United States Patent
Brenneman et al.

(10) Patent No.: US 11,485,736 B2
(45) Date of Patent: Nov. 1, 2022

(54) SUBSTITUTED PYRAZOLOPYRIMIDINES AND SUBSTITUTED PURINES AND THEIR USE AS UBIQUITIN-SPECIFIC-PROCESSING PROTEASE 1 (USP1) INHIBITORS

(71) Applicant: KSQ Therapeutics, Inc., Lexington, MA (US)

(72) Inventors: Jehrod Burnett Brenneman, Marblehead, MA (US); Elsa Beyer Krall, Cambridge, MA (US); Michael Schlabach, Belmont, MA (US); Andrew Alistair Wylie, Newton, MA (US)

(73) Assignee: KSQ Therapeutics, Inc., Lexington, MA (US)

( * ) Notice: Subject to any disclaimer, the term of this patent is extended or adjusted under 35 U.S.C. 154(b) by 157 days.

(21) Appl. No.: 16/721,079

(22) Filed: Dec. 19, 2019

(65) Prior Publication Data

US 2021/0115049 A1   Apr. 22, 2021

Related U.S. Application Data

(60) Provisional application No. 62/946,263, filed on Dec. 10, 2019, provisional application No. 62/868,616, filed on Jun. 28, 2019, provisional application No. 62/857,986, filed on Jun. 6, 2019, provisional application No. 62/799,423, filed on Jan. 31, 2019, provisional application No. 62/783,014, filed on Dec. 20, 2018.

(51) Int. Cl.
*C07D 487/04* (2006.01)
*A61P 35/00* (2006.01)
*C12Q 1/6886* (2018.01)

(52) U.S. Cl.
CPC .......... *C07D 487/04* (2013.01); *A61P 35/00* (2018.01); *C12Q 1/6886* (2013.01); *C12Q 2600/156* (2013.01)

(58) Field of Classification Search
CPC ..... A61K 31/519; A61P 35/00; C07D 487/04; C12Q 1/6886; C12Q 2600/156
See application file for complete search history.

(56) References Cited

U.S. PATENT DOCUMENTS

| | | | |
|---|---|---|---|
| 5,010,175 | A | 4/1991 | Rutter et al. |
| 5,475,096 | A | 12/1995 | Gold et al. |
| 6,453,242 | B1 | 9/2002 | Eisenberg et al. |
| 7,964,356 | B2 | 6/2011 | Zichi et al. |
| 8,541,192 | B2 | 9/2013 | D'Andrea |
| 8,598,184 | B2 | 12/2013 | Zhang |
| 2008/0318838 | A1 | 12/2008 | Bauer et al. |
| 2009/0062196 | A1 | 3/2009 | D'Andrea et al. |
| 2011/0144134 | A1 | 6/2011 | Shokat et al. |
| 2012/0202690 | A1* | 8/2012 | Whittingham ....... C07D 471/04 504/103 |
| 2013/0079512 | A1 | 3/2013 | Nagaraj et al. |
| 2013/0253005 | A1 | 9/2013 | D'Andrea et al. |
| 2017/0145012 | A1 | 5/2017 | Buckmelter et al. |

FOREIGN PATENT DOCUMENTS

| | | |
|---|---|---|
| WO | WO-1996023899 A1 | 8/1996 |
| WO | WO-1998015833 A1 | 4/1998 |
| WO | WO-2014105952 A2 | 7/2014 |
| WO | WO-2015071474 A2 | 5/2015 |
| WO | WO 2017/026718 A1 | 2/2017 |

OTHER PUBLICATIONS

Pubchem CID 129736955,9-Benzyl-2-(2-fluorophenyl)purine, Sep. 13, 2017, accessed at https://pubchem.ncbi.nlm.nih.gov/compound/129736955, accessed on Feb. 12, 2020.

International Search Report and Written Opinion for International Application No. PCT/US19/67521, International Searching Authority, United States, dated May 5, 2020, 14 pages.

Audeh, M.W., et al., "Oral poly(ADP-ribose) polymerase inhibitor olaparib in patients with BRCA1 or BRCA2 mutations and recurrent ovarian cancer: a proof-of-concept trial," Lancet 376:245-251, Elsevier, Netherlands (2010).

Beerli, R.R., et al., "Engineering polydactyl zinc-finger transcription factors," Nat Biotechnol. 20(2): 135-141, Nature Publishing Group, United Kingdom (2002).

(Continued)

*Primary Examiner* — Erich A Leeser
(74) *Attorney, Agent, or Firm* — Sterne, Kessler, Goldstein and Fox P.L.L.C.

(57) ABSTRACT

The present disclosure provides compounds having Formula I:

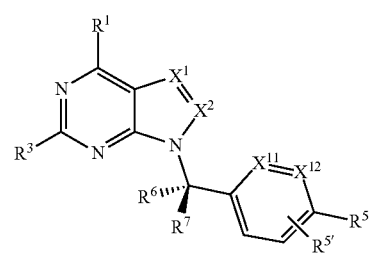

and the pharmaceutically acceptable salts and solvates thereof, wherein $X^1$, $X^2$, $X^{11}$, $X^{12}$, $R^1$, $R^3$, $R^5$, $R^{5'}$, $R^6$, and $R^7$ are defined as set forth in the specification. The present disclosure is also directed to the use of compounds of Formula I to inhibit a USP1 protein and/or to treat a disorder responsive to the inhibition of USP1 proteins and USP1 activity. Compounds of the present disclosure are especially useful for treating cancer.

45 Claims, 7 Drawing Sheets

Specification includes a Sequence Listing.

(56) References Cited

OTHER PUBLICATIONS

Bingham, A. L., et al., "Over one hundred solvates of sulfathiazole," Chemical Communications 7:603-604, Royal Society of Chemistry, England (2001).
Bratkovic, T., et al., "Progress in phage display: evolution of the technique and its applications," Cell Mol Life Sci 67(5):749-767, Springerlink, United States (2010).
Brody, E.N., et al., "High-content affinity-based proteomics: unlocking protein biomarker discovery," Expert Rev Mol. Diagn 10(8):1013-1022, Taylor & Francis, United States (2010).
Caira, M.R., et al., "Preparation and crystal characterization of a polymorph, a monohydrate, and an ethyl acetate solvate of the antifungal fluconazole," Journal of Pharmaceutical Sciences 93(3):601-611, American Pharmacists Association, United States (2003).
Chaturvedi, K., et al.,"Cyclodextrin-based siRNA delivery nanocarriers: a state-of-the-art review," Expert Opin Drug Delivery, 8(11):1455-1468, Taylor and Francis, United States (2011).
Chen, J., et al., "Selective and cell-active inhibitors of the USP1/UAF1 deubiquitinase complex reverse cisplatin resistance in non-small cell lung cancer cells," Chem Biol 18(11):1390-1400, Elsevier, Netherlands (2011).
Chernolovskaya, E.L., et al., "Chemical modification of siRNA," Curr Opin Mol Ther 12(2):158-167, Current Drugs Ltd., United Kingdom (2010).
Choo, Y., et al., "Advances in zinc finger engineering," Curr Opin Struct Biology 10(4):411-416, Elsevier, Netherlands (2000).
Chylinski, K., et al., "The tracrRNA and Cas9 families of type II CRISPR-Cas Immunity systems," RNA Biol 10(5):726-737, Landes Bioscience, United States (2013).
Davis, M.I., et al.,"Ubiquitin-Specific Proteases as Druggable Targets," Drug Target Rev. 2(3):60-64, Bentham Science, United States (2015).
Deveau, H., et al., "Phage Response to CRISPR-Encoded Resistance in *Streptococcus thermophilus*," Journal of Bacteriology 190(4):1390-1400, American Society for Microbiology, United States (2008).
Elington, A.D., et al., "In vitro selection of RNA molecules that bind specific ligands," Nature 346:818-822, Nature Publishing Group, United Kingdom (1990).
Esvelt, K.M., et al., "A system for the continuous directed evolution of biomolecules," Nature 472(7344):499-503, Nature Publishing Group, United Kingdom (2011).
Foged, C., "siRNA delivery with lipid-based systems: promises and pitfalls," Curr Top Med Chem 12(2):97-107, Betham Science, United States (2012).
Gaglione, M., et al., "Recent progress in chemically modified siRNAs," Mini Rev Med Chem 10(7):578-595, Bentham Science, United States (2010).
Gallop, M.A., et al., "Applications of combinatorial technologies to drug discovery. 1. Background and peptide combinatorial libraries," J. Med Chem 37(9):1233-1251, American Chemical Society, United States (1994).
Gao, Y., et al., "Research Progress on siRNA Delivery with Nonviral Carriers," International Journal of Nanomedicine 6:1017-1025, International Jorunal of Nanomedicine, Dovepress, United States (2011).
Geary, R.S., "Antisense oligonucleotide pharmacokinetics and metabolism," Expert Opin Drug Metab Toxicol 5(4):381-391, Taylor & Francis, United States (2009).
Kumari, A., et al., "Nanocarriers: a tool to overcome biological barriers in siRNA delivery," Expert Opinion on Biological therapy 11(10): 1327-1339, Taylor & Francis, United States (2011).
Horvath et al., "CRISPR/Cas, the immune system of bacteria and archaea," Science, 327(5962): 167-70, American Association for the Advancement of Science (2010).
Isalan et al., "A rapid, generally applicable method to engineer zinc fingers illustrated by targeting the HIV-1 promoter," Nature Biotechnol. 19:656-660, Europe PMC, England (2001).
Yamamoto, T., et al., "Antisense drug discovery and development," Future Medicinal chemistry 3(3):339-365, Future Science, United States (2011).

Kanasty et al., "Action and reaction: the biological response to siRNA and its delivery vehicles," Mol. Ther., 20: 513-524, Cell Press, United States (2012).
Kurreck et al., "Design of antisense oligonucleotides stabilized by locked nucleic acids," Nucl. Acids Res., 30(9): 1911-1918, Oxford Academic, England (2002).
Kurreck, J., "Antisense technologies. Improvement through novel chemical modifications," Eur. J. Biochem., 270: 1628-1644, John Wiley & Sons, United States (2003).
Liang, Q., et al., "A selective USP1-UAF1 inhibitor links deubiquitination to DNA damage responses," Nat Chem Biol 10:298-304, Nature Publishing Group, England (2014).
Mali, P., et al., "RNA-guided human genome engineering via Cas9," Science 339(6121): 823-24, American Association for the Advancement of Science (2013).
Lee, S.K., et al., "Cell-specific siRNA delivery by peptides and antibodies," Methods Enzymol., 502: 91-122, Elsevier, Netherlands (2012).
Miller, J., et al., "Repetitive zinc-binding domains in the protein transcription factor IIIA from Xenopus oocytes," Embo J. 4(6):1609-1614, Embo Press, United States (1985).
Mistry, H., et al., "Small-Molecule Inhibitors of USP1 Target ID1 Degradation in Leukemic Cells," Mol. Cancer Ther. 12:2651-2662, American Association for Cancer Research (2013).
Naeye, B., et al., "Matrix systems for siRNA delivery," Curr. Top. Med. Chem. 12: 89-96, Bentham Publishers, Netherlands (2012).
Ni, X. et al., "Nucleic acid aptamers: clinical applications and promising new horizons," Curr. Med. Chem. 18(27): 4206, Bentham Publishers, Netherlands (2011).
Pabo, C., et al., "Design and selection of novel Cys2His2 zinc finger proteins," Ann. Rev. Biochem. 70:313-340, Annual Reviews, United States (2001).
Pande, J., et al., "Phage display: concept, innovations, applications and future," Biotech. Adv. 28: 849-858, Elsevier, Netherlands (2010).
Peacock, H. et al., "Chemical Modification of siRNA Bases to Probe and Enhance RNA Interference," J. Org. Chem., 76: 7295-7300, ACS Publications, United States (2011).
Pasternak, A., et al., "Unlocked nucleic acid—an RNA modification with broad potential," Organic & Biomolecular Chemistry (9): 3591-3597, Royal Society of Chemistry, England (2011).
Prakash, T.P., "An overview of sugar-modified oligonucleotides for antisense therapeutics," Chemistry & Biodiversity 8(9):1616-1641, Europe PMC, United States (2011).
Roon-Mom, W.M., et al., "Overview on applications of antisense-mediated exon skipping," Methods Mol Biol 867:79-96, Springerlink, United States (2012).
S.A., et al., "Pharmacogenomic analysis of patient-derived tumor cells in gynecologic cancers," Genome Biology: 13 pages, Biomed Central, United States (2019).
Segal, D.J., et al., "Custom DNA-binding proteins come of age: polydactyl zinc-finger proteins," Curr Opin Biotechnol 12(6):632-637, Elsevier, Netherlands (2001).
Seth, S., et al., "Delivery and biodistribution of siRNA for cancer therapy: challenges and future prospects," Therapeutic Delivery 3(2):245-261, Future Science, United States (2012).
Sharei, A., et al., "A vector-free microfluidic platform for intracellular delivery," PNAS, 110(6), 2082-2087, National Academy of Sciences, United States (2013).
Shegokar, R., et al., "SiRNA Delivery: challenges and role of carrier systems," Pharmazie 66(5):313-318, Govi-Verlag Pharmazautischer Verlag, Germany, (2011).
Taniguchi, T., et al., "The Fanconi anemia pathway and ubiquitin," BMC Biochemistry 8(1):S10, Biomed Central, United States (2007).
Thompson, L.A., et al., "Synthesis and Applications of Small Molecule Libraries," Chemical Review 96:555-600, American Chemical Society, United States (1996).
Tuerk, C., et al., "Systematic evolution of ligands by exponential enrichment: RNA ligands to bacteriophage T4 DNA polymerase," Science 249(4968):505-510, AAAS, United States (1990).
Vader, P., et al., "Polymeric Carrier Systems for siRNA Delivery," Current Topics in Medicinal Chemistry 12(2):108-119, Bentham Science, United States (2012).

(56) References Cited

OTHER PUBLICATIONS

Van Tonder, E.C., et al., "Preparation and physicochemical characterization of 5 niclosamide solvates and 1 hemisolvate," AAPS PharmSciTech 5(1), Art. 12, 1-10, Springerlink, Germany (2004).
Wang, C., et al., "ATM-Deficient Colorectal Cancer Cells are Sensitive to the PARP Inhibitor Olaparib," Tranl Oncol, 10(2):190-196, Elsevier, Netherlands (2017).
Lim, K.S., et al., "Abstract 333: USP1 is required for replication fork stability in BRCA1-deficient tumors," AACR 78(13): 1 page, Proceedings of the American Association for Cancer Research Annual Meeting, Apr. 14-Apr. 18, United States (2018).
Chan, J.H., et al., "Antisense oligonucleotides: from design to therapeutic application," Clin Exp Pharmacol Physiol. 33(5-6):533-540, Wiley Online Library, United States (2006).
Fire, A., et al., "Potent and specific genetic interference by double-stranded RNA in Caenorhabditis elegans," Nature 391(6669):806-811, Nature Publishing Group, United Kingdom (1998).
McManus, M., et al., "Gene silencing in mammals by small interfering RNAs," Nat Rev Genet 3:737-747, Nature Publishing Group, United Kingdom (2002).
Bramsen, J.B., et al., "Chemical modification of small interfering RNA," Methods Mol Biol. 721:77-103, SpringerLink, Germany (2011).
Rhodes, D., et al., "Zinc Fingers," Scientific American 268(2):56-59,62-65, Scientific American, United States (1993).
Esvelt, K.M., et al., "Orthogonal Cas9 Proteins for RNA-Guided Gene Regulation and editing," Nat Methods 10(11):1116-1121, Nature Publishing Group, United Kingdom (2013).
Zhang, Y,. et al., "Comparison of non-canonical PAMs for CRISPR/Cas9-mediated DNA cleavage in human cells," Sci Rep 5405:1-5, Scientific Reports, United States (2014).
Gentilucci, L., et al., "Chemical modifications designed to improve peptide stability: incorporation of non-natural amino acids, pseudo-peptide bonds, and cyclization," Curr Pharm Des 16(28):3185-3203, Bentham Science, United States (2010).
Berezovski, M.V., et al., "APTAMER-Facilitated Biomarker Discovery (AptaBiD)," JACS Articles 130: 9137-9143, American Chemical Society, United States (2008).
Cadzow, L., "Development Of KSQ-4279 as a First-in-Class USP1 Inhibitor for the Treatment of BRCA-Deficient Cancers," KSQ Therapeutics, poster presented at the *32nd Symposium of the EORTC-NCI-AACR on Molecular Targets and Cancer Therapeutics*, Poster #184, 1 page, American Association for Cancer Research, United States (Oct. 2020).
Cadzow, L., "Development of KSQ-4279 as a First-in-Class USP1 Inhibitor for the Treatment of BRCA-Deficient Cancers," *European Journal of Cancer 138*(S2):S52, Abstract #184, 1 page, Elsevier, Netherlands (Oct. 2020).
Fok, J. H. L., et al., "AZD7648 is a potent and selective DNA-PK inhibitor that enhances radiation, chemotherapy and olaparib activity," *Nat Commun 10*(1):5065, 15 pages, Nature Publishing Group, United Kingdom (Nov. 2019).
Huang, T. T., and D'Andrea, A. D., "Regulation of DNA repair by ubiquitylation," *Nat Rev Mol Cell Biol 7*(5):323-334, Nature Publishing Group, United Kingdom (May 2006).
Kim, J. M., et al., "Inactivation of murine Usp1 results in genomic instability and a Fanconi anemia phenotype," *Dev Cell 16*(2):314-320, Cell Press, United States (Feb. 2009).
Lim, K. S., et al., "USP1 is Required for Replication Fork Protection in BRCA1-Deficient Tumors," *Mol Cell 72*(6):925-941, Cell Press, United States (Dec. 2018).
Lord, C. J., and Ashworth, A., "PARP inhibitors: Synthetic lethality in the clinic," *Science 355*(6330): 1152-1158, American Association for the Advancement of Science, United States (Mar. 2017).
Murai, J., et al., "The USP1/UAF1 complex promotes double-strand break repair through homologous recombination," *Mol Cell Biol 31*(12):2462-2469, American Society for Microbiology, United States (published online Apr. 2011, published in print Jun. 2011).
Parmar, K., et al., "Hematopoietic stem cell defects in mice with deficiency of Fancd2 or Usp1," *Stem Cells 28*(7):1186-1195, Wiley-Blackwell, United States (Jul. 2010).
Rageul, J., and Kim, H., "Fanconi anemia and the underlying causes of genomic instability," *Environ Mol Mutagen 61*(7):693-708, Wiley-Liss Inc., United States (published online Feb. 2020, published in print Aug. 2020).
Sullivan, P., "USP1 inhibitors show robust combination activity and a distinct resistance profile from PARP inhibitors," *European Journal of Cancer 138*(S2):S7-S8, Abstract #ORAL003, 2 pages, Elsevier, Netherlands (Oct. 2020).
Wylie, A., "USP1 inhibitors show robust combination activity and a distinct resistance profile from PARP inhibitors," KSQ Therapeutics, presented at the *32nd Symposium of the EORTC-NCI-AACR on Molecular Targets and Cancer Therapeutics*, Virtual Conference, ORAL003, 17 pages, American Association for Cancer Research, United States (Oct. 24, 2020).

\* cited by examiner

SEQUENCE LISTING

```
<160> NUMBER OF SEQ ID NOS: 1

<210> SEQ ID NO 1
<211> LENGTH: 785
<212> TYPE: PRT
<213> ORGANISM: Homo sapiens

<400> SEQUENCE: 1

Met Pro Gly Val Ile Pro Ser Glu Ser Asn Gly Leu Ser Arg Gly Ser
1               5                   10                  15

Pro Ser Lys Lys Asn Arg Leu Ser Leu Lys Phe Phe Gln Lys Lys Glu
            20                  25                  30

Thr Lys Arg Ala Leu Asp Phe Thr Asp Ser Gln Glu Asn Glu Glu Lys
        35                  40                  45

Ala Ser Glu Tyr Arg Ala Ser Glu Ile Asp Gln Val Val Pro Ala Ala
    50                  55                  60

Gln Ser Ser Pro Ile Asn Cys Glu Lys Arg Glu Asn Leu Leu Pro Phe
65                  70                  75                  80

Val Gly Leu Asn Asn Leu Gly Asn Thr Cys Tyr Leu Asn Ser Ile Leu
                85                  90                  95

Gln Val Leu Tyr Phe Cys Pro Gly Phe Lys Ser Gly Val Lys His Leu
            100                 105                 110

Phe Asn Ile Ile Ser Arg Lys Lys Glu Ala Leu Lys Asp Glu Ala Asn
        115                 120                 125

Gln Lys Asp Lys Gly Asn Cys Lys Glu Asp Ser Leu Ala Ser Tyr Glu
    130                 135                 140

Leu Ile Cys Ser Leu Gln Ser Leu Ile Ile Ser Val Glu Gln Leu Gln
145                 150                 155                 160

Ala Ser Phe Leu Leu Asn Pro Glu Lys Tyr Thr Asp Glu Leu Ala Thr
                165                 170                 175

Gln Pro Arg Arg Leu Leu Asn Thr Leu Arg Glu Leu Asn Pro Met Tyr
            180                 185                 190

Glu Gly Tyr Leu Gln His Asp Ala Gln Glu Val Leu Gln Cys Ile Leu
        195                 200                 205

Gly Asn Ile Gln Glu Thr Cys Gln Leu Leu Lys Lys Glu Glu Val Lys
    210                 215                 220

Asn Val Ala Glu Leu Pro Thr Lys Val Glu Glu Ile Pro His Pro Lys
225                 230                 235                 240

Glu Glu Met Asn Gly Ile Asn Ser Ile Glu Met Asp Ser Met Arg His
```

-continued

```
                245                 250                 255
Ser Glu Asp Phe Lys Glu Lys Leu Pro Lys Gly Asn Gly Lys Arg Lys
            260                 265                 270
Ser Asp Thr Glu Phe Gly Asn Met Lys Lys Val Lys Leu Ser Lys
        275                 280                 285
Glu His Gln Ser Leu Glu Glu Asn Gln Arg Gln Thr Arg Ser Lys Arg
    290                 295                 300
Lys Ala Thr Ser Asp Thr Leu Glu Ser Pro Lys Ile Ile Pro Lys
305                 310                 315                 320
Tyr Ile Ser Glu Asn Glu Ser Pro Arg Pro Ser Gln Lys Lys Ser Arg
                325                 330                 335
Val Lys Ile Asn Trp Leu Lys Ser Ala Thr Lys Gln Pro Ser Ile Leu
            340                 345                 350
Ser Lys Phe Cys Ser Leu Gly Lys Ile Thr Thr Asn Gln Gly Val Lys
        355                 360                 365
Gly Gln Ser Lys Glu Asn Glu Cys Asp Pro Glu Glu Asp Leu Gly Lys
    370                 375                 380
Cys Glu Ser Asp Asn Thr Thr Asn Gly Cys Gly Leu Glu Ser Pro Gly
385                 390                 395                 400
Asn Thr Val Thr Pro Val Asn Val Asn Glu Val Lys Pro Ile Asn Lys
                405                 410                 415
Gly Glu Glu Gln Ile Gly Phe Glu Leu Val Lys Leu Phe Gln Gly
            420                 425                 430
Gln Leu Val Leu Arg Thr Arg Cys Leu Glu Cys Glu Ser Leu Thr Glu
        435                 440                 445
Arg Arg Glu Asp Phe Gln Asp Ile Ser Val Pro Val Gln Glu Asp Glu
    450                 455                 460
Leu Ser Lys Val Glu Ser Ser Glu Ile Ser Pro Glu Pro Lys Thr
465                 470                 475                 480
Glu Met Lys Thr Leu Arg Trp Ala Ile Ser Gln Phe Ala Ser Val Glu
                485                 490                 495
Arg Ile Val Gly Glu Asp Lys Tyr Phe Cys Glu Asn Cys His His Tyr
            500                 505                 510
Thr Glu Ala Glu Arg Ser Leu Leu Phe Asp Lys Met Pro Glu Val Ile
        515                 520                 525
Thr Ile His Leu Lys Cys Phe Ala Ala Ser Gly Leu Glu Phe Asp Cys
    530                 535                 540
Tyr Gly Gly Gly Leu Ser Lys Ile Asn Thr Pro Leu Leu Thr Pro Leu
545                 550                 555                 560
Lys Leu Ser Leu Glu Glu Trp Ser Thr Lys Pro Thr Asn Asp Ser Tyr
                565                 570                 575
Gly Leu Phe Ala Val Val Met His Ser Gly Ile Thr Ile Ser Ser Gly
            580                 585                 590
His Tyr Thr Ala Ser Val Lys Val Thr Asp Leu Asn Ser Leu Glu Leu
        595                 600                 605
Asp Lys Gly Asn Phe Val Val Asp Gln Met Cys Glu Ile Gly Lys Pro
    610                 615                 620
Glu Pro Leu Asn Glu Glu Ala Arg Gly Val Val Glu Asn Tyr Asn
625                 630                 635                 640
Asp Glu Glu Val Ser Ile Arg Val Gly Gly Asn Thr Gln Pro Ser Lys
                645                 650                 655
Val Leu Asn Lys Lys Asn Val Glu Ala Ile Gly Leu Leu Gly Gly Gln
            660                 665                 670
```

```
Lys Ser Lys Ala Asp Tyr Glu Leu Tyr Asn Lys Ala Ser Asn Pro Asp
        675                 680                 685
Lys Val Ala Ser Thr Ala Phe Ala Glu Asn Arg Asn Ser Glu Thr Ser
690                 695                 700
Asp Thr Thr Gly Thr His Glu Ser Asp Arg Asn Lys Glu Ser Ser Asp
705                 710                 715                 720
Gln Thr Gly Ile Asn Ile Ser Gly Phe Glu Asn Lys Ile Ser Tyr Val
                725                 730                 735
Val Gln Ser Leu Lys Glu Tyr Glu Gly Lys Trp Leu Leu Phe Asp Asp
            740                 745                 750
Ser Glu Val Lys Val Thr Glu Glu Lys Asp Phe Leu Asn Ser Leu Ser
        755                 760                 765
Pro Ser Thr Ser Pro Thr Ser Thr Pro Tyr Leu Leu Phe Tyr Lys Lys
770                 775                 780
Leu
785
```

SUBSTITUTED PYRAZOLOPYRIMIDINES AND SUBSTITUTED PURINES AND THEIR USE AS UBIQUITIN-SPECIFIC-PROCESSING PROTEASE 1 (USP1) INHIBITORS

CROSS REFERENCE TO RELATED APPLICATIONS

This application claims the priority benefit of U.S. Provisional Application Nos. 62/946,263, filed Dec. 10, 2019, 62/868,616, filed Jun. 28, 2019, 62/857,986, filed Jun. 6, 2019, 62/799,423, filed Jan. 31, 2019, and 62/783,014, filed Dec. 20, 2018, each of which is hereby incorporated by reference herein in its entirety.

REFERENCE TO A SEQUENCE LISTING SUBMITTED ELECTRONICALLY VIA EFS-WEB

The Sequence Listing submitted Dec. 19, 2019, as a text file named "4195.0070004_SL_ST25," created on Dec. 18, 2019, and having a size of 7,275 bytes, is hereby incorporated by reference pursuant to 37 C.F.R. § 1.52(e)(5).

BACKGROUND OF THE DISCLOSURE

Field of the Invention

The present disclosure provides substituted pyrazolopyrimidines and substituted purines as ubiquitin-specific-processing protease 1 (USP1) inhibitors, and therapeutic methods of treating conditions and diseases wherein inhibition of USP1 provides a benefit. In particular, the present disclosure provides methods of treating cancer by administering a USP1 inhibitor.

Background

Ubiquitin is a small (76 amino acid) protein that is post-transcriptionally attached to target proteins. The consequence of ubiquitination is determined by the number and linkage topology of ubiquitin molecules conjugated to the target protein. For example, proteins exhibiting lysine 48-linked poly-ubiquitin chains are generally targeted to the proteasome for degradation, while mono-ubiquitination or poly-ubiquitin chains linked through other lysines regulate non-proteolytic functions, such as cell cycle regulation, DNA damage repair, transcription, and endocytosis. Ubiquitination is a reversible process, and enzymes called deubiquitinases remove ubiquitin from target proteins.

USP1 is a deubiquitinase that plays a role in DNA damage repair. USP1 interacts with UAF1 (USP1-associated factor 1) to form a complex that is required for the deubiquitinase activity. The USP1/UAF1 complex deubiquitinates mono-ubiquitinated PCNA (proliferating cell nuclear antigen) and mono-ubiquitinated FANCD2 (Fanconi anemia group complementation group D2), which are proteins that play important functions in translesion synthesis (TLS) and the Fanconi anemia (FA) pathway, respectively. The USP1/UAF1 complex also deubiquitinates Fanconi anemia complementation group I (FANCI). These two pathways are essential for repair of DNA damage induced by DNA cross-linking agents, such as cisplatin and mitomycin C (MMC).

Safe and effective treatments targeting deubiquitinases are unknown, not yet commercially available, or have not yet been clinically developed.

BRIEF SUMMARY OF THE DISCLOSURE

In one aspect, the present disclosure relates to compounds, or a pharmaceutically acceptable salt or solvate thereof, having Formula I (also referred to herein as Compounds of the Disclosure):

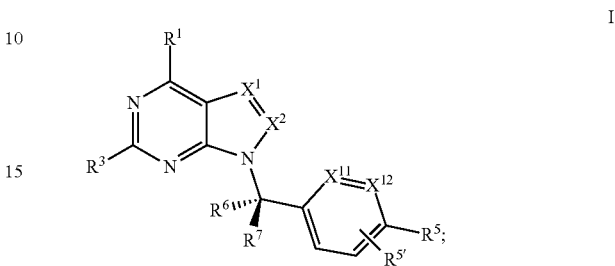

I wherein:
each of $X^1$ and $X^2$ is independently selected from N and $CR^2$;
each of $R^1$ and $R^2$ is independently selected from hydrogen, halo, cyano, optionally substituted alkyl, optionally substituted alkenyl, and optionally substituted alkynyl;
$R^3$ is an optionally substituted phenyl, optionally substituted pyridyl, optionally substituted pyrimidinyl, optionally substituted pyrazinyl, optionally substituted pyridazinyl, or optionally substituted pyrazolyl;
each of $X^{11}$ and $X^{12}$ is independently selected from N and CH;
$R^{5'}$ is independently selected from hydrogen, optionally substituted $(C_1-C_6)$ alkyl, optionally substituted $(C_2-C_6)$ alkenyl, optionally substituted $(C_2-C_6)$ alkynyl, optionally substituted $(C_1-C_6)$ alkoxy, $(C_1-C_6)$ haloalkyl, $(C_1-C_6)$ haloalkoxy, $(C_1-C_6)$ hydroxyalkyl, cyano, halo, sulfonamido, —C(=O)$R^{23}$, —C(=O)O$R^{24}$, —$NR^{32a}R^{32b}$, —$NR^{31a}$C(=O)$R^{25}$, —$NR^{31a}$C(=O)$NR^{31a}R^{31b}$, —C(=O)$NR^{31a}R^{31b}$, —S(O)$_2R^{27}$, —$NR^{31a}SO_2R^{27}$, optionally substituted $(C_6-C_{14})$ aryl, optionally substituted $(C_6-C_{14})$ ar-$(C_1-C_2)$ alkyl, optionally substituted heteroaryl, optionally substituted heteroar-$(C_1-C_2)$ alkyl, optionally substituted $(C_3-C_8)$ cycloalkyl, optionally substituted $((C_3-C_8)$ cycloalkyl)-$(C_1-C_2)$ alkyl, optionally substituted heterocyclo, optionally substituted heterocyclo-$(C_1-C_2)$ alkyl, optionally substituted —O—$(C_6-C_{14})$ aryl, optionally substituted —O—$(C_6-C_{14})$ ar-$(C_1-C_2)$ alkyl, optionally substituted —O-heteroaryl, optionally substituted —O-heteroar-$(C_1-C_2)$ alkyl, optionally substituted —O—$(C_3-C_8)$ cycloalkyl, optionally substituted —O—$((C_3-C_8)$ cycloalkyl)-$(C_1-C_2)$ alkyl, optionally substituted —O-heterocyclo, and optionally substituted —O-heterocyclo-$(C_1-C_2)$ alkyl;
$R^5$ is independently selected from optionally substituted $(C_1-C_6)$ alkyl, optionally substituted $(C_2-C_6)$ alkenyl, optionally substituted $(C_2-C_6)$ alkynyl, optionally substituted $(C_1-C_6)$ alkoxy, $(C_1-C_6)$ haloalkyl, $(C_1-C_6)$ haloalkoxy, $(C_1-C_6)$ hydroxyalkyl, cyano, halo, sulfonamido, —C(=O)$R^{23}$, —C(=O)O$R^{24}$, —$NR^{32a}R^{32b}$, —$NR^{31a}$C(=O)$R^{25}$, —$NR^{31a}$C(=O)$NR^{31a}R^{31b}$, —C(=O)$NR^{31a}R^{31b}$, —S(O)$_2R^{27}$, —$NR^{31a}SO_2R^{27}$, optionally substituted $(C_6-C_{14})$ aryl, optionally substituted $(C_6-C_{14})$ ar-$(C_1-C_2)$ alkyl, optionally substituted heteroaryl, optionally substituted heteroar-$(C_1-C_2)$ alkyl, optionally substituted $(C_3-C_8)$ cycloalkyl, optionally substituted $((C_3-C_8)$ cycloalkyl)-$(C_1-C_2)$ alkyl, optionally substituted heterocyclo, optionally substituted heterocyclo-$(C_1-C_2)$ alkyl, optionally substituted —O—($C_6$-$C_{14}$) aryl, optionally substituted —O—($C_6$-$C_{14}$) ar-($C_1$-$C_2$) alkyl, optionally substituted —O-heteroaryl, optionally substituted —O-heteroar-($C_1$-$C_2$) alkyl, optionally substituted —O—($C_3$-$C_8$) cycloalkyl, optionally substituted —O—(($C_3$-$C_8$) cycloalkyl)-($C_1$-$C_2$) alkyl, optionally substituted —O-heterocyclo, and optionally substituted —O-heterocyclo-($C_1$-$C_2$) alkyl; or one of $R^5$ and one of $R^5$ on adjacent atoms are taken together with the atoms to which they are attached to form an optionally substituted ($C_6$-$C_{14}$) aryl ring; or one of $R^5$ and one of $R^{5'}$ on adjacent atoms are taken together with the atoms to which they are attached to form an optionally substituted heteroaryl ring; or one of $R^5$ and one of $R^{5'}$ on adjacent atoms are taken together with the atoms to which they are attached to form an optionally substituted ($C_3$-$C_8$) cycloalkyl ring; or one of $R^5$ and one of $R^{5'}$ on adjacent atoms are taken together with the atoms to which they are attached to form an optionally substituted heterocycloalkyl ring; or one of $R^5$ and one of $R^{5'}$ on adjacent atoms on the same atom to which they are attached are taken together to form an optionally substituted spirocycloalkyl ring; or one of $R^5$ and one of $R^{5'}$ on adjacent atoms on the same atom to which they are attached are taken together to form an optionally substituted spiroheterocycloalkyl ring;

each of $R^6$ and $R^7$ is independently selected from hydrogen, halo, cyano, optionally substituted alkyl, optionally substituted alkenyl, and optionally substituted alkynyl;

$R^{23}$ is selected from the group consisting of hydrogen, optionally substituted alkyl, optionally substituted alkenyl, optionally substituted alkynyl, amino, alkylamino, dialkylamino, cycloalkylamino, hydroxyalkyl, (amino)alkyl, (alkylamino)alkyl, (dialkylamino)alkyl, (cycloalkylamino)alkyl, (cycloalkyl)alkyl, aralkyl, (heterocyclo)alkyl, (heteroaryl)alkyl, (amino)(hydroxy)alkyl, (aralkylamino)alkyl, optionally substituted heterocyclo, optionally substituted heteroaryl, optionally substituted aryl, and optionally substituted cycloalkyl;

$R^{31a}$ and $R^{31b}$ are each independently selected from the group consisting of hydrogen, optionally substituted alkyl, optionally substituted alkenyl, optionally substituted alkynyl, hydroxyalkyl, (amino)alkyl, (alkylamino)alkyl, (dialkylamino)alkyl, alkoxyalkyl, cycloalkyl, (cycloalkyl)alkyl, (heterocyclo)alkyl, aralkyl, and (heteroaryl)alkyl; and each of $R^{24}$, $R^{25}$, $R^{27}$, $R^{32a}$, and $R^{32b}$ is independently selected from the group consisting of hydrogen, optionally substituted alkyl, optionally substituted alkenyl, optionally substituted alkynyl, amino, alkylamino, dialkylamino, cycloalkylamino, hydroxyalkyl, (amino)alkyl, (alkylamino)alkyl, (dialkylamino)alkyl, (cycloalkylamino)alkyl, (cycloalkyl)alkyl, aralkyl, (heterocyclo)alkyl, (heteroaryl)alkyl, (amino)(hydroxy)alkyl, (aralkylamino)alkyl, alkoxyalkyl, optionally substituted heterocyclo, optionally substituted heteroaryl, optionally substituted aryl, and optionally substituted cycloalkyl.

In some embodiments, the Compounds of the Disclosure exhibit improved solubility, e.g., as measured by an ADME solubility assay as disclosed herein.

In some embodiments, the Compounds of the Disclosure exhibit improved metabolic stability, e.g., as measured by liver microsome and hepatocyte metabolic stability assays as disclosed herein.

In other embodiments, the Compounds of the Disclosure exhibit improved duration of action and oral exposure in vivo.

In some embodiments, a Compound of the Disclosure is a compound having Formula I, wherein $R^{5'}$ is selected from hydrogen, halo, and optionally substituted ($C_1$-$C_6$) alkyl.

In some embodiments, a Compound of the Disclosure is a compound having Formula I, wherein at least one of $X^{11}$ and $X^{12}$ is N. In some embodiments, $X^{11}$ is N. In some embodiments, $X^{12}$ is N.

In another embodiment, a Compound of the Disclosure is a compound having Formula I, wherein at least one of $X^{11}$ and $X^{12}$ is CH. In some embodiments, $X^{11}$ is CH. In some embodiments, $X^{12}$ is CH.

In one embodiment, a Compound of the Disclosure is a compound having Formula I, wherein each of $X^{11}$ and $X^{12}$ is N.

In one embodiment, a Compound of the Disclosure is a compound having Formula I, wherein each of $X^{11}$ and $X^{12}$ is CH.

In some embodiments, one of $X^{11}$ and $X^{12}$ is N and the other of $X^{11}$ and $X^{12}$ is CH. In one embodiment $X^{11}$ is N and $X^{12}$ is CH. In another embodiment, $X^{11}$ is CH and $X^{12}$ is N.

In some embodiments,

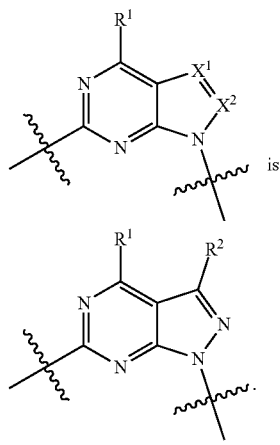

is

In some embodiments,

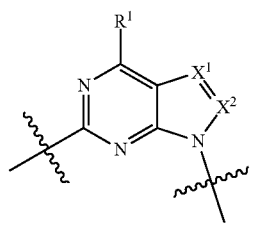

is selected from:

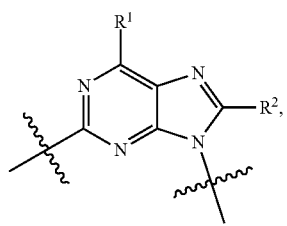

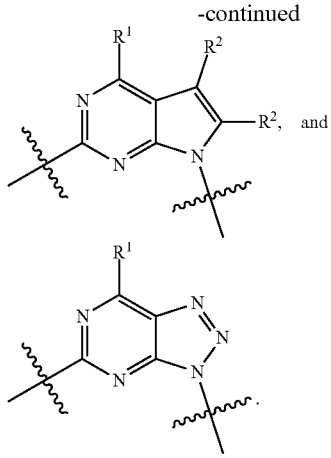

In some embodiments, the optional substituents on R³ are independently selected from hydrogen, halo, nitro, cyano, hydroxy, amino, alkylamino, dialkylamino, haloalkyl, hydroxyalkyl, alkoxy, haloalkoxy, aryloxy, heteroaryloxy, aralkyl aralkyloxy, alkylthio, carboxamido, sulfonamido, alkylcarbonyl, arylcarbonyl, alkylsulfonyl, arylsulfonyl, carboxy, carboxyalkyl, alkyl, optionally substituted cycloalkyl, alkenyl, alkynyl, optionally substituted aryl, optionally substituted heteroaryl, optionally substituted heterocyclo, alkoxyalkyl, (amino)alkyl, hydroxyalkylamino, (alkylamino)alkyl, (dialkylamino)alkyl, (cyano)alkyl, (carboxamido) alkyl, mercaptoalkyl, (heterocyclo)alkyl, (cycloalkylamino) alkyl, (C$_{1-4}$ haloalkoxy)alkyl, and (heteroaryl)alkyl; or two of the optional substituents on R³ are taken together with the carbon or nitrogen atoms to which they are attached to form an optionally substituted cycloalkyl, optionally substituted heterocyclo, optionally substituted aryl, or optionally substituted heteroaryl group.

In some embodiments, R³ is an optionally substituted phenyl, wherein the phenyl is optionally substituted at the 2-position, optionally substituted at the 6-position, optionally disubstituted at the 2- and 6-positions, or optionally disubstituted at the 2- and 3-positions.

In some embodiments, R³ is an optionally substituted pyrid-3-yl or optionally substituted pyrid-4-yl, wherein the pyrid-3-yl is optionally substituted at the 2-position, optionally substituted at the 4-position, or optionally disubstituted at the 2- and 4-positions; and wherein the pyrid-4-yl is optionally substituted at the 3-position, optionally substituted at the 5-position, or optionally disubstituted at the 3- and 5-positions.

In some embodiments, R³ is an optionally substituted pyrimidin-5-yl, wherein the pyrimidin-5-yl is optionally substituted at the 4-position, optionally substituted at the 6-position, optionally disubstituted at the 4- and 6-positions, or optionally trisubstituted at the 2-, 4-, and 6-positions.

In some embodiments, R³ is an optionally substituted pyrazol-5-yl, wherein the pyrazol-5-yl is optionally substituted at the 1-position, optionally substituted at the 4-position, or optionally disubstituted at the 1- and 4-positions.

In some embodiments, R³ is substituted and the substituents are independently selected from methoxy, deuteromethoxy, ethoxy, isopropoxy, t-butoxy, difluoromethoxy, 2-fluoroethoxy, 2-methoxyethoxy, cyclopropoxy, cyclobutoxy, (tetrahydrofuran-3-yl)oxy, benzyloxy, methyl, ethyl, isopropyl, 2-fluoroisopropyl, t-butyl, cyclopropyl, cyclobutyl, methylcyclopropyl, pyrrolidin-1-yl, azetidin-1-yl, methylamino, dimethylamino, cyano, halo, methylthio, methylsulfonyl, and ethylsulfonyl.

In some embodiments, R³ is selected from the group consisting of:

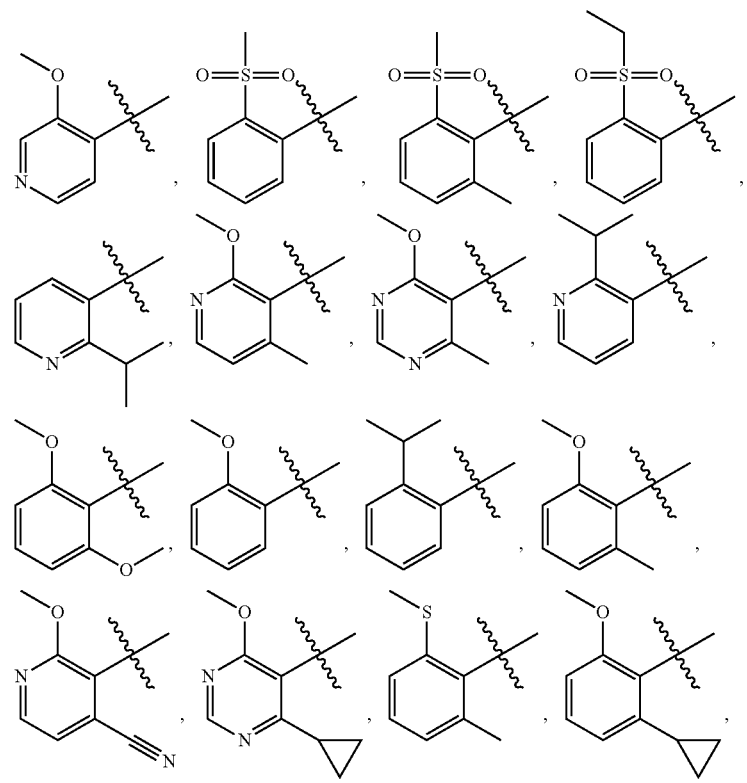

-continued
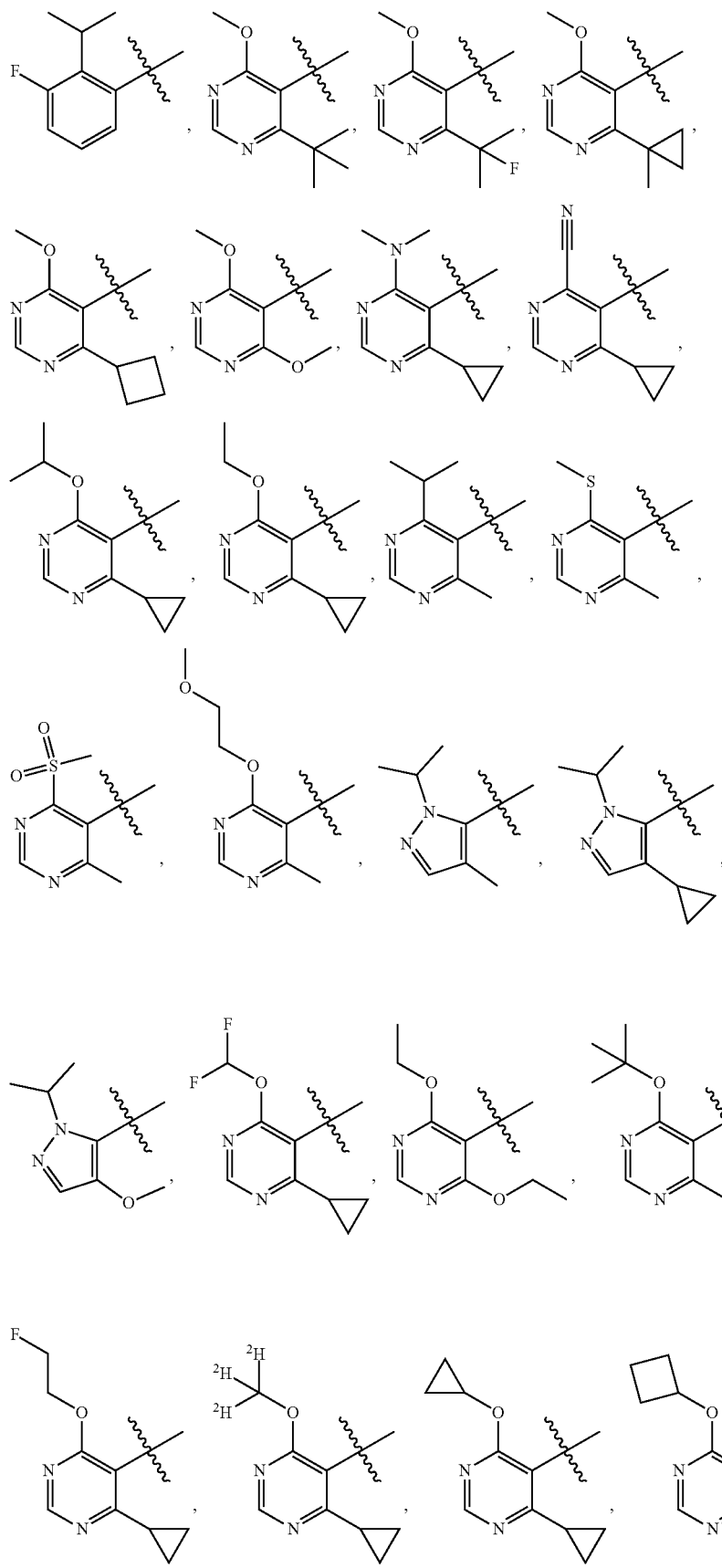

-continued

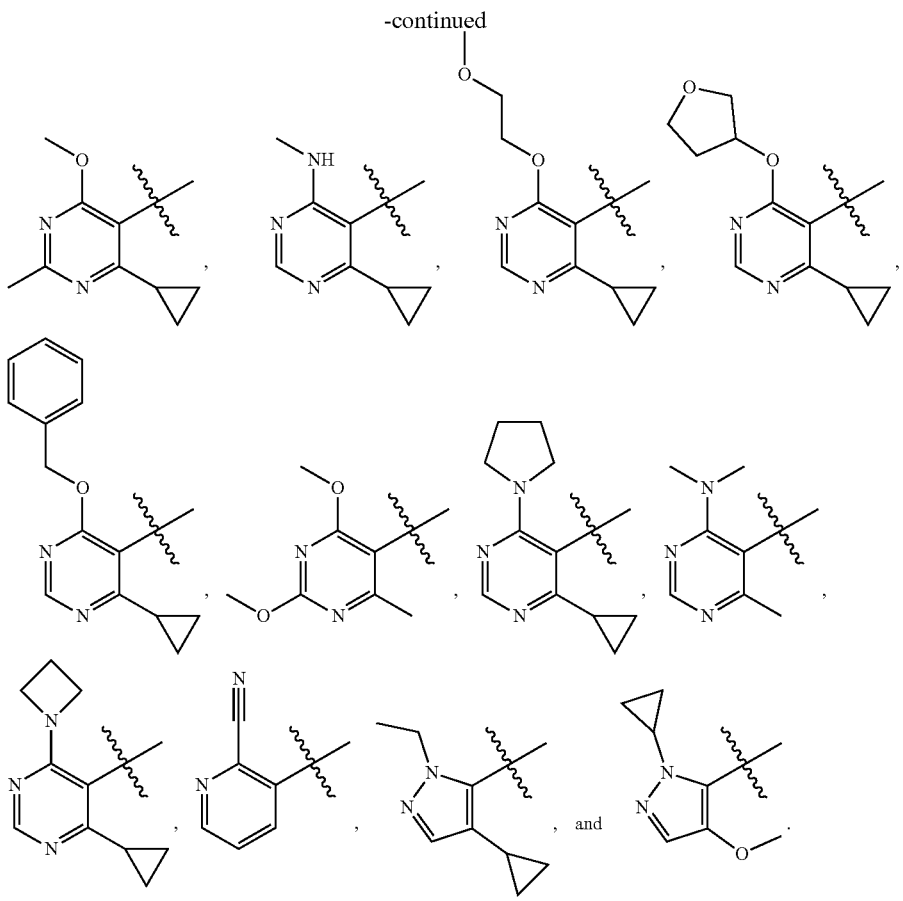

In some embodiments, the optional substituents on $R^5$ are independently selected from hydrogen, halo, nitro, cyano, optionally substituted alkyl, optionally substituted alkenyl, optionally substituted alkynyl, alkoxy, hydroxy, carboxy, carboxyalkyl, amino, alkylamino, dialkylamino, cycloalkylamino, heterocycloalkylamino, aralkylamino, heteroaralkylamino, alkylthio, haloalkyl, haloalkoxy, hydroxyalkyl, hydroxyalkylamino, alkoxyalkyl, (alkoxyalkyl)amino, (amino)alkyl, (alkylamino)alkyl, (dialkylamino)alkyl, (cycloalkylamino)alkyl, (carboxamido)alkyl, mercaptoalkyl, (cyano)alkyl, (cycloalkyl)alkyl, aralkyl, aralkyloxy, alkylcarbonyl, arylcarbonyl, (heterocyclo)alkyl, (heteroaryl)alkyl, (amino)(hydroxy)alkyl, (aralkylamino)alkyl, ($C_{1-4}$ haloalkoxy)alkyl, optionally substituted heterocyclo, optionally substituted heteroaryl, optionally substituted aryl, optionally substituted cycloalkyl, carboxamido, sulfonyl, sulfonamido, sulfamido, alkylsulfonyl, alkylsulfonamido, alkylsulfamido, arylsulfonyl, aryloxy, heteroaryloxy, —C(=O)$R^{23}$, —C(=O)O$R^{24}$, —C(=O)N$R^{31a}R^{31b}$, —N$R^{31a}$C(=O)$R^{25}$, —N$R^{31a}$C(=O)O$R^{26}$, —N$R^{31a}$C(=O)N$R^{31a}R^{31b}$, —N$R^{31a}$SO$_2R^{27}$, —OC(=O)$R^{28}$, —OC(=O)O$R^{29}$, —OC(=O)N$R^{31a}R^{31b}$, —OSO$_2R^{30}$, and —N$R^{32a}R^{32b}$; or two of the optional substituents on $R^5$ are taken together with the carbon or nitrogen atoms to which they are attached to form a cycloalkyl, heterocyclo, aryl, or heteroaryl group; and each of $R^{24}$, $R^{25}$, $R^{26}$, $R^{27}$, $R^{28}$, $R^{29}$, $R^{30}$, $R^{32a}$, and $R^{32b}$ is selected from the group consisting of hydrogen, optionally substituted alkyl, optionally substituted alkenyl, optionally substituted alkynyl, amino, alkylamino, dialkylamino, cycloalkylamino, hydroxyalkyl, (amino)alkyl, (alkylamino)alkyl, (dialkylamino)alkyl, (cycloalkylamino)alkyl, (cycloalkyl)alkyl, aralkyl, (heterocyclo)alkyl, (heteroaryl)alkyl, (amino)(hydroxy)alkyl, (aralkylamino)alkyl, alkoxyalkyl, optionally substituted heterocyclo, optionally substituted heteroaryl, optionally substituted aryl, and optionally substituted cycloalkyl.

In some embodiments, $R^5$ is selected from optionally substituted ($C_1$-$C_6$) alkyl, optionally substituted ($C_2$-$C_6$) alkenyl, optionally substituted ($C_2$-$C_6$) alkynyl, optionally substituted ($C_1$-$C_6$) alkoxy, ($C_1$-$C_6$) haloalkyl, ($C_1$-$C_6$) haloalkoxy, ($C_1$-$C_6$) hydroxyalkyl, cyano, halo, sulfonamido, —C(=O)$R^{23}$, —C(=O)O$R^{24}$, —N$R^{32a}R^{32b}$, —N$R^{31a}$C(=O)$R^{25}$, —N$R^{31a}$C(=O)N$R^{31a}R^{31b}$, —C(=O)N$R^{31a}R^{31b}$, —S(O)$_2R^{27}$, and —N$R^{31a}$SO$_2R^{27}$, optionally substituted —O—($C_6$-$C_{14}$) aryl, optionally substituted —O—($C_6$-$C_{14}$) ar-($C_1$-$C_2$) alkyl, optionally substituted —O-heteroaryl, optionally substituted —O-heteroar-($C_1$-$C_2$) alkyl, optionally substituted —O—($C_3$-$C_8$) cycloalkyl, optionally substituted —O—(($C_3$-$C_8$) cycloalkyl)-($C_1$-$C_2$) alkyl, optionally substituted —O-heterocyclo, optionally substituted —O-heterocyclo-($C_1$-$C_2$) alkyl.

In some embodiments, $R^5$ is selected from optionally substituted ($C_6$-$C_{14}$) aryl, optionally substituted ($C_6$-$C_{14}$) ar-($C_1$-$C_2$) alkyl, optionally substituted heteroaryl, optionally substituted heteroar-($C_1$-$C_2$) alkyl, optionally substituted ($C_3$-$C_8$) cycloalkyl, optionally substituted (($C_3$-$C_8$) cycloalkyl)-($C_1$-$C_2$) alkyl, optionally substituted heterocyclo, optionally substituted heterocyclo-($C_1$-$C_2$) alkyl.

In some embodiments, R⁵ is an optionally substituted pyrrolyl, optionally substituted imidazolyl, optionally substituted pyrazolyl, optionally substituted triazolyl, or optionally substituted tetrazolyl.

In some embodiments, R⁵ is an optionally substituted imidazolyl.

In some embodiments, R⁵ is an optionally substituted pyrazolyl.

In some embodiments, R⁵ is an optionally substituted triazolyl.

In some embodiments, R⁵ is an optionally substituted heteroaryl, such as imidazolyl, pyrazolyl or triazolyl, where the substituents are independently selected from halo, methyl, ethyl, isopropyl, cyclopropyl, cyclobutyl, methoxy, ethoxy, triazolyl, cyano, optionally substituted alkyl, amino, alkylamino, dialkylamino, difluoromethyl, trifluoromethyl, methylsulfonyl, oxetan-3-yl, and methylazetidinyl.

In some embodiments, R⁵ is selected from the group consisting of:

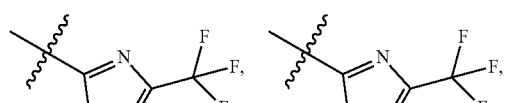
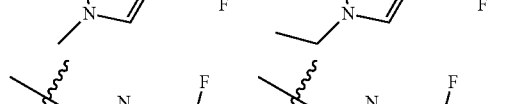
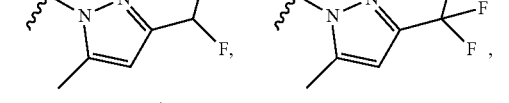
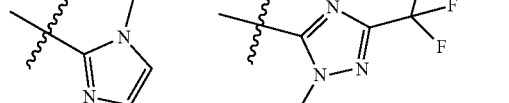
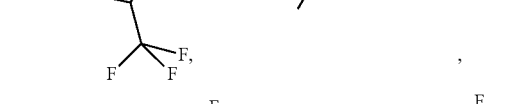
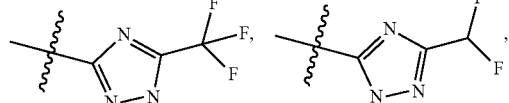
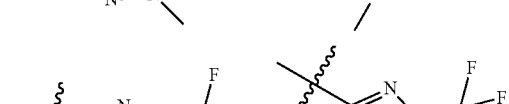

-continued

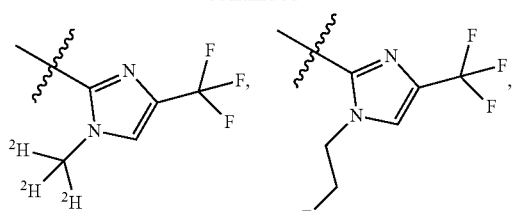
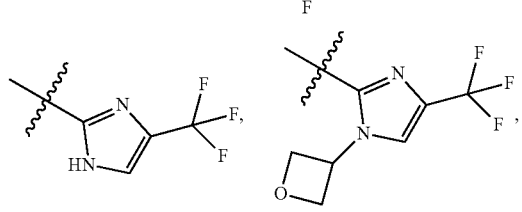
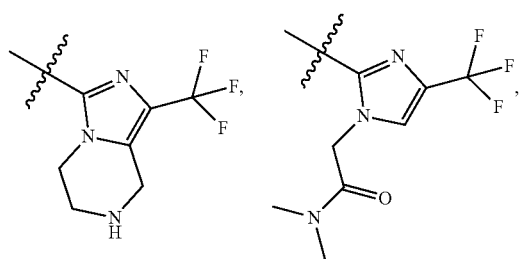
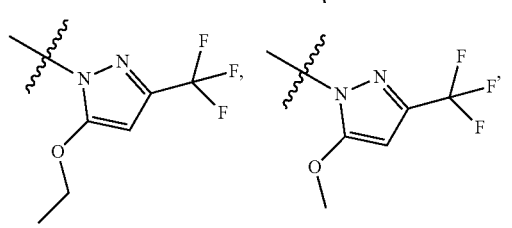
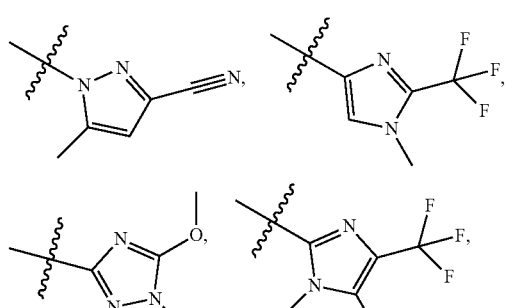
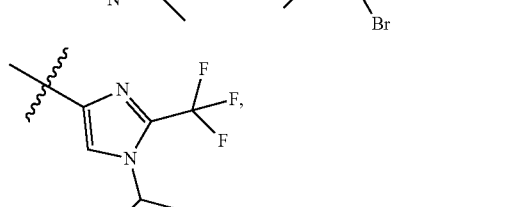
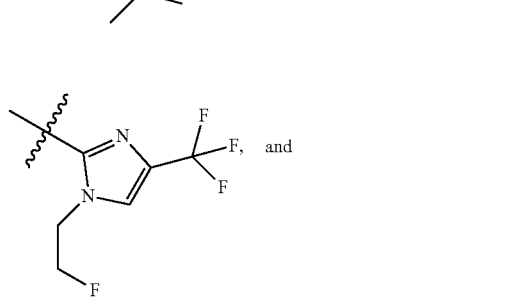

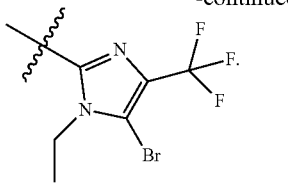

In some embodiments, the compound has Formula II:

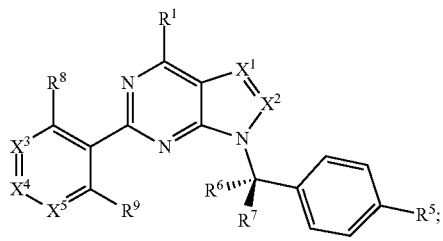

wherein $X^3$ is selected from N and $CR^{10}$; $X^4$ is selected from N and $CR^{11}$; $X^5$ is selected from N and $CR^{12}$; and each of $R^8$, $R^9$, $R^{10}$, $R^{11}$, and $R^{12}$ is independently selected from the group consisting of hydrogen, halo, nitro, cyano, hydroxy, amino, alkylamino, dialkylamino, haloalkyl, hydroxyalkyl, alkoxy, haloalkoxy, aryloxy, heteroaryloxy, aralkyl aralkyloxy, alkylthio, carboxamido, sulfonamido, alkylcarbonyl, arylcarbonyl, alkylsulfonyl, arylsulfonyl, carboxy, carboxyalkyl, alkyl, optionally substituted cycloalkyl, alkenyl, alkynyl, optionally substituted aryl, optionally substituted heteroaryl, optionally substituted heterocyclo, alkoxyalkyl, (amino)alkyl, hydroxyalkylamino, (alkylamino)alkyl, (dialkylamino)alkyl, (cyano)alkyl, (carboxamido)alkyl, mercaptoalkyl, (heterocyclo)alkyl, (cycloalkylamino)alkyl, ($C_{1-4}$ haloalkoxy)alkyl, or (heteroaryl)alkyl.

In some embodiments, the Compounds of the Disclosure has Formula III, Formula IV, Formula V, Formula VI, or Formula VIa:

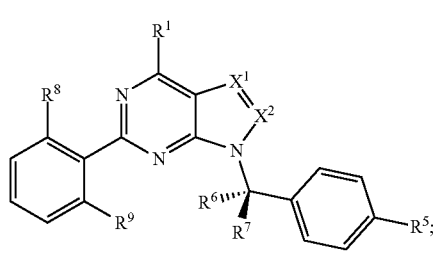

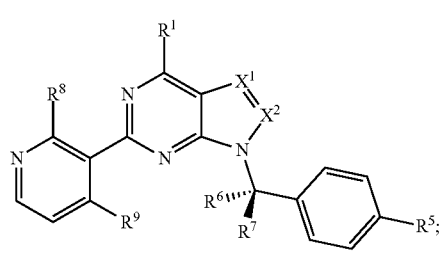

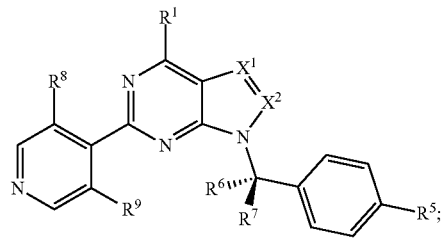

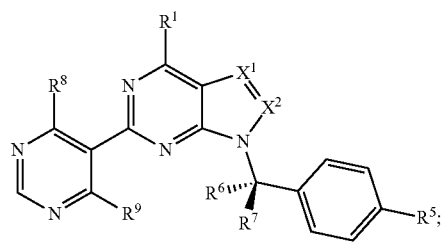

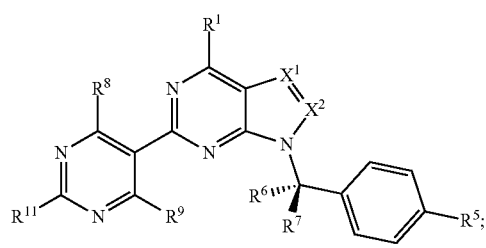

wherein each of $X^1$, $X^2$, $R^1$, $R^5$, $R^6$, $R^7$, $R^8$, $R^9$, and $R^{11}$ are as defined above for Formula II.

In some embodiments, $R^5$ is:

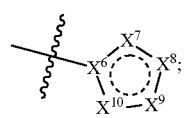

wherein $X^6$ is selected from $NR^{13}$ and $CR^{18}$; $X^7$ is selected from $NR^{14}$ and $CR^{19}$; $X^8$ is selected from $NR^{15}$ and $CR^{20}$; $X^9$ is selected from $NR^{16}$ and $CR^{21}$; $X^{10}$ is selected from $NR^{17}$ and $CR^{22}$; and each of $R^{13}$, $R^{14}$, $R^{5}$, $R^{16}$, and $R^{17}$ is absent, or independently selected from hydrogen, halo, methyl, ethyl, isopropyl, cyclopropyl, methoxy, triazolyl, cyano, optionally substituted alkyl, amino, alkylamino, dialkylamino, difluoromethyl, trifluoromethyl, methylsulfonyl, and methylazetidinyl.

each of $R^{18}$, $R^{19}$, $R^{20}$, $R^{21}$, and $R^{22}$ is independently selected from hydrogen, halo, methyl, ethyl, isopropyl, cyclopropyl, methoxy, triazolyl, cyano, optionally substituted alkyl, amino, alkylamino, dialkylamino, difluoromethyl, trifluoromethyl, methylsulfonyl, and methylazetidinyl.

In some embodiments, the Compounds of the Disclosure has Formula VII, Formula VIII, Formula IX, Formula X, Formula XI, or Formula XII:

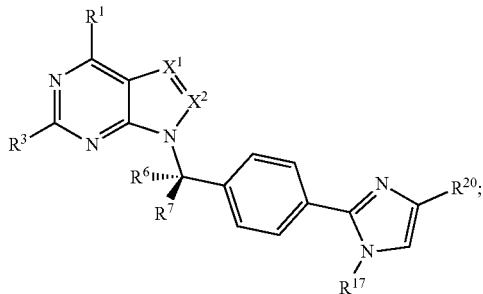

VII

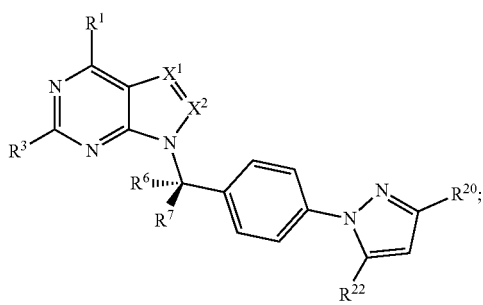

VIII

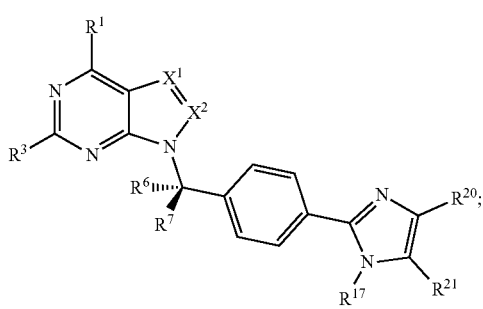

IX

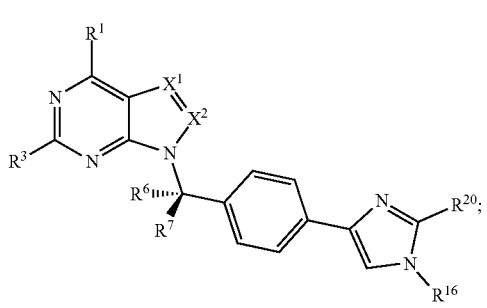

X

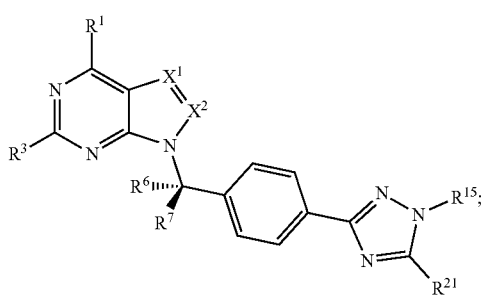

XI

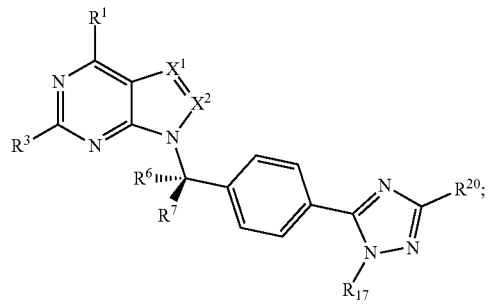

XII wherein each of $X^1$, $X^2$, $R^1$, $R^3$, $R^6$, $R^7$, $R^{15}$, $R^{16}$, $R^{17}$, $R^{20}$, $R^{21}$, and $R^{22}$ are as defined above for Formula II.

In another aspect, the present disclosure relates to Compounds of the Disclosure, or a pharmaceutically acceptable salt or solvate thereof, having Formula XIII:

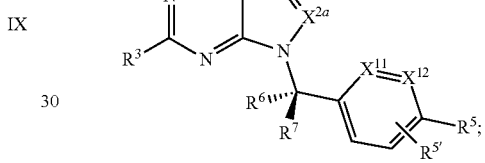

XIII wherein:

each of $X^{1a}$ and $X^{2a}$ is independently selected from N, and $CR^{2a}$;

$R^{2a}$ is independently selected from hydrogen, halo, cyano, optionally substituted alkyl, optionally substituted alkenyl, optionally substituted alkynyl, alkoxy, alkoxyalkyl, alkylsulfonyl, alkylthio, aryl, heteroaryl, and heterocyclo; and each of the remaining substituents is defined as disclosed herein.

In some embodiments, the Compound of the Disclosure is one of the specific compounds listed in the detailed description, or a pharmaceutically acceptable salt or solvate thereof.

In some embodiments, the Compound of the Disclosure inhibits a USP1 protein.

In some embodiments, the Compound of the Disclosure inhibits a USP1 protein with an $IC_{50}$ value of less than about 1 μM in a Ub-Rho deubiquitinating assay.

In some embodiments, the Ub-Rho deubiquitinating assay is the assay disclosed in Example 26.

In one aspect, the present disclosure relates to a method of treating cancer in a patient comprising administering to the patient a therapeutically effective amount of a Compound of the Disclosure, or a pharmaceutically acceptable salt or solvate thereof.

In one aspect, the present disclosure relates to a pharmaceutical composition comprising a Compound of the Disclosure, or a pharmaceutically acceptable salt or solvate thereof, and a pharmaceutically acceptable carrier.

In some embodiments, the present disclosure relates to a pharmaceutical composition for use in treatment of cancer.

In some embodiments, the present disclosure relates to a Compound of the Disclosure for use in treatment of cancer.

In some embodiments, the present disclosure relates to a use of a Compound of the Disclosure for the manufacture of a medicament for treatment of cancer.

In one aspect, the present disclosure relates to a kit comprising a Compound of the Disclosure, or a pharmaceutically acceptable salt or solvate thereof, or a pharmaceutical composition comprising a Compound of the Disclosure, and instructions for administering the compound, or a pharmaceutically acceptable salt or solvate thereof, or the pharmaceutical composition to a patient having cancer.

In one aspect, the present disclosure relates to a method of treating cancer in a patient comprising administering to the patient a Compound of the Disclosure, or a pharmaceutically acceptable salt or solvate thereof, or a pharmaceutical composition comprising a Compound of the Disclosure.

In some embodiments, the cancer is selected from the group consisting of a hematological cancer, a lymphatic cancer, and a DNA damage repair pathway deficient cancer.

In some embodiments, the cancer comprises cancer cells with a mutation in a gene encoding p53. In some embodiments, the mutation in a gene encoding p53 is a germline mutation. In some embodiments, the mutation in a gene encoding p53 is a somatic mutation. In some embodiments, the cancer comprises cancer cells with a loss of function mutation in a gene encoding p53.

In some embodiments, the cancer is selected from the group consisting of lung cancer, non-small cell lung cancer (NSCLC), colon cancer, bladder cancer, osteosarcoma, ovarian cancer, and breast cancer.

In some embodiments, the cancer is non-small cell lung cancer (NSCLC).

In some embodiments, the cancer is colon cancer.

In some embodiments, the cancer is bladder cancer.

In some embodiments, the cancer is ovarian cancer or breast cancer.

In some embodiments, the cancer is ovarian cancer.

In some embodiments, the cancer is breast cancer.

In some embodiments, the cancer is triple negative breast cancer.

In some embodiments, the cancer comprises cancer cells with elevated levels of RAD18.

In some embodiments, the elevated levels of RAD18 are elevated RAD18 protein levels.

In some embodiments, the elevated levels of RAD18 are elevated RAD18 mRNA levels.

In some embodiments, the elevated levels of RAD18 have been detected prior to the administration.

In another aspect, the present disclosure relates to a method that further comprises detecting RAD18 levels in a cancer sample obtained from the subject.

In some embodiments, the cancer is selected from the group consisting of bone cancer, including osteosarcoma and chondrosarcoma; brain cancer, including glioma, glioblastoma, astrocytoma, medulloblastoma, and meningioma; soft tissue cancer, including rhabdoid and sarcoma; kidney cancer; bladder cancer; skin cancer, including melanoma; and lung cancer, including non-small cell lung cancer; colon cancer, uterine cancer; nervous system cancer; head and neck cancer; pancreatic cancer; and cervical cancer.

In some embodiments, the cancer is a DNA damage repair pathway deficient cancer.

In some embodiments, the cancer comprises cancer cells with a mutation in a gene encoding p53. In some embodiments, the mutation in a gene encoding p53 is a germline mutation. In some embodiments, the mutation in a gene encoding p53 is a somatic mutation. In some embodiments, the cancer comprises cancer cells with a loss of function mutation in a gene encoding p53.

In some embodiments, the cancer is a BRCA1 mutant cancer. In some embodiments, the BRCA1 mutation is a germline mutation. In some embodiments, the BRCA1 mutation is a somatic mutation. In some embodiments, the BRCA1 mutation leads to BRCA1 deficiency.

In some embodiments, the cancer is a BRCA2 mutant cancer. In some embodiments, the BRCA2 mutation is a germline mutation. In some embodiments, the BRCA2 mutation is a somatic mutation. In some embodiments, the BRCA2 mutation leads to BRCA2 deficiency.

In some embodiments, the cancer is a BRCA1 mutant cancer and a BRCA2 mutant cancer.

In some embodiments, the cancer is a BRCA1 deficient cancer.

In some embodiments, the cancer is a BRCA2 deficient cancer.

In some embodiments, the cancer is a BRCA1 deficient cancer and a BRCA2 deficient cancer.

In some embodiments, the cancer is a Poly (ADP-ribose) polymerase ("PARP") inhibitor refractory or resistant cancer. In some embodiments, the cancer is a PARP inhibitor resistant or refractory BRCA1, BRCA2, or BRCA1 and BRCA2 mutant cancer. In some embodiments, the cancer is a PARP inhibitor resistant or refractory BRCA1, BRCA2, or BRCA1 and BRCA2-deficient cancer.

In some embodiments, the cancer has a mutation in the gene encoding ataxia telangiectasia mutated (ATM) protein kinase. In some embodiments the ATM mutation is a germline mutation. In some embodiments the ATM mutation is a somatic mutation. In some embodiments the cancer is an ATM-deficient cancer.

In some embodiments the cancer has a mutation in the gene encoding at least two of p53, BRCA1, BRCA2, and ATM.

In another aspect, the present disclosure relates to a method of treating a USP1 protein mediated disorder comprising administering to a patient in need thereof a Compound of the Disclosure, or a pharmaceutically acceptable salt or solvate thereof, or a pharmaceutical composition comprising a Compound of the Disclosure, in an effective amount to treat the USP1 protein mediated disorder.

In some embodiments, the USP1 protein comprises the amino acid sequence of SEQ ID NO:1.

In another aspect, the present disclosure relates to a method of inhibiting a USP1 protein comprising contacting a USP1 protein with a Compound of the Disclosure, or a pharmaceutically acceptable salt or solvate thereof, or a pharmaceutical composition comprising a Compound of the Disclosure.

In some embodiments, the contacting occurs in vitro.

In some embodiments, the contacting occurs in vivo.

In another aspect, the present disclosure relates to a method of treating cancer in a patient comprising administering to the subject a USP1 inhibitor, wherein the cancer comprises cancer cells with a mutation in a gene encoding p53.

In some embodiments, the mutation in a gene encoding p53 has been detected prior to the administration.

In some embodiments, the method further comprises detecting the mutation in the gene encoding p53 in a cancer sample obtained from the patient.

In another aspect, the present disclosure relates to a method of selecting a patient with cancer for treatment with a USP1 inhibitor, comprising detecting whether the cancer comprises cancer cells with a mutation in a gene encoding p53, wherein if the cancer comprises cancer cells with a mutation in a gene encoding p53, the patient is selected for treatment with a USP1 inhibitor.

In another aspect, the present disclosure relates to a USP1 inhibitor for use in the treatment of cancer in a patient, wherein the cancer comprises cancer cells with a mutation in a gene encoding p53.

In some embodiments, the patient is identified to be responsive to the treatment with the USP1 inhibitor by detecting cancer cells with a mutation in a gene encoding p53 in a cancer sample obtained from the patient, wherein cancer cells with a mutation in a gene encoding p53 in the cancer sample identify the patient to be responsive to the treatment with an USP1 inhibitor.

In another aspect, the present disclosure relates to a USP1 inhibitor for use in the treatment of cancer in a subject identified to be responsive to the treatment with the USP1 inhibitor by cancer cells with a mutation in a gene encoding p53 in a cancer sample obtained from the subject, wherein cancer cells with a mutation in a gene encoding p53 in the cancer sample identify the patient to be responsive to the treatment with an USP1 inhibitor.

In some embodiments, the USP1 inhibitor is not administered to a subject in case a mutation in a gene encoding p53 is not detected in a cancer sample obtained from the subject.

In another aspect, the present disclosure relates to an in vitro method for identifying a subject with cancer to be responsive to the treatment with an USP1 inhibitor, comprising detecting a mutation in a gene encoding p53 in a cancer sample obtained from the subject, wherein a mutation in a gene encoding p53 in the cancer sample is indicative for the patient to be responsive to the treatment with an USP1 inhibitor.

In another aspect, the present disclosure relates to an in vitro use of at least one agent capable of specifically detecting a mutation in a gene encoding p53, for identifying a subject with cancer to be responsive to the treatment with an USP1 inhibitor.

In some embodiments, the mutation in the gene encoding p53 is a loss of function mutation.

In another aspect, the present disclosure relates to a method of treating cancer in a patient comprising administering to the subject a USP1 inhibitor, wherein the cancer comprises cancer cells with a mutation in a gene encoding BRCA1.

In some embodiments, the mutation in a gene encoding BRCA1 has been detected prior to the administration.

In some embodiments, the method further comprises detecting the mutation in the gene encoding BRCA1 in a sample (e.g., a cancer sample or blood sample) obtained from the patient.

In another aspect, the present disclosure relates to a method of selecting a patient with cancer for treatment with a USP1 inhibitor, comprising detecting whether the cancer comprises cancer cells with a mutation in a gene encoding BRCA1, wherein if the cancer comprises cancer cells with a mutation in a gene encoding BRCA1, the patient is selected for treatment with a USP1 inhibitor.

In another aspect, the present disclosure relates to a USP1 inhibitor for use in the treatment of cancer in a patient, wherein the cancer comprises cancer cells with a mutation in a gene encoding BRCA1.

In some embodiments, the patient is identified to be responsive to the treatment with the USP1 inhibitor by detecting a mutation in a gene encoding BRCA1 in a sample (e.g., a cancer sample or a blood sample) obtained from the patient, wherein a mutation in a gene encoding BRCA1 in the sample identifies the patient to be responsive to the treatment with a USP1 inhibitor.

In another aspect, the present disclosure relates to a USP1 inhibitor for use in the treatment of cancer in a subject identified to be responsive to the treatment with the USP1 inhibitor by cancer cells with a mutation in a gene encoding BRCA1 in a sample (e.g., a cancer sample or a blood sample) obtained from the subject, wherein cancer cells with a mutation in a gene encoding BRCA1 in the sample identify the patient to be responsive to the treatment with an USP1 inhibitor.

In some embodiments, the USP1 inhibitor is not administered to a subject in case a mutation in a gene encoding BRCA1 is not detected in a sample (e.g., a cancer sample or a blood sample) obtained from the subject.

In another aspect, the present disclosure relates to an in vitro method for identifying a subject with cancer to be responsive to the treatment with an USP1 inhibitor, comprising detecting a mutation in a gene encoding BRCA1 in a sample (e.g., a cancer sample or a blood sample) obtained from the subject, wherein a mutation in a gene encoding BRCA1 in the sample is indicative for the patient to be responsive to the treatment with an USP1 inhibitor.

In another aspect, the present disclosure relates to an in vitro use of at least one agent capable of specifically detecting a mutation in a gene encoding BRCA1, for identifying a subject with cancer to be responsive to the treatment with an USP1 inhibitor.

In some embodiments, the mutation in the gene encoding BRCA1 is a loss of function mutation.

In another aspect, the present disclosure relates to a method of treating cancer in a patient comprising administering to the subject a USP1 inhibitor, wherein the cancer comprises cancer cells with a mutation in a gene encoding BRCA2.

In some embodiments, the mutation in a gene encoding BRCA2 has been detected prior to the administration.

In some embodiments, the method further comprises detecting the mutation in the gene encoding BRCA2 in a sample (e.g., a cancer sample or a blood sample) obtained from the patient.

In another aspect, the present disclosure relates to a method of selecting a patient with cancer for treatment with a USP1 inhibitor, comprising detecting whether the cancer comprises cancer cells with a mutation in a gene encoding BRCA2, wherein if the cancer comprises cancer cells with a mutation in a gene encoding BRCA2, the patient is selected for treatment with a USP1 inhibitor.

In another aspect, the present disclosure relates to a USP1 inhibitor for use in the treatment of cancer in a patient, wherein the cancer comprises cancer cells with a mutation in a gene encoding BRCA2.

In some embodiments, the patient is identified to be responsive to the treatment with the USP1 inhibitor by detecting a mutation in a gene encoding BRCA2 in a sample (e.g., a cancer sample or a blood sample) obtained from the patient, wherein a mutation in a gene encoding BRCA2 in the sample identifies the patient to be responsive to the treatment with an USP1 inhibitor.

In another aspect, the present disclosure relates to a USP1 inhibitor for use in the treatment of cancer in a subject identified to be responsive to the treatment with the USP1 inhibitor by cancer cells with a mutation in a gene encoding BRCA2 in a sample (e.g., a cancer sample or a blood sample) obtained from the subject, wherein cancer cells with a mutation in a gene encoding BRCA2 in the sample identify the patient to be responsive to the treatment with an USP1 inhibitor.

In some embodiments, the USP1 inhibitor is not administered to a subject in case a mutation in a gene encoding BRCA2 is not detected in a sample (e.g., a cancer sample or a blood sample) obtained from the subject.

In another aspect, the present disclosure relates to an in vitro method for identifying a subject with cancer to be responsive to the treatment with an USP1 inhibitor, comprising detecting a mutation in a gene encoding BRCA2 in a sample (e.g., a cancer sample or a blood sample) obtained from the subject, wherein a mutation in a gene encoding BRCA2 in the sample is indicative for the patient to be responsive to the treatment with an USP1 inhibitor.

In another aspect, the present disclosure relates to an in vitro use of at least one agent capable of specifically detecting a mutation in a gene encoding BRCA2, for identifying a subject with cancer to be responsive to the treatment with an USP1 inhibitor.

In some embodiments, the mutation in the gene encoding BRCA2 is a loss of function mutation.

In another aspect, the present disclosure relates to a method of treating cancer in a patient comprising administering to the subject a USP1 inhibitor, wherein the cancer comprises cancer cells with a mutation in a gene encoding ATM.

In some embodiments, the mutation in a gene encoding ATM has been detected prior to the administration.

In some embodiments, the method further comprises detecting the mutation in the gene encoding ATM in a sample obtained from the patient.

In another aspect, the present disclosure relates to a method of selecting a patient with cancer for treatment with a USP1 inhibitor, comprising detecting whether the cancer comprises cancer cells with a mutation in a gene encoding ATM, wherein if the cancer comprises cancer cells with a mutation in a gene encoding ATM, the patient is selected for treatment with a USP1 inhibitor.

In another aspect, the present disclosure relates to a USP1 inhibitor for use in the treatment of cancer in a patient, wherein the cancer comprises cancer cells with a mutation in a gene encoding ATM.

In some embodiments, the patient is identified to be responsive to the treatment with the USP1 inhibitor by detecting cancer cells with a mutation in a gene encoding ATM in a cancer sample obtained from the patient, wherein cancer cells with a mutation in a gene encoding ATM in the cancer sample identify the patient to be responsive to the treatment with an USP1 inhibitor.

In another aspect, the present disclosure relates to a USP1 inhibitor for use in the treatment of cancer in a subject identified to be responsive to the treatment with the USP1 inhibitor by cancer cells with a mutation in a gene encoding ATM in a cancer sample obtained from the subject, wherein cancer cells with a mutation in a gene encoding ATM in the cancer sample identify the patient to be responsive to the treatment with an USP1 inhibitor.

In some embodiments, the USP1 inhibitor is not administered to a subject in case a mutation in a gene encoding ATM is not detected in a cancer sample obtained from the subject.

In another aspect, the present disclosure relates to an in vitro method for identifying a subject with cancer to be responsive to the treatment with an USP1 inhibitor, comprising detecting a mutation in a gene encoding ATM in a cancer sample obtained from the subject, wherein a mutation in a gene encoding ATM in the cancer sample is indicative for the patient to be responsive to the treatment with an USP1 inhibitor.

In another aspect, the present disclosure relates to an in vitro use of at least one agent capable of specifically detecting a mutation in a gene encoding ATM, for identifying a subject with cancer to be responsive to the treatment with an USP1 inhibitor.

In some embodiments, the mutation in the gene encoding ATM is a loss of function mutation.

In some embodiments, the USP1 inhibitor is a Compound of the Disclosure.

In one aspect (A1), the present disclosure provides a method of treating cancer in a subject comprising administering to the subject a USP1 inhibitor, wherein the cancer comprises cancer cells with elevated levels of RAD18.

In one aspect (A2), the present disclosure provides a method of treating a triple negative breast cancer in a subject comprising administering to the subject a USP1 inhibitor. In one aspect of A1 (A3), the cancer comprises cancer cells with elevated levels of RAD18.

In one aspect (A4) of A1 or A3, the elevated levels of RAD18 have been detected prior to the administration. In one aspect (A5) of A4, the method further comprises detecting RAD18 levels in a cancer sample obtained from the subject.

In one aspect (A5), the present disclosure provides a method of selecting a subject with cancer for treatment with a USP1 inhibitor comprising detecting whether the cancer comprises cells with elevated levels of RAD18, wherein if the cancer comprises cells with elevated levels of RAD18, the subject is selected for treatment with a USP1 inhibitor.

In one aspect (A6), the present disclosure provides a USP1 inhibitor for use in the treatment of cancer in a subject, wherein the cancer comprises cancer cells with elevated levels of RAD18.

In one aspect (A7), the present disclosure provides a USP1 inhibitor for use in the treatment of triple negative breast cancer in a subject.

In one aspect (A9) of A7 or A8, the subject is identified to be responsive to the treatment with the USP1 inhibitor by detecting RAD18 levels in a cancer sample obtained from the subject, wherein elevated levels of RAD18 in the cancer sample identify the patient to be responsive to the treatment with an USP1 inhibitor.

In one aspect (A10), the present disclosure provides a USP1 inhibitor for use in the treatment of cancer in a subject identified to be responsive to the treatment with the USP1 inhibitor by detecting elevated RAD18 levels in a cancer sample obtained from the subject, wherein elevated levels of RAD18 in the cancer sample identify the patient to be responsive to the treatment with an USP1 inhibitor.

In one aspect (A11), the present disclosure provides a USP1 inhibitor for use of any of A7-A10, wherein the USP1 inhibitor is not administered to a subject in case non-elevated RAD18 levels are detected in a cancer sample obtained from the subject.

In one aspect (A12), the present disclosure provides an in vitro method for identifying a subject with cancer to be responsive to the treatment with an USP1 inhibitor, comprising detecting RAD18 levels in a cancer sample obtained from the subject, wherein elevated levels of RAD18 in the cancer sample are indicative for the patient to be responsive to the treatment with an USP1 inhibitor.

In one aspect (A13), the present disclosure provides an in vitro use of at least one agent capable of specifically detecting RAD18, for identifying a subject with cancer to be responsive to the treatment with an USP1 inhibitor.

In one aspect (A14), the present disclosure provides a kit or kit-of-parts, comprising: (a) a pharmaceutical composition comprising a USP1 inhibitor and one or more pharmaceutically acceptable excipients, and (b) a diagnostic kit comprising at least one agent capable of specifically detecting RAD18.

In one aspect (A15) of A13 or A14, the at least one agent capable of specifically detecting RAD18 is capable of specifically hybridizing to RAD18 mRNA. In one aspect (A16) of A13 or A14, the at least one agent capable of specifically detecting RAD18 is capable of specifically binding to RAD18 protein.

In one aspect (A17) of A10, A12, or A13, the cancer is triple negative breast cancer.

In one aspect (A18) of A10, A12, A13, or A17, the cancer comprises cancer cells with elevated levels of RAD18.

In one aspect (A19), the present disclosure provides a method for classifying a cancer in a subject, comprising detecting elevated RAD18 levels in a cancer sample obtained from the subject.

In one aspect (A20) of any one of A1-A19, the cancer is not a BRCA1 mutant cancer. In one aspect (A21) of any one of A1-A19, the cancer is not a BRCA2 mutant cancer. In one aspect (A22) of any one of A1-A19, the cancer is not a BRCA1 mutant cancer or a BRCA2 mutant cancer.

In one aspect (A23) of any one of A1-A19, the cancer is not a homologous-recombination deficient cancer. In one aspect (A24) of any one of A1-A19, the cancer is a homologous-recombination deficient cancer.

In one aspect (A25) of any one of A1-A23, the cancer comprises cancer cells with a mutation in a gene encoding p53, optionally wherein the mutation in the gene encoding p53 is a loss of function mutation.

In one aspect (A26) of any one of A1, A3-A7, A9-A12, and A18-A25, the elevated levels of RAD18 are elevated RAD18 protein levels. In one aspect (A27) of A26, the detection of elevated RAD18 protein levels is by Western blot. In one aspect (A28) of A26, the detection of elevated RAD18 protein levels is by fluorescence-activated cell sorting (FACS). In one aspect (A29) of A26, the detection of elevated RAD18 protein levels is by immunohistochemistry.

In one aspect (A30) of any one of A1, A3-A7, A9-A12, and A18-A25, the elevated levels of RAD18 are elevated RAD18 mRNA levels. In one aspect (A31) of A30, the detection of elevated of RAD18 mRNA levels is by quantitative reverse transcriptase (RT)-polymerase chain reaction (PCR), RNA-Seq, or microarray.

In one aspect (A32) of any one of A1, A3-A7, A9-A12, and A18-A31, the elevated levels of RAD18 are at least as high as the RAD18 levels in ES2 cells. In one aspect (A33) of any one of A1, A3-A7, A9-A12, and A18-A31, the elevated levels of RAD18 are higher than the RAD18 levels in HEP3B217 cells.

In one aspect (A34) of any one of A1, A4-A7, A9-A16, and A18-A33, the cancer is an ovarian cancer. In one aspect (A35) of any one of A1, A4-A7, A9-A16, and A18-A33, the cancer is a breast cancer. In one aspect (A36) of A35, the breast cancer is a triple negative breast cancer.

In one aspect (A37) of any one of A1-A19 and A24-A36, the cancer is a BRCA1 mutant cancer. In one aspect (A38) of any one of A1-A19 and A24-A36, the cancer is a BRCA2 mutant cancer. In one aspect (A39) of any one of A1-A19 and A24-A36, the cancer is a BRCA1 mutant cancer and a BRCA2 mutant cancer.

In one aspect (A40) of any one of A1-A18 and A20-A39, the USP1 inhibitor is selected from a small molecule, an siRNA, an antisense oligonucleotide, a peptide, or an aptamer. In one aspect (A41) of any one of A1-A18 and A20-A40, the USP1 inhibitor specifically binds USP1 protein. In one aspect (A42) of A41, the USP1 protein comprises the amino acid sequence

```
                                              (SEQ ID NO: 1)
MPGVIPSESNGLSRGSPSKKNRLSLKFFQKKETKRALDFTDSQENEEKASE

YRASEIDQVVPAAQSSPINCEKRENLLPFVGLNNLGNTCYLNSILQVLYFC

PGFKSGVKHLFNIISRKKEALKDEANQKDKGNCKEDSLASYELICSLQSLI

ISVEQLQASFLLNPEKYTDELATQPRRLLNTLRELNPMYEGYLQHDAQEVL

QCILGNIQETCQLLKKEEVKNVAELPTKVEEIPHPKEEMNGINSIEMDSMR

HSEDFKEKLPKGNGKRKSDTEFGNMKKKVKLSKEHQSLEENQRQTRSKRKA

TSDTLESPPKIIPKYISENESPRPSQKKSRVKINWLKSATKQPSILSKFCS

LGKITTNQGVKGQSKENECDPEEDLGKCESDNTTNGCGLESPGNTVTPVNV

NEVKPINKGEEQIGFELVEKLFQGQLVLRTRCLECESLTERREDFQDISVP

VQEDELSKVEESSEISPEPKTEMKTLRWAISQFASVERIVGEDKYFCENCH

HYTEAERSLLFDKMPEVITIHLKCFAASGLEFDCYGGGLSKINTPLLTPLK

LSLEEWSTKPTNDSYGLFAVVMHSGITISSGHYTASVKVTDLNSLELDKGN

FVVDQMCEIGKPEPLNEEEARGVVENYNDEEVSIRVGGNTQPSKVLNKKNV

EAIGLLGGQKSKADYELYNKASNPDKVASTAFAENRNSETSDTTGTHESDR

NKESSDQTGINISGFENKISYVVQSLKEYEGKWLLFDDSEVKVTEEKDFLN

SLSPSTSPTSTPYLLFYKKL.
```

In one aspect (A43) of any one of A1-A18 and A20-A42, the USP1 inhibitor inhibits formation and/or activity of the USP1/UAF1 complex.

In one aspect (A44) of any one of A1-A18 and A20-A40, the USP1 inhibitor specifically binds to the USP1/UAF1 complex.

In one aspect (A45) of any one of A1-A18 and A20-A40, the USP1 inhibitor specifically binds USP1 mRNA.

In one aspect (A46) of any one of A1-A18 and A20-A45, the USP1 inhibitor increases mono-ubiquitinated PCNA.

In one aspect (A47) of any one of A1-A18 and A20-A46, the USP1 inhibitor increases mono-ubiquitinated FANCD2.

In one aspect (A48) of any one of A1-A18 and A20-A39, the USP1 inhibitor is a purinone. In one aspect (A49) of any one of A1-A18 and A20-A39, the USP1 inhibitor is GW7647. In one aspect (A50) of any one of A1-A18 and A20-A39, the USP1 inhibitor is Pimozide. In one aspect (A51) of any one of A1-A18 and A20-A39, the USP1 inhibitor is ML323.

In one aspect (A52) of any one of A1-A18 and A20-A51, the subject is human.

Additional embodiments and advantages of the disclosure will be set forth, in part, in the description that follows, and will flow from the description, or can be learned by practice of the disclosure. The embodiments and advantages of the disclosure will be realized and attained by means of the elements and combinations particularly pointed out in the appended claims.

It is to be understood that both the foregoing summary and the following detailed description are exemplary and explanatory only, and are not restrictive of the invention as claimed.

DETAILED DESCRIPTION OF THE DISCLOSURE

Figure 1:
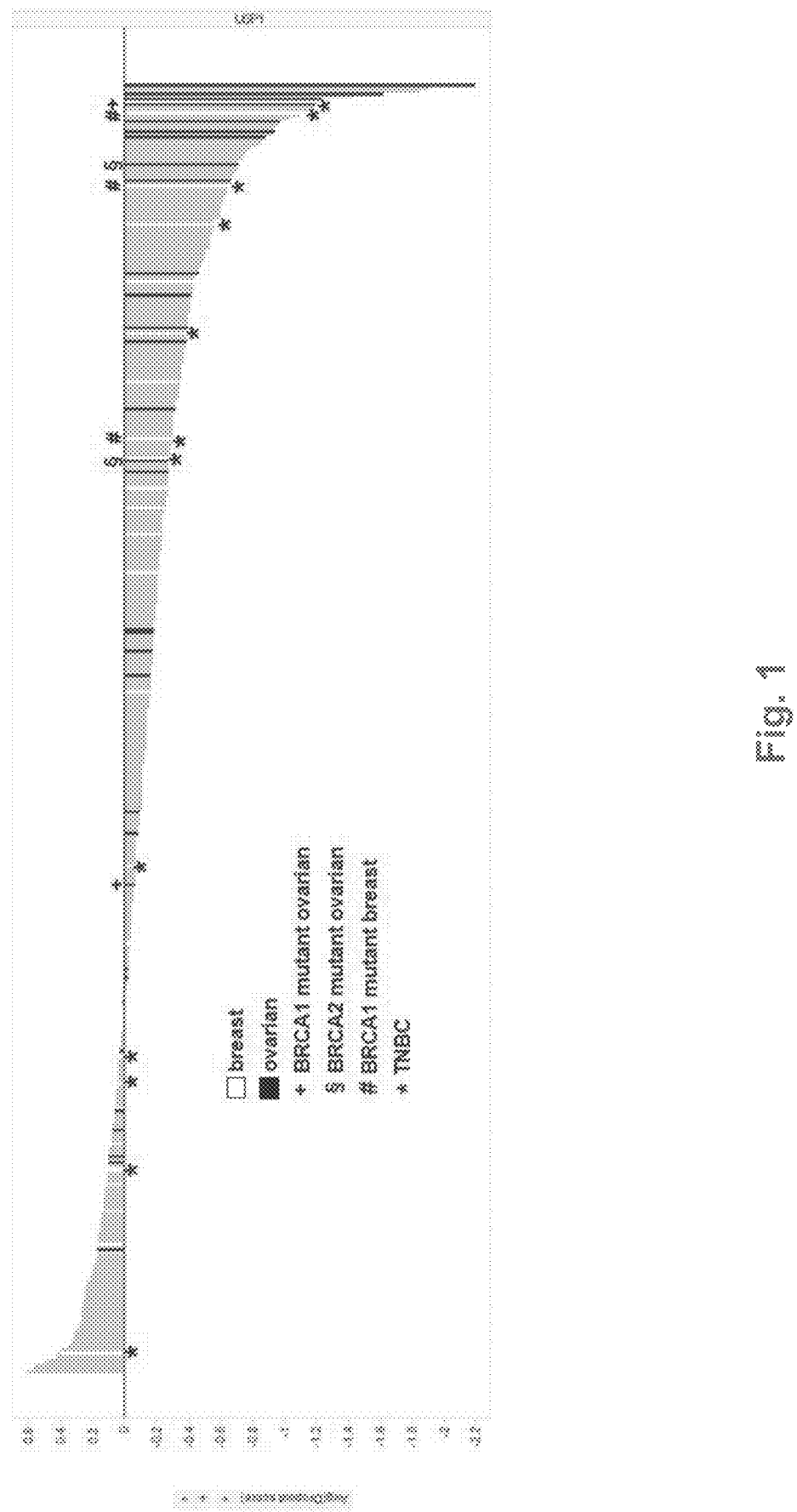
FIG. 1 provides a USP1 dropout profile across approximately 500 cancer cell lines. A lower dropout score indicates a greater sensitivity to loss of USP1. Breast cancer cell lines are shown in white, and ovarian cancer cell lines are shown in black. Symbols indicate BRCA1/2 mutations or triple negative breast cancer (TNBC) status.

One aspect of the present disclosure is based on the use of Compounds of the Disclosure as inhibitors of a ubiquitin-specific-processing protease 1 (USP1) protein. In view of this property, the Compounds of the Disclosure are useful for inhibiting a USP1 protein and for treating diseases, disorders, or conditions, e.g., cancer, that are responsive to inhibition of a USP1 protein.

In some embodiments, the Compounds of the Disclosure exhibit improved solubility, e.g., as measured by an ADME solubility assay as disclosed herein.

In some embodiments, the Compounds of the Disclosure exhibit improved metabolic stability, e.g., as measured by liver microsome metabolic stability assays as disclosed herein.

In other embodiments, the Compounds of the Disclosure exhibit improved duration of action and oral exposure in vivo.

In one embodiment, Compounds of the Disclosure are compounds having Formula I:

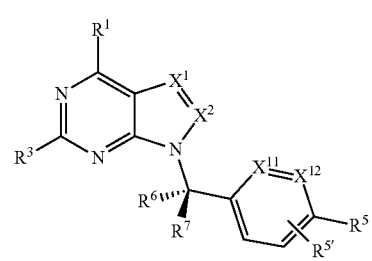

I and the pharmaceutically acceptable salts or solvates, e.g., hydrates, thereof, wherein:

each of $X^1$ and $X^2$ is independently selected from N and $CR^2$;

each of $R^1$ and $R^2$ is independently selected from hydrogen, halo, cyano, optionally substituted alkyl, optionally substituted alkenyl, and optionally substituted alkynyl;

$R^3$ is an optionally substituted phenyl, optionally substituted pyridyl, optionally substituted pyrimidinyl, optionally substituted pyrazinyl, optionally substituted pyridazinyl, or optionally substituted pyrazolyl;

$R^{5'}$ is selected from hydrogen, optionally substituted ($C_1$-$C_6$) alkyl, optionally substituted ($C_2$-$C_6$) alkenyl, optionally substituted ($C_2$-$C_6$) alkynyl, optionally substituted ($C_1$-$C_6$) alkoxy, ($C_1$-$C_6$) haloalkyl, ($C_1$-$C_6$) haloalkoxy, ($C_1$-$C_6$) hydroxyalkyl, cyano, halo, sulfonamido, —C(=O)$R^{23}$, —C(=O)O$R^{24}$, —N$R^{32a}R^{32b}$, —N$R^{31a}$C(=O)$R^{25}$, —N$R^{31a}$C(=O)N$R^{31a}R^{31b}$, —C(=O)N$R^{31a}R^{31b}$, —S(O)$_2$$R^{27}$, —N$R^{31a}$SO$_2R^{27}$, optionally substituted ($C_6$-$C_{14}$) aryl, optionally substituted ($C_6$-$C_{14}$) ar-($C_1$-$C_2$) alkyl, optionally substituted heteroaryl, optionally substituted heteroar-($C_1$-$C_2$) alkyl, optionally substituted ($C_3$-$C_8$) cycloalkyl, optionally substituted (($C_3$-$C_8$) cycloalkyl)-($C_1$-$C_2$) alkyl, optionally substituted heterocyclo, optionally substituted heterocyclo-($C_1$-$C_2$) alkyl, optionally substituted —O—($C_6$-$C_{14}$) aryl, optionally substituted —O—($C_6$-$C_{14}$) ar-($C_1$-$C_2$) alkyl, optionally substituted —O-heteroaryl, optionally substituted —O-heteroar-($C_1$-$C_2$) alkyl, optionally substituted —O—($C_3$-$C_8$) cycloalkyl, optionally substituted —O—(($C_3$-$C_8$) cycloalkyl)-($C_1$-$C_2$) alkyl, optionally substituted —O-heterocyclo, optionally substituted —O-heterocyclo-($C_1$-$C_2$) alkyl;

$R^5$ is selected from optionally substituted ($C_1$-$C_6$) alkyl, optionally substituted ($C_2$-$C_6$) alkenyl, optionally substituted ($C_2$-$C_6$) alkynyl, optionally substituted ($C_1$-$C_6$) alkoxy, ($C_1$-$C_6$) haloalkyl, ($C_1$-$C_6$) haloalkoxy, ($C_1$-$C_6$) hydroxyalkyl, cyano, halo, sulfonamido, —C(=O)$R^{23}$, —C(=O)O$R^{24}$, —N$R^{32a}R^{32b}$, —N$R^{31a}$C(=O)$R^{25}$, —N$R^{31a}$C(=O)N$R^{31a}R^{31b}$, —C(=O)N$R^{31a}R^{31b}$, —S(O)$_2R^{27}$, —N$R^{31a}$SO$_2R^{27}$, optionally substituted ($C_6$-$C_{14}$) aryl, optionally substituted ($C_6$-$C_{14}$) ar-($C_1$-$C_2$) alkyl, optionally substituted heteroaryl, optionally substituted heteroar-($C_1$-$C_2$) alkyl, optionally substituted ($C_3$-$C_8$) cycloalkyl, optionally substituted (($C_3$-$C_8$) cycloalkyl)-($C_1$-$C_2$) alkyl, optionally substituted heterocyclo, optionally substituted heterocyclo-($C_1$-$C_2$) alkyl, optionally substituted —O—($C_6$-$C_{14}$) aryl, optionally substituted —O—($C_6$-$C_{14}$) ar-($C_1$-$C_2$) alkyl, optionally substituted —O-heteroaryl, optionally substituted —O-heteroar-($C_1$-$C_2$) alkyl, optionally substituted —O—($C_3$-$C_8$) cycloalkyl, optionally substituted —O—(($C_3$-$C_8$) cycloalkyl)-($C_1$-$C_2$) alkyl, optionally substituted —O-heterocyclo, optionally substituted —O-heterocyclo-($C_1$-$C_2$) alkyl; or one of $R^5$ and one of $R^{5'}$ on adjacent atoms are taken together with the atoms to which they are attached to form an optionally substituted ($C_6$-$C_{14}$) aryl ring; or one of $R^5$ and one of $R^{5'}$ on adjacent atoms are taken together with the atoms to which they are attached to form an optionally substituted heteroaryl ring; or one of $R^5$ and one of $R^{5'}$ on adjacent atoms are taken together with the atoms to which they are attached to form an optionally substituted ($C_3$-$C_8$) cycloalkyl ring; or one of $R^5$ and one of $R^{5'}$ on adjacent atoms are taken together with the atoms to which they are attached to form an optionally substituted heterocycloalkyl ring; or one of $R^5$ and one of $R^{5'}$ on adjacent atoms on the same atom to which they are attached are taken together to form an optionally substituted spirocycloalkyl ring; or one of $R^5$ and one of $R^{5'}$ on adjacent atoms on the same atom to which they are attached are taken together to form an optionally substituted spiroheterocycloalkyl ring;

each of $R^6$ and $R^7$ is independently selected from hydrogen, halo, cyano, optionally substituted alkyl, optionally substituted alkenyl, and optionally substituted alkynyl;

each of $X^{11}$ and $X^{12}$ is independently selected from N and CH;

$R^{23}$ is selected from the group consisting of hydrogen, optionally substituted alkyl, optionally substituted alkenyl, optionally substituted alkynyl, amino, alkylamino, dialkylamino, cycloalkylamino, hydroxyalkyl, (amino)alkyl, (alkylamino)alkyl, (dialkylamino)alkyl, (cycloalkylamino)alkyl, (cycloalkyl)alkyl, aralkyl, (heterocyclo)alkyl, (heteroaryl)alkyl, (amino)(hydroxy)alkyl, (aralkylamino)alkyl, optionally substituted heterocyclo, optionally substituted heteroaryl, optionally substituted aryl, and optionally substituted cycloalkyl;

$R^{31a}$ and $R^{31b}$ are each independently selected from the group consisting of hydrogen, optionally substituted alkyl, optionally substituted alkenyl, optionally substituted alkynyl, hydroxyalkyl, (amino)alkyl, (alkylamino)alkyl, (dialkylamino)alkyl, alkoxyalkyl, cycloalkyl, (cycloalkyl)alkyl, (heterocyclo)alkyl, aralkyl, and (heteroaryl)alkyl; and each of $R^{24}$, $R^{25}$, $R^{27}$, $R^{32a}$, and $R^{32b}$ is independently selected from the group consisting of hydrogen, optionally substituted alkyl, optionally substituted alkenyl, optionally substituted alkynyl, amino, alkylamino, dialkylamino, cycloalkylamino, hydroxyalkyl, (amino)alkyl, (alkylamino)alkyl, (dialkylamino)alkyl, (cycloalkylamino)alkyl, (cycloalkyl)alkyl, aralkyl, (heterocyclo)alkyl, (heteroaryl)alkyl, (amino)(hydroxy)alkyl, (aralkylamino)alkyl, alkoxyalkyl, optionally substituted heterocyclo, optionally substituted heteroaryl, optionally substituted aryl, and optionally substituted cycloalkyl.

In one embodiment, a Compound of the Disclosure is a compound having Formula I, wherein each of $X^1$ and $X^2$ is $CR^2$.

In another embodiment, a Compound of the Disclosure is a compound having Formula I, wherein at least one of $X^1$ and $X^2$ is N. In some embodiments, $X^1$ is N. In some embodiments, $X^2$ is N.

In another embodiment, a Compound of the Disclosure is a compound having Formula I, wherein at least one of $X^1$ and $X^2$ is $CR^2$. In some embodiments, $X^1$ is $CR^2$. In some embodiments, $X^2$ is $CR^2$.

In another embodiment, a Compound of the Disclosure is a compound having Formula I, wherein each of $X^1$ and $X^2$ is N.

In one embodiment, a Compound of the Disclosure is a compound having Formula I, wherein $R^{5'}$ is selected from hydrogen, halo, and optionally substituted ($C_1$-$C_6$) alkyl.

In one embodiment, a Compound of the Disclosure is a compound having Formula I, wherein

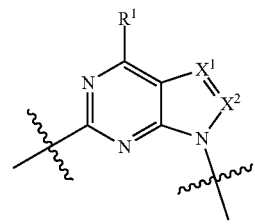

is independently selected from:

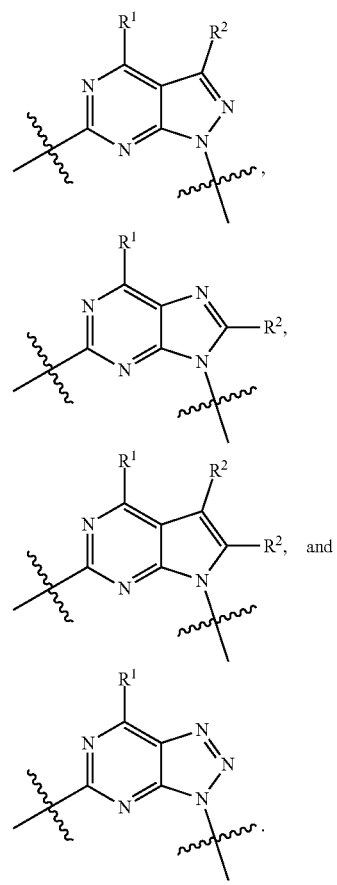

In another embodiment,

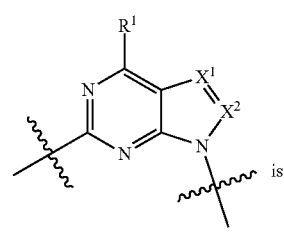

is

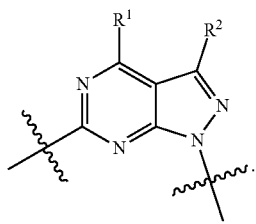
In another embodiment, is
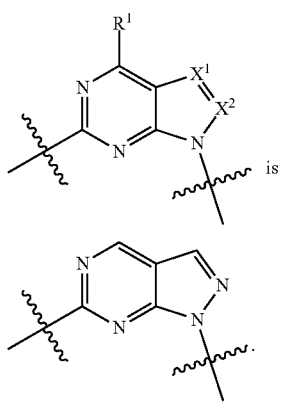
In another embodiment, is
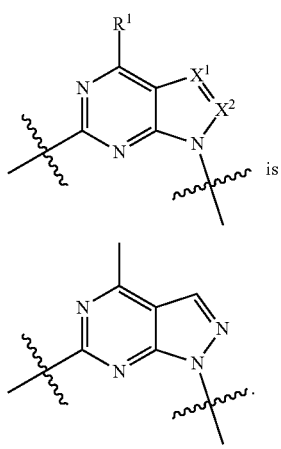
In another embodiment, is
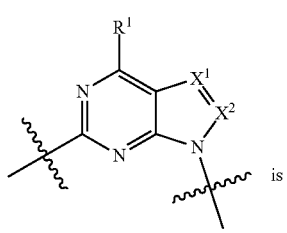
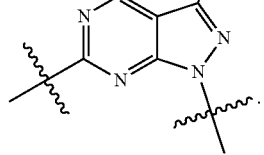
In another embodiment,
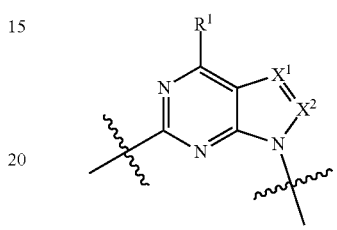
is independently selected from:
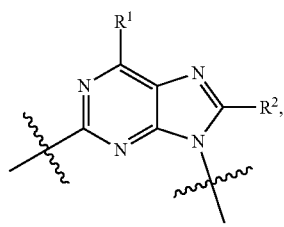
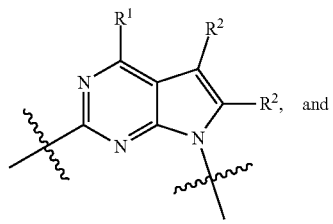
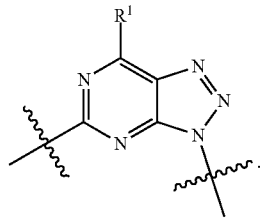
In another embodiment, is
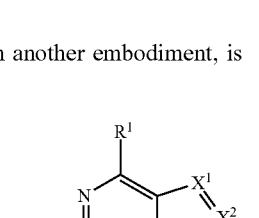

-continued

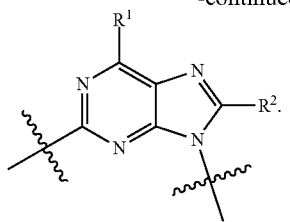

In another embodiment, is

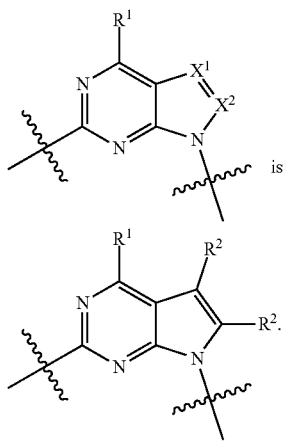

In another embodiment, is

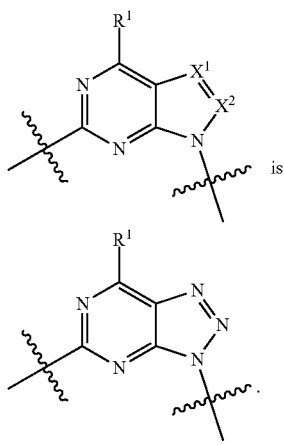

In one embodiment, a Compound of the Disclosure is a compound having Formula I, wherein each of $R^1$ and $R^2$ is independently selected from hydrogen, halo, and cyano.

In another embodiment, a Compound of the Disclosure is a compound having Formula I, wherein each of $R^1$ and $R^2$ is independently selected from optionally substituted ($C_{1-4}$) alkyl, optionally substituted ($C_{2-4}$) alkenyl, and optionally substituted ($C_{2-4}$) alkynyl. In some embodiments, each of $R^1$ and $R^2$ is independently selected from optionally substituted ($C_{1-4}$) alkyl. In some embodiments, each of $R^1$ and $R^2$ is independently selected from optionally substituted ($C_{2-4}$) alkenyl. In some embodiments, each of $R^1$ and $R^2$ is independently selected from optionally substituted ($C_{2-4}$) alkynyl.

In another embodiment, a Compound of the Disclosure is a compound having Formula I, wherein $R^3$ is an optionally substituted phenyl.

In another embodiment, a Compound of the Disclosure is a compound having Formula I, wherein $R^3$ is an optionally substituted pyridyl.

In another embodiment, a Compound of the Disclosure is a compound having Formula I, wherein $R^3$ is an optionally substituted pyrimidinyl.

In another embodiment, a Compound of the Disclosure is a compound having Formula I, wherein $R^3$ is an optionally substituted pyrazinyl.

In another embodiment, a Compound of the Disclosure is a compound having Formula I, wherein $R^3$ is an optionally substituted pyridazinyl.

In another embodiment, a Compound of the Disclosure is a compound having Formula I, wherein $R^3$ is an optionally substituted pyrazolyl.

In one embodiment, a Compound of the Disclosure is a compound having Formula I, wherein the optional substituents on $R^3$ are independently selected from hydrogen, halo, nitro, cyano, hydroxy, amino, alkylamino, dialkylamino, haloalkyl, hydroxyalkyl, alkoxy, haloalkoxy, aryloxy, heteroaryloxy, aralkyl aralkyloxy, alkylthio, carboxamido, sulfonamido, alkylcarbonyl, arylcarbonyl, alkylsulfonyl, arylsulfonyl, carboxy, carboxyalkyl, alkyl, optionally substituted cycloalkyl, alkenyl, alkynyl, optionally substituted aryl, optionally substituted heteroaryl, optionally substituted heterocyclo, alkoxyalkyl, (amino)alkyl, hydroxyalkylamino, (alkylamino)alkyl, (dialkylamino)alkyl, (cyano)alkyl, (carboxamido)alkyl, mercaptoalkyl, (heterocyclo)alkyl, (cycloalkylamino)alkyl, ($C_{1-4}$ haloalkoxy)alkyl, and (heteroaryl)alkyl.

In another embodiment, the optional substituents on $R^3$ are independently selected from hydrogen, halo, nitro, cyano, hydroxy, amino, ($C_1$-$C_4$) alkylamino, di-($C_1$-$C_4$) alkylamino, halo-($C_1$-$C_4$) alkyl, hydroxy-($C_1$-$C_4$) alkyl, ($C_1$-$C_4$) alkoxy, halo-($C_1$-$C_4$) alkoxy, ($C_6$-$C_{10}$) aryloxy, ($C_3$-$C_6$) heteroaryloxy, ar-($C_1$-$C_4$) alkyl, ar-($C_1$-$C_4$) alkyloxy, ($C_1$-$C_4$) alkylthio, carboxamido, sulfonamido, ($C_1$-$C_4$) alkylcarbonyl, ($C_6$-$C_{10}$) arylcarbonyl, ($C_1$-$C_4$) alkylsulfonyl, ($C_6$-$C_{10}$) arylsulfonyl, carboxy, carboxy-($C_1$-$C_4$) alkyl, ($C_1$-$C_4$) alkyl, ($C_2$-$C_4$) alkenyl, ($C_2$-$C_4$) alkynyl, alkoxy-($C_1$-$C_4$) alkyl, (amino)-($C_1$-$C_4$) alkyl, hydroxy-($C_1$-$C_4$) alkylamino, (alkylamino)-($C_1$-$C_4$) alkyl, (dialkylamino)-($C_1$-$C_4$) alkyl, (cyano)-($C_1$-$C_4$) alkyl, (carboxamido)-($C_1$-$C_4$) alkyl, mercapto-($C_1$-$C_4$) alkyl, (heterocyclo)-($C_1$-$C_4$) alkyl, (cycloalkylamino)-($C_1$-$C_4$) alkyl, ($C_{1-4}$ haloalkoxy)-($C_1$-$C_4$) alkyl, and (heteroaryl)-($C_1$-$C_4$) alkyl.

In another embodiment, the optional substituents on $R^3$ are independently selected from ($C_3$-$C_8$) cycloalkyl, ($C_6$-$C_{10}$) aryl, ($C_3$-$C_6$) heteroaryl, and ($C_3$-$C_8$) heterocyclo.

In one embodiment, a Compound of the Disclosure is a compound having Formula I, wherein two of the optional substituents on $R^3$ are taken together with the carbon or nitrogen atoms to which they are attached to form an optionally substituted cycloalkyl, optionally substituted heterocyclo, optionally substituted aryl, or optionally substituted heteroaryl group.

In another embodiment, two of the optional substituents on $R^3$ are taken together with the carbon or nitrogen atoms to which they are attached to form an optionally substituted ($C_3$-$C_8$) cycloalkyl, optionally substituted ($C_3$-$C_8$) heterocyclo, optionally substituted ($C_6$-$C_{10}$) aryl, or optionally substituted ($C_3$-$C_6$) heteroaryl group.

In one embodiment, a Compound of the Disclosure is a compound having Formula I, wherein $R^3$ is an optionally substituted phenyl, wherein the phenyl is optionally substituted at the 2-position. In another embodiment, the phenyl is optionally substituted at the 6-position. In another embodiment, the phenyl is optionally disubstituted at the 2- and 6-positions. In another embodiment, the phenyl is optionally disubstituted at the 2- and 3-positions.

In one embodiment, a Compound of the Disclosure is a compound having Formula I, wherein $R^3$ is an optionally substituted pyrid-3-yl or optionally substituted pyrid-4-yl.

In another embodiment, $R^3$ is an optionally substituted pyrid-3-yl. In another embodiment, the pyrid-3-yl is optionally substituted at the 2-position. In another embodiment, the pyrid-3-yl is optionally substituted at the 4-position. In another embodiment, the pyrid-3-yl is optionally disubstituted at the 2- and 4-positions.

In another embodiment, $R^3$ is an optionally substituted pyrid-4-yl. In another embodiment, the pyrid-4-yl is optionally substituted at the 3-position. In another embodiment, the pyrid-4-yl is optionally substituted at the 5-position. In another embodiment, the pyrid-4-yl is optionally disubstituted at the 3- and 5-positions.

In one embodiment, a Compound of the Disclosure is a compound having Formula I, wherein $R^3$ is an optionally substituted pyrimidin-5-yl. In another embodiment, the pyrimidin-5-yl is optionally substituted at the 2-position. In another embodiment, the the pyrimidin-5-yl is optionally substituted at the 4-position. In another embodiment, the the pyrimidin-5-yl is optionally substituted at the 6-position. In another embodiment, the the pyrimidin-5-yl is optionally disubstituted at the 4- and 6-positions. In another embodiment, the the pyrimidin-5-yl is optionally disubstituted at the 2- and 6-positions. In another embodiment, the the pyrimidin-5-yl is optionally disubstituted at the 2- and 4-positions. In another embodiment, the the pyrimidin-5-yl is optionally trisubstituted at the 2-, 4-, and 6-positions.

In one embodiment, a Compound of the Disclosure is a compound having Formula I, wherein $R^3$ is an optionally substituted pyrazol-3-yl or optionally substituted pyrazol-5-yl.

In one embodiment, a Compound of the Disclosure is a compound having Formula I, wherein $R^3$ is an optionally substituted pyrazol-5-yl. In another embodiment, the the pyrazol-5-yl is optionally substituted at the 1-position. In another embodiment, the the pyrazol-5-yl is optionally substituted at the 3-position. In another embodiment, the the pyrazol-5-yl is optionally substituted at the 4-position. In another embodiment, the the pyrazol-5-yl is optionally disubstituted at the 1- and 4-positions. In another embodiment, the the pyrazol-5-yl is optionally disubstituted at the 1- and 3-positions. In another embodiment, the the pyrazol-5-yl is optionally disubstituted at the 3- and 4-positions.

In one embodiment, a Compound of the Disclosure is a compound having Formula I, wherein $R^3$ is substituted and the substituents are independently selected from methoxy, deuteromethoxy, ethoxy, isopropoxy, t-butoxy, difluoromethoxy, 2-fluoroethoxy, 2-methoxyethoxy, cyclopropoxy, cyclobutoxy, (tetrahydrofuran-3-yl)oxy, benzyloxy, methyl, ethyl, isopropyl, 2-fluoroisopropyl, t-butyl, cyclopropyl, cyclobutyl, methylcyclopropyl, pyrrolidin-1-yl, azetidin-1-yl, methylamino, dimethylamino, cyano, halo, methylthio, methylsulfonyl, and ethylsulfonyl.

In one embodiment, $R^3$ is selected from the group consisting of:

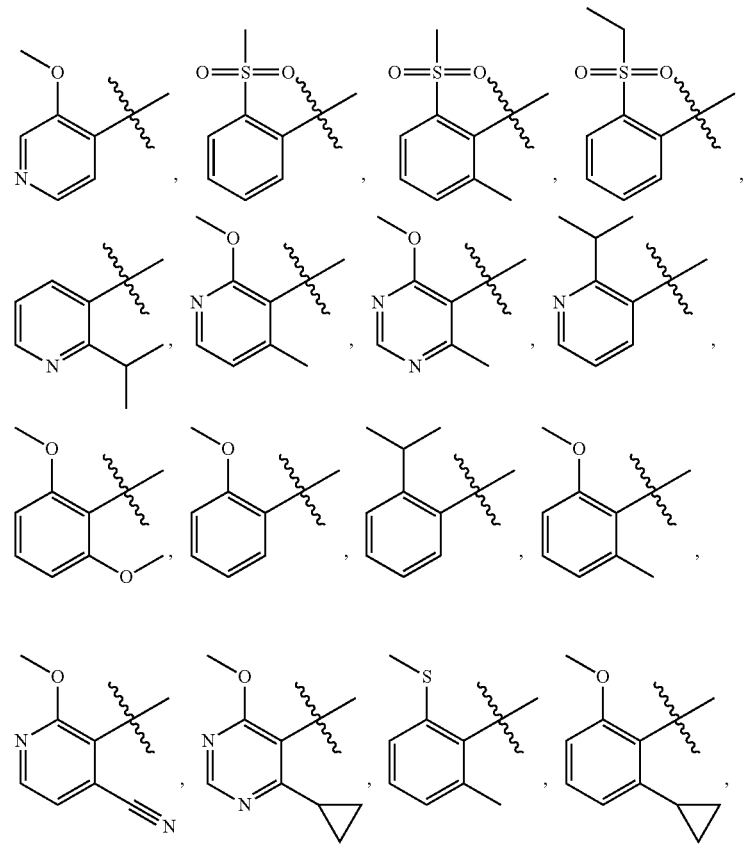

-continued
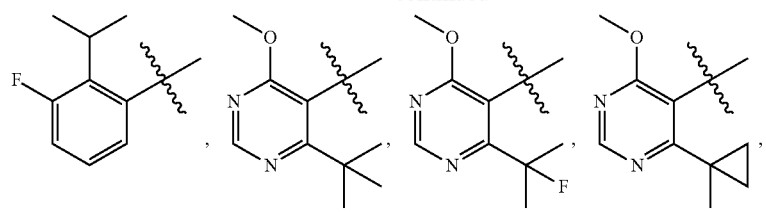
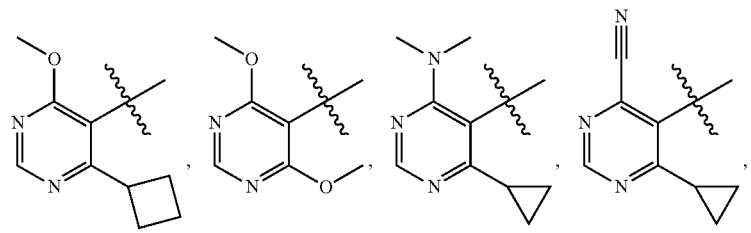
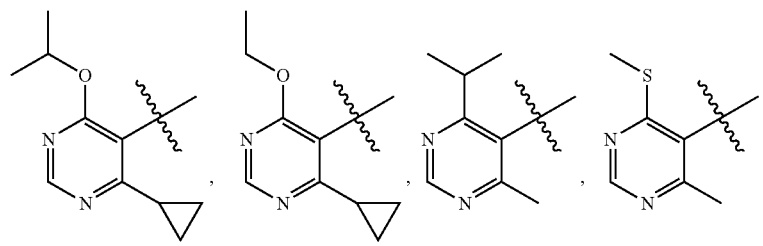
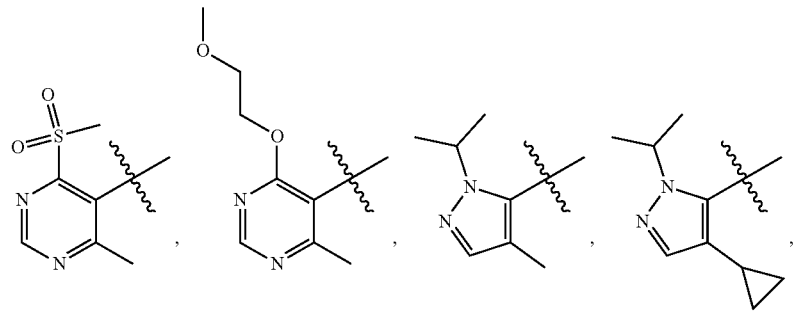
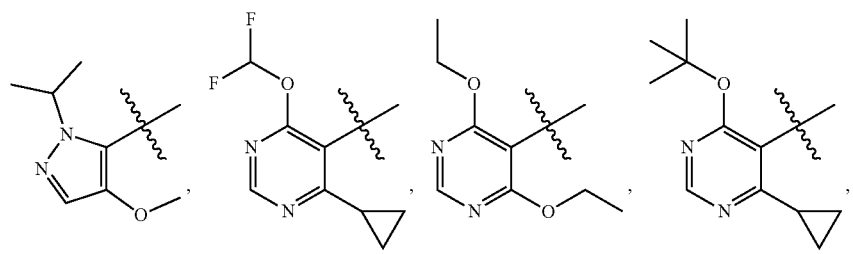
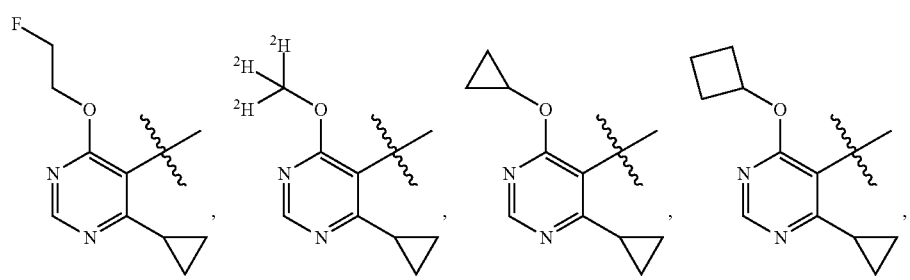

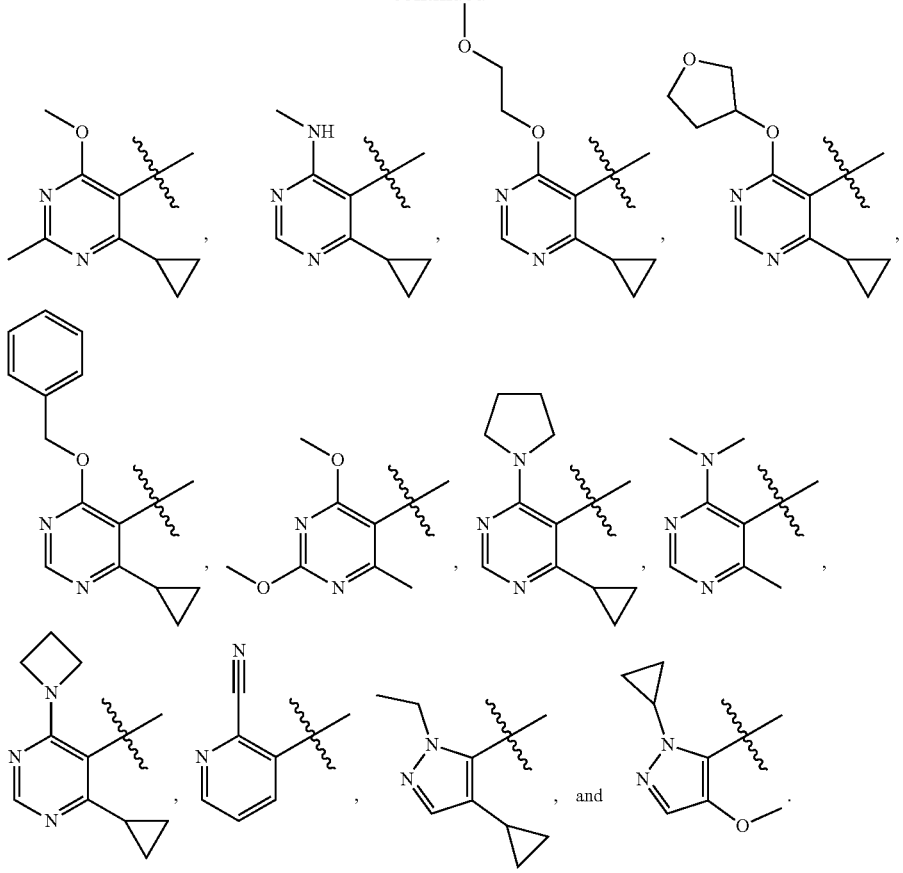

In another embodiment, a Compound of the Disclosure is a compound having Formula I, wherein at least one of $X^{11}$ and $X^{12}$ is N. In some embodiments, $X^{11}$ is N. In some embodiments, $X^{12}$ is N.

In another embodiment, a Compound of the Disclosure is a compound having Formula I, wherein at least one of $X^{11}$ and $X^{12}$ is CH. In some embodiments, $X^{11}$ is CH. In some embodiments, $X^{12}$ is CH.

In one embodiment, a Compound of the Disclosure is a compound having Formula I, wherein each of $X^{11}$ and $X^{12}$ is N.

In one embodiment, a Compound of the Disclosure is a compound having Formula I, wherein each of $X^{11}$ and $X^{12}$ is CH.

In some embodiments, one of $X^{11}$ and $X^{12}$ is N and the other of $X^{11}$ and $X^{12}$ is CH. In one embodiment $X^{11}$ is N and $X^{12}$ is CH. In another embodiment, $X^{11}$ is CH and $X^{12}$ is N.

In one embodiment, a Compound of the Disclosure is a compound having Formula I, wherein $R^5$ is selected from optionally substituted ($C_1$-$C_4$) alkyl, optionally substituted ($C_2$-$C_4$) alkenyl, optionally substituted ($C_2$-$C_4$) alkynyl, optionally substituted ($C_1$-$C_4$) alkoxy, ($C_1$-$C_4$) haloalkyl, ($C_1$-$C_4$) haloalkoxy, ($C_1$-$C_4$) hydroxyalkyl.

In another embodiment, a Compound of the Disclosure is a compound having Formula I, wherein $R^5$ is selected from cyano, halo, sulfonamido, —C(=O)$R^{23}$, —C(=O)O$R^{24}$, —N$R^{32a}R^{32b}$, —N$R^{31a}$C(=O)$R^{25}$, —N$R^{31a}$C(=O)N$R^{31a}R^{31b}$, —C(=O)N$R^{31a}R^{31b}$, —S(O)$_2R^{27}$, —N$R^{31a}$SO$_2R^{27}$.

In another embodiment, a Compound of the Disclosure is a compound having Formula I, wherein $R^5$ is selected from optionally substituted ($C_6$-$C_{10}$) aryl, optionally substituted ($C_6$-$C_{10}$) ar-($C_1$-$C_2$) alkyl, optionally substituted ($C_3$-$C_6$) heteroaryl, optionally substituted ($C_3$-$C_6$) heteroar-($C_1$-$C_2$) alkyl, optionally substituted ($C_3$-$C_8$) cycloalkyl, optionally substituted (($C_3$-$C_8$) cycloalkyl)-($C_1$-$C_2$) alkyl, optionally substituted ($C_3$-$C_8$) heterocyclo, optionally substituted ($C_3$-$C_8$) heterocyclo-($C_1$-$C_2$) alkyl, optionally substituted —O—($C_6$-$C_{10}$) aryl, optionally substituted —O—($C_6$-$C_{10}$) ar-($C_1$-$C_2$) alkyl, optionally substituted —O—($C_3$-$C_6$) heteroaryl, optionally substituted —O—($C_3$-$C_6$) heteroar-($C_1$-$C_2$) alkyl, optionally substituted —O—($C_3$-$C_8$) cycloalkyl, optionally substituted —O—(($C_3$-$C_8$) cycloalkyl)-($C_1$-$C_2$) alkyl, optionally substituted —O—($C_3$-$C_8$) heterocyclo, optionally substituted —O—($C_3$-$C_8$) heterocyclo-($C_1$-$C_2$) alkyl.

In another embodiment, a Compound of the Disclosure is a compound having Formula I, wherein $R^5$ is an optionally substituted heteroaryl. In another embodiment, $R^5$ is an optionally substituted 5- or 6-membered heteroaryl containing one or more nitrogens. In another embodiment, $R^5$ is an optionally substituted 5- or 6-membered heteroaryl containing only nitrogen as the heteroatom or heteroatoms.

In another embodiment, a Compound of the Disclosure is a compound having Formula I, wherein one of $R^5$ and one of $R^{5'}$ on adjacent atoms are taken together with the atoms to which they are attached to form an optionally substituted ($C_6$-$C_{10}$) aryl ring.

In another embodiment, a Compound of the Disclosure is a compound having Formula I, wherein one of $R^5$ and one of $R^{5'}$ on adjacent atoms are taken together with the atoms to which they are attached to form an optionally substituted ($C_3$-$C_6$) heteroaryl ring.

In another embodiment, a Compound of the Disclosure is a compound having Formula I, wherein one of $R^5$ and one of $R^{5'}$ on adjacent atoms are taken together with the atoms to which they are attached to form an optionally substituted ($C_3$-$C_8$) cycloalkyl ring.

In another embodiment, a Compound of the Disclosure is a compound having Formula I, wherein one of $R^5$ and one of $R^{5'}$ on adjacent atoms are taken together with the atoms to which they are attached to form an optionally substituted ($C_3$-$C_8$) heterocycloalkyl ring.

In another embodiment, a Compound of the Disclosure is a compound having Formula I, wherein one of $R^5$ and one of $R^{5'}$ on adjacent atoms are taken together with the atoms to which they are attached to form an optionally substituted spirocycloalkyl ring.

In another embodiment, a Compound of the Disclosure is a compound having Formula I, wherein one of $R^5$ and one of $R^{5'}$ on adjacent atoms are taken together with the atoms to which they are attached to form an optionally substituted spiroheterocycloalkyl ring.

In one embodiment, a Compound of the Disclosure is a compound having Formula I, wherein the optional substituents on $R^5$ are independently selected from hydrogen, halo, nitro, cyano, optionally substituted alkyl, optionally substituted alkenyl, optionally substituted alkynyl, alkoxy, hydroxy, carboxy, carboxyalkyl, amino, alkylamino, dialkylamino, cycloalkylamino, heterocycloalkylamino, aralkylamino, heteroaralkylamino, alkylthio, haloalkyl, haloalkoxy, hydroxyalkyl, hydroxyalkylamino, alkoxyalkyl, (alkoxyalkyl)amino, (amino)alkyl, (alkylamino)alkyl, (dialkylamino)alkyl, (cycloalkylamino)alkyl, (carboxamido)alkyl, mercaptoalkyl, (cyano)alkyl, (cycloalkyl)alkyl, aralkyl, aralkyloxy, alkylcarbonyl, arylcarbonyl, (heterocyclo)alkyl, (heteroaryl)alkyl, (amino)(hydroxy)alkyl, (aralkylamino)alkyl, ($C_{1-4}$ haloalkoxy)alkyl, optionally substituted heterocyclo, optionally substituted heteroaryl, optionally substituted aryl, optionally substituted cycloalkyl, carboxamido, sulfonyl, sulfonamido, sulfamido, alkylsulfonyl, alkylsulfonamido, alkylsulfamido, arylsulfonyl, aryloxy, heteroaryloxy, —C(=O)R$^{23}$, —C(=O)OR$^{24}$, —C(=O)NR$^{31a}$R$^{31b}$, —NR$^{31a}$C(=O)R$^{25}$, —NR$^{31a}$C(=O)OR$^{26}$, —NR$^{31a}$C(=O)NR$^{31a}$R$^{31b}$, —NR$^{31a}$SO$_2$R$^{27}$, —OC(=O)R$^{28}$, —OC(=O)OR$^{29}$, —OC(=O)NR$^{31a}$R$^{31b}$, —OSO$_2$R$^{30}$, and —NR$^{32a}$R$^{32b}$.

In another embodiment, the optional substituents on $R^5$ are independently selected from hydrogen, halo, nitro, cyano, optionally substituted ($C_1$-$C_4$) alkyl, optionally substituted ($C_2$-$C_4$) alkenyl, optionally substituted ($C_2$-$C_4$) alkynyl, ($C_1$-$C_4$) alkoxy, hydroxy, carboxy, carboxy-($C_1$-$C_4$) alkyl, amino, ($C_1$-$C_4$) alkylamino, di-($C_1$-$C_4$) alkylamino, ($C_3$-$C_8$) cycloalkylamino, heterocycl0-($C_1$-$C_4$) alkylamino, ar-($C_1$-$C_4$) alkylamino, heteroar-($C_1$-$C_4$) alkylamino, ($C_1$-$C_4$) alkylthio, halo-($C_1$-$C_4$) alkyl, halo-($C_1$-$C_4$) alkoxy, hydroxy-($C_1$-$C_4$) alkyl, hydroxy-($C_1$-$C_4$) alkylamino, alkoxy-($C_1$-$C_4$) alkyl, (alkoxyalkyl)amino, (amino)-($C_1$-$C_4$) alkyl, (alkylamino)-($C_1$-$C_4$) alkyl, (dialkylamino)-($C_1$-$C_4$) alkyl, (cycloalkylamino)-($C_1$-$C_4$) alkyl, (carboxamido)-($C_1$-$C_4$) alkyl, mercapto-($C_1$-$C_4$) alkyl, (cyano)-($C_1$-$C_4$) alkyl, (cycloalkyl)-($C_1$-$C_4$) alkyl, ar-($C_1$-$C_4$) alkyl, ar-($C_1$-$C_4$) alkyloxy, ($C_1$-$C_4$) alkylcarbonyl, arylcarbonyl, (heterocyclo)-($C_1$-$C_4$) alkyl, (heteroaryl)-($C_1$-$C_4$) alkyl, (amino)(hydroxy)-($C_1$-$C_4$) alkyl, (aralkylamino)-($C_1$-$C_4$) alkyl, and ($C_{1-4}$ haloalkoxy)-($C_1$-$C_4$) alkyl.

In another embodiment, the optional substituents on $R^5$ are independently selected from optionally substituted ($C_3$-$C_8$) heterocyclo, optionally substituted ($C_3$-$C_6$) heteroaryl, optionally substituted ($C_6$-$C_{10}$) aryl, optionally substituted ($C_3$-$C_8$) cycloalkyl.

In another embodiment, the optional substituents on $R^5$ are independently selected from carboxamido, sulfonyl, sulfonamido, sulfamido, ($C_1$-$C_4$) alkylsulfonyl, ($C_1$-$C_4$) alkylsulfonamido, ($C_1$-$C_4$) alkylsulfamido, ($C_6$-$C_{10}$) arylsulfonyl, ($C_6$-$C_{10}$) aryloxy, ($C_3$-$C_6$) heteroaryloxy, —C(=O)R$^{23}$, —C(=O)OR$^{24}$, —C(=O)NR$^{31a}$R$^{31b}$, —NR$^{31a}$C(=O)R$^{25}$, —NR$^{31a}$C(=O)OR$^{26}$, —NR$^{31a}$C(=O)NR$^{31a}$R$^{31b}$, —NR$^{31a}$SO$_2$R$^{27}$, —OC(=O)R$^{28}$, —OC(=O)OR$^{29}$, —OC(=O)NR$^{31a}$R$^{31b}$, —OSO$_2$R$^{30}$, and —NR$^{32a}$R$^{32b}$.

In one embodiment, a Compound of the Disclosure is a compound having Formula I, wherein two of the optional substituents on $R^5$ are taken together with the carbon or nitrogen atoms to which they are attached to form an optionally substituted cycloalkyl, optionally substituted heterocyclo, optionally substituted aryl, or optionally substituted heteroaryl group.

In another embodiment, two of the optional substituents on $R^5$ are taken together with the carbon atoms to which they are attached to form an optionally substituted ($C_3$-$C_8$) cycloalkyl, optionally substituted ($C_3$-$C_8$) heterocyclo, optionally substituted ($C_6$-$C_{10}$) aryl, or optionally substituted ($C_3$-$C_6$) heteroaryl group.

In one embodiment, a Compound of the Disclosure is a compound having Formula I, wherein $R^5$ is selected from optionally substituted ($C_1$-$C_6$) alkyl, optionally substituted ($C_2$-$C_6$) alkenyl, optionally substituted ($C_2$-$C_6$) alkynyl, optionally substituted ($C_1$-$C_6$) alkoxy, ($C_1$-$C_6$) haloalkyl, ($C_1$-$C_6$) haloalkoxy, and ($C_1$-$C_6$) hydroxyalkyl.

In one embodiment, a Compound of the Disclosure is a compound having Formula I, wherein $R^5$ is selected from cyano, halo, sulfonamido, —C(=O)R$^{23}$, —C(=O)OR$^{24}$, —NR$^{32a}$R$^{32b}$, —NR$^{31a}$C(=O)R$^{25}$, —NR$^{31a}$C(=O)NR$^{31a}$R$^{31b}$, —C(=O)NR$^{31a}$R$^{31b}$ S(O)$_2$R$^{27}$, and —NR$^{31a}$SO$_2$R$^{27}$.

In one embodiment, a Compound of the Disclosure is a compound having Formula I, wherein $R^5$ is selected from optionally substituted —O—($C_6$-$C_{14}$) aryl, optionally substituted —O—($C_6$-$C_{14}$) ar-($C_1$-$C_2$) alkyl, optionally substituted —O— heteroaryl, optionally substituted —O-heteroar-($C_1$-$C_2$) alkyl, optionally substituted —O—($C_3$-$C_8$) cycloalkyl, optionally substituted —O—(($C_3$-$C_8$) cycloalkyl)-($C_1$-$C_2$) alkyl, optionally substituted —O-heterocyclo, optionally substituted —O-heterocyclo-($C_1$-$C_2$) alkyl. In another embodiment, $R^5$ is selected from optionally substituted —O—($C_6$-$C_{10}$) aryl, optionally substituted —O—($C_6$-$C_{10}$) ar-($C_1$-$C_2$) alkyl, optionally substituted —O—($C_3$-$C_6$) heteroaryl, optionally substituted —O—($C_3$-$C_6$) heteroar-($C_1$-$C_2$) alkyl, optionally substituted —O—($C_3$-$C_8$) cycloalkyl, optionally substituted —O—(($C_3$-$C_8$) cycloalkyl)-($C_1$-$C_2$) alkyl, optionally substituted —O—($C_3$-$C_8$) heterocyclo, optionally substituted —O—($C_3$-$C_8$) heterocyclo-($C_1$-$C_2$) alkyl.

In one embodiment, a Compound of the Disclosure is a compound having Formula I, wherein $R^5$ is selected from optionally substituted ($C_6$-$C_{14}$) aryl, optionally substituted ($C_6$-$C_{14}$) ar-($C_1$-$C_2$) alkyl, optionally substituted heteroaryl, optionally substituted heteroar-($C_1$-$C_2$) alkyl, optionally substituted ($C_3$-$C_8$) cycloalkyl, optionally substituted (($C_3$-$C_8$) cycloalkyl)-($C_1$-$C_2$) alkyl, optionally substituted heterocyclo, optionally substituted heterocyclo-($C_1$-$C_2$) alkyl. In another embodiment, $R^5$ is selected from optionally substituted ($C_6$-$C_{10}$) aryl, optionally substituted ($C_6$-$C_{10}$) ar-($C_1$-$C_2$) alkyl, optionally substituted ($C_3$-$C_6$) heteroaryl, optionally substituted (C$_3$-C$_6$) heteroar-(C$_1$-C$_2$) alkyl, optionally substituted (C$_3$-C$_8$) cycloalkyl, optionally substituted ((C$_3$-C$_8$) cycloalkyl)-(C$_1$-C$_2$) alkyl, optionally substituted (C$_3$-C$_8$) heterocyclo, optionally substituted (C$_3$-C$_8$) heterocyclo-(C$_1$-C$_2$) alkyl.

In one embodiment, a Compound of the Disclosure is a compound having Formula I, wherein R$^5$ is an optionally substituted pyrrolyl, optionally substituted imidazolyl, optionally substituted pyrazolyl, optionally substituted triazolyl, or optionally substituted tetrazolyl. In another embodiment, R$^5$ is an optionally substituted pyrrolyl. In another embodiment, R$^5$ is an optionally substituted imidazolyl. In another embodiment, R$^5$ is an optionally substituted pyrazolyl. In another embodiment, R$^5$ is an optionally substituted triazolyl. In another embodiment, R$^5$ is an optionally substituted tetrazolyl.

In one embodiment, a Compound of the Disclosure is a compound having Formula I, wherein R$^5$ is substituted and the substituents are independently selected from halo, methyl, ethyl, isopropyl, cyclopropyl, cyclobutyl, methoxy, ethoxy, triazolyl, cyano, optionally substituted alkyl, amino, alkylamino, dialkylamino, difluoromethyl, trifluoromethyl, methylsulfonyl, oxetan-3-yl, and methylazetidinyl.

In one embodiment, a Compound of the Disclosure is a compound having Formula I, wherein R$^5$ is selected from the group consisting of:

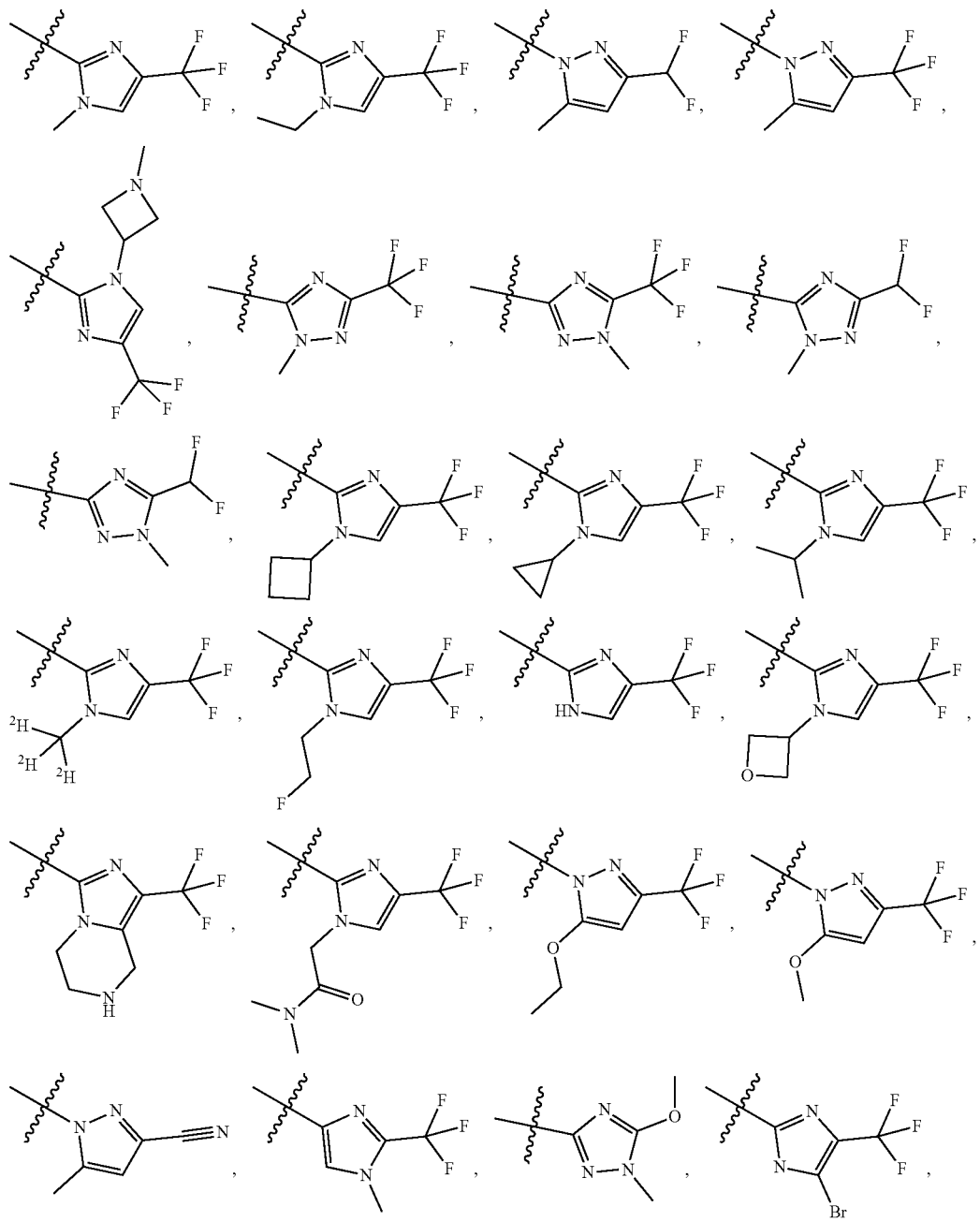

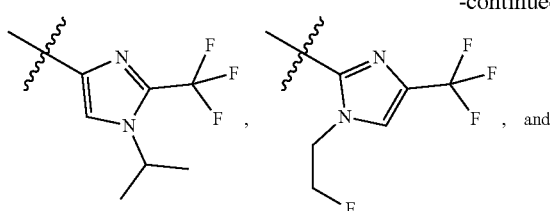

In one embodiment, a Compound of the Disclosure is a compound having Formula I, wherein each of $R^6$ and $R^7$ is independently selected from hydrogen, halo, and cyano.

In another embodiment, a Compound of the Disclosure is a compound having Formula I, wherein each of $R^6$ and $R^7$ is independently selected from optionally substituted $(C_1\text{-}C_4)$ alkyl, optionally substituted $(C_2\text{-}C_4)$ alkenyl, and optionally substituted $(C_2\text{-}C_4)$ alkynyl.

In one embodiment, a Compound of the Disclosure is a compound having Formula I, wherein $R^{23}$ is selected from the group consisting of hydrogen, optionally substituted $(C_1\text{-}C_4)$ alkyl, optionally substituted $(C_2\text{-}C_4)$ alkenyl, optionally substituted $(C_2\text{-}C_4)$ alkynyl, amino, $(C_1\text{-}C_4)$ alkylamino, di-$(C_1\text{-}C_4)$ alkylamino, cyclo-$(C_1\text{-}C_4)$ alkylamino, hydroxy-$(C_1\text{-}C_4)$ alkyl, (amino)-$(C_1\text{-}C_4)$ alkyl, (alkylamino)-$(C_1\text{-}C_4)$ alkyl, (dialkylamino)-$(C_1\text{-}C_4)$ alkyl, (cycloalkylamino)-$(C_1\text{-}C_4)$ alkyl, (cycloalkyl)-$(C_1\text{-}C_4)$ alkyl, ar-$(C_6\text{-}C_{10})$ alkyl, (heterocyclo)-$(C_1\text{-}C_4)$ alkyl, (heteroaryl)-$(C_1\text{-}C_4)$ alkyl, (amino)(hydroxy)-$(C_1\text{-}C_4)$ alkyl, (aralkylamino)-$(C_1\text{-}C_4)$ alkyl, optionally substituted $(C_3\text{-}C_8)$ heterocyclo, optionally substituted $(C_3\text{-}C_6)$ heteroaryl, optionally substituted $(C_6\text{-}C_{10})$ aryl, and optionally substituted $(C_3\text{-}C_8)$ cycloalkyl.

In one embodiment, a Compound of the Disclosure is a compound having Formula I, wherein each of $R^{31a}$ and $R^{31b}$ is independently selected from the group consisting of hydrogen, optionally substituted $(C_1\text{-}C_4)$ alkyl, optionally substituted $(C_2\text{-}C_4)$ alkenyl, optionally substituted $(C_2\text{-}C_4)$ alkynyl, hydroxy-$(C_1\text{-}C_4)$ alkyl, (amino)-$(C_1\text{-}C_4)$ alkyl, (alkylamino)-$(C_1\text{-}C_4)$ alkyl, (dialkylamino)-$(C_1\text{-}C_4)$ alkyl, alkoxy-$(C_1\text{-}C_4)$ alkyl, $(C_3\text{-}C_8)$ cycloalkyl, (cycloalkyl)-$(C_1\text{-}C_4)$ alkyl, (heterocyclo)-$(C_1\text{-}C_4)$ alkyl, ar-$(C_1\text{-}C_4)$ alkyl, and (heteroaryl)-$(C_1\text{-}C_4)$ alkyl.

In one embodiment, a Compound of the Disclosure is a compound having Formula I, wherein each of $R^{24}$, $R^{25}$, $R^{27}$, $R^{32a}$, and $R^{32b}$ is independently selected from the group consisting of hydrogen, optionally substituted $(C_1\text{-}C_4)$ alkyl, optionally substituted $(C_2\text{-}C_4)$ alkenyl, optionally substituted $(C_2\text{-}C_4)$ alkynyl, amino, $(C_1\text{-}C_4)$ alkylamino, di-$(C_1\text{-}C_4)$ alkylamino, $(C_3\text{-}C_8)$ cycloalkylamino, hydroxy-$(C_1\text{-}C_4)$ alkyl, (amino)-$(C_1\text{-}C_4)$ alkyl, (alkylamino)-$(C_1\text{-}C_4)$alkyl, (dialkylamino)-$(C_1\text{-}C_4)$ alkyl, (cycloalkylamino)-$(C_1\text{-}C_4)$ alkyl, (cycloalkyl)-$(C_1\text{-}C_4)$ alkyl, ar-$(C_1\text{-}C_4)$ alkyl, (heterocyclo)-$(C_1\text{-}C_4)$ alkyl, (heteroaryl)-$(C_1\text{-}C_4)$ alkyl, (amino)(hydroxy)-$(C_1\text{-}C_4)$ alkyl, (aralkylamino)-$(C_1\text{-}C_4)$ alkyl, alkoxy-$(C_1\text{-}C_4)$ alkyl, optionally substituted $(C_3\text{-}C_8)$ heterocyclo, optionally substituted $(C_3\text{-}C_6)$ heteroaryl, optionally substituted $(C_6\text{-}C_{10})$ aryl, and optionally substituted $(C_3\text{-}C_8)$ cycloalkyl.

In one embodiment, a Compound of the Disclosure is a compound having Formula I, wherein each of $R^{24}$, $R^{25}$, $R^{26}$, $R^{27}$, $R^{28}$, $R^{29}$, $R^{30}$, $R^{32a}$, and $R^{32b}$ is selected from the group consisting of hydrogen, optionally substituted alkyl, optionally substituted alkenyl, optionally substituted alkynyl, amino, alkylamino, dialkylamino, cycloalkylamino, hydroxyalkyl, (amino)alkyl, (alkylamino)alkyl, (dialkylamino)alkyl, (cycloalkylamino)alkyl, (cycloalkyl)alkyl, aralkyl, (heterocyclo)alkyl, (heteroaryl)alkyl, (amino)(hydroxy)alkyl, (aralkylamino)alkyl, alkoxyalkyl, optionally substituted heterocyclo, optionally substituted heteroaryl, optionally substituted aryl, and optionally substituted cycloalkyl.

In another embodiment, each of $R^{24}$, $R^{25}$, $R^{26}$, $R^{27}$, $R^{28}$, $R^{29}$, $R^{30}$, $R^{32a}$, and $R^{32b}$ is selected from the group consisting of hydrogen, optionally substituted $(C_1\text{-}C_4)$ alkyl, optionally substituted $(C_2\text{-}C_4)$ alkenyl, optionally substituted $(C_2\text{-}C_4)$ alkynyl, amino, $(C_1\text{-}C_4)$ alkylamino, di-$(C_1\text{-}C_4)$ alkylamino, $(C_3\text{-}C_8)$ cycloalkylamino, hydroxy-$(C_1\text{-}C_4)$ alkyl, (amino)-$(C_1\text{-}C_4)$ alkyl, (alkylamino)-$(C_1\text{-}C_4)$ alkyl, (dialkylamino)-$(C_1\text{-}C_4)$ alkyl, (cycloalkylamino)-$(C_1\text{-}C_4)$ alkyl, (cycloalkyl)-$(C_1\text{-}C_4)$ alkyl, ar-$(C_1\text{-}C_4)$ alkyl, (heterocyclo)-$(C_1\text{-}C_4)$ alkyl, (heteroaryl)-$(C_1\text{-}C_4)$ alkyl, (amino)(hydroxy)-$(C_1\text{-}C_4)$ alkyl, (aralkylamino)-$(C_1\text{-}C_4)$ alkyl, alkoxy-$(C_1\text{-}C_4)$ alkyl, optionally substituted $(C_3\text{-}C_8)$ heterocyclo, optionally substituted $(C_3\text{-}C_6)$ heteroaryl, optionally substituted $(C_6\text{-}C_{10})$ aryl, and optionally substituted $(C_3\text{-}C_8)$ cycloalkyl.

In another embodiment, Compounds of the Disclosure are compounds having Formula II:

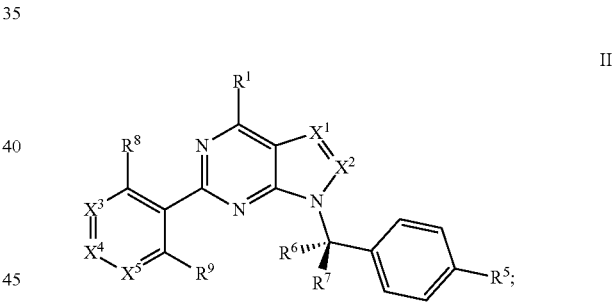

and the pharmaceutically acceptable salts or solvates, e.g., hydrates, thereof, wherein:

each of $X^1$, $X^2$, $R^1$, $R^5$, $R^6$, and $R^7$ are as defined above for Formula I;

$X^3$ is selected from N and $CR^{10}$; $X^4$ is selected from N and $CR^{11}$; and $X^5$ is selected from N and $CR^{12}$; and each of $R^8$, $R^9$, $R^{10}$, $R^{11}$, and $R^{12}$ is independently selected from the group consisting of hydrogen, halo, nitro, cyano, hydroxy, amino, alkylamino, dialkylamino, haloalkyl, hydroxyalkyl, alkoxy, haloalkoxy, aryloxy, heteroaryloxy, aralkyl aralkyloxy, alkylthio, carboxamido, sulfonamido, alkylcarbonyl, arylcarbonyl, alkylsulfonyl, arylsulfonyl, carboxy, carboxalkyl, alkyl, optionally substituted cycloalkyl, alkenyl, alkynyl, optionally substituted aryl, optionally substituted heteroaryl, optionally substituted heterocyclo, alkoxyalkyl, (amino)alkyl, hydroxyalkylamino, (alkylamino)alkyl, (dialkylamino)alkyl, (cyano)alkyl, (carboxamido)alkyl, mercaptoalkyl, (heterocyclo)alkyl, (cycloalkylamino)alkyl, $(C_{1\text{-}4}$ haloalkoxy)alkyl, or (heteroaryl)alkyl.

In another embodiment, each of $R^8$, $R^9$, $R^{10}$, $R^{11}$, and $R^{12}$ is independently selected from hydrogen, halo, nitro, cyano, hydroxy, amino, $(C_1-C_4)$ alkylamino, di-$(C_1-C_4)$ alkylamino, halo-$(C_1-C_4)$ alkyl, hydroxy-$(C_1-C_4)$ alkyl, $(C_1-C_4)$ alkoxy, halo-$(C_1-C_4)$ alkoxy, $(C_6-C_{10})$ aryloxy, $(C_3-C_6)$ heteroaryloxy, ar-$(C_1-C_4)$ alkyl ar-$(C_1-C_4)$ alkyloxy, $(C_1-C_4)$ alkylthio, carboxamido, sulfonamido, $(C_1-C_4)$ alkylcarbonyl, $(C_6-C_{10})$ arylcarbonyl, $(C_1-C_4)$ alkylsulfonyl, $(C_6-C_{10})$ arylsulfonyl, carboxy, carboxy-$(C_1-C_4)$ alkyl, $(C_1-C_4)$ alkyl, $(C_2-C_4)$ alkenyl, $(C_2-C_4)$ alkynyl, alkoxy-$(C_1-C_4)$ alkyl, (amino)-$(C_1-C_4)$ alkyl, hydroxy-$(C_1-C_4)$ alkylamino, (alkylamino)-$(C_1-C_4)$ alkyl, (dialkylamino)-$(C_1-C_4)$ alkyl, (cyano)-$(C_1-C_4)$ alkyl, (carboxamido)-$(C_1-C_4)$ alkyl, mercapto-$(C_1-C_4)$ alkyl, (heterocyclo)-$(C_1-C_4)$ alkyl, (cycloalkylamino)-$(C_1-C_4)$ alkyl, $(C_{1-4}$ haloalkoxy)-$(C_1-C_4)$ alkyl, or (heteroaryl)-$(C_1-C_4)$ alkyl.

In another embodiment, each of $R^8$, $R^9$, $R^{10}$, $R^{11}$, and $R^{12}$ is independently selected from optionally substituted $(C_3-C_8)$ cycloalkyl, optionally substituted $(C_6-C_{10})$ aryl, optionally substituted $(C_3-C_6)$ heteroaryl, and optionally substituted $(C_3-C_8)$ heterocyclo.

In one embodiment, Compounds of the Disclosure are compounds having Formula III, Formula IV, Formula V, Formula VI, or Formula VIa:

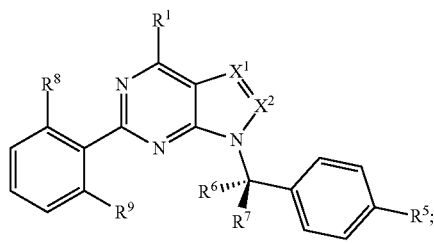

III

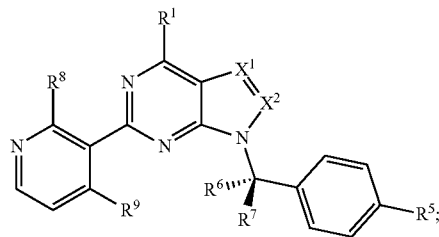

IV

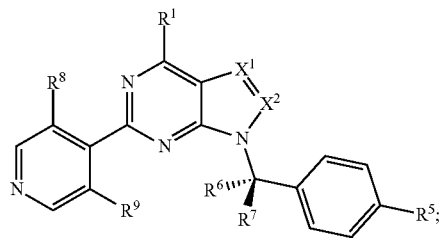

V

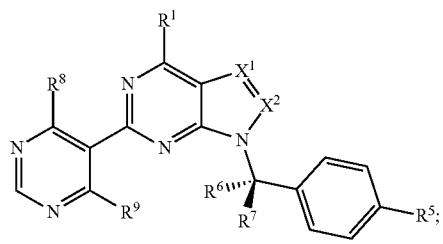

VI

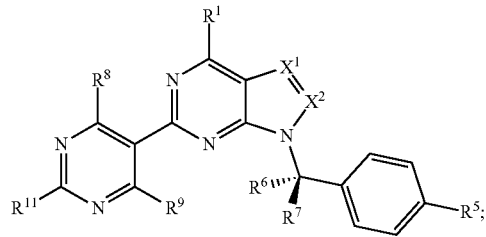

VIa wherein each of $X^1$, $X^2$, $R^1$, $R^5$, $R^6$, $R^7$, $R^8$, $R^9$, and $R^{11}$ are as defined above for Formula II.

In another embodiment, $R^5$ is:

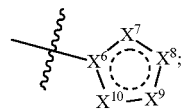

wherein:

$X^6$ is selected from $NR^{13}$ and $CR^{18}$; $X^7$ is selected from $NR^{14}$ and $CR^{19}$; $X^8$ is selected from $NR^{15}$ and $CR^{20}$; $X^9$ is selected from $NR^{16}$ and $CR^{21}$; $X^{10}$ is selected from $NR^{17}$ and $CR^{22}$; and each of $R^{13}$, $R^{14}$, $R^{15}$, $R^{16}$, and $R^{17}$ is absent, or independently selected from hydrogen, halo, methyl, ethyl, isopropyl, cyclopropyl, cyclobutyl, methoxy, ethoxy, triazolyl, cyano, optionally substituted alkyl, amino, alkylamino, dialkylamino, difluoromethyl, trifluoromethyl, methylsulfonyl, oxetan-3-yl, and methylazetidinyl.

each of $R^{18}$, $R^{19}$, $R^{20}$, $R^{21}$, and $R^{22}$ is independently selected from hydrogen, halo, methyl, ethyl, isopropyl, cyclopropyl, methoxy, triazolyl, cyano, optionally substituted alkyl, amino, alkylamino, dialkylamino, difluoromethyl, trifluoromethyl, methylsulfonyl, and methylazetidinyl.

In one embodiment, Compounds of the Disclosure are compounds having Formula VII, Formula VIII, Formula IX, Formula X, Formula XI, or Formula XII:

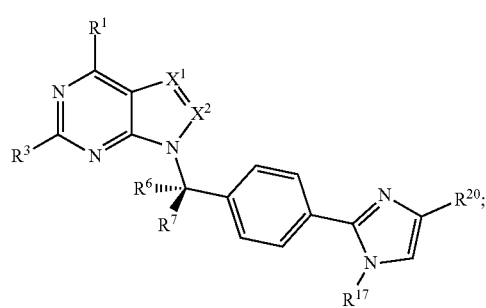

VII

-continued

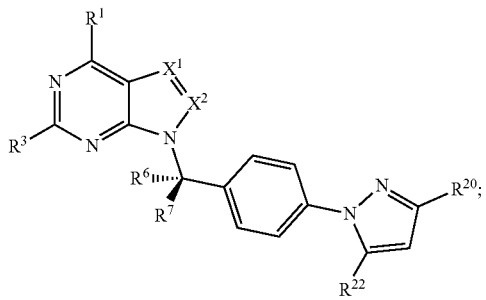

VIII

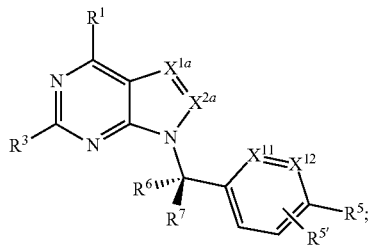

XIII wherein:
each of $X^{1a}$ and $X^{2a}$ is independently selected from N, and $CR^{2a}$;

$R^{2a}$ is independently selected from hydrogen, halo, cyano, optionally substituted alkyl, optionally substituted alkenyl, optionally substituted alkynyl, alkoxy, alkoxyalkyl, alkylsulfonyl, alkylthio, aryl, heteroaryl, and heterocyclo; and each of the remaining substituents is defined as disclosed herein.

In one embodiment, Compounds of the Disclosure are compounds selected from the group consisting of:

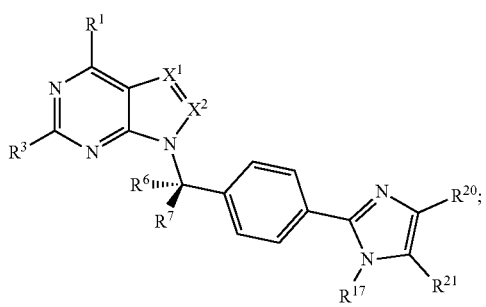

IX 6-(3-methoxypyridin-4-yl)-1-(4-(1-methyl-4-(trifluoromethyl)-1H-imidazol-2-yl)benzyl)-1H-pyrazolo[3,4-d]pyrimidine (Example 8);

1-(4-(1-methyl-4-(trifluoromethyl)-1H-imidazol-2-yl)benzyl)-6-(2-(methylsulfonyl)-phenyl)-1H-pyrazolo[3,4-d]pyrimidine (Example 3);

1-(4-(1-methyl-4-(trifluoromethyl)-1H-imidazol-2-yl)benzyl)-6-(2-methyl-6-(methylsulfonyl)phenyl)-1H-pyrazolo[3,4-d]pyrimidine (Example 23);

X 6-(2-(ethylsulfonyl)phenyl)-1-(4-(1-methyl-4-(trifluoromethyl)-1H-imidazol-2-yl)benzyl)-1H-pyrazolo[3,4-d]pyrimidine (Example 7);

1-(4-(3-(difluoromethyl)-5-methyl-1H-pyrazol-1-yl)benzyl)-6-(2-isopropylpyridin-3-yl)-1H-pyrazolo[3,4-d]pyrimidine (Example 20);

6-(2-methoxy-4-methylpyridin-3-yl)-1-(4-(1-methyl-4-(trifluoromethyl)-1H-imidazol-2-yl)benzyl)-1H-pyrazolo[3,4-d]pyrimidine (Example 6);

XI 6-(4-methoxy-6-methylpyrimidin-5-yl)-1-(4-(1-methyl-4-(trifluoromethyl)-1H-imidazol-2-yl)benzyl)-1H-pyrazolo[3,4-d]pyrimidine (Example 21);

6-(2-isopropylpyridin-3-yl)-1-(4-(5-methyl-3-(trifluoromethyl)-1H-pyrazol-1-yl)benzyl)-1H-pyrazolo[3,4-d]pyrimidine (Example 18);

XII 6-(2,6-dimethoxyphenyl)-1-(4-(1-methyl-4-(trifluoromethyl)-1H-imidazol-2-yl)benzyl)-1H-pyrazolo[3,4-d]pyrimidine (Example 4);

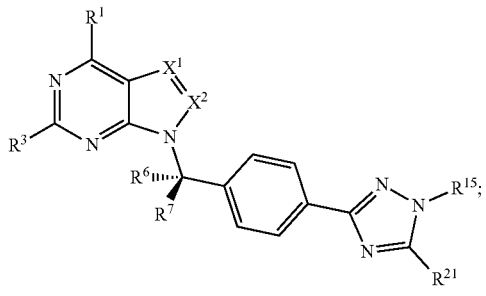

6-(2-methoxyphenyl)-1-(4-(1-methyl-4-(trifluoromethyl)-1H-imidazol-2-yl)benzyl)-1H-pyrazolo[3,4-d]pyrimidine (Example 2);

6-(2-isopropylphenyl)-1-(4-(5-methyl-3-(trifluoromethyl)-1H-pyrazol-1-yl)benzyl)-1H-pyrazolo[3,4-d]pyrimidine (Example 15);

6-(2-methoxy-6-methylphenyl)-1-(4-(1-methyl-4-(trifluoromethyl)-1H-imidazol-2-yl)benzyl)-1H-pyrazolo[3,4-d]pyrimidine (Example 5);

2-methoxy-3-(1-(4-(1-methyl-4-(trifluoromethyl)-1H-imidazol-2-yl)benzyl)-1H-pyrazolo[3,4-d]pyrimidin-6-yl)isonicotinonitrile (Example 22);

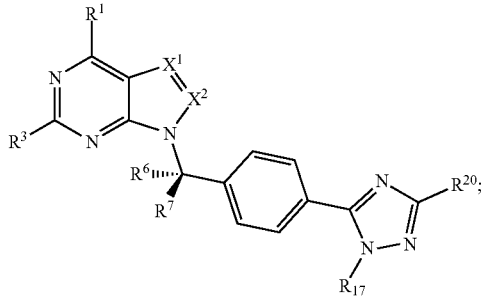

2-(2-isopropylphenyl)-9-(4-(1-methyl-4-(trifluoromethyl)-1H-imidazol-2-yl)benzyl)-9H-purine (Example 24);

wherein each of $X^1$, $X^2$, $R^1$, $R^3$, $R^6$, $R^7$, $R^{15}$, $R^{16}$, $R^{17}$, $R^{20}$, $R^{21}$, and $R^{22}$ are as defined above for Formula II.

In one embodiment, Compounds of the Disclosure are compounds having Formula XIII:

6-(4-cyclopropyl-6-methoxypyrimidin-5-yl)-1-(4-(1-methyl-4-(trifluoromethyl)-1H-imidazol-2-yl)benzyl)-1H-pyrazolo[3,4-d]pyrimidine (Example 12);

6-(2-isopropylpyridin-3-yl)-1-(4-(1-methyl-4-(trifluoromethyl)-1H-imidazol-2-yl)benzyl)-1H-pyrazolo[3,4-d]pyrimidine (Example 9);

1-(4-(1-methyl-4-(trifluoromethyl)-1H-imidazol-2-yl)benzyl)-6-(2-methyl-6-(methylthio)phenyl)-1H-pyrazolo[3,4-d]pyrimidine (Example 13);

6-(4-cyclopropyl-6-methoxypyrimidin-5-yl)-1-(4-(5-methyl-3-(trifluoromethyl)-1H-pyrazol-1-yl)benzyl)-1H-pyrazolo[3,4-d]pyrimidine (Example 19);

6-(2-cyclopropyl-6-methoxyphenyl)-1-(4-(1-methyl-4-(trifluoromethyl)-1H-imidazol-2-yl)benzyl)-1H-pyrazolo[3,4-d]pyrimidine (Example 11);

6-(2-isopropylphenyl)-1-(4-(1-(1-methylazetidin-3-yl)-4-(trifluoromethyl)-1H-imidazol-2-yl)benzyl)-1H-pyrazolo[3,4-d]pyrimidine (Example 25);

6-(2-isopropylphenyl)-1-(1-(4-(1-methyl-4-(trifluoromethyl)-1H-imidazol-2-yl)phenyl)ethyl)-1H-pyrazolo[3,4-d]pyrimidine (Example 16);

6-(2-isopropylphenyl)-4-methyl-1-(4-(1-methyl-4-(trifluoromethyl)-1H-imidazol-2-yl)benzyl)-1H-pyrazolo[3,4-d]pyrimidine (Example 14);

6-(3-fluoro-2-isopropylphenyl)-1-(4-(1-methyl-4-(trifluoromethyl)-1H-imidazol-2-yl)benzyl)-1H-pyrazolo[3,4-d]pyrimidine (Example 10);

6-(2-isopropylphenyl)-3-methyl-1-(4-(1-methyl-4-(trifluoromethyl)-1H-imidazol-2-yl)benzyl)-1H-pyrazolo[3,4-d]pyrimidine (Example 17);

6-(2-isopropylphenyl)-1-(4-(1-methyl-4-(trifluoromethyl)-1H-imidazol-2-yl)benzyl)-1H-pyrazolo[3,4-d]pyrimidine (Example 1);

6-(4-(tert-butyl)-6-methoxypyrimidin-5-yl)-1-(4-(1-methyl-4-(trifluoromethyl)-1H-imidazol-2-yl)benzyl)-1H-pyrazolo[3,4-d]pyrimidine;

6-(4-(2-fluoropropan-2-yl)-6-methoxypyrimidin-5-yl)-1-(4-(1-methyl-4-(trifluoromethyl)-1H-imidazol-2-yl)benzyl)-1H-pyrazolo[3,4-d]pyrimidine;

6-(4-methoxy-6-(1-methylcyclopropyl)pyrimidin-5-yl)-1-(4-(1-methyl-4-(trifluoromethyl)-1H-imidazol-2-yl)benzyl)-1H-pyrazolo[3,4-d]pyrimidine;

6-(4-cyclobutyl-6-methoxypyrimidin-5-yl)-1-(4-(1-methyl-4-(trifluoromethyl)-1H-imidazol-2-yl)benzyl)-1H-pyrazolo[3,4-d]pyrimidine;

(S)-6-(4-cyclopropyl-6-methoxypyrimidin-5-yl)-1-(1-(4-(1-methyl-4-(trifluoromethyl)-1H-imidazol-2-yl)phenyl)ethyl)-1H-pyrazolo[3,4-d]pyrimidine;

(R)-6-(4-cyclopropyl-6-methoxypyrimidin-5-yl)-1-(1-(4-(1-methyl-4-(trifluoromethyl)-1H-imidazol-2-yl)phenyl)ethyl)-1H-pyrazolo[3,4-d]pyrimidine;

6-(4-cyclopropyl-6-ethoxypyrimidin-5-yl)-1-(4-(1-methyl-4-(trifluoromethyl)-1H-imidazol-2-yl)benzyl)-1H-pyrazolo[3,4-d]pyrimidine;

6-(4-cyclopropyl-6-isopropoxypyrimidin-5-yl)-1-(4-(1-methyl-4-(trifluoromethyl)-1H-imidazol-2-yl)benzyl)-1H-pyrazolo[3,4-d]pyrimidine;

6-cyclopropyl-5-(1-(4-(1-methyl-4-(trifluoromethyl)-1H-imidazol-2-yl)benzyl)-1H-pyrazolo[3,4-d]pyrimidin-6-yl)pyrimidine-4-carbonitrile;

6-cyclopropyl-N,N-dimethyl-5-(1-(4-(1-methyl-4-(trifluoromethyl)-1H-imidazol-2-yl)benzyl)-1H-pyrazolo[3,4-d]pyrimidin-6-yl)pyrimidin-4-amine;

6-(4,6-dimethoxypyrimidin-5-yl)-1-(4-(1-methyl-4-(trifluoromethyl)-1H-imidazol-2-yl)benzyl)-1H-pyrazolo[3,4-d]pyrimidine;

6-(4-cyclopropyl-6-methoxypyrimidin-5-yl)-1-(4-(1-ethyl-4-(trifluoromethyl)-1H-imidazol-2-yl)benzyl)-1H-pyrazolo[3,4-d]pyrimidine;

6-(4-isopropyl-6-methylpyrimidin-5-yl)-1-(4-(5-methyl-3-(trifluoromethyl)-1H-pyrrazol-1-yl)benzyl)-1H-pyrazolo[3,4-d]pyrimidine;

1-(4-(5-methyl-3-(trifluoromethyl)-1H-pyrazol-1-yl)benzyl)-6-(4-methyl-6-(methylthio)pyrimidin-5-yl)-1H-pyrazolo[3,4-d]pyrimidine;

2-(4-cyclopropyl-6-methoxypyrimidin-5-yl)-8-methyl-9-(4-(5-methyl-3-(trifluoromethyl)-1H-pyrazol-1-yl)benzyl)-9H-purine;

1-(4-(5-methyl-3-(trifluoromethyl)-1H-pyrazol-1-yl)benzyl)-6-(4-methyl-6-(methylsulfonyl)pyrimidin-5-yl)-1H-pyrazolo[3,4-d]pyrimidine;

6-(4-(2-methoxyethoxy)-6-methylpyrimidin-5-yl)-1-(4-(5-methyl-3-(trifluoromethyl)-1H-pyrazol-1-yl)benzyl)-1H-pyrazolo[3,4-d]pyrimidine;

6-(1-isopropyl-4-methyl-1H-pyrazol-5-yl)-1-(4-(5-methyl-3-(trifluoromethyl)-1H-pyrazol-1-yl)benzyl)-1H-pyrazolo[3,4-d]pyrimidine;

6-(1-isopropyl-4-methoxy-1H-pyrazol-5-yl)-1-(4-(5-methyl-3-(trifluoromethyl)-1H-pyrazol-1-yl)benzyl)-1H-pyrazolo[3,4-d]pyrimidine;

6-(4-cyclopropyl-1-isopropyl-1H-pyrazol-5-yl)-1-(4-(5-methyl-3-(trifluoromethyl)-1H-pyrazol-1-yl)benzyl)-1H-pyrazolo[3,4-d]pyrimidine;

2-(4-cyclopropyl-6-methoxypyrimidin-5-yl)-7-(4-(1-methyl-4-(trifluoromethyl)-1H-imidazol-2-yl)benzyl)-7H-pyrrolo[2,3-d]pyrimidine; and 5-(4-cyclopropyl-6-methoxypyrimidin-5-yl)-3-(4-(1-methyl-4-(trifluoromethyl)-1H-imidazol-2-yl)benzyl)-3H-[1,2,3]triazolo[4,5-d]pyrimidine, or a pharmaceutically acceptable salt or solvate, e.g., hydrate, of any of the above.

In another embodiment, Compounds of the Disclosure are compounds selected from the group consisting of:

6-(4,6-diethoxypyrimidin-5-yl)-1-(4-(1-ethyl-4-(trifluoromethyl)-1H-imidazol-2-yl)benzyl)-1H-pyrazolo[3,4-d]pyrimidine;

6-(4-cyclopropyl-6-methoxypyrimidin-5-yl)-1-(4-(1-(trifluoromethyl)-5,6,7,8-tetrahydroimidazo[1,5-a]pyrazin-3-yl)benzyl)-1H-pyrazolo[3,4-d]pyrimidine;

6-(4-cyclopropyl-6-methoxypyrimidin-5-yl)-1-(4-(1-methyl-5-(trifluoromethyl)-1H-1,2,4-triazol-3-yl)benzyl)-1H-pyrazolo[3,4-d]pyrimidine;

6-(1-cyclopropyl-4-methoxy-1H-pyrazol-5-yl)-1-(4-(1-ethyl-4-(trifluoromethyl)-1H-imidazol-2-yl)benzyl)-1H-pyrazolo[3,4-d]pyrimidine;

6-(4-cyclopropyl-6-methoxypyrimidin-5-yl)-1-((6-(5-methoxy-3-(trifluoromethyl)-1H-pyrazol-1-yl)pyridin-3-yl)methyl)-1H-pyrazolo[3,4-d]pyrimidine;

(R)-6-(4-cyclobutyl-6-methoxypyrimidin-5-yl)-1-(1-(4-(1-ethyl-4-(trifluoromethyl)-1H-imidazol-2-yl)phenyl)ethyl)-1H-pyrazolo[3,4-d]pyrimidine;

(S)-6-(4-cyclobutyl-6-methoxypyrimidin-5-yl)-1-(1-(4-(1-ethyl-4-(trifluoromethyl)-1H-imidazol-2-yl)phenyl)ethyl)-1H-pyrazolo[3,4-d]pyrimidine;

(R)-6-(4-cyclopropyl-6-methoxypyrimidin-5-yl)-1-(1-(4-(1-ethyl-4-(trifluoromethyl)-1H-imidazol-2-yl)phenyl)ethyl)-1H-pyrazolo[3,4-d]pyrimidine;

(S)-6-(4-cyclopropyl-6-methoxypyrimidin-5-yl)-1-(1-(4-(1-ethyl-4-(trifluoromethyl)-1H-imidazol-2-yl)phenyl)ethyl)-1H-pyrazolo[3,4-d]pyrimidine;

6-(4-cyclopropyl-6-methoxypyrimidin-5-yl)-1-(4-(1-methyl-2-(trifluoromethyl)-1H-imidazol-4-yl)benzyl)-1H-pyrazolo[3,4-d]pyrimidine;

6-(4-(2-fluoropropan-2-yl)-6-methoxypyrimidin-5-yl)-1-(4-(1-methyl-4-(trifluoromethyl)-1H-imidazol-2-yl)benzyl)-1H-pyrazolo[3,4-d]pyrimidine;

6-(4-cyclopropyl-6-methoxypyrimidin-5-yl)-1-(4-(5-ethoxy-3-(trifluoromethyl)-1H-pyrazol-1-yl)benzyl)-1H-pyrazolo[3,4-d]pyrimidine;

6-(4-cyclopropyl-6-methoxypyrimidin-5-yl)-1-((6-(1-ethyl-4-(trifluoromethyl)-1H-imidazol-2-yl)pyridin-3-yl)methyl)-1H-pyrazolo[3,4-d]pyrimidine;

1-(4-((6-(4-cyclopropyl-6-methoxypyrimidin-5-yl)-1H-pyrazolo[3,4-d]pyrimidin-1-yl)methyl)phenyl)-5-methyl-1H-pyrazole-3-carbonitrile;

6-(4-cyclopropyl-1-ethyl-1H-pyrazol-5-yl)-1-(4-(1-ethyl-4-(trifluoromethyl)-1H-imidazol-2-yl)benzyl)-1H-pyrazolo[3,4-d]pyrimidine;

6-(4-cyclopropyl-6-(methoxy-d₃)pyrimidin-5-yl)-1-(4-(1-ethyl-4-(trifluoromethyl)-1H-imidazol-2-yl)benzyl)-1H-pyrazolo[3,4-d]pyrimidine;

6-cyclopropyl-5-(1-(4-(1-methyl-4-(trifluoromethyl)-1H-imidazol-2-yl)benzyl)-1H-pyrazolo[3,4-d]pyrimidin-6-yl)pyrimidine-4-carbonitrile;

6-(4-cyclopropoxy-6-cyclopropylpyrimidin-5-yl)-1-(4-(1-ethyl-4-(trifluoromethyl)-1H-imidazol-2-yl)benzyl)-1H-pyrazolo[3,4-d]pyrimidine;

6-(4-cyclobutoxy-6-cyclopropylpyrimidin-5-yl)-1-(4-(1-ethyl-4-(trifluoromethyl)-1H-imidazol-2-yl)benzyl)-1H-pyrazolo[3,4-d]pyrimidine;

6-(4-cyclopropyl-6-(difluoromethoxy)pyrimidin-5-yl)-1-(4-(1-ethyl-4-(trifluoromethyl)-1H-imidazol-2-yl)benzyl)-1H-pyrazolo[3,4-d]pyrimidine;

6-(4-cyclopropyl-6-methoxy-2-methylpyrimidin-5-yl)-1-(4-(1-methyl-4-(trifluoromethyl)-1H-imidazol-2-yl)benzyl)-1H-pyrazolo[3,4-d]pyrimidine;

6-(4-cyclopropyl-6-methoxypyrimidin-5-yl)-1-(4-(1-(oxetan-3-yl)-4-(trifluoromethyl)-1H-imidazol-2-yl)benzyl)-1H-pyrazolo[3,4-d]pyrimidine;

6-(4-(tert-butyl)-6-methoxypyrimidin-5-yl)-1-(4-(1-methyl-4-(trifluoromethyl)-1H-imidazol-2-yl)benzyl)-1H-pyrazolo[3,4-d]pyrimidine;

6-(4-(tert-butoxy)-6-cyclopropylpyrimidin-5-yl)-1-(4-(1-ethyl-4-(trifluoromethyl)-1H-imidazol-2-yl)benzyl)-1H-pyrazolo[3,4-d]pyrimidine;

6-(4-cyclopropyl-6-(2-fluoroethoxy)pyrimidin-5-yl)-1-(4-(1-ethyl-4-(trifluoromethyl)-1H-imidazol-2-yl)benzyl)-1H-pyrazolo[3,4-d]pyrimidine;

6-(4-cyclopropyl-6-methoxypyrimidin-5-yl)-1-(4-(1-(methyl-d3)-4-(trifluoromethyl)-1H-imidazol-2-yl)benzyl)-1H-pyrazolo[3,4-d]pyrimidine;

1-(4-(1-cyclobutyl-4-(trifluoromethyl)-1H-imidazol-2-yl)benzyl)-6-(4-cyclopropyl-6-methoxypyrimidin-5-yl)-1H-pyrazolo[3,4-d]pyrimidine;

6-(4,6-dimethoxypyrimidin-5-yl)-1-(4-(1-ethyl-4-(trifluoromethyl)-1H-imidazol-2-yl)benzyl)-1H-pyrazolo[3,4-d]pyrimidine;

6-(4-cyclopropyl-6-methoxypyrimidin-5-yl)-1-(4-(1-isopropyl-4-(trifluoromethyl)-1H-imidazol-2-yl)benzyl)-1H-pyrazolo[3,4-d]pyrimidine;

1-(4-(1-cyclopropyl-4-(trifluoromethyl)-1H-imidazol-2-yl)benzyl)-6-(4-cyclopropyl-6-methoxypyrimidin-5-yl)-1H-pyrazolo[3,4-d]pyrimidine;

6-(4-cyclopropyl-6-methoxypyrimidin-5-yl)-1-(4-(1-(2-fluoroethyl)-4-(trifluoromethyl)-1H-imidazol-2-yl)benzyl)-1H-pyrazolo[3,4-d]pyrimidine;

6-(4-cyclopropyl-6-methoxypyrimidin-5-yl)-1-(4-(4-(trifluoromethyl)-1H-imidazol-2-yl)benzyl)-1H-pyrazolo[3,4-d]pyrimidine;

6-(4-cyclopropyl-6-methoxypyrimidin-5-yl)-1-(3-fluoro-4-(1-methyl-4-(trifluoromethyl)-1H-imidazol-2-yl)benzyl)-1H-pyrazolo[3,4-d]pyrimidine;

6-(4-cyclopropyl-6-methoxypyrimidin-5-yl)-1-(2-fluoro-4-(1-methyl-4-(trifluoromethyl)-1H-imidazol-2-yl)benzyl)-1H-pyrazolo[3,4-d]pyrimidine;

6-(2,4-dimethoxy-6-methylpyrimidin-5-yl)-1-(4-(1-methyl-4-(trifluoromethyl)-1H-imidazol-2-yl)benzyl)-1H-pyrazolo[3,4-d]pyrimidine;

6-(4-cyclopropyl-6-methoxypyrimidin-5-yl)-1-(4-(5-methoxy-3-(trifluoromethyl)-1H-pyrazol-1-yl)benzyl)-1H-pyrazolo[3,4-d]pyrimidine;

6-(4-cyclopropyl-6-(2-methoxyethoxy)pyrimidin-5-yl)-1-(4-(1-methyl-4-(trifluoromethyl)-1H-imidazol-2-yl)benzyl)-1H-pyrazolo[3,4-d]pyrimidine;

6-(4-cyclopropyl-6-(2-methoxyethoxy)pyrimidin-5-yl)-1-(4-(5-methyl-3-(trifluoromethyl)-1H-pyrazol-1-yl)benzyl)-1H-pyrazolo[3,4-d]pyrimidine;

6-(4-methoxy-6-(1-methylcyclopropyl)pyrimidin-5-yl)-1-(4-(1-methyl-4-(trifluoromethyl)-1H-imidazol-2-yl)benzyl)-1H-pyrazolo[3,4-d]pyrimidine;

6-(1-isopropyl-4-methyl-1H-pyrazol-5-yl)-1-(4-(5-methyl-3-(trifluoromethyl)-1H-pyrazol-1-yl)benzyl)-1H-pyrazolo[3,4-d]pyrimidine;

(S)-6-(4-cyclopropyl-6-methoxypyrimidin-5-yl)-1-(1-(4-(1-methyl-4-(trifluoromethyl)-1H-imidazol-2-yl)phenyl)ethyl)-1H-pyrazolo[3,4-d]pyrimidine;

(R)-6-(4-cyclopropyl-6-methoxypyrimidin-5-yl)-1-(1-(4-(1-methyl-4-(trifluoromethyl)-1H-imidazol-2-yl)phenyl)ethyl)-1H-pyrazolo[3,4-d]pyrimidine;

6-(4-cyclobutyl-6-methoxypyrimidin-5-yl)-1-(4-(1-methyl-4-(trifluoromethyl)-1H-imidazol-2-yl)benzyl)-1H-pyrazolo[3,4-d]pyrimidine;

6-(4-cyclopropyl-6-isopropoxypyrimidin-5-yl)-1-(4-(1-methyl-4-(trifluoromethyl)-1H-imidazol-2-yl)benzyl)-1H-pyrazolo[3,4-d]pyrimidine;

6-(4-isopropyl-6-methylpyrimidin-5-yl)-1-(4-(5-methyl-3-(trifluoromethyl)-1H-pyrrazol-1-yl)benzyl)-1H-pyrazolo[3,4-d]pyrimidine;

6-(4-cyclopropyl-6-ethoxypyrimidin-5-yl)-1-(4-(1-methyl-4-(trifluoromethyl)-1H-imidazol-2-yl)benzyl)-1H-pyrazolo[3,4-d]pyrimidine;

N,N,6-trimethyl-5-(1-(4-(5-methyl-3-(trifluoromethyl)-1H-pyrazol-1-yl)benzyl)-1H-pyrazolo[3,4-d]pyrimidin-6-yl)pyrimidin-4-amine;

1-(4-(5-methyl-3-(trifluoromethyl)-1H-pyrazol-1-yl)benzyl)-6-(4-methyl-6-(methylthio)pyrimidin-5-yl)-1H-pyrazolo[3,4-d]pyrimidine;

6-(4-cyclopropyl-6-methoxypyrimidin-5-yl)-1-(4-(1-ethyl-4-(trifluoromethyl)-1H-imidazol-2-yl)benzyl)-1H-pyrazolo[3,4-d]pyrimidine;

6-(4,6-dimethoxypyrimidin-5-yl)-1-(4-(1-methyl-4-(trifluoromethyl)-1H-imidazol-2-yl)benzyl)-1H-pyrazolo[3,4-d]pyrimidine;

6-(4-(2-methoxyethoxy)-6-methylpyrimidin-5-yl)-1-(4-(5-methyl-3-(trifluoromethyl)-1H-pyrazol-1-yl)benzyl)-1H-pyrazolo[3,4-d]pyrimidine;

6-(4-cyclopropyl-6-methoxypyrimidin-5-yl)-1-(4-(1-(1-methylazetidin-3-yl)-4-(trifluoromethyl)-1H-imidazol-2-yl)benzyl)-1H-pyrazolo[3,4-d]pyrimidine;

6-(4-methoxy-6-methylpyrimidin-5-yl)-1-(4-(5-methyl-3-(trifluoromethyl)-1H-pyrazol-1-yl)benzyl)-1H-pyrazolo[3,4-d]pyrimidine;

3-(1-(4-(5-methyl-3-(trifluoromethyl)-1H-pyrazol-yl)benzyl)-H-pyrazolo[3,4-d]pyrimidin-6-yl)picolinonitrile;

6-(4-cyclopropyl-6-methoxypyrimidin-5-yl)-1-(4-(3-(difluoromethyl)-5-methyl-1H-pyrazol-1-yl)benzyl)-1H-pyrazolo[3,4-d]pyrimidine;

6-cyclopropyl-N-methyl-5-(1-(4-(1-methyl-4-(trifluoromethyl)-1H-imidazol-2-yl)benzyl)-1H-pyrazolo[3,4-d]pyrimidin-6-yl)pyrimidin-4-amine;

1-(4-(5-methoxy-3-(trifluoromethyl)-1H-pyrazol-1-yl)benzyl)-6-(4-methoxy-6-methylpyrimidin-5-yl)-1H-pyrazolo[3,4-d]pyrimidine;

6-(4-cyclopropyl-6-((tetrahydrofuran-3-yl)oxy)pyrimidin-5-yl)-1-(4-(1-methyl-4-(trifluoromethyl)-1H-imidazol-2-yl)benzyl)-1H-pyrazolo[3,4-d]pyrimidine;

6-(4-(benzyloxy)-6-cyclopropylpyrimidin-5-yl)-1-(4-(1-ethyl-4-(trifluoromethyl)-1H-imidazol-2-yl)benzyl)-1H-pyrazolo[3,4-d]pyrimidine;

6-(4-cyclopropyl-6-methoxypyrimidin-5-yl)-1-(4-(3-(difluoromethyl)-1-methyl-1H-1,2,4-triazol-5-yl)benzyl)-1H-pyrazolo[3,4-d]pyrimidine;

6-(4-(benzyloxy)-6-cyclopropylpyrimidin-5-yl)-1-(4-(1-methyl-4-(trifluoromethyl)-1H-imidazol-2-yl)benzyl)-1H-pyrazolo[3,4-d]pyrimidine;

6-(4-cyclopropyl-6-methoxypyrimidin-5-yl)-1-(4-(5-methoxy-1-methyl-1H-1,2,4-triazol-3-yl)benzyl)-1H-pyrazolo[3,4-d]pyrimidine;

2-(2-(4-((6-(4-cyclopropyl-6-methoxypyrimidin-5-yl)-1H-pyrazolo[3,4-d]pyrimidin-1-yl)methyl)phenyl)-4-(trifluoromethyl)-1H-imidazol-1-yl)-N,N-dimethylacetamide;

6-cyclopropyl-N,N-dimethyl-5-(1-(4-(1-methyl-4-(trifluoromethyl)-1H-imidazol-2-yl)benzyl)-1H-pyrazolo[3,4-d]pyrimidin-6-yl)pyrimidin-4-amine;

6-(4-cyclopropyl-6-methoxypyrimidin-5-yl)-1-(4-(5-(difluoromethyl)-1-methyl-1H-1,2,4-triazol-3-yl)benzyl)-1H-pyrazolo[3,4-d]pyrimidine;

6-(4-cyclopropyl-6-(pyrrolidin-1-yl)pyrimidin-5-yl)-1-(4-(1-methyl-4-(trifluoromethyl)-1H-imidazol-2-yl)benzyl)-1H-pyrazolo[3,4-d]pyrimidine;

6-(4-(azetidin-1-yl)-6-cyclopropylpyrimidin-5-yl)-1-(4-(1-methyl-4-(trifluoromethyl)-1H-imidazol-2-yl)benzyl)-1H-pyrazolo[3,4-d]pyrimidine; and 5-(4-cyclopropyl-6-methoxypyrimidin-5-yl)-3-(4-(1-methyl-4-(trifluoromethyl)-1H-imidazol-2-yl)benzyl)-3H-[1,2,3]triazolo[4,5-d]pyrimidine, or a pharmaceutically acceptable salt or solvate, e.g., hydrate, of any of the above.

In another embodiment, Compounds of the Disclosure are compounds selected from the group consisting of:

6-(4-cyclopropyl-6-methoxypyrimidin-5-yl)-1-(4-(1-ethyl-4-(trifluoromethyl)-1H-imidazol-2-yl)benzyl)-3-(methylsulfonyl)-1H-pyrazolo[3,4-d]pyrimidine;

6-(4-cyclopropyl-6-methoxypyrimidin-5-yl)-1-(4-(1-ethyl-4-(trifluoromethyl)-1H-imidazol-2-yl)benzyl)-3-(methylthio)-1H-pyrazolo[3,4-d]pyrimidine;

6-(4-cyclopropyl-6-methoxypyrimidin-5-yl)-1-(4-(1-ethyl-4-(trifluoromethyl)-1H-imidazol-2-yl)benzyl)-3-((4-methoxybenzyl)thio)-1H-pyrazolo[3,4-d]pyrimidine;

(S)-1-(1-(4-(5-bromo-1-methyl-4-(trifluoromethyl)-1H-imidazol-2-yl)phenyl)ethyl)-6-(4-cyclopropyl-6-methoxypyrimidin-5-yl)-3-methoxy-1H-pyrazolo[3,4-d]pyrimidine;

2-(4-cyclopropyl-6-methoxypyrimidin-5-yl)-7-(4-(1-isopropyl-4-(trifluoromethyl)-1H-imidazol-2-yl)benzyl)-7H-pyrrolo[2,3-d]pyrimidine;

2-(4-cyclopropyl-6-methoxypyrimidin-5-yl)-9-(4-(1-isopropyl-4-(trifluoromethyl)-1H-imidazol-2-yl)benzyl)-8-(methoxymethyl)-9H-purine;

2-(4-cyclopropyl-6-methoxypyrimidin-5-yl)-8-isopropyl-9-(4-(1-isopropyl-4-(trifluoromethyl)-1H-imidazol-2-yl)benzyl)-9H-purine;

3-cyclobutoxy-6-(4-cyclopropyl-6-methoxypyrimidin-5-yl)-1-(4-(1-ethyl-4-(trifluoromethyl)-1H-imidazol-2-yl)benzyl)-1H-pyrazolo[3,4-d]pyrimidine;

6-(4-cyclopropyl-6-methoxypyrimidin-5-yl)-1-(4-(1-isopropyl-2-(trifluoromethyl)-1H-imidazol-4-yl)benzyl)-3-methoxy-1H-pyrazolo[3,4-d]pyrimidine;

2-(4-cyclopropyl-6-methoxypyrimidin-5-yl)-8-ethyl-9-(4-(1-isopropyl-4-(trifluoromethyl)-1H-imidazol-2-yl)benzyl)-9H-purine;

(S)-6-(4-cyclopropyl-6-methoxypyrimidin-5-yl)-1-(1-(4-(1-(2-fluoroethyl)-4-(trifluoromethyl)-1H-imidazol-2-yl)phenyl)ethyl)-3-methoxy-1H-pyrazolo[3,4-d]pyrimidine;

3-(azetidin-1-yl)-6-(4-cyclopropyl-6-methoxypyrimidin-5-yl)-1-(4-(1-ethyl-4-(trifluoromethyl)-1H-imidazol-2-yl)benzyl)-1H-pyrazolo[3,4-d]pyrimidine;

1-(4-(5-bromo-1-ethyl-4-(trifluoromethyl)-1H-imidazol-2-yl)benzyl)-6-(4-cyclopropyl-6-methoxypyrimidin-5-yl)-3-methoxy-1H-pyrazolo[3,4-d]pyrimidine;

6-(4-cyclopropyl-6-methoxypyrimidin-5-yl)-1-(1-(4-(1-(2-fluoroethyl)-4-(trifluoromethyl)-1H-imidazol-2-yl)phenyl)ethyl)-3-methoxy-1H-pyrazolo[3,4-d]pyrimidine;

(S)-6-(4-cyclopropyl-6-methoxypyrimidin-5-yl)-1-(1-(4-(1-ethyl-4-(trifluoromethyl)-1H-imidazol-2-yl)phenyl)ethyl)-3-methoxy-1H-pyrazolo[3,4-d]pyrimidine;

(S)-6-(4-cyclopropyl-6-methoxypyrimidin-5-yl)-1-(1-(4-(1-isopropyl-4-(trifluoromethyl)-1H-imidazol-2-yl)phenyl)ethyl)-3-methoxy-1H-pyrazolo[3,4-d]pyrimidine;

6-(4-cyclopropyl-6-ethoxypyrimidin-5-yl)-3-ethoxy-1-(4-(1-ethyl-4-(trifluoromethyl)-1H-imidazol-2-yl)benzyl)-1H-pyrazolo[3,4-d]pyrimidine;

6-(4-cyclopropyl-6-methoxypyrimidin-5-yl)-3-ethoxy-1-(4-(1-ethyl-4-(trifluoromethyl)-1H-imidazol-2-yl)benzyl)-1H-pyrazolo[3,4-d]pyrimidine;

6-(4-cyclopropyl-6-methoxypyrimidin-5-yl)-1-(4-(1-ethyl-4-(trifluoromethyl)-1H-imidazol-2-yl)-3-fluorobenzyl)-3-methoxy-1H-pyrazolo[3,4-d]pyrimidine;

2-(4-cyclopropyl-6-methoxypyrimidin-5-yl)-9-(4-(1-isopropyl-4-(trifluoromethyl)-1H-imidazol-2-yl)benzyl)-9H-purine;

6-(4-cyclopropyl-6-methoxypyrimidin-5-yl)-1-(4-(1-ethyl-4-(trifluoromethyl)-1H-imidazol-2-yl)benzyl)-3-methoxy-1H-pyrazolo[3,4-d]pyrimidine;

2-(4-cyclopropyl-6-methoxypyrimidin-5-yl)-8-methyl-9-(4-(1-methyl-4-(trifluoromethyl)-1H-imidazol-2-yl)benzyl)-9H-purine;

8-cyclopropyl-2-(4-cyclopropyl-6-methoxypyrimidin-5-yl)-9-(4-(5-methyl-3-(trifluoromethyl)-1H-pyrazol-1-yl)benzyl)-9H-purine;

8-cyclobutyl-2-(4-cyclopropyl-6-methoxypyrimidin-5-yl)-9-(4-(5-methyl-3-(trifluoromethyl)-1H-pyrazol-1-yl)benzyl)-9H-purine;

2-(4-cyclopropyl-6-methoxypyrimidin-5-yl)-8-isopropyl-9-(4-(5-methyl-3-(trifluoromethyl)-1H-pyrazol-1-yl)benzyl)-9H-purine;

2-(4-cyclopropyl-6-methoxypyrimidin-5-yl)-8-ethyl-9-(4-(5-methyl-3-(trifluoromethyl)-1H-pyrazol-1-yl)benzyl)-9H-purine;

2-(4-cyclopropyl-6-methoxypyrimidin-5-yl)-7-(4-(1-methyl-4-(trifluoromethyl)-1H-imidazol-2-yl)benzyl)-7H-pyrrolo[2,3-d]pyrimidine;

2-(4-cyclopropyl-6-methoxypyrimidin-5-yl)-8-methyl-9-(4-(5-methyl-3-(trifluoromethyl)-1H-pyrazol-1-yl)benzyl)-9H-purine;

5-(4-cyclopropyl-6-methoxypyrimidin-5-yl)-3-(4-(1-methyl-4-(trifluoromethyl)-1H-imidazol-2-yl)benzyl)-3H-[1,2,3]triazolo[4,5-d]pyrimidine;

2-(4-methoxy-6-methylpyrimidin-5-yl)-9-(4-(5-methyl-3-(trifluoromethyl)-1H-pyrazol-1-yl)benzyl)-9H-purine;

2-(4-cyclopropyl-6-methoxypyrimidin-5-yl)-9-(4-(5-methyl-3-(trifluoromethyl)-1H-pyrazol-1-yl)benzyl)-9H-purine;

2-(4-cyclopropyl-6-methoxypyrimidin-5-yl)-9-(4-(1-methyl-4-(trifluoromethyl)-1H-imidazol-2-yl)benzyl)-9H-purine; and 2-(2-isopropylphenyl)-9-(4-(1-methyl-4-(trifluoromethyl)-1H-imidazol-2-yl)benzyl)-9H-purine.

Definitions

For the purpose of the present disclosure, the term "alkyl" as used by itself or as part of another group refers to a straight- or branched-chain aliphatic hydrocarbon containing one to twelve carbon atoms (i.e., $C_{1-12}$ alkyl) or the number of carbon atoms designated (i.e., a $C_1$ alkyl such as methyl, a $C_2$ alkyl such as ethyl, a $C_3$ alkyl such as propyl or isopropyl, etc.). The alkyl group can be suitably chosen from a straight chain $C_{1-10}$ alkyl group, a branched chain $C_{3-10}$ alkyl group, a straight chain $C_{1-6}$ alkyl group, a branched chain $C_{3-6}$ alkyl group, a straight chain $C_{1-4}$ alkyl group, a branched chain $C_{3-4}$ alkyl group, a straight or branched chain $C_{3-4}$ alkyl group. The alkyl group can be partially or completely deuterated, i.e., one or more hydrogen atoms of the alkyl group are replaced with deuterium atoms. Non-limiting exemplary $C_{1-10}$ alkyl groups include methyl (including —$CD_3$), ethyl, propyl, isopropyl, butyl, sec-butyl, tert-butyl, iso-butyl, 3-pentyl, hexyl, heptyl, octyl, nonyl, and decyl. Non-limiting exemplary $C_{1-4}$ alkyl groups include methyl, ethyl, propyl, isopropyl, butyl, sec-butyl, tert-butyl, and iso-butyl.

For the purpose of the present disclosure, the term "optionally substituted alkyl" as used by itself or as part of another group means that the alkyl as defined above is unsubstituted or substituted with one, two, or three substituents independently chosen from halo, nitro, cyano, hydroxy, amino, alkylamino, dialkylamino, haloalkyl, hydroxyalkyl, alkoxy, haloalkoxy, aryloxy, aralkyl, aralkyloxy, alkylthio, carboxamido, sulfonamido, alkylcarbonyl, arylcarbonyl, alkylsulfonyl, arylsulfonyl, carboxy, carboxyalkyl, alkoxyalkyl, (amino)alkyl, hydroxyalkylamino, (alkylamino)alkyl, (dialkylamino)alkyl, (cyano)alkyl, (carboxamido)alkyl, mercaptoalkyl, (heterocyclo)alkyl, or (heteroaryl)alkyl. The alkyl can be an optionally substituted $C_{1-4}$ alkyl. The optionally substituted alkyl can be substituted with two substituents, or one substituent. Non-limiting exemplary optionally substituted alkyl groups include —$CH_2CH_2NO_2$, —$CH_2CH_2CO_2H$, —$CH_2CH_2SO_2CH_3$, —$CH_2CH_2COPh$, and —$CH_2C_6H_{11}$.

For the purpose of the present disclosure, the term "alkylene" or "alkylenyl" refers to a divalent alkyl radical. Any of the above mentioned monovalent alkyl groups may be an alkylene by abstraction of a second hydrogen atom from the alkyl. The alkylene group may also be a $C_1$-$C_6$ alkylene or a $C_1$-$C_4$ alkylene. Non-limiting exemplary alkylene groups include, —$CH_2$—, —$CH(CH_3)$—, —$C(CH_3)_2$—, —$CH_2CH_2$—, —$CH_2CH(CH_3)$—, —$CH_2C(CH_3)_2$—, —$CH_2CH_2CH_2$—, and —$CH_2CH_2CH_2CH_2$—.

For the purpose of the present disclosure, the term "cycloalkyl" as used by itself or as part of another group refers to saturated and partially unsaturated (containing one or two double bonds) cyclic aliphatic hydrocarbons containing one to three rings having from three to twelve carbon atoms (i.e., $C_{3-12}$ cycloalkyl) or the number of carbons designated. The cycloalkyl group can have two rings, or one ring. The cycloalkyl group can be chosen from a $C_{3-8}$ cycloalkyl group and a $C_{3-6}$ cycloalkyl group. The cycloalkyl group can contain one or more carbon-to-carbon double bonds or one carbon-to-carbon double bond. Non-limiting exemplary cycloalkyl groups include cyclopropyl, cyclobutyl, cyclopentyl, cyclohexyl, cycloheptyl, cyclooctyl, norbornyl, decalin, adamantyl, cyclohexenyl, and spiro [3.3]heptane.

For the purpose of the present disclosure, the term "optionally substituted cycloalkyl" as used by itself or as part of another group means that the cycloalkyl as defined above is either unsubstituted or substituted with one, two, or three substituents independently chosen from halo, nitro, cyano, hydroxy, amino, alkylamino, dialkylamino, haloalkyl, hydroxyalkyl, alkoxy, haloalkoxy, aryloxy, aralkyl, aralkyloxy, alkylthio, carboxamido, sulfonamido, alkylcarbonyl, arylcarbonyl, alkylsulfonyl, arylsulfonyl, carboxy, carboxyalkyl, alkyl, optionally substituted cycloalkyl, alkenyl, alkynyl, optionally substituted aryl, optionally substituted heteroaryl, optionally substituted heterocyclo, alkoxyalkyl, (amino)alkyl, hydroxyalkylamino, (alkylamino)alkyl, (dialkylamino)alkyl, (cyano)alkyl, (carboxamido)alkyl, mercaptoalkyl, (heterocyclo)alkyl, or (heteroaryl)alkyl. The optionally substituted cycloalkyl can be substituted with two substituents or one substituent.

For the purpose of the present disclosure, the term "alkenyl" as used by itself or as part of another group refers to an alkyl group as defined above containing one, two or three carbon-to-carbon double bonds. The alkenyl group can be chosen from a $C_{2-6}$ alkenyl group and a $C_{2-4}$ alkenyl group. Non-limiting exemplary alkenyl groups include ethenyl, propenyl, isopropenyl, butenyl, sec-butenyl, pentenyl, and hexenyl.

For the purpose of the present disclosure, the term "optionally substituted alkenyl" as used herein by itself or as part of another group means the alkenyl as defined above is either unsubstituted or substituted with one, two or three substituents independently chosen from halo, nitro, cyano, hydroxy, amino, alkylamino, dialkylamino, haloalkyl, hydroxyalkyl, alkoxy, haloalkoxy, aryloxy, aralkyloxy, alkylthio, carboxamido, sulfonamido, alkylcarbonyl, arylcarbonyl, alkylsulfonyl, arylsulfonyl, carboxy, carboxyalkyl, optionally substituted cycloalkyl, optionally substituted aryl, optionally substituted heteroaryl, or optionally substituted heterocyclo.

For the purpose of the present disclosure, the term "alkynyl" as used by itself or as part of another group refers to an alkyl group as defined above containing one to three carbon-to-carbon triple bonds. The alkynyl can have one carbon-to-carbon triple bond. The alkynyl group can be chosen from a $C_{2-6}$ alkynyl group and a $C_{2-4}$ alkynyl group. Non-limiting exemplary alkynyl groups include ethynyl, propynyl, butynyl, 2-butynyl, pentynyl, and hexynyl groups.

For the purpose of the present disclosure, the term "optionally substituted alkynyl" as used herein by itself or as part of another group means the alkynyl as defined above is either unsubstituted or substituted with one, two or three substituents independently chosen from halo, nitro, cyano, hydroxy, amino, alkylamino, dialkylamino, haloalkyl, hydroxyalkyl, alkoxy, haloalkoxy, aryloxy, aralkyloxy, alkylthio, carboxamido, sulfonamido, alkylcarbonyl, arylcarbonyl, alkylsulfonyl, arylsulfonyl, carboxy, carboxyalkyl, cycloalkyl, aryl, heteroaryl, or heterocyclo.

For the purpose of the present disclosure, the term "haloalkyl" as used by itself or as part of another group refers to an alkyl group substituted by one or more fluorine, chlorine, bromine and/or iodine atoms. The alkyl group can be substituted by one, two, or three fluorine and/or chlorine atoms. The haloalkyl group can be chosen from a $C_{1-4}$ haloalkyl group. Non-limiting exemplary haloalkyl groups include fluoromethyl, difluoromethyl, trifluoromethyl, pentafluoroethyl, 1,1-difluoroethyl, 2,2-difluoroethyl, 2,2,2-trifluoroethyl, 3,3,3-trifluoropropyl, 4,4,4-trifluorobutyl, and trichloromethyl groups.

For the purpose of the present disclosure, the term "hydroxyalkyl" as used by itself or as part of another group refers to an alkyl group substituted with one or more, e.g., one, two, or three, hydroxy groups. The hydroxyalkyl group can be chosen from a monohydroxyalkyl group, i.e., substituted with one hydroxy group, a dihydroxyalkyl group, i.e., substituted with two hydroxy groups, and a $C_{1-4}$ hydroxyalkyl group. Non-limiting exemplary hydroxyalkyl groups include hydroxymethyl, hydroxyethyl, hydroxypropyl and hydroxybutyl groups, such as 1-hydroxyethyl, 2-hydroxyethyl, 1,2-dihydroxyethyl, 2-hydroxypropyl, 3-hydroxypropyl, 3-hydroxybutyl, 4-hydroxybutyl, 2-hydroxy-1-methylpropyl, and 1,3-dihydroxyprop-2-yl.

For the purpose of the present disclosure, the term "alkoxy" as used by itself or as part of another group refers to an optionally substituted alkyl, optionally substituted cycloalkyl, optionally substituted heterocyclo, optionally substituted alkenyl or optionally substituted alkynyl attached to a terminal oxygen atom. The alkoxy group can be chosen from a $C_{1-4}$ alkoxy group and a $C_{1-4}$ alkyl attached to a terminal oxygen atom, e.g., methoxy, ethoxy, and tert-butoxy.

For the purpose of the present disclosure, the term "alkylthio" as used by itself or as part of another group refers to a sulfur atom substituted by an optionally substituted alkyl group. The alkylthio group can be chosen from a $C_{1-4}$ alkylthio group. Non-limiting exemplary alkylthio groups include —$SCH_3$ (i.e., methylthio), and —$SCH_2CH_3$.

For the purpose of the present disclosure, the term "alkoxyalkyl" as used by itself or as part of another group refers to an alkyl group substituted with an alkoxy group. Non-limiting exemplary alkoxyalkyl groups include methoxymethyl, methoxyethyl, methoxypropyl, methoxybutyl, ethoxymethyl, ethoxyethyl, ethoxypropyl, ethoxybutyl, propoxymethyl, iso-propoxymethyl, propoxyethyl, propoxypropyl, butoxymethyl, tert-butoxymethyl, isobutoxymethyl, sec-butoxymethyl, and pentyloxymethyl.

For the purpose of the present disclosure, the term "halo" as used by itself or as part of another group refers to a halogen atom. Non-limiting exemplary halo groups include fluoro, chloro, bromo, and iodo.

For the purpose of the present disclosure, the term "haloalkoxy" as used by itself or as part of another group refers to a haloalkyl attached to a terminal oxygen atom. Non-limiting exemplary haloalkoxy groups include fluoromethoxy, difluoromethoxy, trifluoromethoxy, and 2,2,2-trifluoroethoxy.

For the purpose of the present disclosure, the term "heteroalkyl" as used by itself or part of another group refers to a stable straight or branched chain hydrocarbon radical containing 1 to 10 carbon atoms and at least two heteroatoms, which can be the same or different, selected from O, N, or S, wherein: 1) the nitrogen atom(s) and sulfur atom(s) can optionally be oxidized; and/or 2) the nitrogen atom(s) can optionally be quaternized. The heteroatoms can be placed at any interior position of the heteroalkyl group or at a position at which the heteroalkyl group is attached to the remainder of the molecule. The heteroalkyl group can contain two oxygen atoms, one oxygen and one nitrogen atom, or two nitrogen atoms. Non-limiting exemplary heteroalkyl groups include —$CH_2OCH$—$_2CH_2OCH_3$, —$OCH_2CH_2OCH_2CH_2OCH_3$, —$CH_2NHCH_2CH_2OCH_2$—, —$OCH_2CH_2NH_2$, —$NHCH_2CH_2N(H)CH_3$, —$NHCH_2CH_2OCH_3$ and —$OCH_2CH_2OCH_3$.

For the purpose of the present disclosure, the term "aryl" as used by itself or as part of another group refers to a monocyclic or bicyclic aromatic ring system having from six to fourteen carbon atoms (i.e., $C_{6-14}$ aryl). The aryl group can be chosen from a $C_{6-14}$ aryl group and a $C_{6-10}$ aryl group. Non-limiting exemplary aryl groups include phenyl (abbreviated as "Ph"), naphthyl, phenanthryl, anthracyl, indenyl, azulenyl, biphenyl, biphenylenyl, and fluorenyl groups. The aryl group can be chosen from phenyl or naphthyl. The aryl group can be phenyl.

For the purpose of the present disclosure, the term "optionally substituted aryl" as used herein by itself or as part of another group means that the aryl as defined above is either unsubstituted or substituted with one to five substituents independently selected from the group consisting of halo, nitro, cyano, hydroxy, amino, alkylamino, dialkylamino, haloalkyl, hydroxyalkyl, alkoxy, haloalkoxy, aryloxy, heteroaryloxy, aralkyl aralkyloxy, alkylthio, carboxamido, sulfonamido, alkylcarbonyl, arylcarbonyl, alkylsulfonyl, arylsulfonyl, carboxy, carboxyalkyl, alkyl, optionally substituted cycloalkyl, alkenyl, alkynyl, optionally substituted aryl, optionally substituted heteroaryl, optionally substituted heterocyclo, alkoxyalkyl, (amino)alkyl, hydroxyalkylamino, (alkylamino)alkyl, (dialkylamino)alkyl, (cyano)alkyl, (carboxamido)alkyl, mercaptoalkyl, (heterocyclo)alkyl, (cycloalkylamino)alkyl, ($C_{1-4}$ haloalkoxy)alkyl, (heteroaryl)alkyl. The optionally substituted aryl can be an optionally substituted phenyl. The optionally substituted phenyl can have four substituents, three substituents, two substituents, or one substituent. The optionally substituted phenyl can have one amino, alkylamino, dialkylamino, (amino)alkyl, (alkylamino)alkyl, or (dialkylamino)alkyl substituent. Non-limiting exemplary substituted aryl groups include 2-methylphenyl, 2-methoxyphenyl, 2-fluorophenyl, 2-chlorophenyl, 2-bromophenyl, 3-methylphenyl, 3-methoxyphenyl, 3-fluorophenyl, 3-chlorophenyl, 4-methylphenyl, 4-ethylphenyl, 4-methoxyphenyl, 4-fluorophenyl, 4-chlorophenyl, 2,6-di-fluorophenyl, 2,6-di-chlorophenyl, 2-methyl, 3-methoxyphenyl, 2-ethyl, 3-methoxyphenyl, 3,4-di-methoxyphenyl, 3,5-di-fluorophenyl 3,5-di-methylphenyl, 3,5-dimethoxy, 4-methylphenyl, 2-fluoro-3-chlorophenyl, 3-chloro-4-fluorophenyl, and 2-phenylpropan-2-amine. The term optionally substituted aryl is meant to include groups having fused optionally substituted cycloalkyl and fused optionally substituted heterocyclo rings. Examples include:

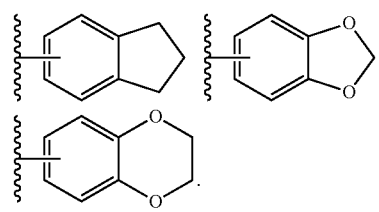

For the purpose of the present disclosure, the term "aryloxy" as used by itself or as part of another group refers to an optionally substituted aryl attached to a terminal oxygen atom. A non-limiting exemplary aryloxy group is PhO—.

For the purpose of the present disclosure, the term "heteroaryloxy" as used by itself or as part of another group refers to an optionally substituted heteroaryl attached to a terminal oxygen atom.

For the purpose of the present disclosure, the term "aralkyloxy" or "arylalkyloxy" as used by itself or as part of another group refers to an aralkyl group attached to a terminal oxygen atom. A non-limiting exemplary aralkyloxy group is $PhCH_2O—$.

For the purpose of the present disclosure, the term "heteroaryl" or "heteroaromatic" refers to monocyclic and bicyclic aromatic ring systems having 5 to 14 ring atoms (i.e., $C_{5-14}$ heteroaryl) and 1, 2, 3, or 4 heteroatoms independently chosen from oxygen, nitrogen or sulfur. The heteroaryl group can be chosen from a $C_{5-14}$ heteroaryl group and a $C_{3-6}$ heteroaryl group. The heteroaryl can have three heteroatoms, two heteroatoms, or one heteroatom. The heteroaryl can be a $C_5$ heteroaryl, or a $C_6$ heteroaryl. Non-limiting exemplary heteroaryl groups include thienyl, benzo[b]thienyl, naphtho[2,3-b]thienyl, thianthrenyl, furyl, benzofuryl, pyranyl, isobenzofuranyl, benzooxazonyl, chromenyl, xanthenyl, 2H-pyrrolyl, pyrrolyl, imidazolyl, pyrazolyl, pyridyl, pyrazinyl, pyrimidinyl, pyridazinyl, isoindolyl, 3H-indolyl, indolyl, indazolyl, purinyl, isoquinolyl, quinolyl, phthalazinyl, naphthyridinyl, cinnolinyl, quinazolinyl, pteridinyl, 4aH-carbazolyl, carbazolyl, β-carbolinyl, phenanthridinyl, acridinyl, phenanthrolinyl, phenazinyl, thiazolyl, isothiazolyl, phenothiazolyl, isoxazolyl, furazanyl, triazolyl, tetrazolyl, and phenoxazinyl. The heteroaryl can be chosen from thienyl (e.g., thien-2-yl and thien-3-yl), furyl (e.g., 2-furyl and 3-furyl), pyrrolyl (e.g., 1H-pyrrol-2-yl and 1H-pyrrol-3-yl), imidazolyl (e.g., 2H-imidazol-2-yl and 2H-imidazol-4-yl), pyrazolyl (e.g., 1H-pyrazol-3-yl, 1H-pyrazol-4-yl, and 1H-pyrazol-5-yl), pyridyl (e.g., pyridin-2-yl, pyridin-3-yl, and pyridin-4-yl), pyrimidinyl (e.g., pyrimidin-2-yl, pyrimidin-4-yl, and pyrimidin-5-yl), thiazolyl (e.g., thiazol-2-yl, thiazol-4-yl, and thiazol-5-yl), isothiazolyl (e.g., isothiazol-3-yl, isothiazol-4-yl, and isothiazol-5-yl), oxazolyl (e.g., oxazol-2-yl, oxazol-4-yl, and oxazol-5-yl) isoxazolyl (e.g., isoxazol-3-yl, isoxazol-4-yl, and isoxazol-5-yl), triazolyl (e.g., 1,2,4-triazolyl and 1,2,3-triazolyl). The term "heteroaryl" is also meant to include possible N-oxides. Exemplary N-oxides include pyridyl N-oxide.

For the purpose of the present disclosure, the term "optionally substituted heteroaryl" as used by itself or as part of another group means that the heteroaryl as defined above is either unsubstituted or substituted with one to four substituents, e.g., one or two substituents, independently chosen from halo, nitro, cyano, hydroxy, amino, alkylamino, dialkylamino, haloalkyl, hydroxyalkyl, alkoxy, haloalkoxy, aralkyl aryloxy, aralkyloxy, alkylthio, carboxamido, sulfonamido, alkylcarbonyl, arylcarbonyl, alkylsulfonyl, arylsulfonyl, carboxy, carboxyalkyl, alkyl, optionally substituted cycloalkyl, alkenyl, alkynyl, optionally substituted aryl, optionally substituted heteroaryl, optionally substituted heterocyclo, alkoxyalkyl, (amino)alkyl, hydroxyalkylamino, (alkylamino)alkyl, (dialkylamino)alkyl, (cyano)alkyl, (carboxamido)alkyl, mercaptoalkyl, (heterocyclo)alkyl, (heteroaryl)alkyl, $—N(R^{33})(R^{34})$, or $—N(H)C(=O)—R^{35}$, wherein $R^{33}$ is hydrogen or $C_{1-4}$ alkyl; $R^{34}$ is alkoxyalkyl, (heterocyclo)alkyl, (amino)alkyl, (alkylamino)alkyl, or (dialkylamino)alkyl; and $R^{35}$ is alkyl, optionally substituted aryl, or optionally substituted heteroaryl. The optionally substituted heteroaryl can have one substituent. The substituent can be amino, alkylamino, dialkylamino, (amino)alkyl, hydroxyalkylamino, (alkylamino)alkyl, (dialkylamino)alkyl, (heterocyclo)alkyl, $—N(R^{33})(R^{34})$, or $—N(H)C(=O)—R^{35}$. The optionally substituted heteroaryl can be an optionally substituted pyridyl, i.e., 2-, 3-, or 4-pyridyl. Any available carbon or nitrogen atom can be substituted.

For the purpose of the present disclosure, the term "heterocycle" or "heterocyclo" as used by itself or as part of another group refers to saturated and partially unsaturated (e.g., containing one or two double bonds) cyclic groups containing one, two, or three rings having from three to fourteen ring members (i.e., a 3- to 14-membered heterocyclo) and at least one heteroatom. The heterocyclo group can be chosen from a $C_{3-14}$ heterocyclo group and a $C_{3-8}$ heterocyclo group. Each heteroatom is independently selected from the group consisting of oxygen, sulfur, including sulfoxide and sulfone, and/or nitrogen atoms, which can be quaternized. The term "heterocyclo" is meant to include cyclic ureido groups such as imidazolidinyl-2-one, cyclic amide groups such as β-lactam, γ-lactam, δ-lactam and ε-lactam, and cyclic carbamate groups such as oxazolidinyl-2-one. The term "heterocyclo" is also meant to include groups having fused optionally substituted aryl groups, e.g., indolinyl, indolinyl-2-one, benzo[d]oxazolyl-2(3H)-one. The term "heterocyclo" is also meant to include groups having fused optionally substituted heteroaryl groups, e.g., 5,6,7,8-tetrahydroimidazo[1,5-a]pyrazine. The heterocyclo group can be chosen from a 4-, 5-, 6-, 7- or 8-membered cyclic group containing one ring and one or two oxygen and/or nitrogen atoms, a 5- or 6-membered cyclic group containing one ring and one or two nitrogen atoms, an 8-, 9-, 10-, 11-, or 12-membered cyclic group containing two rings and one or two nitrogen atoms. The heterocyclo can be optionally linked to the rest of the molecule through a carbon or nitrogen atom. Non-limiting exemplary heterocyclo groups include 2-oxopyrrolidin-3-yl, 2-imidazolidinone, piperidinyl, morpholinyl, piperazinyl, pyrrolidinyl, azetidinyl, 8-azabicyclo[3.2.1]octane (nortropane), 6-azaspiro[2.5]octane, 6-azaspiro[3.4]octane, indolinyl, indolinyl-2-one, 1,3-dihydro-2H-benzo[d]imidazol-2-one.

For the purpose of the present disclosure, the term "optionally substituted heterocyclo" as used herein by itself or part of another group means the heterocyclo as defined above is either unsubstituted or substituted with one to four substituents independently selected from halo, nitro, cyano, hydroxy, amino, alkylamino, dialkylamino, haloalkyl, hydroxyalkyl, alkoxy, haloalkoxy, aryloxy, aralkyl aralkyloxy, alkylthio, carboxamido, sulfonamido, alkylcarbonyl, arylcarbonyl, alkylsulfonyl, arylsulfonyl, carboxy, carboxyalkyl, alkyl, cycloalkyl, alkenyl, alkynyl, aryl, heteroaryl, heterocyclo, alkoxyalkyl, (amino)alkyl, hydroxyalkylamino, (alkylamino)alkyl, (dialkylamino)alkyl, (cyano)alkyl, (carboxamido)alkyl, mercaptoalkyl, (heterocyclo)alkyl, and (heteroaryl)alkyl. Substitution may occur on any available carbon or nitrogen atom, and may form a spirocycle.

For the purpose of the present disclosure, the term "amino" as used by itself or as part of another group refers to $—NH_2$.

For the purpose of the present disclosure, the term "alkylamino" as used by itself or as part of another group refers to $—NHR^{36}$, wherein $R^{36}$ is $C_{1-6}$ alkyl. $R^{36}$ can be $C_{1-4}$ alkyl. Non-limiting exemplary alkylamino groups include $—N(H)CH_3$ and $—N(H)CH_2CH_3$.

For the purpose of the present disclosure, the term "dialkylamino" as used by itself or as part of another group refers to $—NR^{37a}R^{37b}$, wherein $R^{37a}$ and $R^{37b}$ are each independently $C_{1-6}$ alkyl. $R^{37a}$ and $R^{37b}$ can each independently be $C_{1-4}$ alkyl. Non-limiting exemplary dialkylamino groups include $—N(CH_3)_2$ and $—N(CH_3)CH_2CH(CH_3)_2$.

For the purpose of the present disclosure, the term "hydroxyalkylamino" as used by itself or as part of another group refers to —NHR$^{38}$, wherein R$^{38}$ is hydroxyalkyl.

For the purpose of the present disclosure, the term "cycloalkylamino" as used by itself or as part of another group refers to —NR$^{39a}$R$^{39b}$, wherein R$^{39a}$ is optionally substituted cycloalkyl and R$^{39b}$ is hydrogen or C$_{1-4}$ alkyl.

For the purpose of the present disclosure, the term "aralkylamino" as used by itself or as part of another group refers to —NR$^{40a}$R$^{40b}$, wherein R$^{40a}$ is aralkyl and R$^{40b}$ is hydrogen or C$_{1-4}$ alkyl. Non-limiting exemplary aralkylamino groups include —N(H)CH$_2$Ph and —N(CH$_3$)CH$_2$Ph.

For the purpose of the present disclosure, the term "(amino)alkyl" as used by itself or as part of another group refers to an alkyl group substituted with an amino group. The alkyl can be a C$_{1-4}$ alkyl. Non-limiting exemplary (amino)alkyl groups include —CH$_2$NH$_2$, —C(NH$_2$)(H)CH$_3$, —CH$_2$CH$_2$NH$_2$, —CH$_2$C(NH$_2$)(H)CH$_3$, —CH$_2$CH$_2$CH$_2$NH$_2$, —CH$_2$CH$_2$CH$_2$CH$_2$NH$_2$, and —CH$_2$C(CH$_3$)$_2$CH$_2$NH$_2$ For the purpose of the present disclosure, the term "(alkylamino)alkyl" as used by itself or as part of another group refers to an alkyl group substituted with an alkylamino group. The alkyl can be a C$_{1-4}$ alkyl. A non-limiting exemplary (alkylamino)alkyl group is —CH$_2$CH$_2$N(H)CH$_3$.

For the purpose of the present disclosure, the term "(dialkylamino)alkyl" as used by itself or as part of another group refers to an alkyl group substituted by a dialkylamino group. The alkyl can be a C$_{1-4}$ alkyl. Non-limiting exemplary (dialkylamino)alkyl groups are —CH$_2$CH$_2$N(CH$_3$)$_2$.

For the purpose of the present disclosure, the term "(cycloalkylamino)alkyl" as used by itself or as part of another group refers to an alkyl group substituted by a cycloalkylamino group. The alkyl can be a C$_{1-4}$ alkyl. Non-limiting exemplary (cycloalkylamino)alkyl groups include —CH$_2$N(H)cyclopropyl, —CH$_2$N(H)cyclobutyl, and —CH$_2$N(H)cyclohexyl.

For the purpose of the present disclosure, the term "(aralkylamino)alkyl" as used by itself or as part of another group refers to an alkyl group substituted with an aralkylamino group. The alkyl can be a C$_{1-4}$ alkyl. A non-limiting exemplary (aralkylamino)alkyl group is —CH$_2$CH$_2$CH$_2$N(H)CH$_2$Ph.

For the purpose of the present disclosure, the term "(cyano)alkyl" as used by itself or as part of another group refers to an alkyl group substituted with one or more cyano, e.g., —CN, groups. The alkyl can be a C$_{1-4}$ alkyl. Non-limiting exemplary (cyano)alkyl groups include —CH$_2$CH$_2$CN, —CH$_2$CH$_2$CH$_2$CN, and —CH$_2$CH$_2$CH$_2$CH$_2$CN.

For the purpose of the present disclosure, the term "(amino)(hydroxy)alkyl" as used by itself or as part of another group refers to an alkyl group substituted with one amino, alkylamino, or dialkylamino group and one hydroxy group. The alkyl is a C$_{1-6}$ alkyl or a C$_{1-4}$ alkyl.

For the purpose of the present disclosure, the term "(amino)(aryl)alkyl" as used by itself or as part of another group refers to an alkyl group substituted with one amino, alkylamino, or dialkylamino group and one optionally substituted aryl group. The alkyl can be a C$_{1-6}$ alkyl. The optionally substituted aryl group can be an optionally substituted phenyl.

For the purpose of the present disclosure, the term "(cycloalkyl)alkyl" as used by itself or as part of another group refers to an alkyl group substituted with one optionally substituted cycloalkyl group. The alkyl can be a C$_{1-4}$ alkyl or a C$_{3-6}$ cycloalkyl. The optionally substituted cycloalkyl group can be substituted with an amino or (amino)alkyl group.

For the purpose of the present disclosure, the term "(hydroxy)(aryl)alkyl" as used by itself or as part of another group refers to an alkyl group substituted with one hydroxy group and one optionally substituted aryl group. The alkyl can be a C$_{1-6}$ alkyl. The optionally substituted aryl group can be an optionally substituted phenyl. Non-limiting exemplary (hydroxy)(aryl)alkyl groups include:

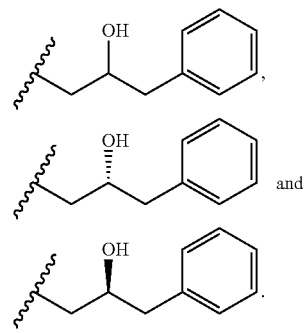

For the purpose of the present disclosure, the term "carboxamido" as used by itself or as part of another group refers to a radical of formula —C(=O)NR$^{41a}$R$^{41b}$, wherein R$^{41a}$ and R$^{41b}$ are each independently hydrogen, optionally substituted alkyl, optionally substituted aryl, or optionally substituted heteroaryl, or R$^{41a}$ and R$^{41b}$ taken together with the nitrogen to which they are attached from a 3- to 8-membered heterocyclo group. R$^{41a}$ and R$^{41b}$ can each independently be hydrogen or optionally substituted alkyl. Non-limiting exemplary carboxamido groups include —CONH$_2$, —CON(H)CH$_3$, —CON(CH$_3$)$_2$, and —CON(H)Ph.

For the purpose of the present disclosure, the term "(carboxamido)alkyl" as used by itself or as part of another group refers to an alkyl group substituted with a carboxamido group. Non-limiting exemplary (carboxamido)alkyl groups include —CH$_2$CONH$_2$, —C(H)CH$_3$—CONH$_2$, and —CH$_2$CON(H)CH$_3$.

For the purpose of the present disclosure, the term "sulfonamido" as used by itself or as part of another group refers to a radical of the formula —SO$_2$NR$^{42a}$R$^{42b}$, wherein R$^{42a}$ and R$^{42b}$ are each independently hydrogen, optionally substituted alkyl, or optionally substituted aryl, or R$^{42a}$ and R$^{42b}$ taken together with the nitrogen to which they are attached from a 3- to 8-membered heterocyclo group. Non-limiting exemplary sulfonamido groups include —SO$_2$NH$_2$, —SO$_2$N(H)CH$_3$, and —SO$_2$N(H)Ph.

For the purpose of the present disclosure, the term "alkylcarbonyl" as used by itself or as part of another group refers to a carbonyl group, i.e., —C(=O)—, substituted by an alkyl group. A non-limiting exemplary alkylcarbonyl group is —COCH$_3$.

For the purpose of the present disclosure, the term "arylcarbonyl" as used by itself or as part of another group refers to a carbonyl group, i.e., —C(=O)—, substituted by an optionally substituted aryl group. A non-limiting exemplary arylcarbonyl group is —COPh.

For the purpose of the present disclosure, the term "alkylsulfonyl" as used by itself or as part of another group refers to a sulfonyl group, i.e., —SO$_2$—, substituted by any of the above-mentioned optionally substituted alkyl groups.

Non-limiting exemplary alkylsulfonyl groups are —SO$_2$CH$_3$ (i.e., methylsulfonyl) and —SO$_2$CH$_2$CH$_3$ (i.e., ethylsulfonyl).

For the purpose of the present disclosure, the term "arylsulfonyl" as used by itself or as part of another group refers to a sulfonyl group, i.e., —SO$_2$—, substituted by any of the above-mentioned optionally substituted aryl groups. A non-limiting exemplary arylsulfonyl group is —SO$_2$Ph.

For the purpose of the present disclosure, the term "mercaptoalkyl" as used by itself or as part of another group refers to any of the above-mentioned alkyl groups substituted by a —SH group.

For the purpose of the present disclosure, the term "carboxy" as used by itself or as part of another group refers to a radical of the formula —COOH.

For the purpose of the present disclosure, the term "carboxyalkyl" as used by itself or as part of another group refers to any of the above-mentioned alkyl groups substituted with a —COOH. A non-limiting exemplary carboxyalkyl group is —CH$_2$CO$_2$H.

For the purpose of the present disclosure, the term "alkoxycarbonyl" as used by itself or as part of another group refers to a carbonyl group, i.e., —C(=O)—, substituted by an alkoxy group. Non-limiting exemplary alkoxycarbonyl groups are —CO$_2$Me and —CO$_2$Et.

For the purpose of the present disclosure, the term "aralkyl" or "arylalkyl" as used by itself or as part of another group refers to an alkyl group substituted with one, two, or three optionally substituted aryl groups. The aralkyl group can be a C$_{1-4}$ alkyl substituted with one optionally substituted aryl group. Non-limiting exemplary aralkyl groups include benzyl, phenethyl, —CHPh$_2$, —CH$_2$(4-OH-Ph), and —CH(4-F-Ph)$_2$.

For the purpose of the present disclosure, the term "(heterocyclo)alkyl" as used by itself or as part of another group refers to an alkyl group substituted with one, two, or three optionally substituted heterocyclo groups. The (heterocyclo)alkyl can be a C$_{1-4}$ alkyl substituted with one optionally substituted heterocyclo group. The heterocyclo can be linked to the alkyl group through a carbon or nitrogen atom. Non-limiting exemplary (heterocyclo)alkyl groups include:

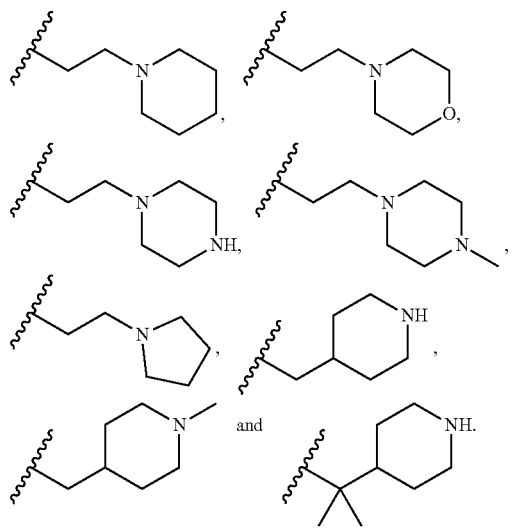

For the purpose of the present disclosure, the term "heteroaralkyl" or "(heteroaryl)alkyl" as used by itself or as part of another group refers to an alkyl group substituted with one, two, or three optionally substituted heteroaryl groups. The (heteroaryl)alkyl group can be a C$_{1-4}$ alkyl substituted with one optionally substituted heteroaryl group. Non-limiting exemplary (heteroaryl)alkyl groups include:

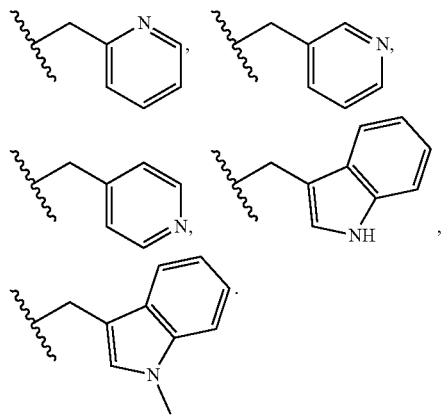

For the purpose of the present disclosure, the term "alkylcarbonylamino" as used by itself or as part of another group refers to an alkylcarbonyl group attached to an amino. A non-limiting exemplary alkylcarbonylamino group is —NHCOCH$_3$.

The present disclosure encompasses any of the Compounds of the Disclosure being isotopically-labelled (i.e., radiolabeled) by having one or more atoms replaced by an atom having a different atomic mass or mass number. Examples of isotopes that can be incorporated into the disclosed compounds include isotopes of hydrogen, carbon, nitrogen, oxygen, phosphorous, fluorine and chlorine, such as $^2$H (or deuterium (D)), $^3$H, $^{11}$C, $^{13}$C, $^{14}$C, $^{15}$N, $^{18}$O, $^{17}$O, $^{31}$P, $^{32}$P, $^{35}$S, $^{18}$F, and $^{36}$Cl, respectively, e.g., $^3$H, $^{11}$C, and $^{14}$C. The present disclosure also provides a composition wherein substantially all of the atoms at a position within the Compound of the Disclosure are replaced by an atom having a different atomic mass or mass number. The present disclosure also provides a composition wherein a portion of the atoms at a position within the Compound of the disclosure are replaced, i.e., the Compound of the Disclosure is enriched at a position with an atom having a different atomic mass or mass number. In one embodiment, the present disclosure provides a composition wherein a Compound of the Disclosure has from 1 to 8 hydrogens replaced with deuterium. Isotopically-labelled Compounds of the Disclosure can be prepared by methods known in the art.

Compounds of the Disclosure may contain one or more asymmetric centers and may thus give rise to enantiomers, diastereomers, and other stereoisomeric forms. The present disclosure is meant to encompass the use of all such possible forms, as well as their racemic and resolved forms and mixtures thereof. The individual enantiomers can be separated according to methods known in the art in view of the present disclosure. When the compounds described herein contain olefinic double bonds or other centers of geometric asymmetry, and unless specified otherwise, it is intended that they include both E and Z geometric isomers. All tautomers are intended to be encompassed by the present disclosure as well.

As used herein, the term "stereoisomers" is a general term for all isomers of individual molecules that differ only in the orientation of their atoms in space. It includes enantiomers and isomers of compounds with more than one chiral center that are not mirror images of one another (diastereomers).

The term "chiral center" or "asymmetric carbon atom" refers to a carbon atom to which four different groups are attached.

The terms "enantiomer" and "enantiomeric" refer to a molecule that cannot be superimposed on its mirror image and hence is optically active wherein the enantiomer rotates the plane of polarized light in one direction and its mirror image compound rotates the plane of polarized light in the opposite direction.

The term "racemic" refers to a mixture of equal parts of enantiomers and which mixture is optically inactive.

The term "absolute configuration" refers to the spatial arrangement of the atoms of a chiral molecular entity (or group) and its stereochemical description, e.g., R or S.

The stereochemical terms and conventions used in the specification are meant to be consistent with those described in Pure & Appl. Chem 68:2193 (1996), unless otherwise indicated.

The term "enantiomeric excess" or "ee" refers to a measure for how much of one enantiomer is present compared to the other. For a mixture of R and S enantiomers, the percent enantiomeric excess is defined as |R−S|*100, where R and S are the respective mole or weight fractions of enantiomers in a mixture such that R+S=1. With knowledge of the optical rotation of a chiral substance, the percent enantiomeric excess is defined as $([\alpha]_{obs}/[\alpha]_{max})*100$, where $[\alpha]_{obs}$ is the optical rotation of the mixture of enantiomers and $[\alpha]_{max}$ is the optical rotation of the pure enantiomer. Determination of enantiomeric excess is possible using a variety of analytical techniques, including NMR spectroscopy, chiral column chromatography or optical polarimetry.

The terms "enantiomerically pure" or "enantiopure" refer to a sample of a chiral substance all of whose molecules (within the limits of detection) have the same chirality sense.

The terms "enantiomerically enriched" or "enantioenriched" refer to a sample of a chiral substance whose enantiomeric ratio is greater than 50:50. Enantiomerically enriched compounds may be enantiomerically pure.

It is understood that embodiments of the invention described herein include "consisting" and/or "consisting essentially of" embodiments. As used herein, the singular form "a," "an," and "the" includes plural references unless indicated otherwise. Use of the term "or" herein is not meant to imply that alternatives are mutually exclusive.

In this application, the use of "or" means "and/or" unless expressly stated or understood by one skilled in the art. In the context of a multiple dependent claim, the use of "or" refers back to more than one preceding independent or dependent claim.

The term "about," as used herein, includes the recited number±10%. Thus, "about 10" means 9 to 11. As is understood by one skilled in the art, reference to "about" a value or parameter herein includes (and describes) instances that are directed to that value or parameter per se. For example, description referring to "about X" includes description of "X."

The present disclosure encompasses the preparation and use of salts of the Compounds of the Disclosure, including non-toxic pharmaceutically acceptable salts. Examples of pharmaceutically acceptable addition salts include inorganic and organic acid addition salts and basic salts. The pharmaceutically acceptable salts include, but are not limited to, metal salts such as sodium salt, potassium salt, cesium salt and the like; alkaline earth metals such as calcium salt, magnesium salt and the like; organic amine salts such as triethylamine salt, pyridine salt, picoline salt, ethanolamine salt, triethanolamine salt, dicyclohexylamine salt, N,N'-dibenzylethylenediamine salt and the like; inorganic acid salts such as hydrochloride, hydrobromide, phosphate, sulphate and the like; organic acid salts such as citrate, lactate, tartrate, maleate, fumarate, mandelate, acetate, dichloroacetate, trifluoroacetate, oxalate, formate and the like; sulfonates such as methanesulfonate, benzenesulfonate, p-toluenesulfonate and the like; and amino acid salts such as arginate, asparginate, glutamate and the like. The term "pharmaceutically acceptable salt" as used herein, refers to any salt, e.g., obtained by reaction with an acid or a base, of a Compound of the Disclosure that is physiologically tolerated in the target patient (e.g., a mammal, e.g., a human).

Acid addition salts can be formed by mixing a solution of the particular Compound of the Disclosure with a solution of a pharmaceutically acceptable non-toxic acid such as hydrochloric acid, fumaric acid, maleic acid, succinic acid, acetic acid, citric acid, tartaric acid, carbonic acid, phosphoric acid, oxalic acid, dichloroacetic acid, or the like. Basic salts can be formed by mixing a solution of the compound of the present disclosure with a solution of a pharmaceutically acceptable non-toxic base such as sodium hydroxide, potassium hydroxide, choline hydroxide, sodium carbonate and the like.

The present disclosure encompasses the preparation and use of solvates of Compounds of the Disclosure. Solvates typically do not significantly alter the physiological activity or toxicity of the compounds, and as such may function as pharmacological equivalents. The term "solvate" as used herein is a combination, physical association and/or solvation of a compound of the present disclosure with a solvent molecule such as, e.g. a disolvate, monosolvate or hemisolvate, where the ratio of solvent molecule to compound of the present disclosure is about 2:1, about 1:1 or about 1:2, respectively. This physical association involves varying degrees of ionic and covalent bonding, including hydrogen bonding. In certain instances, the solvate can be isolated, such as when one or more solvent molecules are incorporated into the crystal lattice of a crystalline solid. Thus, "solvate" encompasses both solution-phase and isolatable solvates. Compounds of the Disclosure can be present as solvated forms with a pharmaceutically acceptable solvent, such as water, methanol, ethanol, and the like, and it is intended that the disclosure includes both solvated and unsolvated forms of Compounds of the Disclosure. One type of solvate is a hydrate. A "hydrate" relates to a particular subgroup of solvates where the solvent molecule is water. Solvates typically can function as pharmacological equivalents. Preparation of solvates is known in the art. See, for example, M. Caira et al, *J. Pharmaceut. Sci.*, 93(3):601-611 (2004), which describes the preparation of solvates of fluconazole with ethyl acetate and with water. Similar preparation of solvates, hemisolvates, hydrates, and the like are described by E. C. van Tonder et al., *AAPS Pharm. Sci. Tech.*, 5(1):Article 12 (2004), and A. L. Bingham et al., *Chem. Commun.* 603-604 (2001). A typical, non-limiting, process of preparing a solvate would involve dissolving a Compound of the Disclosure in a desired solvent (organic, water, or a mixture thereof) at temperatures above 20° C. to about 25° C., then cooling the solution at a rate sufficient to form crystals, and isolating the crystals by known methods, e.g., filtration. Analytical techniques such as infrared spectroscopy can be used to confirm the presence of the solvent in a crystal of the solvate.

Since Compounds of the Disclosure are inhibitors of USP1 proteins, the present disclosure provides a method for inhibiting a USP1 protein comprising contacting a USP1 protein or a composition comprising a USP1 protein with one or more Compounds of the Disclosure.

Since Compounds of the Disclosure are inhibitors of USP1 proteins, a number of diseases, conditions, or disorders mediated by USP1 proteins can be treated by employing these compounds. The present disclosure is thus directed generally to a method for treating a disease, condition, or disorder responsive to the inhibition of USP1 proteins in an animal suffering from, or at risk of suffering from, the disorder, the method comprising administering to the animal an effective amount of one or more Compounds of the Disclosure.

The present disclosure is further directed to a method of inhibiting USP1 proteins in an animal in need thereof, the method comprising administering to the animal a therapeutically effective amount of at least one Compound of the Disclosure.

As used herein, "treatment" is an approach for obtaining beneficial or desired clinical results. "Treatment" as used herein, covers any administration or application of a therapeutic for disease in a mammal, including a human. For purposes of this disclosure, beneficial or desired clinical results include, but are not limited to, any one or more of: alleviation of one or more symptoms, diminishment of extent of disease, preventing or delaying spread (for example, metastasis) of disease, preventing or delaying recurrence of disease, delay or slowing of disease progression, amelioration of the disease state, inhibiting the disease or progression of the disease, inhibiting or slowing the disease or its progression, arresting its development, and remission (whether partial or total). Also encompassed by "treatment" is a reduction of pathological consequence of a proliferative disease. The methods provided herein contemplate any one or more of these aspects of treatment. In-line with the above, the term treatment does not require one-hundred percent removal of all aspects of the disorder.

In the context of cancer, the term "treating" includes, but is not limited to, inhibiting growth of cancer cells, inhibiting replication of cancer cells, lessening of overall tumor burden, and delaying, halting, or slowing tumor growth, progression, or metastasis.

As used herein, "delaying" means to defer, hinder, slow, retard, stabilize, suppress and/or postpone development or progression of the disease (such as cancer). This delay can be of varying lengths of time, depending on the history of the disease and/or individual being treated.

A "therapeutically effective amount" of a substance can vary according to factors such as the disease state, age, sex, and weight of the individual, and the ability of the substance to elicit a desired response in the individual. A therapeutically effective amount is also one in which any toxic or detrimental effects of the substance are outweighed by the therapeutically beneficial effects. A therapeutically effective amount can be delivered in one or more administrations. A therapeutically effective amount refers to an amount effective, at dosages and for periods of time necessary, to achieve the desired therapeutic effect.

The terms "administer," "administering," "administration," and the like refer to methods that can be used to enable delivery of the therapeutic agent to the desired site of biological action. Administration techniques that can be employed with the agents and methods described herein are found in e.g., Goodman and Gilman, *The Pharmacological Basis of Therapeutics*, current ed.; Pergamon; and Remington's, *Pharmaceutical Sciences* (current edition), Mack Publishing Co., Easton, Pa.

The terms "pharmaceutical formulation" and "pharmaceutical composition" refer to a preparation which is in such form as to permit the biological activity of the active ingredient(s) to be effective, and which contains no additional components which are unacceptably toxic to a subject to which the formulation would be administered. Such formulations may be sterile.

A "pharmaceutically acceptable carrier" refers to a non-toxic solid, semisolid, or liquid filler, diluent, encapsulating material, formulation auxiliary, or carrier conventional in the art for use with a therapeutic agent that together comprise a "pharmaceutical composition" for administration to a subject. A pharmaceutically acceptable carrier is non-toxic to recipients at the dosages and concentrations employed and is compatible with other ingredients of the formulation. The pharmaceutically acceptable carrier is appropriate for the formulation employed.

A "sterile" formulation is aseptic or essentially free from living microorganisms and their spores.

The term "container" means any receptacle and closure therefore suitable for storing, shipping, dispensing, and/or handling a pharmaceutical product.

The term "insert" or "package insert" means information accompanying a pharmaceutical product that provides a description of how to administer the product, along with the safety and efficacy data required to allow the physician, pharmacist, and patient to make an informed decision regarding use of the product. The package insert generally is regarded as the "label" for a pharmaceutical product.

The term "disease" or "condition" or "disorder" as used herein refers to a condition where treatment is needed and/or desired and denotes disturbances and/or anomalies that as a rule are regarded as being pathological conditions or functions, and that can manifest themselves in the form of particular signs, symptoms, and/or malfunctions. As demonstrated below, Compounds of the Disclosure inhibit USP1 proteins and can be used in treating diseases and conditions such as proliferative diseases, wherein inhibition of USP1 proteins provides a benefit.

The terms "polypeptide" and "protein" are used interchangeably to refer to a polymer of amino acid residues and are not limited to a minimum length. Such polymers of amino acid residues may contain natural or non-natural amino acid residues, and include, but are not limited to, peptides, oligopeptides, dimers, trimers, and multimers of amino acid residues. Both full-length proteins and fragments thereof are encompassed by the definition. The terms also include post-expression modifications of the polypeptide, for example, glycosylation, sialylation, acetylation, phosphorylation, and the like. Furthermore, for purposes of the present disclosure, a "polypeptide" refers to a protein which includes modifications, such as deletions, additions, and substitutions (generally conservative in nature), to the native sequence, as long as the protein maintains the desired activity. These modifications may be deliberate, as through site-directed mutagenesis, or may be accidental, such as through mutations of hosts which produce the proteins or errors due to PCR amplification.

"USP1" and "ubiquitin-specific-processing protease 1" as used herein refer to any native polypeptide or USP1-encoding polynucleotide. The term "USP1" encompasses "full-length," unprocessed USP1 polypeptide as well as any forms of USP1 that result from processing within the cell (e.g., removal of the signal peptide). The term also encompasses naturally occurring variants of USP1, e.g., those encoded by splice variants and allelic variants. The USP1 polypeptides described herein can be isolated from a variety of sources, such as from human tissue types or from another source, or prepared by recombinant or synthetic methods. Human USP1 sequences are known and include, for example, the sequences publicly available as UniProt No. 094782 (including isoforms). As used herein, the term "human USP1 protein" refers to USP1 protein comprising the amino acid sequence as set forth in SEQ ID NO: 1 in U.S. provisional patent application No. 62/857,986 filed Jun. 6, 2019.

USP1 is a deubiquitinating enzyme that acts as part of a complex with UAF1. USP1's "deubiquitinase activity" includes its ability to deubiquitinate as part of the USP1-UAF1 complex.

The term "specifically binds" to a protein or domain of a protein is a term that is well understood in the art, and methods to determine such specific binding are also well known in the art. A molecule is said to exhibit "specific binding" or "preferential binding" if it reacts or associates more frequently, more rapidly, with greater duration and/or with greater affinity with a particular protein or domain of a protein than it does with alternative proteins or domains. It should be understood that a molecule that specifically or preferentially binds to a first protein or domain may or may not specifically or preferentially bind to a second protein or domain. As such, "specific binding" or "preferential binding" does not necessarily require (although it can include) exclusive binding. Generally, but not necessarily, reference to binding means preferential binding. For example, a USP1 inhibitor that specifically binds to USP1, UAF1, and/or the USP1-UAF1 complex may not bind to other deubiquitinases, other USP proteins, or other UAF1 complexes (e.g., USP46-UAF1) or may bind to other deubiquitinases, other USP proteins, or other UAF1 complexes (e.g., USP46-UAF1) with a reduced affinity as compared to binding to USP1.

The terms "reduction" or "reduce" or "inhibition" or "inhibit" refer to a decrease or cessation of any phenotypic characteristic or to the decrease or cessation in the incidence, degree, or likelihood of that characteristic. To "reduce" or "inhibit" is to decrease, reduce or arrest an activity, function, and/or amount as compared to a reference. In some embodiments, by "reduce" or "inhibit" is meant the ability to cause an overall decrease of 20% or greater. In some embodiments, by "reduce" or "inhibit" is meant the ability to cause an overall decrease of 50% or greater. In some embodiments, by "reduce" or "inhibit" is meant the ability to cause an overall decrease of 75%, 85%, 90%, 95%, or greater. In some embodiments, the amount noted above is inhibited or decreased over a period of time, relative to a control over the same period of time.

In some embodiments inhibiting USP1 proteins is the inhibition of one or more activities or functions of USP1 proteins. It should be appreciated that the activity or function of the one or more USP1 proteins may be inhibited in vitro or in vivo. Non-limiting examples of activities and functions of USP1 include deubiquitinase activity, and formation of a complex with UAF1 and are described herein. Examplary levels of inhibition of the activity of one or more USP1 proteins include at least 10% inhibiton, at least 20% inhibition, at least 30% inhibition, at least 40% inhibition, at least 50% inhibition, at least 60% inhibition, at least 70% inhibition, at least 80% inhibition, at least 90% inhibition, and up to 100% inhibition.

The terms "individual" or "subject" are used interchangeably herein to refer to an animal; for example, a mammal, such as a human. In some instances, methods of treating mammals, including, but not limited to, humans, rodents, simians, felines, canines, equines, bovines, porcines, ovines, caprines, mammalian laboratory animals, mammalian farm animals, mammalian sport animals, and mammalian pets, are provided. In some examples, an "individual" or "subject" refers to an individual or subject in need of treatment for a disease or disorder. In some instances, the subject to receive the treatment can be a patient, designating the fact that the subject has been identified as having a disorder of relevance to the treatment, or being at particular risk of contracting the disorder.

As used herein, the terms "cancer" and "tumor" refer to or describe the physiological condition in mammals in which a population of cells are characterized by unregulated cell growth. The terms encompass solid and hematological/lymphatic cancers. Examples of cancer include but are not limited to, DNA damage repair pathway deficient cancers. Additional examples of cancer include, but are not limited to, ovarian cancer, breast cancer (including triple negative breast cancer), non-small cell lung cancer (NSCLC), and osteosarcoma. The cancer can be BRCA1 or BRCA2 wild-type. The cancer can also be BRCA1 or BRCA2 mutant. The cancer can further be a PARP inhibitor resistant or refractory cancer, or a PARP inhibitor resistant or refractory BRCA1 or BRCA2-mutant cancer.

As used herein, the term "loss of function" mutation refers to a mutation that that results in the absence of a gene, decreased expression of a gene, or the production of a gene product (e.g. protein) having decreased activity or no activity. Loss of function mutations include for example, missense mutations, nucleotide insertions, nucleotide deletions, and gene deletions. Loss of function mutations also include dominant negative mutations. Thus, cancer cells with a loss of function mutation in a gene encoding p53 include cancer cells that contain missense mutations in a gene encoding p53 as well as cancer cells that lack a gene encoding p53.

USP1 Inhibitors

In various embodiments, the Compounds of the Disclosure are USP1 inhibitors that reduce the level of USP1 protein and/or inhibit or reduce at least one biological activity of USP1 protein.

In some embodiments, the Compounds of the Disclosure specifically bind to USP1 protein. In some embodiments, the Compounds of the Disclosure specifically bind to USP1 protein in a USP1-UAF1 complex. In some embodiments, the Compounds of the Disclosure specifically bind to USP1 mRNA. In some embodiments, the Compounds of the Disclosure specifically bind to USP1 protein (alone or in a USP1-UAF1 complex) or USP1 mRNA. In some embodiments, the Compounds of the Disclosure specifically bind to UAF1 (alone or in a USP1-UAF1 complex) and inhibit or reduces formation or activity of the USP1-UAF1 complex.

In some embodiments, the Compounds of the Disclosure decrease the formation of the USP1-UAF1 complex. In some embodiments, the Compounds of the Disclosure decrease the activity of the USP1-UAF1 complex. In some embodiments, the Compounds of the Disclosure decrease the deubiquitinase activity of USP1. In some embodiments, the Compounds of the Disclosure increase mono-ubiquitinated PCNA. In some embodiments, the Compounds of the Disclosure increase mono-ubiquitinated FANCD2. In some embodiments, the Compounds of the Disclosure increase mono-ubiquitinated FANCI.

In some embodiments, the Compounds of the Disclosure do not bind to other deubiquitinases, other USP proteins, or other UAF1 complexes (e.g., USP46-UAF1) or bind deubiquitinases, other USP proteins, or other UAF1 complexes (e.g., USP46-UAF1) with at least 5-fold, at least 10-fold, at least 20-fold, or at least 100-fold reduced affinity compared to the affinity for USP1 (i.e., the $K_D$ of the USP1 inhibitor for other deubiquitinases, other USP proteins, or other UAF1 complexes (e.g., USP46-UAF1) is at least 5-fold, at least 10-fold, at least 20-fold, or at least 100-fold higher than the $K_D$ for USP1).

In some embodiments, the Compounds of the Disclosure inhibit USP1 deubiquitinase activity with an IC50 of less than about 50 nM, between about 50 nM and about 200 nM, between about 200 nM and about 2 pM, or greater than 2 pM, e.g., as measured using the assay disclosed in US Patent Application Publication No. 2017/0145012 or IC50 of 50 nM to 1000 nM, e.g., as measured using the assay disclosed in Liang et al., *Nat Chem Biol* 10: 289-304 (2014). In some embodiments, the Compounds of the Disclosure inhibit USP1 deubiquitinase activity with an IC50 as measured using the assay disclosed in Chen, et al., *Chem Biol.*, 18(11): 1390-1400 (2011). In some embodiments, the Compounds of the Disclosure do not inhibit the activity of other deubiquitinases, other USP proteins, or other UAF1 complexes (e.g., USP46-UAF1) or inhibit the activity of other deubiquitinases, other USP proteins, or other UAF1 complexes (e.g., USP46-UAF1) with at least 5-fold, at least 10-fold, at least 20-fold, or at least 100-fold higher IC50 compared to the IC50 for inhibition of USP1 deubiquitinase activity.

In some embodiments, the Compounds of the Disclosure bind to a USP1 protein with an affinity in the range of 1 pM to 100 µM, or 1 pM to 1 µM, or 1 pM to 500 nM, or 1 pM to 100 nM. In some embodiment, the Compounds of the Disclosure bind to a USP1 protein with an affinity of about 1 pM to about 100 µM, about 1 nM to about 100 µM, about 1 µM to about 100 µM, about 1 µM to about 50 µM, about 1 µM to about 40 µM, about 1 µM to about 30 µM, about 1 µM to about 20 µM, or about 1 µM to about 10 µM, about 1 µM, about 5 µM, about 10 µM, about 15 µM, about 20 µM, about 25 µM, about 30 µM, about 35 µM, about 40 µM, about 45 µM, about 50 µM, about 60 µM, about 70 µM, about 80 µM, about 90 µM, or about 100 µM. In some embodiment, the Compounds of the Disclosure bind to a USP1 protein with an affinity of about 100 nM to about 1 µM, about 100 nM to about 900 nM, about 100 nM to about 800 nM, about 100 nM to about 700 nM, about 100 nM to about 600 nM, about 100 nM to about 500 nM, about 100 nM to about 400 nM, about 100 nM to about 300 nM, about 100 nM to about 200 nM, about 200 nM to about 1 µM, about 300 nM to about 1 µM, about 400 nM to about 1 µM, about 500 nM to about 1 µM, about 600 nM to about 1 µM, about 700 nM to about 1 µM, about 800 nM to about 1 µM, about 900 nM to about 1 µM, about 100 nM, about 200 nM, about 300 nM, about 400 nM, about 500 nM, about 600 nM, about 700 nM, about 800 nM, or about 900 nM. In some embodiment, the Compounds of the Disclosure bind to a USP1 protein with an affinity of about 1 nM to about 100 nM, 1 nM to about 90 nM, 1 nM to about 80 nM, 1 nM to about 70 nM, 1 nM to about 60 nM, 1 nM to about 50 nM, 1 nM to about 40 nM, 1 nM to about 30 nM, 1 nM to about 20 nM, 1 nM to about 10 nM, about 10 nM to about 100 nM, about 20 nM to about 100 nM, about 30 nM to about 100 nM, about 40 nM to about 100 nM, about 50 nM to about 100 nM, about 60 nM to about 100 nM, about 70 nM to about 100 nM, about 80 nM to about 100 nM, about 90 nM to about 100 nM, about 1 nM, about 2 nM, about 3 nM, about 4 nM, about 5 nM, about 6 nM, about 7 nM, about 8 nM, about 9 nM, about 10 nM, about 20 nM, about 30 nM, about 40 nM, about 50 nM, about 60 nM, about 70 nM, about 80 nM, about 90 nM, or about 100 nM. In some embodiment, the Compounds of the Disclosure bind to a USP1 protein with an affinity of less than 1 µM, less than 500 nM, less than 100 nM, less than 10 nM, or less than 1 nM. In some embodiments, the Compounds of the Disclosure bind to a USP1 protein with an affinity of less than 1 nM.

In some embodiments, the Compounds of the Disclosure inhibit USP1 activity with an $IC_{50}$ of 1 pM to 100 µM, or 1 pM to 1 µM, or 1 pM to 500 nM, or 1 pM to 100 nM. In some embodiments, the Compounds of the Disclosure inhibit USP1 activity with an $IC_{50}$ of about 1 pM to about 100 µM, about 1 nM to about 100 µM, about 1 µM to about 100 µM, about 1 µM to about 50 µM, about 1 µM to about 40 µM, about 1 µM to about 30 µM, about 1 µM to about 20 µM, or about 1 µM to about 10 µM, about 1 µM, about 5 µM, about 10 µM, about 15 µM, about 20 µM, about 25 µM, about 30 µM, about 35 µM, about 40 µM, about 45 µM, about 50 µM, about 60 µM, about 70 µM, about 80 µM, about 90 µM, or about 100 µM. In some embodiment, the Compounds of the Disclosure inhibit USP1 activity with an $IC_{50}$ of about 100 nM to about 1 µM, about 100 nM to about 900 nM, about 100 nM to about 800 nM, about 100 nM to about 700 nM, about 100 nM to about 600 nM, about 100 nM to about 500 nM, about 100 nM to about 400 nM, about 100 nM to about 300 nM, about 100 nM to about 200 nM, about 200 nM to about 1 µM, about 300 nM to about 1 µM, about 400 nM to about 1 µM, about 500 nM to about 1 µM, about 600 nM to about 1 µM, about 700 nM to about 1 µM, about 800 nM to about 1 µM, about 900 nM to about 1 µM, about 100 nM, about 200 nM, about 300 nM, about 400 nM, about 500 nM, about 600 nM, about 700 nM, about 800 nM, or about 900 nM. In some embodiment, the Compounds of the Disclosure inhibit USP1 activity with an $IC_{50}$ of about 1 nM to about 100 nM, 1 nM to about 90 nM, 1 nM to about 80 nM, 1 nM to about 70 nM, 1 nM to about 60 nM, 1 nM to about 50 nM, 1 nM to about 40 nM, 1 nM to about 30 nM, 1 nM to about 20 nM, 1 nM to about 10 nM, about 10 nM to about 100 nM, about 20 nM to about 100 nM, about 30 nM to about 100 nM, about 40 nM to about 100 nM, about 50 nM to about 100 nM, about 60 nM to about 100 nM, about 70 nM to about 100 nM, about 80 nM to about 100 nM, about 90 nM to about 100 nM, about 1 nM, about 2 nM, about 3 nM, about 4 nM, about 5 nM, about 6 nM, about 7 nM, about 8 nM, about 9 nM, about 10 nM, about 20 nM, about 30 nM, about 40 nM, about 50 nM, about 60 nM, about 70 nM, about 80 nM, about 90 nM, or about 100 nM. In some embodiments, the Compounds of the Disclosure inhibit USP1 activity with an $IC_{50}$ of less than 1 µM, less than 500 nM, less than 100 nM, less than 10 nM, or less than 1 nM. In some embodiments, the Compounds of the Disclosure inhibit USP1 activity with an $IC_{50}$ of less than 1 nM.

Exemplary Assays

Any suitable assay in the art can be used to determine an activity, detect an outcome or effect, determine efficacy, etc. Certain non-limiting exemplary assays that can be used in the methods provided herein are described.

In some instances, a method of determining whether a Compound of the Disclosure inhibits USP1 deubiquitinase activity measure a change in mass upon di-ubiquitin cleavage of deubiquitinase binding. For example, ubiquitin aldehyde and ubiquitin vinyl sulfone form covalent irreversible linkages to deubiquitinases that result in observable mass changes to the deubiquitinases. Similarly, cleavage of di-ubiquitins results in an observable mass change.

In some instances, a method of determining whether a Compound of the Disclosure inhibits USP1 deubiquitinase activity involves an increase in luminescence or fluorescence upon cleavage, e.g., that can be monitored on a plate reader. Such assays can use ubiquitin linked to a flurophore through a linker linkage, such as ubiquitin-7-amino-4-methylcoumarin (Ub-AMC) or ubiquitin-Rhodamine 110. Such assays can also use a di-ubiquitin containing an isopeptide linkage. Exemplary di-ubiquitins can comprise a flurophore on one ubiquitin and a quencher on the other ubiquitin such that fluorescence increases with then di-ubiquitin is cleaved. Such assays can also use enzyme coupled systems wherein ubiquitin is coupled to an enzyme that is only active in producing a fluorescence enzyme product when released from the ubiquitin.

Exemplary Deubicuitination Assay for USP1/UAF1 Activity and Inhibitor Testing.

Deubiquitinase activity can be measured using ubiquitin-rhodamine 110 as a substrate. Cleavage of the amide bond between rhodamine and the c-terminal glycine of ubiquitin yields an increase in fluorescence signal. The assay can be conducted in 20 ul total volume of assay buffer (50 mM Tris-HCl, pH 7.8, 0.5 mM EDTA, 0.01% Bovine Serum Albumin, 1 mM DTT, 0.01% Tween-20), and 0.05 nM USP1/UAF1 enzyme. Reaction can be initiated by addition of 150 nM Ubiquitin-rhodamine (Boston Biochem) substrate.

Compounds of the Disclosure can be dissolved in DMSO and tested in dose response format, beginning at 10M.

Compounds of the Disclosure can be added to enzyme/assay buffer mix and incubated 10 min. Substrate mix can be added, and reaction mix can be read in kinetic mode for 30 min at Ex480/Em540 and IC50 response curves can be plotted. See, e.g., Chen, et al., *Chem Biol.,* 18(11):1390-1400 (2011).

Methods of Use

In some embodiments, the Compounds of the Disclosure can be used to inhibit the activity of a USP1 protein. For example, in some embodiments, a method of inhibiting a USP1 protein comprises contacting the USP1 protein with a Compound of the Disclosure. The contacting can occur in vitro or in vivo.

In some embodiments, the Compounds of the Disclosure can be used to treat a "USP1 protein mediated disorder." A USP1 protein mediated disorder is any pathological condition in which a USP1 protein is known to play a role. In some embodiments, a USP1 protein mediated disorder is a proliferative disease such as cancer.

Various methods of treating diseases and disorders with the Compounds of the Disclosure are provided herein. Exemplary diseases and disorders that may be treated with the Compounds of the Disclosure include, but are not limited to, cancer.

In some embodiments, methods of treating cancer with Compounds of the Disclosure are provided. Such methods comprise administering to a subject with cancer a therapeutically effective amount of a Compound of the Disclosure.

In some embodiments, the cancer to be treated with a Compound of the Disclosure is selected from a hematological cancer, a lymphatic cancer, and a DNA damage repair pathway deficient cancer. In some embodiments, the cancer to be treated with a Compound of the Disclosure is a cancer that comprises cancer cells with a mutation in a gene encoding p53. In some embodiments, the cancer to be treated with a Compound of the Disclosure is a cancer that comprises cancer cells with a loss of function mutation in a gene encoding p53. In some embodiments, the cancer to be treated with a Compound of the Disclosure is a cancer that comprises cancer cells with a mutation in a gene encoding BRCA1. In some embodiments, the cancer to be treated with a Compound of the Disclosure is a cancer that comprises cancer cells with a mutation in a gene encoding BRCA2. In some embodiments, the cancer to be treated with a Compound of the Disclosure is a cancer that comprises cancer cells with a loss of function mutation in a gene encoding ATM.

In some embodiments, the cancer to be treated with a Compound of the Disclosure is selected from non-small cell lung cancer (NSCLC), osteosarcoma, ovarian cancer, and breast cancer. In some embodiments, the cancer is ovarian cancer or breast cancer. In some embodiments, the cancer is ovarian cancer. In some embodiments, the cancer is breast cancer. In some embodiments, the cancer is a triple negative breast cancer.

In some embodiments, the cancer to be treated with a Compound of the Disclosure is selected from the group consisting of bone cancer, including osteosarcoma and chondrosarcoma; brain cancer, including glioma, glioblastoma, astrocytoma, medulloblastoma, and meningioma; soft tissue cancer, including rhabdoid and sarcoma; kidney cancer; bladder cancer; skin cancer, including melanoma; and lung cancer, including non-small cell lung cancer; colon cancer, uterine cancer; nervous system cancer; head and neck cancer; pancreatic cancer; and cervical cancer.

Various methods of treating cancer with a Compound of the Disclosure are provided herein. In some embodiments, a therapeutically effective amount of Compound of the Disclosure is administered to a subject with cancer, wherein the cancer comprises cancer cells with elevated levels of RAD18. In some embodiments, the elevated levels of RAD18 are elevated RAD18 protein levels. In some embodiments, the elevated levels of RAD18 are elevated RAD18 mRNA levels. In some embodiments, elevated levels of RAD18 (e.g., RAD18 protein and/or RAD18 mRNA) have been detected (e.g., in a cancer sample obtained from the subject) prior to the administration. That is, in some embodiments, a subject's cancer has been tested for RAD18 protein or mRNA prior to beginning treatment with a USP1 inhibitor.

In some embodiments, such methods comprise (a) identifying a cancer in a subject as a USP1 inhibitor-sensitive cancer and then (b) administering a therapeutically effective amount of a Compound of the Disclosure to the subject.

In some embodiments, such methods comprise (a) detecting levels of RAD18 (e.g., RAD18 protein and/or RAD18 mRNA) in cancer cells (e.g., in a cancer sample obtained from the subject) and then (b) administering a therapeutically effective amount of a Compound of the Disclosure to a subject having a cancer comprising cells with elevated levels of RAD18.

In some embodiments, such methods comprise administering to a subject with triple negative breast cancer a therapeutically effective amount of a Compound of the Disclosure.

In some embodiments, a Compound of the Disclosure is used to treat a cancer, wherein the cancer is a homologous-recombination deficient cancer. In some embodiments, a Compound of the Disclosure is used to treat a cancer, wherein the cancer comprises cancer cells with a mutation in a gene encoding p53. In some embodiments, a Compound of the Disclosure is used to treat a cancer, wherein the cancer comprises cancer cells with a loss of function mutation in a gene encoding p53. In some embodiments, a Compound of the Disclosure is used to treat a cancer that does not have a defect in the homologous recombination pathway.

In some embodiments, a Compound of the Disclosure is used to treat a cancer, wherein the cancer is a BRCA1 mutant cancer. In some embodiments, a Compound of the Disclosure is used to treat a cancer, wherein the cancer is a BRCA2 mutant cancer. In some embodiments, a Compound of the Disclosure is used to treat a cancer, wherein the cancer is a BRCA1 mutant cancer and a BRCA2 mutant cancer. In some embodiments, the cancer is not a BRCA1 mutant cancer or a BRCA2 mutant cancer. In some embodiments, the cancer is a BRCA1 deficient cancer. In some embodiments, the cancer is a BRCA2 deficient cancer. In some embodiments, the cancer is a BRCA1 deficient cancer and a BRCA2 mutant cancer.

In some embodiments, a Compound of the Disclosure is used to treat a cancer, wherein the cancer is an ATM mutant cancer. In some embodiments, the cancer is not an ATM mutant cancer. In some embodiments, the cancer is an ATM deficient cancer.

In some embodiments, a Compound of the Disclosure is used to treat a cancer, wherein the cancer is a PARP inhibitor resistant or refractory cancer. In some embodiments, a Compound of the Disclosure is used to treat a cancer, wherein the cancer is a PARP inhibitor resistant or refractory BRCA1-deficient cancer.

In some embodiments, the cancer is a BRCA1 and/or BRCA2 mutant cancer, wherein the cancer comprises cells with elevated levels of RAD18, e.g., wherein the elevated levels of RAD18 are at least as high as the RAD18 protein and/or mRNA levels in ES2 cells or wherein the elevated levels of RAD18 are higher than the RAD18 protein and/or mRNA levels in HEP3B217 cells. In some embodiments, a triple negative breast cancer is a BRCA1 and/or BRCA2 mutant cancer.

In some instances, the cancer is a solid cancer. In some instances, the cancer is a hematological/lymphatic cancer. In some instances, the cancer is a DNA damage repair pathway deficient cancer. In some instances, the cancer is a homolgous-recombination deficient cancer. In some instances, the cancer comprises cancer cells with a mutation in a gene encoding p53. In some instances, the cancer comprises cancer cells with a loss of function mutation in a gene encoding p53. In some instances, the cancer is selected from the group consisting of non-small cell lung cancer (NSCLC), osteosarcoma, ovarian cancer, and breast cancer (including triple negative breast cancer). In some instances, the cancer is ovarian cancer or breast cancer (including triple negative breast cancer). In some instances, the cancer is ovarian cancer. In some instances, the cancer is breast cancer (including triple negative breast cancer.)

In some embodiments, a Compound of the Disclosure is used in combination with one or more additional therapeutic agents to treat cancer. It has been reported that p53 status determines PARP inhibitor sensitization (Sa et al. Genome Biology, (2019) 20:253) and that BRCA1/2 status predicts the efficacy of PARP inhibitors in the clinic (Audeh et al. Lancet (2010) 376 (9737), 245-51). As shown below, p53 mutant cancers and BRCA mutant cancers have increased sensitivity to USP1 inhibitors. Accordingly, in some embodiments, a Compound of the Disclosure is used in combination with a PARP inhibitor to treat cancer.

In some embodiments, provided herein are Compounds of the Disclosure for use as a medicament or for use in preparing a medicament, e.g., for the treatment of cancer. In some embodiments, provided herein are Compounds of the Disclosure for use in a method for the treatment of cancer.

Pharmaceutical Compositions

Compounds of the Disclosure can be administered to a mammal in the form of a raw chemical without any other components present, or Compounds of the Disclosure can also be administered to a mammal as part of a pharmaceutical composition containing the compound combined with a suitable pharmaceutically acceptable carrier (see, for example, Gennaro, Remington: The Science and Practice of Pharmacy with Facts and Comparisons: Drugfacts Plus, 20th ed. (2003); Ansel et al., Pharmaceutical Dosage Forms and Drug Delivery Systems, 7th ed., Lippencott Williams and Wilkins (2004); Kibbe et al., Handbook of Pharmaceutical Excipients, 3rd ed., Pharmaceutical Press (2000)). Such a carrier can be selected from pharmaceutically acceptable excipients and auxiliaries. The term "pharmaceutically acceptable carrier" or "pharmaceutically acceptable vehicle" encompasses any of the standard pharmaceutical carriers, solvents, surfactants, or vehicles. Standard pharmaceutical carriers and their formulations are described in Remington's Pharmaceutical Sciences, Mack Publishing Co., Easton, Pa., 19th ed. 1995.

A pharmaceutical composition of the present disclosure may be prepared as liquid suspensions or solutions using a liquid, such as an oil, water, an alcohol, and combinations of these.

A pharmaceutical composition of the present disclosure may be prepared as a sterile injectable, which may be aqueous or oleaginous suspensions. These suspensions may be formulated according to techniques known in the art.

A pharmaceutical composition of the present disclosure may be orally administered in any orally acceptable dosage form including capsules, tablets, aqueous suspensions or solutions.

A pharmaceutical composition of the present disclosure may be administered in the form of suppositories for rectal administration.

A pharmaceutical composition of the present disclosure may also be administered topically, especially when the target of treatment includes areas or organs readily accessible by topical application, including diseases of the eye, the skin, or the lower intestinal tract. Topical application for the lower intestinal tract may be effected in a rectal suppository formulation (see above) or in a suitable enema formulation. Topically-transdermal patches may also be used. For topical applications, the pharmaceutical compositions may be formulated in a suitable ointment, lotion, or cream containing the active component suspended or dissolved in one or more carriers.

A pharmaceutical composition of the present disclosure may also be administered ophthalmically and formulated as micronized suspensions in isotonic, pH adjusted sterile saline, or, preferably, as solutions in isotonic, pH adjusted sterile saline, either with or without a preservative such as benzylalkonium chloride. Alternatively, for ophthalmic uses, the pharmaceutical compositions may be formulated in an ointment such as petrolatum.

A pharmaceutical composition of the present disclosure may also be administered by nasal aerosol or inhalation. Such compositions are prepared according to techniques well known in the art of pharmaceutical formulation and may be prepared as solutions in saline, employing benzyl alcohol or other suitable preservatives, absorption promoters to enhance bioavailability, fluorocarbons, and/or other conventional solubilizing or dispersing agents.

The pharmaceutical compositions to be used for in vivo administration can be sterile. This is readily accomplished by filtration through, e.g., sterile filtration membranes.

Pharmaceutical compositions within the scope of the present disclosure include all compositions where a Compound of the Disclosure is combined with one or more pharmaceutically acceptable carriers. In one embodiment, the Compound of the Disclosure is present in the composition in an amount that is effective to achieve its intended therapeutic purpose.

A pharmaceutical composition of the present disclosure can be administered to any patient that may experience the beneficial effects of a Compound of the Disclosure. Foremost among such patients are mammals, e.g., humans and companion animals, although the disclosure is not intended to be so limited. In one embodiment, the patient is a human. In another embodiment, a pharmaceutical compositions of the present disclosure can be administered to a patient having PARP inhibitor resistant or refractory cancer. In another embodiment, a pharmaceutical compositions of the present disclosure can be administered to a patient having PARP inhibitor resistant or refractory BRCA1-deficient cancer. In another embodiment, a pharmaceutical compositions of the present disclosure can be administered to a patient in combination with a PARP inhibitor.

In another embodiment, the present disclosure provides kits which comprise a Compound of the Disclosure (or a composition comprising a Compound of the Disclosure) packaged in a manner that facilitates their use to practice methods of the present disclosure. In one embodiment, the kit includes a Compound of the Disclosure (or a composition comprising a Compound of the Disclosure) packaged in a container, such as a sealed bottle or vessel, with a label affixed to the container or included in the kit that describes use of the compound or composition to practice the method of the disclosure. In one embodiment, the compound or composition is packaged in a unit dosage form. The kit further can include a device suitable for administering the composition according to the intended route of administration. In some embodiments, the present disclosure provides a kit which comprise a Compound of the Disclosure, or a pharmaceutically acceptable salt or solvate thereof, and instructions for administering the compound, or a pharmaceutically acceptable salt or solvate thereof, to a patient having cancer.

In some embodiments, the present disclosure provides a pharmaceutical composition comprising a Compound of the Disclosure, or a pharmaceutically acceptable salt or solvate thereof, and a pharmaceutically acceptable carrier.

In some embodiments, the present disclosure provides a pharmaceutical composition comprising a compound having Formula I, or a pharmaceutically acceptable salt or solvate thereof, and a pharmaceutically acceptable carrier.

In some embodiments, the present disclosure provides a pharmaceutical composition comprising a compound having Formula II, or a pharmaceutically acceptable salt or solvate thereof, and a pharmaceutically acceptable carrier.

In some embodiments, the present disclosure provides a pharmaceutical composition comprising a compound having Formula III, or a pharmaceutically acceptable salt or solvate thereof, and a pharmaceutically acceptable carrier.

In some embodiments, the present disclosure provides a pharmaceutical composition comprising a compound having Formula IV, or a pharmaceutically acceptable salt or solvate thereof, and a pharmaceutically acceptable carrier.

In some embodiments, the present disclosure provides a pharmaceutical composition comprising a compound having Formula V, or a pharmaceutically acceptable salt or solvate thereof, and a pharmaceutically acceptable carrier.

In some embodiments, the present disclosure provides a pharmaceutical composition comprising a compound having Formula VI, or a pharmaceutically acceptable salt or solvate thereof, and a pharmaceutically acceptable carrier.

In some embodiments, the present disclosure provides a pharmaceutical composition comprising a compound having Formula VIa, or a pharmaceutically acceptable salt or solvate thereof, and a pharmaceutically acceptable carrier.

In some embodiments, the present disclosure provides a pharmaceutical composition comprising a compound having Formula VII, or a pharmaceutically acceptable salt or solvate thereof, and a pharmaceutically acceptable carrier.

In some embodiments, the present disclosure provides a pharmaceutical composition comprising a compound having Formula VIII, or a pharmaceutically acceptable salt or solvate thereof, and a pharmaceutically acceptable carrier.

In some embodiments, the present disclosure provides a pharmaceutical composition comprising a compound having Formula IX, or a pharmaceutically acceptable salt or solvate thereof, and a pharmaceutically acceptable carrier.

In some embodiments, the present disclosure provides a pharmaceutical composition comprising a compound having Formula X, or a pharmaceutically acceptable salt or solvate thereof, and a pharmaceutically acceptable carrier.

In some embodiments, the present disclosure provides a pharmaceutical composition comprising a compound having Formula XI, or a pharmaceutically acceptable salt or solvate thereof, and a pharmaceutically acceptable carrier.

In some embodiments, the present disclosure provides a pharmaceutical composition comprising a compound having Formula XII, or a pharmaceutically acceptable salt or solvate thereof, and a pharmaceutically acceptable carrier.

In some embodiments, the present disclosure provides a pharmaceutical composition comprising a Compound of the Disclosure, or a pharmaceutically acceptable salt or solvate thereof, and a pharmaceutically acceptable carrier, wherein the compound binds to a protein encoded by the USP1 gene.

In some embodiments, the present disclosure provides a pharmaceutical composition comprising a Compound of the Disclosure, or a pharmaceutically acceptable salt or solvate thereof, and a pharmaceutically acceptable carrier, wherein the pharmaceutical composition is for use in treating cancer.

In some embodiments, the present disclosure provides a pharmaceutical composition comprising a Compound of the Disclosure, or a pharmaceutically acceptable salt or solvate thereof, and a pharmaceutically acceptable carrier, wherein the pharmaceutical composition is for the manufacture of a medicament for treatment of cancer.

EXAMPLES

General Synthetic Methods

Compounds of the Disclosure are prepared using methods known to those skilled in the art in view of this disclosure, or by the illustrative methods shown in the General Schemes below. In any of the General Schemes, suitable protecting groups can be employed in the synthesis. (See, Wuts, P. G. M.; Greene, T. W., "Greene's Protective Groups in Organic Synthesis", 4th Ed., J. Wiley & Sons, N Y, 2007).

Unless otherwise noted, all reagents were used without further purification. $^1$H-NMR spectra were obtained in DMSO-$d_6$ or CD$_3$OD at room temperature on a Bruker 300 MHz instrument. When more than one conformer was detected, the chemical shifts for the most abundant one is reported. Chemical shifts of $^1$H NMR spectra were recorded in parts per million (ppm) on the δ scale from an internal standard of residual solvent. Splitting patterns are designed as s, singlet; d, doublet; t, triplet; q, quartet; m, multiplet; br, broad. LC-MS and prep-HPLC conditions are described below:

LCMS Method A
LCMS Column: Agilent Zorbax XDB C18 4.6×50 mm, 3.5 m
Mobile phase: Solvent A: Water (with 0.1% Formic acid)
Solvent B: MeOH
Flow rate: 1.0 mL/min,
Run time: 2 min gradient (20%-90% B), then 3 min @90% B,
Temperature: 30° C.

LCMS Method B
LCMS Column: X-Select CSH C18 3.0×50 mm, 2.5 m
Mobile phase: Solvent A: Water (with 0.05% Formic acid)/MeCN (95:5)
Solvent B: 0.05% Formic acid in MeCN
Flow rate: 1.2 mL/min,
Run time: 2 min gradient (0%-98% B), hold 1 min, then 0% B up to 4 min
Temperature: 50° C.

LCMS Method C
LCMS Column: X-Select CSH C18 3.0×50 mm, 2.5 m
Mobile phase: Solvent A: 5 mM Ammonium Bicarbonate
Solvent B: MeCN
Flow rate: 1.2 mL/min,
Run time: 2 min gradient (0%-98% B), hold 1 min, then 0% B up to 4 min
Temperature: 50° C.

HPLC Column A: Agilent SB-C18 4.6×150 mm, 3.5 m
Mobile phase: Solvent A: water (with 0.02% TFA)
Solvent B: MeOH
Flow rate: 1.0 mL/min,
Run time: 0.5 min @10% B, 9.5 min gradient (10%-90% B), then 10 min @90% B,
Temperature: 30° C.

Preparative Column A: Phenomenex Luna 5 u 100 A, 21.2×250 mm, 5 m
Mobile phase: Solvent A: Water
Solvent B: MeOH
Flow rate: 10 mL/min,
Run time: 1 min @20% B, 30 min gradient (20%-80% B), then 10 min @90% B,
Temperature: Ambient Preparative Column B: X-Select C18, 30×250 mm, 5 m
Mobile phase: Solvent A: 10 mm Formic acid in Water
Solvent B: MeCN
Flow rate: 30 mL/min,
Run time: 50 min, isocratic 5% A:95% B
Temperature: Ambient Preparative Column C: Nucleodur C18, 30×250 mm, 5 m
Mobile phase: Solvent A: 10 mM Ammonium bicarbonate in Water
Solvent B: MeCN
Flow rate: 30 mL/min,
Run time: 50 min, isocratic 5% A:95% B
Temperature: Ambient Preparative Column D: X-Select C18, 30×250 mm, 5 m
Mobile phase: Solvent A: 10 mM Ammonium bicarbonate in Water
Solvent B: MeCN
Flow rate: 30 mL/min,
Run time: 50 min, isocratic 5% A:95% B
Temperature: Ambient Preparative Column E: Nucleodur C18, 30×250 mm, 5 m
Mobile phase: Solvent A: 10 mM $NH_3$ in Water
Solvent B: MeCN
Flow rate: 30 mL/min,
Run time: 50 min, isocratic 5% A:95% B
Temperature: Ambient SFC Method: Green Sep ES Diol, 250×4.6 mm, 5 m
Mobile Phase Solvent A: $CO_2$
Solvent B: MeCN
Flow rate: 80 mL/min; Diluent: MeCN
Run Time: 10-20% B 3 min, 20-25% B 9 min, 25-30% B 3 min, 30-50% B 6 min, 50% B 50 min Chiral Method A: DIACEL CHIRAL PAK-IC (250×4.6 mm, 5); Wavelength: 260 nm
Mobile Phase Solvent A: $CO_2$
Solvent B: MeOH+DCM (80:20)
Flow rate: 3 mL/min.
Run Time: 25-50% B in 5 min, hold 50% B 4 min, 50-25% B at 10 min, hold 25% B 2 min Chiral Method B: DIACEL CHIRAL PAK-IG (250×4.6 mm, 5); Wavelength: 280 nm
Mobile Phase Solvent A: $CO_2$
Solvent B: MeOH+0.1% $NH_3$
Flow rate: 3 mL/min.
Run Time: 10-40% B 5.0 min, hold 40% B till 4 min, 40-10% B at 10 min, hold 10% B 2 min The following abbreviations are used in the text:
PE=petroleum ether
EA or EtOAc=ethyl acetate
DMSO=dimethyl sulfoxide
DMF=N, N-dimethylformamide
DMA=N,N-dimethylacetamide
MeOH=methanol
MTBE=Methyl tert-butyl ether
DCM=dichloromethane
TEA=trimethylamine
DIPEA=Diisopropylethylamine
TFA=trifluoroacetic acid
MeCN or ACN=acetonitrile
TLC=thin layer chromatography
$(BPin)_2$=Bis(pinacolato)diboron
HFIP=1,1,1,3,3,3-hexafluoropropan-2-ol
DIBAL-H=Diisobutylaluminum hydride
MeI=Iodomethane
hex or n-hex=n-Hexane
DCE=1,2-Dichloroethane
TBSCl=tert-Butyldimethylsilyl chloride
$Tf_2O$=Trifluoromethanesulfonic anhydride
n-BuLi=n-Butyllithium
DMAP=4-Dimethylaminopyridine
KOAc=Potassium acetate
NaOAc=Sodium acetate
TFAA=Trifluoroacetic anhydride
m-CPBA=meta-Chloroperoxybenzoic acid
DME=1,2-Dimethoxyethane
TPP=Triphenylphosphine
DTAD=Di-tert-butyl azodicarboxylate
DEAD=Diethylazodicarboxylate
DIAD=Diisopropyl azodicarboxylate
PS-TPP=Polystyrene supported triphenylphosphine
NBS=N-Bromosuccinimide.

Preparation of Common Intermediate I-1:

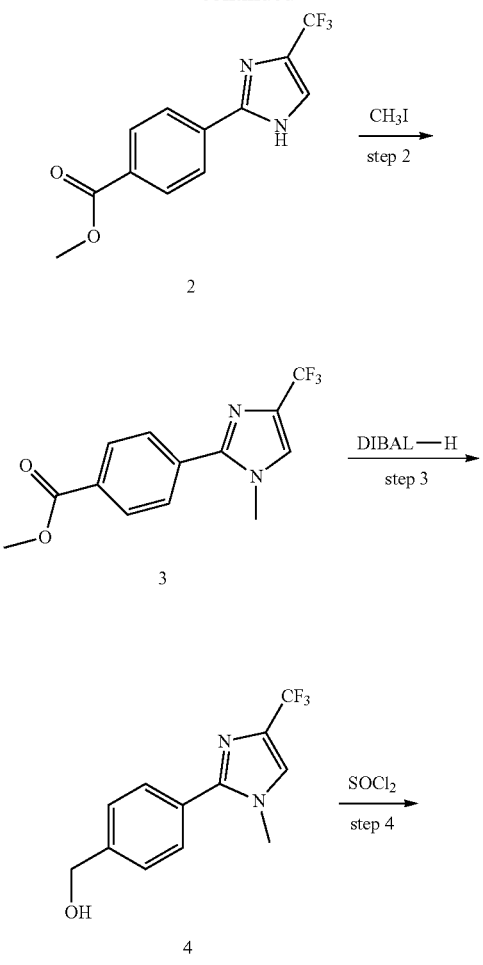

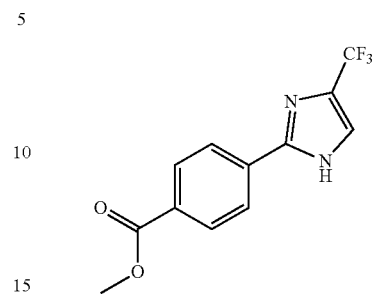

Step 1: Synthesis of Methyl 4-(4-(trifluoromethyl)-1H-imidazol-2-yl) benzoate To a mixture of 3,3-dibromo-1,1,1-trifluoropropan-2-one (3.1 g, 11.49 mmol) in water (6 ml), was added NaOAc (951.8 mg, 11.60 mmol). The mixture was heated at 100° C. for 1 hour, then cooled to room temperature. A solution of methyl 4-formylbenzoate (1.7 g, 10.34 mmol) in MeOH (47 ml) and NH$_4$OH (11 ml), was then added to the reaction mixture at room temperature. After 40 min, the reaction was warmed to 100° C. and stirred for 2 hours. The mixture was quenched with water (50 mL), and then extracted with EA (100 mL×2). The organic layer was dried over Na$_2$SO$_4$ (30 g), filtered and concentrated. The concentrated residue was purified by silica gel chromatography (PE:EA=20:1 to 5:1) to afford 1.9 g of the title compound. LC-MS (Method A) (ESI+): m/z 271 (M+H)$^+$; $^1$H-NMR (300 MHz, CD$_3$OD) δ 8.12 (d, J=8.7 Hz, 2H), 8.01 (d, J=8.7 Hz, 2H), 7.72 (s, 1H), 3.93 (s, 3H).

Step 2: Synthesis of Methyl 4-(1-methyl-4-(trifluoromethyl)-1H-imidazol-2-yl)benzoate

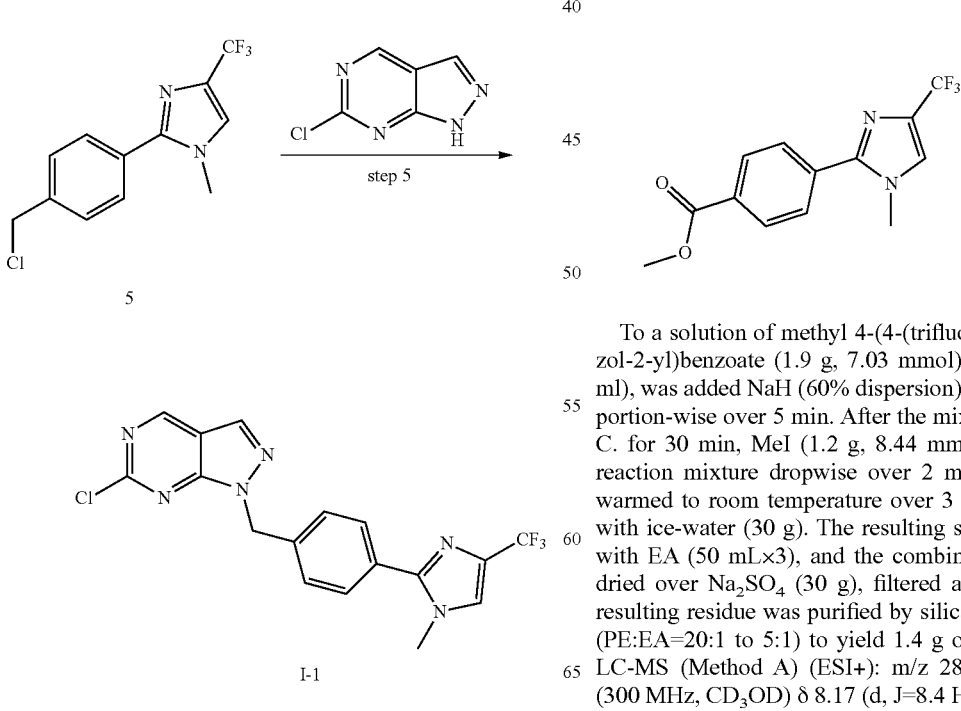

To a solution of methyl 4-(4-(trifluoromethyl)-1H-imidazol-2-yl)benzoate (1.9 g, 7.03 mmol) in THF at 0° C. (50 ml), was added NaH (60% dispersion) (338 mg, 8.44 mmol) portion-wise over 5 min. After the mixture was stirred at 0° C. for 30 min, MeI (1.2 g, 8.44 mmol) was added to the reaction mixture dropwise over 2 min. The reaction was warmed to room temperature over 3 hours, then quenched with ice-water (30 g). The resulting solution was extracted with EA (50 mL×3), and the combined organic layer was dried over Na$_2$SO$_4$ (30 g), filtered and concentrated. The resulting residue was purified by silica gel chromatography (PE:EA=20:1 to 5:1) to yield 1.4 g of the title compound. LC-MS (Method A) (ESI+): m/z 285 (M+H)$^+$; $^1$H-NMR (300 MHz, CD$_3$OD) δ 8.17 (d, J=8.4 Hz, 2H), 7.80 (d, J=8.4 Hz, 2H), 7.75 (s, 1H), 3.94 (s, 3H), 3.83 (s, 3H).

Step 3: Synthesis of (4-(1-Methyl-4-(trifluoromethyl)-1H-imidazol-2-yl)phenyl)methanol

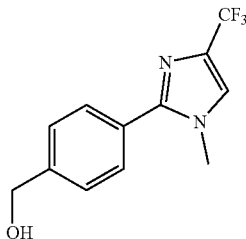 [SMILES: Cn1cc(C(F)(F)F)nc1-c1ccc(CO)cc1]

To a solution of methyl 4-(1-methyl-4-(trifluoromethyl)-1H-imidazol-2-yl)benzoate (1.4 g, 4.93 mmol) in THF (40 ml) at 0° C., was DIBAL-H (24 ml, 24.6 mmol, 1 M in toluene) via syringe. After the addition, the reaction was stirred at 0° C. for 20 min, and then warmed to room temperature over 30 min. After the reaction was complete as indicated by TLC analysis, the mixture was quenched with ice water (10 mL), and the pH was adjusted to 5 with a 1N HCl solution. The resulting mixture was extracted with EA (50 mL×2), and the combined organic layer was washed with brine (30 mL), dried over Na$_2$SO$_4$ (30 g), filtered and concentrated in vacuo. The resulting residue was purified by silica gel chromatography (PE:EA=20:1 to 5:1) to afford 1.2 g of the title compound. LC-MS (Method A) (ESI+): m/z 257 (M+H)$^+$; $^1$H-NMR (300 MHz, CD$_3$OD) δ 7.69 (s, 1H), 7.63 (d, J=8.1 Hz, 2H), 7.52 (d, J=8.1 Hz, 2H), 4.69 (s, 2H), 3.78 (s, 3H).

Step 4: Synthesis of 2-(4-(Chloromethyl)phenyl)-1-methyl-4-(trifluoromethyl)-1H-imidazole

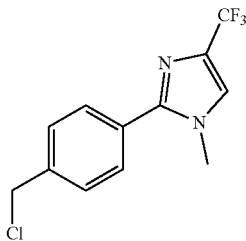 [SMILES: Cn1cc(C(F)(F)F)nc1-c1ccc(CCl)cc1]

To a mixture of (4-(1-methyl-4-(trifluoromethyl)-1H-imidazol-2-yl)phenyl)methanol (1.2 g, 4.68 mmol) in DCE (40 ml), was added SOCl$_2$ (1.7 g, 14.1 mmol) in one portion. After the addition, the reaction was stirred at 50° C. for 20 min, then concentrated to dryness to afford 1.28 g of the crude title compound. LC-MS (Method A) (ESI+): m/z 275, 277 (M+H)$^+$; $^1$H-NMR (300 MHz, CD$_3$OD) δ 8.04 (s, 1H), 7.74 (d, J=8.4 Hz, 2H), 7.68 (d, J=8.4 Hz, 2H), 4.75 (s, 2H), 3.87 (s, 3H).

Step 5: Synthesis of 6-Chloro-1-(4-(1-methyl-4-(trifluoromethyl)-1H-imidazol-2-yl)benzyl)-1H-pyrazolo[3,4-d]pyrimidine (I-1)

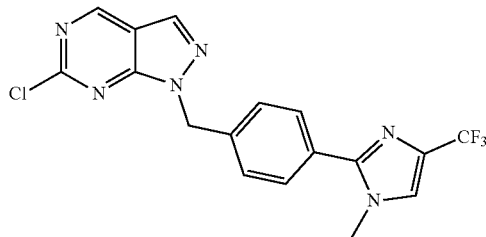 [SMILES: Cn1cc(C(F)(F)F)nc1-c1ccc(Cn2ncc3cnc(Cl)nc32)cc1]

To a solution of 2-(4-(chloromethyl)phenyl)-1-methyl-4-(trifluoromethyl)-1H-imidazole (1 g, 3.64 mmol) in DMF (25 ml), was added 6-chloro-1H-pyrazolo[3,4-d]pyrimidine (675 mg, 4.37 mmol) and K$_2$CO$_3$ (1.26 g, 9.10 mmol). The resulting mixture was stirred at 35° C. for 20 hours, then quenched with water (50 mL) and extracted with EA (100 mL×2). The combined organic phase was washed with water and brine, dried over Na$_2$SO$_4$ (50 g), filtered and concentrated in vacuo. The resulting residue was purified by silica gel chromatography (PE:EA=20:1 to 10:1) to afford 580 mg of the title compound with a small amount of its regioisomer. LC-MS (Method A) (ESI+): m/z 393, 395 (M+H)$^+$; $^1$H-NMR (300 MHz, CDCl$_3$) δ 9.06 (s, 1H), 8.18 (s, 1H), 7.61 (d, J=8.1 Hz, 2H), 7.47 (d, J=8.1 Hz, 2H), 7.30 (s, 1H), 5.69 (s, 2H), 3.74 (s, 3H).

The following intermediates were prepared from the appropriate heterocycles and alkylating reagents according to the method of preparation for I-1.

| Intermediate | Structure | Analytics |
|---|---|---|
| I-2 | ![structure] | LC-MS (Method A) (ESI+): m/z 407, 409 (M + H)$^+$; $^1$H-NMR (300 MHz, CDCl$_3$) δ 8.16 (s, 1H), 7.60 (d, J = 8.1 Hz, 2H), 7.45 (d, J = 8.1 Hz, 2H), 7.29 (s, 1H), 5.66 (s, 2H), 3.74 (s, 3H), 2.81 (s, 3H). |

| Intermediate | Structure | Analytics |
| --- | --- | --- |
| I-3 | 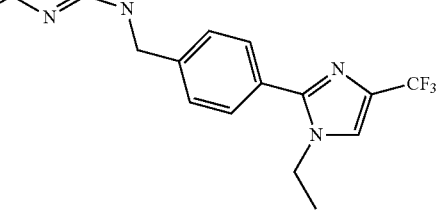 | LC-MS (Method B) (ESI+): m/z 421.00 (M + H)+. |
| I-4 | 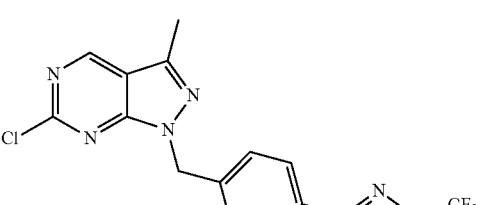 | LC-MS (Method A) (ESI+): m/z 407 (M + H); $^1$H-NMR (300 MHz, CDCl$_3$) δ 8.95 (s, 1H), 7.60 (d, J = 8.1 Hz, 2H), 7.44 (d, J = 8.1 Hz, 2H), 7.29 (s, 1H), 5.60 (s, 2H), 3.74 (s, 3H), 2.61 (s, 3H). |
| I-5 | 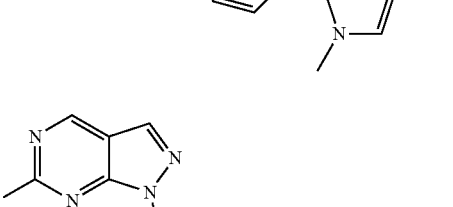 | LC-MS (Method A) (ESI+): m/z 407 (M + H)+; $^1$H-NMR (300 MHz, CDCl$_3$) δ 9.07 (s, 1H), 8.20 (s, 1H), 7.56 (d, J = 8.4 Hz, 2H), 7.46 (d, J = 8.4 Hz, 2H), 7.38 (s, 1H), 5.70 (s, 2H), 4.04 (q, J = 7.2 Hz, 2H), 1.26 (t, J = 7.2 Hz, 3H). |
| I-6 | 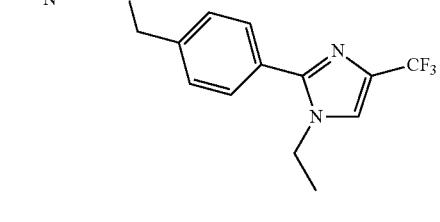 | LCMS (Method B) (ESI+): m/z 421.00 (M + H)+; $^1$H-NMR (400 MHz, DMSO-d$_6$) δ 9.32 (s, 1H), 8.53 (s, 1H), 8.13-8.21 (m, 1H), 7.54 (d, J = 7.48 Hz, 2H), 7.39 (d, J = 7.98 Hz, 2H), 5.74 (s, 2H), 4.44 (td, J = 6.48, 12.96 Hz, 1H), 1.38 (d, J = 6.48 Hz, 6H). |
| I-7 | 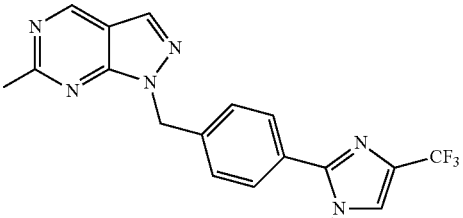 | LC-MS (Method A) (ESI+): m/z 408 (M + H)+; $^1$H-NMR (300 MHz, CDCl$_3$) δ 9.07 (s, 1H), 8.65 (d, J = 2.1 Hz, 1H), 8.22 (d, J = 8.1 Hz, 1H), 8.20 (s, 1H), 7.81 (dd, J = 8.1, 2.1 Hz, 1H), 7.34 (s, 1H), 5.68 (s, 2H), 4.63 (q, J = 7.2 Hz, 2H), 1.45 (t, J = 7.2 Hz, 3H). |

Preparation of Common Intermediate I-8

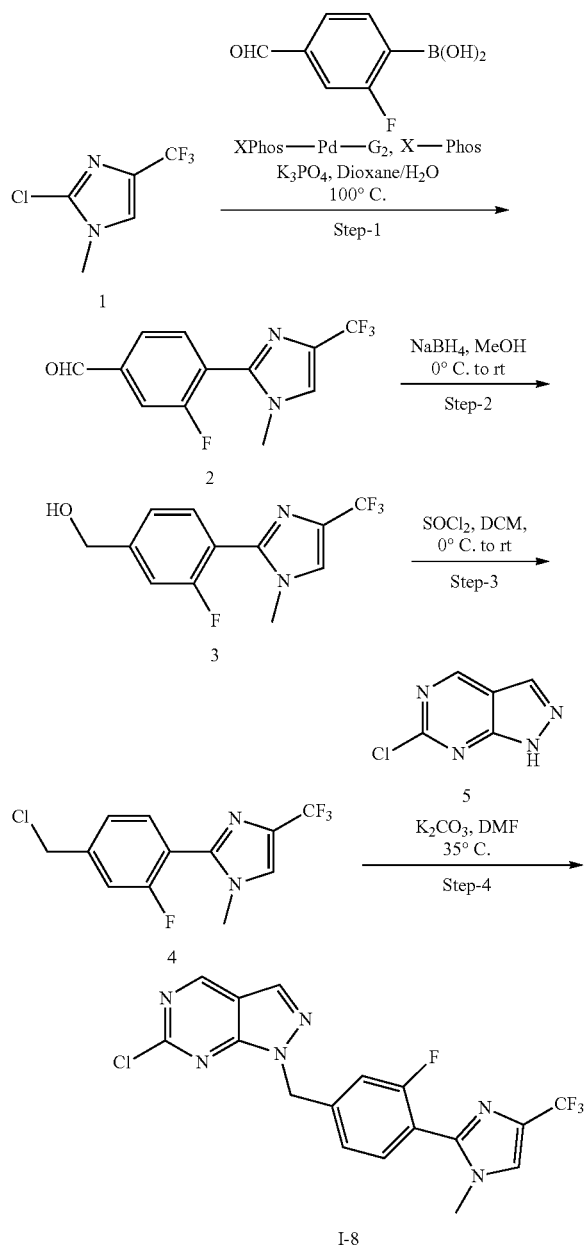

Step 1: Synthesis of 3-Fluoro-4-(1-methyl-4-(trifluoromethyl)-1H-imidazol-2-yl)benzaldehyde A solution of 2-chloro-1-methyl-4-(trifluoromethyl)-1H-imidazole (1.00 g, 5.40 mmol), (2-fluoro-4-formylphenyl) boronic acid (1.00 g, 6.50 mmol) and $K_3PO_4$ (3.40 g, 16.30 mmol) in dioxane (20 mL) and $H_2O$ (5 mL), was degassed with argon for 5 min. To the resulting reaction mixture were added Xphos-Pd-$G_2$ (0.42 g, 0.54 mmol) and X-Phos (1.03 g, 2.10 mmol) sequentially, and the reaction mixture was heated in a sealed tube at 100° C. for 16 h. Progress of the reaction was monitored by TLC. After completion, the reaction mixture was diluted with water and extracted with EA. The organic layer was dried over anhydrous sodium sulfate, filtered, and concentrated under reduced pressure. The crude compound thus obtained was purified by silica gel chromatography using 0-30% EA in hexane to afford 1.40 g the title compound. LC-MS (Method B) (ESI+): m/z 272.90 $(M+H)^+$; $^1$H-NMR (400 MHz, DMSO-$d_6$) δ 10.09 (s, 1H), 8.08 (s, 1H), 7.83-7.94 (m, 3H), 3.66 (s, 3H).

Step 2: Synthesis of (3-Fluoro-4-(1-methyl-4-(trifluoromethyl)-1H-imidazol-2-yl)phenyl)methanol To an ice cooled solution of 3-fluoro-4-(1-methyl-4-(trifluoromethyl)-1H-imidazol-2-yl)benzaldehyde (1.40 g, 5.14 mmol) in MeOH (30 mL) was added $NaBH_4$ (0.293 g 7.70 mmol), and the reaction mixture was stirred at room temperature for 2 h. Progress of the reaction was monitored by TLC. After completion, the reaction mixture was concentrated under reduced pressure. The crude reaction mixture was dissolved in water and extracted with EA. The organic layer was dried over anhydrous sodium sulfate, filtered, and concentrated under reduced pressure to afford 1.40 g of the title compound that was used without further purification. LC-MS (Method B) (ESI+): m/z 274.85 $(M+H)^+$; $^1$H-NMR (400 MHz, DMSO-$d_6$) δ 7.99 (s, 1H), 7.54 (t, J=7.8 Hz, 1H), 7.28-7.34 (m, 2H), 5.46 (t, J=5.6 Hz, 1H), 4.60 (d, J=5.4 Hz, 2H), 3.59 (s, 3H).

Step 3: Synthesis of 2-(4-(Chloromethyl)-2-fluorophenyl)-1-methyl-4-(trifluoromethyl)-1H-imidazole To an ice-cooled solution of (3-fluoro-4-(1-methyl-4-(trifluoromethyl)-1H-imidazol-2-yl)phenyl)-methanol (1.40 g, 5.10 mmol) in DCM (15 mL), was added $SOCl_2$ (1.80 g, 15.0 mmol) and the reaction mixture was stirred at room temperature for 2 h. Progress of the reaction was monitored by TLC. After completion, the reaction mixture was quenched with saturated $NaHCO_3$ solution and extracted with DCM. Organic layer was dried over anhydrous sodium sulfate, filtered, and concentrated under reduced pressure to afford 1.42 g of the title compound, which was used without further purification. LC-MS (Method B) (ESI+): m/z 292.85 $(M+H)^+$.

Step 4: Synthesis of 6-Chloro-1-(3-fluoro-4-(1-methyl-4-(trifluoromethyl)-1H-imidazol-2-yl)benzyl)-1H-pyrazolo[3,4-d]pyrimidine (I-8)

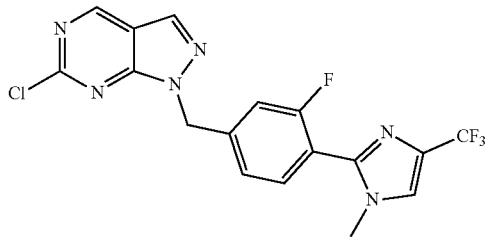 [SMILES: Cn1cc(C(F)(F)F)nc1-c1ccc(Cn2ncc3cnc(Cl)nc32)cc1F]

A solution of 2-(4-(chloromethyl)-2-fluorophenyl)-1-methyl-4-(trifluoromethyl)-1H-imidazole (1.41 g, 4.80 mmol), 6-chloro-1H-pyrazolo[3,4-d]pyrimidine 5 (0.65 g, 4.20 mmol) and $K_2CO_3$ (1.45 g, 10.50 mmol) in DMF (12 mL), was stirred at 35° C. for 16 h. Progress of the reaction was monitored by TLC. After completion, the reaction mixture was quenched with water and extracted with EA. The organic layer was dried over anhydrous sodium sulfate, filtered, and concentrated under reduced pressure. The crude compound was purified by silica gel chromatography using 0-15% EA in hexane to afford 0.70 g of the title compound. LC-MS (Method B) (ESI+): m/z 410.85 (M+H)$^+$; $^1$H-NMR (400 MHz, DMSO-d$_6$) δ 9.33 (s, 1H), 8.54 (s, 1H), 7.99 (s, 1H), 7.57 (t, J=7.6 Hz, 1H), 7.31 (d, J=10.8 Hz, 1H), 7.19 (d, J=7.8 Hz, 1H), 5.76 (s, 2H), 3.58 (s, 3H).

The following intermediate was made from the appropriate aldehyde and alkylating reagents according to the procedure for Intermediate I-8.

| Intermediate | Structure | Analytics |
| --- | --- | --- |
| I-9 | 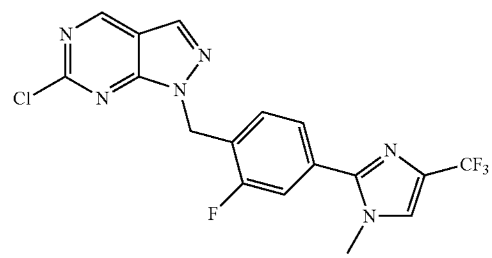 [SMILES: Cn1cc(C(F)(F)F)nc1-c1ccc(Cn2ncc3cnc(Cl)nc32)c(F)c1] | LC-MS (Method C) (ESI+): m/z 410.90 (M + H)$^+$. |
| I-10 | 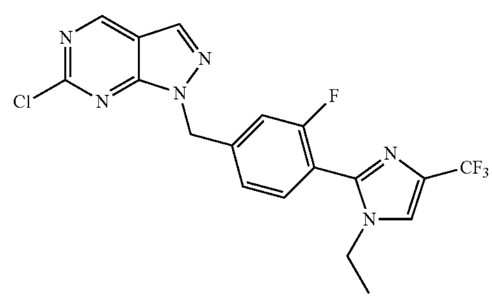 [SMILES: CCn1cc(C(F)(F)F)nc1-c1ccc(Cn2ncc3cnc(Cl)nc32)cc1F] | LC-MS (Method B) (ESI+): m/z 424.90 (M + H)$^+$; $^1$H-NMR (400 MHz, DMSO-d$_6$) δ 9.33 (s, 1H), 8.54 (s, 1H), 8.10 (s, 1H), 7.51-7.57 (m, 1H), 7.31 (d, J = 10.97 Hz, 1H), 7.19 (d, J = 7.98 Hz, 1H), 5.77 (s, 2H), 3.86 (q, J = 7.15 Hz, 2H), 1.25 (t, J = 6.98 Hz, 3H). |
| I-11 | 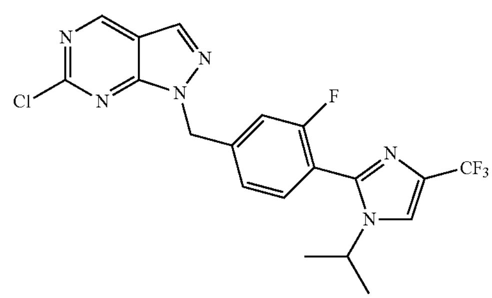 [SMILES: CC(C)n1cc(C(F)(F)F)nc1-c1ccc(Cn2ncc3cnc(Cl)nc32)cc1F] | LC-MS (Method B) (ESI+): m/z 439.10 (M + H)$^+$; $^1$H-NMR (300 MHz, CDCl$_3$) δ 8.86 (s, 1H), 7.53 (t, J = 7.5 Hz, 1H), 7.44 (s, 1H), 7.19 (s, 1H), 7.12 (d, J = 7.8 Hz, 1H), 6.97 (d, J = 10.2 Hz, 1H), 6.65 (d, J = 3.6 Hz, 1H), 5.49 (s, 2H), 4.23 (m, 1H), 1.41 (d, J = 6.6 Hz, 6H). |
| I-12 | 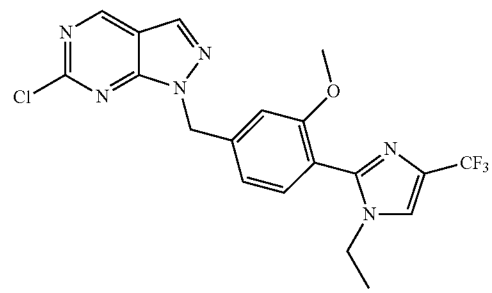 [SMILES: CCn1cc(C(F)(F)F)nc1-c1ccc(Cn2ncc3cnc(Cl)nc32)cc1OC] | LC-MS (Method B) (ESI+): m/z 437.10 (M + H)$^+$; $^1$H-NMR (400 MHz, DMSO-d$_6$) δ 9.32 (s, 1H), 8.53 (s, 1H), 7.98 (s, 1H), 7.29 (d, J = 7.98 Hz, 1H), 7.19 (s, 1H), 6.81 (d, J = 7.48 Hz, 1H), 5.73 (s, 2H), 3.77 (s, 3H), 3.70-3.76 (m, 2H), 1.21 (t, J = 6.98 Hz, 3H). |

| Intermediate | Structure | Analytics |
|---|---|---|
| I-13 | 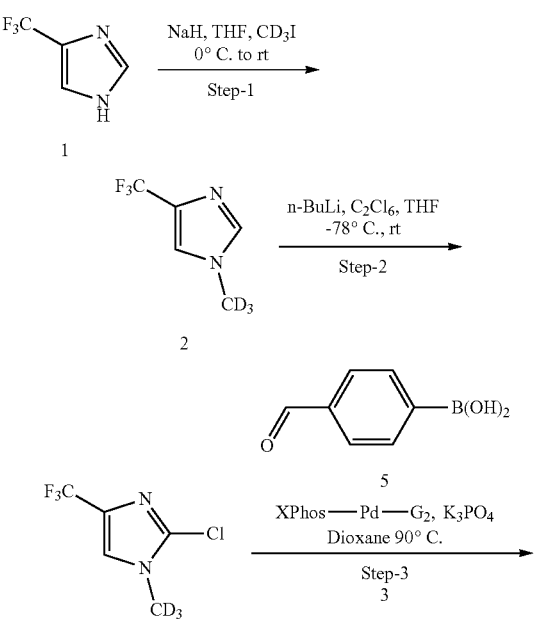 | LC-MS (Method B) (ESI+): m/z 455.09 (M + H)+. |
| I-14 | 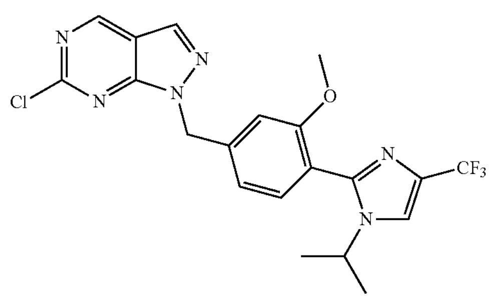 [SMILES: COc1cc(Cn2ncc3cnc(Cl)nc32)ccc1-c1nc(C(F)(F)F)cn1C(C)C] | LC-MS (Method C) (ESI+): m/z 450.85 (M + H)+; $^1$H-NMR (400 MHz, DMSO-$d_6$) δ 9.31-9.34 (m, 1H), 8.54 (s, 1H), 8.12 (s, 1H), 7.28 (d, J = 7.48 Hz, 1H), 7.19 (s, 1H), 6.80 (d, J = 7.48 Hz, 1H), 5.73 (s, 2H), 4.10 (q, J = 4.99 Hz, 1H), 3.76 (s, 3H), 1.30 (d, J = 6.48 Hz, 6H). |
Preparation of Common Intermediate I-15
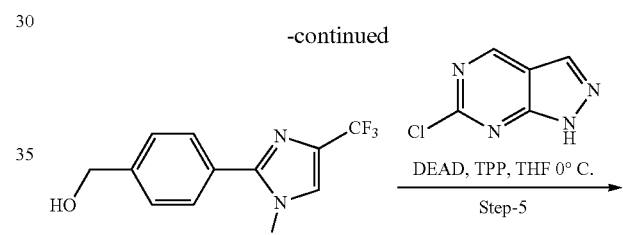
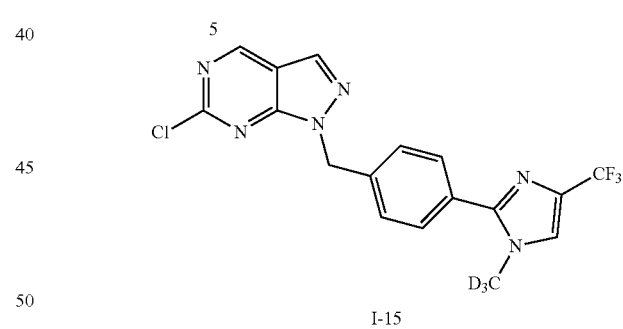
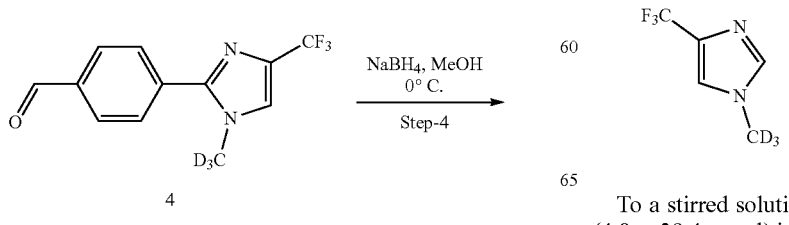
Step 1: Synthesis of 1-(Methyl-d3)-4-(trifluoromethyl)-1H-imidazole
To a stirred solution of 4-(trifluoromethyl)-1H-imidazole (4.0 g, 29.4 mmol) in dry THF (100 mL) at 0° C., was added sodium hydride (60% dispersion, 1.294 g, 32.35 mmol). The resulting mixture was stirred for 15 min, and then iodomethane-d3 (4.26 g, 29.4 mmol) was added at 0° C., and the reaction was stirred for 30 min. The reaction mixture was then allowed to warm to room temperature and stirred for 4 h. After completion of the reaction (monitored by TLC), the reaction mixture was quenched with saturated ammonium chloride solution (50 mL) and extracted with EA (3×50 mL). The combined organic layer was dried over anhydrous Na$_2$SO$_4$, filtered, and dried under vacuum. The crude product was purified by silica gel chromatography (50-100% EA in n-hexane) to afford 3.0 g of the title compound. LC-MS (Method B) (ESI+): m/z 154.45 (M+H)$^+$; $^1$H-NMR (400 MHz, CDCl$_3$) δ 7.48 (s, 1H), 7.27 (s, 1H)

Step 2: Synthesis of 2-Chloro-1-(methyl-d3)-4-(trifluoromethyl)-1H-imidazole

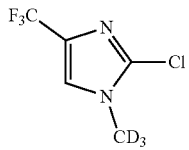

To a stirred solution of 1-(methyl-d3)-4-(trifluoromethyl)-1H-imidazole (2.70 g, 17.6 mmol) in THF (50 mL) at −78° C., was added a 2.5M solution of n-butyl lithium in n-hexane (7 mL, 17.64 mmol). The resulting mixture was stirred at −78° C. for 30 min, and then treated with hexachloroethane (2.08 g, 8.82 mmol). After 1 h, the reaction mixture was warmed to room temperature, whereupon stirring was continued for an additional 3 h. After completion of the reaction (monitored by TLC), the reaction mixture was quenched with saturated ammonium chloride solution (25 mL) and extracted with EA (3×50 mL). The combined organic layer was dried over anhydrous Na$_2$SO$_4$, filtered, and concentrated under vacuum. The crude compound was purified by silica gel chromatography (30-100% EA in n-hexane) to afford 1.30 g of the title compound. LC-MS (Method B) (ESI+): m/z 188.30 (M+H)$^+$.

Step 3: Synthesis of 4-(1-(Methyl-d3)-4-(trifluoromethyl)-1H-imidazol-2-yl)benzaldehyde

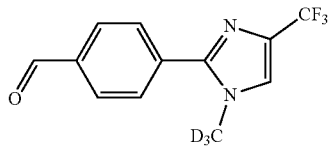 [SMILES: [2H]C([2H])([2H])n1cc(C(F)(F)F)nc1-c1ccc(C=O)cc1]

To the solution of 2-chloro-1-(methyl-d3)-4-(trifluoromethyl)-1H-imidazole (1.40 g, 7.49 mmol) in 1,4-dioxane (60 mL), was added X-Phos-Pd-G2 catalyst (0.294 g, 0.374 mmol). The resulting mixture was purged with argon gas for 10 min, whereupon solid K$_3$PO$_4$ (4.76 g, 22.5 mmol) and (4-formylphenyl)boronic acid (2.24 g, 14.97 mmol) were added, followed by additional purging with argon gas for another 5 min. The reaction mixture was then heated at 90° C. for 16 h. After completion of the reaction (monitored by TLC), the mixture was diluted with water (60 mL) and EA (60 mL). The organic layer was separated, and the aqueous layer was extracted with EA (2×50 mL). The combined organic layer was dried over anhydrous Na$_2$SO$_4$, filtered, and concentrated under reduced pressure. The crude compound was purified by silica gel chromatography (0-30% EA in n-hexane) to afford 1.62 g of the title compound. LC-MS (Method B) (ESI+): m/z 258.00 (M+H)$^+$; $^1$H-NMR (400 MHz, CDCl$_3$) δ 10.09 (s, 1H), 8.00 (d, J=7.88 Hz, 2H), 7.86 (d, J=7.88 Hz, 2H), 7.37 (s, 1H).

Step 4: Synthesis of (4-(1-(Methyl-d3)-4-(trifluoromethyl)-1H-imidazol-2-yl)phenyl)methanol

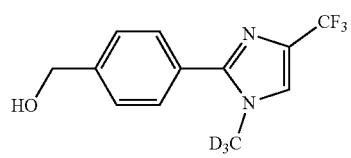

To a stirred solution of 4-(1-(methyl-d3)-4-(trifluoromethyl)-1H-imidazol-2-yl)benzaldehyde (1.60 g, 6.23 mmol) in methanol (50 mL) at 0° C., was added NaBH$_4$ (0.118 g, 3.11 mmol). After completion of the reaction (monitored by TLC), the mixture was quenched with ice water (30 mL) and extracted with 10% methanol in DCM (4×50 mL). The combined organic layer was dried over anhydrous Na$_2$SO$_4$, filtered and concentrated under vacuum. The crude compound was purified by silica gel chromatography (0-60% EA in n-hexane) to afford 1.30 g of the title compound. LC-MS (Method B) (ESI+): m/z 259.80 (M+H)$^+$; $^1$H-NMR (400 MHz, CDCl$_3$) δ 7.60 (d, J=8.31 Hz, 2H), 7.45 (d, J=7.83 Hz, 2H), 7.31 (s, 1H), 4.76 (s, 2H).

Step 5: Synthesis of 6-Chloro-1-(4-(1-(methyl-d3)-4-(trifluoromethyl)-1H-imidazol-2-yl)benzyl)-1H-pyrazolo[3,4-d]pyrimidine (I-15)

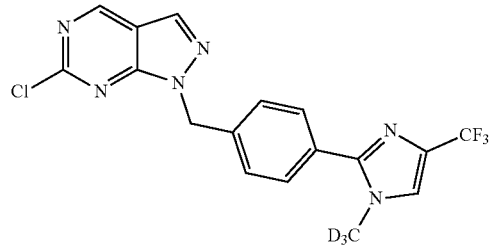 [SMILES: [2H]C([2H])([2H])n1cc(C(F)(F)F)nc1-c1ccc(Cn2ncc3cnc(Cl)nc32)cc1]

To a mixture of (4-(1-(methyl-d3)-4-(trifluoromethyl)-1H-imidazol-2-yl)phenyl)methanol (0.500 g, 1.930 mmol) and 6-chloro-1H-pyrazolo[3,4-d]pyrimidine 7 (0.335 g, 2.181 mmol) in dry THF (5 mL) at 0° C., was added triphenylphosphine (0.657 g, 2.509 mmol). The resulting mixture was stirred for 5 min, and then treated with diethyl azodicarboxylate (0.434 g, 2.509 mmol) dropwise. The mixture was further stirred at 0° C. for 2 h. After completion of the reaction (monitored by TLC), the mixture was diluted with water (30 mL) and extracted with EA (3×30 mL). The combined organic layer was washed with brine (3×30 mL), dried over anhydrous Na$_2$SO$_4$, filtered, and concentrated under vacuum. The crude compound was purified by silica gel chromatography (0-3% methanol in DCM) to afford 0.400 g of the title compound. LC-MS (Method B) (ESI+):

m/z 396.00 (M+H)+; 1H-NMR (400 MHz, CDCl3) δ 9.05 (s, 1H), 8.18 (s, 1H), 7.61 (d, J=8.31 Hz, 2H), 7.47 (d, J=7.82 Hz, 2H), 7.30 (s, 1H), 5.69 (s, 2H).

Preparation of Common Intermediate I-16

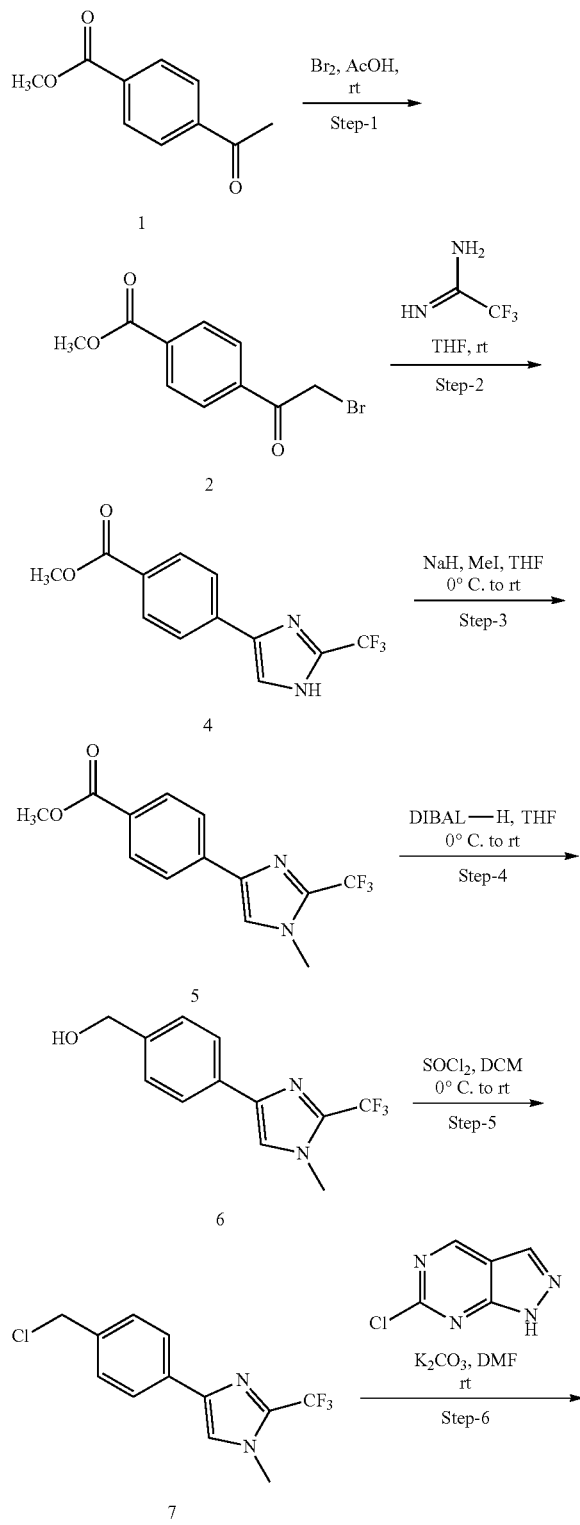

I-16

Step 1: Synthesis of Methyl 4-(2-bromoacetyl)benzoate

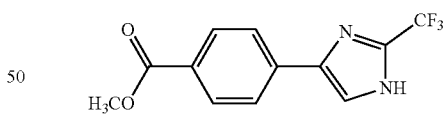

To a stirred solution of methyl 4-acetylbenzoate (5.00 g, 28.0 mmol) in AcOH (40 mL), was added Br2 (1.00 mL, 19.6 mmol) in AcOH (10 mL) dropwise, and the reaction mixture was stirred at room temperature for 6 h. Progress of the reaction was monitored by TLC. After completion, the reaction mixture was poured onto ice water (100 mL), and the solid obtained was filtered and dried. The crude compound was purified by silica gel chromatography using 5-7% EA in hexane to afford 3.50 g of the title compound. LC-MS (Method C) (ESI+): m/z 278.95 (M+Na)+; 1H-NMR (400 MHz, DMSO-d6) δ 8.04-8.15 (m, 4H), 5.00 (s, 2H), 3.89 (s, 3H).

Step 2: Synthesis of Methyl 4-(2-(trifluoromethyl)-1H-imidazol-4-yl)benzoate

To a stirred solution of 2,2,2-trifluoroacetimidamide (4.37 g, 39.0 mmol) in THF (30 mL), was added methyl 4-(2-bromoacetyl)benzoate (2.00 g, 7.80 mmol), and the reaction mixture was stirred at room temperature for 5 h. Progress of the reaction was monitored by TLC. After completion, the reaction mixture was diluted with EA (20 mL) and washed with brine (2×20 mL). The combined organic layer was dried over anhydrous sodium sulfate, filtered, and concentrated under reduced pressure. The crude compound was purified by silica gel chromatography using 10-15% EA in hexane to afford 0.81 g of the title compound. LC-MS (Method B) (ESI+): m/z 270.90 (M+H)+; 1H-NMR (400 MHz, DMSO-d6) δ 13.89 (s, 1H), 8.14 (s, 1H), 7.98 (s, 4H), 3.86 (s, 3H).

Step 3: Synthesis of Methyl 4-(1-methyl-2-(trifluoromethyl)-1H-imidazol-4-yl)benzoate

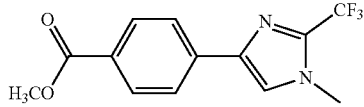

To a stirred solution of methyl 4-(2-(trifluoromethyl)-1H-imidazol-4-yl)benzoate (0.80 g, 2.9 mmol) in THF (15 mL) at 0° C., was added NaH (60% dispersion in mineral oil, 0.178 g, 4.40 mmol) portion wise, and the reaction mixture was stirred at same temperature for 15 min. To the resulting reaction mixture, methyl iodide (0.624 g, 4.40 mmol) was added, and the reaction mixture was stirred at room temperature for 16 h. Progress of the reaction was monitored by TLC. After completion, the reaction mixture was quenched with ice water (50 mL) and extracted with EA (2×30 mL). The combined organic layer was washed with brine (2×30 mL), dried over anhydrous sodium sulfate, filtered, and concentrated under reduced pressure to afford 0.80 g of the title compound. LC-MS (Method B) (ESI+): m/z 284.95 (M+H)$^+$; $^1$H-NMR (400 MHz, DMSO-d$_6$) δ 8.12-8.17 (m, 1H), 7.96-8.02 (m, 2H), 7.88-7.94 (m, 2H), 3.86 (s, 6H).

Step 4: Synthesis of (4-(1-Methyl-2-(trifluoromethyl)-1H-imidazol-4-yl)phenyl)methanol

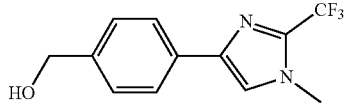 [SMILES: Cn1cc(-c2ccc(CO)cc2)nc1C(F)(F)F]

To a stirred solution of methyl 4-(1-methyl-2-(trifluoromethyl)-1H-imidazol-4-yl)benzoate (0.80 g, 2.8 mmol) in THF (10 mL) at 0° C., was added DIBAL-H (1M in toluene, 5.63 mL, 5.63 mmol) dropwise, and the reaction mixture was stirred at room temperature for 1 h. Progress of the reaction was monitored by TLC. After completion, the reaction mixture was quenched with 2N HCl (20 mL) and extracted with EA (2×30 mL). The combined organic layer was dried over anhydrous sodium sulfate, filtered, and concentrated under reduced pressure to afford 0.65 g of the title compound, which was used in subsequent reactions without further purification. LC-MS (Method B) (ESI+): m/z 256.85 (M+H)$^+$.

Step 5: Synthesis of 4-(4-(Chloromethyl)phenyl)-1-methyl-2-(trifluoromethyl)-1H-imidazole

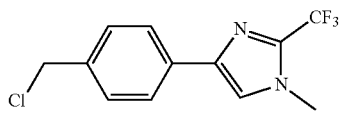 [SMILES: Cn1cc(-c2ccc(CCl)cc2)nc1C(F)(F)F]

To a stirred solution of (4-(1-methyl-2-(trifluoromethyl)-1H-imidazol-4-yl)phenyl)methanol (0.65 g, 2.5 mmol) in DCM (10 mL) at 0° C., was added SOCl$_2$ (0.27 mL, 3.80 mmol), and the reaction mixture was stirred at room temperature for 1 h. Progress of the reaction was monitored by TLC. After completion, the reaction mixture was diluted with DCM (50 mL) and washed with saturated NaHCO$_3$ solution (3×30 mL). The combined organic layer was dried over anhydrous sodium sulfate, filtered, and concentrated under reduced pressure to afford 0.65 g of the title compound, which was used in subsequent reactions without further purification. LC-MS (Method B) (ESI+): m/z 274.90 (M+H)$^+$; $^1$H-NMR (400 MHz, DMSO-d$_6$) δ 8.00 (s, 1H), 7.77 (d, J=7.8 Hz, 2H), 7.46 (d, J=7.8 Hz, 2H), 4.78 (s, 2H), 3.84 (s, 3H).

Step 6: Synthesis of 6-Chloro-1-(4-(1-methyl-2-(trifluoromethyl)-1H-imidazol-4-yl)benzyl)-1H-pyrazolo[3,4-d]pyrimidine (I-16)

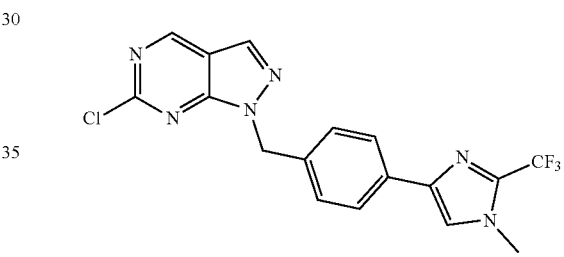

To a stirred solution of 6-chloro-1H-pyrazolo[3,4-d]pyrimidine (0.40 g, 2.5 mmol) in DMF (10 mL), was added K$_2$CO$_3$ (0.517 g, 3.70 mmol) in one portion. After stirring for 10 minutes at room temperature, 4-(4-(chloromethyl)phenyl)-1-methyl-2-(trifluoromethyl)-1H-imidazole (0.638 g, 2.30 mmol) was added, and the reaction mixture was stirred at room temperature for 16 h. Progress of the reaction was monitored by TLC. After completion, the reaction mixture was poured onto ice water (50 mL) and extracted with EA (2×30 mL). The combined organic layer was dried over anhydrous sodium sulfate, filtered, and concentrated under reduced pressure. The crude compound was purified by silica gel chromatography using 0-50% EA in hexane to afford 0.15 g of the title compound. LC-MS (Method B) (ESI+): m/z 392.95 (M+H)$^+$; $^1$H-NMR (400 MHz, DMSO-d$_6$) δ 9.30 (s, 1H), 8.49 (s, 1H), 7.94 (s, 1H), 7.72 (d, J=8.3 Hz, 2H), 7.29 (d, J=8.3 Hz, 2H), 5.63 (s, 2H), 3.82 (s, 3H).

The following intermediate was made from the appropriate reagents according to the procedure for Intermediate I-16.

| Intermediate | Structure | Analytics |
|---|---|---|
| I-17 | 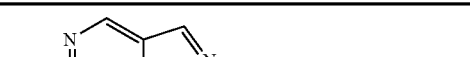 | LC-MS (Method B) (ESI+): m/z 421.00 (M + H)+; $^1$H-NMR (400 MHz, DMSO-$d_6$) δ 9.30 (s, 1H), 8.49 (s, 1H), 8.24 (s, 1H), 7.76 (d, J = 7.98 Hz, 2H), 7.30 (d, J = 7.98 Hz, 2H), 5.63 (s, 2H), 4.56 (td, J = 6.48, 12.96 Hz, 1H), 1.48 (d, J = 6.48 Hz, 6H). |
Preparation of Common Intermediate I-18
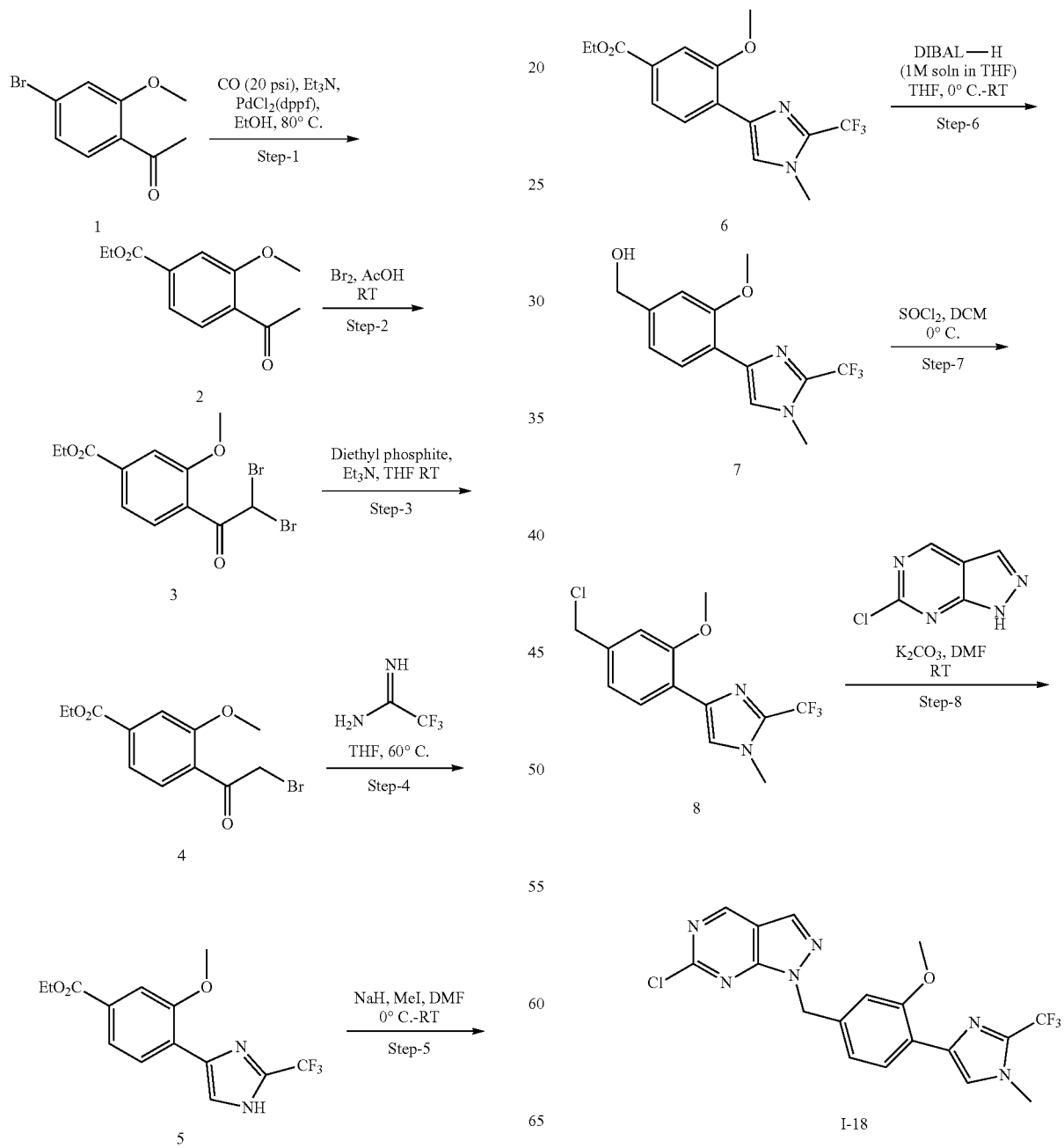

Step 1: Synthesis of ethyl 4-acetyl-3-methoxybenzoate

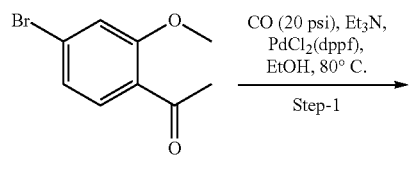

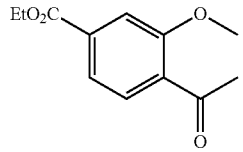

To a stirred solution of 1-(4-bromo-2-methoxyphenyl)ethan-1-one 1 (3.00 g, 13.1 mmol) in ethanol (60 mL), was added triethylamine (3.67 mL, 26.2 mmol) and the mixture was degassed with argon for 10 min. To the reaction mixture was added PdCl$_2$(dppf) (0.957 g, 0.131 mmol) at room temperature, and the resulting mixture was heated at 80° C. under carbon monoxide (20 psi pressure) for 3 h. Progress of the reaction was monitored by TLC. After completion, the reaction mixture was concentrated under reduced pressure. The crude compound was purified by silica gel chromatography using 0-5% EA in hexane as eluent to afford the title compound (2.50 g). LC-MS (Method B) (ESI+): m/z 223.00 (M+H)$^+$; H-NMR (400 MHz, CDCl$_3$) δ 7.72-7.76 (m, 1H), 7.64-7.70 (m, 2H), 4.42 (dq, J=3.99, 7.15 Hz, 2H), 4.00 (br s, 1H), 3.99 (s, 2H), 2.65 (s, 1H), 2.64 (s, 2H), 1.43 (dt, J=3.99, 6.98 Hz, 3H).

Step 2: Synthesis of ethyl 4-(2,2-dibromoacetyl)-3-methoxybenzoate

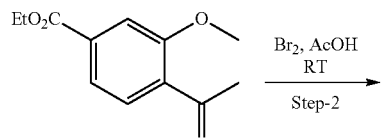

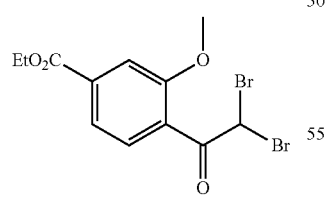

To a stirred solution of ethyl 4-acetyl-3-methoxybenzoate 2 (1.00 g, 4.50 mmol) in acetic acid (10 mL), was added bromine (0.16 mL, 3.153 mmol) at room temperature. The resulting mixture was stirred for 3 h, and progress of the reaction was monitored by TLC. After completion, the reaction mixture was concentrated under reduced pressure. The crude residue was diluted with water (30 mL) and EA (50 mL), and then neutralized using saturated Na$_2$CO$_3$ solution. The organic layer was washed with brine (30 mL), dried over anhydrous sodium sulfate, filtered and concentrated under reduced pressure to afford the title compound (1.20 g). $^1$H-NMR (400 MHz, CDCl$_3$) δ 7.83 (d, J=7.98 Hz, 1H), 7.69 (d, J=8.48 Hz, 1H), 7.67 (s, 1H), 4.59 (s, 1H), 4.41 (q, J=7.15 Hz, 2H), 4.01 (s, 3H), 1.42 (t, J=6.98 Hz, 3H).

Step 3: Synthesis of ethyl 4-(2-bromoacetyl)-3-methoxybenzoate

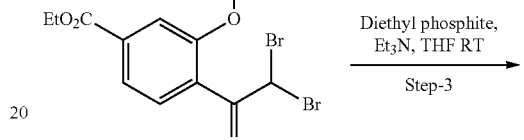

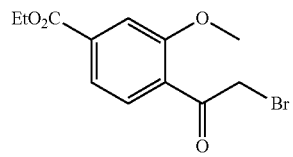

To a stirred solution of ethyl 4-(2,2-dibromoacetyl)-3-methoxybenzoate 3 (1.20 g, 3.17 mmol) in THF (15 mL), was added triethyl amine (0.44 mL, 3.17 mmol) and diethylphosphite (0.433 g, 3.166 mmol) at room temperature. The resulting mixture was stirred for 3 h, and progress of the reaction was monitored by TLC. After completion, the reaction mixture diluted with EA (30 mL) and washed with brine (3×10 mL). The organic layer was dried over anhydrous sodium sulfate, filtered and concentrated under reduced pressure. The crude compound was purified by silica gel chromatography using 10-15% EA in hexane as eluent to afford the title compound (0.900 g). LC-MS (Method B) (ESI+): m/z 300.80 (M)$^+$; $^1$H-NMR (400 MHz, CDCl$_3$) δ 7.84 (d, J=7.98 Hz, 1H), 7.69 (d, J=7.98 Hz, 1H), 7.67 (s, 1H), 4.60 (s, 2H), 4.41 (q, J=7.15 Hz, 2H), 4.02 (s, 3H), 1.42 (t, J=6.98 Hz, 3H).

Step 4: Synthesis of ethyl 3-methoxy-4-(2-(trifluoromethyl)-1H-imidazol-4-yl)benzoate

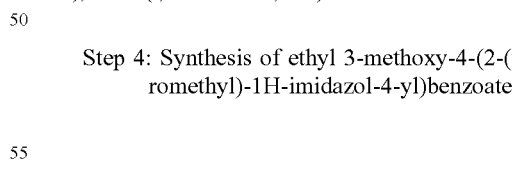

-continued

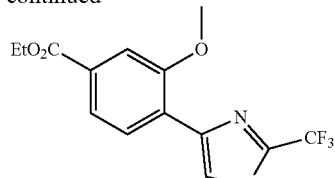

To a stirred solution of ethyl 4-(2-bromoacetyl)-3-methoxybenzoate 4 (0.900 g, 3.00 mmol) in THF (20 mL), was added 2,2,2-trifluoroacetimidamide (1.68 g, 15.0 mmol) at room temperature. The reaction mixture was then heated at 60° C. for 16 h. Progress of the reaction was monitored by TLC. After completion, the reaction mixture was diluted with EA (50 mL) and washed with saturated NaHCO₃ solution (2×30 mL). The organic layer was dried over anhydrous sodium sulfate, filtered and concentrated under reduced pressure. The crude residue was purified by silica gel chromatography using 20-30% EA in hexane as eluent to afford the title compound (0.300 g). LC-MS (Method B) (ESI+): m/z 315.10 (M+H)⁺; ¹H-NMR (400 MHz, DMSO-d₆) δ 13.82 (br s, 1H), 8.17 (d, J=7.48 Hz, 1H), 7.92 (br s, 1H), 7.64 (d, J=7.98 Hz, 1H), 7.59 (s, 1H), 4.33 (q, J=7.31 Hz, 2H), 4.00 (s, 3H), 1.34 (t, J=6.98 Hz, 3H).

Step 5: Synthesis of ethyl 3-methoxy-4-(1-methyl-2-(trifluoromethyl)-1H-imidazol-4-yl)benzoate

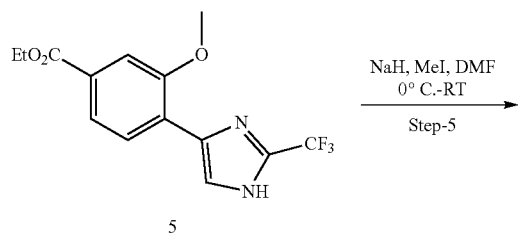

To a stirred solution of ethyl 3-methoxy-4-(2-(trifluoromethyl)-1H-imidazol-4-yl)benzoate 5 (0.300 g, 0.955 mmol) in DMF (10 mL) at 0° C., was added 60% dispersion of sodium hydride in oil (0.057 g, 1.43 mmol) and methyl iodide (0.089 mL, 1.43 mmol). The reaction mixture was allowed to warm to room temperature, and then stirred for 2 h. Progress of the reaction was monitored by TLC. After completion, the reaction mixture was poured over ice cold water (50 mL) and extracted with EA (2×30 mL). The combined organic layer was dried over anhydrous sodium sulfate, filtered and concentrated under reduced pressure. The crude compound was purified by silica gel chromatography using 0-15% EA in hexane as eluent to afford the title compound (0.240 g). LC-MS (Method B) (ESI+); m/z 328.90 (M+H)⁺; ¹H-NMR (400 MHz, DMSO-d₆) δ 8.14 (d, J=8.48 Hz, 1H), 8.04 (s, 1H), 7.64 (dd, J=1.50, 7.98 Hz, 1H), 7.59 (s, 1H), 4.33 (q, J=7.15 Hz, 2H), 4.00 (s, 3H), 3.87 (s, 3H), 1.33 (t, J=7.23 Hz, 3H).

Step 6: Synthesis of (3-methoxy-4-(1-methyl-2-(trifluoromethyl)-1H-imidazol-4-yl)phenyl)methanol

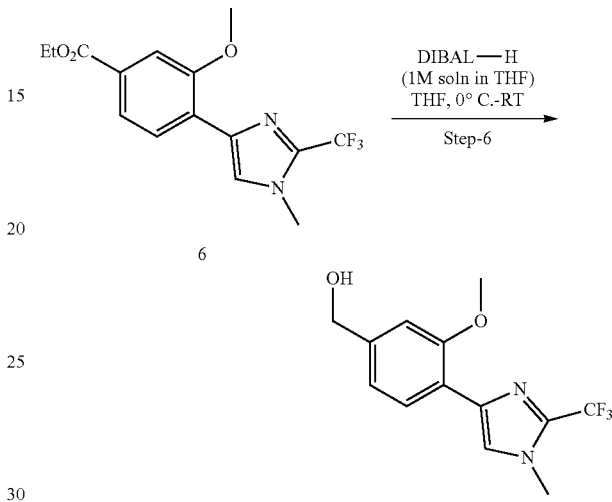

To a stirred solution of ethyl 3-methoxy-4-(1-methyl-2-(trifluoromethyl)-1H-imidazol-4-yl) benzoate 6 (0.320 g, 0.975 mmol) in dry THF (10 mL) at 0° C., was added DIBAL-H (1M solution in toluene, 1.46 mL, 1.46 mmol). The reaction mixture was allowed to warm to room temperature, and then stirred for 2 h. Progress of the reaction was monitored by TLC. After completion, the reaction mixture was quenched with 1N HCl (20 mL) and extracted with EA (3×20 mL). The combined organic layer was dried over anhydrous sodium sulfate, filtered and concentrated under reduced pressure to afford the crude title compound (0.260 g). LC-MS (Method B) (ESI+): m/z 287.30 (M+H)⁺; ¹H-NMR (400 MHz, DMSO-d₆) δ 7.94 (d, J=7.83 Hz, 1H), 7.84 (s, 1H), 7.05 (s, 1H), 6.95 (d, J=7.82 Hz, 1H), 5.21 (t, J=4.89 Hz, 1H), 4.51 (d, J=4.89 Hz, 2H), 3.92 (s, 3H), 3.84 (s, 3H).

Step 7: Synthesis of 4-(4-(chloromethyl)-2-methoxyphenyl)-1-methyl-2-(trifluoromethyl)-1H-imidazole

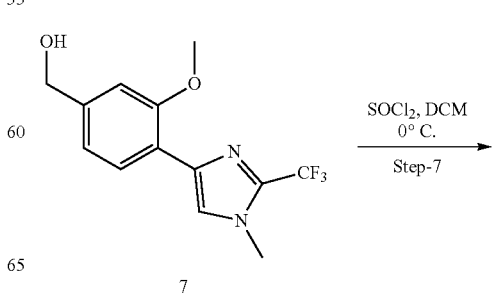

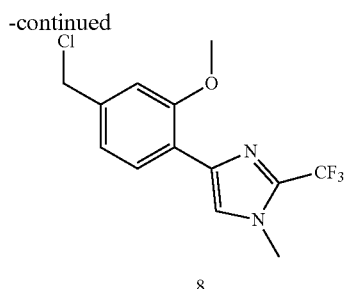

To a stirred solution of (3-methoxy-4-(1-methyl-2-(trifluoromethyl)-1H-imidazol-4-yl)phenyl)methanol 7 (0.260 g, 0.909 mmol) in DCM (10 mL) at 0° C., was added thionyl chloride (0.065 mL, 0.91 mmol). The mixture was stirred for 1 h, and progress of the reaction was monitored by TLC. After completion, the reaction mixture was diluted with DCM (20 mL) and washed with saturated $Na_2CO_3$ solution (3×20 mL). The organic layer was dried over anhydrous sodium sulfate, filtered and concentrated under reduced pressure to afford the crude title compound (0.260 g). LC-MS (Method B) (ESI+): m/z 304.80 (M+H)+; $^1$H-NMR (400 MHz, DMSO-d$_6$) δ 8.00 (d, J=7.98 Hz, 1H), 7.90 (s, 1H), 7.18 (s, 1H), 7.08 (d, J=7.98 Hz, 1H), 4.78 (s, 2H), 3.94 (s, 3H), 3.85 (s, 3H).

Step 8: Synthesis of 6-chloro-1-(3-methoxy-4-(1-methyl-2-(trifluoromethyl)-1H-imidazol-4-yl)benzyl)-1H-pyrazolo[3,4-d]pyrimidine (I-18)

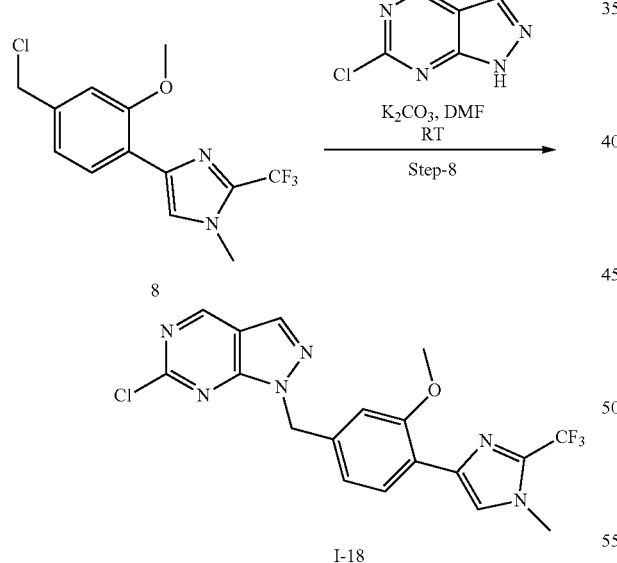

To a stirred solution of 4-(4-(chloromethyl)-2-methoxyphenyl)-1-methyl-2-(trifluoromethyl)-1H-imidazole 8 (0.250 g, 0.822 mmol) in DMF (5 mL), was added potassium carbonate (0.170 g, 1.23 mmol) and 6-chloro-1H-pyrazolo[3,4-d]pyrimidine (0.126 g, 0.822 mmol) at room temperature. The resulting mixture was stirred for 16 h, and progress of the reaction was monitored by TLC. After completion, the reaction mixture was poured over ice cold water (30 mL) and extracted with EA (2×30 mL). The combined organic layer was washed with brine (2×30 mL), dried over anhydrous sodium sulfate, filtered and concentrated under reduced pressure. The crude compound was purified by silica gel chromatography using 30-50% EA in hexane as eluent to afford the title compound (0.150 g). LC-MS (Method B) (ESI+): m/z 423.00 (M+H)+; $^1$H-NMR (400 MHz, DMSO-d$_6$) δ 9.31 (s, 1H), 8.50 (s, 1H), 7.92 (d, J=7.98 Hz, 1H), 7.86 (s, 1H), 7.11 (s, 1H), 6.82 (d, J=7.98 Hz, 1H), 5.64 (s, 2H), 3.89 (s, 3H), 3.83 (s, 3H).

Preparation of Common Intermediate I-19

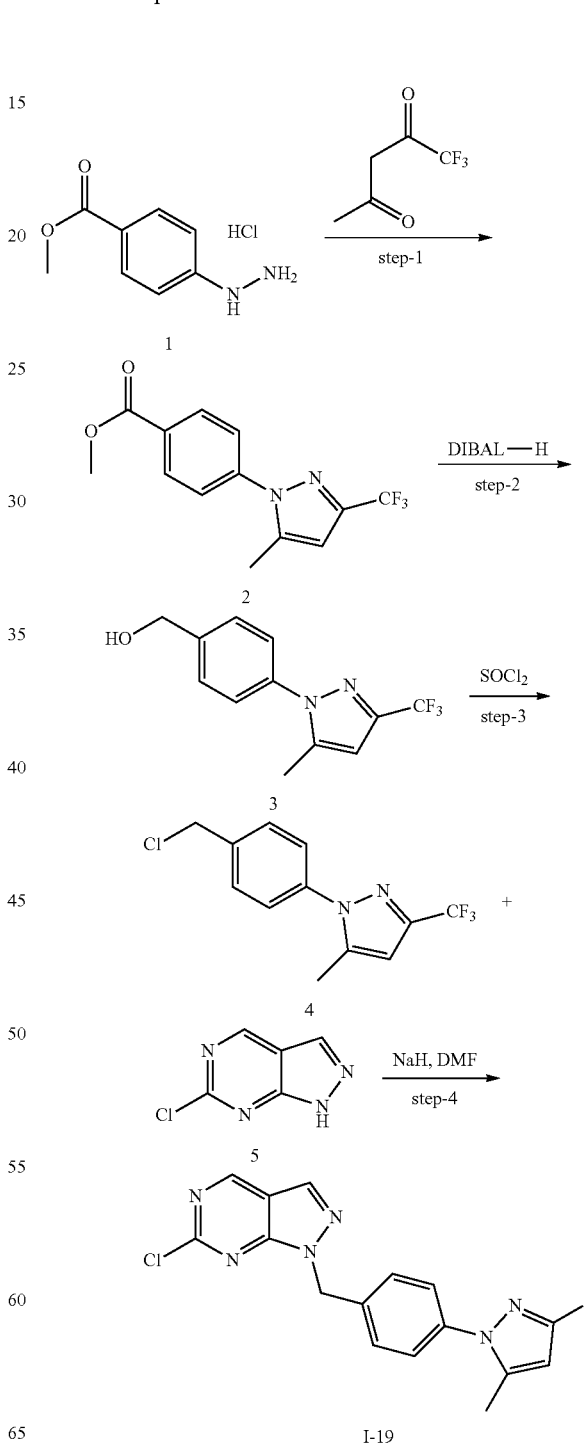

Step 1: Synthesis of Methyl 4-(5-methyl-3-(trifluoromethyl)-1H-pyrazol-1-yl)benzoate

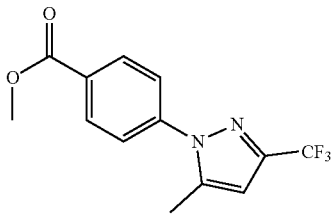 [SMILES: COC(=O)c1ccc(-n2nc(C(F)(F)F)cc2C)cc1]

To a solution of methyl 4-hydrazinylbenzoate hydrochloride (1.0 g, 4.92 mmol) and 1,1,1-trifluoropentane-2,4-dione (758 mg, 4.92 mmol) in HFIP (5 mL) cooled to 0° C., was added a solution of TEA (994 mg, 9.84 mmol) in HFIP (3 mL) dropwise over 5 min. After addition, the resulting mixture was stirred at room temperature for 1 hour, then quenched with water (20 mL) and extracted with DCM (100 mL×3). The combined organics were dried with anhydrous Na$_2$SO$_4$ (30 g), filtered and concentrated in vacuo. The residue was purified by silica gel chromatography (EA:n-Hex=1:20) to provide 1.1 g of the title compound. LC-MS (Method A) (ESI+): m/z 285 (M+H)$^+$; $^1$H-NMR (300 MHz, CDCl$_3$) δ 8.18 (d, J=8.7 Hz, 2H), 7.57 (d, J=8.7 Hz, 2H), 6.50 (s, 1H), 3.96 (s, 3H), 2.41 (s, 3H).

Step 2: Synthesis of (4-(5-Methyl-3-(trifluoromethyl)-1H-pyrazol-1-yl)phenyl)methanol

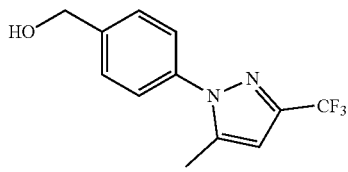 [SMILES: Cc1cc(C(F)(F)F)nn1-c1ccc(CO)cc1]

To a solution of methyl 4-(5-methyl-3-(trifluoromethyl)-1H-pyrazol-1-yl)-benzoate (1.0 g, 3.52 mmol) in dry THF (20 mL) at 0° C., was added DIBAL-H (10.5 mL, 10.56 mmol, 1 M in toluene) over 10 min. After the addition, the reaction mixture was warmed to rt. After the reaction was complete as indicated by TLC analysis, the reaction was quenched with a saturated NH$_4$Cl solution (20 mL), extracted with EA (100 ml×3). The combined organic layers were dried with anhydrous Na$_2$SO$_4$ (50 g), filtered and concentrated. The crude product was purified by silica gel chromatography (PE:EA=20:1 to 10:1) to give 1.1 g of the title compound. $^1$H-NMR (300 MHz, CDCl$_3$) δ 7.40-7.49 (m, 4H), 6.46 (s, 1H), 4.76 (s, 2H), 2.34 (s, 3H), 2.17 (br s, 1H).

Step 3: Synthesis of 1-(4-(Chloromethyl)phenyl)-5-methyl-3-(trifluoromethyl)-1H-pyrazole

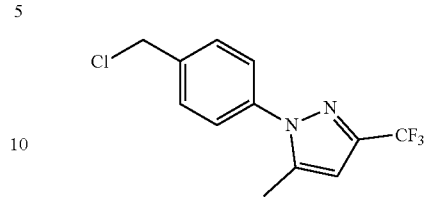

To a solution of (4-(5-methyl-3-(trifluoromethyl)-1H-pyrazol-1-yl)phenyl)methanol (0.82 g, 3.20 mmol) in DCE (20 mL), was added in SOCl$_2$ (1.14 g, 9.61 mmol) in one portion. After the reaction was stirred at 50° C. for 30 min, the mixture was cooled to 0° C. and quenched with water (10 mL). The resulting solution was neutralized with saturated NaHCO$_3$ (aq) solution and extracted with DCM (3×100 mL). The combined organic layer was dried over anhydrous Na$_2$SO$_4$ (50 g), filtered and concentrated to dryness to afford 480 mg of crude product, which was used for the next step directly. LC-MS (Method A) (ESI+): m/z 275 (M+H)$^+$; $^1$H-NMR (300 MHz, CDCl$_3$) δ 7.53 (d, J=8.7 Hz, 2H), 7.46 (d, J=8.7 Hz, 2H), 6.47 (s, 1H), 4.64 (s, 2H), 2.37 (s, 3H).

Step 4: Synthesis of 6-Chloro-1-(4-(5-methyl-3-(trifluoromethyl)-1H-pyrazol-1-yl)benzyl)-1H-pyrazolo[3,4-d]pyrimidine (I-19)

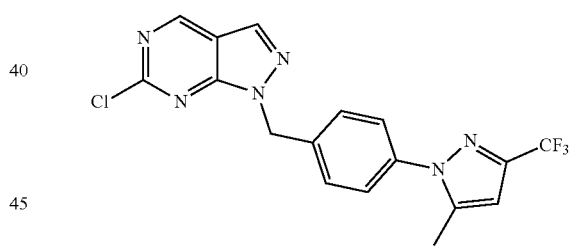

To a solution of 1-(4-(chloromethyl)phenyl)-5-methyl-3-(trifluoromethyl)-1H-pyrazole (0.48 g, 1.75 mmol) in DMF (8 mL), was added 6-chloro-1H-pyrazolo[3,4-d]pyrimidine (0.27 g, 1.75 mmol) and K$_2$CO$_3$ (0.60 g, 4.38 mmol). The reaction was stirred at room temperature for 2 hours, and then quenched by water (20 mL) and extracted with EA (50 mL×3). The combined organic layer was dried over anhydrous Na$_2$SO$_4$ (30 g), filtered and concentrated in vacuo. The resulting residue was purified by silica gel chromatography (PE:EA=20:1 to 10:1) to give 370 mg of the title product with a small amount of regioisomer. LC-MS (Method A) (ESI+): m/z 393,395 (M+H)$^+$; $^1$H-NMR (300 MHz, CDCl$_3$) δ 9.06 (s, 1H), 8.19 (s, 1H), 7.51 (d, J=8.7 Hz, 2H), 7.42 (d, J=8.7 Hz, 2H), 6.44 (s, 1H), 5.70 (s, 2H), 2.33 (s, 3H).

The following common intermediates were prepared according the procedure of I-19 from the appropriate reagents:

| Intermediate | Structure | Analytics |
|---|---|---|
| I-20 | 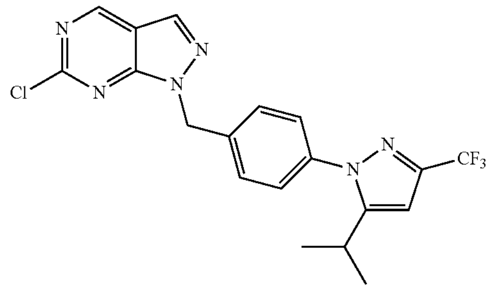 [SMILES: CC(C)c1cc(C(F)(F)F)nn1-c1ccc(Cn2ncc3cnc(Cl)nc32)cc1] | LC-MS (Method B) (ESI+): m/z 421.00 (M + H)+; 1H-NMR (300 MHz, DMSO-d6) δ 9.33 (s, 1H), 8.53 (s, 1H), 7.41-7.53 (m, 4H), 6.81 (s, 1H), 5.76 (s, 2H), 2.94 (td, J = 6.73, 13.46 Hz, 1H), 1.12 (d, J = 6.98 Hz, 6H). |
| I-21 | 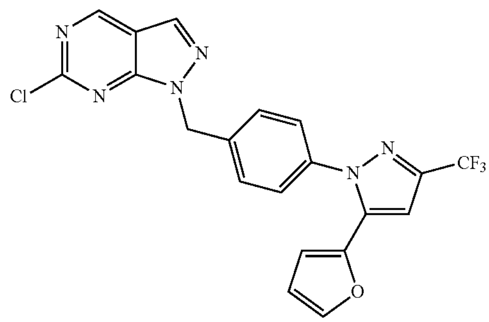 [SMILES: FC(F)(F)c1cc(-c2ccco2)n(-c2ccc(Cn3ncc4cnc(Cl)nc43)cc2)n1] | LC-MS (Method B) (ESI+): m/z 445.00 (M + H)+; 1H-NMR (300 MHz, DMSO-d6) δ 9.33 (s, 1H), 8.54 (s, 1H), 7.76 (s, 1H), 7.45-7.49 (m, 2H), 7.38-7.42 (m, 2H), 7.21-7.27 (m, 1H), 6.52-6.56 (m, 1H), 6.28 (d, J = 3.49 Hz, 1H), 5.77 (s, 2H). |

Preparation of Common Intermediate I-22

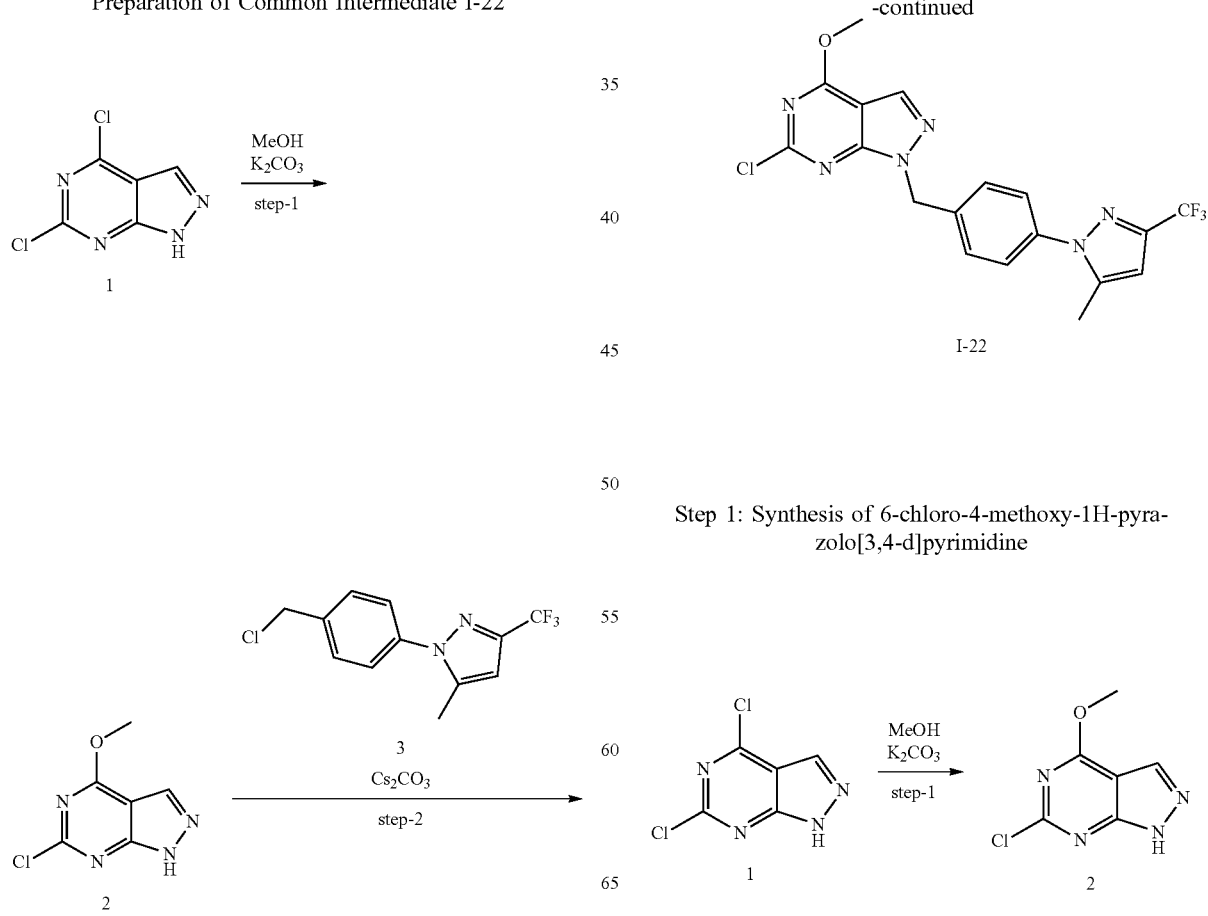

Step 1: Synthesis of 6-chloro-4-methoxy-1H-pyrazolo[3,4-d]pyrimidine

To a solution of 4,6-dichloro-1H-pyrazolo[3,4-d]pyrimidine 1 (330 mg, 1.74 mmol) in methanol (10 mL) was added potassium carbonate (240 mg, 1.74 mmol). After the mixture was stirred at rt for 24 h, the reaction was quenched with saturated ammonium chloride (30 mL) solution and extracted with EA (20 mL×3). The combined organic layer was dried over sodium sulfate (30 g), filtered and concentrated. The residue was purified by silica gel chromatography (eluent: EA/n-Hex=1/10) to afford 120 mg of the title compound. LC-MS (Method A) (ESI+): m/z 185 (M+H)+; ¹H-NMR (300 MHz, CDCl₃) δ 10.69 (br s, 1H), 8.09 (s, 1H), 4.19 (s, 3H).

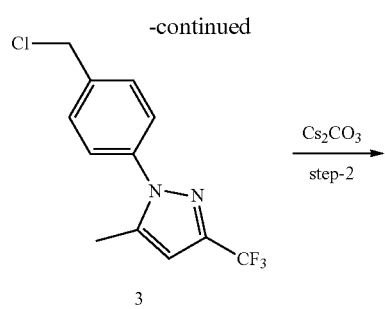

Step 2: Synthesis of 6-chloro-4-methoxy-1-(4-(5-methyl-3-(trifluoromethyl)-1H-pyrazol-1-yl)benzyl)-1H-pyrazolo[3,4-d]pyrimidine (I-22)

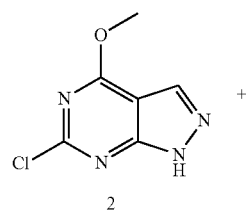

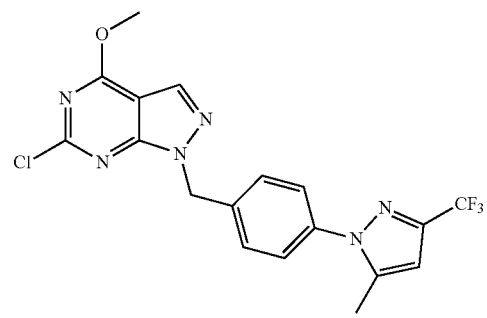

The compound was synthesized according to the procedure for the preparation of common intermediate I-19. LC-MS (Method A) (ESI+): m/z 423 (M+H)+; ¹H-NMR (300 MHz, CDCl₃) δ 8.05 (s, 1H), 7.45 (m, 4H), 6.44 (s, 1H), 5.63 (s, 2H), 4.15 (s, 3H), 2.31 (s, 3H).

The following common intermediate was prepared according the procedure of I-22 from the appropriate reagents:

| Intermediate | Structure | Analytics |
|---|---|---|
| I-22b | (structure shown) | LC-MS (Method A) (ESI+): m/z 437 (M + H)+; ¹H-NMR (300 MHz, CDCl₃) δ 7.97 (s, 1H), 7.47 (d, J = 8.1 Hz, 2H), 7.35 (d, J = 8.1 Hz, 2H), 7.28 (s, 1H), 5.56 (s, 2H), 4.11 (s, 3H), 3.96 (q, J = 7.5 Hz, 2H), 1.34 (t, J = 7.5 Hz, 3H). |

Preparation of Common Intermediate I-23

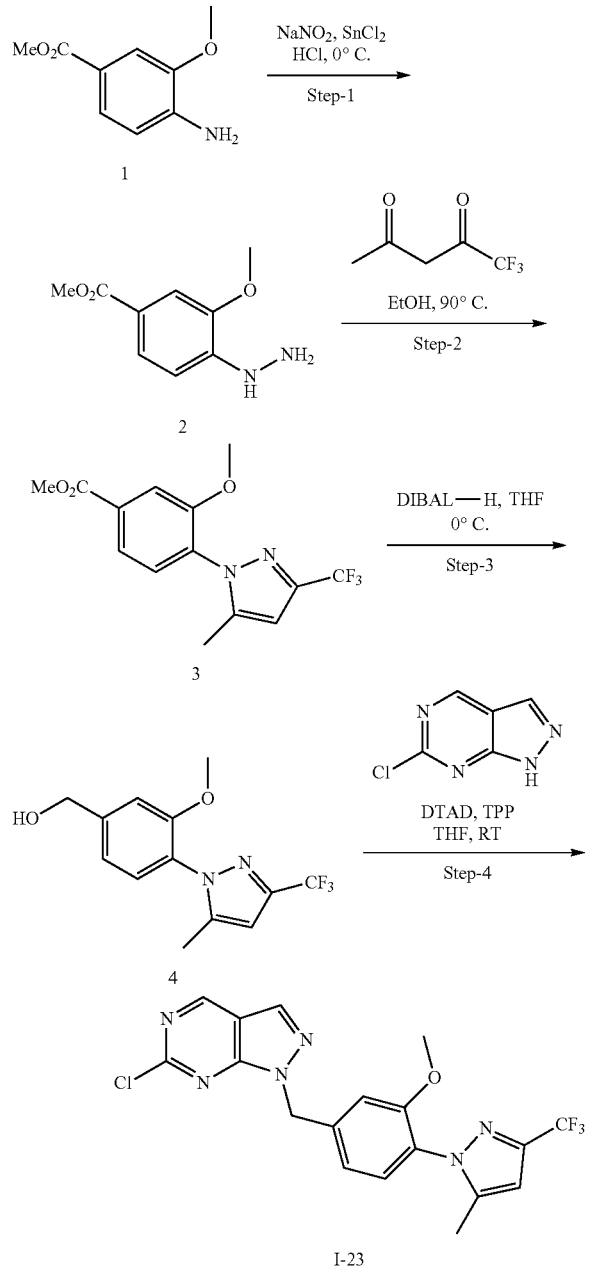

Step 1: Synthesis of methyl 4-hydrazineyl-3-methoxybenzoate

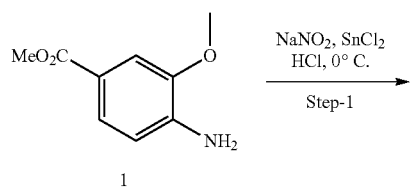

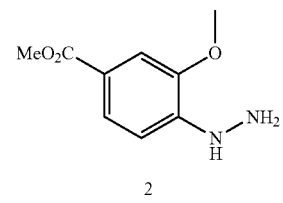

To a stirred solution of methyl 4-amino-3-methoxybenzoate 1 (5.0 g, 27.6 mmol) in conc. HCl (55 mL) at −10° C., was added dropwise an aqueous solution of NaNO$_2$ (1.99 g, 29.0 mmol) in water (5 mL). To the resulting reaction mixture was added dropwise a solution of SnCl$_2$ (26.0 g, 138 mmol) in conc. HCl (35 mL), and the reaction was stirred for 2 h. Progress of the reaction was monitored by TLC. After completion, the solid obtained was filtered and dried under reduced pressure. The crude compound was washed with diethyl ether (50 mL), filtered and dried under reduced pressure to afford the crude title compound (8.0 g) that was used in the next step without purification. $^1$H-NMR (400 MHz, DMSO-d$_6$) δ 10.43 (br s, 2H), 7.95-8.40 (m, 1H), 7.57 (d, J=8.31 Hz, 1H), 7.44 (s, 1H), 7.09 (d, J=8.31 Hz, 1H), 3.88 (s, 3H).

Step 2: Synthesis of methyl 3-methoxy-4-(5-methyl-3-(trifluoromethyl)-1H-pyrazol-1-yl)benzoate

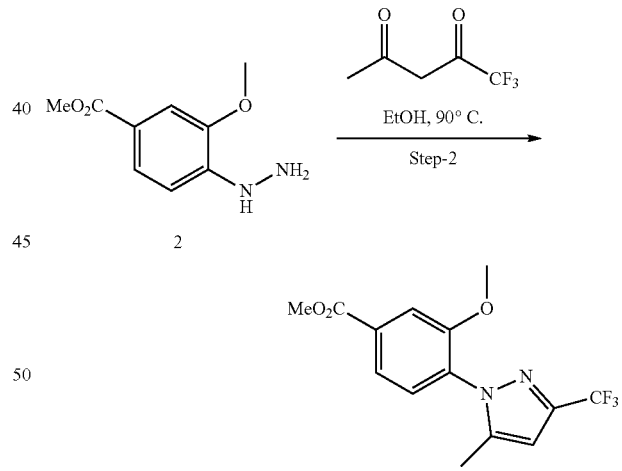

A stirred solution of methyl 4-hydrazinyl-3-methoxybenzoate 2 (2.0. g, 12.98 mmol) and 1,1,1-trifluoropentane-2,4-dione (6.09 g, 25.97 mmol) in ethanol (20 mL), was heated at 90° C. for 16 h. Progress of the reaction was monitored by TLC. After completion, the reaction mixture was cooled to room temperature and concentrated under reduced pressure. The crude compound was purified by size silica gel chromatography using 0-30% EA in hexane to afford the title compound (2.5 g). LC-MS (Method B) (ESI+): m/z 315.05 (M+H)$^+$.

Step 3: Synthesis of (3-methoxy-4-(5-methyl-3-(trifluoromethyl)-1H-pyrazol-1-yl) phenyl) methanol

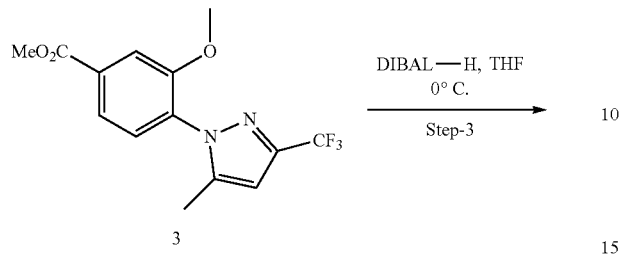

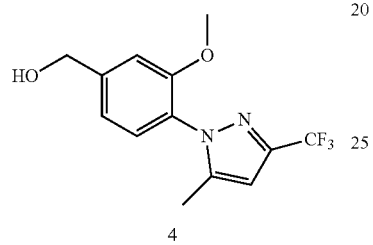

To a stirred solution of methyl 3-methoxy-4-(5-methyl-3-(trifluoromethyl)-1H-pyrazol-1-yl) benzoate 3 (2.5 g, 7.96 mmol) in THF (40 mL) at 0° C., was added dropwise DIBAL-H (16 mL, 15.9 mmol, 1.0 M solution in THF). The resulting mixture was stirred for 2 h at 0° C., and progress of the reaction was monitored by TLC. After completion, the reaction mixture was quenched with 1N HCl (4 mL) at 0° C. and extracted with EA (100 mL). The combined organic layer was dried over anhydrous sodium sulfate, filtered and concentrated under reduced pressure to afford the crude 4 (1.5 g). The crude product was used as is without purification. LC-MS (Method B) (ESI+): m/z 287.45 (M+H)$^+$; $^1$H-NMR (400 MHz, DMSO-d$_6$) δ 7.31 (d, J=7.98 Hz, 1H), 7.21 (s, 1H), 7.05 (d, J=7.98 Hz, 1H), 6.67 (s, 1H), 5.40 (br s, 1H), 4.59 (br s, 2H), 3.79 (s, 3H), 2.09 (s, 3H).

Step 4: Synthesis of 6-chloro-1-(3-methoxy-4-(5-methyl-3-(trifluoromethyl)-1H-pyrazol-1-yl)benzyl)-1H-pyrazolo[3,4-d]pyrimidine (I-23)

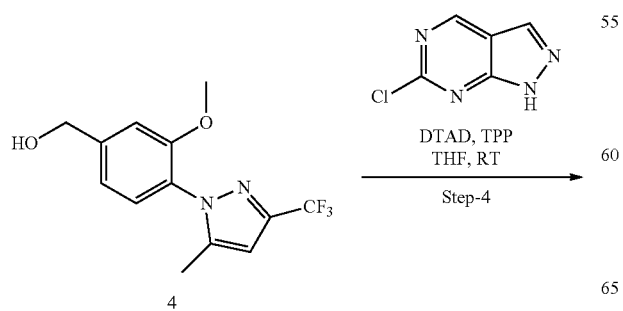

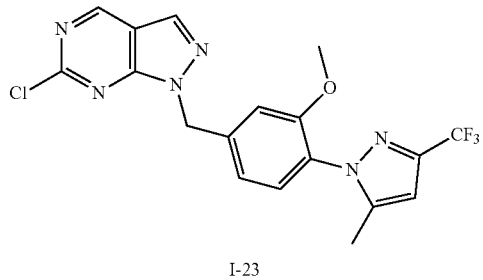

To an ice cooled solution of (3-methoxy-4-(5-methyl-3-(trifluoromethyl)-1H-pyrazol-1-yl) phenyl) methanol 4 (1.0 g, 3.494 mmol) in THF (10 mL), was added 6-chloro-1H-pyrazolo[3,4-d]pyrimidine (0.486 g, 3.144 mmol), DTAD (1.20 g, 5.240 mmol) and TPP (2.747 g, 10.48 mmol). The reaction mixture was stirred at room temperature for 2 h. Progress of the reaction was monitored by TLC. After completion, the reaction mixture was quenched with water (30 mL) and extracted with EA (3×50 mL). The combined organic layer was dried over anhydrous sodium sulfate, filtered and concentrated under reduced pressure. The crude compound was purified by size silica gel chromatography using 0-40% EA in hexane as eluent to afford the title compound (1.0 g). LC-MS (Method B) (ESI+): m/z 423 (M+H)$^+$.

Preparation of Common Intermediate I-24

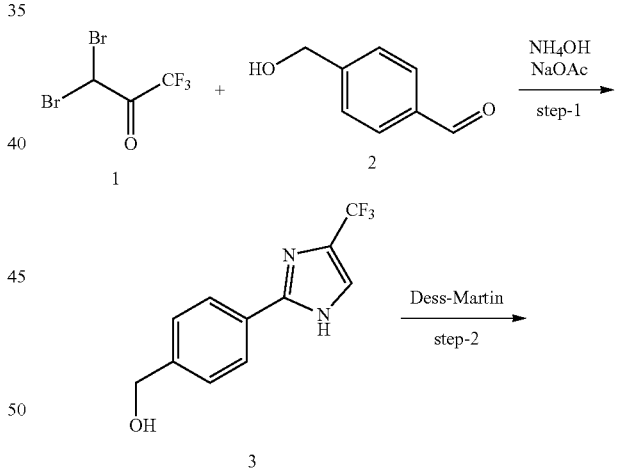

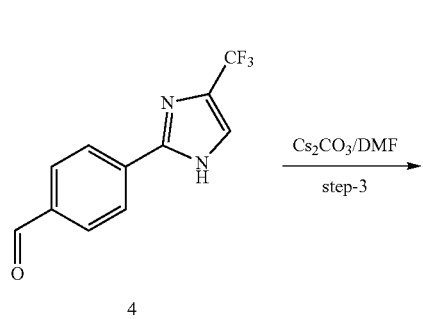

-continued

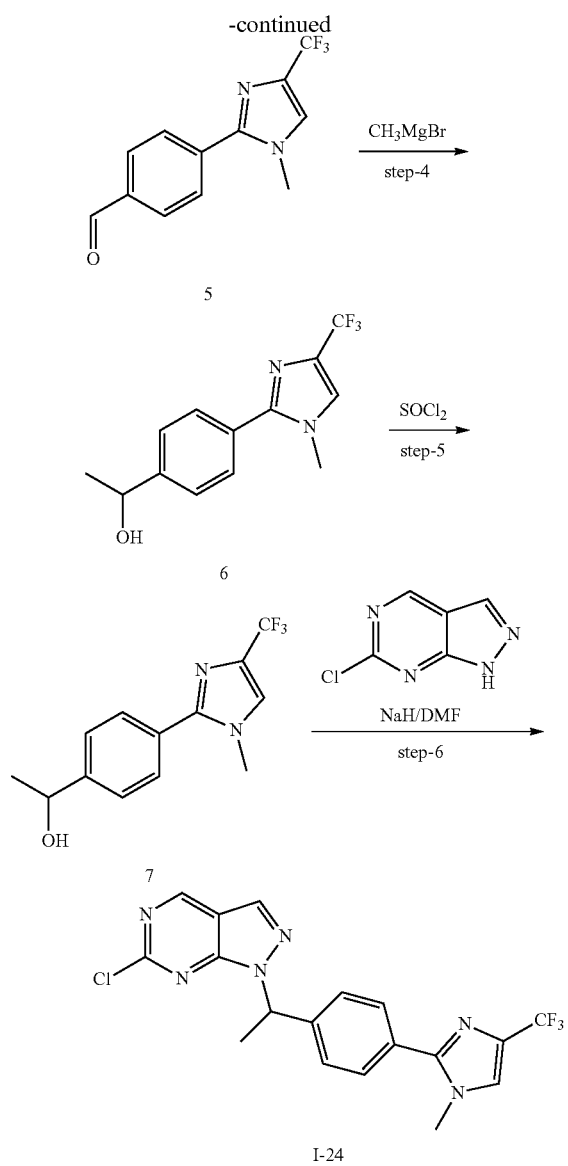

Step 1: Synthesis of (4-(4-(Trifluoromethyl)-1H-imidazol-2-yl)phenyl)methanol

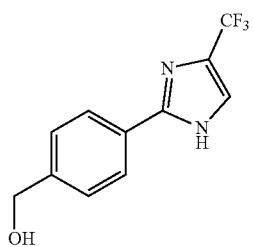 [SMILES: OCc1ccc(-c2nc(C(F)(F)F)c[nH]2)cc1]

A solution of 3,3-dibromo-1,1,1-trifluoropropan-2-one (1.0 g, 7.3 mmol) and NaOAc (533.5 mg, 8.1 mmol) in H₂O (7.3 mL), was stirred at 100° C. for 1 hour. The reaction mixture was then cooled to 0° C. and the solution of 4-(hydroxymethyl)benzaldehyde (2.18 g, 8.08 mmol) and NH₄OH (9.3 mL) in MeOH (37 mL), was added over 10 min. After addition, the reaction mixture was stirred at ambient temperature overnight. The resulting mixture was concentrated under reduced pressure to remove most of the solvent. To the concentrated residue was added water (20 mL) and the mixture was extracted with EA (100 mL×3). The combined organic layer was washed with brine, dried over anhydrous Na₂SO₄ (50 g), filtered, and concentrated to dryness in vacuo. The resulting crude product was slurried in DCM (30 mL), collected by filtration, and dried in vacuo to afford 1.1 g of the title compound. $^1$H-NMR (300 MHz, CD₃OD) δ 7.88 (d, J=8.4 Hz, 2H), 7.64 (s, 1H), 7.48 (d, J=8.4 Hz, 2H), 4.66 (s, 2H).

Step 2: Synthesis of 4-(4-(Trifluoromethyl)-1H-imidazol-2-yl)benzaldehyde


To a solution of (4-(4-(trifluoromethyl)-1H-imidazol-2-yl)phenyl)methanol (1 g, 4.1 mmol) in EA (80 mL), was added Dess-Martin reagent (2.6 g, 6.2 mmol) portion-wise at 0° C. over 5 min. After addition, the reaction was stirred at ambient temperature overnight. The resulting suspension was filtered, and the filter cake was rinsed with EA (20 mL). The filtrate was washed with saturated aqueous NH₄Cl solution (20 mL), dried with anhydrous Na₂SO₄ (20 g), filtered and concentrated in vacuo. The concentrated residue was purified by silica gel chromatography (PE:EA=20:1 to 5:1) to give 0.9 g of the title compound. $^1$H-NMR (300 MHz, CD₃OD) δ 10.04 (s, 1H), 8.12 (d, J=8.4 Hz, 2H), 8.03 (d, J=8.4 Hz, 2H), 7.74 (s, 1H).

Step 3: Synthesis of 4-(1-Methyl-4-(trifluoromethyl)-1H-imidazol-2-yl)benzaldehyde

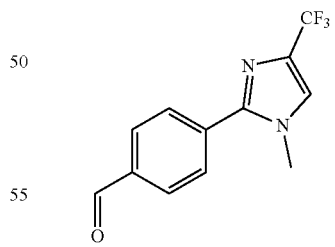

To a solution of 4-(4-(trifluoromethyl)-1H-imidazol-2-yl)benzaldehyde (0.9 g, 3.8 mmol) in DMF (40 mL) at room temperature, was added Cs₂CO₃ (3.7 g, 11.2 mmol) and MeI (1.1 g, 7.5 mmol) in one portion. After the reaction was stirred at ambient temperature for 1 hour, the reaction was quenched with water (100 mL) and extracted with EA (100 mL×2). The combined organic layer was washed with water (50 mL×2), dried with anhydrous Na₂SO₄ (50 g) and concentrated in vacuo. The concentrated residue was purified by silica gel chromatography (PE:EA=20:1 to 5:1) to give 0.8 g of the title compound. ¹H-NMR (300 MHz, CDCl₃) δ 10.09 (s, 1H), 8.00 (d, J=8.4 Hz, 2H), 7.86 (d, J=8.4 Hz, 2H), 7.38 (s, 1H), 3.85 (s, 3H).

Step 4: Synthesis of 1-(4-(1-Methyl-4-(trifluoromethyl)-1H-imidazol-2-yl)phenyl)ethan-1-ol

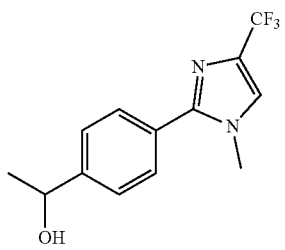 [SMILES: CC(O)c1ccc(-c2nc(C(F)(F)F)cn2C)cc1]

To a solution of 4-(1-methyl-4-(trifluoromethyl)-1H-imidazol-2-yl)benzaldehyde (0.8 g, 3.2 mmol) in THF (30 mL), was added CH₃MgBr (4.7 mL, 4.7 mmol, 1 M in THF) dropwise over 10 min at 0° C. After addition, the reaction was stirred at 0° C. for 1.5 hr, and then quenched by addition of a saturated aqueous NH₄Cl (20 mL) solution. The resulting mixture was extracted with EA (100 mL×2), and the combined organic layer was washed with brine (20 mL), dried over anhydrous Na₂SO₄ (30 g) and concentrated in vacuo to give 0.9 g of the crude title compound. ¹H-NMR (300 MHz, CDCl₃) δ 7.60 (d, J=8.1 Hz, 2H), 7.47 (d, J=8.1 Hz, 2H), 7.31 (s, 1H), 4.97 (q, J=6.3 Hz, 1H), 3.81 (s, 3H), 1.52 (d, J=6.3 Hz, 3H).

Step 5: Synthesis of 2-(4-(1-Chloroethyl)phenyl)-1-methyl-4-(trifluoromethyl)-1H-imidazole

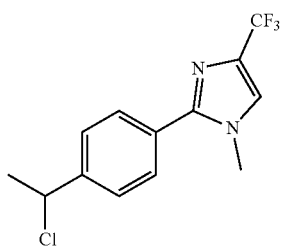 [SMILES: CC(Cl)c1ccc(-c2nc(C(F)(F)F)cn2C)cc1]

To a solution of 1-(4-(1-methyl-4-(trifluoromethyl)-1H-imidazol-2-yl)phenyl)ethan-1-ol (570 mg, 2.1 mmol) in DCE (20 mL), was added SOCl₂ (753.8 mg, 6.3 mmol) in one portion. After addition, the reaction was stirred at 60° C. for 1 hour, and then concentrated to dryness in vacuo. The residue was dissolved in EA (100 mL), and then treated with a saturated NaHCO₃ solution. After separation, the organic layer was dried with anhydrous Na₂SO₄ (30 g) and concentrated in vacuo. The concentrated crude product was purified by silica gel chromatography (PE:EA=20:1) to give 330 mg of the title compound. ¹H-NMR (300 MHz, CDCl₃) δ 7.64 (d, J=8.4 Hz, 2H), 7.53 (d, J=8.4 Hz, 2H), 7.32 (s, 1H), 5.13 (q, J=6.6 Hz, 1H), 3.79 (s, 3H), 1.87 (d, J=6.6 Hz, 3H).

Step 6: Synthesis of 6-Chloro-1-(1-(4-(1-methyl-4-(trifluoromethyl)-1H-imidazol-2-yl)phenyl)ethyl)-1H-pyrazolo[3,4-d]pyrimidine (I-24)

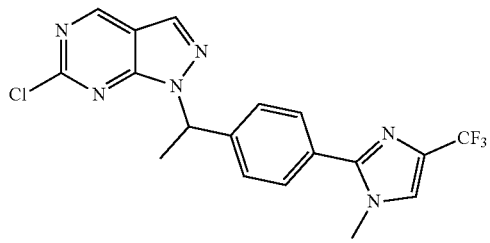 [SMILES: CC(c1ccc(-c2nc(C(F)(F)F)cn2C)cc1)n1ncc2cnc(Cl)nc21]

To a solution of 6-chloro-1H-pyrazolo[3,4-d]pyrimidine (321.2 mg, 2.1 mmol) in DMF (14 mL), was added 2-(4-(1-chloroethyl)phenyl)-1-methyl-4-(trifluoromethyl)-1H-imidazole (400 mg, 1.4 mmol) and K₂CO₃ (574.5 mg, 4.2 mmol). After addition, the reaction mixture was stirred at 65° C. overnight, then quenched with water (30 mL) and extracted with EA (50 mL×2). The combined organic layer was washed with water (20 mL×2), dried over anhydrous Na₂SO₄ (30 g), filtered and concentrated to dryness in vacuo. The concentrated residue was purified by silica gel chromatography (PE:EA=5:1 to 3:1) to give 40 mg of the title compound. Its regioisomer was obtained as the major product after purification. ¹H-NMR (300 MHz, CDCl₃) δ 9.03 (s, 1H), 8.19 (s, 1H), 7.50-7.64 (m, 4H), 7.29 (s, 1H), 6.26 (q, J=7.2, 1H), 3.75 (s, 3H), 2.04 (d, J=7.2 Hz, 3H).

The following common intermediates were prepared according the procedure of I-24 from the appropriate reagents:

| Intermediate | Structure | Analytics |
| --- | --- | --- |
| I-25 | 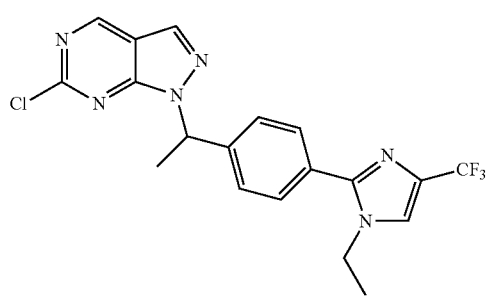 [SMILES: CCn1cc(C(F)(F)F)nc1-c1ccc(C(C)n2ncc3cnc(Cl)nc32)cc1] | ¹H-NMR (300 MHz, CDCl₃) δ 9.05 (s, 1H), 8.17 (s, 1H), 7.70 (d, J = 8.4 Hz, 2H), 7.46 (d, J = 8.4 Hz, 2H), 5.90 (s, 1H), 5.67 (s, 2H), 4.20 (q, J = 7.2 Hz, 2H), 1.45 (t, J = 7.2 Hz, 3H). |

| Intermediate | Structure | Analytics |
|---|---|---|
| I-26 | 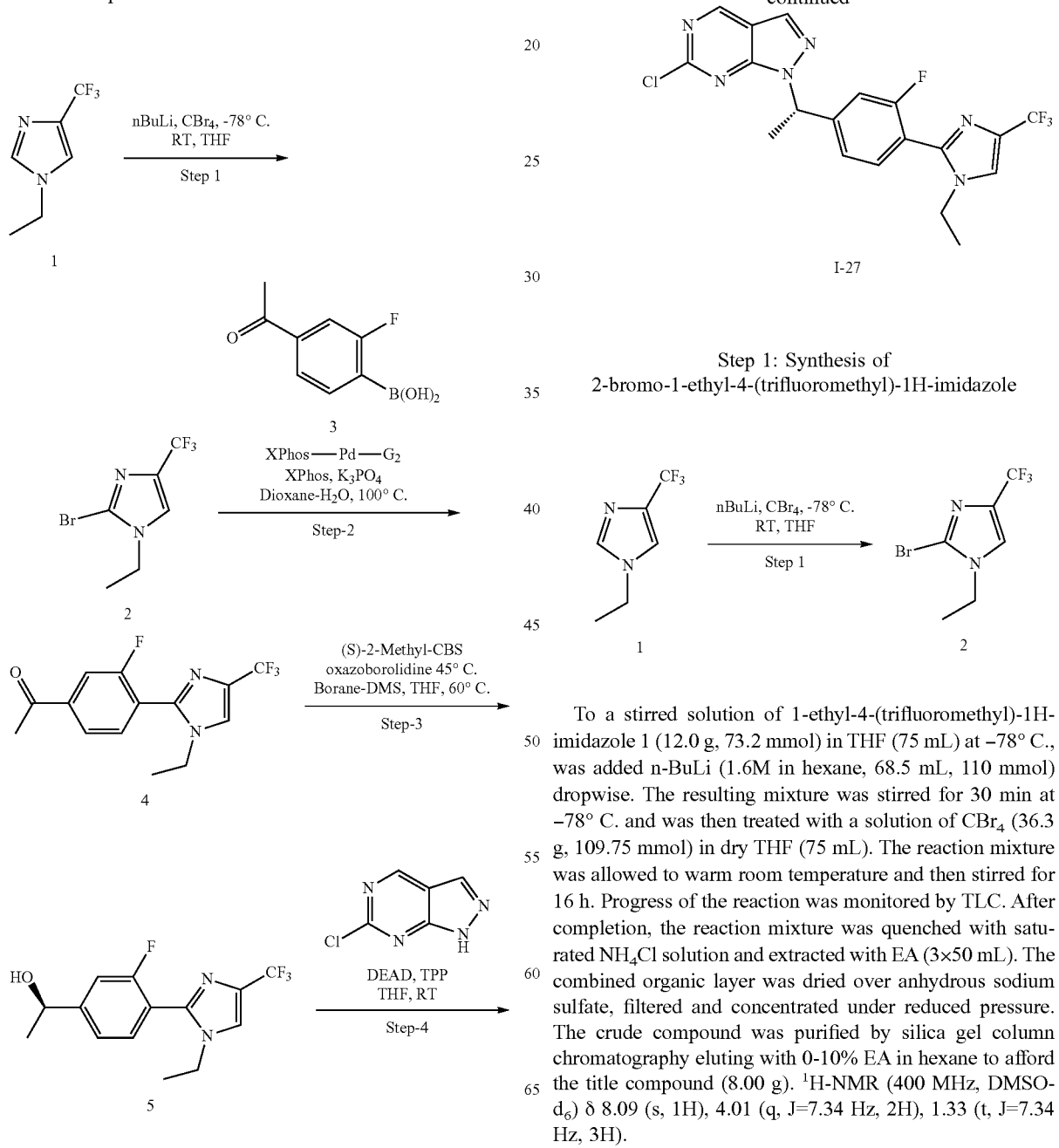 | LC-MS (Method C) (ESI+): m/z 439.29 (M + H)+; 1H-NMR (300 MHz, DMSO-d6) δ 9.31 (s, 1H), 8.56 (s, 1H), 8.10 (d, J = 0.98 Hz, 1H), 7.53 (t, J = 7.83 Hz, 1H), 7.39 (dd, J = 0.98, 11.25 Hz, 1H), 7.27 (dd, J = 1.47, 7.83 Hz, 1H), 6.30 (q, J = 7.17 Hz, 1H), 3.85 (q, J = 7.17 Hz, 2H), 1.95 (d, J = 6.85 Hz, 3H), 1.25 (t, J = 7.34 Hz, 3H). |

Preparation of Common Intermediate I-27

Step 1: Synthesis of 2-bromo-1-ethyl-4-(trifluoromethyl)-1H-imidazole

To a stirred solution of 1-ethyl-4-(trifluoromethyl)-1H-imidazole 1 (12.0 g, 73.2 mmol) in THF (75 mL) at −78° C., was added n-BuLi (1.6M in hexane, 68.5 mL, 110 mmol) dropwise. The resulting mixture was stirred for 30 min at −78° C. and was then treated with a solution of CBr$_4$ (36.3 g, 109.75 mmol) in dry THF (75 mL). The reaction mixture was allowed to warm room temperature and then stirred for 16 h. Progress of the reaction was monitored by TLC. After completion, the reaction mixture was quenched with saturated NH$_4$Cl solution and extracted with EA (3×50 mL). The combined organic layer was dried over anhydrous sodium sulfate, filtered and concentrated under reduced pressure. The crude compound was purified by silica gel column chromatography eluting with 0-10% EA in hexane to afford the title compound (8.00 g). 1H-NMR (400 MHz, DMSO-d$_6$) δ 8.09 (s, 1H), 4.01 (q, J=7.34 Hz, 2H), 1.33 (t, J=7.34 Hz, 3H).

Step 2: Synthesis of 1-(4-(1-ethyl-4-(trifluoromethyl)-1H-imidazol-2-yl)-3-fluorophenyl)ethan-1-one

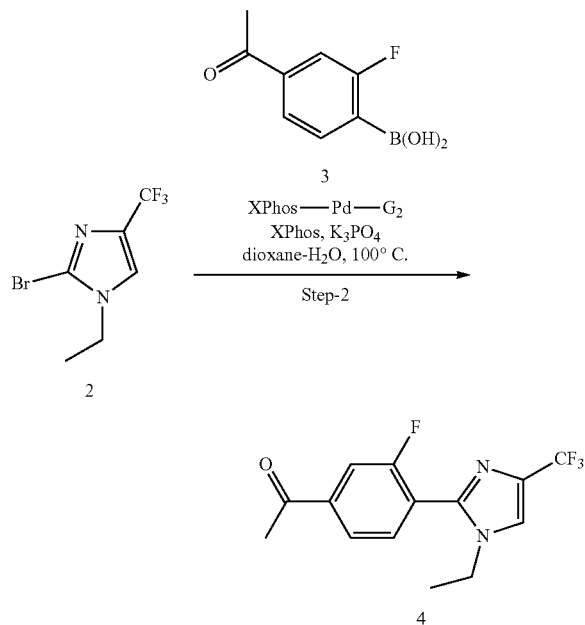

To a stirred solution of 2-bromo-1-ethyl-4-(trifluoromethyl)-1H-imidazole 2 (1.80 g, 7.44 mmol) in dioxane:H$_2$O (8:2 mL) was added K$_3$PO$_4$ (3.94 g, 18.6 mmol) and (4-acetyl-2-fluorophenyl)boronic acid 3 (1.48 g, 8.18 mmol). The resulting mixture was degassed with argon for 10 min, and then treated with X-Phos (0.708 g, 1.49 mmol) and X-Phos-Pd-G$_2$ (0.292 g, 0.372 mmol) in a sealed tube at room temperature. The reaction mixture was further degassed with argon for 10 min and then heated at 100° C. for 2 h. Progress of the reaction was monitored by TLC. After completion, the reaction mixture was cooled to room temperature and concentrated under reduced pressure. The crude compound was purified by silica gel chromatography eluting with 0-20% EA in hexane to afford the title compound (1.85 g). LC-MS (Method B) (ESI+): m/z 301.15 (M+H)$^+$; $^1$H-NMR (400 MHz, DMSO-d$_6$) δ 8.14-8.20 (m, 1H), 7.93 (d, J=9.29 Hz, 2H), 7.76 (t, J=7.34 Hz, 1H), 3.93 (q, J=7.01 Hz, 2H), 2.66 (s, 3H), 1.29 (t, J=7.34 Hz, 3H).

Step 3: Synthesis of (R)-1-(4-(1-ethyl-4-(trifluoromethyl)-1H-imidazol-2-yl)-3-fluorophenyl)ethan-1-ol

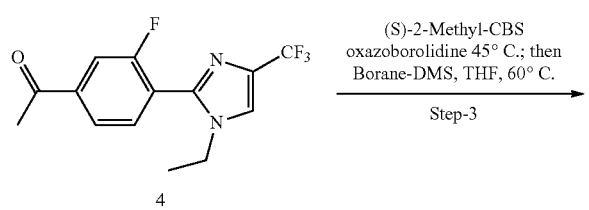

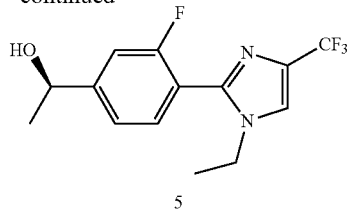

To a stirred solution of 1-(4-(1-ethyl-4-(trifluoromethyl)-1H-imidazol-2-yl)-3-fluorophenyl)ethan-1-one 4 (2.30 g, 7.67 mmol) in THF (18 mL), was added (S)-2-Methyl-CBS-oxazoborolidine (0.42 mL 1.53 mmol) at room temperature. The resulting mixture was then heated at 45° C. for 1 h. To the resulting reaction mixture was added borane-DMS (1.09 mL, 11.5 mmol), and the mixture was heated at 60° C. for 16 h. Progress of the reaction was monitored by TLC. After completion, the reaction mixture was cooled to room temperature, quenched with methanol (10 mL) and concentrated under reduced pressure. The crude compound was purified by silica gel column chromatography eluting with 0-30% EA in hexane to afford the title compound (2.10 g). LC-MS (Method B) (ESI+): m/z 303.00 (M+H)$^+$; $^1$H-NMR (400 MHz, DMSO-d$_6$) δ 8.10 (s, 1H), 7.50 (t, J=7.82 Hz, 1H), 7.30-7.37 (m, 2H), 5.43 (d, J=4.40 Hz, 1H), 4.81 (m, J=5.87 Hz, 1H), 3.88 (q, J=7.17 Hz, 2H), 1.37 (d, J=6.36 Hz, 3H), 1.27 (t, J=7.09 Hz, 3H).

Step 3: Synthesis of (S)-6-chloro-1-(1-(4-(1-ethyl-4-(trifluoromethyl)-1H-imidazol-2-yl)-3-fluorophenyl)ethyl)-1H-pyrazolo[3,4-d]pyrimidine (I-27)

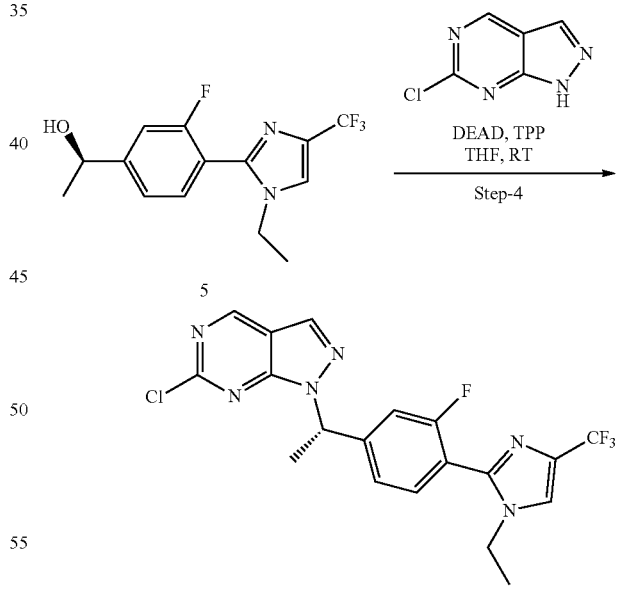

To a stirred solution of (R)-1-(4-(1-ethyl-4-(trifluoromethyl)-1H-imidazol-2-yl)-3-fluorophenyl)ethan-1-ol 5 (2.10 g, 6.95 mmol) in THF (12 mL) at 0° C., was added 6-chloro-1H-pyrazolo[3,4-d]pyrimidine (1.07 g, 6.95 mmol), DEAD (2.41 g, 13.9 mmol) and TPP (2.25 g, 13.9 mmol). The reaction mixture was stirred at room temperature for 2 h. Progress of the reaction was monitored by TLC. After completion, the reaction mixture was quenched with water (10 mL) and extracted with EA (3×10 mL). The combined organic layer was dried over anhydrous sodium sulfate, filtered and concentrated under reduced pressure. The crude product was purified by silica gel column chromatography using 0-30% EA in hexane to afford the title compound (2.20 g). LC-MS (Method B) (ESI+): m/z 439.22 (M+H)+.

The following common intermediates were prepared according the procedure of I-27 from the appropriate ketones and CBS reducing reagents:

| Intermediate | Structure | Analytics |
|---|---|---|
| I-28 | 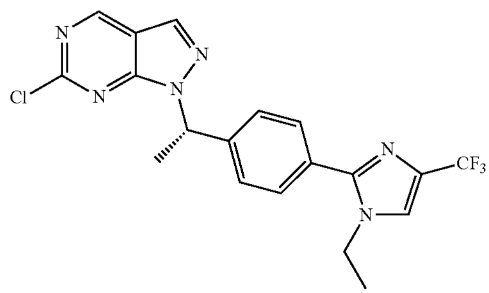 [SMILES: CCn1cc(C(F)(F)F)nc1-c1ccc([C@H](C)n2ncc3cnc(Cl)nc32)cc1] | 1H-NMR (400 MHz, DMSO-$d_6$) δ 9.30 (s, 1H), 8.54 (s, 1H), 8.01 (s, 1H), 7.60 (d, J = 8.31 Hz, 2H), 7.46 (d, J = 8.31 Hz, 2H), 6.27 (q, J = 7.01 Hz, 1H), 4.05 (q, J = 7.34 Hz, 2H), 1.95 (d, J = 7.34 Hz, 3H), 1.30 (t, J = 7.34 Hz, 3H). |
| I-29 | 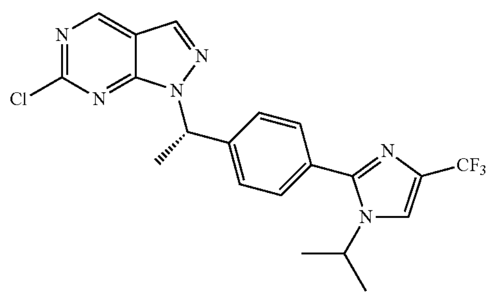 [SMILES: CC(C)n1cc(C(F)(F)F)nc1-c1ccc([C@H](C)n2ncc3cnc(Cl)nc32)cc1] | LC-MS (Method C) (ESI+): m/z 435.00 (M + H)+; 1H-NMR (400 MHz, DMSO-$d_6$) δ 9.30 (s, 1H), 8.54 (s, 1H), 8.16 (s, 1H), 7.53-7.59 (m, 1H), 7.52-7.56 (m, 1H), 7.45-7.49 (m, 2H), 6.23-6.31 (m, 1H), 4.43 (td, J = 6.55, 13.34 Hz, 1H), 1.96 (d, J = 6.98 Hz, 3H), 1.38 (d, J = 6.48 Hz, 6H). |
| I-30 | 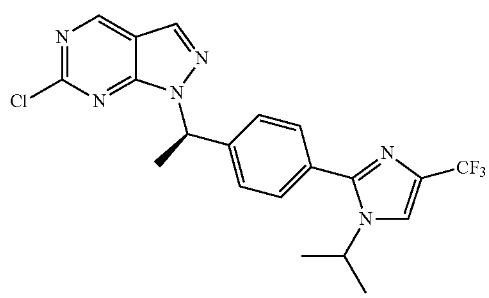 [SMILES: CC(C)n1cc(C(F)(F)F)nc1-c1ccc([C@@H](C)n2ncc3cnc(Cl)nc32)cc1] | LC-MS (Method C) (ESI+): m/z 435.00 (M + H)+; 1H-NMR (400 MHz, DMSO-d6) δ 9.30 (s, 1H), 8.55 (s, 1H), 8.17 (s, 1H), 7.52-7.55 (m, 2H), 7.45-7.50 (m, 2H), 6.27 (q, J = 6.65 Hz, 1H), 4.40-4.48 (m, 1H), 1.96 (d, J = 6.98 Hz, 3H), 1.38 (d, J = 6.48 Hz, 6H). |

Preparation of Common Intermediate I-31

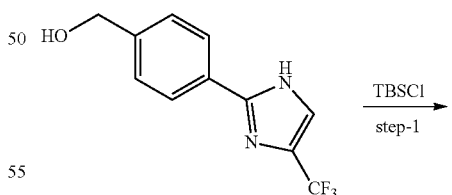

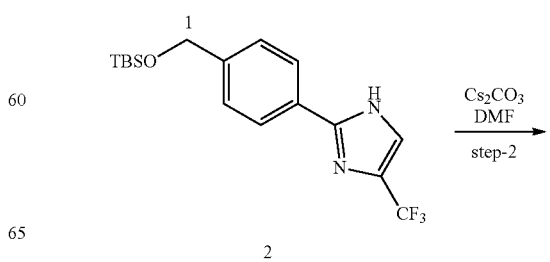

-continued

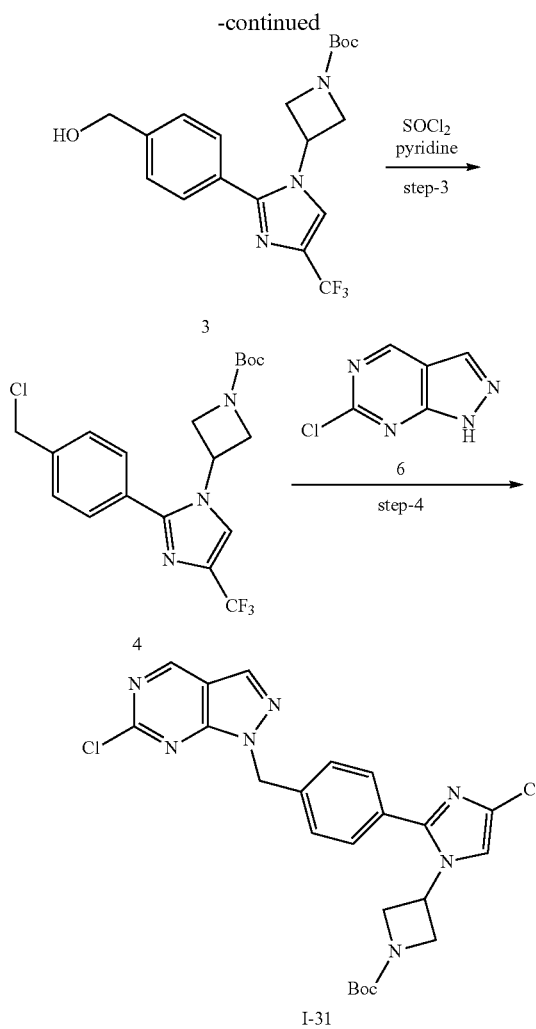

Step 1: Synthesis of 2-(4-(((Tert-butyldimethylsilyl)oxy)methyl)phenyl)-4-(trifluoromethyl)-1H-imidazole

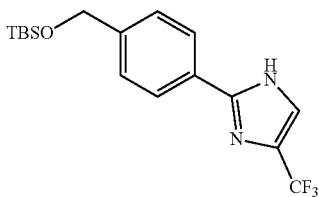 [SMILES: CC(C)(C)[Si](C)(C)OCc1ccc(-c2nc(C(F)(F)F)c[nH]2)cc1]

To a solution of (4-(4-(trifluoromethyl)-1H-imidazol-2-yl)phenyl)methanol (1.90 g, 7.85 mmol), DMAP (95.8 mg, 0.79 mmol) and TEA (1.19 g, 11.78 mmol) in THF (40 mL) at room temperature, was added TBSCl (1.42 g, 9.42 mmol) in one portion. After addition, the reaction mixture was stirred at room temperature for 1.5 hours. The reaction was then quenched with water (20 mL) and extracted with EA (150 ml×3). The combined organic layer was dried over anhydrous $Na_2SO_4$ (50 g), filtered and concentrated in vacuo. The concentrated residue was purified by silica gel chromatography (EA:n-Hex=1:10 to 1:1) to give 2.69 g of the title compound. LC-MS (Method A) (ESI+): m/z 357 (M+H)$^+$; $^1$H-NMR (300 MHz, $CDCl_3$) δ 9.82 (br s, 1H), 7.68 (d, J=8.7 Hz, 2H), 7.26-7.31 (m, 3H), 4.66 (s, 2H), 0.84 (s, 9H), 0.00 (s, 6H).

Step 2: Synthesis of 3-(2-(4-(Hydroxymethyl)phenyl)-4-(trifluoromethyl)-1H-imidazol-1-yl)azetidine-1-carboxylate

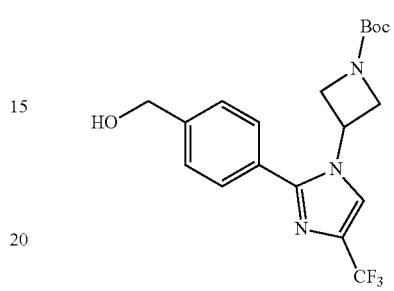

To a solution of 2-(4-(((tert-butyldimethylsilyl)oxy)methyl)phenyl)-4-(trifluoromethyl)-1H-imidazole (2.50 g, 7.02 mmol) in DMF (40 mL), was added tert-butyl 3-iodoazetidine-1-carboxylate (2.58 g, 9.13 mmol) and $Cs_2CO_3$ (6.87 g, 21.06 mmol). The reaction mixture was stirred at 120° C. for 4 hours. The reaction was then quenched with water (80 mL) and extracted with EA (150 mL×3). The combined organic layer was washed with water (50 mL×2), dried with anhydrous $Na_2SO_4$ (100 g), filtered and concentrated in vacuo. The residue was purified by silica gel chromatography (DCM:MeOH=100:1 to 20:1) to give 917 mg of the title compound. LC-MS (Method A) (ESI+): m/z 398 (M+H)$^+$; $^1$H-NMR (300 MHz, $CDCl_3$) δ 7.73 (s, 1H), 7.37-7.44 (m, 4H), 5.06 (m, 1H), 4.74 (s, 2H), 4.37-4.43 (m, 2H), 4.07-4.16 (m, 2H), 2.86 (br s, 1H), 1.46 (s, 9H).

Step 3: Synthesis of tert-Butyl 3-(2-(4-(Chloromethyl)phenyl)-4-(trifluoromethyl)-1H-imidazol-1-yl)azetidine-1-carboxylate

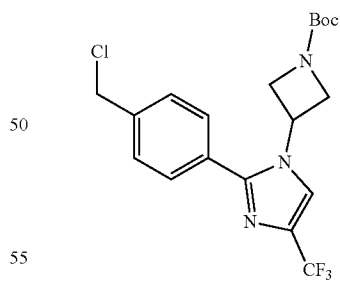

To a solution of tert-butyl 3-(2-(4-(hydroxymethyl)phenyl)-4-(trifluoromethyl)-1H-imidazol-1-yl) azetidine-1-carboxylate (0.92 g, 2.32 mmol) in DCE (22 mL), was added pyridine (1.10 g, 13.92 mmol) and $SOCl_2$ (0.83 g, 6.95 mmol). The reaction was then stirred at room temperature overnight before concentration to dryness in vacuo. The resulting residue was purified by column chromatography (EA:n-Hex=1:10 to 1:4) to give 480 mg of the title compound. LC-MS (Method A) (ESI+): m/z 416 (M+H)$^+$; $^1$H-NMR (300 MHz, $CDCl_3$) δ 7.75 (s, 1H), 7.52 (d, J=8.1

Hz, 2H), 7.46 (d, J=8.1 Hz, 2H), 5.07 (m, 1H), 4.64 (s, 2H), 4.41-4.47 (t, J=9.0 Hz, 2H), 4.09-4.14 (m, 2H), 4.47 (s, 9H).

Step 4: Synthesis of tert-Butyl 3-(2-(4-((6-chloro-1H-pyrazolo[3,4-d]pyrimidin-1-yl)methyl)phenyl)-4-(trifluoromethyl)-1H-imidazol-1-yl)azetidine-1-carboxylate (I-31)

A solution of tert-butyl 3-(2-(4-(chloromethyl)phenyl)-4-(trifluoromethyl)-1H-imidazol-1-yl) azetidine-1-carboxylate (0.45 g, 1.07 mmol), 6-chloro-1H-pyrazolo[3,4-d]pyrimidine (0.18 g, 1.18 mmol) and K$_2$CO$_3$ (0.37 g, 2.68 mmol) in DMF (13 mL) was stirred at room temperature for 3 hours. The mixture was then quenched with water (30 mL) and extracted with EA (100 mL×3). The combined organic layer was washed with water (20 mL) and dried over anhydrous Na$_2$SO$_4$ (50 g), filtered and concentrated in vacuo. The residue was purified by silica gel chromatography (EA:Hex=1:10 to 1:0) to give 280 mg of the title compound. LC-MS (Method A) (ESI+): m/z 534 (M+H)$^+$; $^1$H-NMR (300 MHz, CDCl$_3$) δ 9.07 (s, 1H), 8.19 (s, 1H), 7.72 (s, 1H), 7.41-7.49 (m, 4H), 5.70 (s, 2H), 5.01 (m, 1H), 4.36-4.42 (t, J=8.7 Hz, 2H), 4.06-4.13 (m, 2H), 1.42 (s, 9H).

Preparation of Common Intermediate I-32

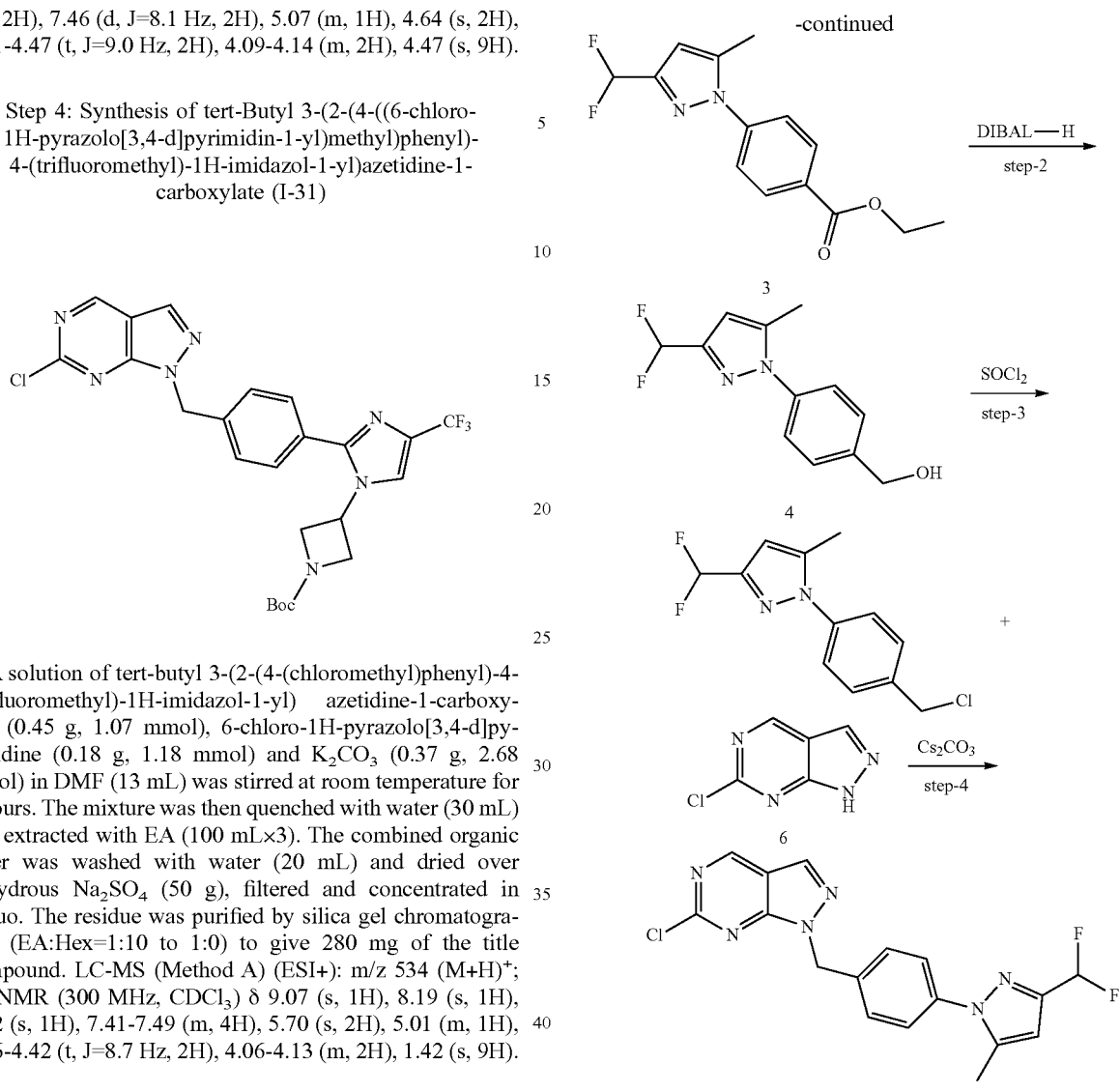

Step 1: Synthesis of Ethyl 4-(3-(difluoromethyl)-5-methyl-1H-pyrazol-1-yl)benzoate

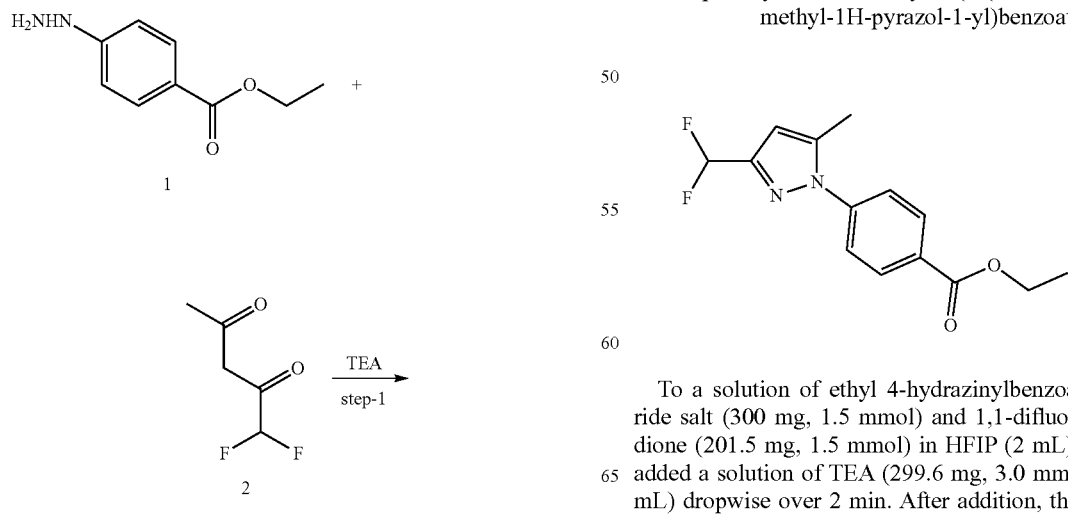

To a solution of ethyl 4-hydrazinylbenzoate hydrochloride salt (300 mg, 1.5 mmol) and 1,1-difluoropentane-2,4-dione (201.5 mg, 1.5 mmol) in HFIP (2 mL) at 0° C., was added a solution of TEA (299.6 mg, 3.0 mmol) in HFIP (1 mL) dropwise over 2 min. After addition, the reaction was stirred at room temperature for 2.5 hours. The reaction was then quenched with water (10 mL) and extracted with DCM (20 mL×2). The combined organic layer was washed with water (10 mL), dried over anhydrous Na$_2$SO$_4$ (20 g) and concentrated in vacuo. The residue was purified by silica gel chromatography (PE:EA=15:1 to 3:1) to give 300 mg of the title compound. $^1$H-NMR (300 MHz, CDCl$_3$) δ 8.17 (dd, J=6.9, 1.8 Hz, 2H), 7.56 (dd, J=6.9, 1.8 Hz, 2H), 6.71 (t, J=54.9 Hz, 1H), 6.48 (s, 1H), 3.96 (s, 3H), 2.42 (s, 3H).

Step 2: Synthesis of (4-(3-(Difluoromethyl)-5-methyl-1H-pyrazol-1-yl)phenyl)methanol

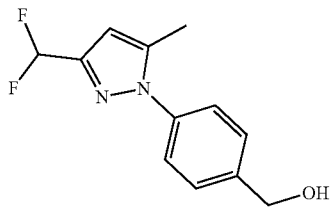 [SMILES: Cc1cc(C(F)F)nn1-c1ccc(CO)cc1]

The title compound was synthesized according to the step 3 of common intermediate I-1. $^1$H-NMR (300 MHz, CDCl$_3$) δ 7.49 (dd, J=6.3, 2.1 Hz, 2H), 7.42 (dd, J=6.3, 2.1 Hz, 2H), 6.70 (t, J=55.2 Hz, 1H), 6.44 (s, 1H), 4.78 (d, J=5.7 Hz, 2H), 2.35 (s, 3H), 1.90 (t, J=5.7 Hz, 1H).

Step 3: Synthesis of 1-(4-(Chloromethyl)phenyl)-3-(difluoromethyl)-5-methyl-1H-pyrazole

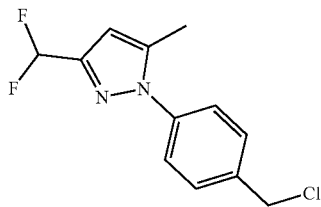 [SMILES: Cc1cc(C(F)F)nn1-c1ccc(CCl)cc1]

To a solution of (4-(3-(difluoromethyl)-5-methyl-1H-pyrazol-1-yl)phenyl)methanol (290 mg, 1.2 mmol) in DCE (10 mL), was added SOCl$_2$ (426.4 mg, 3.6 mmol) in one portion. After addition, the reaction was stirred at 60° C. for 1 hour, then concentrated in vacuo to give 300 mg of the crude title compound. $^1$H-NMR (300 MHz, CDCl$_3$) δ 7.52 (dd, J=6.3, 2.1 Hz, 2H), 7.44 (dd, J=6.3, 2.1 Hz, 2H), 6.70 (t, J=54.9 Hz, 1H), 6.44 (s, 1H), 4.65 (s, 2H), 2.37 (s, 3H).

Step 4: Synthesis of 6-Chloro-1-(4-(3-(difluoromethyl)-5-methyl-1H-pyrazol-1-yl)benzyl)-1H-pyrazolo[3,4-d]pyrimidine (I-32)

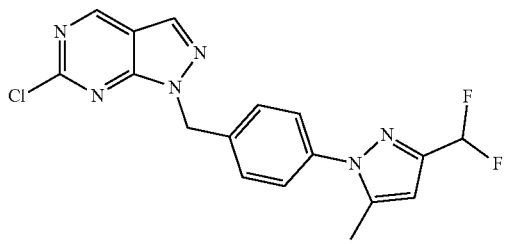 [SMILES: Cc1cc(C(F)F)nn1-c1ccc(Cn2ncc3cnc(Cl)nc32)cc1]

A solution of 1-(4-(chloromethyl)phenyl)-3-(difluoromethyl)-5-methyl-1H-pyrazole (300 mg, 1.2 mmol), 6-chloro-1H-pyrazolo[3,4-d]pyrimidine (270.9 mg, 1.8 mmol) and K$_2$CO$_3$ (484.6 mg, 351 mmol) in DMF (12 mL) was stirred at 90° C. for 1.5 hours. The reaction was then quenched with water (25 mL) and extracted with EA (50 mL×2). The combined organic layer was washed with water (20 mL×2), dried over anhydrous Na$_2$SO$_4$ (30 g) and concentrated in vacuo. The residue was purified by silica gel chromatography (PE:EA=5:1 to 3:1) to give 150 mg of title compound with a small amount of the regioisomer. $^1$H-NMR (300 MHz, CDCl$_3$) δ 9.06 (s, 1H), 8.19 (s, 1H), 7.50 (dd, J=6.6, 1.8 Hz, 2H), 7.41 (dd, J=6.6, 1.8 Hz, 2H), 6.67 (t, J=54.9 Hz, 1H), 6.42 (s, 1H), 5.69 (s, 2H), 2.33 (s, 3H).

Preparation of Common Intermediate I-33 and I-34

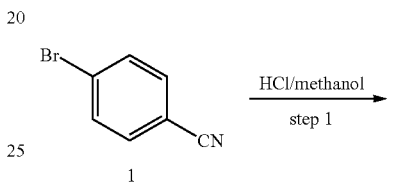

1

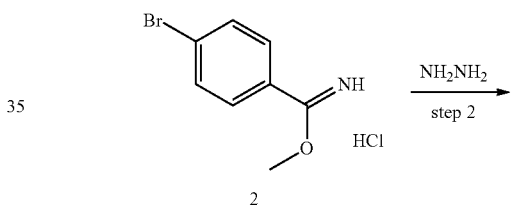

2

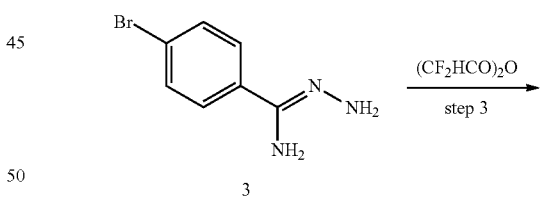

3

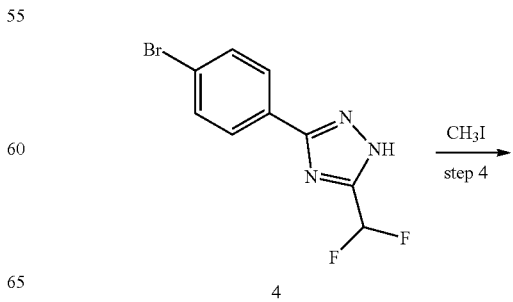

4

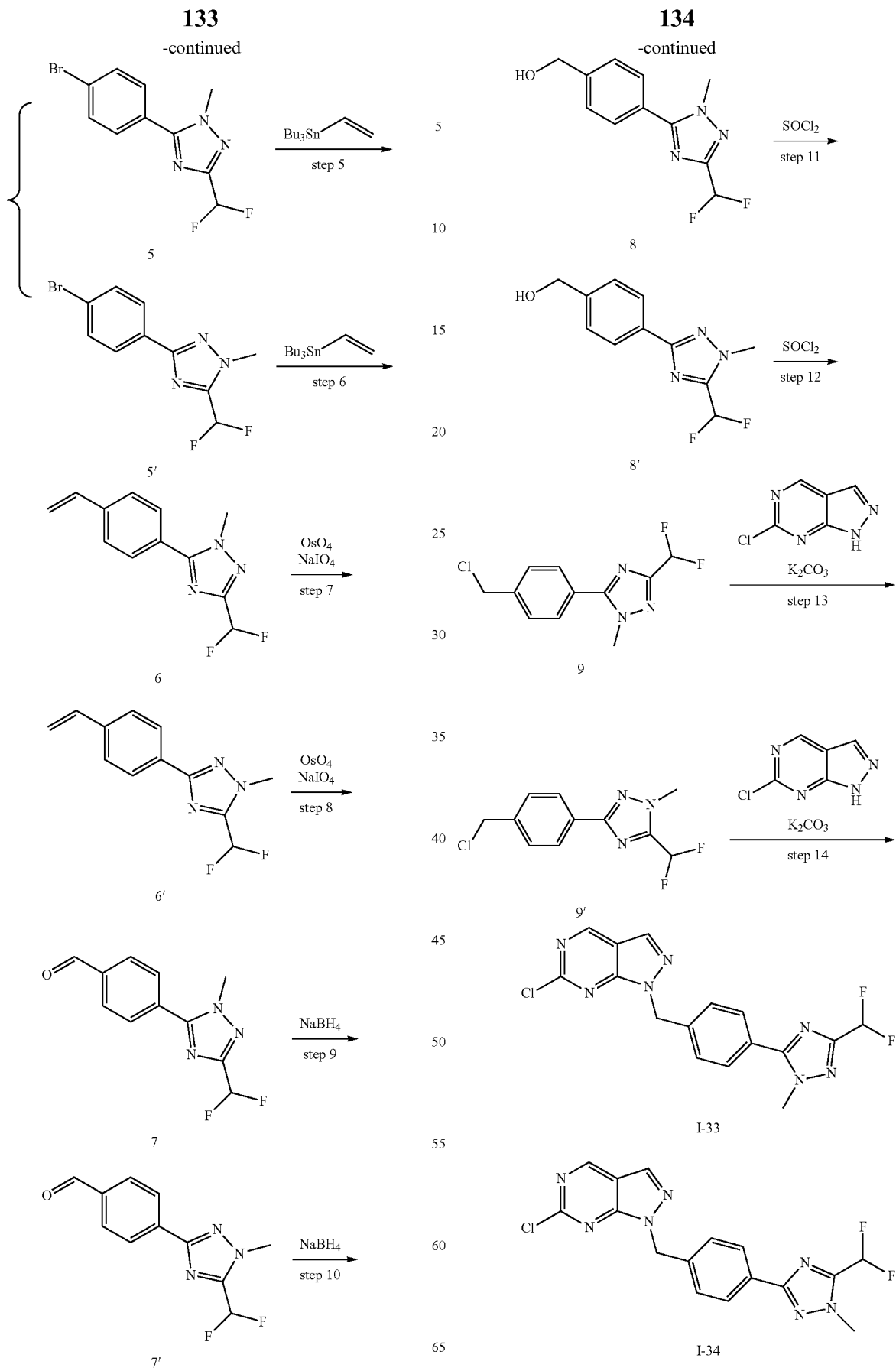

Step 1: Synthesis of Ethyl 4-bromobenzimidate hydrochloride Salt

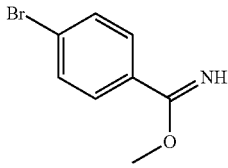

Gaseous HCl was bubbled through a vigorously stirred solution of 4-bromobenzonitrile (4.2 g, 23.07 mmol) in anhydrous MeOH (40 mL) at 0° C. for 3 h. The mixture was then stirred at rt overnight. The resulting reaction mixture was poured into Et$_2$O (40 mL), and the resulting solid precipitate was collected by filtration. The solid was suspended in cold DCM (80 mL) and neutralized by a saturated aqueous NaHCO$_3$ solution (80 mL). After the organic phase was separated, the aqueous phase was extracted with DCM (40 mL×2). The combined organic phase was dried with sodium sulfate (40 g), filtered and concentrated to afford 5.0 g of the title compound. LC-MS (Method A) (ESI+): m/z 214 (M+H)$^+$; $^1$H-NMR (300 MHz, CDCl$_3$) δ 7.81 (br s, 1H), 7.51-7.68 (m, 4H), 3.92 (s, 3H).

Step 2: Synthesis of 4-Bromobenzohydrazonamide

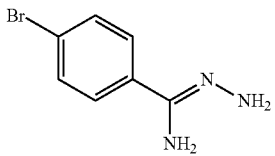 [SMILES: N/N=C(\N)c1ccc(Br)cc1]

To a solution of methyl 4-bromobenzimidate (4.6 g, 21.6 mmol) in IPA (80 mL) at 0° C., was added hydrazine hydrate (1.6 g, 25.9 mmol) in IPA (20 mL) dropwise over 30 min. The reaction mixture was stirred in an ice-water bath for 1 h and then warmed to rt overnight. After the reaction was completed as indicated by TLC analysis, the reaction mixture was concentrated to dryness. The residue was diluted with Et$_2$O (35 mL) and a large amount of solid was precipitated. The suspension was stirred at rt for 1 h, then the solid was collected by filtration to afford 3.8 g of the crude title compound. LC-MS (Method A) (ESI+): m/z 214 (M+H)$^+$; $^1$H-NMR (300 MHz, DMSO) δ 7.63 (d, J=8.7 Hz, 2H), 7.52 (d, J=8.7 Hz, 2H), 5.66 (br s, 2H), 5.08 (br s, 2H).

Step 3: Synthesis of 3-(4-Bromophenyl)-5-(difluoromethyl)-1H-1,2,4-triazole

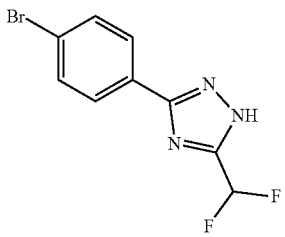 [SMILES: FC(F)c1nc(-c2ccc(Br)cc2)n[nH]1]

A solution of 2,2-difluoroacetic anhydride (1.63 g, 9.38) in DCM (20 mL) was added dropwise over 5 min to a mixture of 4-bromobenzohydrazonamide (2.0 g, 9.38 mmol) and TEA (2.84 g, 28.14 mmol) in DCM (70 mL) at 0° C. After the addition, the reaction mixture was warmed to rt and stirred overnight. After the reaction was completed as indicated by TLC analysis, the mixture was quenched with brine (80 mL) and extracted with DCM (80 mL×2). The combined organic layer was dried with sodium sulfate (30 g), filtered and concentrated. The residue was purified by silica gel chromatography (PE:EA=8:1 to 4:1) to yield 1.2 g of the title compound. LC-MS (Method A) (ESI+): m/z 274 (M+H)$^+$; $^1$H-NMR (300 MHz, CDCl$_3$) (7.85 (d, J=8.4 Hz, 2H), 7.66 (d, J=8.4 Hz, 2H), 6.81 (t, J=53.4 Hz, 1H).

Step 4: Synthesis of 5-(4-Bromophenyl)-3-(difluoromethyl)-1-methyl-1H-1,2,4-triazole and 3-(4-bromophenyl)-5-(difluoromethyl)-1-methyl-1H-1,2,4-triazole

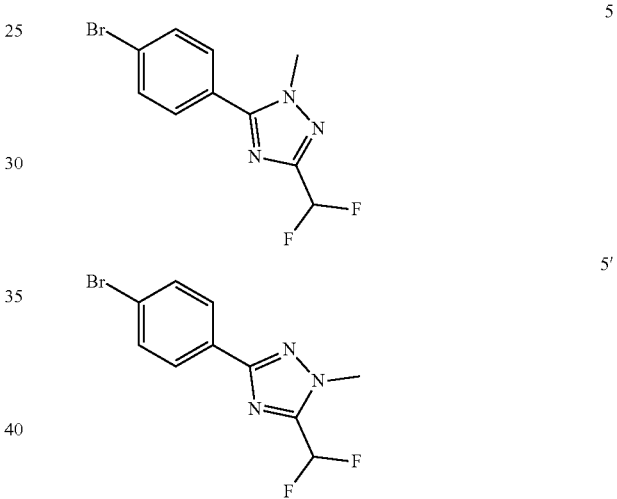

To a solution of 3-(4-bromophenyl)-5-(difluoromethyl)-1H-1,2,4-triazole (1.05 g, 3.85 mmol) in DMF (25 mL) at 0° C., was added sodium hydride (200 mg, 5.0 mmol) portionwise over 5 min. After the resulting mixture was stirred at 0° C. for 20 min, MeI (1.09 g, 7.69 mmol) was added dropwise over 1 min. The reaction was warmed to rt and stirred for 1 h. After the reaction was completed as indicated by TLC analysis, the reaction was quenched with ice-water (50 mL) and extracted with EA (70 mL×2). The combined organic layer was washed with water (60 mL×2), dried with sodium sulfate (30 g), filtered and concentrated. The residue was purified by silica gel chromatography (PE:EA=20:1 to 15:1) to yield 260 mg of 5-(4-bromophenyl)-3-(difluoromethyl)-1-methyl-1H-1,2,4-triazole and 750 mg of 3-(4-bromophenyl)-5-(difluoromethyl)-1-methyl-1H-1,2,4-triazole.

5-(4-bromophenyl)-3-(difluoromethyl)-1-methyl-1H-1,2,4-triazole

LC-MS (Method A) (ESI+): m/z 288 (M+H)$^+$; $^1$H-NMR (300 MHz, CDCl$_3$) (7.70 (d, J=6.6, 1.8 Hz, 2H), 7.59 (d, J=6.6, 1.8 Hz, 2H), 6.73 (t, J=53.7 Hz, 1H), 4.03 (s, 3H).

3-(4-bromophenyl)-5-(difluoromethyl)-1-methyl-1H-1,2,4-triazole

LC-MS (Method A) (ESI+): m/z 288 (M+H)+; 1H-NMR (300 MHz, CDCl3) (7.93 (d, J=8.7 Hz, 2H), 7.58 (d, J=8.7 Hz, 2H), 6.87 (t, J=53.7 Hz, 1H), 4.09 (s, 3H).

Step 5: Synthesis of 3-(Difluoromethyl)-1-methyl-5-(4-vinylphenyl)-1H-1,2,4-triazole

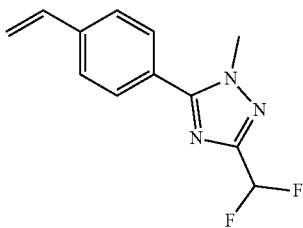 [SMILES: C=Cc1ccc(-c2nc(C(F)F)nn2C)cc1]

Under nitrogen protection, a solution of 5-(4-bromophenyl)-3-(difluoromethyl)-1-methyl-1H-1,2,4-triazole (1.6 g, 5.57 mmol) in toluene (50 ml) was treated with tributylvinylstannane (2.65 g, 8.36 mmol) and Pd(PPh3)4 (644 mg, 0.56 mmol) in one portion. The reaction was stirred at 90° C. for 5 hours, then quenched with water (50 mL) and extracted with EA (50 mL×2). The combined organic layer was washed with brine (60 mL), dried over sodium sulfate (30 g), filtered and concentrated. The residue was purified by flash silica chromatography (PE:EA=10:1) to yield 1.2 g of the title compound. LC-MS (Method A) (ESI+): m/z 236 (M+H)+; 1H-NMR (300 MHz, CDCl3) δ 7.68 (d, J=8.1 Hz, 2H), 7.56 (d, J=8.1 Hz, 2H), 6.74 (t, J=53.7 Hz, 1H), 6.73 (m, 1H), 5.88 (d, J=17.4 Hz, 1H), 5.40 (d, J=11.1 Hz, 1H), 4.05 (s, 3H).

Step 6: Synthesis of 5-(Difluoromethyl)-1-methyl-3-(4-vinylphenyl)-1H-1,2,4-triazole

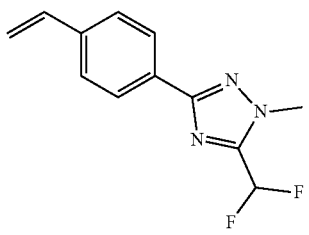 [SMILES: C=Cc1ccc(-c2nc(C(F)F)n(C)n2)cc1]

The compound was synthesized according to the procedure of step 5 of common intermediate I-33. LC-MS (Method A) (ESI+): m/z 236 (M+H)+; 1H-NMR (300 MHz, CDCl3) δ 8.02 (d, J=8.1 Hz, 2H), 7.51 (d, J=8.1 Hz, 2H), 6.90 (t, J=53.7 Hz, 1H), 6.78 (m, 1H), 5.83 (d, J=17.2 Hz, 1H), 5.31 (d, J=10.8 Hz, 1H), 4.10 (s, 3H).

Step 7: Synthesis of 4-(3-(Difluoromethyl)-1-methyl-1H-1,2,4-triazol-5-yl)benzaldehyde

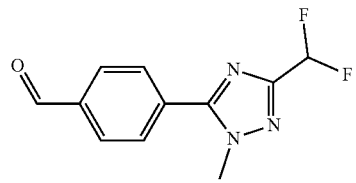 [SMILES: Cn1nc(C(F)F)nc1-c1ccc(C=O)cc1]

To a solution of 3-(difluoromethyl)-1-methyl-5-(4-vinylphenyl)-1H-1,2,4-triazole (450 mg, 1.91 mmol) in THF (15 mL) and water (8 mL) at rt, was added NaIO4 (1.23 g, 5.75 mmol) and OsO4 (4.2 mg, 1 mol %) in one portion. After the reaction was completed as indicated by TLC analysis, the reaction mixture was quenched by a saturated ammonium chloride solution (20 mL) and extracted with EA (30 mL×2). The combined organic layer was washed with brine (40 mL), dried over sodium sulfate (20 g), filtered and concentrated to afford 450 mg of the crude title compound. LC-MS (Method A) (ESI+): m/z 238 (M+H)+.

Step 8: Synthesis of 4-(5-(Difluoromethyl)-1-methyl-1H-1,2,4-triazol-3-yl)benzaldehyde

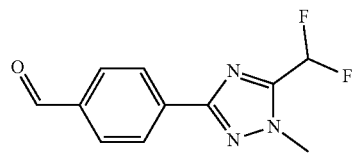 [SMILES: Cn1nc(-c2ccc(C=O)cc2)nc1C(F)F]

The compound was synthesized according to the procedure of step 7 of common intermediate I-33. LC-MS (Method A) (ESI+): m/z 238 (M+H)+. 1H-NMR (300 MHz, CDCl3) δ 9.99 (s, 1H), 8.17 (d, J=8.1 Hz, 2H), 7.90 (d, J=8.1 Hz, 2H), 6.84 (t, J=52.5 Hz, 1H), 4.06 (s, 3H).

Step 9: Synthesis of (4-(3-(Difluoromethyl)-1-methyl-1H-1,2,4-triazol-5-yl)phenyl)methanol

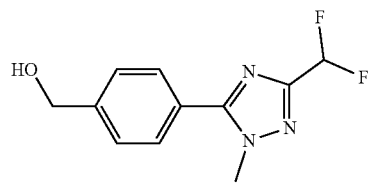 [SMILES: Cn1nc(C(F)F)nc1-c1ccc(CO)cc1]

To a solution of 4-(3-(difluoromethyl)-1-methyl-1H-1,2,4-triazol-5-yl)benzaldehyde (450 mg, 1.90 mmol) in THF (15 mL), was added NaBH4 (94 mg, 2.47 mmol) in one portion. After the reaction was completed as indicated by TLC analysis, the reaction was quenched by ice-water (20 mL) and extracted with EA (40 mL×2). The combined organic layer was washed with brine (40 mL), dried over sodium sulfate (30 g), filtered and concentrated. The residue was purified by silica gel chromatography (PE:EA=3:2) to yield 340 mg of the title compound. LC-MS (Method A)

(ESI+): m/z 240 (M+H)+; 1H-NMR (300 MHz, CDCl3) δ 7.71 (d, J=8.1 Hz, 2H), 7.54 (d, J=8.1 Hz, 2H), 6.74 (t, J=53.7 Hz, 1H), 4.81 (d, J=5.7 Hz, 2H) 4.04 (s, 3H).

Step 10: Synthesis of (4-(5-(Difluoromethyl)-1-methyl-1H-1,2,4-triazol-3-yl)phenyl)methanol

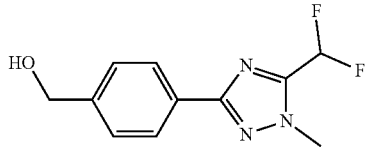 [SMILES: Cn1nc(-c2ccc(CO)cc2)nc1C(F)F]

The compound was synthesized according to the procedure of step 9 of common intermediate I-14. LC-MS (Method A) (ESI+): m/z 240 (M+H)+; 1H-NMR (300 MHz, CDCl3) (8.06 (d, J=8.4 Hz, 2H), 7.45 (d, J=8.4 Hz, 2H), 7.89 (t, J=52.5 Hz, 1H), 4.75 (d, J=6.0 Hz, 2H) 4.13 (s, 3H).

Step 11: Synthesis of 5-(4-(Chloromethyl)phenyl)-3-(difluoromethyl)-1-methyl-1H-1,2,4-triazole

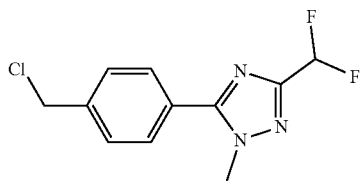 [SMILES: Cn1nc(C(F)F)nc1-c1ccc(CCl)cc1]

To a solution of (4-(3-(difluoromethyl)-1-methyl-1H-1,2,4-triazol-5-yl)phenyl)methanol (320 mg, 1.34 mmol) in DCE (15 mL), was added SOCl2 (318 mg, 2.68 mmol) in one portion. The reaction was stirred at 60° C. for 1 h. After the reaction was completed as indicated by TLC analysis, the reaction mixture was concentrated to dryness to afford 340 mg of the crude title compound. LC-MS (Method A) (ESI+): m/z 258 (M+H)+; 1H-NMR (300 MHz, CDCl3) (7.72 (d, J=8.1 Hz, 2H), 7.57 (d, J=8.1 Hz, 2H), 6.74 (t, J=53.7 Hz, 1H), 4.66 (s, 2H), 4.05 (s, 3H).

Step 12: Synthesis of 3-(4-(Chloromethyl)phenyl)-5-(difluoromethyl)-1-methyl-1H-1,2,4-triazole

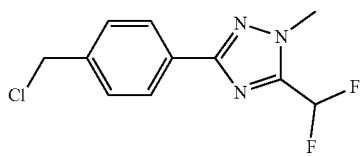 [SMILES: Cn1nc(-c2ccc(CCl)cc2)nc1C(F)F]

The compound was synthesized according to the procedure of step 11 of common intermediate I-33. LC-MS (Method A) (ESI+): m/z 258 (M+H)+; 1H-NMR (300 MHz, CDCl3) δ 8.06 (d, J=8.1 Hz, 2H), 7.45 (d, J=8.1 Hz, 2H), 6.89 (t, J=52.5 Hz, 1H), 4.63 (s, 2H), 4.10 (s, 3H).

Step 13: Synthesis of 6-Chloro-1-(4-(3-(difluoromethyl)-1-methyl-1H-1,2,4-triazol-5-yl)benzyl)-1H-pyrazolo[3,4-d]pyrimidine (I-33)

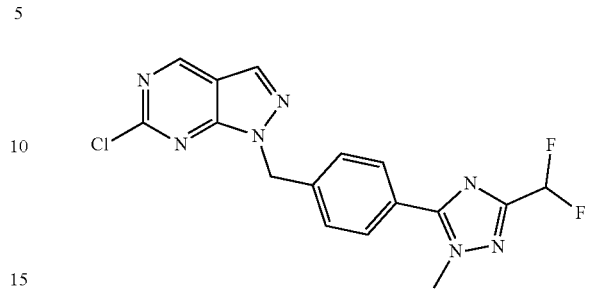

To a solution of 5-(4-(chloromethyl)phenyl)-3-(difluoromethyl)-1-methyl-1H-1,2,4-triazole (340 mg, 1.32 mmol) and 6-chloro-1H-pyrazolo[3,4-d]pyrimidine (244 mg, 1.58 mmol) in DMF (15 mL), was added Cs2CO3 (474 mg, 1.45 mmol) in one portion. The reaction was stirred at 80° C. for 1 h, then cooled to rt. The reaction was then quenched by ice-water (40 mL), and then extracted with EA (50 mL×2). The combined organic layer was washed with water (40 mL×3), dried over sodium sulfate (30 g), filtered and concentrated. The residue was purified by silica gel chromatography (PE:EA=1:1 to 1:3) to yield 180 mg of the title compound. LC-MS (Method A) (ESI+): m/z 376 (M+H)+; 1H-NMR (300 MHz, CDCl3) δ 9.07 (s, 1H), 8.20 (s, 1H), 7.69 (d, J=8.4 Hz, 2H), 7.52 (d, J=8.4 Hz, 2H), 6.71 (t, J=53.7 Hz, 1H), 5.72 (s, 2H), 4.00 (s, 3H).

Step 14: Synthesis of 6-Chloro-1-(4-(5-(difluoromethyl)-1-methyl-1H-1,2,4-triazol-3-yl)benzyl)-1H-pyrazolo[3,4-d]pyrimidine (I-34)

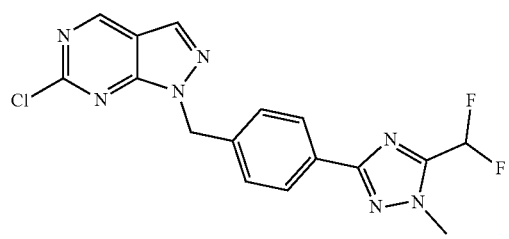 [SMILES: Cn1nc(-c2ccc(Cn3ncc4cnc(Cl)nc43)cc2)nc1C(F)F]

The compound was synthesized according to the procedure of step 13 of common intermediate I-33. LC-MS (Method A) (ESI+): m/z 376 (M+H)+; 1H-NMR (300 MHz, CDCl3) δ 9.05 (s, 1H), 8.18 (s, 1H), 8.03 (d, J=8.4 Hz, 2H), 7.43 (d, J=8.4 Hz, 2H), 6.86 (t, J=58.2 Hz, 1H), 5.67 (s, 2H), 4.10 (s, 3H).

Preparation of Common Intermediate I-35

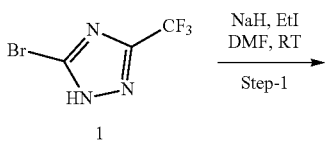

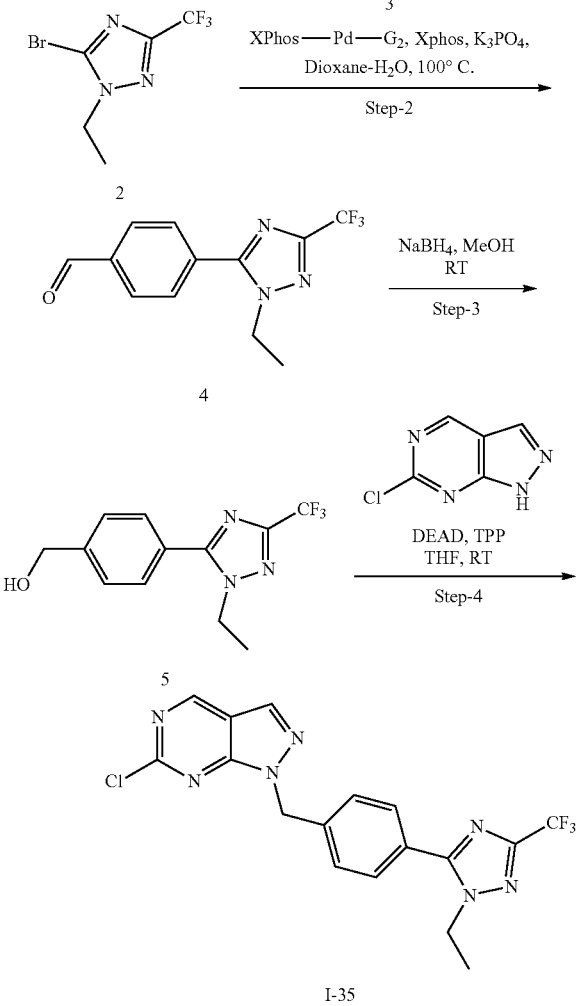

Step 1: Synthesis of 5-bromo-1-ethyl-3-(trifluoromethyl)-1H-1,2,4-triazole

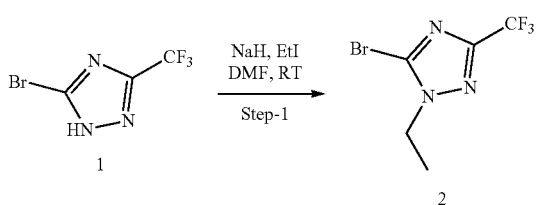

To an ice cooled solution of 5-bromo-3-(trifluoromethyl)-1H-1,2,4-triazole 1 (0.500 g, 2.31 mmol) in DMF (10 mL), was added sodium hydride (0.138 g, 3.47 mmol) portion-wise. The resulting mixture was stirred for 15 min, and then ethyl iodide (0.360 mL, 0.708 g, 0.462 mmol) was added. The reaction mixture was allowed to warm to room temperature and then stirred for 16 h. Progress of the reaction was monitored by TLC. After completion, the reaction mixture was quenched with water (20 mL) and extracted with EA (2×30 mL). The combined organic layer was washed with water (20 mL), and brine (20 mL), then dried over anhydrous sodium sulfate, filtered and concentrated under reduced pressure. The crude compound was purified by silica gel chromatography using 0-5% EA in n-hexane to afford the title compound (0.280 g). $^1$H-NMR (400 MHz, DMSO-$d_6$) δ 4.28 (q, J=7.01 Hz, 2H), 1.40 (t, J=7.09 Hz, 3H).

Step 2: Synthesis of 4-(1-ethyl-3-(trifluoromethyl)-1H-1,2,4-triazol-5-yl)benzaldehyde

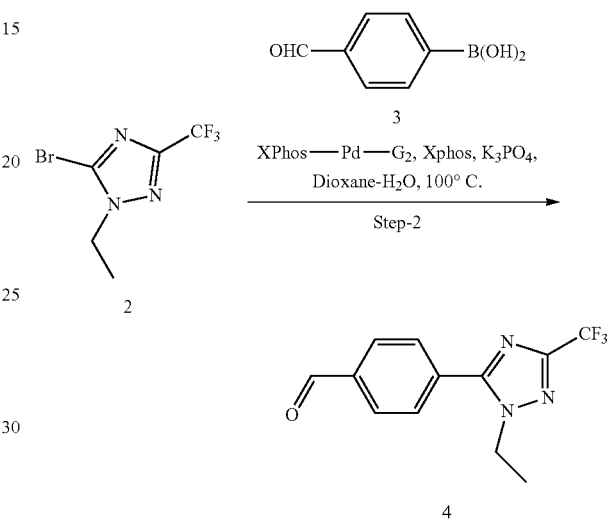

To a stirred solution of 5-bromo-1-ethyl-3-(trifluoromethyl)-1H-1,2,4-triazole 2 (0.250 g, 1.03 mmol) in dioxane:H$_2$O (10:4 mL) in a sealed tube were added K$_3$PO$_4$ (0.436 g, 2.07 mmol) and (4-formylphenyl)boronic acid 3 (0.200 g, 1.34 mmol). The resulting mixture was degassed with argon for 10 min, and then X-Phos (0.049 g, 0.102 mmol) and X-Phos-Pd-G$_2$ (0.040 g, 0.051 mmol) were added at room temperature. The reaction mixture was further degassed with argon for 10 min and then heated at 100° C. for 2 h. Progress of the reaction was monitored by TLC. After completion, the reaction mixture was cooled to room temperature, quenched with water (20 mL) and extracted with EA (3×30 mL). The organic layer was dried over anhydrous sodium sulfate, filtered and concentrated under reduced pressure. The crude compound was purified by silica gel chromatography eluting with 0-25% EA in hexane to afford the title compound (0.220 g). $^1$H-NMR (400 MHz, DMSO-$d_6$) δ 10.13 (s, 1H), 8.11 (d, J=6.85 Hz, 2H), 8.00 (d, J=7.34 Hz, 2H), 4.38 (q, J=6.85 Hz, 2H), 1.44 (t, J=6.85 Hz, 3H).

Step 3: Synthesis of (4-(1-ethyl-3-(trifluoromethyl)-1H-1,2,4-triazol-5-yl)phenyl)methanol

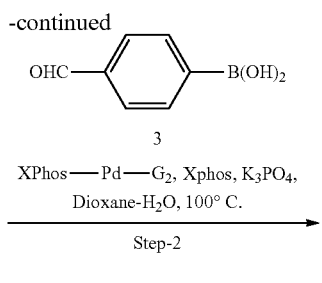

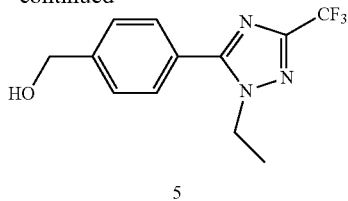

5

To a stirred solution of 4-(1-ethyl-3-(trifluoromethyl)-1H-1,2,4-triazol-5-yl) benzaldehyde 4 (0.200 g, 0.743 mmol) in methanol (5 mL) was added sodium borohydride (0.056 g, 1.49 mmol) portion-wise. The reaction mixture was allowed to warm to room temperature and was further stirred for 2 h. Progress of the reaction was monitored by TLC. After completion, the reaction mixture was cooled to room temperature, quenched with water (20 mL) and extracted with EA (3×30 mL). The organic layer was dried over anhydrous sodium sulfate, filtered and concentrated under reduced pressure. The crude compound was purified by silica gel chromatography eluting with 0-40% EA in hexane to afford the title compound (0.150 g). LC-MS (Method B) (ESI+): m/z 271.40 (M+H)$^+$; $^1$H-NMR (400 MHz, DMSO-d$_6$) δ 7.72 (d, J=8.31 Hz, 2H), 7.53 (d, J=7.82 Hz, 2H), 5.38 (t, J=5.62 Hz, 1H), 4.61 (d, J=5.87 Hz, 2H), 4.34 (q, J=7.34 Hz, 2H), 1.42 (t, J=7.34 Hz, 3H).

Step 4: Synthesis of 6-chloro-1-(4-(1-ethyl-3-(trifluoromethyl)-1H-1,2,4-triazol-5-yl)benzyl)-1H-pyrazolo[3,4-d]pyrimidine (I-35)

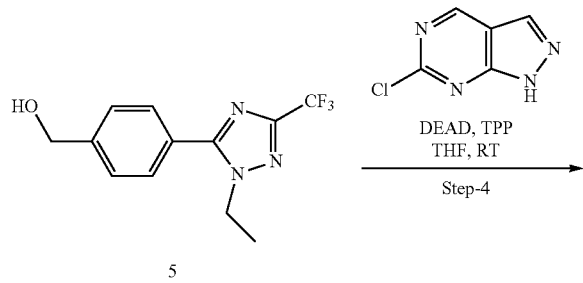

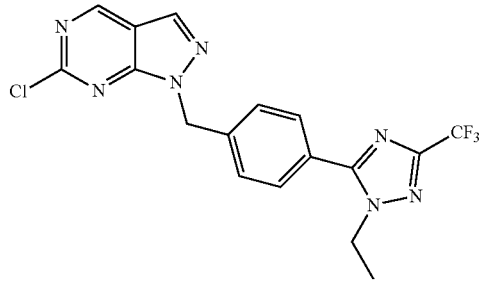

I-35

To a stirred solution of (4-(1-ethyl-3-(trifluoromethyl)-1H-1,2,4-triazol-5-yl)phenyl)methanol 5 (0.130 g, 0.479 mmol) in THF (5 mL) at 0° C., was added 6-chloro-1H-pyrazolo[3,4-d]pyrimidine (0.066 g, 0.43 mmol), DEAD (0.163 g, 0.959 mmol) and TPP (0.246 g, 0.959 mmol). The reaction mixture was allowed to warm to room temperature and was then stirred for 6 h. Progress of the reaction was monitored by TLC. After completion, the reaction mixture was quenched with water (20 mL) and extracted with EA (3×30 mL). The combined organic layer was dried over anhydrous sodium sulfate, filtered and concentrated under reduced pressure. The crude compound was purified by silica gel chromatography using 0-30% EA in hexane as eluent to afford the title compound (0.100 g). $^1$H-NMR (400 MHz, DMSO-d$_6$) δ 9.33 (s, 1H), 8.53 (s, 1H), 7.73 (d, J=8.31 Hz, 2H), 7.45 (d, J=7.83 Hz, 2H), 5.77 (s, 2H), 4.30 (q, J=7.17 Hz, 2H), 1.39 (t, J=7.34 Hz, 3H).

The following intermediates were prepared from the appropriate heterocycles and alkylating reagents according to the method of preparation for I-35:

| Intermediate | Structure | Analytics |
| --- | --- | --- |
| I-36 | 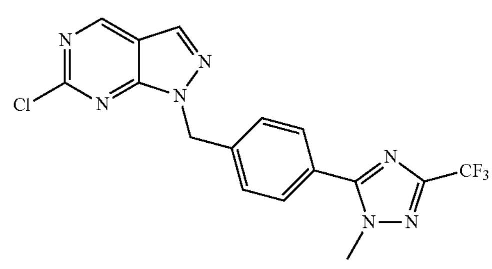 [SMILES: Cn1nc(C(F)(F)F)nc1-c1ccc(Cn2ncc3cnc(Cl)nc32)cc1] | LC-MS (Method A) (ESI+): m/z 394 (M + H)$^+$; $^1$HNMR (300 MHz, CDCl$_3$) δ 9.07 (s, 1H), 8.20 (s, 1H), 7.69 (d, J = 8.1 Hz, 2H), 7.53 (d, J = 8.1 Hz, 2H), 5.72 (s, 2H), 4.03 (s, 3H). |

| Intermediate | Structure | Analytics |
|---|---|---|
| I-37 | 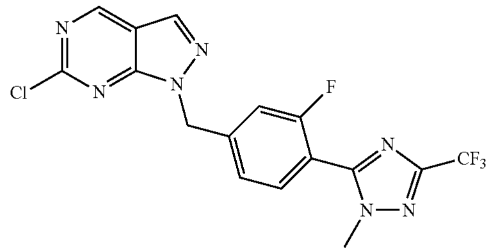 [SMILES: Cn1nc(C(F)(F)F)nc1-c1ccc(Cn2ncc3cnc(Cl)nc32)cc1F] | LC-MS (Method B) (ESI+): m/z 412 (M + H)+; 1H-NMR (400 MHz, DMSO-d6) δ 9.33 (s, 1H), 8.54 (s, 1H), 7.70 (t, J = 7.83 Hz, 1H), 7.38 (d, J = 10.76 Hz, 1H), 7.26 (d, J = 8.31 Hz, 1H), 5.79 (s, 2H), 3.88 (s, 3H). |
| I-38 | 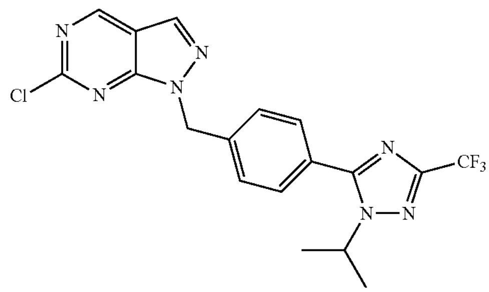 [SMILES: CC(C)n1nc(C(F)(F)F)nc1-c1ccc(Cn2ncc3cnc(Cl)nc32)cc1] | LC-MS (Method B) (ESI+): m/z 422.13 (M + H)+. |
Preparation of Common Intermediate I-39
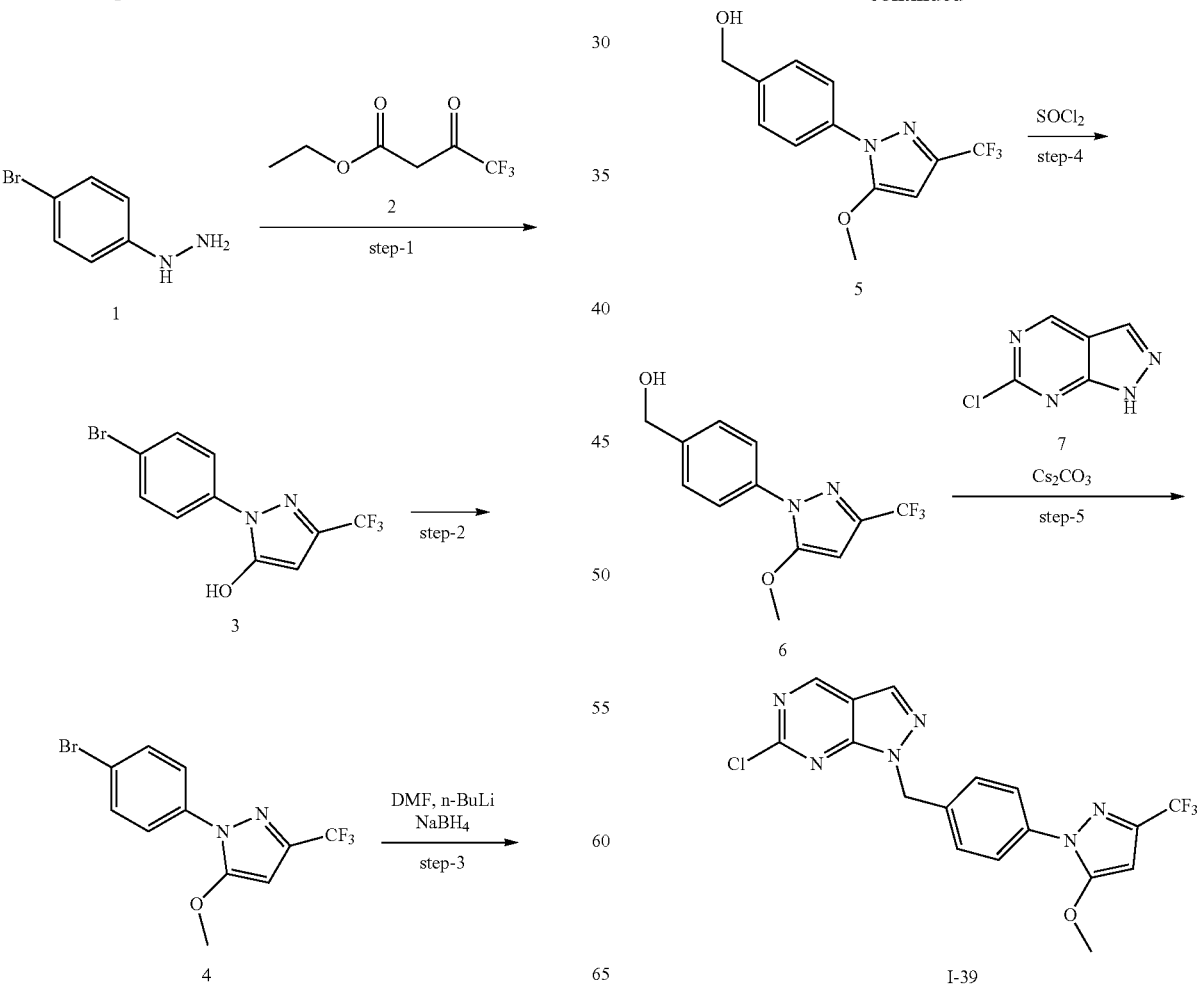

Step 1: Synthesis of 1-(4-Bromophenyl)-3-(trifluoromethyl)-1H-pyrazol-5-ol

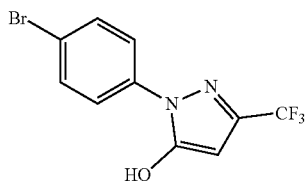 [SMILES: Oc1cc(C(F)(F)F)nn1-c1ccc(Br)cc1]

To a solution of (4-bromophenyl)hydrazine hydrochloride (4.9 g, 22 mmol) in ethanol (60 mL) at rt, was added sodium hydroxide (898 mg, 22.5 mmol) in one portion. The resulting mixture was stirred at rt for 30 min, a then a solution of ethyl 4,4,4-trifluoro-3-oxobutanoate (4.9 g, 27 mmol) in ethanol (10 mL) was added in one portion to the reaction mixture. The reaction was heated to reflux and stirred overnight. After the reaction was completed as indicated by TLC analysis, the reaction was cooled to rt and quenched with water (150 mL). The resulting mixture was acidified to pH 5 with diluted HCl solution (1 N) and extracted with EA (100 mL×3). The combined organic layer was dried over sodium sulfate (50 g), filtered and concentrated in vacuo. The residue was purified by silica gel chromatography (PE:EA=30:1 to 6:1) to afford 6.2 g of the title compound. LC-MS (Method A) (ESI+): m/z 307 (M+H)+; 1H-NMR (300 MHz, CD3OD) δ 7.62-7.74 (m, 4H), 5.84 (s, 1H).

Step 2: Synthesis of 1-(4-Bromophenyl)-5-methoxy-3-(trifluoromethyl)-1H-pyrazole

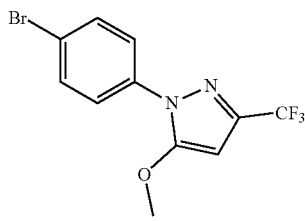 [SMILES: COc1cc(C(F)(F)F)nn1-c1ccc(Br)cc1]

To a solution of methyl 1-(4-bromophenyl)-3-(trifluoromethyl)-1H-pyrazol-5-ol (6.2 g, 20 mmol) in DMF (65 ml) at 0° C., was added sodium hydride (60% dispersion, 973 mg, 0.024 mmol) portion-wise over 5 min. After the mixture was stirred at 0° C. for 30 min, iodomethane (4.26 g, 0.03 mmol) was added dropwise to the reaction mixture over 2 min. The reaction was stirred at rt for 3 h, and then quenched with ice-water (200 mL) and extracted with EA (100 mL×3). The organic phase was washed with water (100 mL×2), dried over sodium sulfate (40 g), filtered and concentrated in vacuo. The residue was purified by silica gel chromatography (PE to PE:EA=100:1) to yield 4.4 g of the title compound. LC-MS (Method A) (ESI+): m/z 321 (M+H)+; 1H-NMR (300 MHz, CD3OD) δ 7.55-7.63 (m, 4H), 5.95 (s, 1H), 4.00 (s, 3H).

Step 3: Synthesis of 4-(5-Methoxy-3-(trifluoromethyl)-1H-pyrazol-1-yl)benzaldehyde

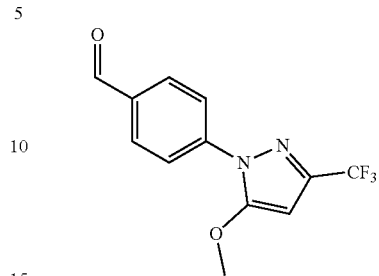

To solution of 1-(4-bromophenyl)-5-methoxy-3-(trifluoromethyl)-1H-pyrazole (1 g, 3.13 mmol) in THF (10 mL) at −78° C., was added n-BuLi (1.5 mL, 3.76 mmol) dropwise over 15 min. After the reaction was stirred at −78° C. for 1 h, anhydrous DMF (0.48 mL, 6.26 mmol) was added dropwise to the reaction mixture over 5 min. After addition, the reaction mixture was stirred at −78° C. for additional 30 min and then warmed to rt. After the reaction was completed as indicated by TLC analysis, the reaction was quenched with ice-water (20 mL). The resulting mixture was extracted with EA (30 mL×2), dried over sodium sulfate (30 g), filtered and concentrated in vacuo. The residue was purified by silica gel chromatography (PE:EA=30:1 to 20:1) to yield 570 mg of the title compound. LC-MS (Method A) (ESI+): m/z 271 (M+H)+; 1H-NMR (300 MHz, CD3OD) δ 10.04 (s, 1H), 7.97 (d, J=6.6 Hz, 4H), 3.99 (s, 1H), 4.05 (s, 3H).

Step 4: Synthesis of (4-(5-Methoxy-3-(trifluoromethyl)-1H-pyrazol-1-yl)phenyl)methanol

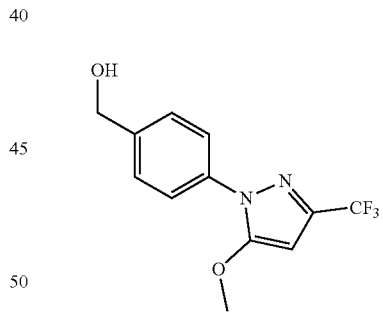

To a solution of 4-(5-methoxy-3-(trifluoromethyl)-1H-pyrazol-1-yl)benzaldehyde (570 mg, 2.11 mmol) in THF (10 mL) at rt, was added NaBH4 (80 mg, 2.11 mmol) in one portion. The reaction was stirred at rt for 1 h. After the reaction was completed as indicated by TLC analysis, the reaction was quenched with water (20 mL) and extracted with EA (20 mL×2). The combined organic layer was dried over sodium sulfate (20 g), filtered and concentrated in vacuo to afford 620 mg of the title compound that was used without purification in subsequent steps. LC-MS (Method A) (ESI+): m/z 273 (M+H)+; 1H-NMR (300 MHz, CD3OD) δ 7.68 (d, J=8.4 Hz, 2H), 7.45 (d, J=8.4 Hz, 2H), 5.96 (s, 1H), 4.75 (d, J=5.1 Hz, 2H), 3.99 (s, 3H), 1.58 (s, 1H).

Step 5: Synthesis of 1-(4-(Chloromethyl)phenyl)-5-methoxy-3-(trifluoromethyl)-1H-pyrazole

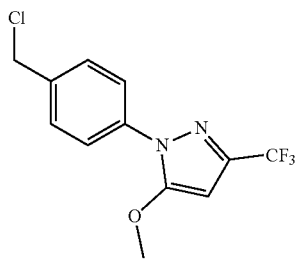 [SMILES: COc1cc(C(F)(F)F)nn1-c1ccc(CCl)cc1]

To a solution of (4-(5-methoxy-3-(trifluoromethyl)-1H-pyrazol-1-yl)phenyl)methanol (570 mg, 2.10 mmol) in DCE (20 ml), was added $SOCl_2$ (748 mg, 6.29 mmol) in one portion. After the addition, the reaction was stirred at 50° C. for 20 min. After the reaction mixture was completed as indicated by TLC analysis, the reaction mixture was concentrated to dryness in vacuo to afford 500 mg of the crude title compound that was used without purification in subsequent steps. LC-MS (Method A) (ESI+): m/z 291 (M+H)+.

Step 6: Synthesis of 6-Chloro-1-(4-(5-methoxy-3-(trifluoromethyl)-1H-pyrazol-1-yl)benzyl)-1H-pyrazolo[3,4-d]pyrimidine (I-39)

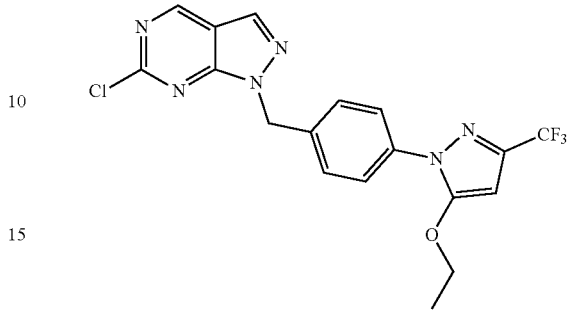

To a solution of 1-(4-(chloromethyl)phenyl)-5-methoxy-3-(trifluoromethyl)-1H-pyrazole (520 mg, 1.79 mmol) in DMF (25 mL), was added 6-chloro-1H-pyrazolo[3,4-d]pyrimidine (276 mg, 1.79 mmol) and potassium carbonate (741 mg, 5.37 mmol). After the addition, the reaction was stirred at 70° C. for 1 h. After the reaction was completed as indicated by TLC analysis, the reaction was quenched with water (30 mL) and extracted with EA (30 mL×2). The combined organic phase was washed with water and brine, dried over sodium sulfate (20 g), filtered and concentrated in vacuo. The residue was purified by silica gel chromatography (PE:EA=10:1 to 5:1) to afford 330 mg of the title compound. LC-MS (Method A) (ESI+): m/z 409 (M+H)+; 1H-NMR (300 MHz, CD3OD) δ 9.05 (s, 1H), 8.17 (s, 1H), 7.67 (d, J=8.4 Hz, 2H), 7.47 (d, J=8.4 Hz, 2H), 5.93 (s, 1H), 5.66 (s, 2H), 3.99 (s, 3H).

The following intermediates were prepared from the appropriate heterocycles and alkylating reagents according to the method of preparation for I-39:

| Intermediate | Structure | Analytics |
|---|---|---|
| I-40 | 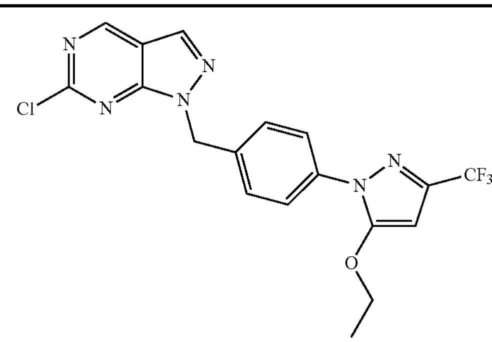 | LC-MS (Method A) (ESI+): m/z 423 (M + H)+; 1H-NMR (300 MHz, CDCl3) δ 9.05 (s, 1H), 8.17 (s, 1H), 7.70 (d, J = 8.4 Hz, 2H), 7.46 (d, J = 8.4 Hz, 2H), 5.90 (s, 1H), 5.67 (s, 2H), 4.20 (q, J = 7.2 Hz, 2H), 1.45 (t, J = 7.2 Hz, 3H). |
| I-41 | 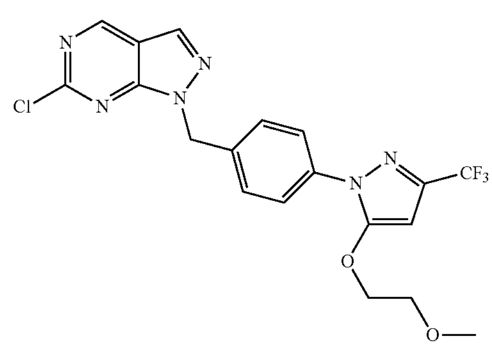 [SMILES: COCCOc1cc(C(F)(F)F)nn1-c1ccc(Cn2ncc3cnc(Cl)nc32)cc1] | 1H-NMR (300 MHz, CDCl3) δ 9.05 (s, 1H), 8.17 (s, 1H), 7.70 (d, J = 8.4 Hz, 2H), 7.46 (d, J = 8.4 Hz, 2H), 5.94 (s, 1H), 5.66 (s, 2H), 4.27(d, J = 4.5 Hz, 2H), 3.73 (d, J = 4.5 Hz, 2H), 3.73 (s, 1H). |

-continued
| Intermediate | Structure | Analytics |
|---|---|---|
| I-42 | 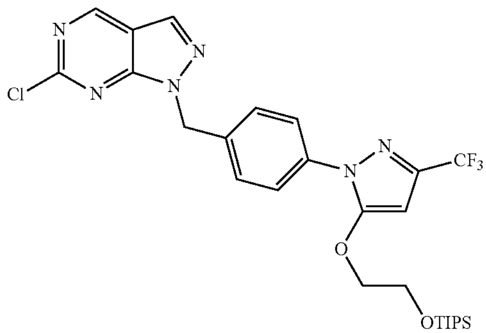 | LC-MS (Method A) (ESI+): m/z 595 (M + H)+; 1H-NMR (300 MHz, CDCl3) δ 9.05 (s, 1H), 8.17 (s, 1H), 7.70 (d, J = 8.4 Hz, 2H), 7.44 (d, J = 8.4 Hz, 2H), 5.94 (s, 1H), 5.66 (s, 2H), 4.21 (t, J = 4.8 Hz, 2H), 4.01 (t, J = 4.8 Hz, 2H), 1.08-1.02 (m, 3H), 0.98 (d, J = 5.4 Hz, 18H). |
| I-43 | 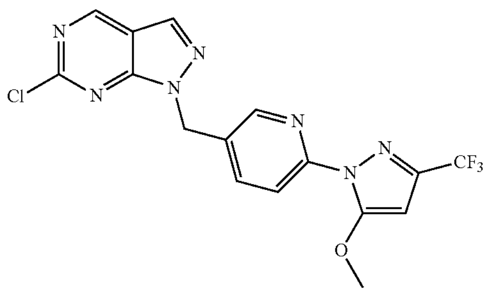 [SMILES: COc1cc(C(F)(F)F)nn1-c1ccc(Cn2ncc3cnc(Cl)nc32)cn1] | LC-MS (Method A) (ESI+): m/z 410 (M + H)+; 1H-NMR (300 MHz, CDCl3) δ 9.06 (s, 1H), 8.66 (d, J = 2.1 Hz, 1H), 8.17 (s, 1H), 7.90 (dd, J = 8.4, 2.1 Hz, 1H), 7.71 (d, J = 8.4 Hz, 1H), 5.96 (s, 1H), 5.69 (s, 2H), 4.02 (s, 3H). |
| I-44 | 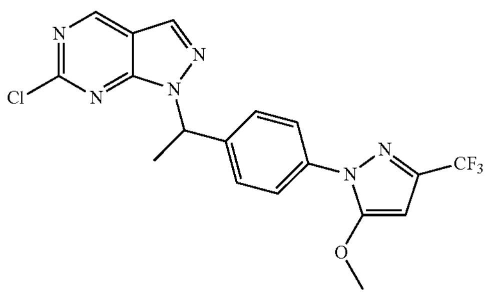 | LC-MS (Method A) (ESI+): m/z 511.24 (M + H)+. |
Preparation of Common Intermediate I-45
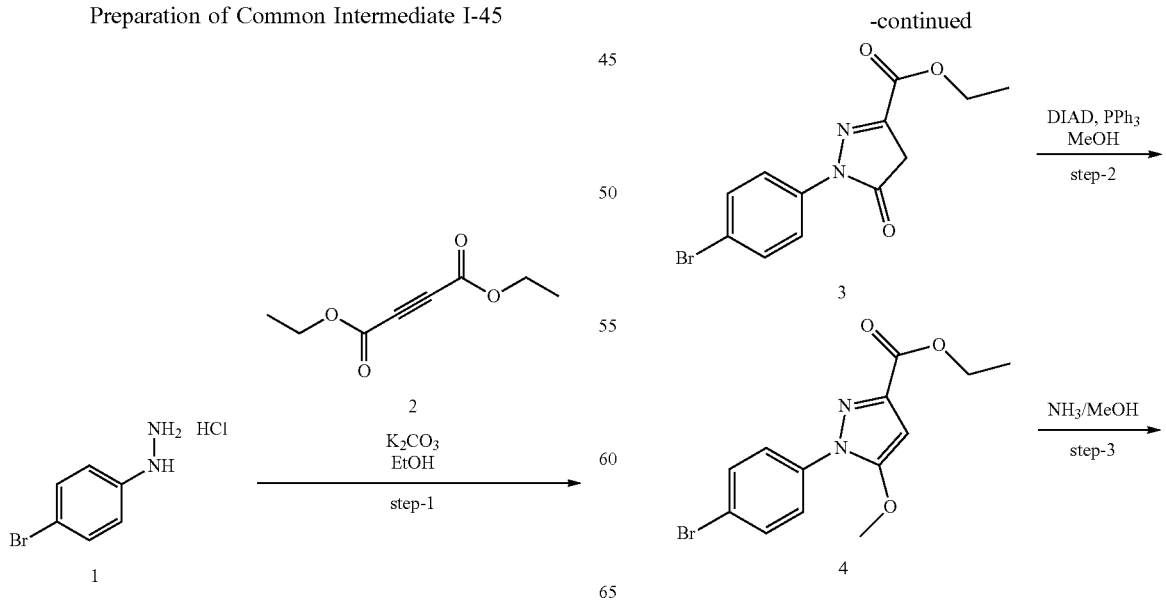

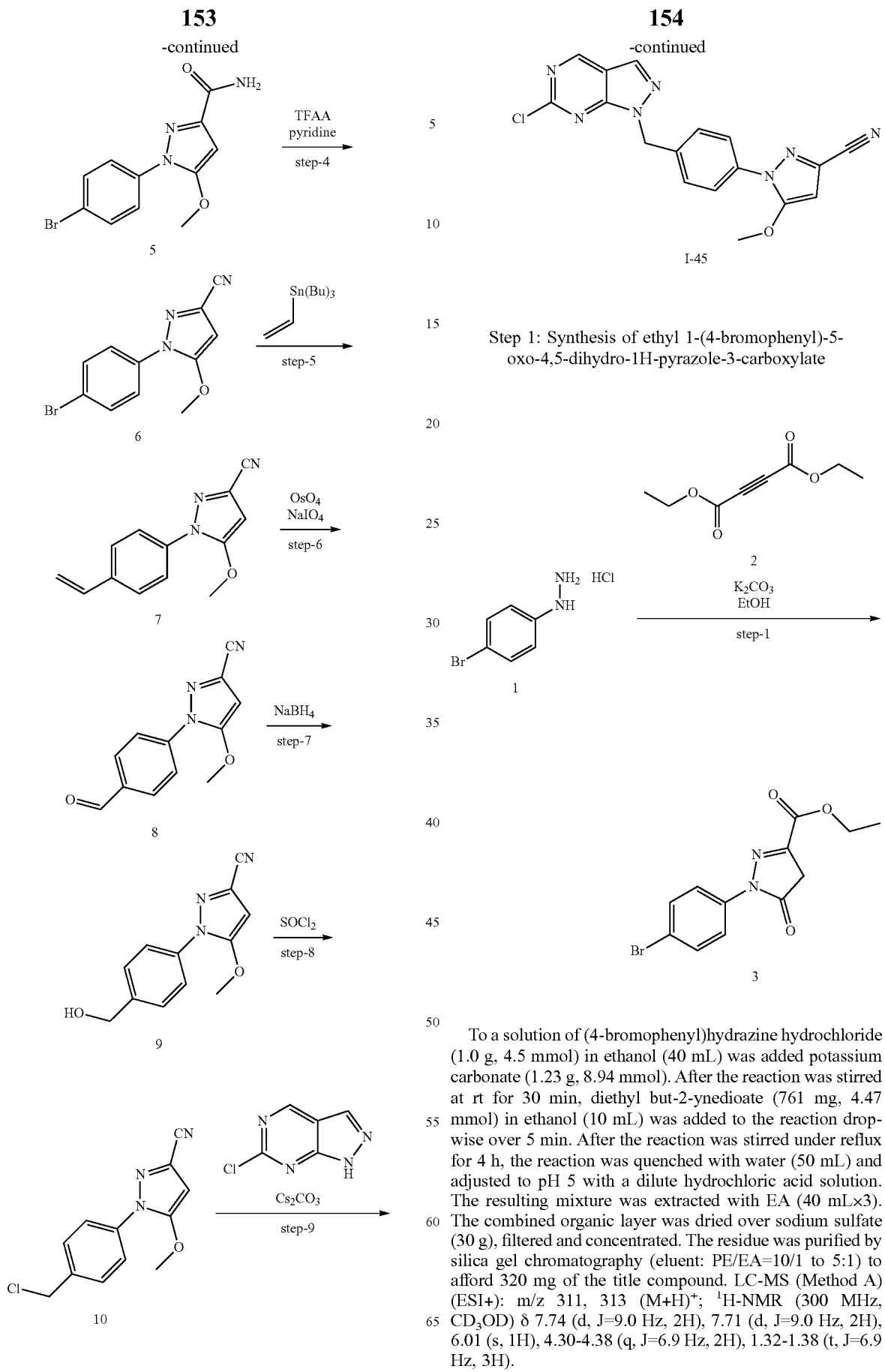

Step 1: Synthesis of ethyl 1-(4-bromophenyl)-5-oxo-4,5-dihydro-1H-pyrazole-3-carboxylate To a solution of (4-bromophenyl)hydrazine hydrochloride (1.0 g, 4.5 mmol) in ethanol (40 mL) was added potassium carbonate (1.23 g, 8.94 mmol). After the reaction was stirred at rt for 30 min, diethyl but-2-ynedioate (761 mg, 4.47 mmol) in ethanol (10 mL) was added to the reaction dropwise over 5 min. After the reaction was stirred under reflux for 4 h, the reaction was quenched with water (50 mL) and adjusted to pH 5 with a dilute hydrochloric acid solution. The resulting mixture was extracted with EA (40 mL×3). The combined organic layer was dried over sodium sulfate (30 g), filtered and concentrated. The residue was purified by silica gel chromatography (eluent: PE/EA=10/1 to 5:1) to afford 320 mg of the title compound. LC-MS (Method A) (ESI+): m/z 311, 313 (M+H)$^+$; $^1$H-NMR (300 MHz, CD$_3$OD) δ 7.74 (d, J=9.0 Hz, 2H), 7.71 (d, J=9.0 Hz, 2H), 6.01 (s, 1H), 4.30-4.38 (q, J=6.9 Hz, 2H), 1.32-1.38 (t, J=6.9 Hz, 3H).

Step 2: Synthesis of ethyl 1-(4-bromophenyl)-5-methoxy-1H-pyrazole-3-carboxylate

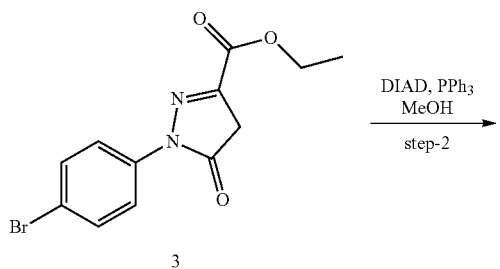

To a mixture of ethyl 1-(4-bromophenyl)-5-oxo-4,5-dihydro-1H-pyrazole-3-carboxylate (720 mg, 2.32 mmol), triphenylphosphine (913 mg, 3.48 mmol) and methanol (96 mg, 3.02 mmol) in toluene (40 mL) at 0° C., was added DIAD (704 mg, 3.48 mmol) dropwise over 5 min. After the mixture was stirred at 0° C. for 30 min, the reaction was warmed to rt slowly and stirred overnight. After the reaction was complete as indicated by TLC analysis, the mixture was quenched with water (20 mL) and extracted with EA (30 mL×3). The combined organic layer was dried over sodium sulfate (30 g), filtered and concentrated. The residue was purified by silica gel chromatography (eluent: PE/EA=20/1 to 10/1) to yield 650 mg of the title compound. LC-MS (Method A) (ESI+): m/z 325, 327 (M+H)$^+$; $^1$H-NMR (300 MHz, CDCl$_3$) δ 7.65 (d, J=8.7 Hz, 2H), 7.56 (d, J=8.7 Hz, 2H), 6.22 (s, 1H), 4.39-4.46 (q, J=7.2 Hz, 2H), 3.98 (s, 3H), 1.39-1.44 (t, J=7.2 Hz, 3H).

Step 3: Synthesis of methyl 1-(4-bromophenyl)-5-methoxy-1H-pyrazole-3-carboxamide

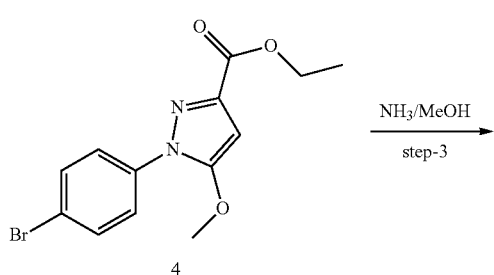

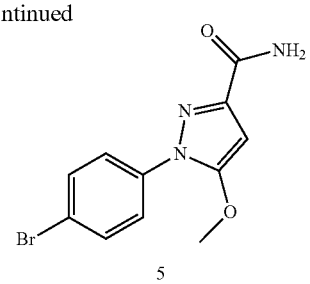

In a seal tube, a solution of ethyl 1-(4-bromophenyl)-5-methoxy-1H-pyrazole-3-carboxylate (650 mg, 2.01 mmol) in a saturated methanolic ammonia solution (30 mL) was stirred at 60° C. for 7 h, After the reaction was complete as indicated by TLC analysis, the mixture was quenched with water (30 mL), and extracted with EA (20 mL×3). The combined organic layer was dried over sodium sulfate (30 g), filtered and concentrated. The residue was purified by silica gel chromatography (eluent: PE/EA=5/1 to 0/1) to yield 405 mg of the title compound. LC-MS (Method A) (ESI+): m/z 296, 298 (M+H)$^+$; $^1$H-NMR (300 MHz, CDCl$_3$) δ 7.55-7.65 (m, 4H), 6.82 (s, 1H), 6.26 (s, 1H), 5.40 (s, 1H), 3.99 (s, 3H).

Step 4: Synthesis of 1-(4-bromophenyl)-5-methoxy-1H-pyrazole-3-carbonitrile

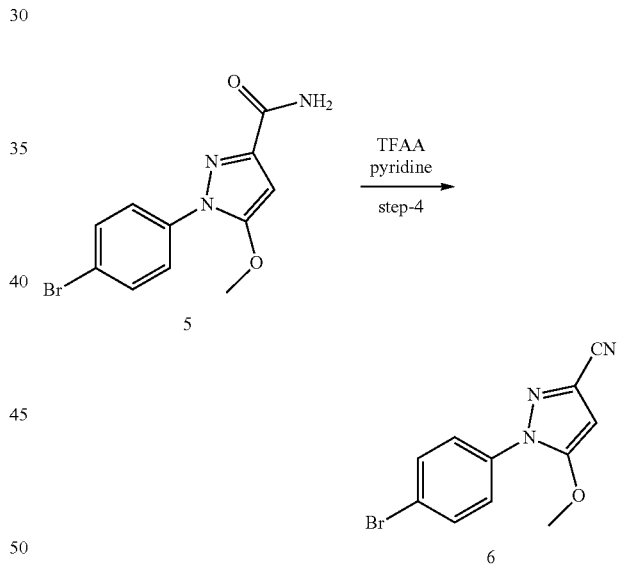

To a solution of methyl 1-(4-bromophenyl)-5-methoxy-1H-pyrazole-3-carboxamide (400 mg, 1.36 mmol) in DCM (40 mL) and pyridine (2 mL) at 0° C. was added trifluoroacetic anhydride (1.6 mL) dropwise over 5 min. The reaction was stirred at 0° C. for 1 h. After the reaction was complete as indicated by TLC analysis, the mixture was quenched with a saturated aqueous NH$_4$Cl solution (40 mL) and extracted with DCM (40 mL×3). The organic layer was washed with water (20 mL) and brine (20 mL), and dried over sodium sulfate (40 g), filtered and concentrated. The resulting residue was purified by silica gel chromatography (eluent: PE/EA=20/1 to 10/1) to yield 295 mg of the title compound. LC-MS (Method A) (ESI+): m/z 278, 280 (M+H)$^+$; $^1$H-NMR (300 MHz, CDCl$_3$) δ 7.59 (s, 4H), 6.06 (s, 1H), 4.00 (s, 3H).

Step 5: Synthesis of 5-methoxy-1-(4-vinylphenyl)-1H-pyrazole-3-carbonitrile

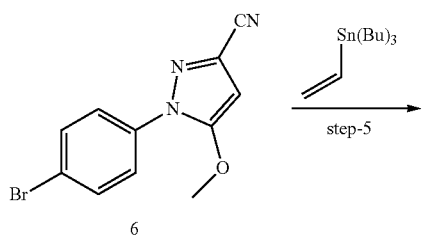

To a solution of 1-(4-bromophenyl)-5-methoxy-1H-pyrazole-3-carbonitrile (290 mg, 1.05 mmol) in toluene (8 mL) was added tributyl(vinyl)stannane (498 mg, 1.57 mmol) and Pd(Ph$_3$)$_4$ (121 mg, 0.11 mmol). The reaction was stirred at 90° C. for 6 h. After the reaction was complete as indicated by LC-MS analysis, the mixture was quenched with water (10 mL) and extracted with EA (10 mL×2). The combined organic layer was dried over sodium sulfate (20 g), filtered and concentrated. The resulting residue was purified by silica gel chromatography (eluent: PE/EA=20/1 to 10/1) to yield 200 mg of the title compound. LC-MS (Method A) (ESI+): m/z 226 (M+H)$^+$; $^1$H-NMR (300 MHz, CDCl$_3$) δ 7.64 (d, J=8.7 Hz, 2H), 7.49 (d, J=8.7 Hz, 2H), 6.74 (dd, J=17.7 Hz, J=10.8 Hz, 1H), 6.06 (s, 1H), 5.80 (d, J=17.7 Hz, 1H), 5.33 (d, J=10.8 Hz, 1H), 3.99 (s, 3H).

Step 6: Synthesis of 1-(4-formylphenyl)-5-methoxy-1H-pyrazole-3-carbonitrile

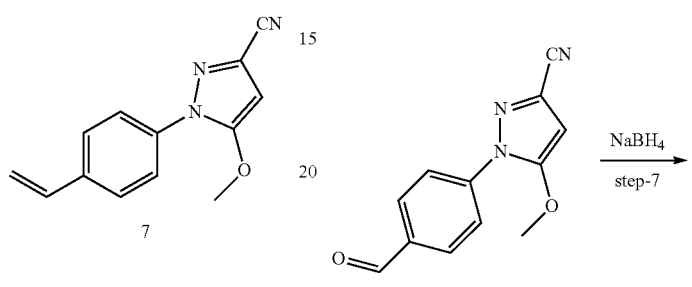

To a solution of 5-methoxy-1-(4-vinylphenyl)-1H-pyrazole-3-carbonitrile (20 mg, 0.89 mmol) in THF/H$_2$O (10 mL/5 mL) and was added NaIO$_4$ (570 mg, 2.67 mmol) and OsO$_4$ (22 mg, 0.09 mmol) in one portion. The reaction was stirred at room temperature for 30 min. After the reaction was complete as indicated by TLC analysis, the mixture was quenched with an aqueous NH$_4$Cl solution (10 mL) and extracted with EA (20 mL×2). The combined organic was dried over sodium sulfate (20 g), filtered and concentrated to afford 210 mg of the crude title compound. LC-MS (Method A) (ESI+): m/z 228 (M+H)$^+$; $^1$H-NMR (300 MHz, CDCl$_3$) δ 10.05 (s, 1H), 7.84-8.05 (m, 4H), 6.01 (s, 1H), 3.99 (s, 3H).

Step 7: Synthesis of 1-(4-(hydroxymethyl)phenyl)-5-methoxy-1H-pyrazole-3-carbonitrile

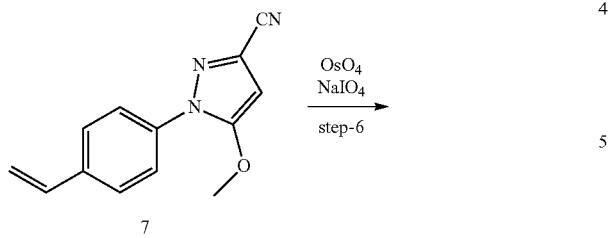

To a solution of 1-(4-formylphenyl)-5-methoxy-1H-pyrazole-3-carbonitrile (210 mg, 0.93 mmol) in THF (30 mL) was added NaBH$_4$ (46 mg, 1.2 mmol) portion-wise over 5 min. The reaction was stirred at room temperature for 1 h. After the reaction was complete as indicated by TLC analysis, the mixture was quenched with water (20 mL) and extracted with EA (30 mL×2). The combined organic layer was dried over sodium sulfate (20 g) and concentrated. The residue was purified by silica gel chromatography (eluent: PE/EA=5/1 to 2/1) to yield 170 mg of the title compound. LC-MS (Method A) (ESI+): m/z 230 (M+H)$^+$; $^1$H-NMR (300 MHz, CDCl$_3$) δ 7.67 (d, J=8.7 Hz, 2H), 7.47 (d, J=8.7 Hz, 2H), 6.07 (s, 1H), 4.76 (d, J=6 Hz, 2H), 3.99 (s, 3H), 1.75 (t, J=6 Hz, 1H).

Step 8: Synthesis of 1-(4-(chloromethyl)phenyl)-5-methoxy-1H-pyrazole-3-carbonitrile

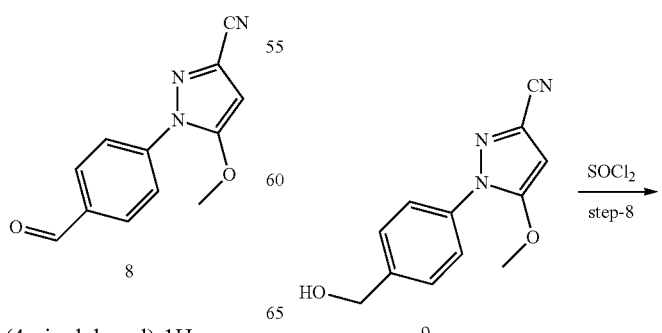

-continued

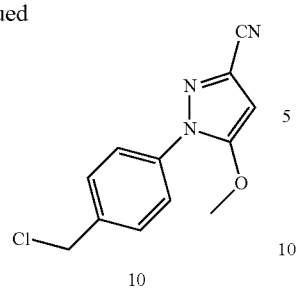

To a solution of 1-(4-(hydroxymethyl)phenyl)-5-methoxy-1H-pyrazole-3-carbonitrile (170 mg, 0.74 mmol) in DCE (10 mL) was added SOCl$_2$ (176 mg, 1.48 mmol) in one portion, and the reaction was stirred at 50° C. for 1 h. After the reaction mixture was complete as indicated by TLC analysis, the reaction mixture was concentrated to dryness to afford 205 mg of the crude title compound. LC-MS (Method A) (ESI+): m/z 248 (M+H)$^+$; $^1$H-NMR (300 MHz, CDCl$_3$) δ 7.70 (d, J=8.4 Hz, 2H), 7.49 (d, J=8.4 Hz, 2H), 6.07 (s, 1H), 4.62 (s, 2H), 4.00 (s, 3H).

Step 9: Synthesis of 1-(4-((6-chloro-1H-pyrazolo[3,4-d]pyrimidin-1-yl)methyl)phenyl)-5-methoxy-1H-pyrazole-3-carbonitrile (I-45)

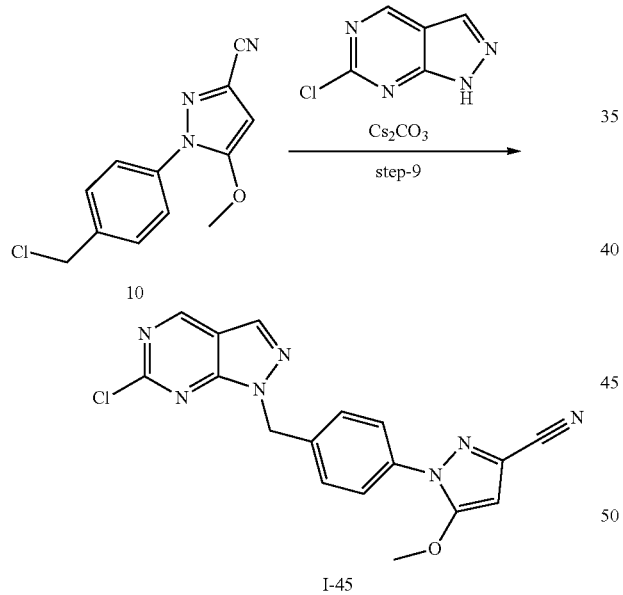

To a solution of 1-(4-(chloromethyl)phenyl)-5-methoxy-1H-pyrazole-3-carbonitrile (205 mg, 0.83 mmol) in DMF (5 mL) was added 6-chloro-1H-pyrazolo[3,4-d]pyrimidine (153 mg, 1.0 mmol) and potassium carbonate (812 mg, 2.49 mmol) in one portion. After the addition, the reaction was stirred at 70° C. for 1 h. After the reaction mixture was complete as indicated by TLC analysis, the mixture was quenched with water (10 mL) and extracted with EA (30 mL×2). The combined organic layer was washed with water (20 mL) and brine (10 mL), dried over sodium sulfate (30 g), filtered and concentrated. The residue was purified by silica gel chromatography (eluent: PE/EA=10/1 to 5/1) to afford 57 mg of the title compound. LC-MS (Method A) (ESI+): m/z 366 (M+H)$^+$; $^1$H-NMR (300 MHz, CDCl$_3$) δ 9.05 (s, 1H), 8.18 (s, 1H), 7.66 (d, J=8.4 Hz, 2H), 7.48 (d, J=8.4 Hz, 2H), 6.04 (s, 1H), 5.67 (s, 2H), 3.97 (s, 3H).

Preparation of Common Intermediate I-46

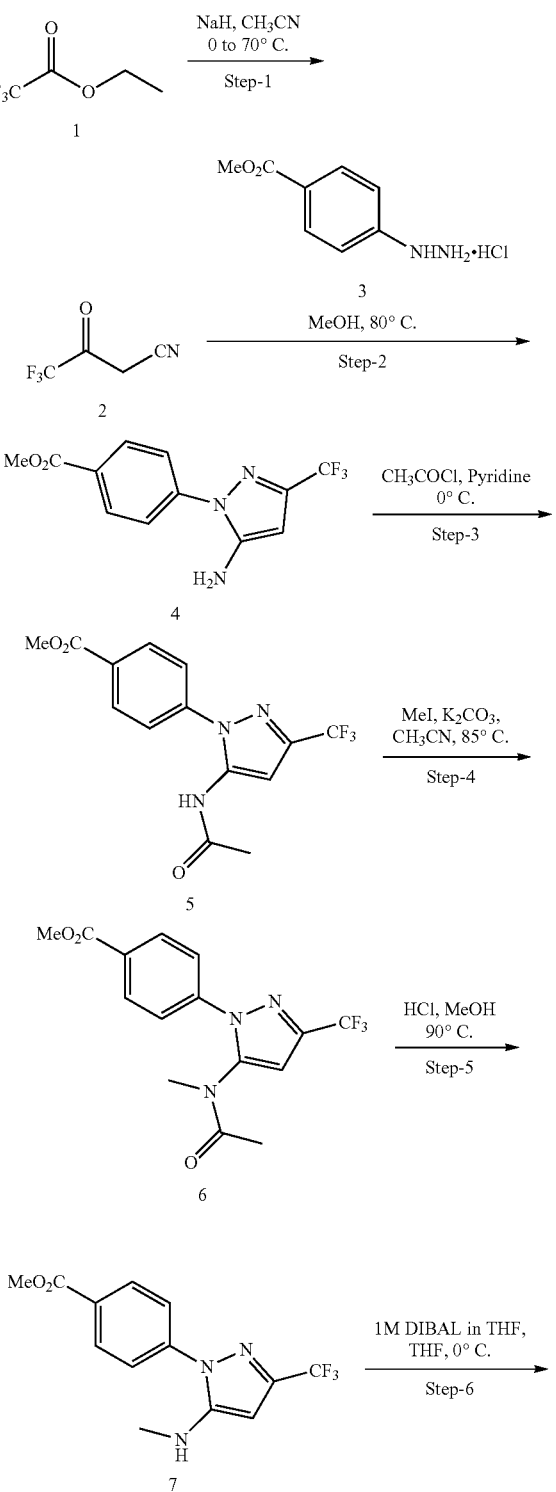

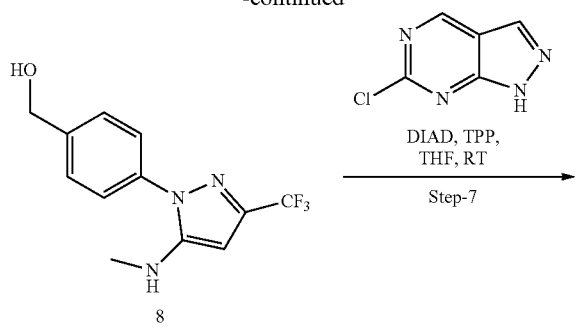

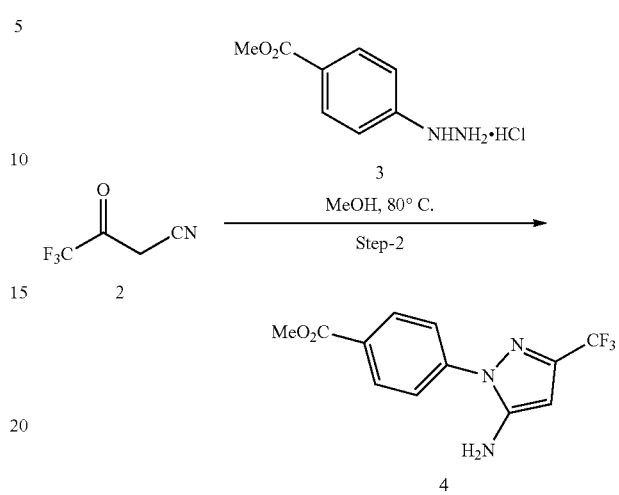

Step 2: Synthesis of ethyl 4-(5-amino-3-(trifluoromethyl)-1H-pyrazol-1-yl)benzoate

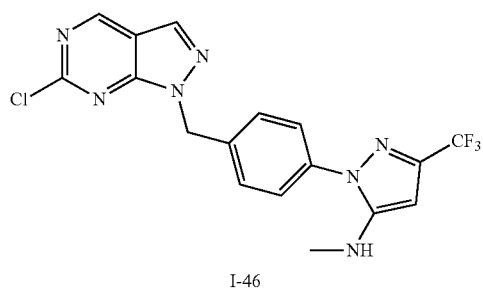

I-46

Step 1: Synthesis of 4,4,4-trifluoro-3-oxobutanenitrile

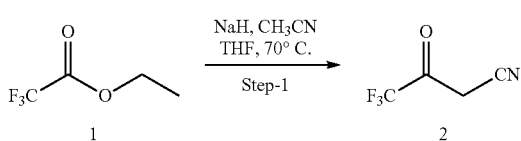

To a stirred suspension of NaH (10.5 g, 264 mmol) in THF (150 mL) at 0° C., were simultaneously added ethyl 2,2,2-trifluoroacetate 1 (15.0 g, 106 mmol) and MeCN (12.4 g, 159 mmol) under argon atmosphere. The resulting mixture was stirred was at room temperature for 10 min, and then heated to 70° C. for 16 h. Progress of the reaction was monitored by TLC. After completion, the reaction mixture was quenched with ice cold water (50 mL) and concentrated under reduced pressure to remove the organic phase. The remaining aqueous layer was extracted with diethyl ether (2×30 mL). The aqueous layer was then adjusted to pH 2 using conc. HCl, then extracted with diethyl ether (3×50 mL). The combined organic layer was dried over anhydrous sodium sulfate, filtered and concentrated under reduced pressure to afford the crude title compound 2 (18.0 g) that was used in subsequent steps without further purification.

To a stirred solution of 4,4,4-trifluoro-3-oxobutanenitrile 2 (3.39 g, 24.8 mmol) in methanol (30 mL), was added methyl 4-hydrazineylbenzoate hydrochloride 3 (2.50 g, 12.47 mmol) at room temperature. The reaction mixture was heated to 80° C. for 16 h. Progress of the reaction was monitored by TLC. After completion, the reaction mixture was concentrated under reduced pressure. The crude compound was purified by silica gel chromatography using 20-25% EA in hexane as eluent to afford the title compound (2.00 g). $^1$H-NMR (400 MHz, DMSO-$d_6$) δ 8.09 (d, J=8.48 Hz, 2H), 7.79 (d, J=8.48 Hz, 2H), 5.98 (br s, 2H), 5.84 (s, 1H), 3.89 (s, 3H).

Step 3: Synthesis of methyl 4-(5-acetamido-3-(trifluoromethyl)-1H-pyrazol-1-yl)benzoate

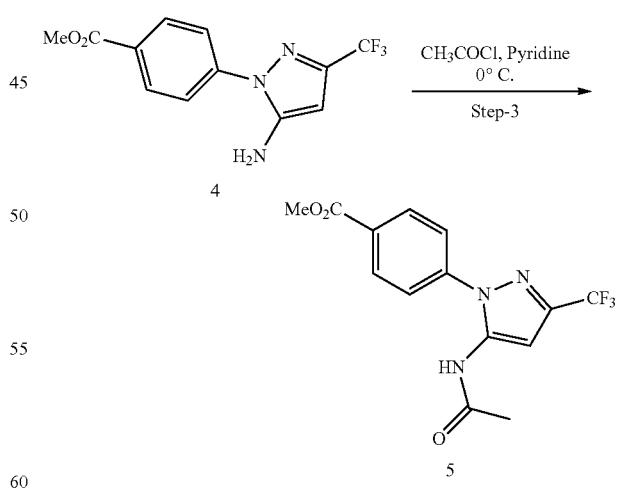

To an ice cooled solution of ethyl 4-(5-amino-3-(trifluoromethyl)-1H-pyrazol-1-yl)benzoate 4 (1.00 g, 3.51 mmol) in pyridine (10 mL), was added CH$_3$COCl (0.37 mL, 5.3 mmol) dropwise. The resulting mixture was stirred for 30 min, and progress of the reaction was monitored by TLC. After completion, the reaction mixture was quenched with saturated CuSO₄ solution (30 mL) and extracted with EA (2×50 mL). The combined organic layer was dried over anhydrous sodium sulfate, filtered and concentrated under reduced pressure. The crude compound was purified by silica gel chromatography using 0-40% EA in hexane as eluent to afford the title compound (0.800 g). LC-MS (Method B) (ESI+): Obs.: 328.05 (M+H)$^+$; $^1$H-NMR (400 MHz, CDCl₃) δ 8.21 (d, J=8.48 Hz, 2H), 7.59 (d, J=8.48 Hz, 2H), 6.95-7.00 (m, 1H), 3.96 (s, 3H), 2.17 (s, 3H).

Step 3: Synthesis of methyl 4-(5-(N-methylacetamido)-3-(trifluoromethyl)-1H-pyrazol-1-yl)benzoate

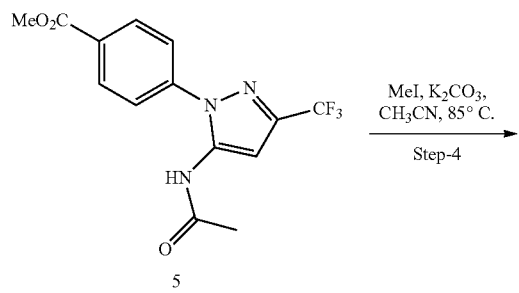

To a stirred solution of methyl 4-(5-acetamido-3-(trifluoromethyl)-1H-pyrazol-1-yl)benzoate 5 (0.800 g, 2.45 mmol) in CH₃CN (15 mL), was added potassium carbonate (0.506 g, 3.67 mmol) and methyl iodide (0.45 mL, 7.34 mmol) at room temperature. The reaction mixture was then heated in a sealed tube at 85° C. for 16 h. Progress of the reaction was monitored by TLC. After completion, the reaction mixture was diluted with EA (100 mL) and washed with water (2×25 mL) followed by brine (20 mL). The organic layer was dried over anhydrous sodium sulfate, filtered and concentrated under reduced pressure. The crude compound was purified by silica gel chromatography using 0-30% EA in hexane as eluent to afford the title compound (0.650 g). LC-MS (Method B) (ESI+): Obs.: 342.10 (M+H)$^+$; $^1$H-NMR (400 MHz, CDCl₃) (8.19 (d, J=8.48 Hz, 2H), 7.57 (d, J=8.48 Hz, 2H), 6.62 (s, 1H), 3.96 (s, 3H), 3.15 (s, 3H), 1.85 (s, 3H).

Step 5: Synthesis of methyl 4-(5-(methylamino)-3-(trifluoromethyl)-1H-pyrazol-1-yl)benzoate

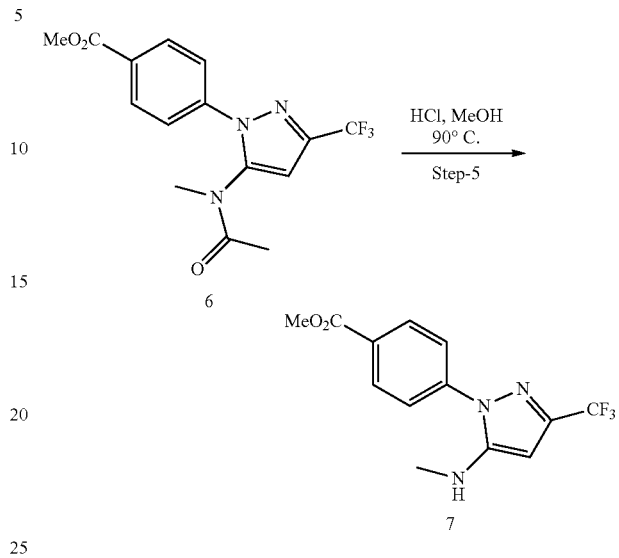

To a stirred solution of methyl 4-(5-(N-methylacetamido)-3-(trifluoromethyl)-1H-pyrazol-1-yl) benzoate 6 (0.650 g, 1.91 mmol) in methanol (10 mL), was added conc. HCl (7 mL) at room temperature. The reaction mixture was then heated at 90° C. for 4 h. Progress of the reaction was monitored by TLC. After completion, the reaction mixture was cooled to room temperature, diluted with water (20 mL) and extracted with EA (3×25 mL). The combined organic layer was dried over anhydrous sodium sulfate, filtered and concentrated under reduced pressure. The crude compound was purified by silica gel chromatography using 0-30% EA in hexane as eluent to afford the title compound (0.500 g). LC-MS (Method C) (ESI+): m/z 299.98 (M+H)$^+$; $^1$H-NMR (400 MHz, CDCl₃) δ 8.16 (d, J=8.48 Hz, 2H), 7.68 (d, J=8.48 Hz, 2H), 5.80 (s, 1H), 3.95 (s, 3H), 2.89 (s, 3H).

Step 6: Synthesis of (4-(5-(methylamino)-3-(trifluoromethyl)-1H-pyrazol-1-yl)phenyl)methanol

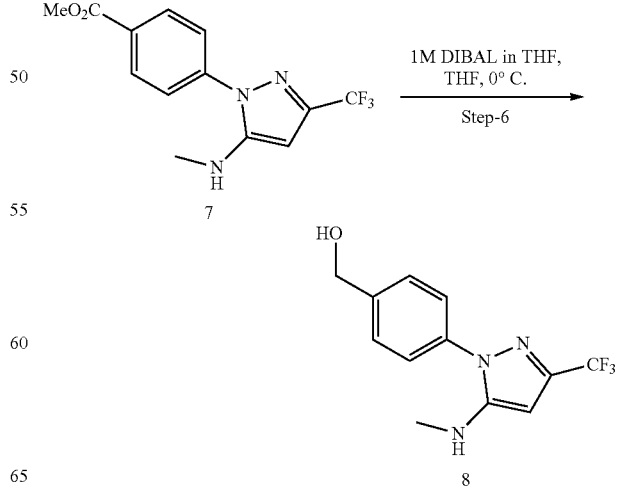

To a stirred solution of methyl 4-(5-(methylamino)-3-(trifluoromethyl)-1H-pyrazol-1-yl)benzoate 7 (0.500 g, 1.67 mmol) in THF (15 mL) at 0° C., was added DIBAL-H (1M in toluene, 5.00 mL, 5.02 mmol). The resulting mixture was stirred for 30 min, and progress of the reaction was monitored by TLC. After completion, the reaction mixture was quenched with aqueous NH₄Cl (10 mL). The resulting solution was diluted with EA (20 mL) and filtered through a pad of Celite. The aqueous layer was separated and re-extracted with EA (3×15 mL). The combined organic layer was washed with brine (10 mL), dried over anhydrous sodium sulfate, filtered and concentrated under reduced pressure. The crude compound was purified by silica gel chromatography using 50-80% EA in hexane as eluent to afford the title compound (0.400 g). $^1$H-NMR (400 MHz, DMSO-$d_6$) δ 7.42-7.51 (m, 4H), 5.89 (s, 1H), 5.83 (d, J=4.40 Hz, 1H), 5.33 (t, J=5.62 Hz, 1H), 4.56 (d, J=5.87 Hz, 2H), 2.69 (d, J=4.89 Hz, 3H).

Step 7: Synthesis of 1-(4-((6-chloro-1H-pyrazolo[3,4-d]pyrimidin-1-yl)methyl)phenyl)-N-methyl-3-(trifluoromethyl)-1H-pyrazol-5-amine (I-46)

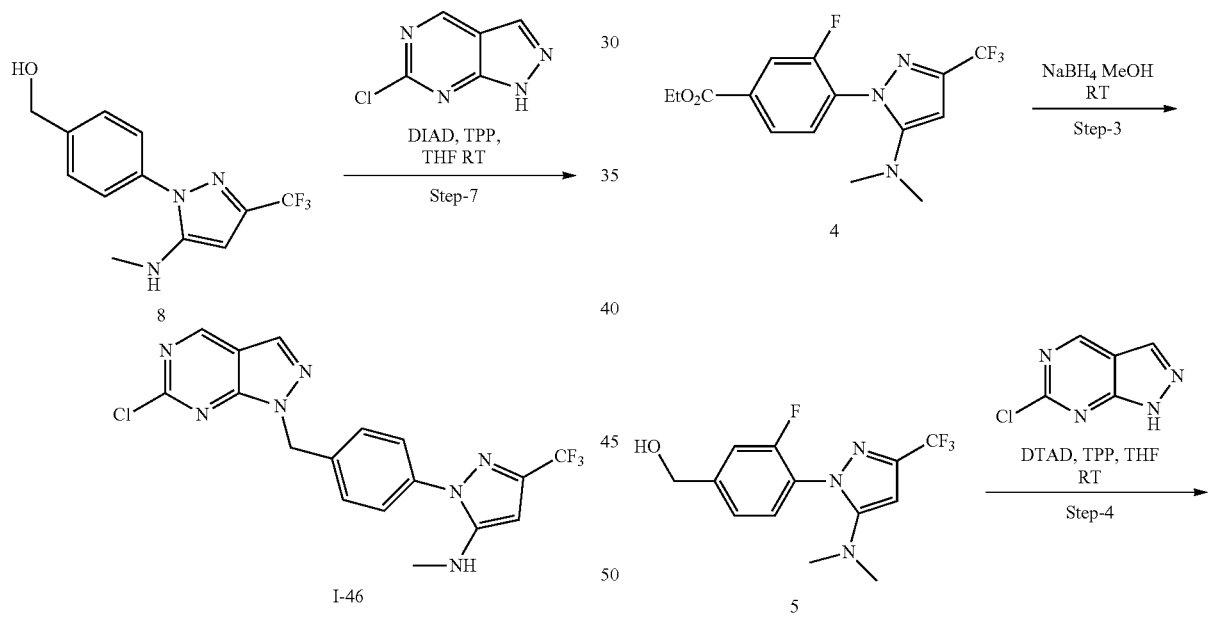

To a stirred solution of (4-(5-(methylamino)-3-(trifluoromethyl)-1H-pyrazol-1-yl)phenyl)methanol 8 (0.200 g, 0.738 mmol) in THF (10 mL), was added 6-chloro-1H-pyrazolo[3,4-d]pyrimidine (0.102 g, 0.664 mmol), DIAD (0.336 g, 1.48 mmol) and TPP (0.382 g, 1.48 mmol). The reaction mixture was stirred at room temperature for 1 h, and progress of the reaction was monitored by TLC. After completion, the reaction mixture was quenched with water (20 mL) and extracted with EA (3×30 mL). The combined organic layer was dried over anhydrous sodium sulfate, filtered and concentrated under reduced pressure. The crude compound was purified by silica gel chromatography using 0-40% EA in hexane as eluent to get the title compound (0.160 g). LC-MS (Method C) (ESI+): m/z 407.86 (M+H)⁺.

Preparation of Common Intermediate I-47

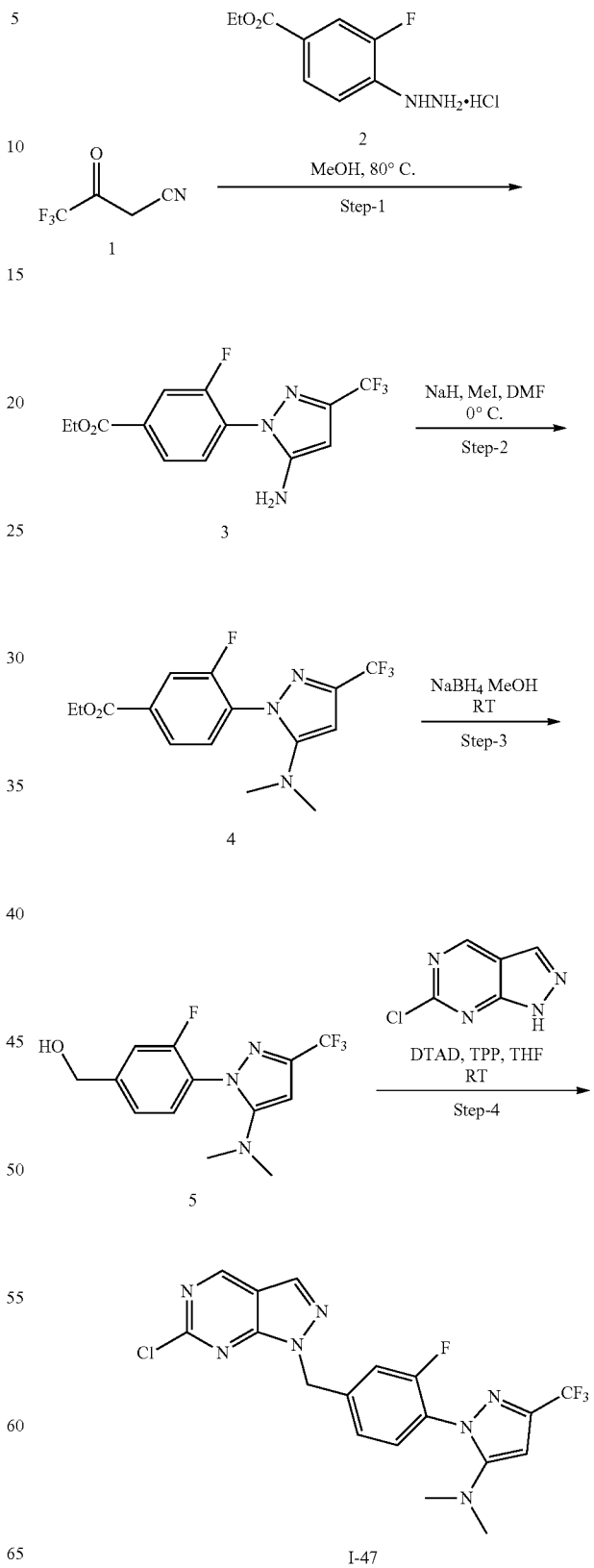

Step 1: Synthesis of ethyl 4-(5-amino-3-(trifluoromethyl)-1H-pyrazol-1-yl)-3-fluorobenzoate

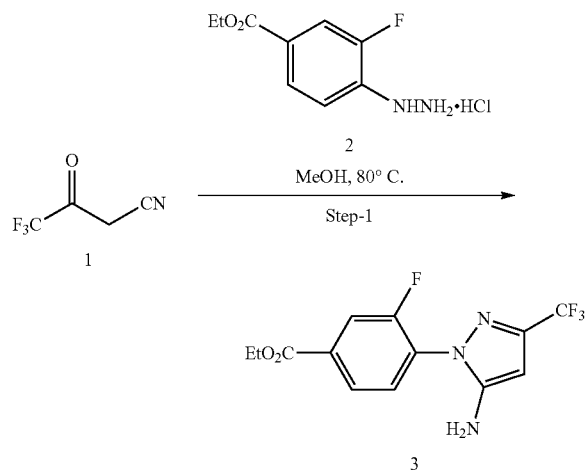

To a stirred solution of 4,4,4-trifluoro-3-oxobutanenitrile 1 (0.500 g, 2.136 mmol) in methanol (20 mL), was added ethyl 3-fluoro-4-hydrazineylbenzoate hydrochloride 2 (0.731 g, 5.341 mmol) at room temperature. The reaction mixture was then heated to 80° C. for 16 h. Progress of the reaction was monitored by TLC. After completion, the reaction mixture was concentrated under reduced pressure. The crude compound was purified by silica gel chromatography using 15-25% EA in hexane as eluent to afford the title compound (0.070 g). $^1$H-NMR (400 MHz, DMSO-$d_6$) δ 7.92 (d, J=9.29 Hz, 2H), 7.72 (t, J=7.83 Hz, 1H), 5.91 (s, 2H), 5.75 (s, 1H), 4.37 (q, J=6.85 Hz, 2H), 1.35 (t, J=7.09 Hz, 3H).

Step 2: Synthesis of ethyl 4-(5-(dimethylamino)-3-(trifluoromethyl)-1H-pyrazol-1-yl)-3-fluorobenzoate

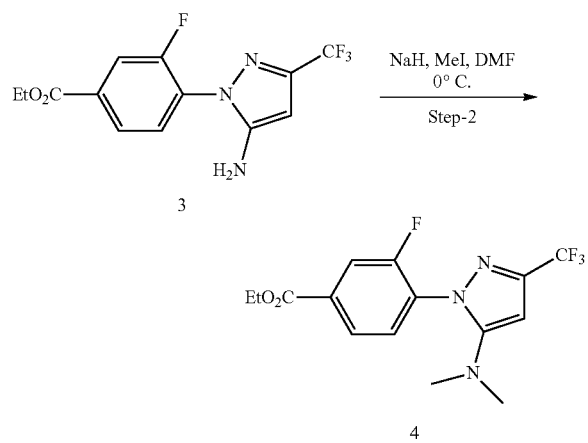

To a stirred solution of ethyl 4-(5-amino-3-(trifluoromethyl)-1H-pyrazol-1-yl)-3-fluorobenzoate 3 (0.250 g, 0.788 mmol) in DMF (10 mL) at 0° C., was added 60% dispersion of sodium hydride in oil (0.063 g, 1.577 mmol) and methyl iodide (0.145 mL, 2.365 mmol). The resulting mixture was stirred for 16 h, and the progress of the reaction was monitored by TLC. After completion, the reaction mixture was quenched with ice cold water (10 mL) and extracted with EA (2×20 mL). The combined organic layer was dried over anhydrous sodium sulfate, filtered and concentrated under reduced pressure. The crude compound was purified by silica gel chromatography using 0-10% EA in hexane as eluent to afford the title compound (0.070 g). $^1$H-NMR (400 MHz, DMSO-$d_6$) δ 7.94-8.00 (m, 2H), 7.79-7.85 (m, 1H), 6.40 (s, 1H), 4.37 (q, J=6.85 Hz, 2H), 2.56 (s, 6H), 1.35 (t, J=7.09 Hz, 3H).

Step 3: Synthesis of (4-(5-(dimethylamino)-3-(trifluoromethyl)-1H-pyrazol-1-yl)-3-fluorophenyl)methanol

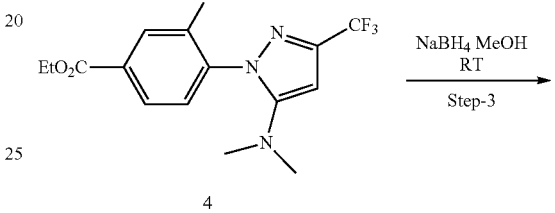

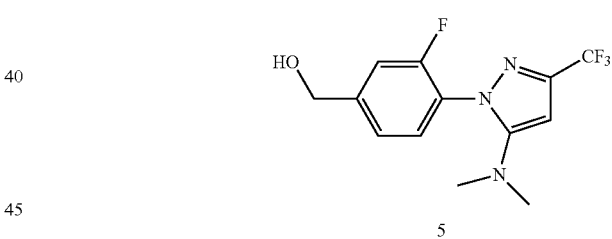

To an ice cooled solution of ethyl 4-(5-(dimethylamino)-3-(trifluoromethyl)-1H-pyrazol-1-yl)-3-fluorobenzoate 4 (0.150 g, 0.434 mmol) in methanol (10 mL), was added sodium borohydride (0.066 g, 1.739 mmol) portion-wise. Upon complete addition, the reaction mixture was stirred for 5 h and progress of the reaction was monitored by TLC. After completion, the reaction mixture was quenched with aqueous NH$_4$Cl solution (10 mL) and extracted with EA (3×20 mL). The combined organic layer was dried over anhydrous sodium sulfate, filtered and concentrated under reduced pressure. The crude compound was purified by silica gel chromatography eluting with 40-50% EA in hexane to afford the title compound (0.090 g). LC-MS (Method B) (ESI+): m/z 304.00 (M+H)$^+$; $^1$H-NMR (400 MHz, DMSO-$d_6$) δ 7.56 (t, J=7.98 Hz, 1H), 7.38 (d, J=11.47 Hz, 1H), 7.32 (d, J=7.98 Hz, 1H), 6.35 (s, 1H), 5.49 (t, J=5.73 Hz, 1H), 4.59 (d, J=5.49 Hz, 2H), 2.54 (s, 6H).

Step 4: Synthesis of 1-(4-((6-chloro-1H-pyrazolo[3,4-d]pyrimidin-1-yl)methyl)-2-fluorophenyl)-N,N-dimethyl-3-(trifluoromethyl)-1H-pyrazol-5-amine (I-47)

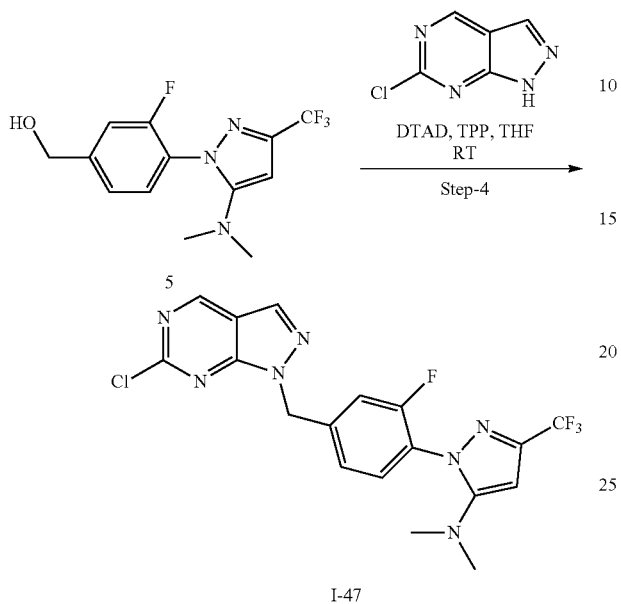

To a stirred solution of (4-(5-(dimethylamino)-3-(trifluoromethyl)-1H-pyrazol-1-yl)-3-fluorophenyl)-methanol (0.080 g, 0.264 mmol) in THF (5 mL), was added 6-chloro-1H-pyrazolo[3,4-d]pyrimidine (0.036 g, 0.237 mmol), DTAD (0.119 g, 0.528 mmol) and TPP (0.136 g, 0.528 mmol) at room temperature. The resulting mixture was stirred for 1 h, and progress of the reaction was monitored by TLC. After completion, the reaction mixture was concentrated under reduced pressure. The crude compound was purified by silica gel chromatography eluting with 0-60% EA in hexane to afford the title compound (0.060 g). LC-MS (Method B) (ESI+): m/z 440.00 (M+H)$^+$; $^1$H-NMR (400 MHz, DMSO-d$_6$) δ 9.33 (s, 1H), 8.54 (s, 1H), 7.60 (t, J=8.07 Hz, 1H), 7.38 (d, J=10.76 Hz, 1H), 7.21 (d, J=8.31 Hz, 1H), 6.35 (s, 1H), 5.77 (s, 2H), 2.52 (s, 6H).

The following intermediates were prepared from the appropriate heterocycles and alkylating reagents according to the method of preparation for I-47:

| Intermediate | Structure | Analytics |
|---|---|---|
| I-48 | 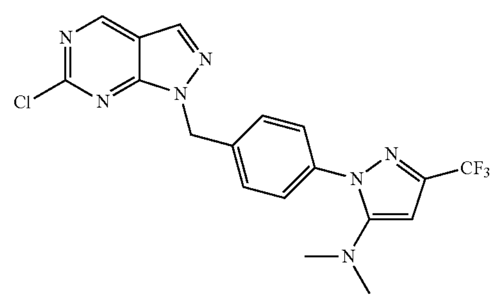 [SMILES: CN(C)c1cc(C(F)(F)F)nn1-c1ccc(Cn2ncc3cnc(Cl)nc32)cc1] | LC-MS (Method A) (ESI+): m/z 422 (M + H)$^+$; $^1$H-NMR (300 MHz, CDCl$_3$) δ 9.19 (s, 1H), 8.12 (s, 1H) 7.80 (d, J = 8.4 Hz, 2H), 7.47 (d, J = 8.4 Hz, 2H), 6.08 (s, 1H), 5.87 (s, 2H), 2.62 (s, 6H). |
| I-49 | 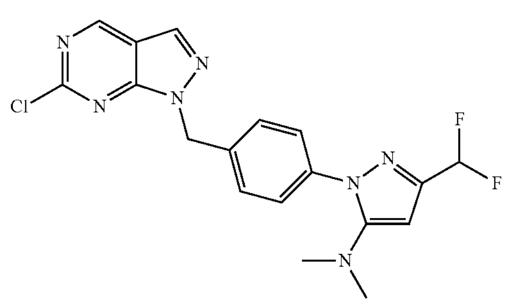 [SMILES: CN(C)c1cc(C(F)F)nn1-c1ccc(Cn2ncc3cnc(Cl)nc32)cc1] | LC-MS (Method B) (ESI+): m/z 404.00 (M + H)$^+$. |

Preparation of Common Intermediate I-50

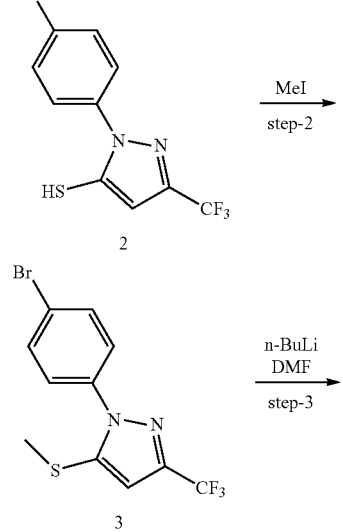

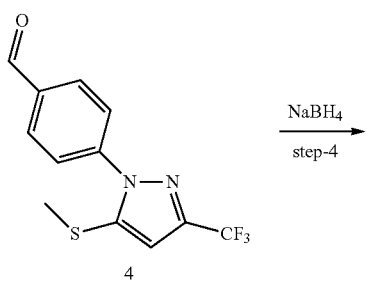

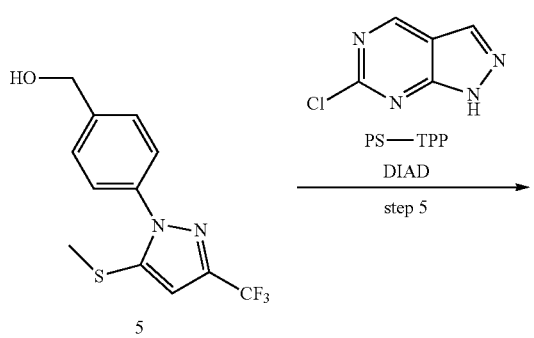

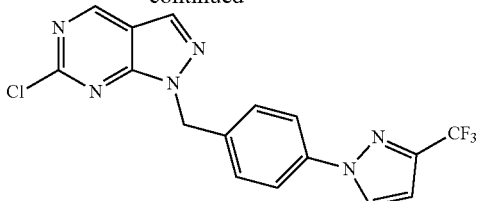

I-50

Step 1: Synthesis of 1-(4-bromophenyl)-3-(trifluoromethyl)-1H-pyrazole-5-thiol

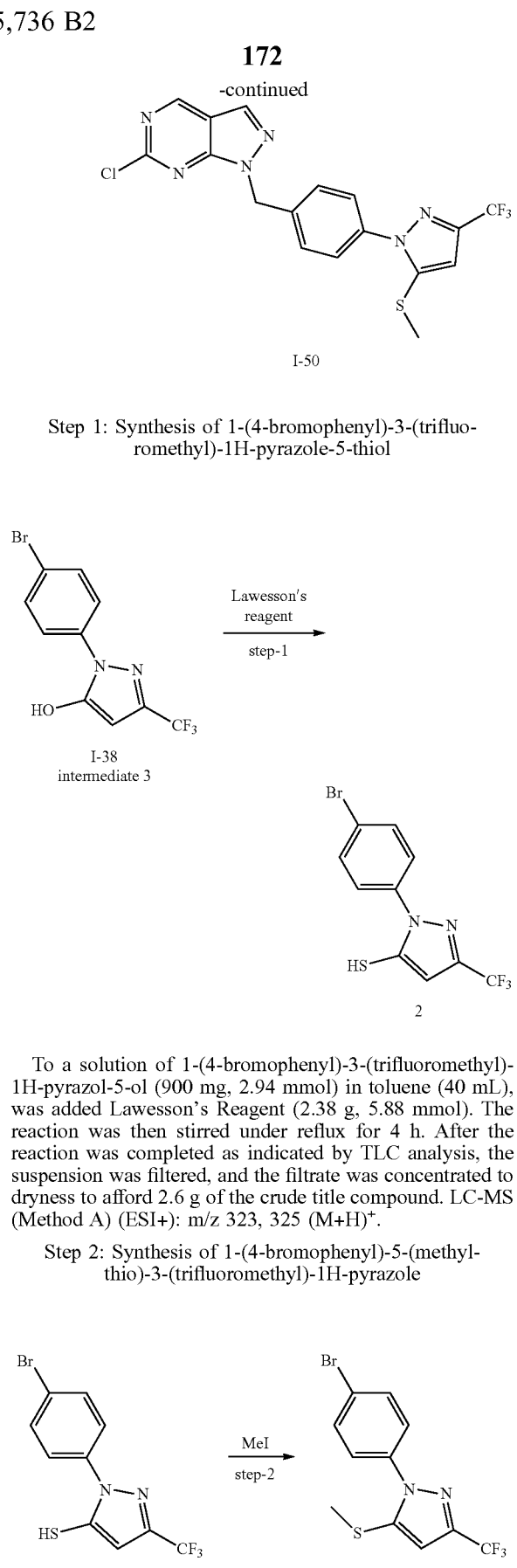

To a solution of 1-(4-bromophenyl)-3-(trifluoromethyl)-1H-pyrazol-5-ol (900 mg, 2.94 mmol) in toluene (40 mL), was added Lawesson's Reagent (2.38 g, 5.88 mmol). The reaction was then stirred under reflux for 4 h. After the reaction was completed as indicated by TLC analysis, the suspension was filtered, and the filtrate was concentrated to dryness to afford 2.6 g of the crude title compound. LC-MS (Method A) (ESI+): m/z 323, 325 (M+H)$^+$.

Step 2: Synthesis of 1-(4-bromophenyl)-5-(methylthio)-3-(trifluoromethyl)-1H-pyrazole To a solution of crude methyl 1-(4-bromophenyl)-3-(trifluoromethyl)-1H-pyrazole-5-thiol (2.6 g, 8.1 mol) in DMF (20 mL) at 0° C., was added NaH (388 mg, 9.69 mmol) portion-wise over 5 min. After the mixture was stirred at 0° C. for 30 min, MeI (1.72 g, 12.1 mmol) was added dropwise over 2 min. The reaction was stirred at 0° C. initially, and then warmed to room temperature over 3 h. After the reaction was completed as indicated by TLC analysis, the mixture was quenched with ice-water (20 mL) and extracted with EA (20 mL×3). The organic layer was washed with water (20 mL×2) and brine (20 mL), dried over sodium sulfate (20 g), filtered and concentrated. The residue was purified by silica gel chromatography (eluent: PE/EA=50/0 to 50/1) to yield 650 mg of the title compound. LC-MS (Method A) (ESI+): m/z 337, 339 (M+H)$^+$; $^1$H-NMR (300 MHz, CDCl$_3$) δ 7.63 (d, J=6.9 Hz, 2H), 7.48 (d, J=6.9 Hz, 2H), 6.57 (s, 1H), 2.44 (s, 3H).

Step 3: Synthesis of 4-(5-(methylthio)-3-(trifluoromethyl)-1H-pyrazol-1-yl)benzaldehyde

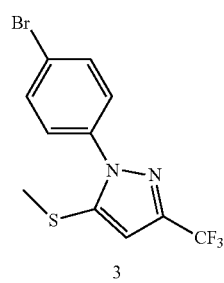

Step 4: Synthesis of (4-(5-(methylthio)-3-(trifluoromethyl)-1H-pyrazol-1-yl)phenyl)methanol

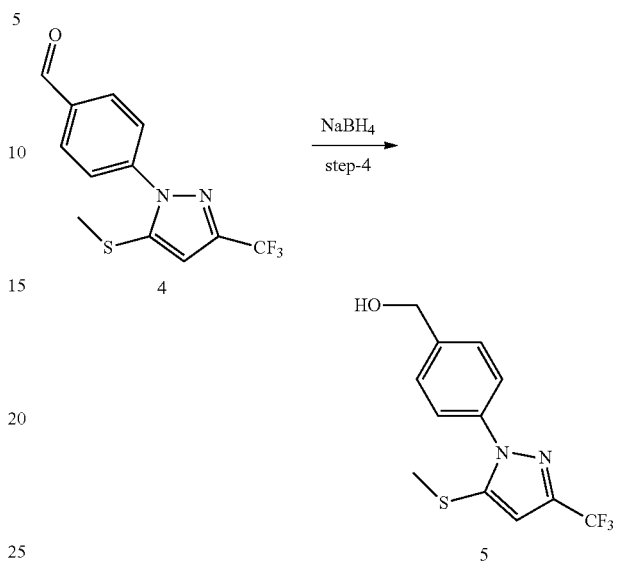

Prepared according to the reduction procedure of 1-8. LC-MS (Method A) (ESI+): m/z 289 (M+H)$^+$; $^1$H-NMR (300 MHz, CDCl$_3$) δ 7.57 (d, J=8.4 Hz, 2H), 7.49 (d, J=8.4 Hz, 2H), 6.57 (s. 1H), 4.78 (s, 2H), 2.43 (s, 3H), 1.83 (br s, 1H).

Step 5: Synthesis of 6-chloro-1-(4-(5-(methylthio)-3-(trifluoromethyl)-1H-pyrazol-1-yl)benzyl)-1H-pyrazolo[3,4-d]pyrimidine (I-50)

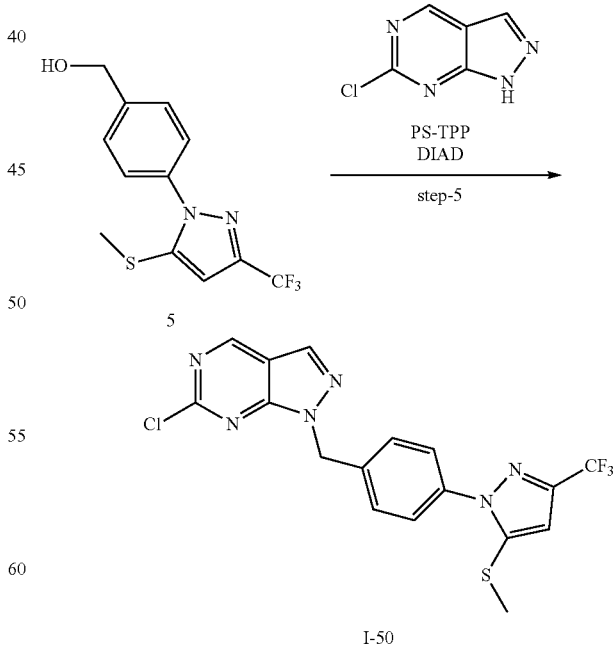

To a solution of 1-(4-bromophenyl)-5-(methylthio)-3-(trifluoromethyl)-1H-pyrazole 3 (550 mg, 1.64 mmol) in anhydrous THF (10 mL) at −78° C., was added n-BuLi (0.98 mL, 2.46 mmol) dropwise over 5 min. After stirring for 1 h at −78° C., DMF (240 mg, 3.28 mmol) was added dropwise over 5 min, and the mixture was warmed to rt slowly over 2 h. After the reaction was complete as indicated by TLC analysis, the mixture was quenched with ice water (20 mL). The resulting mixture was extracted with EA (30 mL×2). The organic layer was dried over sodium sulfate (30 g), filtered and concentrated. The resulting residue was purified by silica gel chromatography (eluent: PE/EA=100/1 to 50/1) to yield 100 mg of the title compound. LC-MS (Method A) (ESI+): m/z 287 (M+H)$^+$; $^1$H-NMR (300 MHz, CDCl$_3$) δ 10.08 (s, 1H), 8.02 (d, J=8.7 Hz, 2H), 7.84 (d, J=8.7 Hz, 2H), 6.61 (s, 1H), 2.48 (s, 3H).

To a suspension of 5 (130 mg, 0.45 mol), 6-chloro-1H-pyrazolo[3,4-d]pyrimidine (90 mg, 0.59 mmol) and PS-TPP (300 mg, 0.9 mmol) in anhydrous THF (10 mL) at 0° C., was added DIAD (136 mg, 0.68 mmol) dropwise over 5 min. The reaction was stirred in an ice-water bath for 30 min and then warmed to rt slowly overnight. After the reaction was completed as indicated by TLC analysis, the reaction was quenched with water (20 mL) and extracted with EA (20 mL×2). The combined organic layer was dried and concentrated. The residue was purified by silica gel chromatography (eluent: PE/EA=10/1 to I/O) to afford 160 mg of the crude product. The crude product was further purified by preparative HPLC (Method A) to give 30 mg of the title compound. LC-MS (Method A) (ESI+): m/z 425 (M+H)$^+$; $^1$H-NMR (300 MHz, CDCl$_3$) δ 9.06 (s, 1H), 8.19 (s, 1H), 7.59-7.45 (m, 4H), 6.55 (s, 1H), 5.70 (s, 2H), 2.42 (s, 3H).

Preparation of Common Intermediate I-51

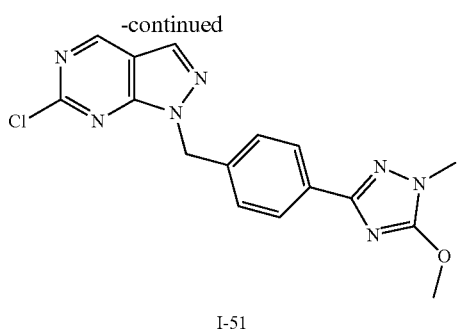

I-51

Step 1: Synthesis of Methyl 4-(5-methoxy-1-methyl-1H-1,2,4-triazol-3-yl)benzoate

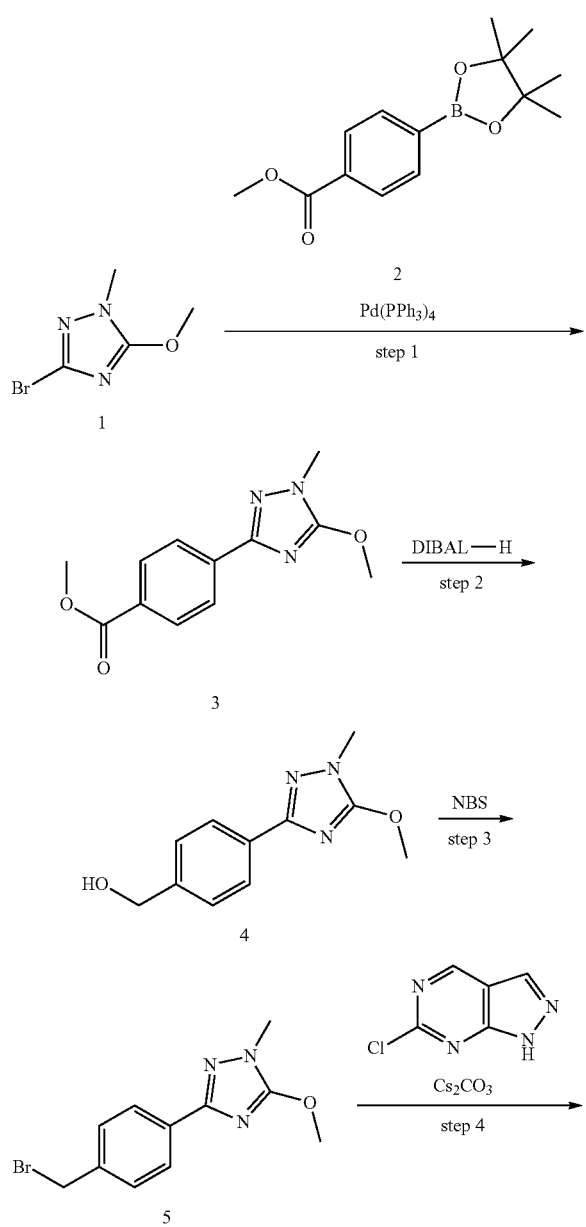

To a mixture of 3-bromo-5-methoxy-1-methyl-1H-1,2,4-triazole (500 mg, 2.60 mmol), methyl 4-(4,4,5,5-tetramethyl-1,3,2-dioxaborolan-2-yl)benzoate (1.02 g, 3.91 mmol), tricyclohexylphosphine (219.07 mg, 0.78 mmol), K$_3$PO$_4$·3H$_2$O (2.08 g, 7.81 mmol) in dioxane (26 mL) and H$_2$O (1.3 mL) was added Pd$_2$(dba)$_3$ (238.45 mg, 0.26 mmol) under nitrogen. The resulting mixture was stirred at 90° C. for 1 hr. After the reaction was completed as indicated by TLC analysis, the reaction was quenched with water (30 mL) and extracted with EA (25 mL×3). The combined organic layer was dried over anhydrous Na$_2$SO$_4$ (30 g), filtered, and concentrated to give the crude product. The crude product was purified by silica gel chromatography (PE:EA=10:1) to provide 650 mg of the title compound. $^1$H-NMR (300 MHz, CDCl$_3$) δ 8.08 (s, 0.4H), 4.17 (s, 3H), 3.93 (s, 3H), 3.68 (s, 3H).

Step 2: Synthesis of (4-(5-Methoxy-1-methyl-1H-1,2,4-triazol-3-yl)phenyl)methanol

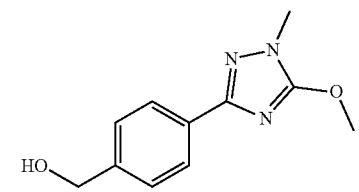 [SMILES: COc1nc(-c2ccc(CO)cc2)nn1C]

To a solution of methyl 4-(5-methoxy-1-methyl-1H-1,2,4-triazol-3-yl) benzoate (650 mg, 2.63 mmol) in THF (26 mL) at 0° C., was added DIBAL-H (1.5 M, 7.9 mL, 11.9 mmol) dropwise over 15 min. The resulting mixture was stirred at 0° C. for 1 h, then slowly diluted with a saturated aqueous NH$_4$Cl solution (10 mL). The resulting suspension was stirred in an ice-water bath for additional 30 min and then filtered to remove the solids. The filter cake was washed with EA (30 mL×4), and the resulting filtrate was washed with brine (50 mL). After separation, the organic layer was dried over anhydrous $Na_2SO_4$ (30 g), filtered, and concentrated to give a crude residue that was purified by silica gel chromatography (PE:EA=3:1 to 2:1) to give 500 mg of the title compound. $^1$H-NMR (300 MHz, $CDCl_3$) δ 8.00 (d, J=8.4 Hz, 2H), 7.41 (d, J=8.4 Hz, 2H), 4.73 (d, J=6.0 Hz, 2H), 4.16 (s, 3H), 3.67 (s, 3H), 1.70 (t, J=6.0 Hz, 1H).

Step 3: Synthesis of 3-(4-(Chloromethyl)phenyl)-5-methoxy-1-methyl-1H-1,2,4-triazole Step 4: Synthesis of 6-Chloro-1-(4-(5-methoxy-1-methyl-1H-1,2,4-triazol-3-yl)benzyl)-1H-pyrazolo[3,4-d]pyrimidine (I-51)

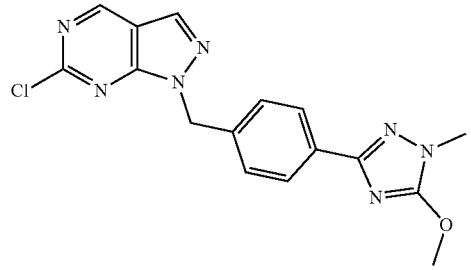

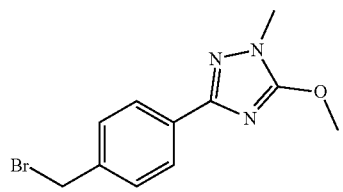 [SMILES: COc1nc(-c2ccc(CBr)cc2)nn1C]

To a solution of (4-(5-methoxy-1-methyl-1H-1,2,4-triazol-3-yl)phenyl)methanol (450 mg, 2.05 mmol) in DCM (25 mL) at rt, was added $PPh_3$ (592 mg, 2.26 mmol) and NBS (438 mg, 2.05 mmol) in one portion. The reaction mixture was stirred at rt for 1.5 h. After the reaction was completed, as indicated by TLC analysis, the reaction mixture was concentrated in vacuo and the crude residue was purified by silica gel chromatography (PE:EA=5:1 to 3:1) to give 480 mg of the title compound. $^1$H-NMR (300 MHz, $CDCl_3$) δ 7.98 (d, J=8.4 Hz, 2H), 7.43 (d, J=8.4 Hz, 2H), 4.53 (s, 2H), 4.16 (s, 3H), 3.66 (s, 3H).

To a solution of 3-(4-(chloromethyl)phenyl)-5-methoxy-1-methyl-1H-1,2,4-triazole (480 mg, 1.70 mmol) and 6-chloro-1H-pyrazolo[3,4-d]pyrimidine (316 mg, 2.04 mmol) in DMF (17 mL), was added $Cs_2CO_3$ (1.66 g, 5.10 mmol) in one portion and the reaction was stirred at 80° C. for 1 h. After the reaction was completed (as indicated by TLC analysis), the mixture was cooled to rt. The reaction was then quenched by ice-water (30 mL) and extracted with EA (50 mL×2). The combined organic layer was washed with water (40 mL×3), dried over sodium sulfate (30 g), filtered and concentrated. The residue was purified by silica gel chromatography (PE:EA=1:1 to 1:3) to yield 220 mg of the title compound. LC-MS (Method A) (ESI+): m/z 356 (M+H)$^+$; $^1$H-NMR (300 MHz, $CDCl_3$) δ 9.03 (s, 1H), 8.16 (s, 1H), 7.95 (d, J=81 Hz, 2H), 7.40 (d, J=8.1 Hz, 2H), 5.65 (s, 2H), 4.13 (s, 3H), 3.64 (s, 3H).

The following intermediate was prepared from the appropriate heterocycle and alkylating reagent according to the method of preparation for I-51:

| Intermediate | Structure | Analytics |
|---|---|---|
| I-52 | (6-chloro-pyrazolo[3,4-d]pyrimidine with benzyl-triazole-CF3 structure, N-methyl) | $^1$H-NMR (300 MHz, $CDCl_3$) δ 9.05 (s, 1H), 8.18 (s, 1H), 8.05 (d, J = 8.4 Hz, 2H), 7.43 (d, J = 8.4 Hz, 2H), 5.67 (s, 2H), 4.08 (s, 3H). |

Preparation of Common Intermediate I-53

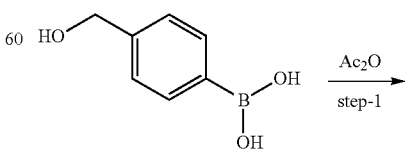

179
-continued

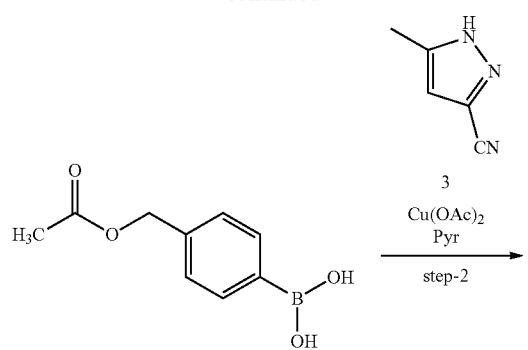

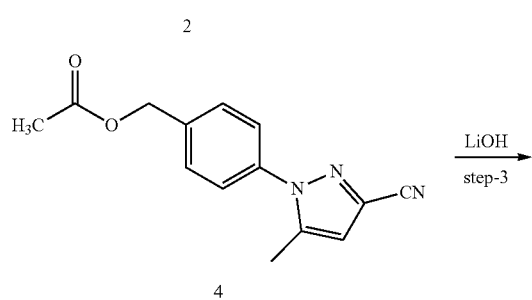

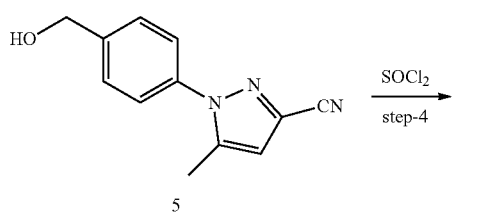

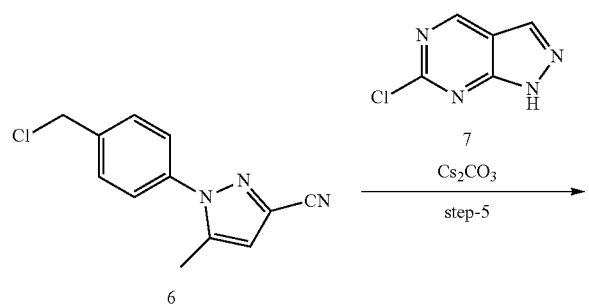

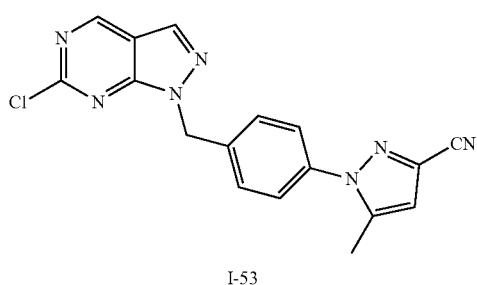

180

Step 1: Synthesis of (4-(Acetoxymethyl)phenyl)boronic Acid

A mixture of (4-(hydroxymethyl)phenyl)boronic acid (3 g, 0.02 mol) and acetic anhydride (4.08 g, 0.04 mol) in pyridine (5 mL, 0.062 mol), was a stirred at rt for 4 h. After the reaction was complete as indicated by TLC analysis, the mixture was poured into dilute aqueous HCl solution (2 N, 20 mL) and extracted with EA (30 mL×2). The combined organic phase was washed with saturated sodium bicarbonate solution (50 mL), dried over sodium sulfate (30 g), filtered, and concentrated in vacuo to afford 4.5 g of the crude title compound. $^1$H-NMR (300 MHz, CD$_3$OD) δ 8.04 (d, J=7.8 Hz, 2H), 7.38 (d, J=7.8 Hz, 2H), 5.13 (s, 2H), 2.11 (s, 3H).

Step 2: Synthesis of 4-(3-Cyano-5-methyl-1H-pyrazol-1-yl)benzyl acetate

To a mixture of (4-(acetoxymethyl)phenyl)boronic acid (1.087 g, 5.60 mmol), 5-methyl-1H-pyrazole-3-carbonitrile (500 mg, 11.60 mmol), triethylamine (709 mg, 4.67 mmol), pyridine (1.11 g, 14.07 mmol) in DCM (20 mL), was added cupric acetate monohydrate (1.14 g, 6.26 mmol) and the resulting mixture was stirred at 40° C. overnight. After the reaction was complete as indicated by TLC analysis, the reaction was quenched by addition of water (20 mL) and extracted with DCM (20 mL×2). The combined organic phase was washed with water (20 mL), dried over sodium sulfate (30 g), filtered, and concentrated in vacuo. The residue was purified by silica gel chromatography on silica (PE:EA=30:1 to 6:1) to afford 390 mg of the title compound. LC-MS (Method A) (ESI+): m/z 256 (M+H)$^+$; $^1$H-NMR (300 MHz, CD$_3$OD) δ 7.51 (d, J=8.7 Hz, 2H), 7.44 (d, J=8.7 Hz, 2H), 6.60 (s, 1H), 5.18 (s, 2H), 2.36 (s, 3H), 2.15 (s, 3H).

Step 3 Synthesis of 1-(4-(Hydroxymethyl)phenyl)-5-methyl-1H-pyrazole-3-carbonitrile

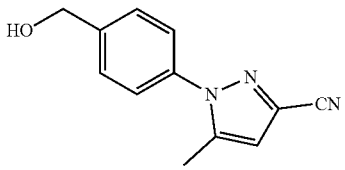 [SMILES: Cc1cc(C#N)nn1-c1ccc(CO)cc1]

To a solution of 4-(3-cyano-5-methyl-1H-pyrazol-1-yl) benzyl acetate (390 mg, 1.53 mmol) in THF (40 mL) and water (5 mL), was added lithium hydroxide (128 mg, 3.06 mmol) in one portion. The reaction was stirred at rt for 3 h. After the reaction was complete as indicated by TLC analysis, the reaction was quenched with ice-water (10 mL). The resulting mixture was extracted with EA (10 mL×2) and the layers separated. The combined organic layer was dried over sodium sulfate (10 g), filtered, and concentrated to afford 300 mg of the crude title compound. LC-MS (Method A) (ESI+): m/z 214 (M+H)$^+$; $^1$H-NMR (300 MHz, CD$_3$OD) δ 7.56 (d, J=8.4 Hz, 2H), 7.47 (d, J=8.4 Hz, 2H), 6.75 (s, 1H), 4.70 (s, 2H), 2.37 (s, 3H).

Step 4: Synthesis of 1-(4-(Chloromethyl)phenyl)-5-methyl-1H-pyrazole-3-carbonitrile

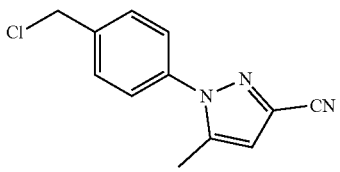 [SMILES: Cc1cc(C#N)nn1-c1ccc(CCl)cc1]

To a solution of 1-(4-(hydroxymethyl)phenyl)-5-methyl-1H-pyrazole-3-carbonitrile (300 mg, 0.96 mmol) in DCE (6 mL), was added SOCl$_2$ (341 mg, 2.87 mmol) in one portion. After the addition, the reaction was stirred at 60° C. for 1 h. After the reaction mixture was complete as indicated by TLC analysis, the reaction mixture was concentrated to dryness in vacuo to afford 330 mg of the crude title compound. LC-MS (Method A) (ESI+): m/z 232 (M+H)$^+$; $^1$H-NMR (300 MHz, CD$_3$OD) δ 7.55 (d, J=8.4 Hz, 2H), 7.44 (d, J=8.4 Hz, 2H), 6.10 (s, 1H), 4.65 (s, 2H), 2.38 (s, 3H).

Step 5: Synthesis of 1-(4-((6-Chloro-1H-pyrazolo[3,4-d]pyrimidin-1-yl)methyl)phenyl)-5-methyl-1H-pyrazole-3-carbonitrile (I-53)

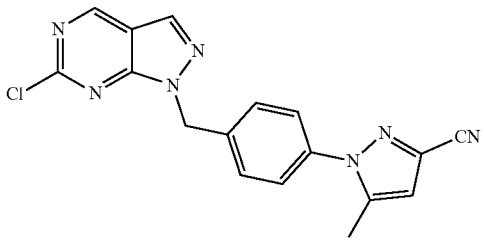 [SMILES: Cc1cc(C#N)nn1-c1ccc(Cn2ncc3cnc(Cl)nc32)cc1]

To a solution of 1-(4-(chloromethyl)phenyl)-5-methyl-1H-pyrazole-3-carbonitrile (330 mg, 1.43 mmol) in DMF (5 mL), was added 6-chloro-1H-pyrazolo[3,4-d]pyrimidine (220 mg, 1.43 mmol) and potassium carbonate (590 mg, 4.29 mmol). After the addition, the reaction was stirred at 70° C. for 1 h. After the reaction was complete as indicated by TLC analysis, the reaction was quenched with water (10 mL) and extracted with EA (10 mL×2). The combined organic phase was washed with water, dried over sodium sulfate (10 g), filtered, and concentrated in vacuo. The residue was purified by silica gel chromatography (PE:EA=10:1 to 2:1) to afford 188 mg of the title compound. LC-MS (Method A) (ESI+): m/z 350 (M+H)$^+$; $^1$H-NMR (300 MHz, CD$_3$OD) δ 9.07 (s, 1H), 8.20 (s, 1H), 7.52 (d, J=8.4 Hz, 2H), 7.41 (d, J=8.4 Hz, 2H), 6.58 (s, 1H), 5.71 (s, 2H), 2.36 (s, 3H).

Preparation of Common Intermediate I-54

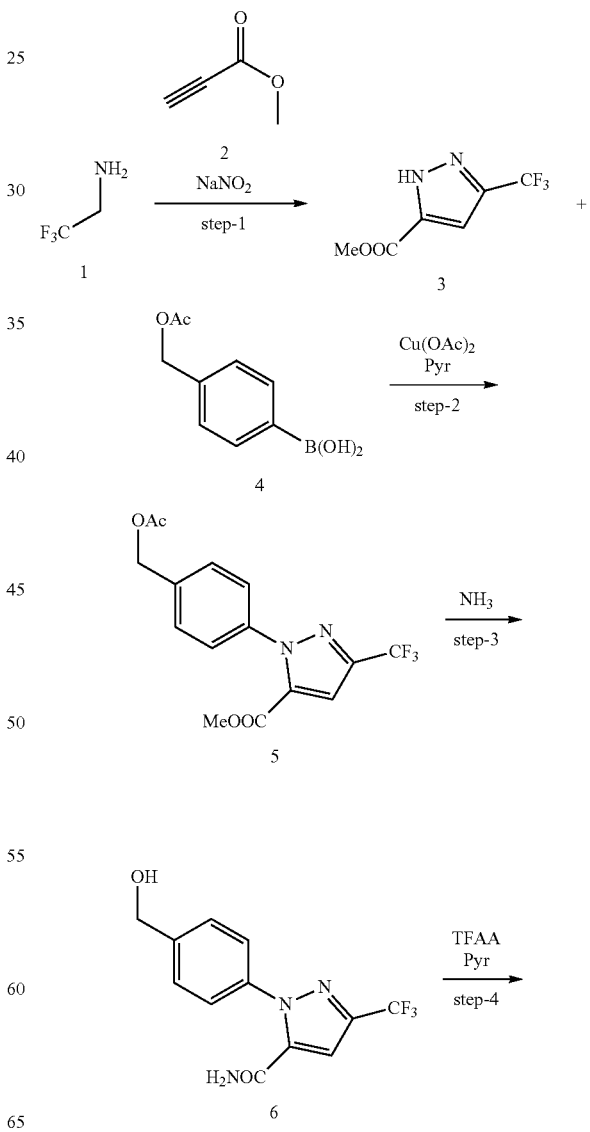

-continued

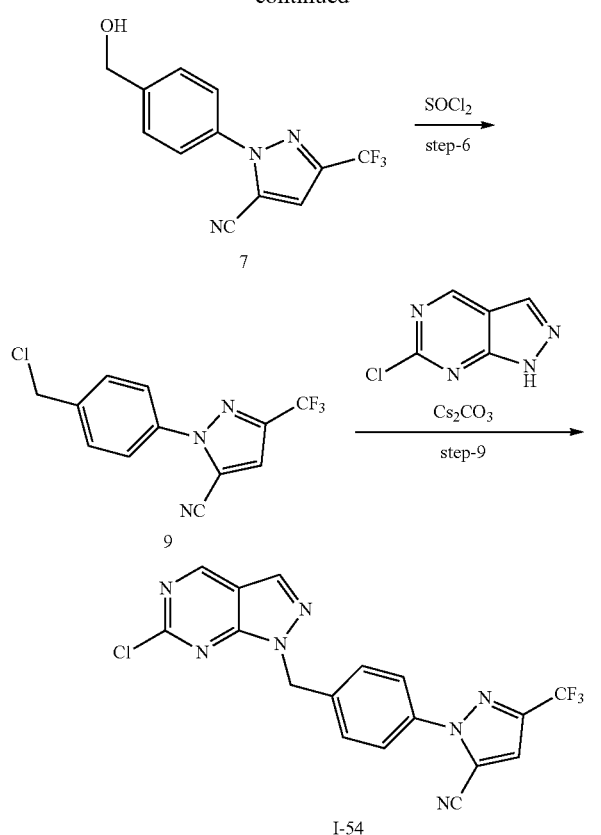

Step 2: Synthesis of methyl 1-(4-(acetoxymethyl)phenyl)-3-(trifluoromethyl)-1H-pyrazole-5-carboxylate

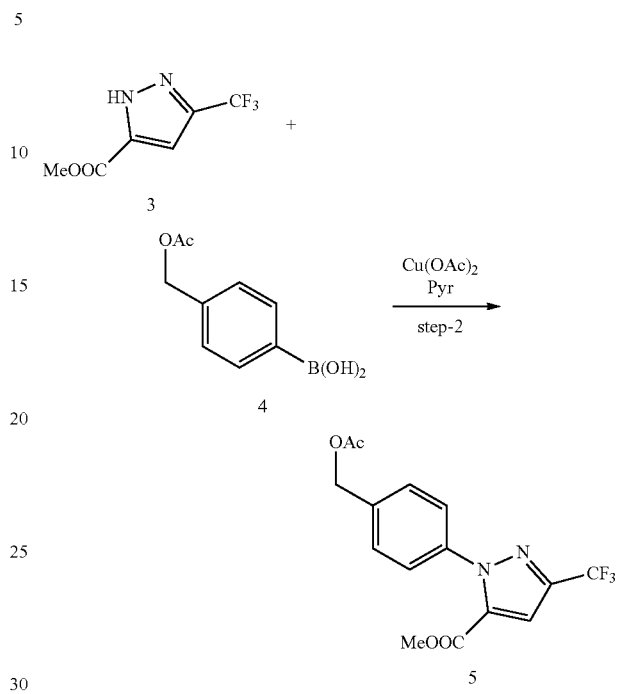

To a mixture of methyl 3-(trifluoromethyl)-1H-pyrazole-5-carboxylate 3 (870 mg, 4.48 mmol) and (4-(acetoxymethyl)phenyl)boronic acid (1.1 g, 5.8 mmol) in DCM (20 mL) and DCE (20 mL), was added Cu(OAc)$_2$ (1.2 g, 6.7 mmol) and pyridine (709 mg, 8.96 mmol). The reaction was then stirred at 40° C. overnight. After the reaction was completed as indicated by TLC analysis, the mixture was filtered, and the filter cake was washed with DCM (30 mL). The combined filtrate was washed with water (30 mL×2), dried over sodium sulfate (30 g), filtered and concentrated. The residue was purified by silica gel chromatography (eluent: PE/EA=9/1) to yield 1.1 g of the title compound. LC-MS (Method A) (ESI+): m/z 343 (M+H)$^+$; $^1$H-NMR (300 MHz, CDCl$_3$) δ 7.43-7.51 (m, 4H), 7.08 (s, 1H), 5.18 (s, 2H), 3.84 (s, 3H), 2.14 (s, 3H).

Step 1: Synthesis of methyl 3-(trifluoromethyl)-1H-pyrazole-5-carboxylate

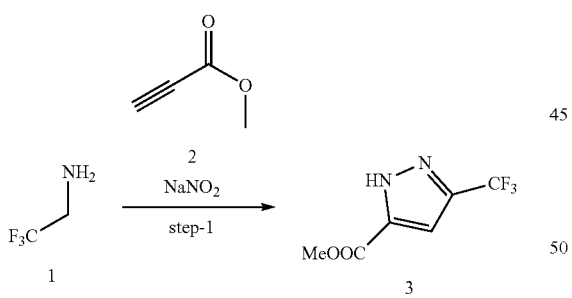

To a solution of methyl propiolate 2 (500 mg, 5.94 mmol) in DCM (4.0 mL) at rt was added an aqueous NaNO$_2$ solution (613 mg of NaNO$_2$ in 2.0 mL of water) in portion. After the addition, the reaction was cooled with ice-water bath and 2,2,2-trifluoroethanamine HCl salt 1 (1.2 g, 8.9 mmol) was added to the reaction portion-wise over 5 min. The reaction was then stirred at 0° C. for 1 h, and then at rt overnight. The mixture was quenched with water (30 mL) and extracted with DCM (30 mL×2). The organic layer was dried over sodium sulfate (20 g), filtered and concentrated to yield 1.1 g of the crude title compound. LC-MS (Method A) (ESI+): m/z 195 (M+H)$^+$; $^1$H-NMR (300 MHz, CDCl$_3$) δ 11.41 (br s, 1H), 7.10 (s, 1H), 3.98 (s, 3H).

Step 3: Synthesis of 1-(4-(hydroxymethyl)phenyl)-3-(trifluoromethyl)-1H-pyrazole-5-carboxamide

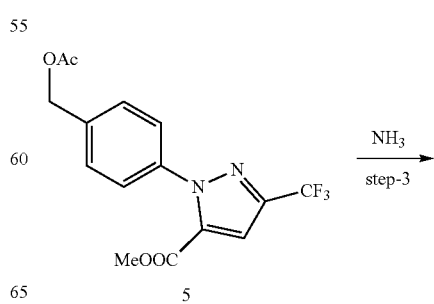

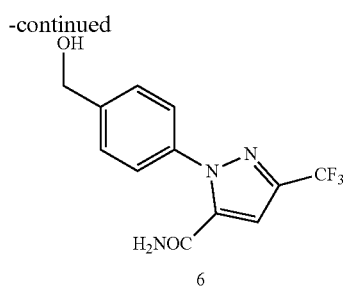

To a saturated methanolic ammonia solution (10 mL, 7 N) was added methyl 1-(4-(acetoxymethyl) phenyl)-3-(trifluoromethyl)-1H-pyrazole-5-carboxylate 5 (1.1 g, 3.2 mmol) in one portion. The reaction was stirred in a sealed tube at 50° C. for 6 h. After the reaction was completed as indicated by TLC analysis, the mixture was quenched with a saturated ammonium chloride solution (40 mL) and extracted with EA (50 mL×2). The combined organic layer was washed with water (30 mL), brine (30 mL), dried over sodium sulfate (30 g), filtered and concentrated. The residue was purified by silica gel chromatography (eluent: DCM/MeOH=50/1 to 20/1) to yield 530 mg of the title compound. LC-MS (Method A) (ESI+): m/z 286 (M+H)+; 1H-NMR (300 MHz, CD3OD) δ 7.43-7.51 (m, 4H), 7.19 (s, 1H), 4.68 (s, 2H).

Step 4: Synthesis of 1-(4-(hydroxymethyl)phenyl)-3-(trifluoromethyl)-1H-pyrazole-5-carbonitrile

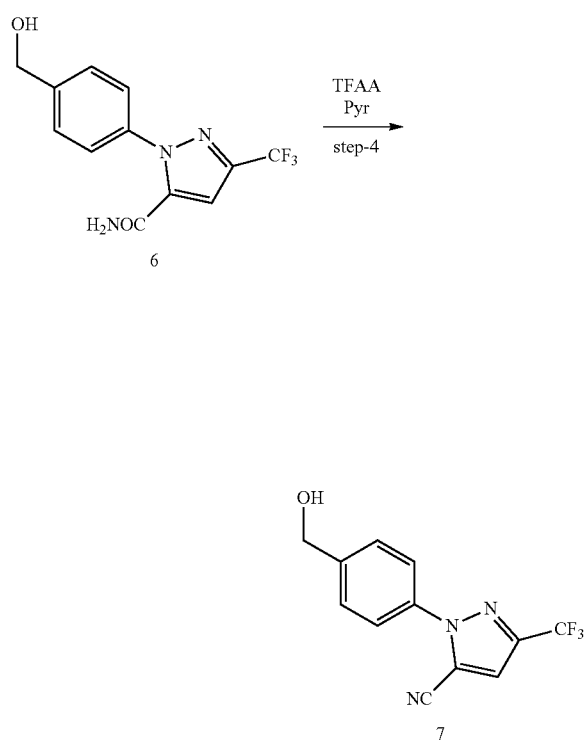

The compound was synthesized according to the procedure from 1-44 step 4. LC-MS (Method A) (ESI+): m/z 267 (M+H)+; 1H-NMR (300 MHz, CDCl3) δ 7.72 (d, J=8.7 Hz, 2H), 7.58 (d, J=8.4 Hz, 2H), 7.27 (s, 1H), 4.83 (s, 2H).

Step 5: Synthesis of 1-(4-(chloromethyl)phenyl)-3-(trifluoromethyl)-1H-pyrazole-5-carbonitrile

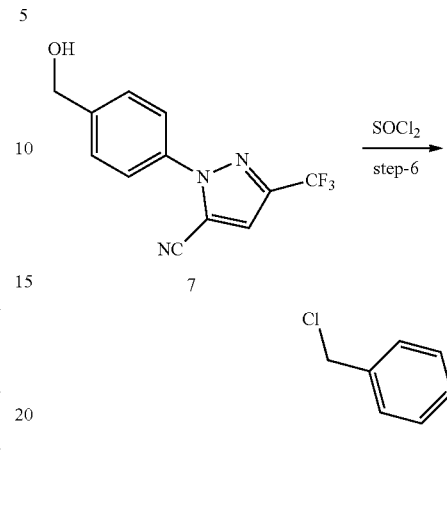

The compound was synthesized according to the procedure for the preparation of common intermediate I-8. LC-MS (Method A) (ESI+): m/z 286 (M+H)+; 1H-NMR (300 MHz, CDCl3) δ 7.74 (d, J=8.1 Hz, 2H), 7.61 (d, J=8.1 Hz, 2H), 7.29 (s, 1H), 4.66 (s, 2H).

Step 6: Synthesis of 1-(4-((6-chloro-1H-pyrazolo[3,4-d]pyrimidin-1-yl)methyl)phenyl)-3-(trifluoromethyl)-1H-pyrazole-5-carbonitrile (I-54)

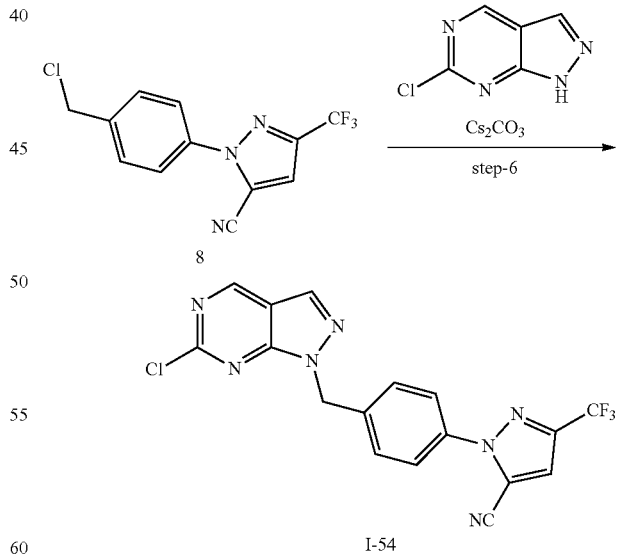

The compound was synthesized according to the procedure for the preparation of common intermediate I-8. LC-MS (Method A) (ESI+): m/z 404 (M+H)+; 1H-NMR (300 MHz, CDCl3) δ 9.08 (s, 1H), 8.20 (s, 1H) 7.71 (d, J=8.4 Hz, 2H), 7.58 (d, J=8.4 Hz, 2H), 7.27 (s, 1H), 5.72 (s, 2H).

Preparation of Common Intermediate I-56

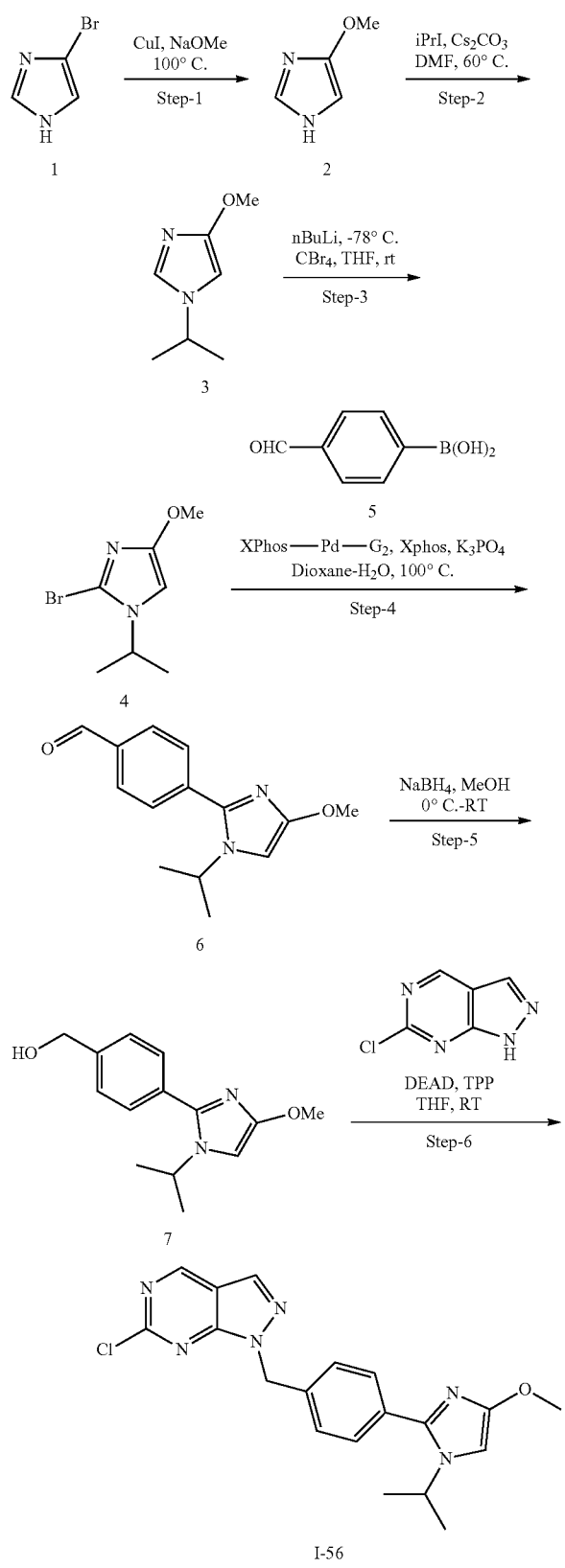

Step 1: Synthesis of 4-methoxy-1H-imidazole

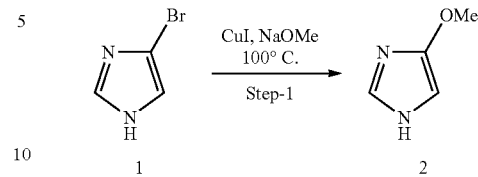

To a stirred solution of 4-bromo-1H-imidazole 1 (15.0 g, 102 mmol) in NaOMe solution (150 mL), was added copper iodide (3.87 g, 20.4 mmol) at room temperature. The reaction mixture was heated to 100° C. for 16 h. Progress of the reaction was monitored by TLC. After completion, the reaction mixture was concentrated under reduced pressure. The crude compound was purified by silica gel chromatography eluting with 0-80% EA in hexane to afford the title compound (1.50 g). $^1$H-NMR (400 MHz, DMSO-$d_6$) 11.61 (br. s, 1H), 7.25 (br s, 1H), 6.39 (br s, 1H), 3.64 (s, 3H).

Step 2: Synthesis of 1-isopropyl-4-methoxy-1H-imidazole

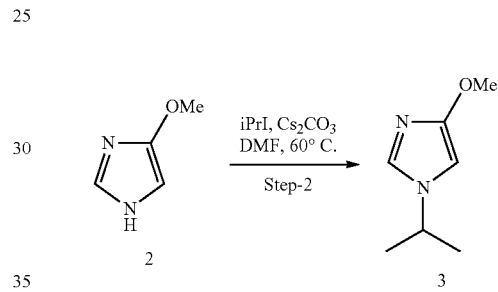

To a stirred solution of 4-methoxy-1H-imidazole 2 (1.50 g, 15.3 mmol) in THF (15 mL), was added $Cs_2CO_3$ (9.90 g, 30.6 mmol) and isopropyl iodide (3.88 g, 23.0 mmol) at room temperature. The reaction mixture was then heated to 60° C. for 16 h. Progress of the reaction was monitored by TLC. After completion, the reaction mixture was quenched with water (50 mL) and extracted with EA (3×30 mL). The organic layer was dried over anhydrous sodium sulfate, filtered and concentrated under reduced pressure. The crude compound was purified by size silica gel chromatography using 0-50% EA in hexane as eluent to afford the title compound (1.00 g). LC-MS (Method B) (ESI+): m/z 140.98 (M+H)$^+$; $^1$H-NMR (400 MHz, DMSO-$d_6$) δ 7.29 (s, 1H), 6.55 (s, 1H), 4.26 (td, J=6.79, 13.33 Hz, 1H), 3.63 (d, J=0.98 Hz, 3H), 1.35 (dd, J=0.98, 6.85 Hz, 6H).

Step 3: Synthesis of 2-bromo-1-isopropyl-4-methoxy-1H-imidazole

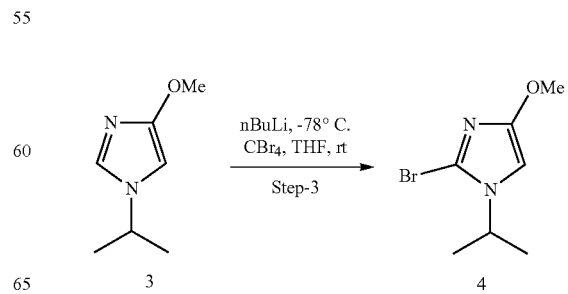

To a stirred solution of 1-isopropyl-4-methoxy-1H-imidazole 3 (1.00 g, 7.14 mmol) in THF (10 mL) at −78° C., was added n-BuLi (1.6M in hexane, 6.69 mL, 10.7 mmol) dropwise. The resulting solution was stirred for 15 min at −78° C., and then CBr₄ (3.50 g, 10.7 mmol) was added. The reaction mixture was allowed to warm to room temperature and was stirred for 16 h. Progress of the reaction was monitored by TLC. After completion, the reaction mixture was quenched with saturated NH₄Cl solution (30 mL) and extracted with EA (3×50 mL). The organic layer was dried over anhydrous sodium sulfate, filtered and concentrated under reduced pressure. The crude compound was purified by silica gel chromatography using 0-30% EA in hexane as eluent to afford the title compound (0.700 g). LC-MS (Method B) (ESI+): m/z 221.19 (M+H)⁺; ¹H-NMR (400 MHz, DMSO-d₆) δ 6.81 (s, 1H), 4.34 (td, J=6.79, 13.33 Hz, 1H), 3.65 (s, 3H), 1.34 (d, J=6.85 Hz, 6H).

Step 4: Synthesis of 4-(1-isopropyl-4-methoxy-1H-imidazol-2-yl)benzaldehyde

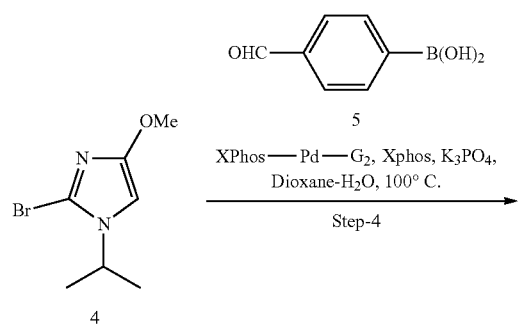

To a stirred solution of 2-bromo-1-isopropyl-4-methoxy-1H-imidazole 4 (0.700 g, 3.21 mmol) in dioxane:H₂O (15:3 mL), was added K₃PO₄ (1.36 g, 6.42 mmol) and (4-formylphenyl)boronic acid 5 (0.621 g, 4.17 mmol). The resulting mixture was degassed with argon for 10 min, and then treated with XPhos (0.152 g, 0.321 mmol) and X-Phos-Pd-G₂ (0.126 g, 0.160 mmol) in a seal tube. The reaction mixture was further degassed with argon for 10 min, and then heated at 100° C. for 2 h. Progress of the reaction was monitored by TLC. After completion, the reaction mixture was cooled to room temperature, quenched with water (20 mL) and extracted with EA (3×30 mL). The organic layer was dried over anhydrous sodium sulfate, filtered and concentrated under reduced pressure. The crude compound was purified by silica gel chromatography using 0-20% EA in hexane as eluent to afford the title compound (0.400 g).

Step 5: Synthesis of (4-(1-isopropyl-4-methoxy-1H-imidazol-2-yl)phenyl)methanol

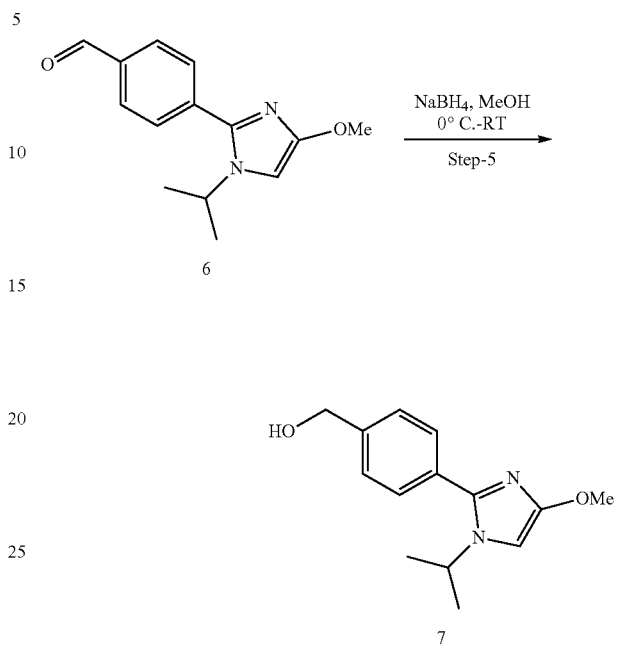

To a stirred solution of 4-(1-isopropyl-4-methoxy-1H-imidazol-2-yl)benzaldehyde 6 (0.400 g, 1.64 mmol) in methanol (4 mL) at 0° C., was added sodium borohydride (0.063 g, 1.64 mmol). The reaction mixture was allowed to warm to room temperature and was stirred for 2 h. Progress of the reaction was monitored by TLC. After completion, the reaction mixture was quenched with water (10 mL) and extracted with EA (3×30 mL). The organic layer was dried over anhydrous sodium sulfate, filtered and concentrated under reduced pressure. The crude compound was purified by silica gel chromatography using 0-70% EA in hexane as eluent to afford the title compound (0.250 g). LC-MS (Method B) (ESI+): m/z 247.04 (M+H)⁺; ¹H-NMR (400 MHz, DMSO-d₆) δ 7.37-7.46 (m, 4H), 6.75 (s, 1H), 4.54 (d, J=5.87 Hz, 2H), 4.43 (tt, J=6.79, 13.27 Hz, 2H), 3.70 (s, 3H), 1.35 (d, J=6.85 Hz, 6H).

Step 6: Synthesis of 6-chloro-1-(4-(1-isopropyl-4-methoxy-1H-imidazol-2-yl)benzyl)-1H-pyrazolo[3,4-d]pyrimidine (I-56)

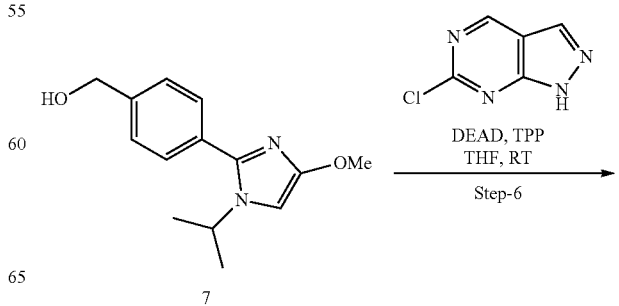

-continued

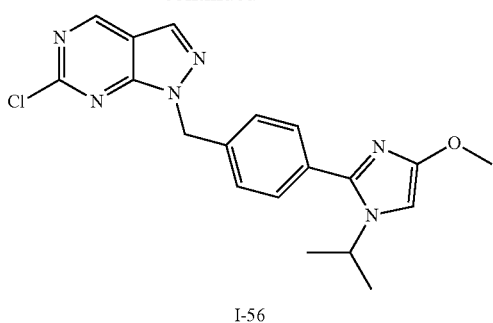

I-56

To a stirred solution of (4-(1-isopropyl-4-methoxy-1H-imidazol-2-yl)phenyl)methanol 7 (0.250 g, 1.02 mmol) in THF (4 mL) at 0° C., was added 6-chloro-1H-pyrazolo[3,4-d]pyrimidine (0.156 g, 1.02 mmol), DEAD (0.357 g, 2.03 mmol) and TPP (0.532 g, 2.03 mmol). The reaction mixture was stirred at room temperature for 1 h. Progress of the reaction was monitored by TLC. After completion, the reaction mixture was quenched with water (20 mL) and extracted with EA (3×30 mL). The organic layer was dried over anhydrous sodium sulfate, filtered and concentrated under reduced pressure. The crude compound was purified by silica gel chromatography using 0-50% EA in hexane as eluent to afford the title compound (0.120 g). LC-MS (Method B) (ESI+): m/z 383.04 (M+H)+; 1H-NMR (400 MHz, DMSO-d6) δ 9.32 (s, 1H), 8.51 (s, 1H), 7.45 (d, J=8.31 Hz, 2H), 7.34 (d, J=8.31 Hz, 2H), 6.76 (s, 1H), 5.70 (s, 2H), 4.36-4.42 (m, 1H), 3.68 (s, 3H), 1.33 (d, J=6.85 Hz, 6H).

Preparation of Common Intermediate I-57:

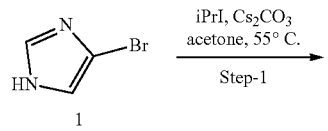

Step-1

1

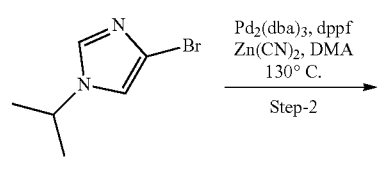

Step-2

2

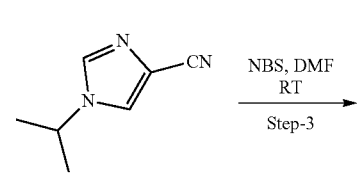

Step-3

3

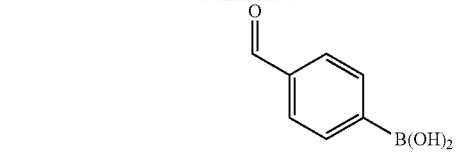

Step-4

4

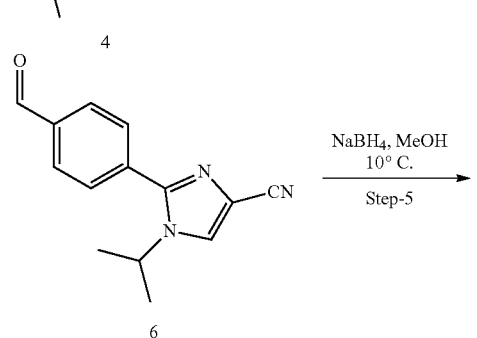

Step-5

6

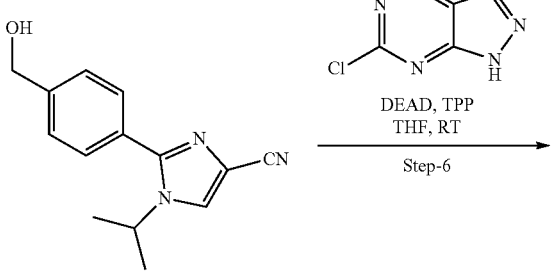

Step-6

7

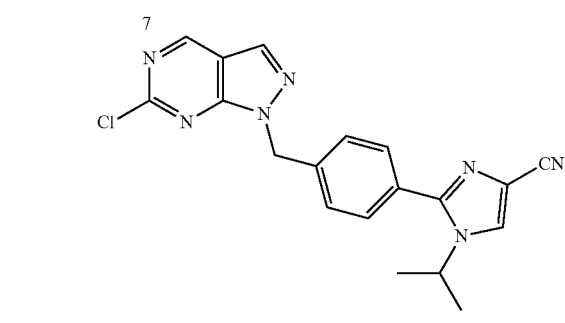

I-57

Step 1: Synthesis of
4-bromo-1-isopropyl-1H-imidazole

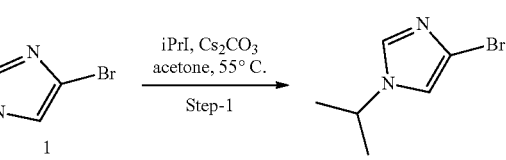

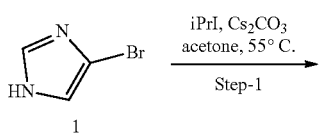

Step-1

1

2

To a stirred solution of 4-bromo-1H-imidazole 1 (10.0 g, 68.0 mmol) in acetone (200 mL), was added Cs2CO3 (22.1 g, 74.8 mmol) and isopropyl iodide (12.7 g, 74.8 mmol) at room temperature. The reaction mixture was then heated at 55° C. for 15 h. Progress of the reaction was monitored by TLC. After completion, the reaction mixture was cooled to room temperature and filtered through a pad of Celite. The filtrate was concentrated under reduced pressure. The crude compound was purified by silica gel chromatography using 0-30% EA in hexane as eluent to afford the title compound (9.00 g). LC-MS (Method C) (ESI+): m/z 191 (M+H)$^+$; $^1$H-NMR (400 MHz, DMSO-d$_6$) δ 7.69 (d, J=1.00 Hz, 1H), 7.43 (d, J=1.50 Hz, 1H), 4.39 (td, J=6.73, 13.46 Hz, 1H), 1.38 (d, J=6.98 Hz, 6H).

Step 2: Synthesis of
1-isopropyl-1H-imidazole-4-carbonitrile

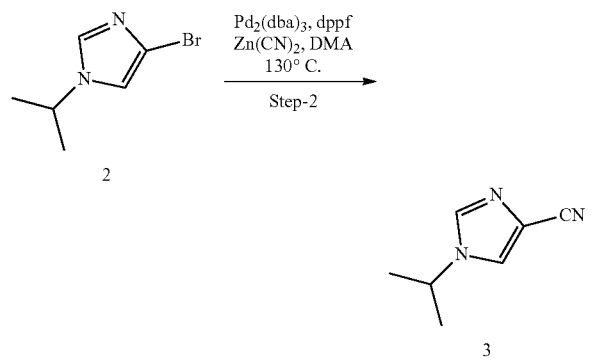

To a stirred solution 4-bromo-1-isopropyl-1H-imidazole 2 (5.00 g, 26.4 mmol) in DMA (50 mL) at room temperature, was added Zn(CN)$_2$ (6.17 g, 52.9 mmol). The resulting mixture was then degassed with argon for 10 min. To the resulting reaction mixture was added Pd$_2$(dba)$_3$ (2.40 g, 2.64 mmol) and 1,1'-bis(diphenylphosphino)ferrocene (2.92 g, 5.29 mmol) at room temperature. The reaction mixture was then heated in a sealed tube at 130° C. for 6 h. Progress of the reaction was monitored by TLC. After completion, the reaction mixture was cooled to room temperature, quenched with aqueous ammonia (30 mL) and extracted with EA (100 mL). The organic layer was washed with water (2×200 mL), dried over anhydrous sodium sulfate, filtered and concentrated under reduced pressure. The crude compound was purified by silica gel chromatography using 10-40% EA in hexane as eluent to afford the title compound (2.10 g). LC-MS (Method B) (ESI+): m/z 135.9 (M+H)$^+$; $^1$H-NMR (400 MHz, DMSO-d$_6$) δ 8.27 (s, 1H), 7.98 (s, 1H), 4.49 (quin, J=6.60, 13.21 Hz, 1H), 1.41 (d, J=6.85 Hz, 6H).

Step 3: Synthesis of
2-bromo-1-isopropyl-1H-imidazole-4-carbonitrile

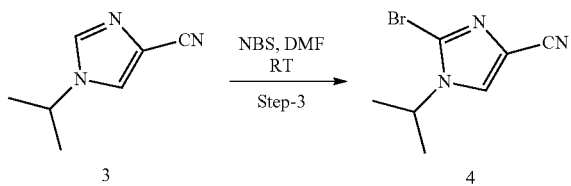

To a stirred solution of methyl 1-isopropyl-1H-imidazole-4-carbonitrile 3 (2.00 g, 14.79 mmol) in DMF (20 mL), was added NBS (5.26 g, 29.6 mmol) at room temperature. The resulting mixture was stirred for 4 h, and progress of the reaction was monitored by TLC. After completion, the reaction mixture was quenched with water (50 mL) and extracted with EA (3×50 mL). The combined organic layer was dried over anhydrous sodium sulfate, filtered and concentrated under reduced pressure. The crude compound was purified by silica gel chromatography using 10-60% EA in hexane to afford the title compound (1.50 g). LC-MS (Method B) (ESI−); m/z 213.8 (M−H); $^1$H-NMR (400 MHz, DMSO-d$_6$) δ 8.25 (s, 1H), 4.40-4.49 (m, 1H), 1.45 (d, J=6.48 Hz, 6H).

Step 4: Synthesis of 2-(4-formylphenyl)-1-isopropyl-1H-imidazole-4-carbonitrile

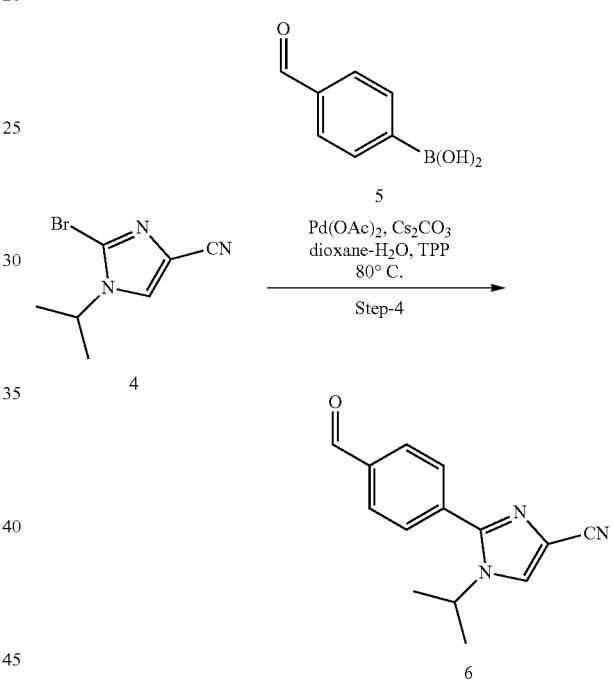

To a stirred solution of 2-bromo-1-isopropyl-1H-imidazole-4-carbonitrile 4 (0.840 g, 5.60 mmol) in dioxane:H$_2$O (2:1) (75 mL), was added Cs$_2$CO$_3$ (3.64 g, 11.2 mmol) and (4-formylphenyl)boronic acid 5 (1.2 g, 5.60 mmol). The resulting mixture was degassed with argon for 10 min. To the reaction mixture was added triphenylphosphine (0.586 g, 2.24 mmol) and Pd(OAc)$_2$ (0.251 g, 1.12 mmol) at room temperature. The reaction mixture was heated in a sealed tube at 80° C. for 2 h. Progress of the reaction was monitored by TLC. After completion, the reaction mixture was cooled to room temperature, diluted with water (10 mL) and extracted with EA (60 mL). The organic layer was separated, dried over anhydrous sodium sulfate, filtered and concentrated under reduced pressure. The crude compound was purified by silica gel chromatography using 10-40% EA in hexane as eluent to afford the title compound (0.800 g). LC-MS (Method B) (ESI+): m/z 240.10 (M+H)$^+$; $^1$H-NMR (400 MHz, DMSO-d$_6$) δ 10.11 (s, 1H), 8.32 (s, 1H), 8.11 (d, J=7.83 Hz, 2H), 7.78 (d, J=7.83 Hz, 2H), 4.33 (td, J=6.42, 13.08 Hz, 1H), 1.42 (d, J=6.85 Hz, 6H).

Step 5: Synthesis of 2-(4-(hydroxymethyl)phenyl)-1-isopropyl-1H-imidazole-4-carbonitrile

Step 6: Synthesis of 2-(4-((6-chloro-1H-pyrazolo[3,4-d]pyrimidin-1-yl)methyl)phenyl)-1-isopropyl-1H-imidazole-4-carbonitrile (I-57)

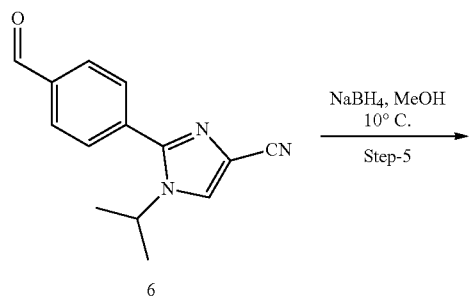

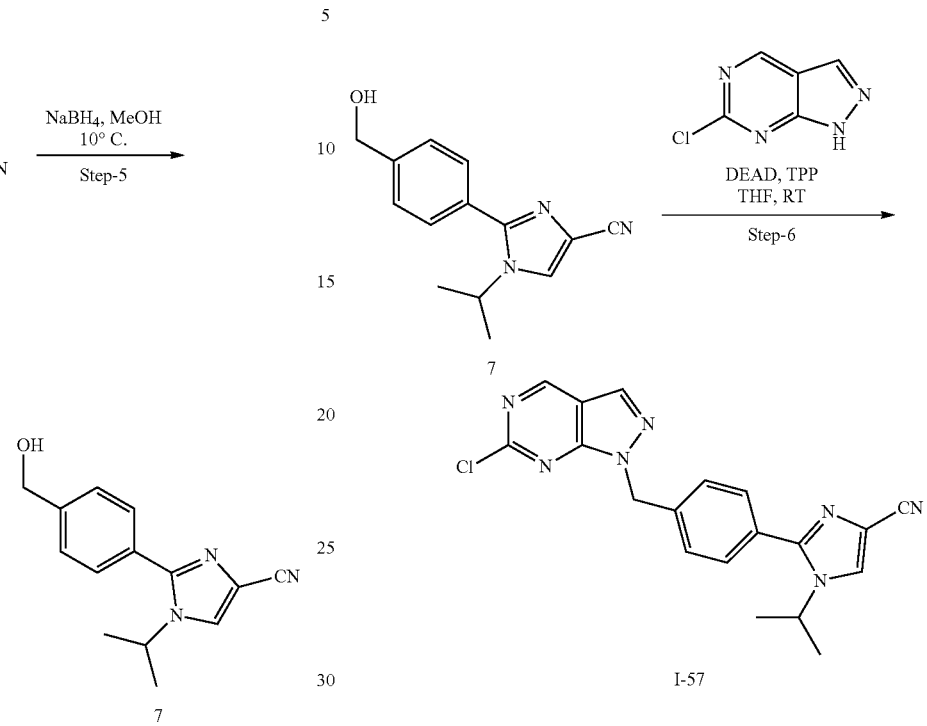

To a stirred solution of 2-(4-formylphenyl)-1-isopropyl-1H-imidazole-4-carbonitrile 6 (0.750 g, 3.134 mmol) in methanol (15 mL) at 10° C., was added sodium borohydride (0.059 g, 1.567 mmol). The resulting mixture was stirred at the same temperature for 30 min. Progress of the reaction was monitored by TLC. After completion, the reaction mixture was quenched with water (50 mL) and extracted with DCM (100 mL). The organic layer was dried over anhydrous sodium sulfate, filtered and concentrated under reduced pressure. The crude compound was purified by silica gel chromatography using 10-80% EA in hexane as eluent to afford the title compound (0.700 g). LC-MS (Method B) (ESI+): m/z 242 (M+H)$^+$; $^1$H-NMR (400 MHz, DMSO-$d_6$) δ 8.23 (s, 1H), 7.51-7.55 (m, 2H), 7.44-7.49 (m, 2H), 5.34 (t, J=5.87 Hz, 1H), 4.59 (d, J=5.87 Hz, 2H), 4.29 (td, J=6.60, 13.21 Hz, 1H), 1.40 (d, J=6.85 Hz, 6H).

To a stirred solution of 2-(4-(hydroxymethyl)phenyl)-1-isopropyl-1H-imidazole-4-carbonitrile 7 (0.319 g, 2.07 mmol) and TPP (0.812 g, 3.11 mmol) in THF (5 mL), was added DEAD (0.540 g, 3.11 mmol) and 6-chloro-1H-pyrazolo[3,4-d]pyrimidine (0.500 g, 2.07 mmol) at room temperature. The resulting mixture was stirred for 1 h at room temperature, and progress of the reaction was monitored by TLC. After completion, the reaction mixture was concentrated under reduced pressure, and the remaining residue was dissolved in water (50 mL) and extracted with EA (50 mL). The organic layer was dried over anhydrous sodium sulfate, filtered and concentrated under reduced pressure. The crude compound was purified by silica gel chromatography using 0-50% EA in hexane to afford the title compound (0.250 g). LC-MS (Method B) (ESI+): m/z 377.9 (M+H)$^+$.

The following intermediate was prepared from the 4-nitro-1H-imidazole according to the method of preparation for I-57:

| Intermediate | Structure | Analytics |
|---|---|---|
| I-58 | ![structure] | LC-MS (Method B) (ESI+): m/z 397.90 (M + H)$^+$; $^1$H-NMR (400 MHz, DMSO-$d_6$) δ 9.33 (s, 1H), 8.54 (s, 1H), 8.19 (s, 1H), 7.48 (d, J = 7.98 Hz, 2H), 7.38 (d, J = 7.98 Hz, 2H), 5.76 (s, 2H), 3.97 (td, J = 6.54, 13.34 Hz, 1H), 1.35 (d, J = 6.48 Hz, 6H). |

Preparation of Common Intermediate I-59

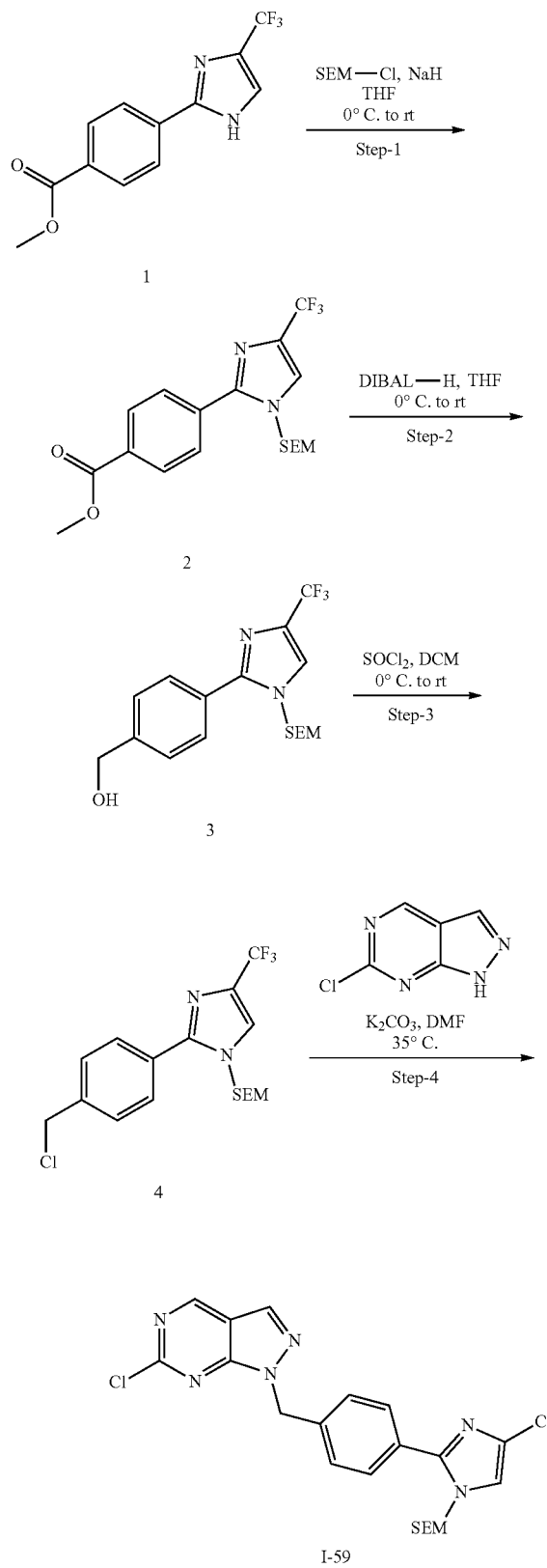

Step 1: Synthesis of Methyl 4-(4-(trifluoromethyl)-1-((2-(trimethylsilyl)ethoxy)methyl)-1H-imidazol-2-yl)benzoate

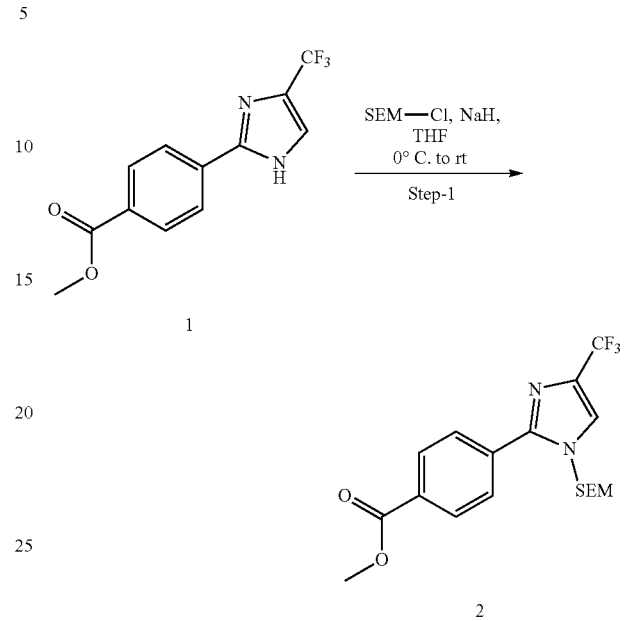

To an ice cooled solution of methyl 4-(4-(trifluoromethyl)-1H-imidazol-2-yl)benzoate (14.5 g, 53.0 mmol) in THF (300 mL), was added NaH (60% dispersion in mineral oil) (3.23 g, 80.0 mmol) portion wise over a period of 5 min. The resulting mixture was stirred at same temperature for 30 min, then SEM-Cl (14.2 mL, 80.0 mmol) was added dropwise over a period of 30 min. The reaction mixture was stirred at room temperature for a further 3 h. Progress of the reaction was monitored by TLC. After completion, the reaction mixture was quenched with ice water and extracted with EA. The organic layer was dried over anhydrous sodium sulfate, filtered, and concentrated under reduced pressure. The crude compound was purified by silica gel chromatography using 0-3.5% EA in hexane to afford 15.00 g the title compound and 1.20 g of the undesired regioisomer. LC-MS (Method B) (ESI+): m/z 400.98 (M+H)$^+$; $^1$H-NMR (400 MHz, DMSO-$d_6$) δ 8.23 (s, 1H), 8.06 (d, J=7.8 Hz, 2H), 7.96 (d, J=8.3 Hz, 2H), 5.44 (s, 2H), 3.87 (s, 3H), 3.57 (t, J=7.8 Hz, 2H), 0.83 (t, J=8.1 Hz, 2H), −0.06 (s, 9H).

Step 3: Synthesis of (4-(4-(Trifluoromethyl)-1-((2-(trimethylsilyl) ethoxy) methyl)-1H-imidazol-2-yl) phenyl)methanol

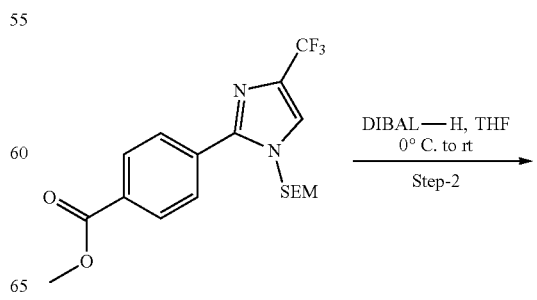

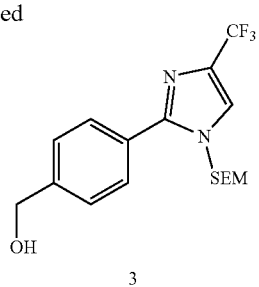

To a stirred solution of methyl 4-(4-(trifluoromethyl)-1-((2-(trimethylsilyl)ethoxy)methyl)-1H-imidazol-2-yl)benzoate (10.0 g, 25.0 mmol) in THF (200 mL) at 0° C., was added DIBAL-H (1M in toluene, 125 mL, 125 mmol), and the reaction mixture was stirred at room temperature for 2 h. Progress of the reaction was monitored by TLC. After completion, water was added to the reaction mixture and extracted with EA. The organic layer was dried over anhydrous sodium sulfate, filtered, and concentrated under reduced pressure to afford 8.10 g of the title compound. LC-MS (Method B) (ESI+): m/z 372.97 (M+H)+; 1H-NMR (400 MHz, DMSO-$d_6$) δ 8.13 (s, 1H), 7.73 (d, J=8.3 Hz, 2H), 7.43 (d, J=8.3 Hz, 2H), 5.36 (s, 2H), 5.29 (t, J=5.6 Hz, 1H), 4.54 (d, J=5.9 Hz, 2H), 3.56 (t, J=8.1 Hz, 2H), 0.79-0.86 (m, 2H), −0.04 (s, 9H).

Step 4: Synthesis of 2-(4-(chloromethyl)phenyl)-4-(trifluoromethyl)-1-((2-(trimethylsilyl)ethoxy)methyl)-1H-imidazole To a stirred solution of (4-(4-(trifluoromethyl)-1-((2-(trimethylsilyl)ethoxy)methyl)-1H-imidazol-2-yl)phenyl)methanol (2.50 g, 6.72 mmol) in DCM (50 mL) at 0° C., was added SOCl₂ (1.46 mL, 20.1 mmol) and the reaction mixture was stirred at room temperature for 30 min. Progress of the reaction was monitored by TLC. After completion, the reaction mixture was quenched with saturated NaHCO₃ solution (~50 mL) at 0° C., diluted with water (200 mL), and extracted with DCM (2×200 mL). The combined organic layer was dried over anhydrous sodium sulfate, filtered, and concentrated under reduced pressure to afford 2.40 g of the title compound, which was used as such for the next reaction without further purification. LC-MS (Method B) (ESI+): m/z 390.85 (M+H)+; 1H-NMR (400 MHz, CDCl₃) δ 7.81 (d, J=7.9 Hz, 2H), 7.51 (d, J=8.4 Hz, 2H), 7.47 (s, 1H), 5.30 (s, 2H), 4.64 (s, 2H), 3.62 (t, J=8.1 Hz, 2H), 0.91-1.01 (m, 2H), −0.06 (m, 9H).

Step 5: Synthesis of 6-Chloro-1-(4-(4-(trifluoromethyl)-1-((2-(trimethylsilyl)ethoxy)methyl)-1H-imidazol-2-yl)benzyl)-1H-pyrazolo[3,4-d]pyrimidine (I-59)

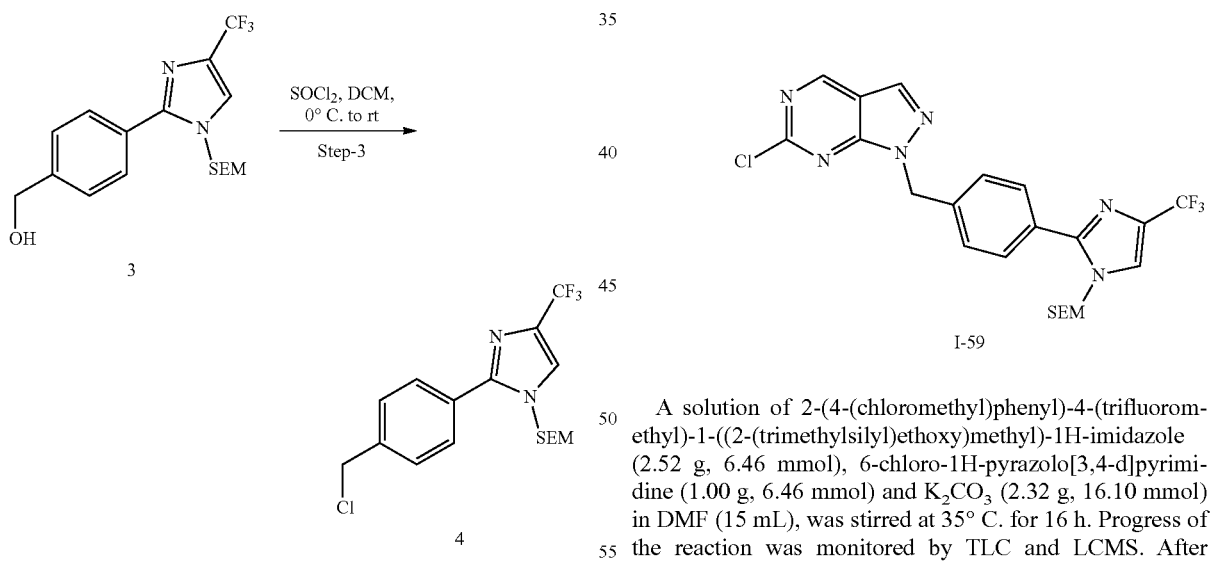

A solution of 2-(4-(chloromethyl)phenyl)-4-(trifluoromethyl)-1-((2-(trimethylsilyl)ethoxy)methyl)-1H-imidazole (2.52 g, 6.46 mmol), 6-chloro-1H-pyrazolo[3,4-d]pyrimidine (1.00 g, 6.46 mmol) and K₂CO₃ (2.32 g, 16.10 mmol) in DMF (15 mL), was stirred at 35° C. for 16 h. Progress of the reaction was monitored by TLC and LCMS. After completion, the reaction mixture was diluted with cold water (100 mL) and extracted with EA (3×200 mL). The combined organic layer was washed with ice cold water (3×200 mL), followed by brine (200 mL). The organic layer was dried over anhydrous sodium sulfate, filtered, and concentrated under reduced pressure. The crude compound was purified by silica gel chromatography using 50-100% EA in hexane to afford 1.25 g of the title compound. LC-MS (Method B) (ESI+): m/z 509.01 (M+H)+; 1H-NMR (400 MHz, CDCl₃) δ 9.06 (s, 1H), 8.19 (s, 1H), 7.78 (d, J=7.4 Hz, 2H), 7.41-7.49 (m, 3H), 5.70 (s, 2H), 5.26 (s, 2H), 3.59 (t, J=7.9 Hz, 2H), 0.94 (t, J=8.1 Hz, 2H), −0.01 (s, 9H).

Preparation of Common Intermediate I-60

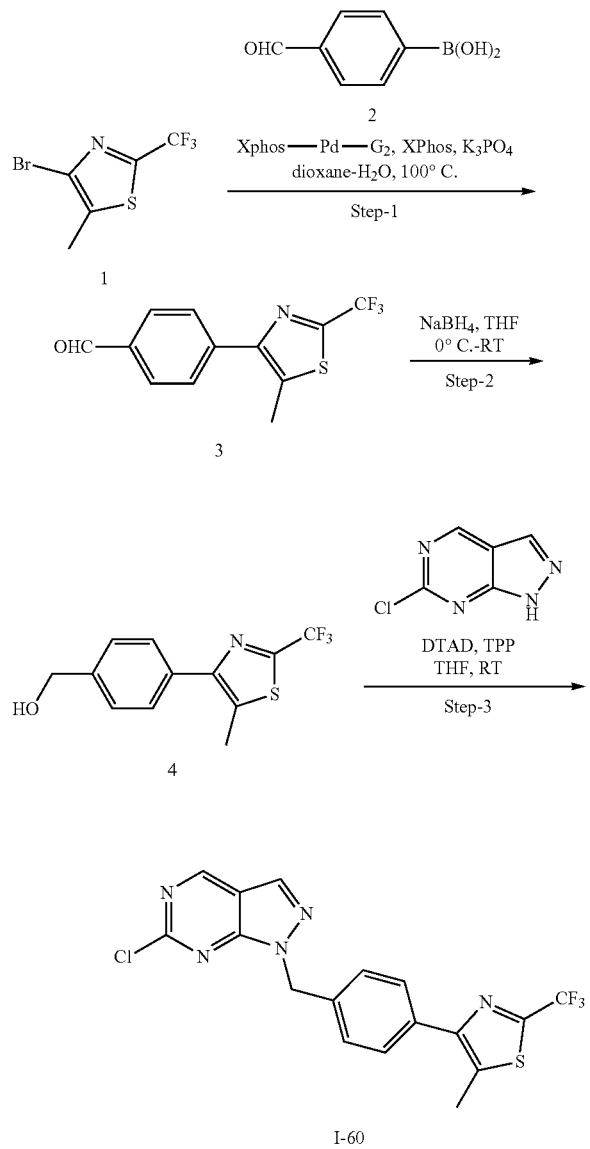

Step 1: Synthesis of 4-(5-methyl-2-(trifluoromethyl)thiazol-4-yl)benzaldehyde

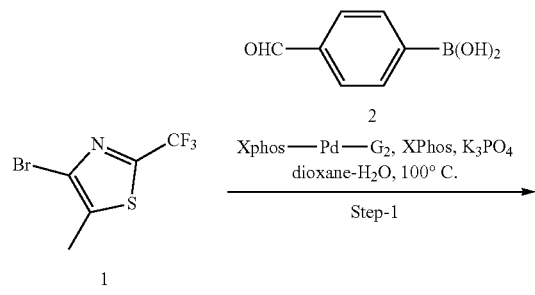

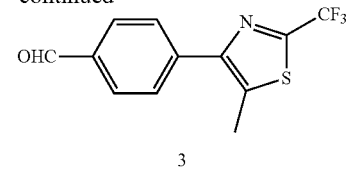

To a stirred solution of 4-bromo-5-methyl-2-(trifluoromethyl)thiazole 1 (1.00 g, 4.10 mmol) in dioxane: H₂O (4:1, 12.5 mL) was added K₃PO₄ (1.73 g, 8.20 mmol), (4-formylphenyl)boronic acid 2 (0.730 g, 4.92 mmol) and the mixture was degassed with argon for 15 min. To the resulting reaction mixture was added X-Phos (0.195 g, 0.410 mmol) and Pd-XPhos-G₂ (0.161 g, 0.205 mmol) at room temperature. The reaction mixture was further heated in a seal tube at 100° C. for 4 h. Progress of the reaction was monitored by TLC. After completion, the reaction mixture was cooled to room temperature, diluted with water (50 mL) and extracted with EA (3×50 mL). The combined organic layer was dried over anhydrous sodium sulfate, filtered and concentrated under reduced pressure. The crude compound was purified by silica gel chromatography using 10-50% EA in hexane as eluent to afford the title compound (1.00 g). LC-MS (Method B) (ESI+): m/z 271.99 (M+H)⁺; ¹H-NMR (400 MHz, DMSO-d₆) δ 10.08 (s, 1H), 8.05 (d, J=7.98 Hz, 2H), 7.94-7.98 (m, 2H), 2.73 (s, 3H).

Step 2: Synthesis of (4-(5-methyl-2-(trifluoromethyl)thiazol-4-yl)phenyl)methanol

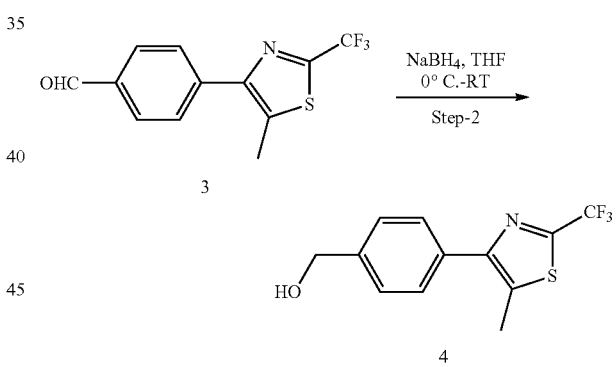

To an ice cooled solution of 4-(5-methyl-2-(trifluoromethyl) thiazol-4-yl) benzaldehyde 3 (1.00 g, 3.690 mmol) in methanol (10 mL), was added sodium borohydride (0.140 g, 3.690 mmol). The reaction mixture was allowed to warm to room temperature, and then stirred for 1 h. Progress of the reaction was monitored by TLC. After completion, the reaction mixture was quenched with water (10 mL) and concentrated under reduced pressure to dryness. The crude residue obtained was dissolved in water (20 mL) and extracted with EA (2×30 mL). Combined organic layer was dried over anhydrous sodium sulfate, filtered and concentrated under reduced pressure. The crude compound was purified by silica gel chromatography using 0-50% EA in hexane to afford the title compound (0.800 g). LC-MS (Method B) (ESI+): m/z 273.95 (M+H)⁺; ¹H-NMR (400 MHz, DMSO-d₆) δ 7.66 (d, J=7.82 Hz, 2H), 7.45 (d, J=7.83 Hz, 2H), 5.27 (t, J=5.62 Hz, 1H), 4.56 (d, J=5.87 Hz, 2H), 2.66 (s, 3H).

Step 3: Synthesis of 4-(4-((6-chloro-1H-pyrazolo[3,4-d]pyrimidin-1-yl)methyl)phenyl)-5-methyl-2-(trifluoromethyl)thiazole (I-60)

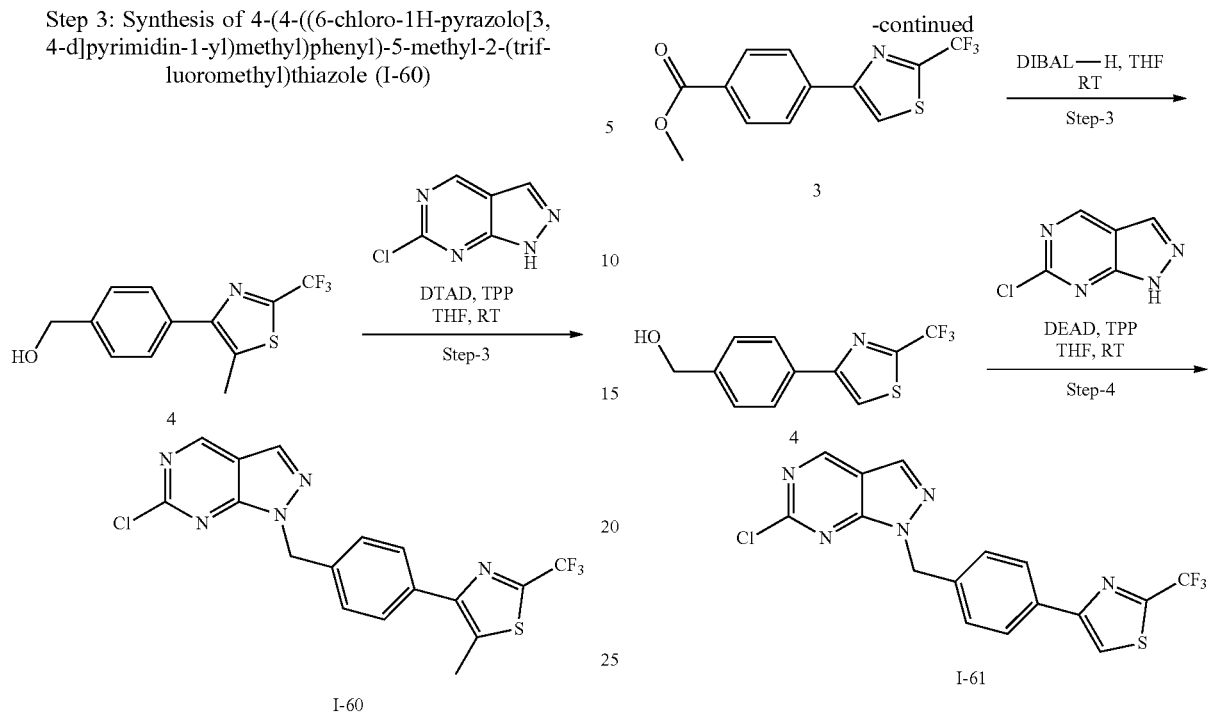

To a stirred solution of (4-(5-methyl-2-(trifluoromethyl)thiazol-4-yl)phenyl)methanol 4 (0.500 g, 1.831 mmol) in THF (10 mL) was added 6-chloro-1H-pyrazolo[3,4-d]pyrimidine (0.282 g, 1.831 mmol), DTAD (0.842 g, 3.662 mmol) and TPP (0.959 g, 3.662 mmol) at room temperature, and the mixture was stirred for 2 h. Progress of the reaction was monitored by TLC. After completion, the reaction mixture was quenched with water (20 mL) and extracted with EA (2×30 mL). The combined organic layer was dried over anhydrous sodium sulfate, filtered and concentrated under reduced pressure. The crude compound was purified by silica gel chromatography using 0-50% EA in hexane to afford the title compound (0.450 g). LC-MS (Method B): (ESI+): m/z 410.02 (M+H)$^+$; $^1$H-NMR (400 MHz, DMSO-d$_6$) δ 9.32 (s, 1H), 8.52 (s, 1H), 7.67 (d, J=7.98 Hz, 2H), 7.39 (d, J=7.98 Hz, 2H), 5.71 (s, 2H), 2.63 (s, 3H).

Preparation of Common Intermediate I-61

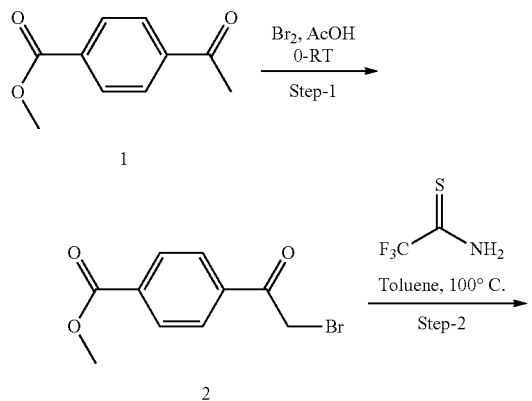

Step 1: Synthesis of 4-(2-bromoacetyl) phenyl acetate

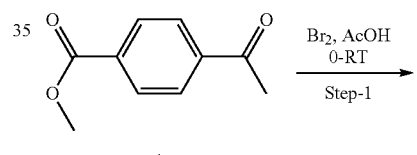

To an ice cooled solution of 4-acetylphenyl acetate 1 (5.00 g, 28.08 mmol) in acetic acid (50 mL) was added bromine (1.15 mL, 22.47 mmol), and the reaction mixture was stirred for 4 h at room temperature. Progress of the reaction was monitored by TLC. After completion, the reaction mixture was poured onto ice cold water (10 mL) and the resulting solid was collected on a Buchner funnel. The solid was washed with water (20 mL) and dried under reduced pressure to afford the crude title compound (5.10 g). LC-MS (Method B) (ESI+): m/z 258.95 (M+H)$^+$; $^1$H-NMR (400 MHz, CDCl$_3$) δ 8.16 (d, J=7.98 Hz, 2H), 8.05 (d, J=8.48 Hz, 2H), 4.47 (s, 2H), 3.96 (s, 3H).

Step 2: Synthesis of methyl 4-(2-(trifluoromethyl)thiazol-4-yl)benzoate

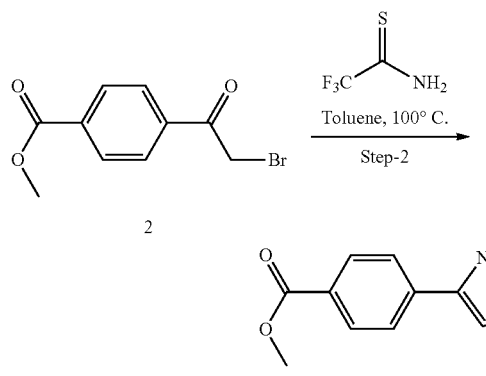

To a stirred solution 4-(2-bromoacetyl)phenyl acetate 2 (0.700 g, 2.73 mmol) in toluene (15 mL), was added 2,2,2-trifluoroethanethioamide (1.05 g, 8.20 mmol) at room temperature, and the reaction mixture was heated in a sealed tube at 100° C. for 16 h. Progress of the reaction was monitored by TLC. After completion, the reaction mixture was cooled to room temperature and concentrated under reduced pressure. The crude compound was purified by silica gel chromatography using 5-20% EA in hexane to afford the title compound (0.700 g). $^1$H-NMR (400 MHz, CDCl$_3$) δ 8.13 (d, J=7.98 Hz, 2H), 8.01 (d, J=8.48 Hz, 2H), 7.82 (s, 1H), 3.95 (s, 3H).

Step 3: Synthesis of (4-(2-(trifluoromethyl)thiazol-4-yl)phenyl)methanol

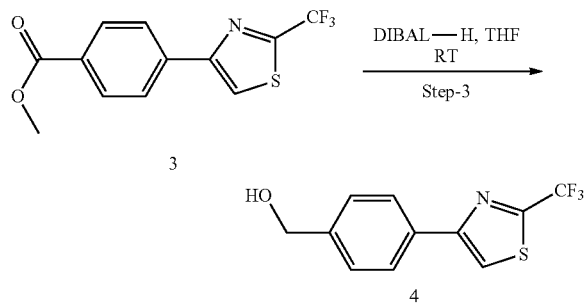

To an ice cooled solution of methyl 4-(2-(trifluoromethyl) thiazol-4-yl) benzoate 3 (0.500 g, 1.74 mmol) in THF (5 mL), was added DIBAL-H (5.22 mL, 5.22 mmol, 1.0 M solution in THF) dropwise. After addition, the mixture was stirred for 1 h at room temperature. Progress of the reaction was monitored by TLC. After completion, the reaction mixture was quenched with saturated solution of NH$_4$Cl (5 mL) and extracted with EA (3×10 mL). The combined organic layer was dried over anhydrous sodium sulfate, filtered and concentrated under reduced pressure. The crude compound was purified by silica gel chromatography using 1-20% EA in hexane as eluent to afford (0.400 g). LC-MS (Method B) (ESI+): m/z 260.00 (M+H)$^+$; $^1$H-NMR (400 MHz, DMSO-d$_6$) δ 8.54 (s, 1H), 7.96 (d, J=7.83 Hz, 2H), 7.44 (d, J=8.31 Hz, 2H), 5.27 (t, J=5.87 Hz, 1H), 4.55 (d, J=5.38 Hz, 2H).

Step 4: Synthesis of 4-(4-((6-chloro-1H-pyrazolo[3,4-d]pyrimidin-1-yl)methyl)phenyl)-2-(trifluoromethyl)thiazole (I-61)

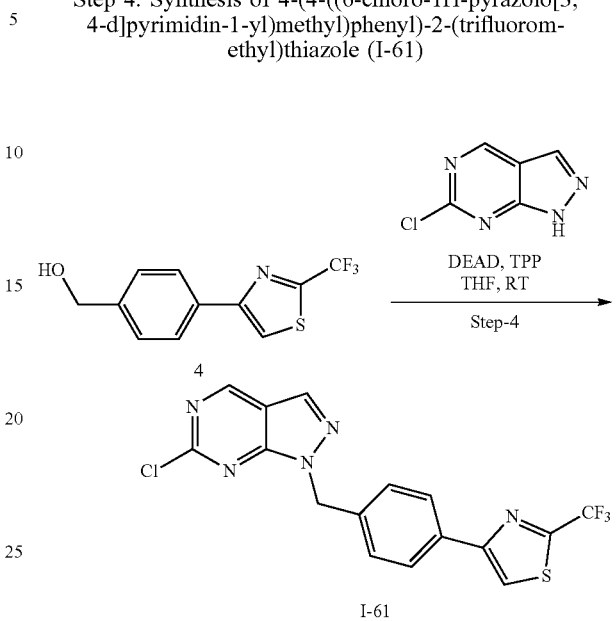

To a stirred solution of (4-(2-(trifluoromethyl) thiazol-4-yl) phenyl)methanol 4 (0.400 g, 1.544 mmol) and TPP (0.606 g, 2.316 mmol) in THF (5 mL) was added DEAD (0.363 g, 2.316 mmol) and 6-chloro-1H-pyrazolo[3,4-d] pyrimidine (0.214 g, 1.389 mmol) at room temperature and stirred for 30 min at room temperature. Progress of the reaction was monitored by TLC. After completion, the reaction mixture was concentrated under reduced pressure. The crude compound was purified by silica gel chromatography using 0-30% EA in hexane as eluent to afford the title compound (0.350 g). $^1$H-NMR (400 MHz, DMSO-d$_6$) δ 9.31 (s, 1H), 8.55 (s, 1H), 8.51 (s, 1H), 7.96 (d, J=8.31 Hz, 2H), 7.38 (d, J=7.83 Hz, 2H), 5.69 (s, 2H).

Preparation of Common Intermediate I-62

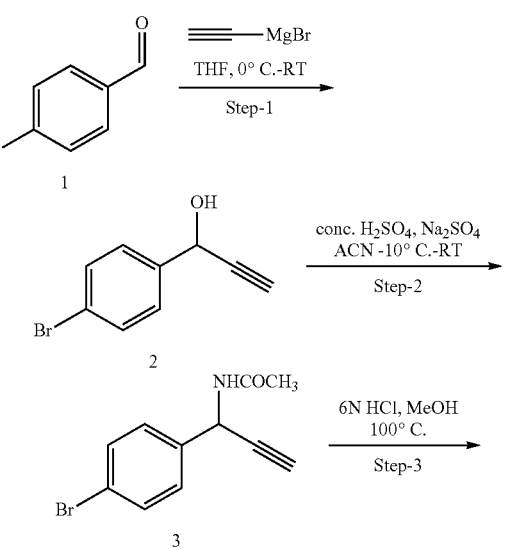

Step 1: Synthesis of 1-(4-bromophenyl)prop-2-yn-1-ol

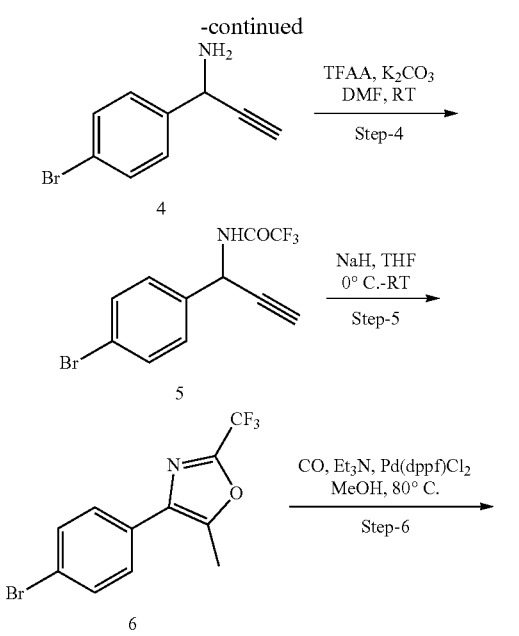

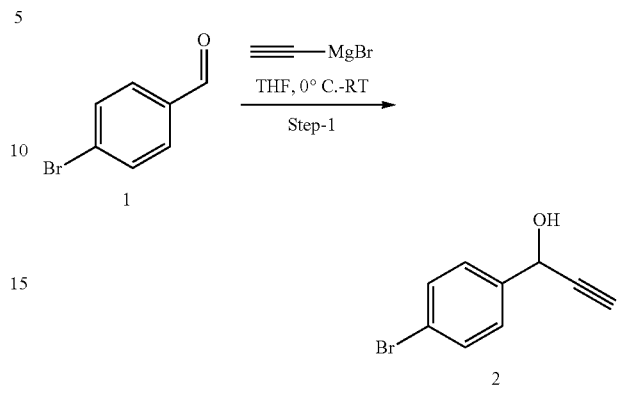

To an ice cooled solution of 4-bromobenzaldehyde 1 (5.00 g, 27.0 mmol) in dry THF (75 mL), was added ethynylmagnesium bromide (0.5M solution in THF, 119 mL, 67.6 mmol) dropwise under nitrogen atmosphere. The reaction mixture was allowed to warm to room temperature, and then stirred for 3 h. Progress of the reaction was monitored by TLC. After completion, the reaction mixture was quenched with dilute HCl (150 mL) and extracted with EA (3×50 mL). The combined organic layer was dried over anhydrous sodium sulfate, filtered and concentrated under reduced pressure. The crude compound was purified by silica gel chromatography using 10-20% EA in hexane as eluent to afford the title compound (3.00 g). LC-MS (Method B) (ESI+): m/z 212.00 (M+H)$^+$; $^1$H-NMR (400 MHz, DMSO-$d_6$) δ 7.56 (d, J=7.98 Hz, 2H), 7.41 (d, J=7.98 Hz, 2H), 6.15 (d, J=5.98 Hz, 1H), 5.33-5.37 (m, 1H), 3.54 (d, J=2.49 Hz, 1H).

Step 2: Synthesis of N-(1-(4-bromophenyl)prop-2-yn-1-yl)acetamide

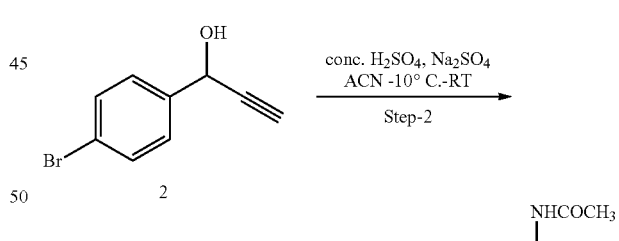

To a stirred solution of 1-(4-bromophenyl)prop-2-yn-1-ol 2 (1.00 g, 4.76 mmol) in acetonitrile (20 mL) at −10° C., was added sodium sulphate (0.676 g, 4.76 mmol) and stirred for 5 min. To the reaction mixture, was added conc. H$_2$SO$_4$ (2.33 g, 23.8 mmol) dropwise. The resulting reaction was stirred for 16 h at room temperature. Progress of the reaction was monitored by TLC. After completion, the reaction mixture was poured over ice cold water (50 mL), basified using sodium carbonate and extracted with EA (3×30 mL).

The combined organic layer was dried over anhydrous sodium sulfate, filtered and concentrated under reduced pressure. The crude compound was purified by silica gel chromatography using 30-40% EA in hexane as eluent to afford the title compound (0.710 g). LC-MS (Method C) (ESI+): m/z 252.00 (M)+; $^1$H-NMR (400 MHz, DMSO-$d_6$) δ 8.87 (d, J=8.31 Hz, 1H), 7.58 (d, J=8.31 Hz, 2H), 7.37 (d, J=8.31 Hz, 2H), 5.79 (d, J=8.31 Hz, 1H), 3.50 (d, J=2.45 Hz, 1H), 1.86 (s, 3H).

Step 3: Synthesis of 1-(4-bromophenyl)prop-2-yn-1-amine

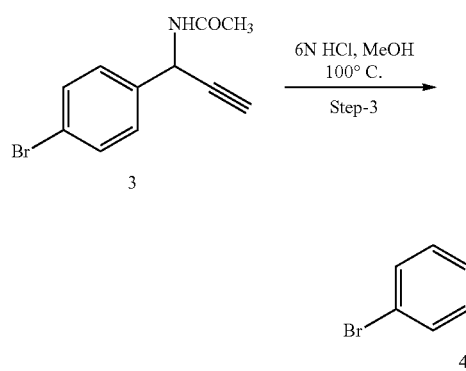

To a stirred solution of N-(1-(4-bromophenyl)prop-2-yn-1-yl)acetamide 3 (0.700 g, 2.79 mmol) in methanol (15 mL), was added 6N HCl (10 mL) at room temperature. The reaction mixture was heated at 100° C. for 16 h. Progress of the reaction was monitored by TLC. After completion, the reaction mixture was concentrated under reduced pressure. The crude residue obtained was dissolved in a mixture of water (20 mL) and EA (30 mL), and then neutralized using solid Na$_2$CO$_3$. The aqueous layer was extracted with EA (2×10 mL). The combined organic layer was dried over anhydrous sodium sulfate, filtered and concentrated under reduced pressure. The crude compound was purified by silica gel chromatography using 25-30% EA in hexane to afford the title compound (0.400 g). $^1$H-NMR (400 MHz, DMSO-$d_6$) δ 7.51-7.56 (m, 2H), 7.45 (d, J=7.98 Hz, 2H), 4.67 (s, 1H), 3.33 (br s, 1H, merged in H$_2$O peak of DMSO solvent), 2.28 (br s, 2H).

Step 4: Synthesis of N-(1-(4-bromophenyl)prop-2-yn-1-yl)-2,2,2-trifluoroacetamide

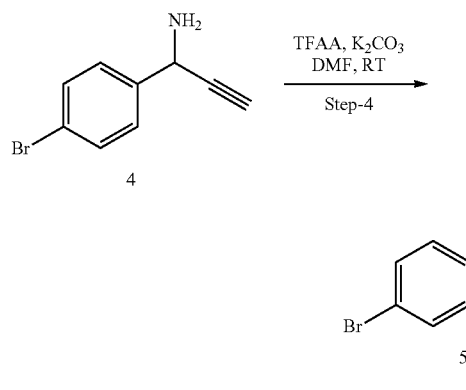

To a stirred solution of 1-(4-bromophenyl)prop-2-yn-1-amine 4 (0.350 g, 1.67 mmol) in DMF (5 mL), was added potassium carbonate (0.277 g, 2.01 mmol), followed by trifluoroacetic anhydride (0.28 mL, 0.42 g, 2.01 mmol) at room temperature. The reaction mixture was stirred at room temperature for 1 h. Progress of the reaction was monitored by TLC. After completion, the reaction mixture was poured over ice water (30 mL) and extracted with EA (2×20 mL). The combined organic layer was dried over anhydrous sodium sulfate, filtered and concentrated under reduced pressure. The crude compound was purified by silica gel chromatography using 4-5% EA in hexane as eluent to afford the title compound (0.260 g). $^1$H-NMR (400 MHz, CDCl$_3$) δ 7.54 (d, J=8.48 Hz, 2H), 7.40 (d, J=8.48 Hz, 2H), 6.70 (br s, 1H), 5.95 (dd, J=1.75, 8.23 Hz, 1H), 2.63 (d, J=2.49 Hz, 1H).

Step 5: Synthesis of 4-(4-bromophenyl)-5-methyl-2-(trifluoromethyl)oxazole

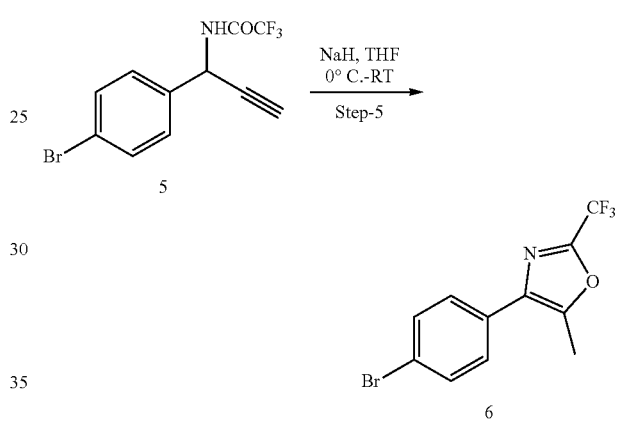

To a stirred solution of N-(1-(4-bromophenyl)prop-2-yn-1-yl)-2,2,2-trifluoroacetamide 5 (0.250 g, 0.819 mmol) in dry THF (5 mL) at 0° C., was added 60% dispersion of sodium hydride in oil (0.033 g, 0.82 mmol). The reaction mixture was allowed to warm to room temperature and was then stirred for 1 h. Progress of the reaction was monitored by TLC. After completion, the reaction mixture was poured over ice cold water (30 mL), stirred well and extracted with EA (2×20 mL). The combined organic layer was dried over anhydrous sodium sulfate, filtered and concentrated under reduced pressure. The crude compound was purified by silica gel chromatography using 3-5% EA in hexane as eluent to afford the title compound (0.200 g). LC-MS (Method B) (ESI+): m/z 308.08 (M+H)+; $^1$H-NMR (400 MHz, CDCl$_3$) δ 7.52-7.61 (m, 4H), 2.61 (s, 3H).

Step 6: Synthesis of ethyl 4-(5-methyl-2-(trifluoromethyl)oxazol-4-yl)benzoate

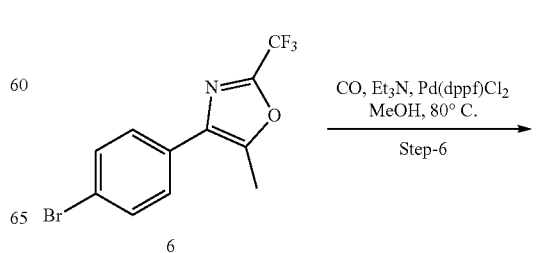

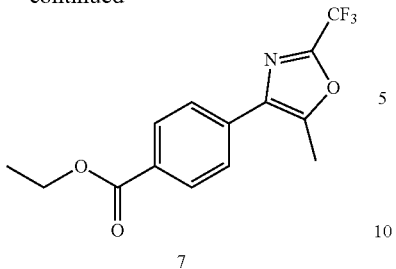

To a stirred solution of 4-(4-bromophenyl)-5-methyl-2-(trifluoromethyl)oxazole 6 (0.200 g, 0.655 mmol) and ethanol (10 mL) in a pressure vial, was added triethylamine (0.180 mL, 1.31 mmol). The resulting mixture was degassed with argon for 10 min, and then treated with Pd(dppf)Cl$_2$ (0.048 g, 0.065 mmol) at room temperature. The reaction mixture was then heated at 80° C. under an atmosphere of carbon monoxide (30 psi pressure) for 16 h. Progress of the reaction was monitored by TLC. After completion, the reaction mixture was concentrated under reduced pressure. The crude compound was purified by silica gel chromatography using 5-10% EA in hexane as eluent to afford the title compound (0.170 g). LC-MS (Method B) (ESI+): m/z 299.80 (M+H)$^+$; $^1$H-NMR (400 MHz, CDCl$_3$) δ 8.13 (d, J=8.31 Hz, 2H), 7.76 (d, J=8.31 Hz, 2H), 4.40 (q, J=7.17 Hz, 2H), 2.66 (s, 3H), 1.42 (t, J=7.09 Hz, 3H).

Step 7: Synthesis of (4-(5-methyl-2-(trifluoromethyl)oxazol-4-yl)phenyl)methanol

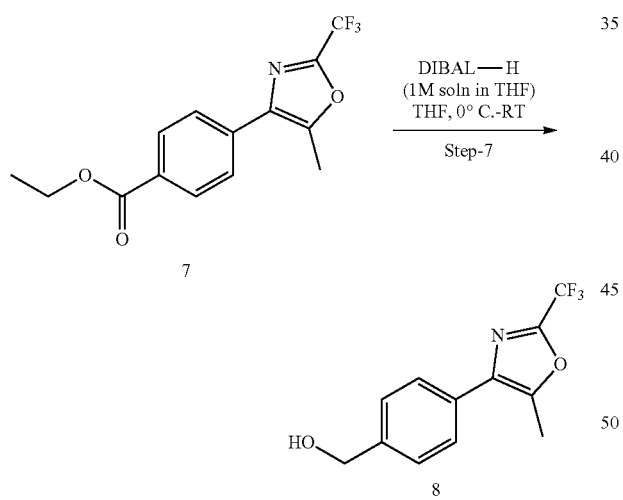

To a stirred solution of ethyl 4-(5-methyl-2-(trifluoromethyl)oxazol-4-yl)benzoate 7 (0.170 g, 0.568 mmol) in dry THF (5 mL) at 0° C., was added DIBAL-H (1M solution in toluene, 0.850 mL, 0.850 mmol). The reaction mixture was allowed to warm to room temperature and was then stirred for 1 h. Progress of the reaction was monitored by TLC. After completion, the reaction mixture was quenched with dilute HCl (5 mL) and extracted with EA (2×20 mL). The combined organic layer was dried over anhydrous sodium sulfate, filtered and concentrated under reduced pressure to afford the crude title compound (0.130 g). $^1$H-NMR (400 MHz, CDCl$_3$) (7.67 (d, J=7.83 Hz, 2H), 7.46 (d, J=7.83 Hz, 2H), 4.75 (s, 2H), 2.62 (s, 3H).

Step 8: Synthesis of 4-(4-((6-chloro-1H-pyrazolo[3,4-d]pyrimidin-1-yl)methyl)phenyl)-5-methyl-2-(trifluoromethyl)oxazole (I-62)

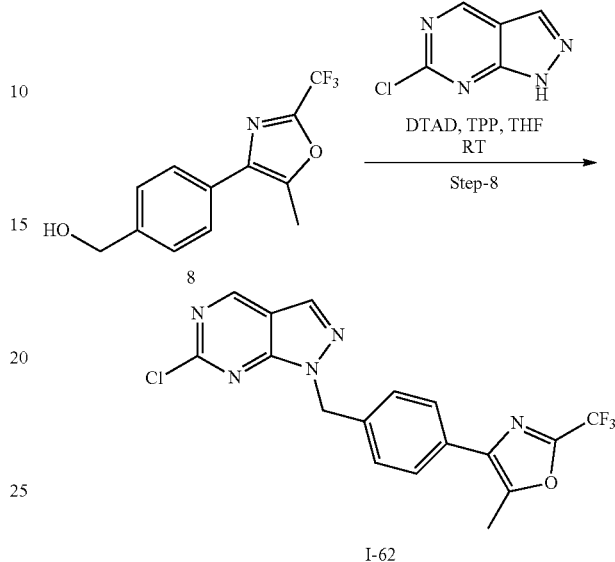

To a stirred solution of (4-(5-methyl-2-(trifluoromethyl)oxazol-4-yl)phenyl)methanol 8 (0.120 g, 0.466 mmol) in THF (5 mL), was added 6-chloro-1H-pyrazolo[3,4-d]pyrimidine (0.072 g, 0.47 mmol), DTAD (0.161 g, 0.699 mmol) and TPP (0.183 g, 0.699 mmol) at room temperature. The resulting mixture was stirred for 3 h, and progress of the reaction was monitored by TLC. After completion, the reaction mixture was quenched with water (10 mL) and extracted with EA (3×10 mL). The combined organic layer was dried over anhydrous sodium sulfate, filtered and concentrated under reduced pressure. The crude was purified by silica gel chromatography using 15-20% EA in hexane as eluent to afford the title compound (0.100 g). LC-MS (Method B) (ESI+): m/z 393.95 (M+H)$^+$; $^1$H-NMR (400 MHz, DMSO-d$_6$) δ 9.31 (s, 1H), 8.51 (s, 1H), 7.67 (d, J=8.31 Hz, 2H), 7.38 (d, J=8.31 Hz, 2H), 5.69 (s, 2H), 2.61 (s, 3H).

Preparation of Common Intermediate I-63

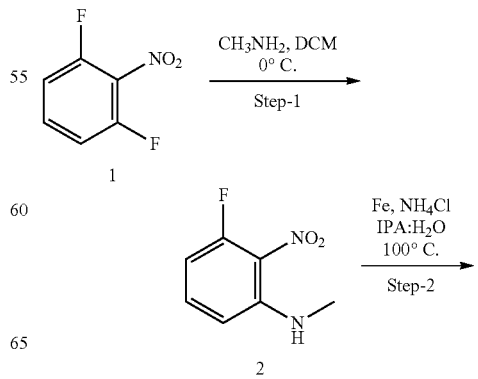

Step 1: Synthesis of 3-fluoro-N-methyl-2-nitroaniline

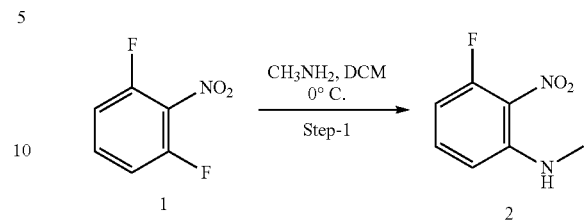

To a stirred solution of 1,3-difluoro-2-nitrobenzene 1 (14.0 g, 88.1 mmol) in DCM (150 mL) at 0° C., was added methylamine (7.00 g, 228 mmol) and the mixture was stirred for 3 h. Progress of the reaction was monitored by TLC. After completion, the reaction mixture was quenched with ice water (50 mL). The organic layer was separated, dried over anhydrous sodium sulfate, filtered and concentrated under reduced pressure to afford the crude title compound (9.00 g). $^1$H-NMR (400 MHz, DMSO-d$_6$) δ 8.29 (s, 1H), 7.41 (dd, J=4.24, 8.73 Hz, 1H), 7.01 (dd, J=8.73, 10.22 Hz, 1H), 4.09 (s, 3H).

Step 2: Synthesis of 3-fluoro-N$^1$-methylbenzene-1,2-diamine

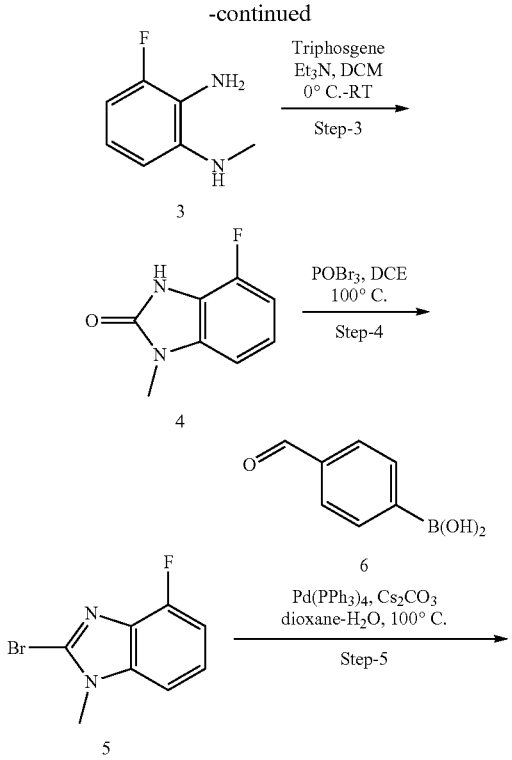

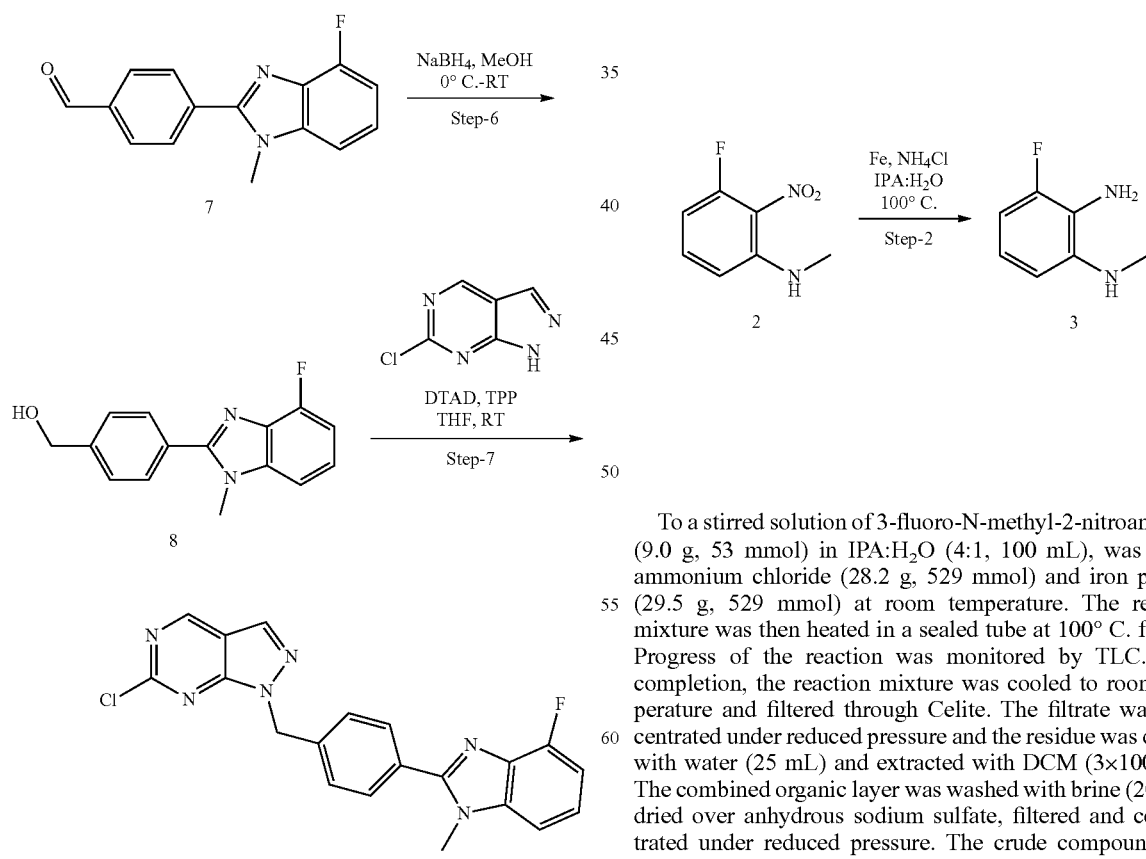

To a stirred solution of 3-fluoro-N-methyl-2-nitroaniline 2 (9.0 g, 53 mmol) in IPA:H$_2$O (4:1, 100 mL), was added ammonium chloride (28.2 g, 529 mmol) and iron powder (29.5 g, 529 mmol) at room temperature. The reaction mixture was then heated in a sealed tube at 100° C. for 3 h. Progress of the reaction was monitored by TLC. After completion, the reaction mixture was cooled to room temperature and filtered through Celite. The filtrate was concentrated under reduced pressure and the residue was diluted with water (25 mL) and extracted with DCM (3×100 mL). The combined organic layer was washed with brine (20 mL), dried over anhydrous sodium sulfate, filtered and concentrated under reduced pressure. The crude compound thus obtained was purified by silica gel chromatography using 0-15% EA in hexane as eluent to afford the title compound (4.67 g). LC-MS (Method B) (ESI+): m/z 141.0 (M+H)$^+$.

Step 3: Synthesis of 4-fluoro-1-methyl-1,3-dihydro-2H-benzo[d]imidazol-2-one

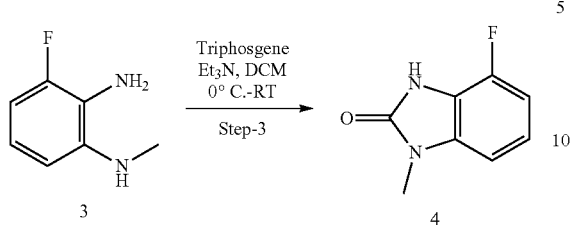

To a stirred solution of 3-fluoro-N¹-methylbenzene-1,2-diamine 3 (1.5 g, 10.70 mmol) in DCM, was added triethylamine (1.4 g, 14 mmol) and triphosgene (0.950 g, 3.21 mmol) at room temperature. The mixture was stirred for 12 h, and the progress of the reaction was monitored by TLC. After completion, the reaction mixture was diluted with DCM (10 mL) and washed with saturated solution of NaHCO$_3$ (10 mL). The organic layer was separated, dried over anhydrous sodium sulfate, filtered and concentrated under reduced pressure. The crude compound was purified by silica gel chromatography eluting with 0-40% EA in hexane to afford the title compound (0.770 g). LC-MS (Method B) (ESI+): m/z 166 (M+H)$^+$.

Step 4: Synthesis of 2-bromo-4-fluoro-1-methyl-1H-benzo[d]imidazole

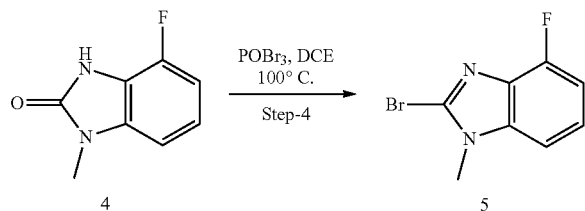

To a stirred solution of 4-fluoro-1-methyl-1,3-dihydro-2H-benzo[d]imidazol-2-one 4 (0.770 g, 4.63 mmol) in dichloroethane (15 mL) at 0° C., was added POBr$_3$ (0.650 g, 2.27 mmol). The reaction mixture was further heated at 90° C. for 12 h. Progress of the reaction was monitored by TLC. After completion, the reaction mixture was cooled to room temperature and concentrated under reduced pressure. The crude residue obtained was diluted with ice cold water (20 mL), and the pH was adjusted to 8 using NaHCO$_3$ 0.500 g). The mixture was then extracted with DCM (3×10 mL). The organic layer was dried over anhydrous sodium sulfate, filtered and concentrated under reduced pressure. The crude compound was purified by silica gel chromatography using 0-5% EA in hexane as eluent to afford the title compound (0.806 g). LC-MS (Method B) (ESI+): m/z 230.95 (M+H)$^+$; $^1$H-NMR (400 MHz, DMSO-d$_6$) δ 7.46 (d, J=7.98 Hz, 1H), 7.27 (dt, J=4.74, 8.10 Hz, 1H), 7.05 (dd, J=7.98, 10.97 Hz, 1H), 3.81 (s, 3H).

Step 5: Synthesis of 4-(4-fluoro-1-methyl-1H-benzo[d]imidazol-2-yl)benzaldehyde

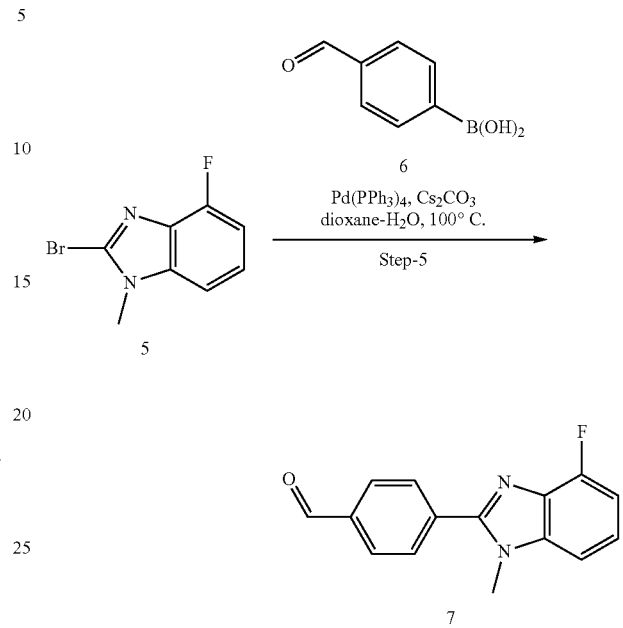

To a stirred solution of 2-bromo-4-fluoro-1-methyl-1H-benzo[d]imidazole 5 (0.600 g, 2.62 mmol) in dioxane:H$_2$O (7:3 mL) was added K$_3$PO$_4$ (1.2 g, 7.9 mmol) and (4-formylphenyl) boronic acid 6 (0.471 g, 3.14 mmol) at room temperature. The mixture was then degassed with argon for 15 min, followed by addition of X-phos (0.099 g, 0.21 mmol) and X-phos-Pd-G$_2$ (0.082 g, 0.10 mmol) at room temperature. The reaction mixture was further degassed with argon for 5 min, and then heated in a sealed tube at 100° C. for 1 h. Progress of the reaction was monitored by TLC. After completion, the reaction mixture was concentrated under reduced pressure. The residue obtained was dissolved in DCM (10 mL) and washed with H$_2$O (10 mL). The organic layer was dried over anhydrous sodium sulfate, filtered and concentrated under reduced pressure. The crude compound was purified by silica gel chromatography using 0-20% EA in hexane as eluent to afford the title compound (0.433 g). LC-MS (Method C) (ESI+): m/z 255.0 (M+H)$^+$; $^1$H-NMR (400 MHz, DMSO-d$_6$) δ 10.14 (s, 1H), 8.09-8.15 (m, 4H), 7.53 (d, J=8.48 Hz, 1H), 7.32 (dt, J=4.74, 8.10 Hz, 1H), 7.10 (dd, J=7.98, 10.97 Hz, 1H), 3.95 (s, 3H).

Step 6: Synthesis of (4-(4-fluoro-1-methyl-1H-benzo[d]imidazol-2-yl)phenyl)methanol

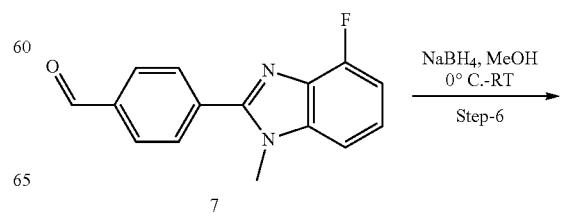

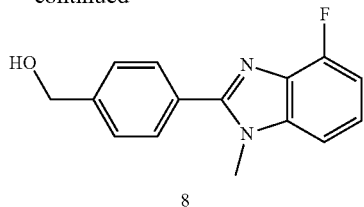

To a stirred solution of 4-(4-fluoro-1-methyl-1H-benzo[d]imidazol-2-yl)benzaldehyde 5 (0.432 g, 1.70 mmol) in methanol (15 mL) at 0° C., was added sodium borohydride (0.128 g, 3.40 mmol). The reaction mixture was allowed to warm to room temperature and then stirred for 3 h. Progress of the reaction was monitored by TLC. After completion, the reaction mixture was quenched with saturated NH$_4$Cl solution (5 mL) and concentrated under reduced pressure. The crude residue obtained was dissolved DCM (20 mL) and washed with brine (5 mL). The organic layer was dried over anhydrous sodium sulfate, filtered and concentrated under reduced pressure. The crude compound was purified by silica gel chromatography using 10-50% EA in hexane as eluent to afford the title compound (0.300 g). LC-MS (Method B) (ESI+): m/z 256.90 (M+H)$^+$.

Step 7: Synthesis of 6-chloro-1-(4-(4-fluoro-1-methyl-1H-benzo[d]imidazol-2-yl)benzyl)-1H-pyrazolo[3,4-d]pyrimidine (I-63)

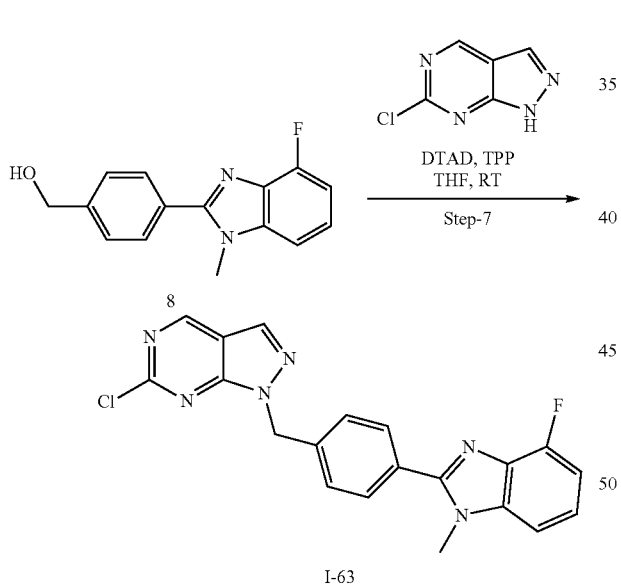

To an ice cooled solution of (4-(4-fluoro-1-methyl-1H-benzo[d]imidazol-2-yl)phenyl)methanol 8 (0.300 g, 1.17 mmol) in THF (10 mL), was added 6-chloro-1H-pyrazolo[3,4-d]pyrimidine (0.162 g, 1.05 mmol), DTAD (0.403 g, 1.76 mmol) and TPP (0.460 g, 1.76 mmol). The reaction mixture was allowed to warm to room temperature and was then stirred for 2 h. Progress of the reaction was monitored by TLC. After completion, the reaction mixture was quenched with water (10 mL) and extracted with DCM (2×20 mL). The combined organic layer was dried over anhydrous sodium sulfate, filtered and concentrated under reduced pressure. The crude compound was purified by silica gel chromatography using 10-60% EA in hexane as eluent to afford the title compound (0.160 g). LC-MS (Method C) (ESI+): m/z 393.00 (M+H)$^+$; $^1$H-NMR (400 MHz, DMSO-d$_6$) δ 9.33 (s, 1H), 8.54 (s, 1H), 7.85 (d, J=7.98 Hz, 2H), 7.43-7.49 (m, 3H), 7.27 (dt, J=4.49, 7.98 Hz, 1H), 7.05 (dd, J=8.23, 10.72 Hz, 1H), 5.77 (s, 2H), 3.87 (s, 3H).

Preparation of Common Intermediate I-64

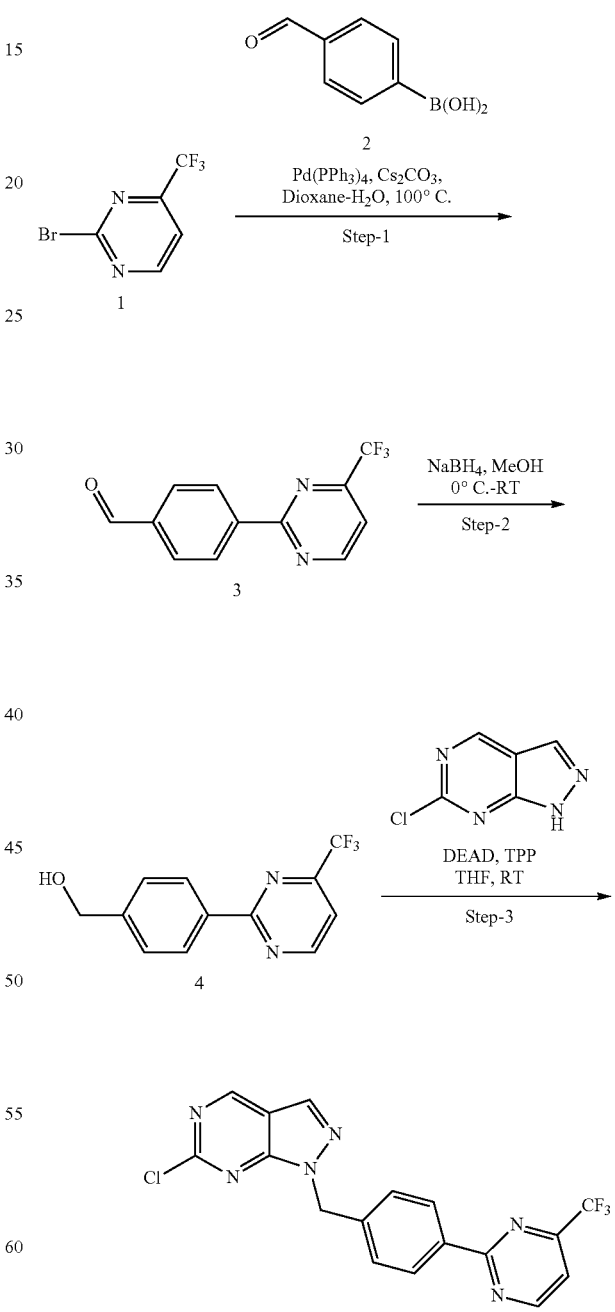

Step 1: Synthesis of 4-(4-(trifluoromethyl)pyrimidin-2-yl)benzaldehyde

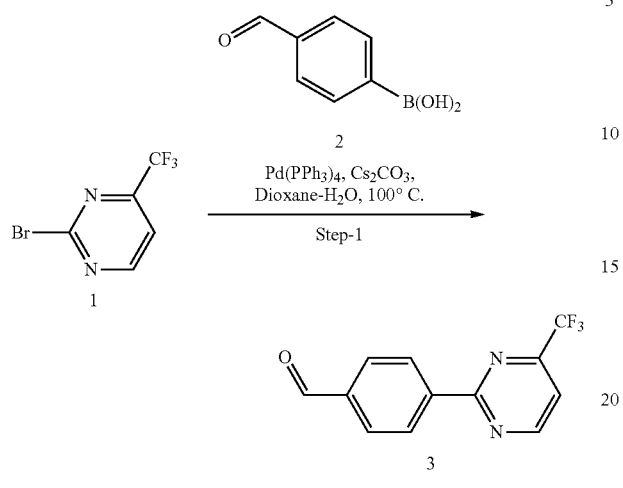

A solution of 2-bromo-4-(trifluoromethyl) pyrimidine 1 (2.00 g, 8.81 mmol), (4-formylphenyl) boronic acid 2 (1.50 g, 10.6 mmol) and Cs$_2$CO$_3$ (7.15 g, 22.0 mmol) in dioxane-H$_2$O (5:1, 25 mL), was purged with argon for 30 min. To the resulting reaction mixture was added Pd(PPh$_3$)$_4$ (1.01 g, 0.881 mmol) at room temperature. The reaction mixture was heated in a sealed tube at 100° C. for 12 h. Progress of the reaction was monitored by TLC and LCMS. After completion, the reaction mixture was cooled to room temperature, diluted with water (250 mL) and extracted with EA (2×250 mL). The combined organic layer was dried over anhydrous sodium sulfate and concentrated under reduced pressure. The crude compound was purified by silica gel chromatography using 20-50% EA in hexane as eluent to afford the title compound (1.50 g). LC-MS (Method B) (ESI+): m/z 253.2 (M+H)$^+$; $^1$H-NMR (400 MHz, CDCl$_3$) δ 10.14 (s, 1H), 9.11 (d, J=4.99 Hz, 1H), 8.70 (d, J=8.48 Hz, 2H), 8.04 (d, J=7.98 Hz, 2H), 7.60 (d, J=4.99 Hz, 1H).

Step 2: Synthesis (4-(4-(trifluoromethyl)pyrimidin-2-yl)phenyl)methanol

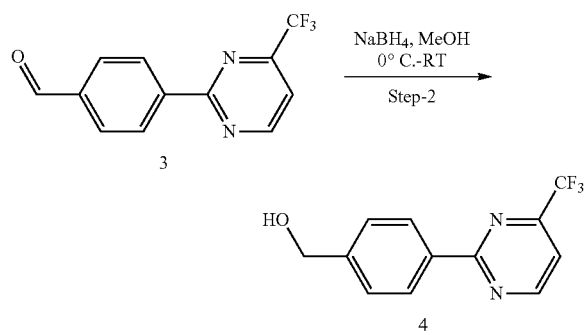

To a stirred solution of 4-(4-(trifluoromethyl) pyrimidin-2-yl) benzaldehyde 3 (1.50 g, 5.95 mmol) in methanol (30 mL) at 0° C., was added NaBH$_4$ (0.449 g, 11.9 mmol) portion-wise. The reaction mixture was further stirred at room temperature for 2 h, and progress of the reaction was monitored by TLC. After completion, the reaction mixture was concentrated under reduced pressure, quenched with ice cold water (50 mL) and extracted with EA (100 mL). The combined organic layer was dried over anhydrous sodium sulfate, filtered and concentrated under reduced pressure. The crude compound was purified by silica gel chromatography using 20-40% EA in hexane as eluent to afford the title compound (0.400 g).

Step 3: Synthesis of 6-chloro-1-(4-(4-(trifluoromethyl)pyrimidin-2-yl)benzyl)-1H-pyrazolo[3,4-d]pyrimidine (I-64)

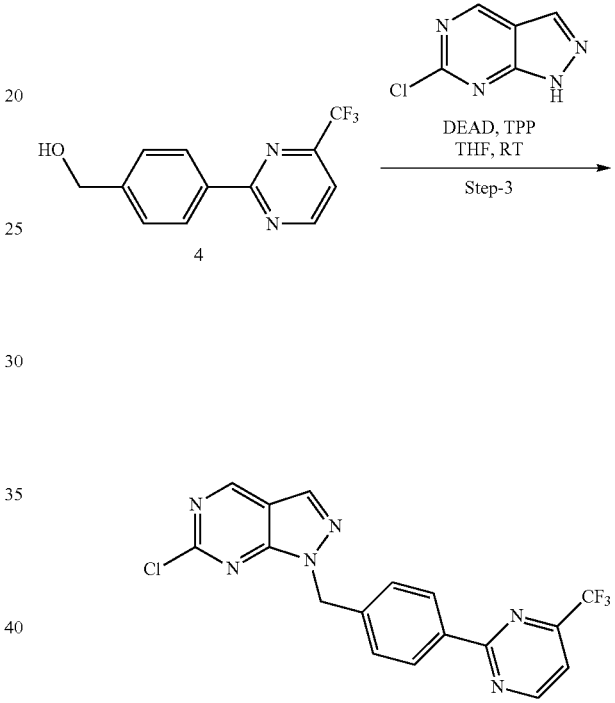

To a stirred solution of (4-(4-(trifluoromethyl)pyrimidin-2-yl)phenyl)methanol 4 (0.700 g, 2.75 mmol) in THF (7 mL), was added 6-chloro-1H-pyrazolo[3,4-d]pyrimidine (0.388 g, 2.48 mmol) and triphenylphosphine (1.083 g, 4.130 mmol) at room temperature. The resulting mixture was stirred for 5 min. The mixture was then cooled to 0° C., and was treated with DEAD (0.719 g, 4.13 mmol). The reaction mixture was allowed to warm to room temperature and was then stirred for 2 h. Progress of the reaction was monitored by TLC. After completion, the reaction mixture was quenched with water (100 mL) and extracted with EA (2×250 mL). The combined organic layer was dried over anhydrous sodium sulfate, filtered and concentrated under reduced pressure. The crude compound was purified by silica gel chromatography using 10-30% EA in hexane as eluent to afford the title compound (0.550 g). LC-MS (Method B) (ESI+): m/z 390.90 (M+H)$^+$; $^1$H-NMR (400 MHz, DMSO-d$_6$) δ 9.32 (s, 1H), 9.26 (d, J=4.49 Hz, 1H), 8.53 (s, 1H), 8.37 (d, J=7.98 Hz, 2H), 7.95 (d, J=4.49 Hz, 1H), 7.44 (d, J=7.98 Hz, 2H), 5.73-5.77 (m, 2H).

Preparation of Common Building Block (BB-1)

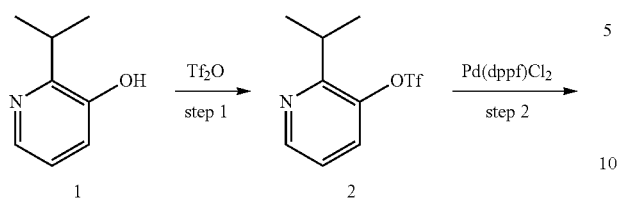

BB-1

Step 1: Synthesis of 2-Isopropylpyridin-3-yl trifluoromethanesulfonate

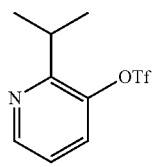 [SMILES: CC(C)c1ncccc1OS(=O)(=O)C(F)(F)F]

To a solution of 2-isopropylpyridin-3-ol (0.40 g, 2.92 mmol) in pyridine (4 mL) was added Tf$_2$O (0.82 g, 2.92 mmol) dropwise at 0° C. over 2 min. After addition, the mixture was warmed to room temperature, and stirred for 2 hours. After the reaction was complete as indicated by TLC analysis, the mixture was quenched with cold water (10 mL) and neutralized with saturated aqueous NaHCO$_3$ solution. The resulting mixture was extracted with DCM (50 mL×3), dried with anhydrous Na$_2$SO$_4$ (30 g), filtered and concentrated in vacuo. The residue was purified by column chromatography (EA:Hex=0:1 to 1:100) to give 420 mg of the title compound. $^1$H-NMR (300 MHz, CDCl$_3$) δ 8.60 (d, J=4.2 Hz, 1H), 7.57 (m, 1H), 7.24 (m, 1H), 3.42 (m, 1H), 1.32-1.37 (d, J=7.2 Hz, 6H).

Step 2: Synthesis of 2-Isopropyl-3-(4,4,5,5-tetramethyl-1,3,2-dioxaborolan-2-yl)pyridine (BB-1)

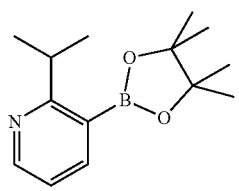 [SMILES: CC(C)c1ncccc1B1OC(C)(C)C(C)(C)O1]

Under N$_2$ atmosphere, a mixture of 2-isopropylpyridin-3-yl trifluoromethanesulfonate (0.28 g, 1.04 mmol), (Bpin)$_2$ (0.53 g, 2.08 mmol), KOAc (0.20 g, 2.08 mmol) and Pd(dppf)Cl$_2$ (85 mg, 10 mol %) in dioxane (5 mL), was stirred at 95° C. for 5 hours. The mixture was then quenched with water (15 mL) and extracted with EA (50 mL×3). The combined organic layer was dried over anhydrous Na$_2$SO$_4$ (30 g), filtered and concentrated in vacuo. The residue was purified by silica gel chromatography (EA:n-Hex=1:20 to 1:5) to give 300 mg of the title compound. $^1$H-NMR (300 MHz, CDCl$_3$) δ 8.60 (dd, J=4.8, 2.1 Hz, 1H), 8.00 (m, 1H), 7.08 (m, 1H), 3.75 (m, 1H), 1.32-1.37 (d, J=7.2 Hz, 6H), 1.24-1.29 (s, 12H).

Preparation of Common Building Block (BB-2)

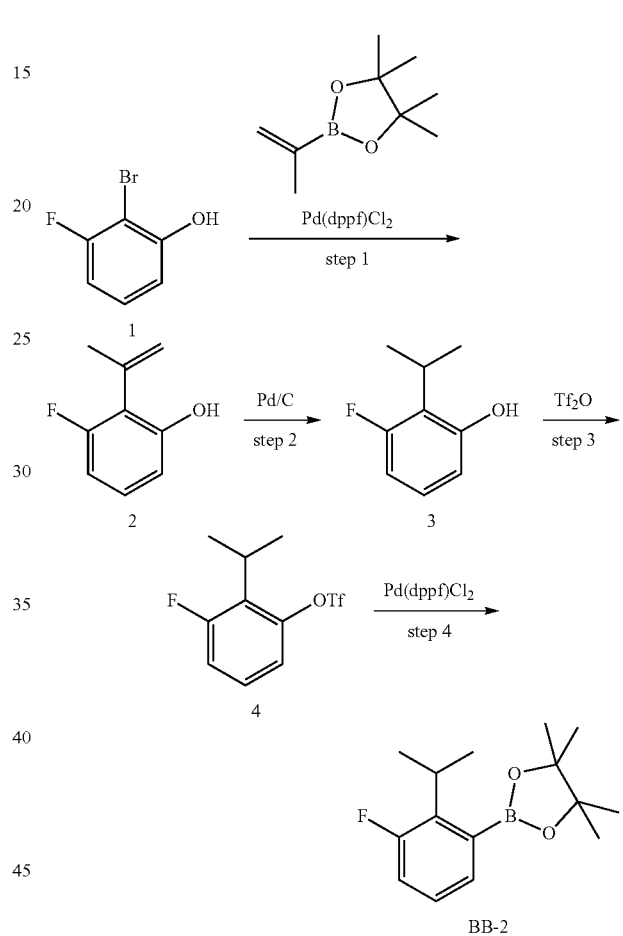

BB-2

Step 1: Synthesis of 3-Fluoro-2-(prop-1-en-2-yl)phenol

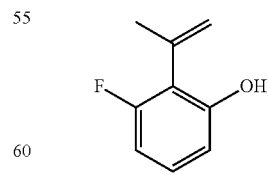

To a mixture of 2-bromo-3-fluorophenol (2 g, 10.5 mmol), 4,4,5,5-tetramethyl-2-(prop-1-en-2-yl)-1,3,2-dioxaborolane (2.37 g, 14.1 mmol), and K$_2$CO$_3$ (2.9 g, 21 mmol) in dioxane and water (30 mL:6 mL), was added Pd(dppf)Cl$_2$ (800 mg, 1 mmol) under nitrogen atmosphere. The resulting mixture was stirred at 90° C. overnight, and then quenched with water (50 mL) and extracted with EA (100 mL×2). The combined organic layer was dried over Na$_2$SO$_4$ (30 g) and concentrated in vacuo. The residue was purified by silica gel chromatography (PE:EA=20:1 to 5:1) to afford 1.5 g of the title compound. $^1$H-NMR (300 MHz, CDCl$_3$) δ 7.12 (m, 1H), 6.74 (d, J=8.1 Hz, 1H), 6.63 (t, J=8.4 Hz, 1H), 5.72 (s, 1H), 5.54 (s, 1H), 5.16 (s, 1H), 2.08 (s, 3H).

Step 2: Synthesis of 3-Fluoro-2-isopropylphenol

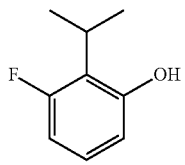

To a solution of 3-fluoro-2-(prop-1-en-2-yl)phenol (1.5 g, 0.98 mmol) in MeOH (20 mL) was added Pd/C (100 mg, 10% wt) and stirred under hydrogen atmosphere. After the reaction was complete as indicated by TLC analysis, the suspension was filtered through a pad of Celite. The filter cake was washed with MeOH (10 mL). The filtrate was concentrated to dryness to afford 1.3 g of the crude title compound, which was used for the next step directly. $^1$H-NMR (300 MHz, CDCl$_3$) δ 6.96 (m, 1H), 6.59 (m, 1H), 6.51 (d, J=8.1 Hz, 1H), 4.96 (br s, 1H), 3.40 (m, 1H), 1.32-1.35 (d, J=6.6 Hz, 6H).

Step 3: Synthesis of 3-Fluoro-2-isopropylphenyl trifluoromethanesulfonate

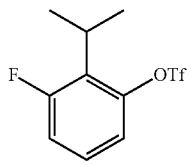

To a solution of 3-fluoro-2-isopropylphenol (1.2 g, 7.8 mmol) and pyridine (3 mL) in DCM (20 mL) at 0° C., was added an excess amount of Tf$_2$O (2 mL). The reaction was stirred at 0-5° C. for 2 hours, then quenched by pouring into cold water (20 mL). The resulting mixture was treated with a saturated NH$_4$Cl solution (20 mL), and then extracted with DCM (100 mL×2). The combined organic layer was dried with Na$_2$SO$_4$ (30 g) and concentrated to dryness to afford the crude product. The crude product was purified by silica gel chromatography (PE:EA=100:1) to afford 1.8 g of the title compound. $^1$H-NMR (300 MHz, CDCl$_3$) (7.19 (m, 1H), 7.04-7.10 (m, 2H), 3.32 (m, 1H), 1.33-1.37 (d, J=6.6 Hz, 6H)

Step 4: Synthesis of 2-(3-Fluoro-2-isopropylphenyl)-4,4,5,5-tetramethyl-1,3,2-dioxaborolane (BB-2)

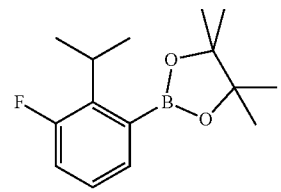 [SMILES: CC(C)c1c(F)cccc1B1OC(C)(C)C(C)(C)O1]

To a solution of 3-fluoro-2-isopropylphenyl trifluoromethanesulfonate (100 mg, 0.35 mmol), (Bpin)$_2$ (178 mg, 0.7 mmol) and KOAc (69 mg, 0.7 mmol) in dioxane (3 mL), was added Pd(dppf)Cl$_2$ (29 mg, 0.035 mmol). After addition, the resulting mixture was warmed to 90° C. and stirred for 16 hours. The reaction mixture was filtered, and the filter cake was washed with EA (5 mL). The filtrate was concentrated to dryness and the residue was purified by silica gel chromatography (eluent: PE/EA=100:1 to 30:1) to afford 47 mg of the title compound. $^1$H-NMR (300 MHz, CDCl$_3$) δ 7.43 (d, J=6.3 Hz, 1H), 7.14 (m, 1H), 7.02 (m, 1H), 3.62 (m, 1H), 1.35 (s, 12H), 1.24-1.26 (d, J=6.0 Hz, 6H)

Preparation of Common Building Block (BB-3)

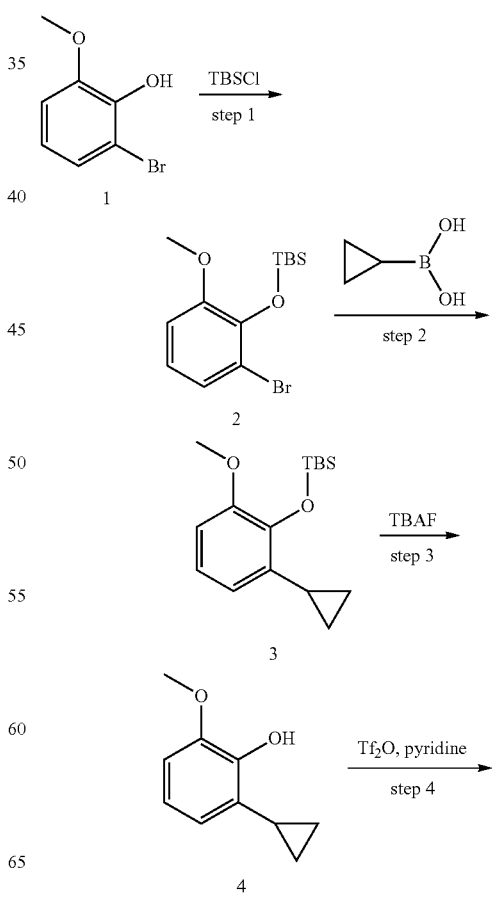

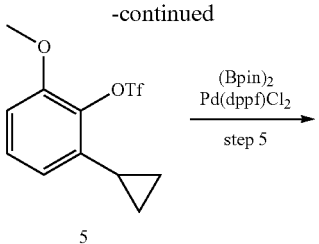

step 5

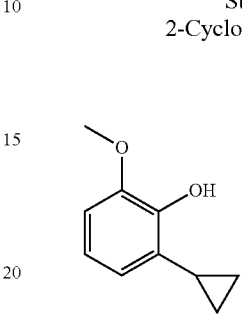

BB-3

Step 1: Synthesis of (2-Bromo-6-methoxyphenoxy)(tert-butyl)dimethylsilane

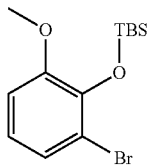

To a solution of 2-bromo-6-methoxyphenol (500 mg, 2.46 mmol) in DCM (10 mL), was added TBSCl (446 mg, 2.96 mmol), DMAP (30 mg, 0.246 mmol) and TEA (373 mg, 3.69 mmol). After the reaction was complete as indicated by TLC analysis, the reaction was quenched with water (10 mL) and extracted with EA (20 mL×3). The combined organic layer was dried over anhydrous $Na_2SO_4$ (20 g), filtered and concentrated to dryness in vacuo to give 800 mg of the crude title compound. $^1$H-NMR (300 MHz, $CDCl_3$) δ 7.10 (m, 1H), 6.74-6.78 (m, 2H), 3.78 (s, 3H), 1.05 (s, 9H), 0.25 (s, 6H).

Step 2: Synthesis of tert-Butyl(2-cyclopropyl-6-methoxyphenoxy)dimethylsilane

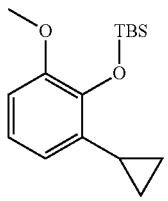

A mixture of (2-bromo-6-methoxyphenoxy)(tert-butyl)dimethylsilane (700 mg, 2.21 mmol), cyclopropylboronic acid (379 mg, 4.42 mmol), $K_3PO_4$ (2.81 mg, 13.3 mmol), and $Pd(PPh_3)_4$ (255 mg, 0.220 mmol) in toluene (35 mL) and $H_2O$ (1.75 mL), was stirred at 95° C. overnight. The resulting mixture was extracted with EA (50 mL×3). The combined organic layer was dried over anhydrous $Na_2SO_4$ (30 g), filtered and concentrated to dryness in vacuo. The concentrated residue was purified by silica gel chromatography (EA:n-hex=0:1 to 1:200) to give 500 mg of the title compound. $^1$H-NMR (300 MHz, $CDCl_3$) δ 6.78 (t, J=7.8 Hz, 1H), 6.67 (d, J=8.1 Hz, 1H), 6.38 (d, J=8.1 Hz, 1H), 3.77 (s, 3H), 2.21 (m, 1H), 1.05 (s, 9H), 0.89-0.95 (m, 2H), 0.63-0.68 (m, 2H), 0.19 (s, 6H).

Step 3: Synthesis of 2-Cyclopropyl-6-methoxyphenol

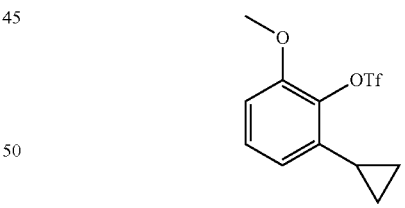

To a solution of tert-butyl-(2-cyclopropyl-6-methoxyphenoxy)dimethylsilane (500 mg, 1.8 mmol) in THF (5 mL) at room temperature, was added TBAF solution (3.6 mL, 1M) in one portion. After the addition, the reaction was stirred at room temperature for 1 hour, then quenched by water (15 mL) and extracted with EA (10 mL×3). The combined organic layer was dried over anhydrous $Na_2SO_4$ (30 g), filtered and concentrated to dryness in vacuo. The concentrated residue was purified by silica gel chromatography (EA:n-hex=0:1 to 1:100) to give 210 mg of the title compound. $^1$H-NMR (300 MHz, $CDCl_3$) (6.69-6.79 (m, 2H), 6.47 (d, J=7.8 Hz, 1H), 5.77 (s, 1H), 3.88 (s, 3H), 2.13 (m, 1H), 0.91-0.98 (m, 2H), 0.65-0.71 (m, 2H).

Step 4: Synthesis of 2-Cyclopropyl-6-methoxyphenyl trifluoromethanesulfonate A solution of 2-cyclopropyl-6-methoxyphenol (90 mg, 0.55 mmol), pyridine (0.5 mL) and $Tf_2O$ (0.5 mL) in DCM (5 mL), was stirred under reflux for 30 min. The reaction mixture was then cooled to room temperature and quenched with saturated $NH_4Cl$ solution (15 mL). The mixture was then extracted with DCM (10 mL×3), and the combined organic layer was dried over anhydrous $Na_2SO_4$ (20 g), filtered and concentrated to dryness in vacuo. The residue was purified by silica gel chromatography (EA:n-Hex=1:200 to 1:100) to give 160 mg of the title compound. $^1$H-NMR (300 MHz, $CDCl_3$) δ 7.19 (t, J=8.1 Hz, 1H), 6.82 (dd, J=8.1, 0.9 Hz, 1H), 6.54 (dd, J=8.1, 0.9 Hz, 1H), 3.88 (s, 3H), 2.08 (m, 1H), 1.01-1.09 (m, 2H), 0.71-0.79 (m, 2H).

Step 5: Synthesis of 2-(2-Cyclopropyl-6-methoxyphenyl)-4,4,5,5-tetramethyl-1,3,2-dioxaborolane (BB-3)

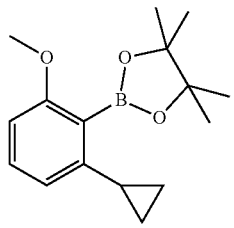 [SMILES: COc1cccc(C2CC2)c1B1OC(C)(C)C(C)(C)O1]

Under N₂ atmosphere, a mixture of 2-cyclopropyl-6-methoxyphenyl trifluoromethanesulfonate (96 mg, 0.33 mmol), (BPin)₂ (166 mg, 0.650 mmol), KOAc (96 mg, 0.98 mmol) and Pd(PPh₃)₄ (35 mg, 0.03 mmol) in dioxane (2 mL) was stirred at 80° C. overnight. The reaction mixture was then diluted with water (10 mL) and extracted with EA (10 mL×3). The combined organic phases were dried over anhydrous Na₂SO₄ (20 g), filtered and concentrated in vacuo. The residue was purified by silica gel chromatography (EA:n-Hex=1:200 to 1:100) to give 30 mg of the title compound. $^1$H-NMR (300 MHz, CDCl₃) δ 7.16-7.21 (t, J=8.1 Hz, 1H), 6.62 (d, J=8.1 Hz, 1H), 6.50 (d, J=8.1 Hz, 1H), 3.76 (s, 3H), 1.96 (m, 1H), 1.37 (s, 12H), 0.85-0.91 (m, 2H), 0.71-0.73 (m, 2H).

Preparation of Common Building Block (BB-4)

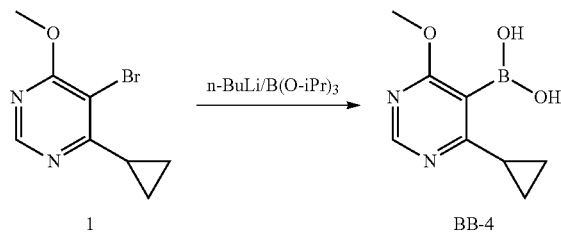

Step 1: Synthesis of (4-Cyclopropyl-6-methoxypyrimidin-5-yl)boronic Acid

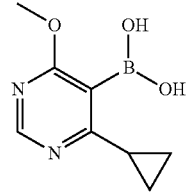

To a solution of 5-bromo-4-cyclopropyl-6-methoxypyrimidine (500 mg, 2.2 mmol) and triisopropyl-borate (533.7 mg, 2.8 mmol) in toluene (5 mL) and THF (1.5 mL) at −78° C., was added n-BuLi (1.1 mL, 2.8 mmol) dropwise over 30 min. After the reaction mixture was stirred at −78° C. for 30 min, the reaction was warmed to −20° C. for 1 hour. The reaction was then quenched with aqueous 1N HCl solution (3.4 mL). After the mixture was stirred at room temperature for 30 min, the mixture was treated with saturated aqueous Na₂CO₃ solution to adjust the pH to 8. The mixture was extracted with EA (100 mL×2). The combined organic layer was dried over anhydrous Na₂SO₄ (30 g) and concentrated in vacuo to give the crude title compound (0.450 g). $^1$H-NMR (300 MHz, CDCl₃) δ 8.61 (s, 1H), 6.56 (br s, 2H), 4.01 (s, 3H), 3.02 (m, 1H), 1.38-1.35 (m, 1H), 1.18-1.23 (m, 2H), 1.00-1.06 (m, 2H).

The following compound was prepared from the commercial bromide according to the procedure of BB-4:

| Example | Structure | Analytical data |
|---|---|---|
| BB-5 | 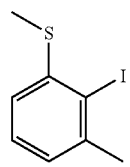 | LC-MS (Method A) (ESI+): m/z 169 (M + H)⁺; $^1$H-NMR (300 MHz, CDCl₃) δ 8.68 (s, 1H), 6.17 (br s, 2H), 4.06 (s, 3H), 2.73 (s, 3H). |

Preparation of Common Building Block (BB-6)

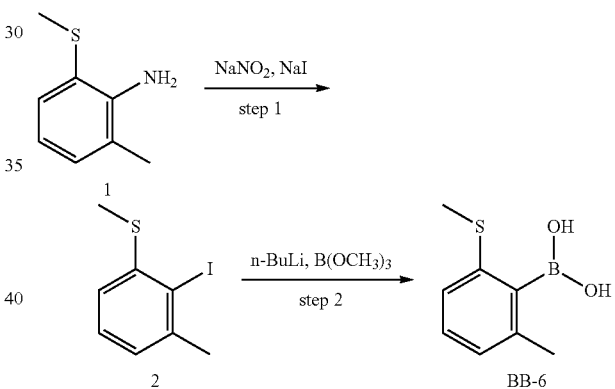

Step 1: Synthesis of (2-Iodo-3-methylphenyl)(methyl)sulfane

A solution of 2-methyl-6-(methylthio)aniline (1.0 g, 6.53 mmol) in acetone (20 mL) and conc. HCl (1.36 mL) was stirred at 0° C. for 10 min. A solution of NaNO₂ (540 mg, 7.84 mmol) in H₂O (8 mL) and a solution of NaI (2.06 g, 13.7 mmol) in H₂O (8 mL) were added to the resulting mixture subsequently over 10 min. After addition, the reaction was stirred at room temperature for 1 hour. The reaction mixture was then quenched with a saturated NH₄Cl solution (20 mL) and extracted with EA (10 mL×3). The combined organic layer was dried over anhydrous Na$_2$SO$_4$ (20 g), filtered and concentrated in vacuo. The residue was purified by column chromatography (EA:n-Hex=0:100 to 1:100) to give 970 mg of the title compound. $^1$H-NMR (300 MHz, CDCl$_3$) δ 7.22 (m, 1H), 7.02 (dd, J=8.4, 0.6 Hz, 1H), 6.88 (d, J=8.4, 0.6 Hz, 1H), 2.47 (s, 3H), 2.45 (s, 3H).

Step 2: Synthesis of (2-Methyl-6-(methylthio)phenyl)boronic acid (BB-6)

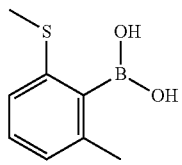

To a solution of (2-iodo-3-methylphenyl)(methyl)sulfane (200 mg, 0.76 mmol) in anhydrous THF (4 mL), was added n-BuLi (0.37 mL, 2.5 M) at −78° C. over 10 min. After the reaction was stirred at −78° C. for 45 min, B(OCH$_3$)$_3$ (237 mg, 2.28 mmol) was added dropwise over 10 min. After addition, the resulting mixture was stirred at −78° C. for additional 30 min and allowed to warm to rt over 40 min. After the reaction was quenched by aqueous 1N HCl solution (2 mL), the reaction mixture was stirred at room temperature for about 30 min. The resulting mixture was extracted with EA (5 mL×3). The combined organics were dried over anhydrous Na$_2$SO$_4$ (10 g), filtered and concentrated in vacuo. The residue was slurried in n-hex (5 mL), then filtered to collect the solids that were subsequently dried in vacuo to give 75 mg of the title compound. $^1$H-NMR (300 MHz, DMSO-d$_6$) δ 7.11-7.21 (m, 2H), 6.95 (d, J=7.2 Hz, 1H), 2.40 (s, 3H), 2.23 (s, 3H).

General Procedure for the Preparation of Alkylated Pyrimidine Boronic Acid Building Blocks by S$_N$Ar: Synthesis of (4-Cyclopropyl-6-((tetrahydrofuran-3-yl)oxy)pyrimidin-5-yl)boronic acid (BB-7)

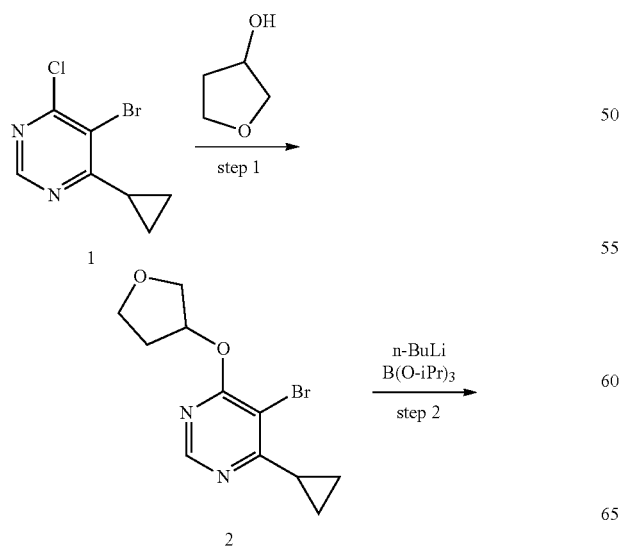

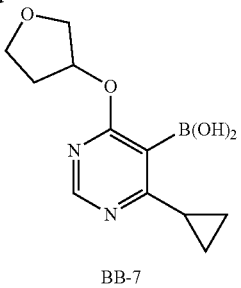

Step 1: Synthesis of 5-Bromo-4-cyclopropyl-6-((tetrahydrofuran-3-yl)oxy)pyrimidine

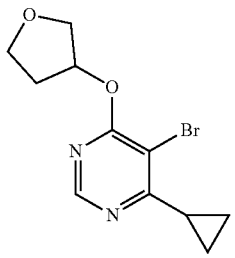 [SMILES: Brc1c(OC2CCOC2)ncnc1C1CC1]

To a solution of tetrahydrofuran-3-ol (107 mg, 1.95 mmol) in dry THF (5 mL) at 0° C. was added 60% sodium hydride dispersion (76 mg, 1.95 mmol) portion-wise over 5 min. After the mixture was stirred at 0° C. for 1 h, a solution of 5-bromo-4-chloro-6-cyclopropylpyrimidine (300 mg, 1.30 mmol) in dry THF (5 mL) was added to the reaction mixture dropwise over 5 min. After the reaction was stirred at rt for 1 h, the reaction was quenched with water (10 mL) and extracted with EA (5 mL×3). The combined organic layer was dried over sodium sulfate (20 g), filtered and concentrated in vacuo. The residue was purified by silica gel chromatography (PE:EA=20:1) to afford 358 mg of the title compound. LC-MS (Method A) (ESI+): m/z 285 (M+H)$^+$; $^1$H-NMR (300 MHz, CDCl$_3$) δ 8.33 (s, 1H), 5.53 (m, 1H), 3.98-4.06 (m, 2H), 3.84-3.97 (m, 2H), 2.45 (m, 1H), 2.12-2.23 (m, 2H), 1.06-1.13 (m, 2H), 1.00-1.06 (m, 2H).

Step 2: Synthesis of (4-Cyclopropyl-6-((tetrahydrofuran-3-yl)oxy)pyrimidin-5-yl)boronic acid (BB-7)

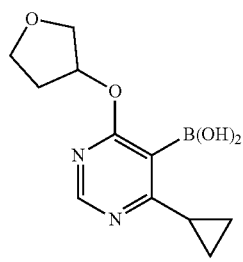 [SMILES: OB(O)c1c(OC2CCOC2)ncnc1C1CC1]

To a mixture of 5-bromo-4-cyclopropyl-6-((tetrahydrofuran-3-yl)oxy) pyrimidine (200 mg, 0.7 mmol) and triisopropylborate (171 mg, 0.9 mmol) in toluene (4 mL) and THF (1 mL) at −78° C., was added n-butyl lithium (0.36 mL, 0.9 mmol) dropwise over 10 min. The mixture was stirred at −78° C. for 30 min, then warmed to −20° C. and stirred for 1 h. The reaction was quenched with aqueous 1N HCl solution (3 mL), and then stirred at rt for 30 min. Saturated aqueous Na$_2$CO$_3$ solution was added to adjust the pH to 8, and then the mixture was extracted with EA (25 mL×3). The combined organic layer was dried over anhydrous Na$_2$SO$_4$ (30 g), filtered and concentrated in vacuo to give 146 mg of the crude title compound. LC-MS (Method A) (ESI+): m/z 251 (M+H)$^+$; $^1$H-NMR (300 MHz, DMSO-d$_6$) δ 8.51 (s, 1H), 8.44 (s, 2H), 5.50 (m, 1H), 3.90 (m, 1H), 3.70-3.88 (m, 3H), 2.18 (m, 1H), 1.86-1.98 (m, 2H), 0.90-1.05 (m, 4H).

The following compounds were prepared according to the method for the preparation of BB-7:

| Example | Structure | Analytical data |
|---|---|---|
| BB-8 | 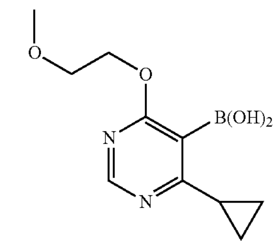 [SMILES: COCCOc1ncnc(C2CC2)c1B(O)O] | LC-MS (Method A) (ESI+): m/z 239 (M + H)$^+$; $^1$H-NMR (300 MHz, CD$_3$OD) δ 8.49 (s, 1H), 4.50 (t, J = 4.5 Hz, 2H), 3.71 (t, J = 4.5 Hz, 2H), 3.38 (s, 3H), 1.80 (m, 1H), 1.10-1.14 (m, 2H), 0.95-1.05 (m, 2H) |
| BB-9 | 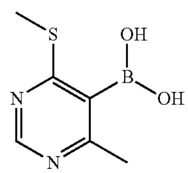 | LC-MS (Method A) (ESI+): m/z 185 (M + H)$^+$ |
| BB-10 | 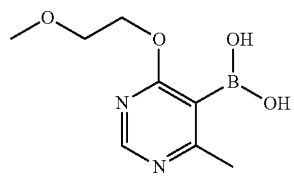 | $^1$H-NMR (300 MHz, CD$_3$OD) δ 8.67 (s, 1H), 4.51-4.59 (m, 2H), 3.69-3.76 (m, 2H), 3.48 (s, 3H), 2.69 (s, 3H). |
| BB-11 | 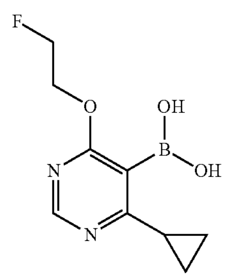 [SMILES: OB(O)c1c(OCCF)ncnc1C1CC1] | LC-MS (Method A) (ESI+): m/z 227 (M + H)$^+$; $^1$H-NMR (300 MHz, CD$_3$OD) δ 8.51 (s, 1H), 4.78 (m, 1H), 4.60-4.70 (m, 2H), 4.56 (m, 1H), 1.82 (m, 1H), 1.00-1.16 (m, 2H), 0.98-1.03 (m, 2H) |
| BB-12 | 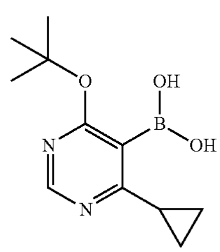 [SMILES: CC(C)(C)Oc1ncnc(C2CC2)c1B(O)O] | LC-MS (Method A) (ESI+): m/z 235 (M + H)$^+$; |
| BB-13 | 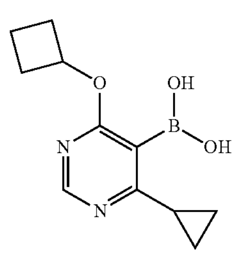 [SMILES: OB(O)c1c(OC2CCC2)ncnc1C1CC1] | LC-MS (Method A) (ESI+): m/z 235 (M + H)$^+$; $^1$H-NMR (300 MHz, DMSO-d$_6$) δ 8.47 (s, 1H), 8.44 (s, 2H), 5.12 (m, 1H), 2.29-2.41 (m, 2H), 2.01-2.2.15 (m, 2H), 1.88 (m, 1H), 1.77 (m, 1H), 1.62 (m, 1H), 0.93-0.98 (m, 4H) |

-continued
| Example | Structure | Analytical data |
|---|---|---|
| BB-14 | 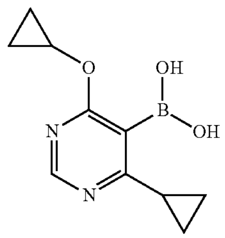 [SMILES: OB(O)c1c(OC2CC2)ncnc1C1CC1] | $^1$H-NMR (300 MHz, CDCl$_3$) δ 8.69 (s, 1H), 5.69 (s, 2H), 4.40 (m, 1H), 2.99 (m, 1H), 1.18-1.25 (m, 2H), 1.01-1.18 (m, 2H), 0.85-0.91 (m, 2H), 0.78-0.84 (m, 2H). |
| BB-15 | 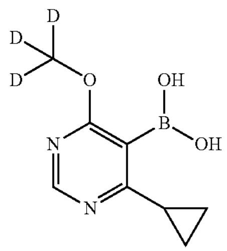 [SMILES: [2H]C([2H])([2H])Oc1ncnc(C2CC2)c1B(O)O] | LC-MS (Method A) (ESI+): m/z 198 (M + H)$^+$; $^1$H-NMR (300 MHz, CD$_3$OD) δ 8.58 (s, 1H), 8.54 (s, 2H), 1.94 (m, 1H), 1.01-1.04 (m, 4H) |
| BB-16 | 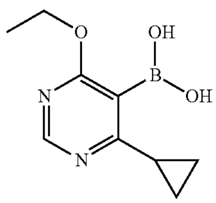 | LC-MS (Method B): (ESI+); m/z 209.10 (M + H)$^+$, $^1$H-NMR (400 MHz, DMSO-d$_6$) δ 8.49 (s, 1H), 8.40 (s, 2H), 4.31 (q, J = 6.8 Hz, 2H), 1.85-1.93 (m, 1H), 1.28 (t, J = 7.1 Hz, 3H), 0.91-1.02 (m, 4H). |
| BB-17 | 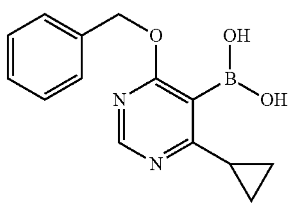 [SMILES: OB(O)c1c(OCc2ccccc2)ncnc1C1CC1] | LC-MS (Method C): (ESI+); m/z 270.95 (M + H)$^+$; $^1$H-NMR (400 MHz, DMSO-d$_6$) δ 8.48-8.54 (m, 3H), 7.29-7.44 (m, 5H), 5.37 (s, 2H), 1.90-1.94 (m, 1H), 0.93-1.04 (m, 4H). |
Preparation of Common Building Block (BB-18)
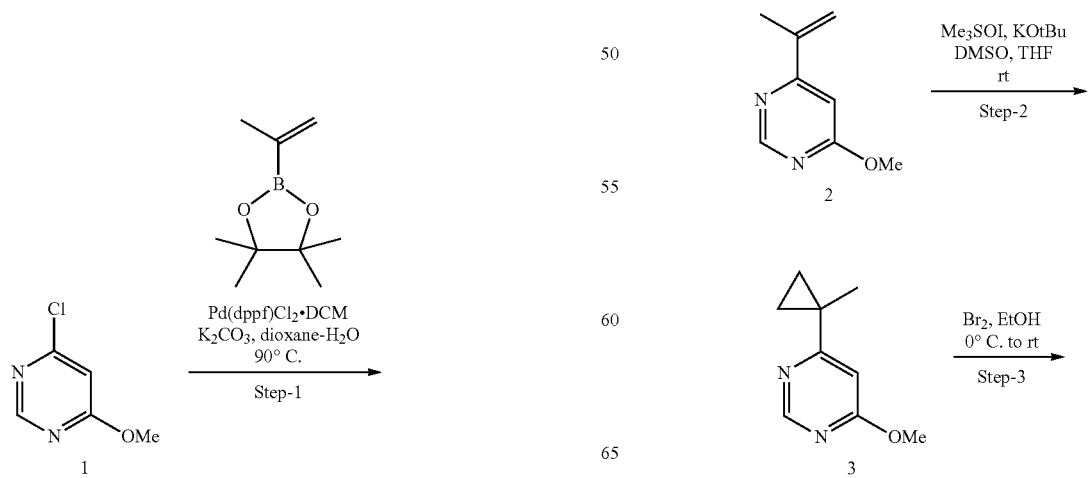

-continued

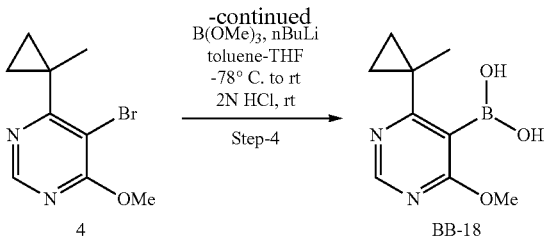

Step 1: Synthesis of 4-Methoxy-6-(prop-1-en-2-yl)pyrimidine

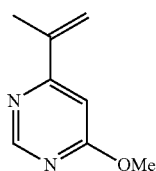

To a stirred solution of 4-chloro-6-methoxypyrimidine (10.0 g, 69.2 mmol) in dioxane (100 mL) and water (15 mL), was added K$_2$CO$_3$ (19.1 g, 138 mmol). The resulting mixture was degassed with argon for 15 min, followed by addition of 4,4,5,5-tetramethyl-2-(prop-1-en-2-yl)-1,3,2-dioxaborolane (13.90 g, 83.00 mmol) and Pd(dppf)Cl$_2$-DCM (2.80 g, 3.40 mmol). The reaction mixture was further degassed with argon for 10 min and heated to 90° C. for 16 h. Progress of the reaction was monitored by TLC. After completion, the reaction mixture was diluted with EA and filtered through Celite bed. The organic layer was collected and dried over anhydrous sodium sulfate, filtered, and concentrated under reduced pressure. The crude compound was purified by silica gel chromatography using 10-15% EA in hexane to afford 7.80 g of the title compound. LC-MS (Method B) (ESI+): m/z 150.85 (M+H)$^+$; $^1$H-NMR (400 MHz, DMSO-d$_6$) δ 8.74 (s, 1H), 7.00 (s, 1H), 6.18 (s, 1H), 5.44 (s, 1H), 3.93 (s, 3H), 2.09 (s, 3H)

Step 2: Synthesis of 4-Methoxy-6-(1-methylcyclopropyl)pyrimidine

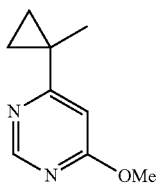

To a stirred solution of trimethylsulfoxonium iodide (16.5 g, 74.9 mmol) in DMSO (100 mL) was added KOtBu (8.42 g, 74.9 mmol), and the reaction mixture was stirred at room temperature for 1 h. To the resulting reaction mixture was added a solution of 4-methoxy-6-(prop-1-en-2-yl)pyrimidine 2 (7.50 g, 49.9 mmol) in THF (10 mL), and the reaction mixture was further stirred at room temperature for 3 h. Progress of the reaction was monitored by TLC. After completion, the reaction mixture was diluted with saturated NaHCO$_3$ solution and extracted with EA (2×20 mL). The combined organic layer was dried over anhydrous sodium sulfate, filtered, and concentrated under reduced pressure. The crude compound was purified by column chromatography using 5-10% EA in hexane to afford 3.80 g of the title compound. LCMS (Method B) (ESI+): m/z 164.85 (M+H)$^+$; $^1$H-NMR (400 MHz, DMSO-d$_6$) δ 8.59 (s, 1H), 6.79 (s, 1H), 3.89 (s, 3H), 1.40 (s, 3H), 1.19-1.25 (m, 2H), 0.85 (q, J=3.4 Hz, 2H).

Step 3: Synthesis of 5-Bromo-4-methoxy-6-(1-methylcyclopropyl)pyrimidine

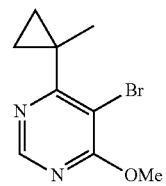

To a stirred solution of 4-methoxy-6-(1-methylcyclopropyl)pyrimidine (3.00 g, 18.2 mmol) in EtOH (50 mL) at 0° C., was added Br$_2$ (2.91 mL, 54.0 mmol), and the resulting reaction mixture was stirred at room temperature for 72 h. Progress of the reaction was monitored by TLC. After completion, the reaction mixture was quenched with saturated sodium bisulfite solution and extracted with EA (2×50 mL). The combined organic layer was dried over anhydrous sodium sulfate, filtered, and concentrated under reduced pressure. The crude compound was purified by silica gel chromatography using 2-5% EA in hexane to afford 3.0 g of the title compound. LCMS (Method B) (ESI+): m/z 244.80 (M+H)$^+$; $^1$H-NMR (400 MHz, DMSO-d$_6$) δ 8.63 (s, 1H), 3.98 (s, 3H), 1.35 (s, 3H), 0.88-0.93 (m, 2H), 0.78-0.84 (m, 2H).

Step 4: Synthesis of (4-Methoxy-6-(1-methylcyclopropyl)pyrimidin-5-yl)boronic acid (BB-18)

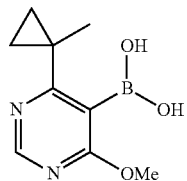

To a stirred solution 5-bromo-4-methoxy-6-(1-methylcyclopropyl)pyrimidine (0.50 g, 2.1 mmol) in toluene:THF (3:1, 8 mL), was added trimethyl borate (0.32 g, 3.1 mmol). To the resulting reaction mixture at −78° C., was added n-BuLi (1.6M, 1.93 mL, 3.1 mmol) and the reaction mixture was stirred at room temperature for 2 h. Progress of the reaction was monitored by TLC. After completion, the reaction mixture was quenched with 2N HCl (10 mL) and stirred at room temperature for 2 h. Then the pH was adjusted to 7 by addition of aq. NaHCO$_3$ solution. The mixture was then extracted with EA (2×10 mL), and the combined organic layer was dried over anhydrous sodium sulfate, filtered and concentrated under reduced pressure. The crude compound was triturated with Et$_2$O, filtered and dried to afford the 0.11 g of the title compound. LCMS (Method C) (ESI+): m/z 209.00 (M+H)+; 1H-NMR (400 MHz, DMSO-d6) δ 8.56 (s, 1H), 8.29 (s, 2H), 3.84 (s, 3H), 1.41 (s, 3H), 1.10 (d, J=2.0 Hz, 2H), 0.65-0.69 (m, 2H)

Preparation of Common Building Block (BB-19)

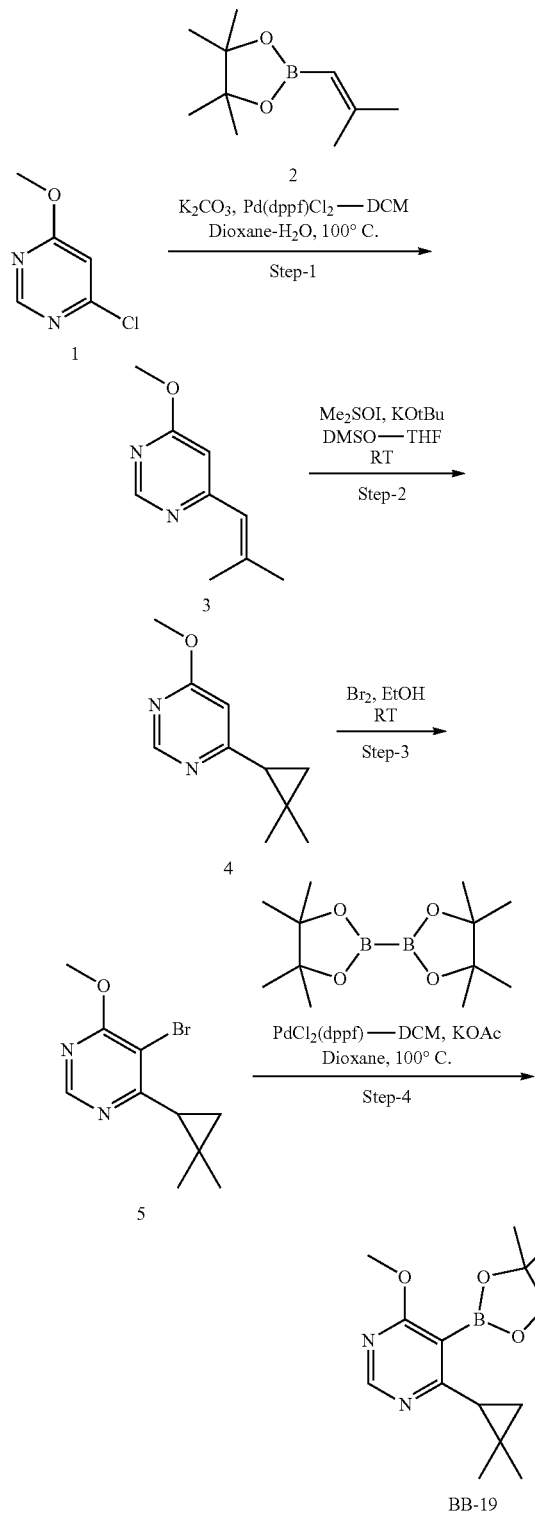

Step 1: Synthesis of 4-methoxy-6-(2-methylprop-1-en-1-yl)pyrimidine

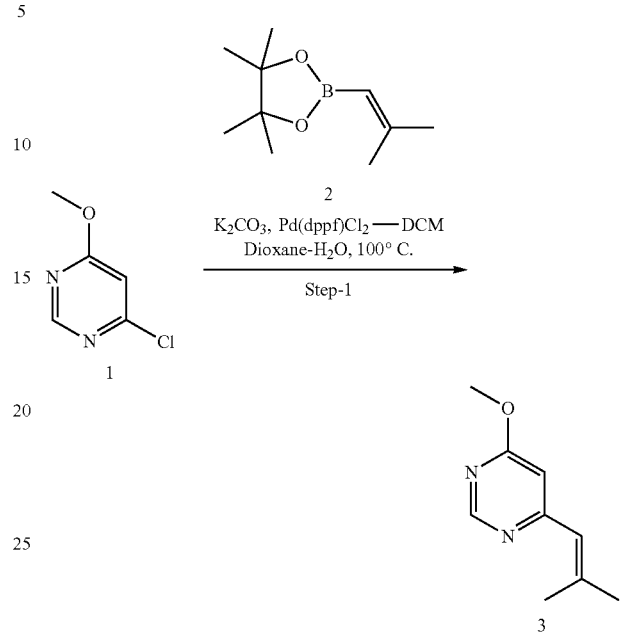

To a stirred solution of 4-chloro-6-methoxypyrimidine 1 (5.00 g, 34.7 mmol), 4,4,5,5-tetramethyl-2-(2-methylprop-1-en-1-yl)-1,3,2-dioxaborolane 2 (7.50 g, 41.7 mmol) in dioxane (50 mL) and water (8 mL), was added K₂CO₃ (14.30 g, 104.2 mmol) at room temperature. The mixture was purged with argon for 30 min, and then treated with Pd(dppf)Cl₂-DCM (2.83 g, 3.47 mmol). The mixture was then heated in a sealed tube at 100° C. for 16 h, and progress of the reaction was monitored by TLC. After completion, the reaction mixture was cooled to room temperature, diluted with water (50 mL) and extracted with EA (2×30 mL). The combined organic layer was dried over anhydrous sodium sulfate and concentrated under reduced pressure. The crude compound was purified by silica gel chromatography using 0-2% EA in hexane as eluent to afford the title compound (5.20 g). LC-MS (Method B) (ESI+): m/z 164.8 (M+H)+; 1H-NMR (400 MHz, DMSO-d6) δ 8.70 (s, 1H), 6.70 (s, 1H), 6.20 (s, 1H), 3.90 (s, 3H), 2.18 (s, 3H), 1.93 (s, 3H).

Step 2: Synthesis of 4-(2,2-dimethylcyclopropyl)-6-methoxypyrimidine

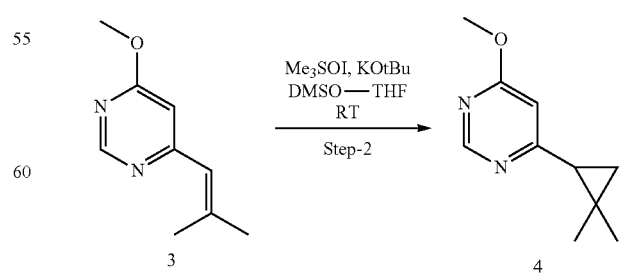

To a stirred solution of trimethylsulfoxonium iodide (9.09 g, 41.1 mmol) and potassium tert-butoxide (4.5 g, 41.1 mmol) in DMSO (50 mL) and THF (5 mL), was added 4-methoxy-6-(2-methylprop-1-en-1-yl) pyrimidine 3 (4.5 g, 27.4 mmol) at room temperature. The resulting mixture was stirred for 16 h, and progress of the reaction was monitored by TLC. After completion, the reaction mixture was quenched with water (50 mL) and extracted with EA (2×40 mL). The combined organic layer was dried over anhydrous sodium sulfate and concentrated under reduced pressure to afford the title compound (4.5 g) which was used as such in next step without further purification. LC-MS (Method B) (ESI+): m/z 178.9 (M+H)+.

Step 3: Synthesis of 4-(2,2-dimethylcyclopropyl)-6-methoxypyrimidine

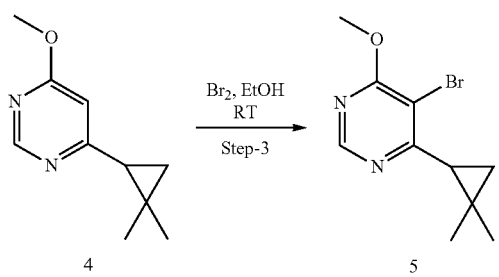

To a stirred solution of 4-(2,2-dimethylcyclopropyl)-6-methoxypyrimidine 4 (4.50 g, 2.53 mmol) in ethanol (50 mL) at 0° C., was added bromine (6.02 g, 3.79 mmol) dropwise. Upon complete addition, the reaction mixture was stirred at room temperature for 16 h. Progress of the reaction was monitored by TLC. After completion, the reaction mixture was quenched with water (50 mL) and extracted with hexane (3×20 mL). The combined organic layer was dried over anhydrous sodium sulfate and concentrated under reduced pressure to afford the crude title compound (1.50 g) that was used without purification in the next step. LC-MS (Method B) (ESI+): m/z 256.8 (M+); ¹H-NMR (400 MHz, DMSO-d₆) δ 8.60 (s, 1H), 3.99 (s, 3H), 2.21 (dd, J=5.98, 7.48 Hz, 1H), 1.47 (t, J=4.74 Hz, 1H), 1.30 (s, 3H), 0.97 (dd, J=3.99, 7.48 Hz, 1H), 0.84 (s, 3H).

Step 4: Synthesis of 4-(2,2-dimethylcyclopropyl)-6-methoxy-5-(4,4,5,5-tetramethyl-1,3,2-dioxaborolan-2-yl) pyrimidine (BB-19)

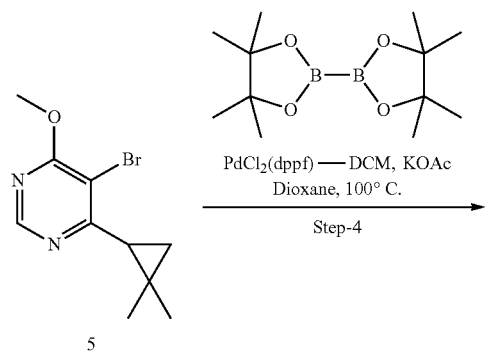

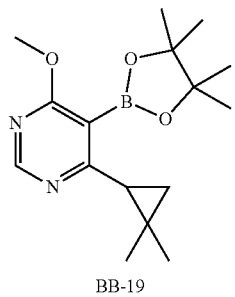

To a solution of 5-bromo-4-(2,2-dimethylcyclopropyl)-6-methoxypyrimidine 5 (0.500 g, 1.95 mmol) and 4,4,4',4',5,5,5',5'-octamethyl-2,2'-bi(1,3,2-dioxaborolane) (2.40 g, 9.77 mmol) in dioxane (10 mL), was added KOAc (0.382 g, 3.91 mmol) at room temperature. The resulting mixture was purged with argon for 30 min, and then treated with Pd(dppf)Cl₂-DCM (0.159 g, 0.195 mmol). The reaction mixture was then heated in a sealed tube at 100° C. for 2 h. Progress of the reaction was monitored by TLC. After completion, the reaction mixture was cooled to room temperature and concentrated under reduced pressure. The crude compound was purified by silica gel chromatography using 0-20% EA in hexane as eluent to afford the title compound (0.330 g). LC-MS (Method B) (ESI+): m/z 304.00 (M+).

Preparation of Common Building Block (BB-20)

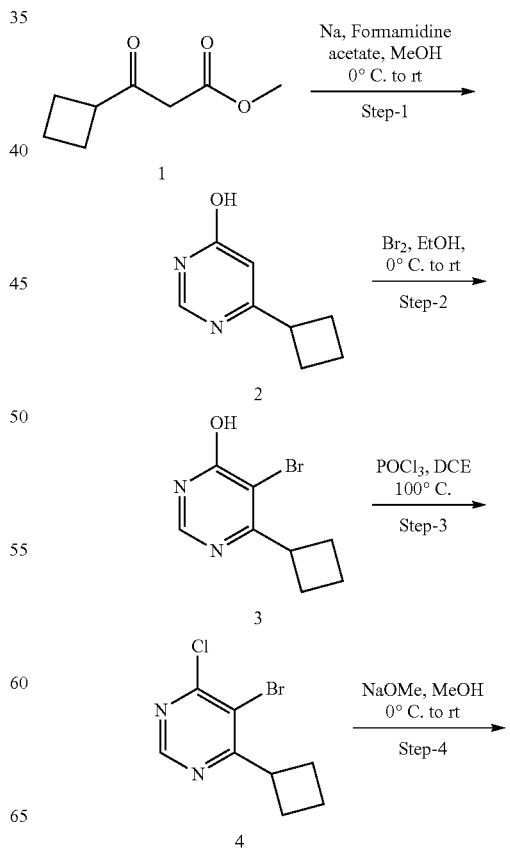

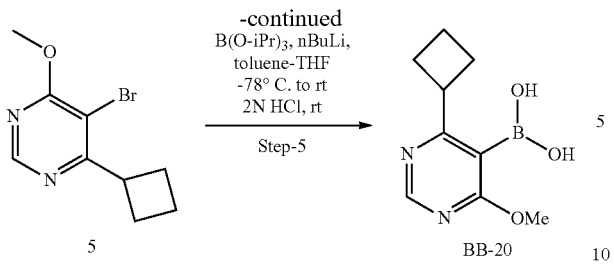

washed with excess Na$_2$S$_2$O$_3$ solution, and dried to afford 2.0 g of the title compound. LC-MS (Method C) (ESI+): m/z 230.86 (M+H)+ $^{81}$Br.

Step 3: Synthesis of 5-Bromo-4-chloro-6-cyclobutylpyrimidine

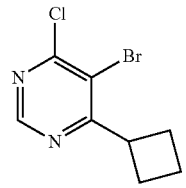

To a stirred solution of 5-bromo-6-cyclobutylpyrimidin-4-ol (2.00 g, 8.70 mmol) in 1,2-DCE (30 mL), was added POCl$_3$ (5 mL) and the reaction mixture was heated to 100° C. for 3 h. Progress of the reaction was monitored by TLC. After completion, the reaction mixture was concentrated under reduced pressure. The crude reaction mixture was diluted with H$_2$O (15 mL), basified to pH=8 using saturated NaHCO$_3$ solution, and extracted with EA (3×30 mL). The combined organic layer was dried over anhydrous sodium sulfate, filtered, and concentrated under reduced pressure. The crude compound was purified by flash chromatography on silica using 0-10% EA in hexane to afford 1.30 g of the title compound. LC-MS (Method C) (ESI+): m/z 248.80 (M+H)+ $^{81}$Br; $^1$H-NMR (400 MHz, DMSO-d$_6$) δ 8.96 (s, 1H), 3.92-4.02 (m, 1H), 2.29-2.39 (m, 4H), 1.96-2.10 (m, 1H), 1.76-1.88 (m, 1H).

Step 4: Synthesis of 5-Bromo-4-cyclobutyl-6-methoxypyrimidine

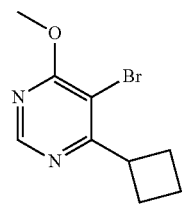

To an ice cooled solution of 5-bromo-4-chloro-6-cyclobutylpyrimidine (1.30 g, 5.20 mmol) in MeOH (30 mL) was added sodium methoxide (1.17 g, 21.00 mmol). The reaction mixture was stirred at room temperature for 16 h and the progress of the reaction was monitored by TLC. After completion, the reaction mixture was concentrated under reduced pressure. The residue was dissolved in water (10 mL) and extracted with EA (3×20 mL). The combined organic layer was dried over anhydrous sodium sulfate, filtered, and concentrated under reduced pressure to afford 1.0 g of the title compound. LC-MS (Method C) (ESI+): m/z 244.90 (M+H)+$^{81}$Br; $^1$H-NMR (400 MHz, DMSO-d$_6$) δ 8.71 (s, 1H), 3.98 (s, 3H), 3.85-3.94 (m, 1H), 2.23-2.39 (m, 4H), 1.95-2.08 (m, 1H), 1.77-1.87 (m, 1H).

Step 1: Synthesis of 6-Cyclobutylpyrimidin-4-ol

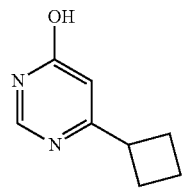 [SMILES: Oc1cc(C2CCC2)ncn1]

Sodium metal (1.47 g, 64.0 mmol) was added to MeOH (40 mL) and stirred at room temperature for 1 h. To the resulting reaction mixture were added formamidine acetate (4.00 g, 38.4 mmol) and methyl 3-cyclobutyl-3-oxopropanoate (4.00 g, 25.6 mmol) at 0° C. The resulting mixture was stirred at room temperature for 16 h. Progress of the reaction was monitored by TLC. After completion, the reaction mixture was quenched with water (20 mL) and adjusted to pH=4 with AcOH. Then the reaction mixture was concentrated under reduced pressure. The crude reaction mixture was extracted with 10% MeOH in DCM (3×50 mL), and the combined organic layer was dried over anhydrous sodium sulfate, filtered and concentrated under reduced pressure. The crude compound was purified by silica gel chromatography on silica using 5-10% MeOH in DCM to afford 1.70 g of the title compound. LC-MS (Method C) (ESI+): m/z 150.93 (M+H)+; $^1$H-NMR (400 MHz, DMSO-d$_6$) δ 11.66-12.56 (m, 1H), 8.12 (s, 1H), 6.09 (s, 1H), 3.27-3.40 (m, 1H), 2.08-2.19 (m, 4H), 1.87-2.01 (m, 1H), 1.74-1.86 (m, 1H).

Step 2: Synthesis of 5-Bromo-6-cyclobutylpyrimidin-4-ol

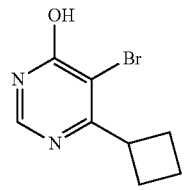 [SMILES: Oc1ncnc(C2CCC2)c1Br]

To an ice cooled solution of 6-cyclobutylpyrimidin-4-ol (1.70 g, 11.3 mmol) in EtOH (30 mL), was slowly added Br$_2$ (1.80 g, 11.3 mmol) and the resulting mixture was stirred at room temperature for 16 h. Progress of the reaction was monitored by TLC. After completion, the reaction mixture was concentrated under reduced pressure. The crude reaction mixture was quenched with saturated aq. Na$_2$S$_2$O$_3$ solution (50 mL), and the solid obtained was filtered,

Step 5: Synthesis of (4-Cyclobutyl-6-methoxypyrimidin-5-yl)boronic acid (BB-20)

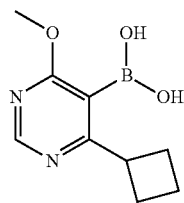

To a stirred solution of 5-bromo-4-cyclobutyl-6-methoxypyrimidine (1.00 g, 4.11 mmol) in toluene: THF (5:1, 30 mL) under nitrogen atmosphere was added triisopropylborate (2.86 mL, 12.30 mmol) and the reaction mixture was cooled to −78° C. Then n-BuLi (1.6M, 3.85 mL, 6.17 mmol) was added dropwise over a period of 45 min. Stirring was continued at the same temperature for 30 min, and then the reaction mixture was further stirred at room temperature for 3 h. Progress of the reaction was monitored by TLC. After completion, the reaction mixture was quenched with 2N HCl (10 mL) and stirred at room temperature for 16 h. The reaction mixture was basified to pH=8 using $K_2CO_3$ (solid) and extracted with EA (3×50 mL). The combined organic layer was dried over anhydrous sodium sulfate, filtered, and concentrated under reduced pressure. The crude compound was triturated with $Et_2O$ and n-pentane (10 mL), filtered to collect the solid, and dried to afford 0.42 g of the title compound. LC-MS (Method C) (ESI+): m/z 209.03 (M+H)$^+$; $^1$H-NMR (400 MHz, DMSO-$d_6$) δ 8.70 (s, 1H), 8.33 (s, 2H), 3.85 (s, 3H), 3.46-3.58 (m, 1H), 2.26-2.38 (m, 2H), 2.10-2.20 (m, 2H), 1.89-2.03 (m, 1H), 1.74-1.86 (m, 1H).

The following building blocks were prepared according to the procedure of BB-20 from the appropriate β-ketoester or 6-alkylpyrimidin-4-ol:

| Example | Structure | Analytical data |
|---|---|---|
| BB-21 | 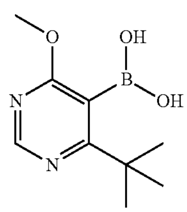 | LC-MS (Method C) (ESI+): m/z 210.95 (M + H)$^+$; $^1$H-NMR (400 MHz, DMSO-$d_6$) δ 8.65 (s, 1H), 8.24 (s, 2H), 3.86 (s, 3H), 1.30 (s, 9H). |
| BB-22 | 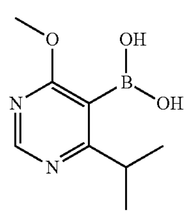 | LC-MS (Method C) (ESI+): m/z 196.85 (M + H)$^+$; $^1$H-NMR (400 MHz, DMSO-$d_6$) δ 8.66 (d, J = 1.47 Hz, 1H), 8.37 (d, J = 1.47 Hz, 2H), 3.86 (d, J = 1.96 Hz, 3H), 2.79-2.89 (m, 1H), 1.14-1.21 (m, 6H). |
| BB-23 | 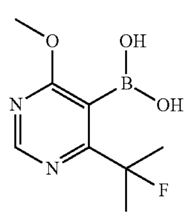 | LC-MS (Method C) (ESI+): m/z 214.95 (M + H)$^+$; $^1$H-NMR (400 MHz, DMSO-$d_6$) δ 8.68 (s, 1H), 7.89 (s, 2H), 3.89 (s, 3H), 1.63 (s, 3H), 1.57 (s, 3H). |
| BB-24 | 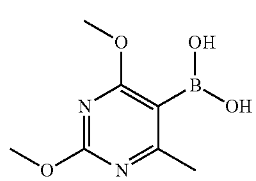 | LC-MS (Method C) (ESI+): m/z 198.80 (M + H)$^+$; $^1$H-NMR (400 MHz, DMSO-$d_6$) δ 8.19 (s, 2H), 3.85 (s, 3H), 3.83 (s, 3H), 2.29 (s, 3H) |

Preparation of Common Building Block (BB-25)

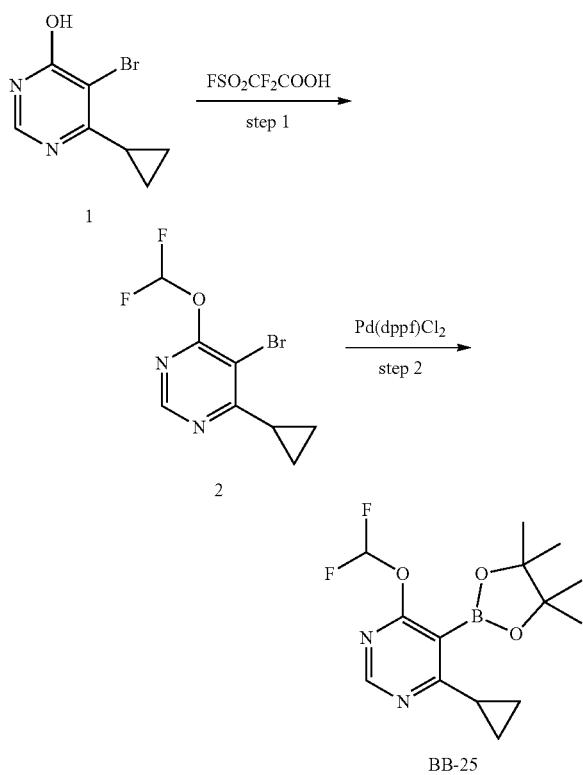

Step 1: Synthesis of 5-Bromo-4-cyclopropyl-6-(difluoromethoxy)pyrimidine

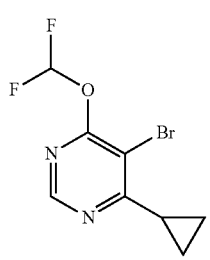 [SMILES: FC(F)Oc1ncnc(C2CC2)c1Br]

To a suspension of 5-bromo-6-cyclopropylpyrimidin-4-ol (1.0 g, 4.7 mmol) in ACN (100 mL) at rt, was added NaH (60% dispersion, 560 mg, 14.0 mmol) portion-wise over 10 min. After the mixture was stirred at rt for 20 min, 2,2-difluoro-2-(fluorosulfonyl)acetic acid (1.4 g, 7.9 mmol) was added dropwise over 10 min. After the addition, the mixture was stirred at rt overnight. After the reaction was completed as indicated by TLC analysis, the reaction was quenched with a saturated $NH_4Cl$ solution (20 mL) and extracted with EA (50 mL×2). The combined organic layer was dried over sodium sulfate (30 g), filtered, and concentrated. The residue was purified by silica gel chromatography (PE:EA=20:1 to 10:1) to afford 600 mg of the title compound. $^1$H-NMR (300 MHz, $CDCl_3$) δ 8.46 (s, 1H), 7.48 (t, J=71.4 Hz), 2.58 (m, 1H), 1.10-1.30 (m, 4H).

Step 2: Synthesis of 4-Cyclopropyl-6-(difluoromethoxy)-5-(4,4,5,5-tetramethyl-1,3,2-dioxaborolan-2-yl)pyrimidine (BB-25)

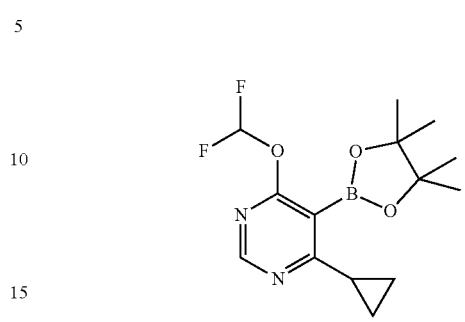

To a mixture of 5-bromo-4-cyclopropyl-6-(difluoromethoxy)pyrimidine (100 mg, 0.38 mmol), 4,4,4',4',5,5,5',5'-octamethyl-2,2'-bi(1,3,2-dioxaborolane) (192 mg, 0.75 mmol), and KOAc (112 mg, 1.14 mmol) in dioxane (3 mL) under nitrogen, was added $Pd(dppf)Cl_2$ (33.00 mg, 10 mol %). The resulting mixture was stirred at 95° C. overnight. After the reaction was completed based on TLC analysis, the reaction was quenched with water (15 mL) and extracted with EA (20 ml×3). The combined organic phase was dried over anhydrous $Na_2SO_4$ (20 g), filtered, and concentrated. The residue was purified by silica gel chromatography (EA:n-Hex=1:20) to give 93 mg of the title compound. LC-MS (Method A) (ESI+): m/z 313 (M+H)$^+$.

Preparation of Common Building Block (BB-26)

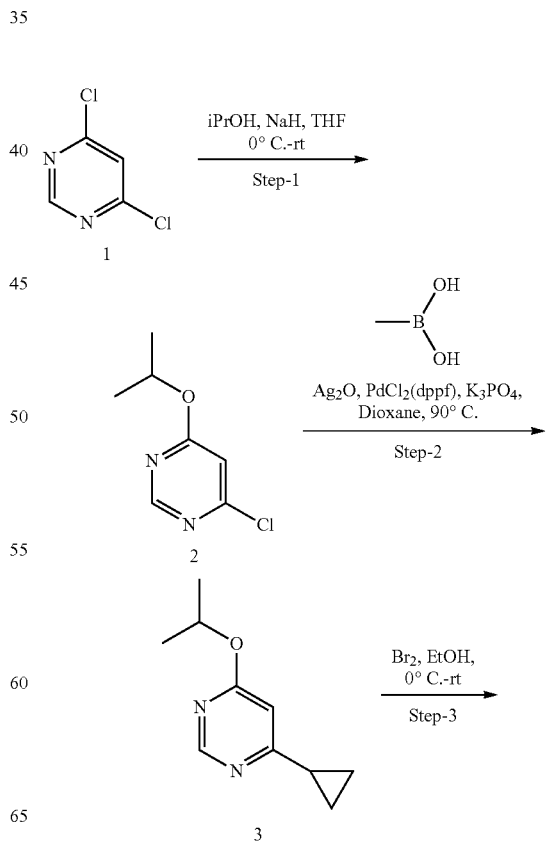

-continued

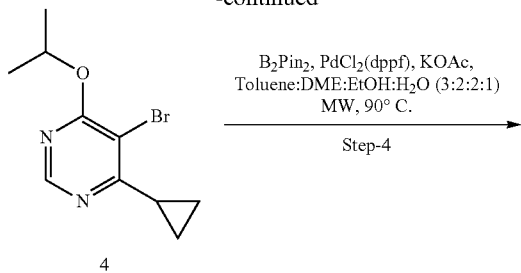

4

B$_2$Pin$_2$, PdCl$_2$(dppf), KOAc,
Toluene:DME:EtOH:H$_2$O (3:2:2:1)
MW, 90° C.
———————————→
Step-4

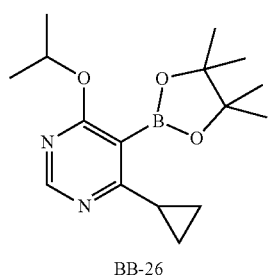

BB-26

Step 1: Synthesis of 4-Chloro-6-isopropoxypyrimidine

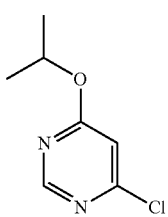

2

A mixture of sodium hydride (60% dispersion, 1.07 g, 26.8 mmol) in THF (40 mL) was cooled to 0° C. and a solution of isopropyl alcohol (2.04 mL, 26.8 mmol) in THF (15 mL) was added dropwise. Upon addition, the reaction was stirred at room temperature for 30 min, and then 4,6-dichloropyrimidine (4.0 g, 26.84 mmol) in THF (15 mL) was added dropwise at room temperature. The resulting mixture was stirred for another 1.5 h, and then quenched with cold water (100 mL) and extracted with EA (3×50 mL). The combined organic layer was dried over anhydrous Na$_2$SO$_4$, filtered, and dried under vacuum. The crude compound was purified by silica gel chromatography (0-10% EA in n-hexane) to afford 1.75 g of the title compound. $^1$H-NMR (400 MHz, CDCl$_3$) δ 8.55 (s, 1H), 6.70 (s, 1H), 5.34-5.42 (m, 1H), 1.36 (dd, J=1.22, 6.11 Hz, 6H).

Step 2: Synthesis of 4-Cyclopropyl-6-isopropoxypyrimidine

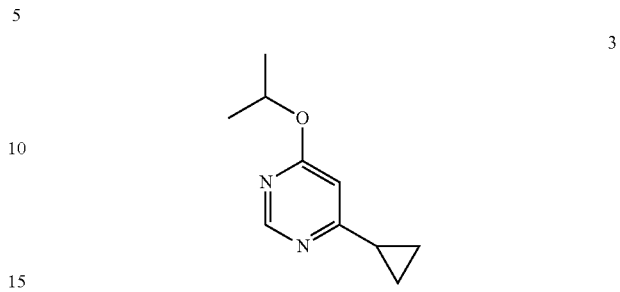

3

A mixture of 4-chloro-6-isopropoxypyrimidine (1.50 g, 8.720 mmol), cyclopropylboronic acid (1.49 g, 17.4 mmol), tripotassium phosphate (5.54 g, 26.2 mmol) and Ag$_2$O (1.00 g, 4.36 mmol) in 1,4 dioxane (15 mL) was purged with argon gas for 20 min. To the resulting solution was added PdCl$_2$(dppf) (0.637 g, 0.872 mmol) at room temperature. The reaction mixture was then heated at 90° C. for 8 h. After completion of the reaction (monitored by TLC), the mixture was filtered through a pad of Celite and washed with DCM (50 mL). The filtrate was concentrated under reduced pressure. The resulting crude compound was purified by silica gel chromatography (0-5% EA in n-hexane) to afford 0.700 g of the title compound. $^1$H-NMR (400 MHz, DMSO-d$_6$) δ 8.53 (s, 1H), 6.76 (s, 1H), 5.27 (td, J=6.11, 12.23 Hz, 1H), 1.95-2.05 (m, 1H), 1.35 (d, J=6.36 Hz, 2H), 1.28 (d, J=6.36 Hz, 6H), 0.98 (d, J=3.91 Hz, 2H).

Step 3: Synthesis of 5-Bromo-4-cyclopropyl-6-isopropoxypyrimidine

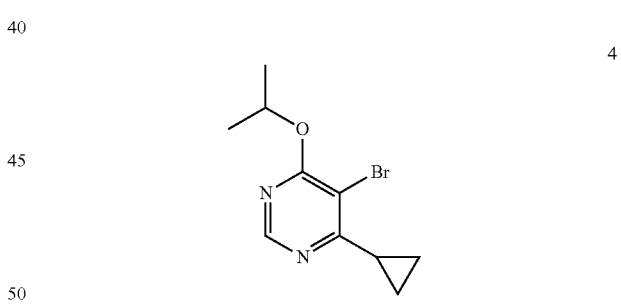

4

To a stirred solution of 4-cyclopropyl-6-isopropoxypyrimidine (0.600 g, 3.370 mmol) in ethanol (7 mL) at 0° C., was added bromine (0.20 mL, 4.04 mmol) dropwise. The reaction mixture was warmed to room temperature and stirred for 4 h. After completion of the reaction (monitored by TLC), the mixture was quenched with saturated NaHCO$_3$ solution (30 mL). The aqueous layer was extracted with EA (3×30 mL) and the combined organic layer was dried over anhydrous Na$_2$SO$_4$, filtered, and concentrated under reduced pressure. The resulting crude compound was purified by silica gel chromatography (0-10% EA in n-hexane) to afford 0.610 g of the title compound. $^1$H-NMR (400 MHz, CDCl$_3$) δ 8.40 (s, 1H), 5.38 (td, J=6.11, 12.23 Hz, 1H), 2.47-2.57 (m, 1H), 1.40 (d, J=5.87 Hz, 6H), 1.16 (d, J=1.96 Hz, 2H), 1.08 (dd, J=3.18, 4.65 Hz, 2H).

Step 4: Synthesis of 4-Cyclopropyl-6-isopropoxy-5-(4,4,5,5-tetramethyl-1,3,2-dioxaborolan-2-yl)pyrimidine (BB-26)

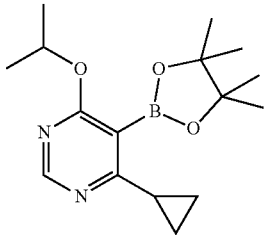

A mixture of 5-bromo-4-cyclopropyl-6-isopropoxypyrimidine 4 (0.250 g, 0.972 mmol), bispinacolato diborane (0.246 g, 0.972 mmol), and KOAc (0.095 g, 0.972 mmol) in Toluene:DME:EtOH:H₂O (3:2:2:1, 3 mL) was combined at room temperature and purged with argon gas for 20 min. To the resulting solution, was added PdCl₂(dppf) (0.071 g, 0.097 mmol). The reaction mixture was heated in a microwave at 90° C. for 20 min. After completion of the reaction (monitored by TLC), the mixture was used without work up in subsequent coupling reactions.

Preparation of Common Building Block (BB-27)

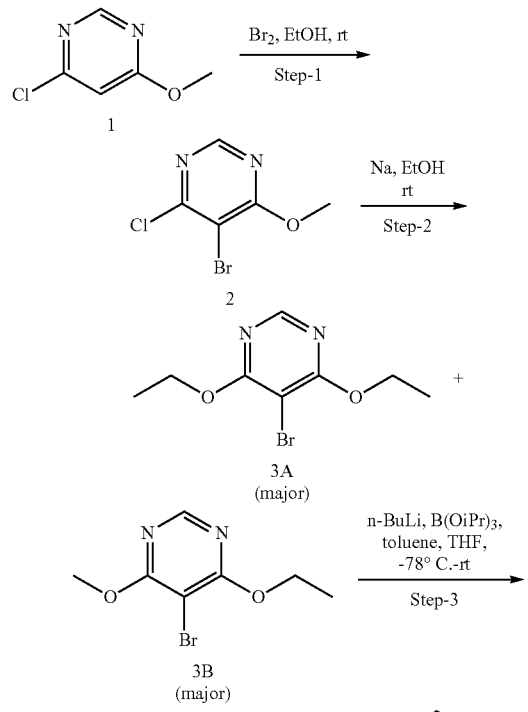

Step 1: Synthesis of 5-Bromo-4-chloro-6-methoxypyrimidine

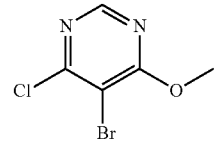

To a stirred solution of 4-chloro-6-methoxypyrimidine (5.00 g, 34.70 mmol) in EtOH (50 mL) was added Br₂ (3.20 g, 41.60 mmol) at room temperature, and the reaction mixture was stirred at room temperature for 16 h. Progress of the reaction was monitored by TLC. After completion, the reaction mixture was quenched with sodium bisulfate solution and extracted with n-hexane (3×100 mL). Combined organic layer was dried over anhydrous sodium sulfate, filtered, and concentrated under reduced pressure. The crude compound was purified by silica gel chromatography on silica using 0-3% EA in hexane to afford 3.90 g of the title compound. LC-MS (Method B) (ESI+): m/z 224.70 (M+H)⁺ ⁸¹Br; ¹H-NMR (400 MHz, DMSO-d₆) δ 8.64 (s, 1H), 4.04 (s, 3H).

Step 2: Synthesis of 5-Bromo-4,6-diethoxypyrimidine

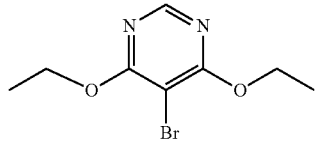

To a stirred solution of EtOH (20 mL) was added sodium metal (0.092 g) in portion at room temperature under argon atmosphere. To the resulting reaction mixture, 5-bromo-4-chloro-6-methoxypyrimidine (0.90 g, 4.00 mmol) was added, and the reaction mixture was stirred at room temperature for 2 h. Progress of the reaction was monitored by TLC. After completion, the reaction mixture was concentrated under reduced pressure, and the residue thus obtained was quenched with water (50 mL) and extracted with EA (2×25 mL). The combined organic layer was dried over anhydrous sodium sulfate, filtered, and concentrated under reduced pressure. The same sequence was repeated on another 500 mg scale batch of starting material, and the combined crude compound of the two batches was purified together by prep HPLC to afford 0.38 g of the title compound. LC-MS (Method C) (ESI+): m/z 246.85 (M+H)⁺; ¹H-NMR (400 MHz, DMSO-d₆) δ 8.40 (s, 1H), 4.44 (q, J=7.2 Hz, 4H), 1.33 (t, J=7.1 Hz, 6H).

Step 3: Synthesis of (4,6-Diethoxypyrimidin-5-yl)boronic acid (BB-27)

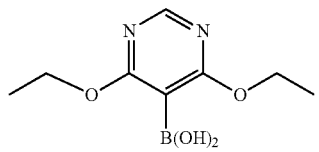

To a stirred solution of 5-bromo-4,6-diethoxypyrimidine (0.38 g, 1.54 mmol) in THF (2.5 mL) and toluene (5 mL) was added triisopropylborate (0.435 g, 2.31 mmol) under argon atmosphere. To the resulting reaction mixture n-BuLi (1.6M in hexane, 1.35 mL, 2.16 mmol) was added dropwise at −76° C., stirred for 30 min at same temperature and further stirred at room temperature for 30 min. Progress of the reaction was monitored by TLC. After completion, the reaction mixture was quenched with 2N HCl (5 mL), stirred for 2 h and adjusted to pH=7.5-8 using Na₂CO₃ (2 g). The aqueous layer was extracted with EA (3×20 mL). The combined organic layer was dried over anhydrous sodium sulfate, filtered, and concentrated under reduced pressure. The crude compound was triturated with n-pentane (10 mL), and the resulting solid was collected and dried to afford 0.065 g of the crude title compound which was used as is in next step without further purification. LC-MS (Method C) (ESI+): m/z 212.90 (M+H)$^+$; $^1$H-NMR (400 MHz, DMSO-d$_6$) δ 8.35-8.43 (m, 1H), 8.11 (s, 1H), 4.27-4.37 (m, 4H), 1.21-1.35 (m, 6H).

The following intermediate was made from the commercially available aryl bromide via the procedure described to prepare BB-27:

| Example | Structure | Analytical data |
|---|---|---|
| BB-28 | 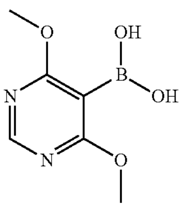 | LC-MS (Method B) (ESI+): m/z 184.80 (M + H)$^+$ |
| BB-29 | 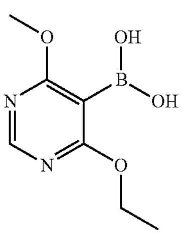 | LC-MS (Method B) (ESI+): m/z 198.90 (M + H)$^+$ |
| BB-30 | 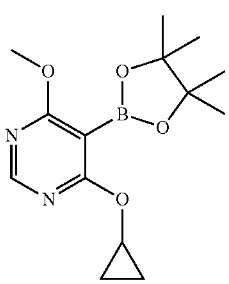 [SMILES: COc1ncnc(OC2CC2)c1B1OC(C)(C)C(C)(C)O1] | Prepared in situ via Pd-catalyzed borylation according to the procedure of BB-26 step-4, and used in next step without isolation |

Preparation of Common Building Block (BB-31)

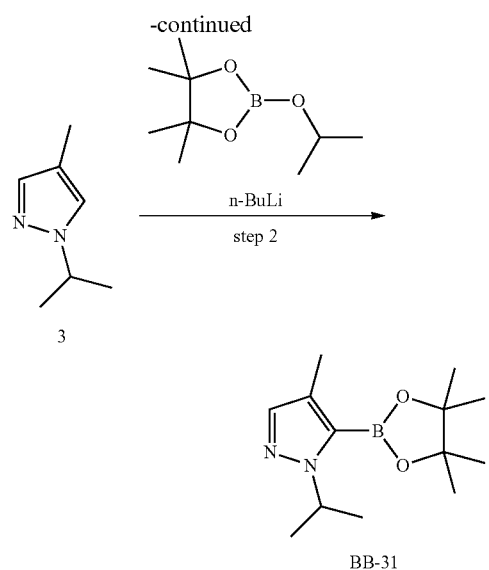

Step 1: Synthesis of 1-Isopropyl-4-methyl-1H-pyrazole

To a solution of 4-methyl-1H-pyrazole (1.0 g, 12.2 mmol) in THF (30 mL) at 0° C., was added NaH (60% dispersion, 730 mg, 18.3 mmol) portion-wise over 5 min. The mixture was stirred at 0° C. for 30 min, then allowed to warm to rt. A solution of isopropyl 4-methylbenzenesulfonate (2.6 g, 12.2 mmol) in THF (10 mL) was added to the reaction mixture in one portion. After addition, the reaction was heated to reflux overnight. The reaction was then quenched with water (50 mL) and extracted with EA (50 mL×2). The combined organic layer was dried over sodium sulfate (30 g), filtered, and concentrated. The residue was purified by silica gel chromatography (PE:EA=50:1 to 10:1) to afford 0.44 g of the title compound. $^1$H-NMR (300 MHz, CD$_3$OD) δ 7.30 (s, 1H), 7.20 (s, 3H), 4.44 (m, 1H), 2.07 (s, 3H), 1.48 (d, J=6.6 Hz, 6H).

Step 2: Synthesis of 1-Isopropyl-4-methyl-5-(4,4,5,5-tetramethyl-1,3,2-dioxaborolan-2-yl)-1H-pyrazole (BB-31)

To a solution of 1-isopropyl-4-methyl-1H-pyrazole (350 mg, 2.82 mmol) in THF (10 ml) at 0° C., was added n-BuLi (2.3 mL, 5.7 mmol) dropwise over 10 min. After the mixture was stirred at 0° C. for 1 h, the reaction was cooled to −78° C. A solution of 2-isopropoxy-4,4,5,5-tetramethyl-1,3,2-dioxaborolane (1.05 g, 5.65 mmol) in THF (5 mL) was added dropwise to the reaction mixture over 5 min. After the reaction was stirred at −78° C. for 30 min, the reaction was warmed to rt and stirred for 4 h. The reaction was quenched with water (20 mL) and extracted with EA (20 mL×2). The combined organic layer was dried over sodium sulfate (10 g), filtered, and concentrated. The residue was purified by column chromatography on silica (eluent: PE/EA=100/1 to 20/1) to afford 180 mg of the title compound. LC-MS (Method A) (ESI+): m/z 251 (M+H)$^+$; $^1$H-NMR (300 MHz, CD$_3$OD) δ 7.34 (s, 1H), 5.05 (m, 1H), 2.22 (s, 3H), 1.45 (d, J=6.6 Hz, 6H), 1.33 (s, 12H).

The following compounds were made from the appropriate heterocycle and alkylating agent according the procedure described for BB-31:

| Example | Structure | Analytical data |
|---------|-----------|-----------------|
| BB-32 | 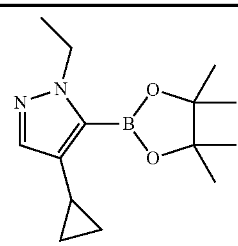 | LC-MS (Method A) (ESI+): m/z 263 (M + H)$^+$; $^1$H-NMR (300 MHz, CDCl$_3$) δ 7.03 (s, 1H), 4.35-4.45 (q, J = 7.2 Hz, 2H), 2.21 (m, 1H), 1.30-1.45 (m, 15H), 0.85-0.94 (m, 2H), 0.51-0.59 (m, 2H). |
| BB-33 | 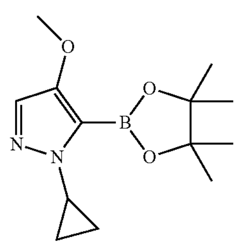 [SMILES: COc1cnn(C2CC2)c1B1OC(C)(C)C(C)(C)O1] | LC-MS (Method A) (ESI+): m/z 265 (M + H)$^+$. |
| BB-34 | 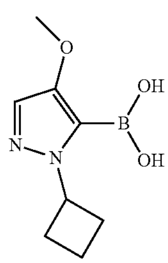 | LC-MS (Method A) (ESI+): m/z 197 (M + H)$^+$. |

Preparation of Common Building Block BB-35

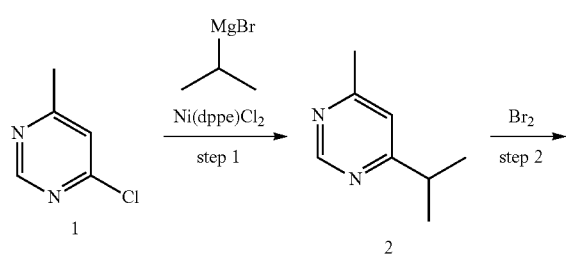

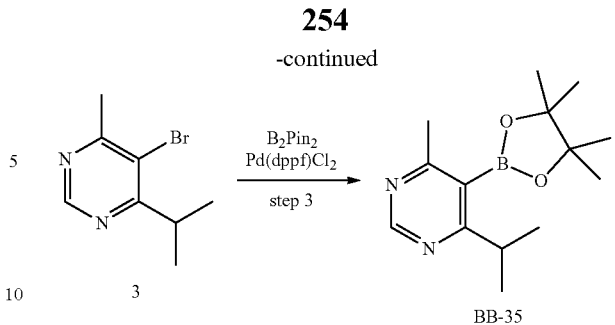

Step 1: Synthesis of 4-Isopropyl-6-methylpyrimidine

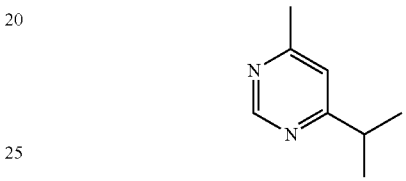

To a solution of 4-chloro-6-methylpyrimidine (2 g, 15.63 mmol) in Et$_2$O (10 mL) at rt, was added Ni(dppe)Cl$_2$ (165 mg, 0.3 mmol) in one portion. After the mixture was cooled −10° C. for 10 min, isopropyl magnesium bromide solution (1 M, 18.75 mmol, 18.75 mL) was added dropwise to the reaction mixture over 5 min. The mixture was stirred at −10° C. for 1 h, and then quenched with water (30 mL) and extracted with EA (30 mL×3). The combined organic layer was dried over sodium sulfate (50 g), filtered, and concentrated. The residue was purified by silica gel chromatography on silica (PE:EA=100:1 to 20:1) to afford 2.02 g of the title compound. LC-MS (Method A) (ESI+): m/z 137 (M+H)$^+$; $^1$H-NMR (300 MHz, CDCl$_3$) δ 9.00 (s, 1H), 7.06 (s, 1H), 2.98 (m, 1H), 2.51 (s, 3H), 1.30 (d, J=6.9 Hz, 6H).

Step 2: Synthesis of 5-Bromo-4-isopropyl-6-methylpyrimidine

To a solution of 4-isopropyl-6-methylpyrimidine (500 mg, 3.6 mmol) in EtOH (5 mL) at 0° C., was added Br$_2$ (588 mg, 3.6 mmol) in one portion. The resulting mixture was stirred at rt overnight, then quenched with water (20 mL) and extracted with EA (15 mL×3). The combined organic layer was dried over sodium sulfate (20 g), filtered, and concentrated. The residue was purified by silica gel chromatography (PE:EA=20:1) to afford 400 mg of the title compound. LC-MS (Method A) (ESI+): m/z 215 (M+H)$^+$; $^1$H-NMR (300 MHz, CDCl$_3$) (8.88 (s, 1H), 3.56 (m, 1H), 2.66 (s, 3H), 1.25-1.31 (m, 6H).

Step 3: Synthesis of 4-Isopropyl-6-methyl-5-(4,4,5,5-tetramethyl-1,3,2-dioxaborolan-2-yl)pyrimidine (BB-35)

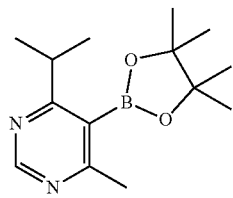 [SMILES: Cc1ncnc(C(C)C)c1B1OC(C)(C)C(C)(C)O1]

To a solution of 5-bromo-4-isopropyl-6-methylpyrimidine (400 mg, 1.86 mmol) and triisopropylborate (457 mg, 2.43 mmol) in toluene (4 mL) and THF (1 mL) at −78° C., was added n-butyllithium (1 mL, 2.6 mmol) dropwise over 10 min. After 30 min at −78° C., the reaction was warmed to −20° C. and stirred for 1 h. The reaction was then quenched with aqueous HCl solution (3 mL, 1 N), and stirred at rt for 30 min. The pH was then adjusted to 8 with a saturated aqueous $Na_2CO_3$ solution and extracted with EA (25 mL×3). The combined organic layer was dried over anhydrous $Na_2SO_4$ (30 g), filtered, and concentrated in vacuo to give 140 mg of the crude title compound. LC-MS (Method A) (ESI+): m/z 181 (M+H)$^+$; $^1$H-NMR (300 MHz, $CD_3OD$) δ 8.91 (s, 1H), 2.78 (m, 1H), 2.44 (s, 3H), 1.26-1.32 (d, J=6.6 Hz, 6H).

Preparation of Common Building Block BB-36

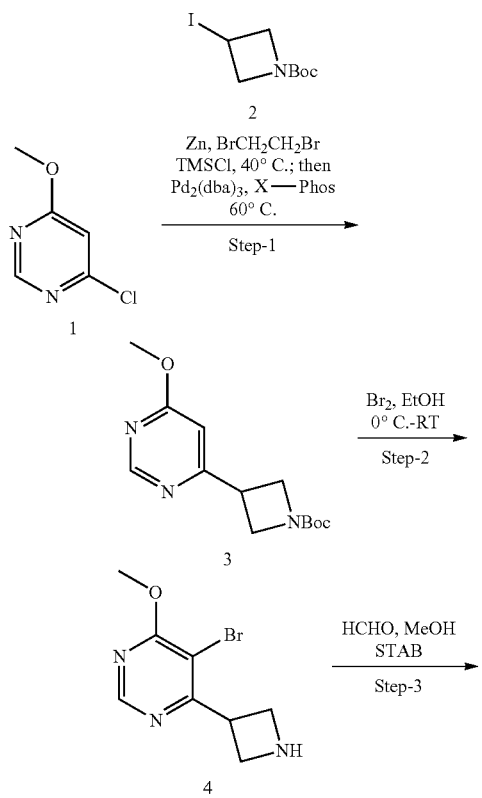

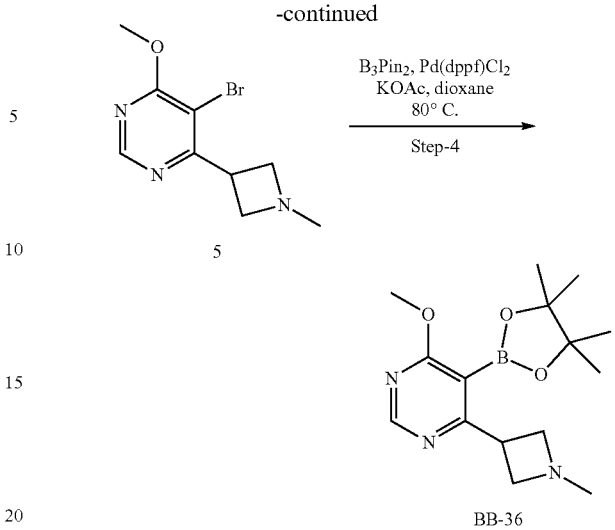

Step 1: Synthesis of tert-butyl 3-(6-methoxypyrimidin-4-yl)azetidine-1-carboxylate

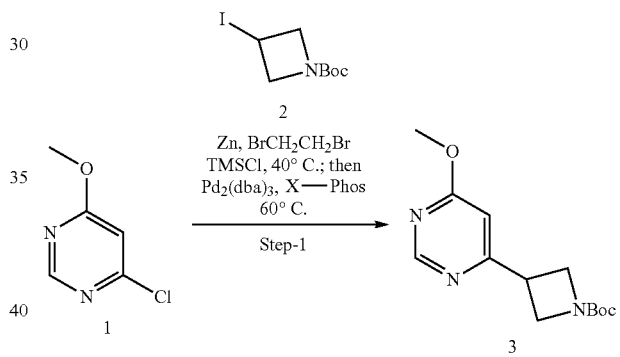

To a stirred solution of zinc (3.78 g, 58.3 mmol) in THF (150 mL), was added TMSCl (0.574 g, 5.30 mmol) and 1,2-dibromoethane (0.962 g, 5.30 mmol). The mixture was stirred for 5 min at room temperature, and was then treated with tert-butyl 3-iodoazetidine-1-carboxylate 2 (15 g, 53.0 mmol) at a rate that maintained the internal reaction temperature below 40° C. The resulting mixture was further stirred for 30 min at room temperature. To the resulting reaction mixture was added 4-chloro-6-methoxypyrimidine 1 (7.64 g, 53.0 mmol), X-Phos (5 g, 10.6 mmol) and $Pd_2(dba)_3$ (4.84 g, 5.30 mmol). The reaction mixture was heated to 60° C. in a sealed tube for 4 h. Progress of the reaction was monitored by TLC. After completion, the reaction mixture was diluted with water (200 mL), extracted with EA (200 mL), and filtered through Celite. The organic layer was separated, dried over anhydrous sodium sulfate, filtered and concentrated under reduced pressure. The crude compound was purified by silica gel chromatography using 10-70% EA in hexane to afford title compound (10.00 g). LC-MS (Method C) (ESI+): m/z 266.3 (M+H)$^+$; $^1$H-NMR (400 MHz, DMSO-$d_6$) δ 8.80 (s, 1H), 6.89 (s, 1H), 4.09-4.20 (m, 2H), 3.95-4.06 (m, 2H), 3.91 (s, 3H), 3.79-3.86 (m, 1H), 1.39 (s, 9H).

Step 2: Synthesis of 4-(azetidin-3-yl)-5-bromo-6-methoxypyrimidine

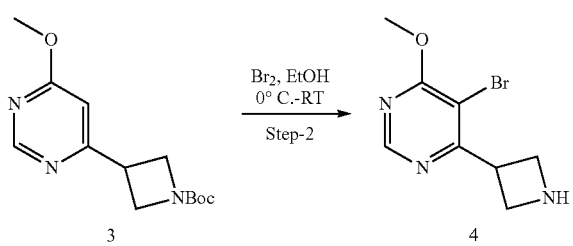

To a stirred solution of tert-butyl 3-(6-methoxypyrimidin-4-yl)azetidine-1-carboxylate 3 (3.0 g, 11.3 mmol) in ethanol (100 mL), was added bromine (5.42 g, 33.9 mmol) at 0° C. The resulting mixture was allowed to warm to room temperature and was stirred for 16 h. Progress of the reaction was monitored by TLC. After completion, the reaction mixture was concentrated under reduced pressure. The residue was dissolved in aqueous ammonia solution (30 mL) and extracted with DCM (100 mL). The organic layer was separated, dried over anhydrous sodium sulfate, filtered and concentrated under reduced pressure. The crude compound was purified by silica gel chromatography using 0-10% methanol in DCM as eluent to afford title compound (1.7 g). LC-MS (Method C) (ESI+): m/z 245.90 (M+H)$^+$; $^1$H-NMR (400 MHz, DMSO-d$_6$) δ 8.77 (s, 1H), 4.31 (td, J=8.35, 16.21 Hz, 2H), 4.01 (s, 3H), 3.87-3.94 (m, 3H).

Step 3: Synthesis of 5-bromo-4-methoxy-6-(1-methylazetidin-3-yl)pyrimidine

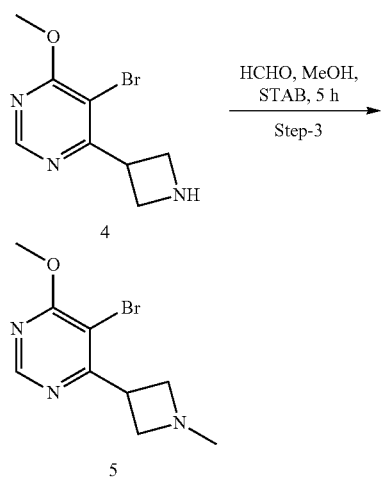

To a stirred solution of 4-(azetidin-3-yl)-5-bromo-6-methoxypyrimidine 4 (1.0 g, 4.08 mmol) in methanol (20 mL), was added formaldehyde solution (10 mL, 37% in water) and the reaction mixture was stirred at room temperature for 1 h. To the resulting reaction mixture was added sodium triacetoxyborohydride (4.3 g, 20.4 mmol) at room temperature. The resulting mixture was stirred for 5 h, and progress of the reaction was monitored by TLC. After completion, the reaction mixture was diluted with DCM (50 mL) and the solution was adjusted to pH 8 using saturated sodium bicarbonate solution (10 mL). The organic layer was separated, dried over anhydrous sodium sulfate, filtered and concentrated under reduced pressure. The crude compound was purified by silica gel chromatography using 0-10% methanol in DCM as eluent to afford title compound (0.719 g). LC-MS (Method C) (ESI): m/z 257.88 (M+H)$^+$; $^1$H-NMR (400 MHz, DMSO-d$_6$) δ 8.75 (s, 1H), 4.11 (quin, J=7.83 Hz, 1H), 4.01 (s, 3H), 3.90 (t, J=8.07 Hz, 2H), 3.62 (t, J=7.58 Hz, 2H), 2.45 (s, 3H).

Step 4: Synthesis of 4-methoxy-6-(1-methylazetidin-3-yl)-5-(4,4,5,5-tetramethyl-1,3,2-dioxaborolan-2-yl)pyrimidine (BB-36)

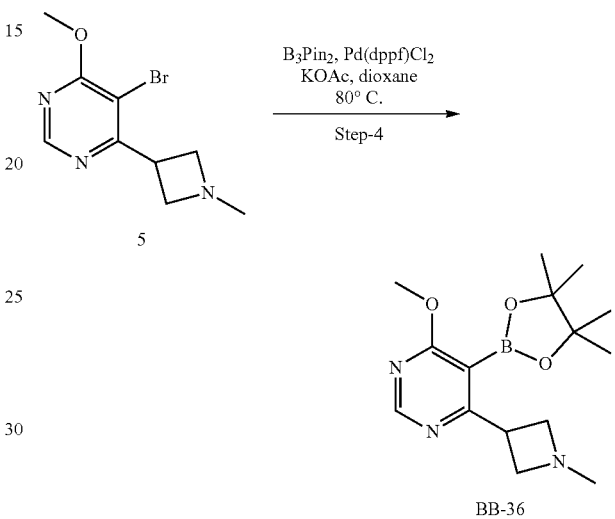

To a stirred solution of 5-bromo-4-methoxy-6-(1-methylazetidin-3-yl)pyrimidine 5 (0.600 g, 2.32 mmol) and B$_2$Pin$_2$ (1.77 g, 6.97 mmol) in dioxane (30 mL), was added KOAc (0.676 g, 6.97 mmol) and the reaction mixture was degassed with argon gas for 15 min. To the resulting reaction mixture was added Pd(dppf)Cl$_2$-DCM (0.375 g, 0.465 mmol) at room temperature, and the mixture was heated in a sealed tube at 80° C. for 2 h. Progress of the reaction was monitored by TLC. After completion, the reaction mixture was cooled to room temperature, diluted with EA (100 mL) and filtered through a pad of Celite. The filtrate obtained was concentrated under reduced pressure to afford the crude title compound (0.709 g). The crude compound was used as such in next step without further purification.

Preparation of Common Building Block BB-37

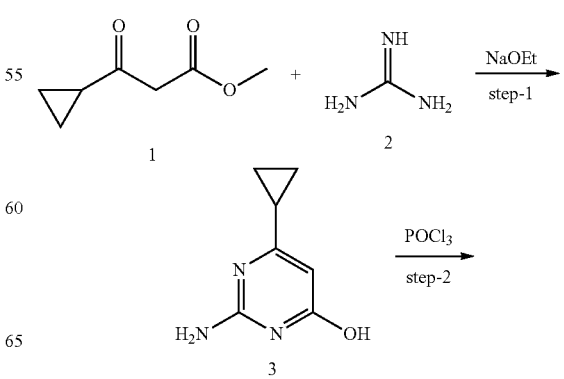

-continued

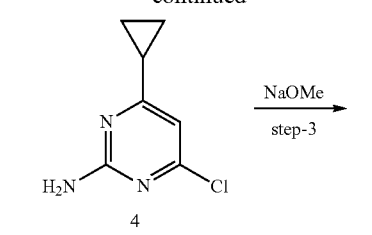

4

NaOMe
step-3

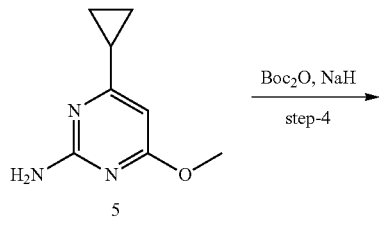

5

Boc₂O, NaH
step-4

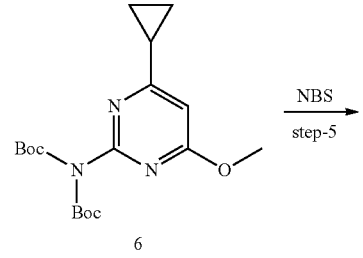

6

NBS
step-5

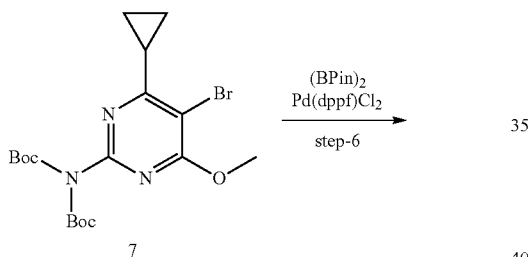

7

(BPin)₂
Pd(dppf)Cl₂
step-6

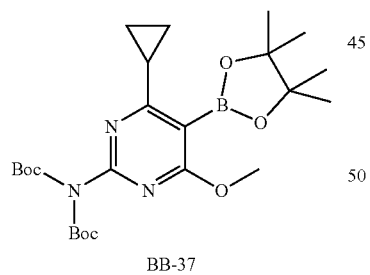

BB-37

Step 1: 2-amino-6-cyclopropylpyrimidin-4-ol

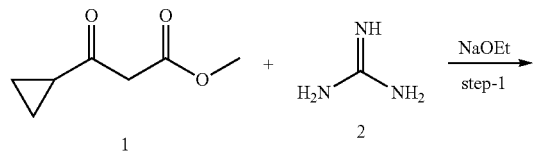

1        2

NaOEt
step-1

-continued

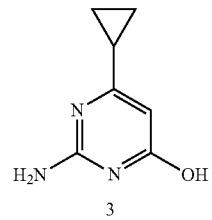

3

To a suspension of methyl 3-cyclopropyl-3-oxopropanoate (8.1 g, 57 mmol) and guanidine carbonate (5.65 g, 63 mmol) in ethanol (70 mL) at rt, was added NaOEt (7.75 g, 114 mmol) portion-wise over 20 min. After the addition, the resulting mixture was warmed to reflux and stirred overnight. After the reaction was complete as indicated by TLC analysis, the resulting suspension was concentrated under reduced pressure to remove most of the ethanol. The residue was diluted with a saturated NH₄Cl solution (100 mL) and extracted with EA (3×200 mL). The combined organic layer was dried with Na₂SO₄ (50 g), filtered and concentrated to give 9 g of crude product. The crude product was slurried in a mixed solvent (Methanol/MTBE=1/10, 33 mL) at rt overnight. After filtration and drying, 7.2 g of the title compound was obtained. LC-MS (Method A) (ESI+): m/z 152 (M+H)⁺; ¹H-NMR (300 MHz, DMSO-d₆) δ 10.45 (s, 1H), 6.37 (s, 2H), 5.48 (s, 1H), 1.65 (m, 1H), 078-0.83 (m, 4H).

Step 2: 4-chloro-6-cyclopropylpyrimidin-2-amine

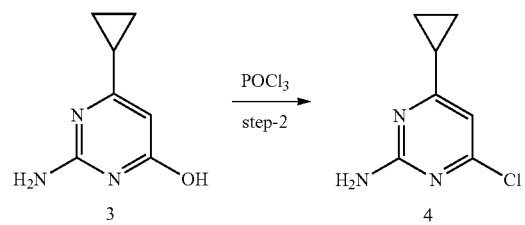

3        4

POCl₃
step-2

To a suspension of 2-amino-6-cyclopropylpyrimidin-4-ol (1.5 g, 9.9 mmol) in DCE (30 mL), was added POCl₃ (20 mL). The reaction was stirred at 75° C. overnight. After the reaction was complete as indicated by TLC, the mixture was concentrated to dryness. The residue was quenched with a cold saturated sodium carbonate solution (60 mL) and extracted with DCM (100 mL×2). The combined organic layer was dried over sodium sulfate (30 g), filtered and concentrated. The residue was purified by silica gel chromatography (PE/EA=10:1) to provide 1.0 g of the title compound. LC-MS (Method A) (ESI+): m/z 170 (M+H)⁺; ¹H-NMR (300 MHz, CDCl₃) δ 6.52 (s, 1H), 5.05 (br s, 2H), 1.79 (m, 1H), 0.94-1.10 (m, 4H).

Step 3: 4-cyclopropyl-6-methoxypyrimidin-2-amine

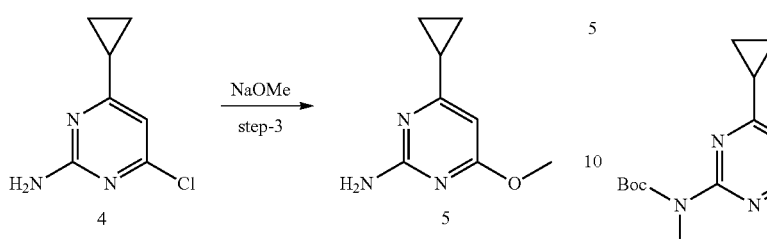

To a solution of 4-chloro-6-cyclopropylpyrimidin-2-amine (850 mg, 5.03 mmol) in MeOH (50 mL), was added NaOMe solution (2.72 g, 15.1 mmol, 30 wt. % in MeOH) in one portion. The reaction was stirred at 60° C. for 3 h. After the reaction was complete as indicated by TLC, the mixture was quenched with water (60 mL) and extracted with EA (100 mL×2). The combined organic layer was washed with brine (120 mL), dried over sodium sulfate (30 g), filtered and concentrated to provide 800 mg of the crude title compound. LC-MS (Method A) (ESI+): m/z 166 (M+H)$^+$; $^1$H-NMR (300 MHz, CDCl$_3$) δ 5.91 (s, 1H), 4.80 (br s, 2H), 3.84 (s, 3H), 1.79 (m, 1H), 0.91-1.08 (m, 2H), 0.85-0.91 (m, 2H).

Step 4: Di-Boc protected 4-cyclopropyl-6-methoxypyrimidin-2-amine

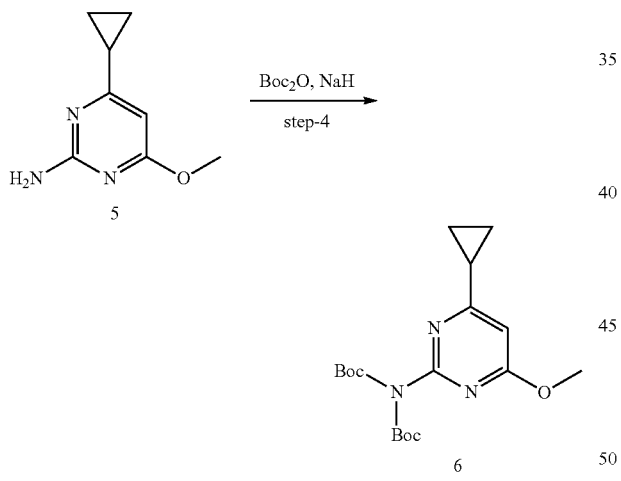

To a solution of 4-cyclopropyl-6-methoxypyrimidin-2-amine (900 mg, 5.45 mmol) and Boc$_2$O (5.96 g, 27.3 mmol) in THF (50 mL), was added NaH (654 mg, 16.4 mmol, 60 wt. %) portion-wise over 5 min. The reaction was stirred at 60° C. overnight. After the reaction was complete as indicated by TLC analysis, the mixture was quenched with an aqueous NH$_4$Cl solution (100 mL) and extracted with EA (100 mL×2). The combined organic layer was washed with brine (120 mL), dried over sodium sulfate (30 g), filtered and concentrated. The residue was purified by silica gel chromatography (PE/EA=50:1 to 25:1) to provide 1.27 g of the title compound. LC-MS (Method A) (ESI+): m/z 366 (M+H)$^+$; $^1$H-NMR (300 MHz, CDCl$_3$) δ 6.43 (s, 1H), 3.92 (s, 3H), 1.89 (m, 1H), 1.44 (s, 18H), 1.02-1.10 (m, 2H), 0.91-1.02 (m, 2H).

Step 5: Di-Boc protected 5-bromo-4-cyclopropyl-6-methoxypyrimidin-2-amine

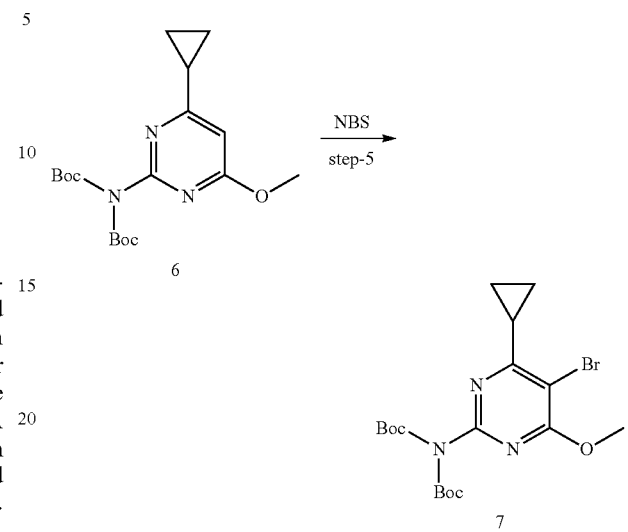

To a solution of di-Boc protected 4-cyclopropyl-6-methoxypyrimidin-2-amine (1.27 g, 3.47 mmol) in DCM (35 mL) at 0° C., was added NBS (1.24 g, 6.96 mmol) portion-wise over 5 min. The reaction was stirred at rt overnight. After the reaction was complete as indicated by TLC, the mixture was quenched with water (30 mL) and extracted with DCM (40 mL×2). The organic layer was washed with brine (60 mL), dried over sodium sulfate (30 g), filtered and concentrated. The residue was purified by silica gel chromatography (PE/EA=60:1 to 30:1) to provide 1.4 g of the title compound. LC-MS (Method A) (ESI+): m/z 444 (M+H)$^+$; $^1$H-NMR (300 MHz, CDCl$_3$) δ 4.01 (s, 3H), 2.52 (m, 1H), 1.45 (s, 18H), 1.09-1.17 (m, 2H), 1.02-1.09 (m, 2H).

Step 6: Di-Boc protected 4-cyclopropyl-6-methoxy-5-(4,4,5,5-tetramethyl-1,3,2-dioxaborolan-2-yl)pyrimidin-2-amine (BB-37)

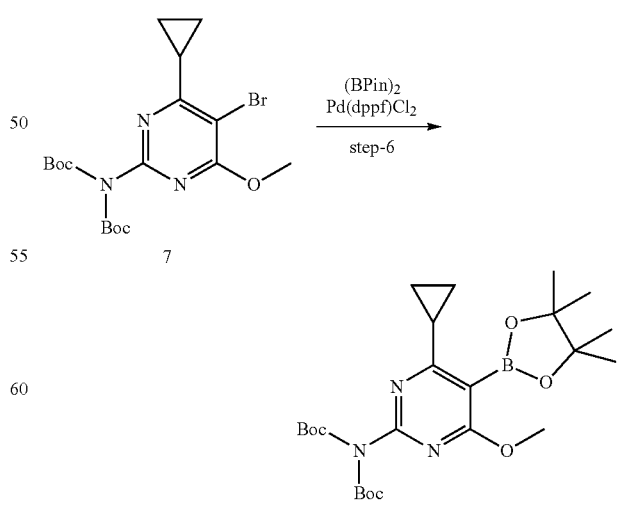

To a solution of di-Boc protected 5-bromo-4-cyclopropyl-6-methoxy-pyrimidin-2-amine (1.5 g, 3.4 mmol) in 1,4-dioxane (34 mL), was added bis(pinacolato)diboron (1.72 g, 6.77 mmol), potassium acetate (997 mg, 10.2 mmol) and Pd(dppf)Cl$_2$ (249 mg, 0.34 mmol). The reaction was then heated to 95° C. overnight. After most of bromo starting material was consumed based on TLC analysis, the mixture was quenched with water (40 mL), and the un-dissolved solid was filtered. The filtrate was extracted with EA (100 mL×2). The combined organic layer was washed with brine (60 mL), dried over sodium sulfate (30 g), filtered and concentrated. The resulting residue was purified by silica gel chromatography (PE/EA=30:1 to 10:1) to provide 650 mg of the title compound. LC-MS (Method A) (ESI+): m/z 492 (M+H)$^+$; $^1$H-NMR (300 MHz, CDCl$_3$) δ 3.90 (s, 3H), 2.18 (m, 1H), 1.45 (s, 18H), 1.33 (s, 12H), 1.09-1.13 (m, 2H), 0.89-0.96 (m, 2H).

General Experimental Procedure 1. Preparation of Example 1:

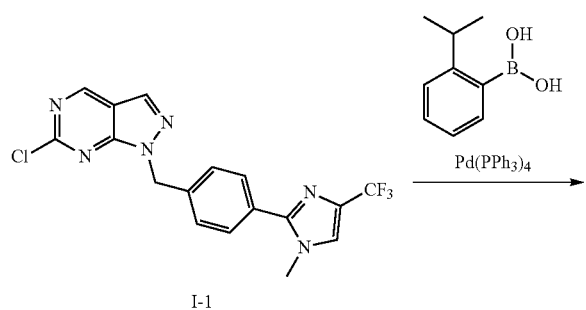

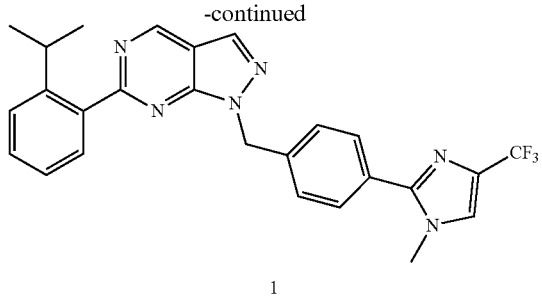

A mixture of 6-chloro-1-(4-(1-methyl-4-(trifluoromethyl)-1H-imidazol-2-yl)benzyl)-1H-pyrazolo[3,4-d]pyrimidine (100 mg, 0.25 mmol), K$_3$PO$_4$.3H$_2$O (208 mg, 0.78 mmol), (2-isopropylphenyl)boronic acid (84 mg, 0.51 mmol) and Pd(PPh$_3$)$_4$ (30 mg, 0.025 mmol) in 1,4-dioxane (4 ml) and water (0.3 ml), was stirred at 100° C. for 2 hours. The resulting mixture was diluted with water (10 mL) and extracted with EA (20 mL×2). The combined organic layer was dried with Na$_2$SO$_4$ (10 g), filtered and concentrated to dryness. The concentrated residue was purified by silica gel chromatography (PE:EA=30:1 to 5:1), followed by preparative HPLC to afford 62 mg of the title compound. LC-MS (Method A) (ESI+): m/z 477 (M+H)$^+$; $^1$H-NMR (300 MHz, CDCl$_3$) (9.30 (s, 1H), 8.20 (s, 1H), 7.72 (d, J=7.2 Hz, 1H), 7.59 (d, J=8.1 Hz, 2H), 7.44-7.51 (m, 4H), 7.26-7.35 (m, 2H), 5.75 (s, 2H), 3.73 (s, 3H), 3.56 (m, 1H), 1.27 (d, J=6.9 Hz, 6H).

The following compounds were prepared according to the General Experimental Procedure 1 using Pd(PPh$_3$)$_4$/K$_3$PO$_4$ or XPhos-Pd-G2/XPhos/K$_3$PO$_4$ and the appropriate boron species (structures of commercial boronic acids and boronates indicated):

| Example | Structure | Starting material | Analytical data |
|---|---|---|---|
| 2 | (structure) | I-1, (structure) | LC-MS (Method A) (ESI+): m/z 465 (M + H)$^+$; $^1$H-NMR (300 MHz, CDCl$_3$) δ 9.31 (s, 1H), 8.18 (s, 1H), 7.80 (d, J = 7.5 Hz, 1H), 7.60 (d, J = 8.1 Hz, 2H), 7.52 (d, J = 8.1 Hz, 2H), 7.47 (d, J = 7.5 Hz, 1H), 7.29 (s, 1H), 7.07-7.15 (m, 2H), 5.77 (s, 2H), 3.91 (s, 3H), 3.73 (s, 3H). |
| 3 | (structure) | I-1, (structure) | LC-MS (Method A) (ESI+): m/z 513 (M + H)$^+$; $^1$H-NMR (300 MHz, DMSO-d$_6$) δ 9.50 (s, 1H), 8.55 (s, 1H), 8.11 (d, J = 7.8 Hz, 1H), 7.91 (s, 1H), 7.86 (d, J = 7.8 Hz, 1H), 7.79-7.84 (m, 2H), 7.68 (d, J = 8.1 Hz, 2H), 7.39 (d, J = 8.1 Hz, 2H), 5.80 (s, 2H), 3.75 (s, 3H), 3.50 (s, 3H). |

| Example | Structure | Starting material | Analytical data |
|---|---|---|---|
| 4 | 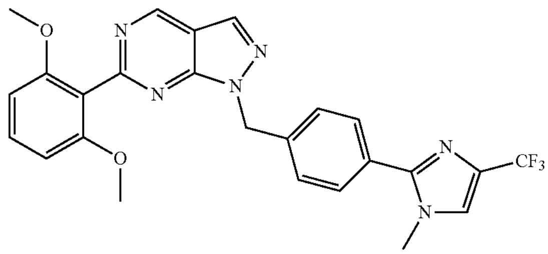 [SMILES: COc1cccc(OC)c1-c1ncc2cnn(Cc3ccc(-c4nc(C(F)(F)F)cn4C)cc3)c2n1] | I-1, | LC-MS (Method A) (ESI+): m/z 495 (M + H)+; 1H-NMR (300 MHz, CD3OD) δ 9.31 (s, 1H), 8.37 (s, 1H), 7.67 (s, 1H), 7.62 (d, J = 8.4 Hz, 2H), 7.52 (d, J = 8.4 Hz, 2H), 7.44 (t, J = 8.4 Hz, 1H), 6.79 (d, J = 8.4 Hz, 2H), 5.79 (s, 2H), 3.74 (s, 3H), 3.72 (s, 6H). |
| 5 | 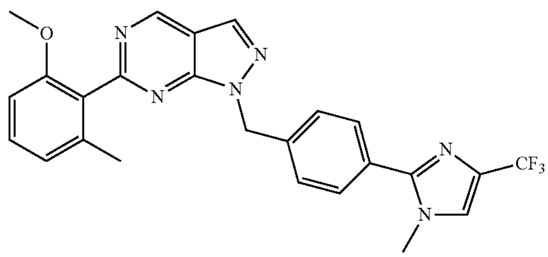 [SMILES: COc1cccc(C)c1-c1ncc2cnn(Cc3ccc(-c4nc(C(F)(F)F)cn4C)cc3)c2n1] | I-1, | LC-MS (Method A) (ESI+): m/z 479 (M + H)+; 1H-NMR (300 MHz, CDCl3) δ 9.32 (s, 1H), 8.21 (s, 1H), 7.57 (d, J = 8.4 Hz, 2H), 7.47 (d, J = 8.4 Hz, 2H), 7.26-7.32 (m, 2H), 6.88-6.95 (m, 2H), 5.76 (s, 2H), 3.75 (s, 3H), 3.73 (s, 3H), 2.08 (s, 3H). |
| 6 | 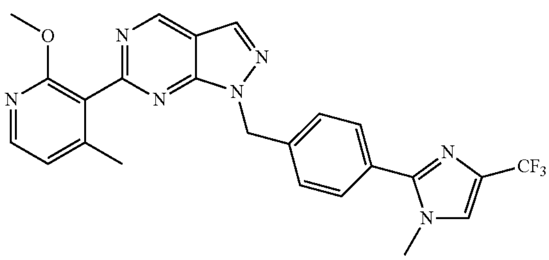 [SMILES: COc1nccc(C)c1-c1ncc2cnn(Cc3ccc(-c4nc(C(F)(F)F)cn4C)cc3)c2n1] | I-1, | LC-MS (Method A) (ESI+): m/z 480 (M + H)+; 1H-NMR (300 MHz, CDCl3) δ 9.32 (s, 1H), 8.22 (s, 1H), 8.14 (d, J = 5.1 Hz, 1H), 7.59 (d, J = 8.1 Hz, 2H), 7.48 (d, J = 8.1 Hz, 2H), 7.30 (s, 1H), 6.88 (d, J = 5.1 Hz, 1H), 5.75 (s, 2H), 3.90 (s, 3H), 3.73 (s, 3H), 2.13 (s, 3H). |
| 7 | 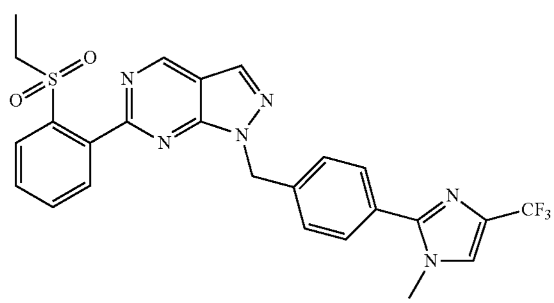 [SMILES: CCS(=O)(=O)c1ccccc1-c1ncc2cnn(Cc3ccc(-c4nc(C(F)(F)F)cn4C)cc3)c2n1] | I-1, | LC-MS (Method A) (ESI+): m/z 527 (M + H)+; 1H-NMR (300 MHz, CD3OD) δ 9.37 (s, 1H), 8.42 (s, 1H), 8.12 (d, J = 7.5 Hz, 1H), 7.72-7.90 (m, 3H), 7.67 (s, 1H), 7.62 (d, J = 8.1 Hz, 2H), 7.42 (d, J = 8.1 Hz, 2H), 5.82 (s, 2H), 3.74 (s, 3H), 3.61-3.68 (q, J = 7.5 Hz, 2H), 1.17-1.28 (t, J = 7.5 Hz, 3H). |
| 8 | 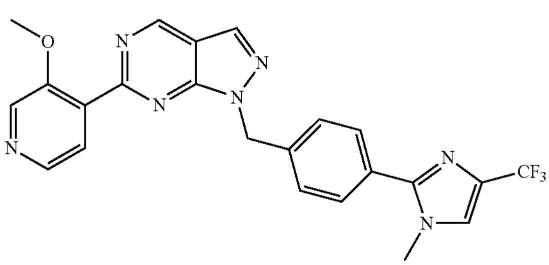 [SMILES: COc1cnccc1-c1ncc2cnn(Cc3ccc(-c4nc(C(F)(F)F)cn4C)cc3)c2n1] | I-1, | LC-MS (Method A) (ESI+): m/z 466 (M + H)+; 1H-NMR (300 MHz, CDCl3) δ 9.33 (s, 1H), 8.53 (s, 1H), 8.42 (d, J = 5.1 Hz, 1H), 8.22 (s, 1H), 7.72 (d, J = 5.1 Hz, 1H), 7.61 (d, J = 8.4 Hz, 2H), 7.53 (d, J = 8.4 Hz, 2H), 7.30 (s, 1H), 5.78 (s, 2H), 4.02 (s, 3H), 3.73 (s, 3H). |

-continued

| Example | Structure | Starting material | Analytical data |
|---|---|---|---|
| 9 | 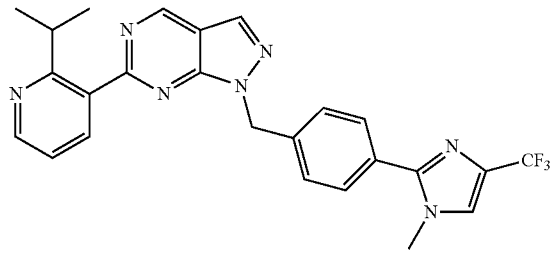 [SMILES: CC(C)c1ncccc1-c1ncc2cnn(Cc3ccc(-c4nc(C(F)(F)F)cn4C)cc3)c2n1] | I-1 and BB-1 | LC-MS (Method A) (ESI+): m/z 478 (M + H)+; $^1$H-NMR (300 MHz, CD$_3$OD) δ 9.40 (s, 1H), 8.61 (dd, J = 4.8, 1.5 Hz, 1H), 8.39 (s, 1H), 8.14 (dd, J = 7.8, 1.5 Hz, 1H), 7.67 (s, 1H), 7.62 (d, J = 8.1 Hz, 2H), 7.50 (d, J = 8.1 Hz, 2H), 7.39 (m, 1H), 5.82 (s, 2H), 3.74 (s, 3H), 3.65 (m, 1H), 1.24-1.29 (d, J = 6.6 Hz, 6H). |
| 10 | 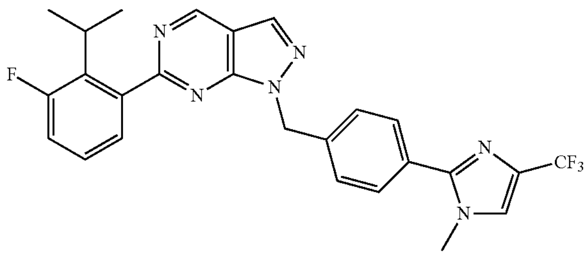 [SMILES: CC(C)c1c(F)cccc1-c1ncc2cnn(Cc3ccc(-c4nc(C(F)(F)F)cn4C)cc3)c2n1] | I-1 and BB-2 | LC-MS (Method A) (ESI+): m/z 495 (M + H)+; $^1$H-NMR (300 MHz, CD$_3$OD) δ 9.36 (s, 1H), 8.39 (s, 1H), 7.67 (s, 1H), 7.62 (d, J = 8.1 Hz, 2H), 7.49 (d, J = 8.1 Hz, 2H), 7.28-7.40 (m, 2H), 7.18 (m, 1H), 5.80 (s, 2H), 3.74 (s, 3H), 3.21 (m, 1H), 1.31 (dd, J = 7.2, 1.2 Hz, 6H). |
| 11 | 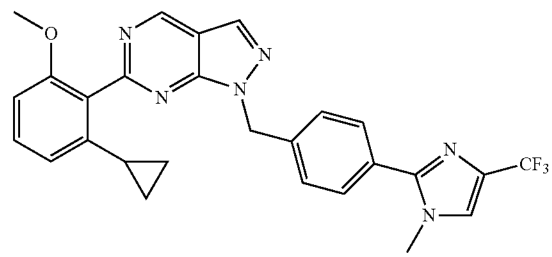 [SMILES: COc1cccc(C2CC2)c1-c1ncc2cnn(Cc3ccc(-c4nc(C(F)(F)F)cn4C)cc3)c2n1] | I-1 and BB-3 | LC-MS (Method A) (ESI+): m/z 505 (M + H)+; $^1$H-NMR (300 MHz, CD$_3$OD) δ 9.35 (s, 1H), 8.39 (s, 1H), 7.67 (s, 1H), 7.60 (d, J = 8.4 Hz, 2H), 7.49 (d, J = 8.4 Hz, 2H), 7.36 (t, J = 8.1 Hz, 2H), 6.96 (d, J = 8.1 Hz, 1H), 6.70 (d, J = 8.1 Hz, 1H), 5.80 (s, 2H), 3.74 (s, 3H), 3.71 (s, 3H), 1.49 (m, 1H), 0.55-0.57 (d, J = 6.9 Hz, 4H). |
| 12 | 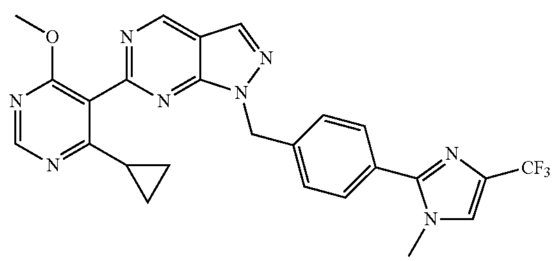 [SMILES: COc1ncnc(C2CC2)c1-c1ncc2cnn(Cc3ccc(-c4nc(C(F)(F)F)cn4C)cc3)c2n1] | I-1 and BB-4 | LC-MS (Method A) (ESI+): m/z 507 (M + H)+; $^1$H-NMR (300 MHz, CD$_3$OD) δ 9.40 (s, 1H), 8.64 (s, 1H), 8.41 (s, 1H), 7.68 (s, 1H), 7.61 (d, J = 8.1 Hz, 2H), 7.51 (d, J = 8.1 Hz, 2H), 5.80 (s, 2H), 3.91 (s, 3H), 3.74 (s, 3H), 1.68 (m, 1H), 1.12-1.19 (m, 2H), 0.85-0.92 (m, 2H). |
| 13 | 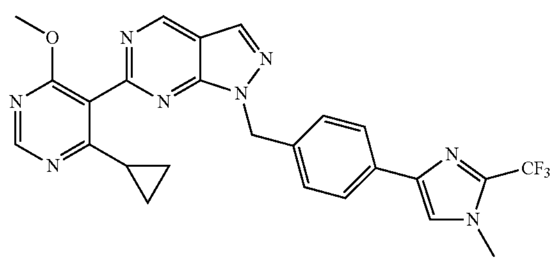 [SMILES: COc1ncnc(C2CC2)c1-c1ncc2cnn(Cc3ccc(-c4cn(C)c(C(F)(F)F)n4)cc3)c2n1] | I-16 and BB-4 | LC-MS (Method B) (ESI+): m/z 507.10 (M + H)+; $^1$H-NMR (400 MHz, DMSO-d$_6$) δ 9.49 (s, 1H), 8.71 (s, 1H), 8.49(s, 1H), 7.94 (s,1H), 7.70 (d, J = 7.8 Hz, 2H), 7.33 (d, J = 8.3 Hz, 2H), 5.69 (s, 2H), 3.86 (s, 3H), 3.82 (s, 3H), 1.60-1.69 (m, 1H), 1.03-1.09 (m, 2H), 0.85 (dd, J = 3.2, 7.6 Hz, 2H). |
| 14 | 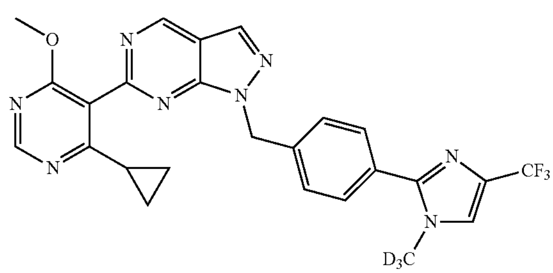 [SMILES: [2H]C([2H])([2H])n1cc(C(F)(F)F)nc1-c1ccc(Cn2ncc3cnc(-c4c(OC)ncnc4C4CC4)nc32)cc1] | I-15 and BB-4 | LC-MS (Method C) (ESI+): m/z 510.20 (M + H)+; $^1$H-NMR (400 MHz, DMSO-d$_6$) δ 9.51 (s, 1H), 8.71 (s, 1H), 8.52 (s, 1H), 7.92 (s, 1H), 7.68 (d, J = 8.31 Hz, 2H), 7.41 (d, J = 8.31 Hz, 2H), 5.78 (s, 2H), 3.85 (s, 3H), 1.65 (td, J = 3.73, 7.70 Hz, 1H), 1.04-1.08 (m, 2H), 0.86 (dd, J = 2.93, 7.83 Hz, 2H). |

-continued

| Example | Structure | Starting material | Analytical data |
|---|---|---|---|
| 15 | 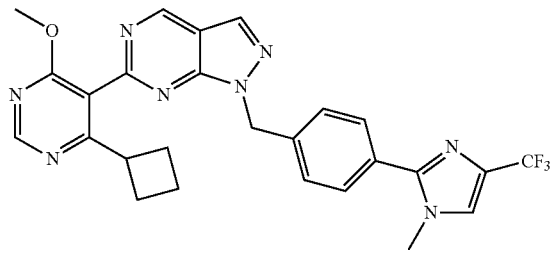 [SMILES: COc1ncnc(C2CCC2)c1-c1ncc2cnn(Cc3ccc(-c4nc(C(F)(F)F)cn4C)cc3)c2n1] | I-1 and BB-20 | LC-MS (Method B) (ESI+): m/z 521.20 (M + H)+; $^1$H-NMR (400 MHz, DMSO-$d_6$) δ 9.48 (s, 1H), 8.89 (s, 1H), 8.53 (s, 1H), 7.92 (s, 1H), 7.68 (d, J = 8.31 Hz, 2H), 7.38 (d, J = 8.31 Hz, 2H), 5.77 (s, 2H), 3.86 (s, 3H), 3.74 (s, 3H), 3.35-3.40 (m, 1H), 2.24 (t, J = 9.54 Hz, 2H), 1.65-1.78 (m, 4H). |
| 16 | 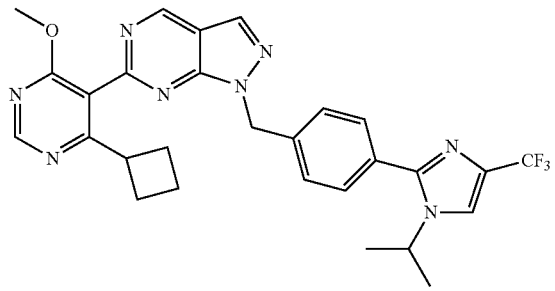 [SMILES: COc1ncnc(C2CCC2)c1-c1ncc2cnn(Cc3ccc(-c4nc(C(F)(F)F)cn4C(C)C)cc3)c2n1] | I-6 and BB-20 | LC-MS (Method B) (ESI+): m/z 549.20 (M + H)+; $^1$H-NMR (400 MHz, DMSO-$d_6$) δ 9.48 (s, 1H), 8.89 (s, 1H), 8.53 (s, 1H), 8.17 (s, 1H), 7.53 (d, J = 8.03 Hz, 2H), 7.39 (d, J = 8.03 Hz, 2H), 5.78 (s, 2H), 4.41 (td, J = 6.43, 12.99 Hz, 1H), 3.86 (s, 3H), 2.19-2.28 (m, 2H), 1.62-1.84 (m, 5H), 1.37 (d, J = 6.53 Hz, 6H). |
| 17 | 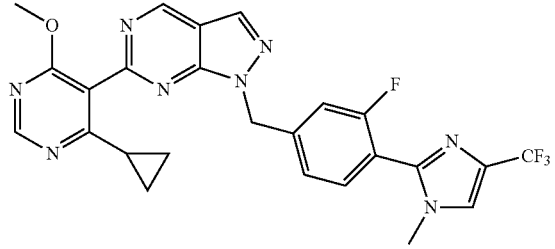 | I-8 and BB-4 | LC-MS (Method B) (ESI+): m/z 525.05 (M + H)+; $^1$H-NMR (400 MHz, DMSO-$d_6$) δ 9.42 (s, 1H), 8.61 (s, 1H), 8.44 (s, 1H), 7.89 (s, 1H), 7.46 (t, J = 7.6 Hz, 1H), 7.25 (d, J = 11.2 Hz, 1H), 7.14 (d, J = 7.8 Hz, 1H), 5.72 (s, 2H), 3.74 (s, 3H), 3.46 (s, 3H), 1.52-1.61 (m, 1H), 0.96 (s, 2H), 0.73-0.80 (m, 2H). |
| 18 | 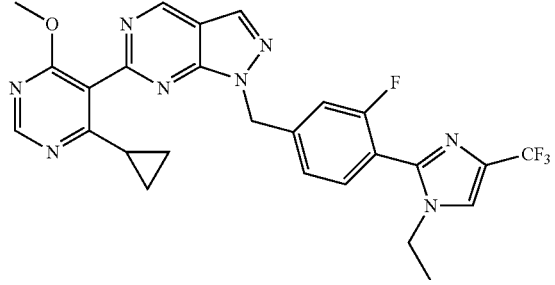 [SMILES: CCn1cc(C(F)(F)F)nc1-c1ccc(Cn2ncc3cnc(-c4c(OC)ncnc4C4CC4)nc32)cc1F] | I-10 and BB-4 | LC-MS (Method B) (ESI+): m/z 539.05 (M + H)+; $^1$H-NMR (400 MHz, DMSO-$d_6$) δ 9.52 (s, 1H), 8.71 (s, 1H), 8.54 (s, 1H), 8.10 (s, 1H), 7.54 (t, J = 7.73 Hz, 1H), 7.35 (d, J = 10.97 Hz, 1H), 7.23 (d, J = 7.98 Hz, 1H), 5.82 (s, 2H), 3.86-3.88 (m, 1H), 3.85 (s, 3H), 3.81-3.84 (m, 1H), 1.63-1.71 (m, 1H), 1.24 (t, J = 7.23 Hz, 3H), 1.03-1.08 (m, 2H), 0.82-0.89 (m, 2H). |
| 19 | 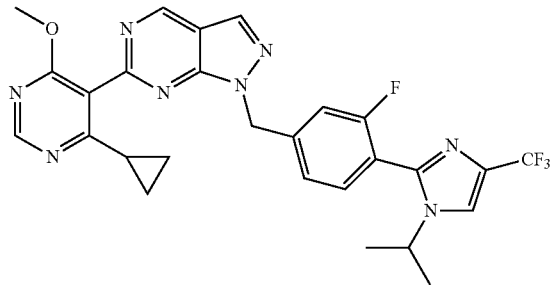 [SMILES: COc1ncnc(C2CC2)c1-c1ncc2cnn(Cc3ccc(-c4nc(C(F)(F)F)cn4C(C)C)c(F)c3)c2n1] | I-11 and BB-4 | LC-MS (Method B) (ESI+): m/z 553.30 (M + H)+; $^1$H-NMR (400 MHz, DMSO-$d_6$) δ 9.52 (s, 1H), 8.70-8.73 (m, 1H), 8.54 (s, 1H), 8.24 (s, 1H), 7.52 (t, J = 7.83 Hz, 1H), 7.35 (d, J = 10.76 Hz, 1H), 7.23 (d, J = 9.29 Hz, 1H), 5.82 (s, 2H), 4.09 (td, J = 6.54, 12.84 Hz, 1H), 3.85 (s, 3H), 1.62-1.70 (m, 1H), 1.33 (d, J = 6.36 Hz, 6H), 1.06 (td, J = 3.61, 6.97 Hz, 2H), 0.83-0.88 (m, 2H). |

-continued

| Example | Structure | Starting material | Analytical data |
|---|---|---|---|
| 20 | 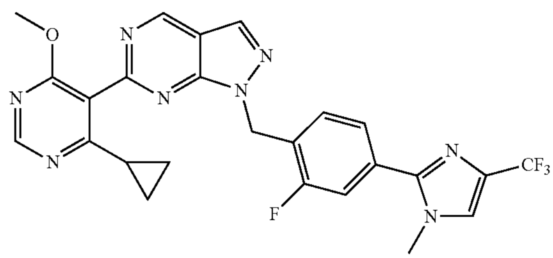 [SMILES: COc1ncnc(C2CC2)c1-c1ncc2cnn(Cc3ccc(-c4nc(C(F)(F)F)cn4C)cc3F)c2n1] | I-9 and BB-4 | LC-MS (Method C) (ESI+): m/z 525.05 (M + H)+; 1H-NMR (400 MHz, DMSO-d6) δ 9.50 (s, 1H), 8.72 (s, 1H), 8.51 (s, 1H), 7.96 (s, 1H), 7.52-7.61 (m, 2H), 7.42 (t, J = 7.8 Hz, 1H), 5.80 (s, 2H), 3.85 (s, 3H), 3.78 (s, 3H), 1.61-1.70 (m, 1H), 1.06 (s, 2H), 0.87 (dd, J = 3.2, 8.1 Hz, 2H). |
| 21 | 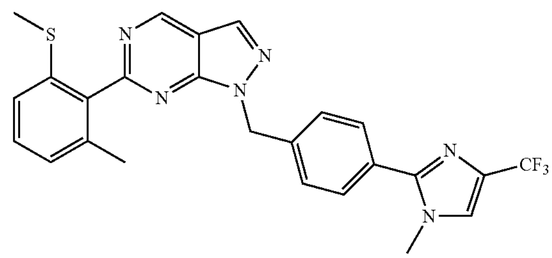 [SMILES: CSc1cccc(C)c1-c1ncc2cnn(Cc3ccc(-c4nc(C(F)(F)F)cn4C)cc3)c2n1] | I-1 and BB-6 | LC-MS (Method A) (ESI+): m/z 495 (M + H)+; 1H-NMR (300 MHz, CDCl3) δ 9.33 (s, 1H), 8.22 (s, 1H), 7.57 (d, J = 8.1 Hz, 2H), 7.49 (d, J = 8.4 Hz, 2H), 7.26-7.35 (m, 3H), 7.12 (d, J = 5.1 Hz, 1H), 5.76 (s, 2H), 3.73 (s, 3H), 2.38 (s, 3H), 2.11 (s, 3H). |
| 22 | 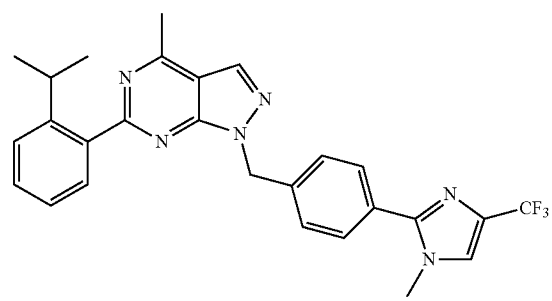 [SMILES: Cc1nc(-c2ccccc2C(C)C)nc2c1cnn2Cc1ccc(-c2nc(C(F)(F)F)cn2C)cc1] | I-2 and | LC-MS (Method A) (ESI+): m/z 491 (M + H)+; 1H-NMR (300 MHz, CDCl3) δ 8.19 (s, 1H), 7.67 (d, J = 7.5 Hz, 1H), 7.58 (d, J = 8.1 Hz, 2H), 7.42-7.52 (m, 4H), 7.27-7.35 (m, 2H), 5.73 (s, 2H), 3.72 (s, 3H), 3.49 (m, 1H), 2.87 (s, 3H), 1.25-1.28 (d, J = 6.9 Hz, 6H). |
| 23 | 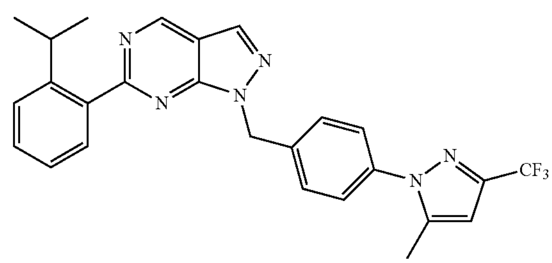 [SMILES: Cc1cc(C(F)(F)F)nn1-c1ccc(Cn2ncc3cnc(-c4ccccc4C(C)C)nc32)cc1] | I-19 and | LC-MS (Method A) (ESI+): m/z 477 (M + H)+; 1H-NMR (300 MHz, CDCl3) δ 9.31 (s, 1H), 8.21 (s, 1H), 7.71 (d, J = 7.5 Hz, 1H), 7.50-7.70 (m, 4H), 7.42-7.49 (m, 2H), 7.30-7.39 (m, 1H), 6.44 (s, 1H), 5.76 (s, 2H), 3.56 (m, 1H), 2.30 (s, 3H), 1.27 (d, J = 6.6 Hz, 6H). |
| 24 | 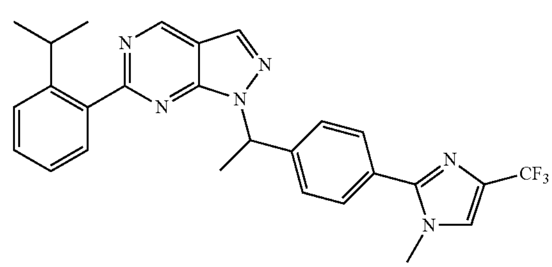 [SMILES: CC(C)c1ccccc1-c1ncc2cnn(C(C)c3ccc(-c4nc(C(F)(F)F)cn4C)cc3)c2n1] | I-24 and | LC-MS (Method A) (ESI+): m/z 491 (M + H)+; 1H-NMR (300 MHz, CDCl3) δ 9.28 (s, 1H), 8.21 (s, 1H), 7.70 (d, J = 7.5 Hz, 1H), 7.50-7.60 (m, 4H), 7.40-7.49 (m, 2H), 7.27-7.35 (m, 2H), 6.35 (q, J = 7.2 Hz, 1H), 3.73 (s, 3H), 3.56 (m, 1H), 2.06-2.08 (d, J = 7.2 Hz, 3H), 1.29-1.31 (d, J = 6.6 Hz, 3H), 1.21-1.23 (d, J = 6.6 Hz, 3H). |

-continued

| Example | Structure | Starting material | Analytical data |
|---|---|---|---|
| 25 | 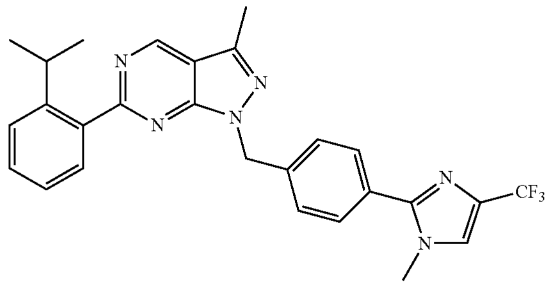 [SMILES: Cc1nn(Cc2ccc(-c3nc(C(F)(F)F)cn3C)cc2)c2nc(-c3ccccc3C(C)C)ncc12] | I-4 and <br> (2-isopropylphenyl)boronic acid | LC-MS (Method A) (ESI+): m/z 491 (M + H)+; 1H-NMR (300 MHz, CDCl3) δ 9.21 (s, 1H), 7.69 (d, J = 7.2 Hz, 1H), 7.57 (d, J = 8.1 Hz, 2H), 7.42-7.50 (m, 4H), 7.27-7.35 (m, 2H), 5.67 (s, 2H), 3.73 (s, 3H), 3.54 (m, 1H), 2.66 (s, 3H), 1.24-1.26 (d, J = 6.9 Hz, 6H). |
| 26 | 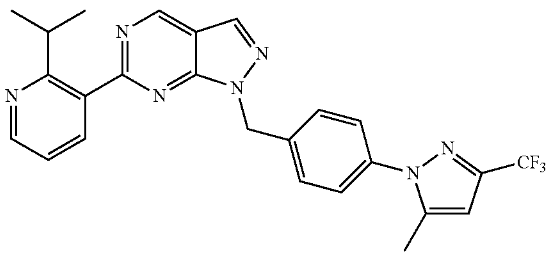 [SMILES: Cc1cc(C(F)(F)F)nn1-c1ccc(Cn2ncc3cnc(-c4cccnc4C(C)C)nc32)cc1] | I-19 and BB-1 | LC-MS (Method A) (ESI+): m/z 478 (M + H)+; 1H-NMR (300 MHz, CD3OD) 9.41 (s, 1H), 8.62 (dd, J = 4.8, 1.8 Hz, 1H), 8.41 (s, 1H), 8.17 (d, J = 8.1 Hz, 1H), 7.45-7.53 (m, 4H), 7.41 (m, 1H), 6.56 (s, 1H), 5.84 (s, 2H), 3.66 (m, 1H), 2.31 (s, 3H), 1.27-1.29 (d, J = 6.9 Hz, 6H). |
| 27 | 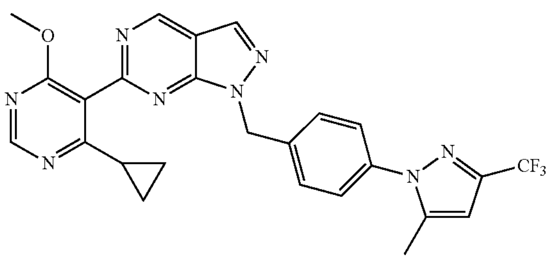 [SMILES: COc1ncnc(C2CC2)c1-c1ncc2cnn(Cc3ccc(-n4nc(C(F)(F)F)cc4C)cc3)c2n1] | I-19 and BB-4 | LC-MS (Method A) (ESI+): m/z 507 (M + H)+; 1H-NMR (300 MHz, CD3OD) δ 9.40 (s, 1H), 8.64 (s, 1H), 8.42 (s, 1H), 7.54 (d, J = 8.4 Hz, 2H), 7.46 (d, J = 8.4 Hz, 2H), 6.56 (s, 1H), 5.82 (s, 2H), 3.91 (s, 3H), 2.31 (s, 3H), 1.61 (m, 1H), 1.12-1.19 (m, 2H), 0.82-0.91 (m, 2H). |
| 28 | 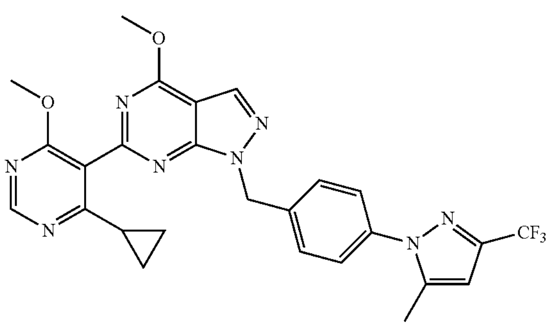 [SMILES: COc1ncnc(C2CC2)c1-c1nc(OC)c2cnn(Cc3ccc(-n4nc(C(F)(F)F)cc4C)cc3)c2n1] | I-22 and BB-4 | LC-MS (Method A) (ESI+): m/z 537 (M + H)+; 1H-NMR (300 MHz, CD3OD) δ 8.61 (s, 1H), 8.22 (s, 1H), 7.40-7.64 (m, 4H), 6.56 (s, 1H), 5.75 (s, 2H), 4.17 (s, 3H), 3.92 (s, 3H), 2.31 (s, 3H), 1.77 (m, 1H), 1.10-1.20 (m, 2H), 0.85-0.97 (m, 2H). |
| 29 | 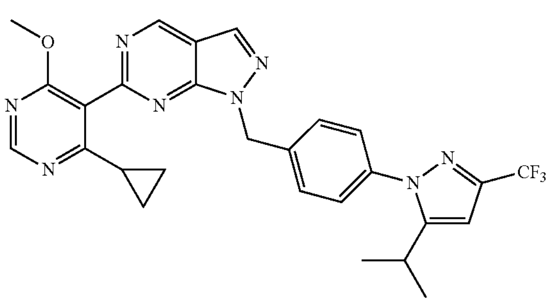 | I-20 and BB-4 | LC-MS (Method B) (ESI+): m/z 535.15 (M + H)+; 1H-NMR (400 MHz, DMSO-d6) δ 9.52 (s, 1H), 8.71 (s, 1H), 8.54 (s, 1H), 7.43-7.52 (m, 4H), 6.81 (s, 1H), 5.82 (s, 2H), 3.85 (s, 3H), 2.92 (td, J = 6.73, 13.46 Hz, 1H), 1.61-1.68 (m, 1H), 1.11 (d, J = 6.98 Hz, 6H), 1.03-1.07 (m, 2H), 0.85 (dd, J = 3.24, 7.73 Hz, 2H). |

| Example | Structure | Starting material | Analytical data |
|---|---|---|---|
| 30 | 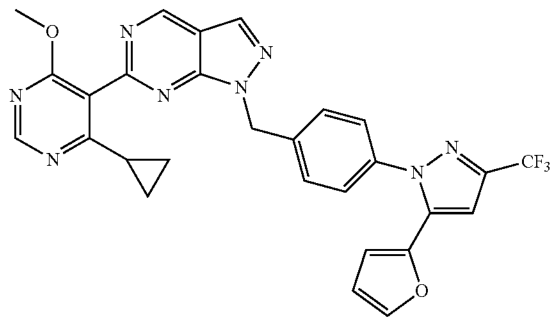 [SMILES: COc1ncnc(C2CC2)c1-c1ncc2cnn(Cc3ccc(-n4nc(C(F)(F)F)cc4-c4ccco4)cc3)c2n1] | I-21 and B-4 | LC-MS (Method B) (ESI+): m/z 559.30 (M + H)+; $^1$H-NMR (400 MHz, DMSO-$d_6$) δ 9.52 (s, 1H), 8.71 (s, 1H), 8.53-8.55 (m, 1H), 7.75 (s, 1H), 7.41-7.49 (m, 4H), 7.26 (s, 1H), 6.53 (dd, J = 1.75, 3.24 Hz, 1H), 6.26 (d, J = 2.99 Hz, 1H), 5.82 (s, 2H), 3.84 (s, 3H), 1.60-1.68 (m, 1H), 1.02-1.07 (m, 2H), 0.82-0.87 (m, 2H). |
| 31 | 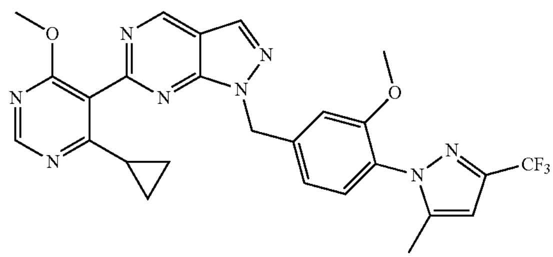 [SMILES: COc1cc(Cn2ncc3cnc(-c4c(OC)ncnc4C4CC4)nc32)ccc1-n1nc(C(F)(F)F)cc1C] | I-23 and BB-4 | LC-MS (Method B) (ESI+): m/z 537.3 (M + H)+; $^1$H-NMR (300 MHz, DMSO-d6) δ 9.52 (s, 1H), 8.71 (s, 1H), 8.54 (s, 1H), 7.30-7.34 (m, 2H), 6.87 (d, J = 7.48 Hz, 1H), 6.66 (s, 1H), 5.80 (s, 2H), 3.84 (s, 3H), 3.74 (s, 3H), 2.06 (s, 3H), 1.62 (dt, J = 3.99, 7.73 Hz, 1H), 1.06 (d, J = 2.49 Hz, 2H), 0.84 (dd, J = 2.99, 7.48 Hz, 2H). |
| 32 | 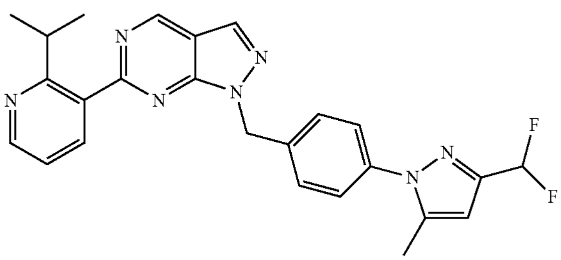 [SMILES: Cc1cc(C(F)F)nn1-c1ccc(Cn2ncc3cnc(-c4cccnc4C(C)C)nc32)cc1] | I-32 and BB-1 | LC-MS (Method A) (ESI+): m/z 460 (M + H)+; $^1$H-NMR (300 MHz, $CD_3OD$) δ 9.40 (s, 1H), 8.61 (dd, J = 4.8, 1.5 Hz, 1H), 8.40 (s, 1H), 8.14 (dd, J = 7.8, 1.5 Hz, 1H), 7.52 (d, J = 8.7 Hz, 2H), 7.46 (d, J = 8.7 Hz, 2H), 7.39 (m, 1H), 6.70 (t, J = 54.9 Hz, 1H), 6.45 (s, 1H), 5.83 (s, 2H), 3.64 (m, 1H), 2.30 (s, 3H), 1.26-1.28 (d, J = 6.6 Hz, 6H). |
| 33 | 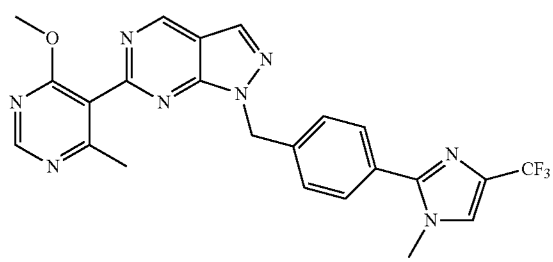 [SMILES: COc1ncnc(C)c1-c1ncc2cnn(Cc3ccc(-c4nc(C(F)(F)F)cn4C)cc3)c2n1] | I-1 and BB-5 | LC-MS (Method A) (ESI+): m/z 481 (M + H)+; $^1$H-NMR (300 MHz, $CD_3OD$) δ 9.40 (s, 1H), 8.74 (s, 1H), 8.42 (s, 1H), 7.68 (s, 1H), 7.65 (d, J = 8.7 Hz, 2H), 7.51 (d, J = 8.7 Hz, 2H), 5.80 (s, 2H), 3.95 (s, 3H), 3.74 (s, 3H), 2.29 (s, 3H). |
| 34 | 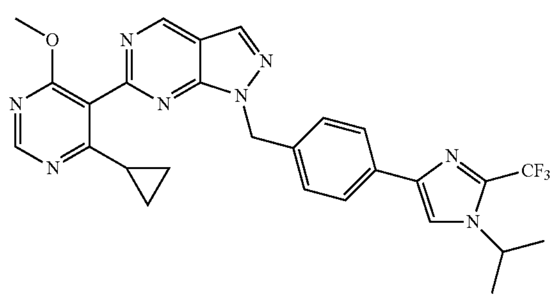 [SMILES: COc1ncnc(C2CC2)c1-c1ncc2cnn(Cc3ccc(-c4cn(C(C)C)c(C(F)(F)F)n4)cc3)c2n1] | I-17 and BB-4 | LC-MS (Method B) (ESI+): m/z 535.15 (M + H)+; $^1$H-NMR (400 MHz, DMSO-$d_6$) δ 9.49 (s, 1H), 8.72 (s, 1H), 8.50 (s, 1H), 8.25 (s, 1H), 7.75 (d, J = 8.48 Hz, 2H), 7.34 (d, J = 7.98 Hz, 2H), 5.69 (s, 2H), 4.56 (td, J = 6.48, 12.96 Hz, 1H), 3.86 (s, 3H), 1.62-1.69 (m, 1H), 1.48 (d, J = 6.48 Hz, 6H), 1.07 (td, J = 3.49, 6.98 Hz, 2H), 0.84-0.89 (m, 2H). |

| Example | Structure | Starting material | Analytical data |
|---|---|---|---|
| 35 | 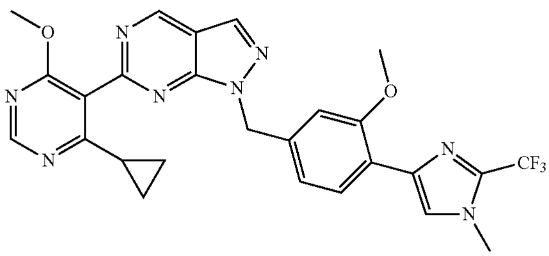 [SMILES: COc1cc(Cn2ncc3cnc(-c4c(OC)ncnc4C4CC4)nc32)ccc1-c1cn(C)c(C(F)(F)F)n1] | I-18 and BB-4 | LC-MS (Method B) (ESI+): m/z 537.15 (M + H)+; 1H-NMR (400 MHz, DMSO-d6) δ 9.50 (s, 1H), 8.71 (s, 1H), 8.50 (s, 1H), 7.90 (d, J = 7.98 Hz, 1H), 7.85 (s, 1H), 7.11 (s, 1H), 6.86 (d, J = 7.98 Hz, 1H), 5.70 (s, 2H), 3.85 (br s, 3H), 3.84 (br. s, 6H), 1.61 (td, J = 3.62, 7.73 Hz, 1H), 1.02-1.07 (m, 2H), 0.83 (dd, J = 2.74, 7.23 Hz, 2H). |
| 36 | 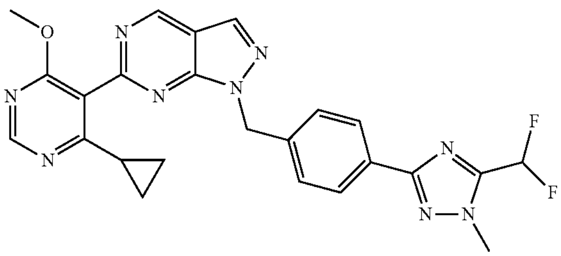 [SMILES: COc1ncnc(C2CC2)c1-c1ncc2cnn(Cc3ccc(-c4nc(C(F)F)n(C)n4)cc3)c2n1] | I-34 and BB-4 | LC-MS (Method A) (ESI+): m/z 490 (M + H)+; 1H-NMR (300 MHz, CDCl3) δ 9.34 (s, 1H), 8.69 (s, 1H), 8.23 (s, 1H), 8.00 (d, J = 8.1 Hz, 2H), 7.48 (d, J = 8.1 Hz, 2H), 6.86 (t, J = 52.5 Hz, 1H), 5.75 (s, 2H), 4.08 (s, 3H), 3.94 (s, 3H), 1.68 (m, 1H), 1.21-1.25 (m, 2H), 0.85-0.93 (m, 2H). |
| 37 | 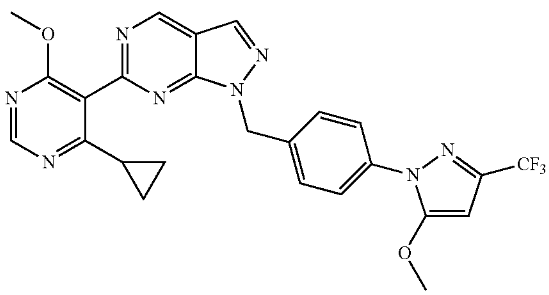 | I-39 and BB-4 | LC-MS (Method A) (ESI+): m/z 523 (M + H)+; 1H-NMR (300 MHz, CD3OD) δ 9.39 (s, 1H), 8.64 (s, 1H), 8.41 (s, 1H), 7.63 (d, J = 8.4 Hz, 2H), 7.47 (d, J = 8.4 Hz, 2H), 6.20 (s, 1H), 5.78 (s, 2H), 3.99 (s, 3H), 3.91 (s, 3H), 1.63 (m, 1H), 1.13-1.17 (m, 2H), 0.86-0.90 (m, 2H). |
| 38 | 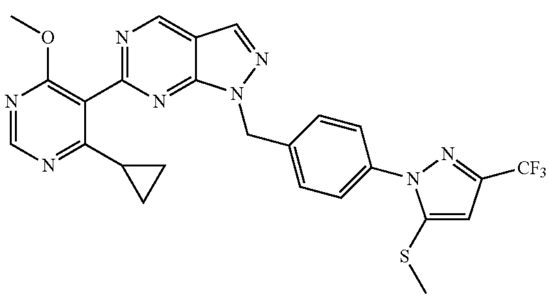 | I-50 and BB-4 | LC-MS (Method A) (ESI+): m/z 539 (M + H)+; 1H-NMR (300 MHz, CD3OD) δ 9.40 (s, 1H), 8.64 (s, 1H), 8.43 (s, 1H), 7.53 (s, 4H), 6.77 (s, 1H), 5.82 (s, 2H), 3.91 (s, 3H), 2.46 (s, 1H), 1.65 (m, 1H), 1.11-1.19 (m, 2H), 0.84-0.93 (m, 2H). |
| 39 | 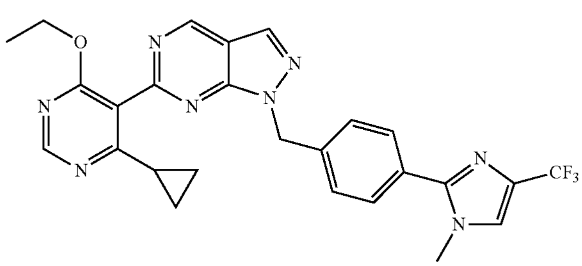 [SMILES: CCOc1ncnc(C2CC2)c1-c1ncc2cnn(Cc3ccc(-c4nc(C(F)(F)F)cn4C)cc3)c2n1] | I-1 and BB-16 | LC-MS (Method B) (ESI+): m/z 520.20 (M + H)+; 1H-NMR (400 MHz, DMSO-d6) δ 9.48 (s, 1H), 8.65 (s, 1H), 8.49 (s, 1H), 7.89 (s, 1H), 7.64 (br d, J = 8.31 Hz, 2H), 7.37 (br d, J = 8.31 Hz, 2H), 5.76 (s, 2H), 4.32 (q, J = 7.01 Hz, 2H), 3.71 (s, 3H), 1.57-1.65 (m, 1H), 1.10 (t, J = 6.85 Hz, 3H), 1.02 (s, 2H), 0.82 (dd, J = 3.18, 7.58 Hz, 2H). |

-continued

| Example | Structure | Starting material | Analytical data |
|---|---|---|---|
| 40 | 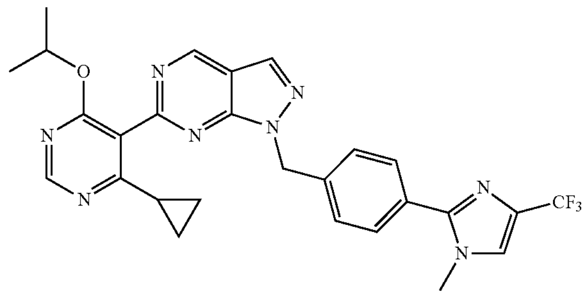 [SMILES: CC(C)Oc1ncnc(C2CC2)c1-c1ncc2cnn(Cc3ccc(-c4nc(C(F)(F)F)cn4C)cc3)c2n1] | I-1 and BB-26 | LC-MS (Method C) (ESI+): m/z 535.15 (M + H)+; $^1$H-NMR (400 MHz, DMSO-$d_6$) δ 9.51 (s, 1H), 8.67 (s, 1H), 8.52 (s, 1H), 7.92 (s, 1H), 7.66 (d, J = 8.31 Hz, 2H), 7.38 (d, J = 8.31 Hz, 2H), 5.79 (s, 2H), 5.30 (td, J = 6.30, 12.35 Hz, 1H), 3.74 (s, 3H), 1.60-1.68 (m, 1H), 1.12 (d, J = 5.87 Hz, 6H), 1.02-1.07 (m, 2H), 0.82-0.87 (m, 2H). |
| 41 | 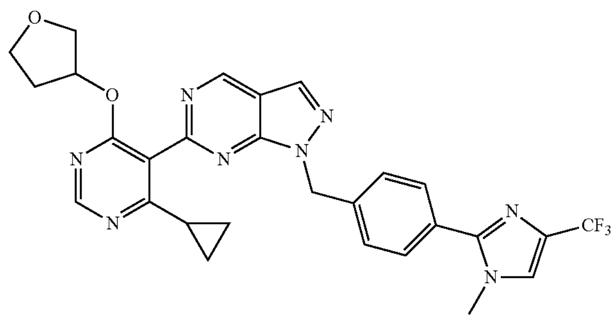 [SMILES: Cn1cc(C(F)(F)F)nc1-c1ccc(Cn2ncc3cnc(-c4c(OC5CCOC5)ncnc4C4CC4)nc32)cc1] | I-1 and BB-7 | LC-MS (Method A) (ESI+): m/z 563 (M + H)+; $^1$H-NMR (300 MHz, CD$_3$OD) δ 9.41 (s, 1H), 8.63 (s, 1H), 8.42 (s, 1H), 7.67 (s, 1H), 7.62 (d, J = 8.1 Hz, 2H), 7.49 (d, J = 8.1 Hz, 2H), 5.81 (s, 2H), 5.67 (m, 1H), 3.92 (m, 1H), 3.74 (s, 3H), 3.55-3.73 (m, 3 H), 2.18 (m, 1H), 1.92 (m, 1H), 1.66 (m, 1H), 1.12-1.21 (m, 2H), 0.85-0.95 (m, 2H). |
| 42 | 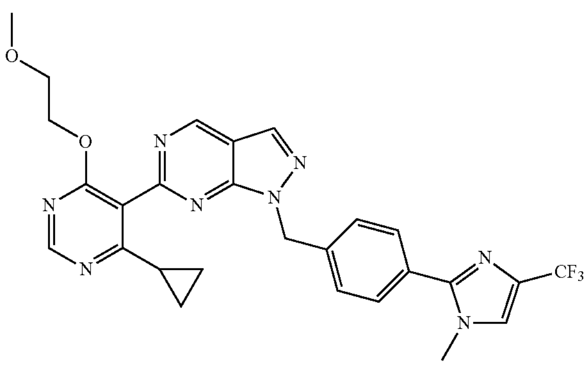 [SMILES: COCCOc1ncnc(C2CC2)c1-c1ncc2cnn(Cc3ccc(-c4nc(C(F)(F)F)cn4C)cc3)c2n1] | I-1 and BB-8 | LC-MS (Method A) (ESI+): m/z 551 (M + H)+; $^1$H-NMR (300 MHz, CDCl$_3$) δ 9.33 (s, 1H), 8.66 (s, 1H), 8.24 (s, 1H), 7.59 (d, J = 8.4 Hz, 2H), 7.50 (d, J = 8.4 Hz, 2H), 7.30 (s, 1H), 5.76 (s, 2H), 4.54 (t, J = 4.8 Hz, 2H), 3.73 (s, 3H), 3.61 (t, J = 4.8 Hz, 2H), 3.23 (s, 3H), 1.70 (m, 1H), 1.22-1.28 (m, 2H), 0.85-0.92 (m, 2H). |
| 43 | 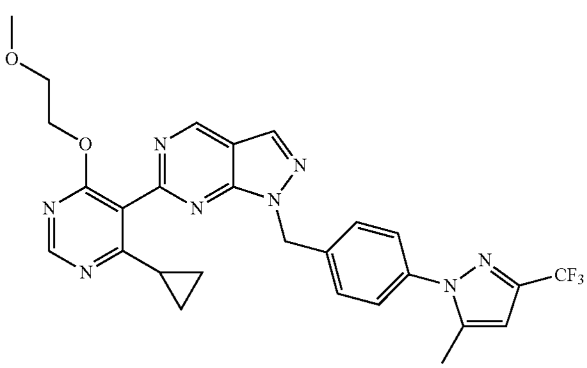 [SMILES: COCCOc1ncnc(C2CC2)c1-c1ncc2cnn(Cc3ccc(-n4nc(C(F)(F)F)cc4C)cc3)c2n1] | I-19 and BB-8 | LC-MS (Method A) (ESI+): m/z 551 (M + H)+; $^1$H-NMR (300 MHz, CDCl$_3$) δ 9.33 (s, 1H), 8.66 (s, 1H), 8.24 (s, 1H), 7.55 (d, J = 8.4 Hz, 2H), 7.41 (d, J = 8.4 Hz, 2H), 6.44 (s, 1H), 5.76 (s, 2H), 4.54 (t, J = 4.8 Hz, 2H), 3.61 (t, J = 4.8 Hz, 2H), 3.23 (s, 3H), 2.32 (s, 3H), 1.69 (m, 1H), 1.22-1.28 (m, 2H), 0.86-0.93 (m, 2H). |

| Example | Structure | Starting material | Analytical data |
|---|---|---|---|
| 44 | 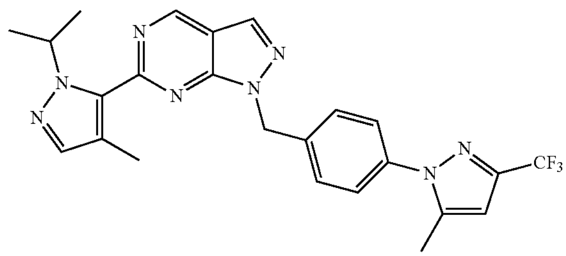 [SMILES: Cc1cnn(C(C)C)c1-c1ncc2cnn(Cc3ccc(-n4nc(C(F)(F)F)cc4C)cc3)c2n1] | I-19 and BB-31 | LC-MS (Method A) (ESI+): m/z 481 (M + H)$^+$; $^1$H-NMR (300 MHz, CD$_3$OD) δ 9.39 (s, 1H), 8.36 (s, 1H), 7.46-7.54 (m, 4H), 7.44 (s, 1H), 6.56 (s, 1H), 5.82 (s, 2H), 5.48 (m, 1H), 2.35 (s, 3H), 2.30 (s, 3H), 1.46 (d, J = 6.6 Hz, 6H). |
| 45 | 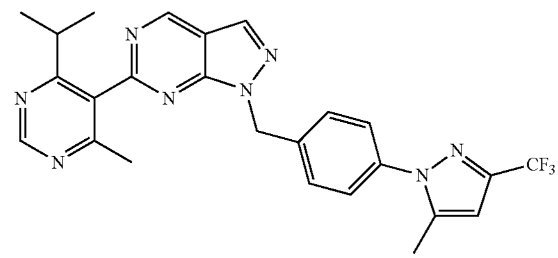 [SMILES: Cc1ncnc(C(C)C)c1-c1ncc2cnn(Cc3ccc(-n4nc(C(F)(F)F)cc4C)cc3)c2n1] | I-19 and BB-35 | LC-MS (Method A) (ESI+): m/z 515 (M + H)$^+$; $^1$H-NMR (300 MHz, CD$_3$OD) δ 9.44 (s, 1H), 9.04 (s, 1H), 8.46 (s, 1H), 7.52 (d, J = 8.4 Hz, 2H), 7.46 (d, J = 8.4 Hz, 2H), 6.56 (s, 1H), 5.83 (s, 2H), 2.73 (m, 1H), 2.31 (s, 3H), 2.27 (s, 3H), 1.16 (d, J = 6.6 Hz, 6H). |
| 46 | 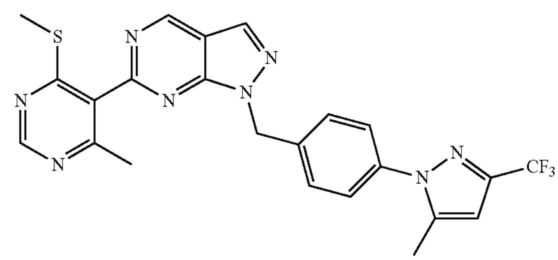 [SMILES: CSc1ncnc(C)c1-c1ncc2cnn(Cc3ccc(-n4nc(C(F)(F)F)cc4C)cc3)c2n1] | I-19 and BB-9 | LC-MS (Method A) (ESI+): m/z 497 (M + H)$^+$; $^1$H-NMR (300 MHz, CD$_3$OD) δ 9.43 (s, 1H), 8.88 (s, 1H), 8.44 (s, 1H), 7.56 (d, J = 8.4 Hz, 2H), 7.47 (d, J = 8.4 Hz, 2H), 6.57 (s, 1H), 5.83 (s, 2H), 2.52 (s, 3H), 2.31 (s, 3H), 2.30 (s, 3H). |
| 47 | 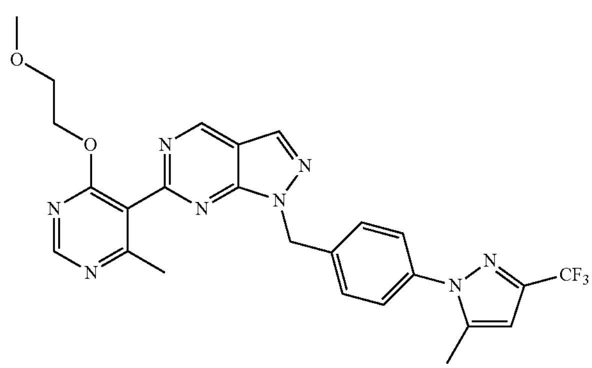 [SMILES: COCCOc1ncnc(C)c1-c1ncc2cnn(Cc3ccc(-n4nc(C(F)(F)F)cc4C)cc3)c2n1] | I-19 and BB-10 | LC-MS (Method A) (ESI+): m/z 525 (M + H)$^+$; $^1$H-NMR (300 MHz, CD$_3$OD) δ 9.40 (s, 1H), 8.72 (s, 1H), 8.42 (s, 1H), 7.54 (d, J = 8.4 Hz, 2H), 7.47 (d, J = 8.4 Hz, 2H), 6.56 (s, 1H), 5.82 (s, 2H), 4.53 (t, J = 4.5 Hz, 2H), 3.57 (t, J = 4.5 Hz, 2H), 3.16 (s, 3H), 2.31 (s, 3H), 2.29 (s, 3H). |
| 48 | 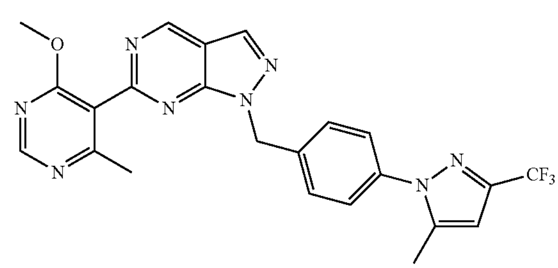 [SMILES: COc1ncnc(C)c1-c1ncc2cnn(Cc3ccc(-n4nc(C(F)(F)F)cc4C)cc3)c2n1] | I-19 and BB-5 | LC-MS (Method A) (ESI+): m/z 481 (M + H)$^+$; $^1$H-NMR (300 MHz, CDCl$_3$) δ 9.33 (s, 1H), 8.77 (s, 1H), 8.25 (s, 1H), 7.53 (d, J = 8.7 Hz, 2H), 7.41 (d, J = 8.7 Hz, 2H), 6.44 (s, 1H), 5.76 (s, 2H), 3.96 (s, 3H), 2.34 (s, 3H), 2.32 (s, 3H). |

-continued

| Example | Structure | Starting material | Analytical data |
|---|---|---|---|
| 49 | 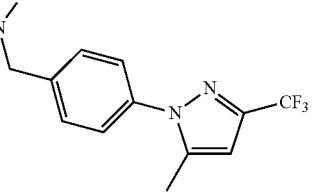 | I-19 and  | LC-MS (Method A) (ESI+): m/z 461 (M + H)+; 1H-NMR (300 MHz, CDCl3) δ 9.34 (s, 1H), 8.93 (d, J = 8.1 Hz, 1H), 8.84 (t, J = 1.5 Hz, 1H), 8.25 (s, 1H), 7.68-7.72 (m, 3H), 7.41 (d, J = 8.4 Hz, 2H), 6.43 (s, 1H), 5.86 (s, 2H), 2.32 (s, 2H). |
| 50 | 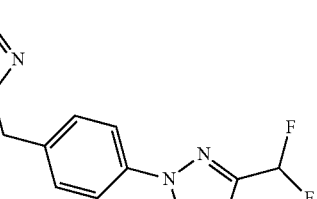 | I-32 and BB-4 | LC-MS (Method A) (ESI+): m/z 489 (M + H)+; 1H-NMR (300 MHz, CD3OD) δ 9.40 (s, 1H), 8.64 (s, 1H), 8.41 (s, 1H), 7.52 (d, J = 8.1 Hz, 2H), 7.44 (d, J = 8.1 Hz, 2H), 6.70 (t, J = 54.9 Hz, 1H), 6.45 (s, 1H), 5.81 (s, 2H), 3.91 (s, 3H), 2.30 (s, 3H), 1.67 (m, 1H), 1.22-1.28 (m, 2H), 0.86-0.93 (m, 2H). |
| 51 | 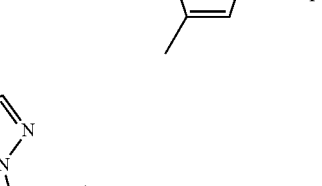 | I-5 and BB-4 | LC-MS (Method C) (ESI+): m/z 521.20 (M + H)+; 1H-NMR (400 MHz, DMSO-d6) δ 9.51 (s, 1H), 8.71 (s, 1H), 8.52 (s, 1H), 8.01 (s, 1H), 7.59 (d, J = 8.31 Hz, 2H), 7.41 (d, J = 7.83 Hz, 2H), 5.79 (s, 2H), 4.04 (q, J = 7.01 Hz, 2H), 3.85 (s, 3H), 1.61-1.69 (m, 1H), 1.29 (t, J = 7.34 Hz, 3H), 1.03-1.08 (m, 2H), 0.85 (dd, J = 3.18, 7.58 Hz, 2H). |
| 52 | 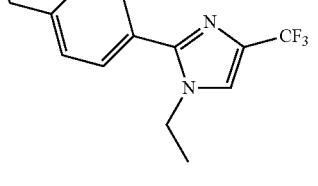 | I-22b and BB-4 | LC-MS (Method A) (ESI+): m/z 551 (M + H)+; 1H-NMR (300 MHz, CD3OD) δ 8.61 (s, 1H), 8.22 (s, 1H), 7.54 (d, J = 8.4 Hz, 2H), 7.48 (d, J = 8.4 Hz, 2H), 5.74 (s, 1H), 4.19 (3, 3H), 4.04-4.11 (q, J = 7.5 Hz, 2H), 3.93 (s, 3H), 1.78 (m, 1H), 1.11-1.19 (m, 2H), 0.84-0.93 (m, 2H). |
| 53 | 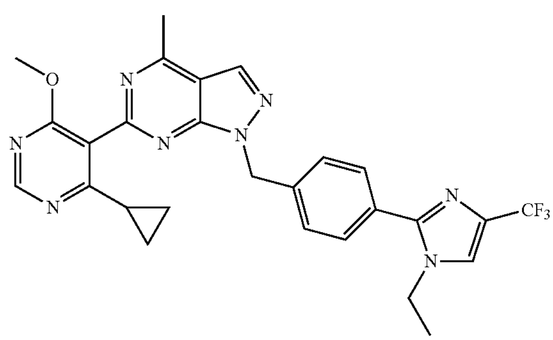 [SMILES: CCn1cc(C(F)(F)F)nc1-c1ccc(Cn2ncc3c(C)nc(-c4c(OC)ncnc4C4CC4)nc32)cc1] | I-3 and BB-4 | LC-MS (Method B) (ESI+): m/z 535.15 (M + H)+; 1H-NMR (400 MHz, DMSO-d6) δ 8.68 (s, 1H), 8.57 (s, 1H), 7.98 (s, 1H), 7.57 (d, J = 7.83 Hz, 2H), 7.38 (d, J = 7.82 Hz, 2H), 5.74 (s, 2H), 4.00-4.07 (m, 2H), 3.84 (s, 3H), 2.83 (s, 3H), 1.58-1.62 (m, 1H), 1.27 (t, J = 7.09 Hz, 3H), 1.01-1.06 (m, 2H), 0.84 (d, J = 4.40 Hz, 2H). |

| Example | Structure | Starting material | Analytical data |
|---|---|---|---|
| 54 | 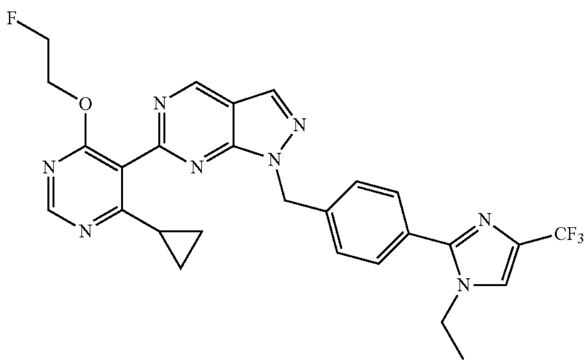 [SMILES: CCn1cc(C(F)(F)F)nc1-c1ccc(Cn2ncc3cnc(-c4c(OCCF)ncnc4C4CC4)nc32)cc1] | I-5 and BB-11 | LC-MS (Method A) (ESI+): m/z 553 (M + H)+; 1H-NMR (300 MHz, CD3OD) δ 9.42 (s, 1H), 8.64 (s, 1H), 8.42 (s, 1H), 7.78 (s, 1H), 7.50-7.57 (m, 4H), 5.81 (s, 2H), 4.64 (s, 2H), 4.55 (m, 1H), 4.47 (m, 1H), 4.06 (q, J = 7.2 Hz, 2H), 1.68 (m, 1H), 1.34 (t, J = 7.2 Hz, 3H), 1.16-1.19 (m, 2H), 0.87-0.94 (m, 2H). |
| 55 | 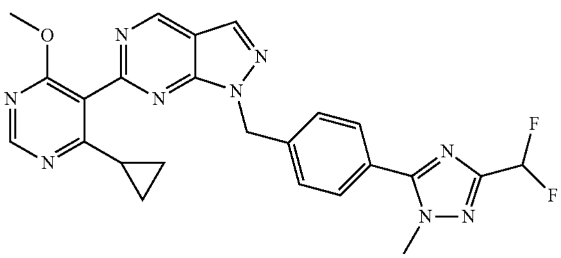 [SMILES: COc1ncnc(C2CC2)c1-c1ncc2cnn(Cc3ccc(-c4nc(C(F)F)nn4C)cc3)c2n1] | I-33 and BB-4 | LC-MS (Method A) (ESI+): m/z 490 (M + H)+; 1H-NMR (300 MHz, CDCl3) δ 9.36 (s, 1H), 8.69 (s, 1H), 8.23 (s, 1H), 7.66 (d, J = 8.4 Hz, 2H), 7.56 (d, J = 8.4 Hz, 2H), 6.72 (t, J = 53.7 Hz, 1H), 5.79 (s, 2H), 4.00 (s, 3H), 3.94 (s, 3H), 1.68 (m, 1H), 1.21-1.24 (m, 2H), 0.85-0.93 (m, 2H). |
| 56 | 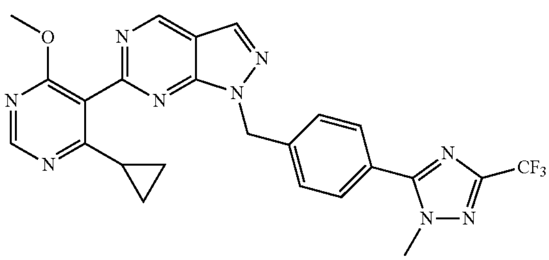 [SMILES: COc1ncnc(C2CC2)c1-c1ncc2cnn(Cc3ccc(-c4nc(C(F)(F)F)nn4C)cc3)c2n1] | I-36 and BB-4 | LC-MS (Method A) (ESI+): m/z 509 (M + H)+; 1HNMR (300 MHz, CDCl3) δ 9.36 (s, 1H), 8.69 (s, 1H), 8.26 (s, 1H), 7.67 (d, J = 8.1 Hz, 2H), 7.57 (d, J = 8.1 Hz, 2H), 5.79 (s, 2H), 4.02 (s, 3H), 3.94 (s, 3H), 1.67 (m, 1H), 1.25-1.28 (m, 2H), 0.87-0.92 (m, 2H). |
| 57 | 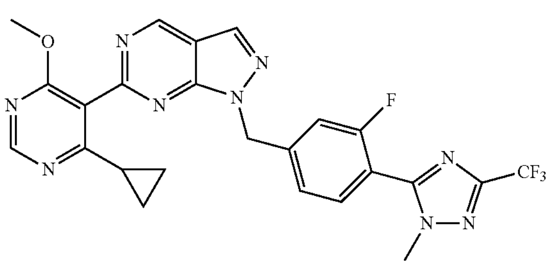 [SMILES: COc1ncnc(C2CC2)c1-c1ncc2cnn(Cc3ccc(-c4nc(C(F)(F)F)nn4C)c(F)c3)c2n1] | I-37 and BB-4 | LC-MS (Method B) (ESI+): m/z 526.30 (M + H)+; 1H-NMR (400 MHz, DMSO-d6) δ 9.52 (s, 1H), 8.71 (s, 1H), 8.55 (s, 1H), 7.70 (t, J = 7.83 Hz, 1H), 7.42 (d, J = 10.76 Hz, 1H), 7.31 (d, J = 7.83 Hz, 1H), 5.85 (s, 2H), 3.87 (s, 3H), 3.85 (s, 3H), 1.63-1.71 (m, 1H), 1.03-1.09 (m, 2H), 0.82-0.89 (m, 2H). |
| 58 | 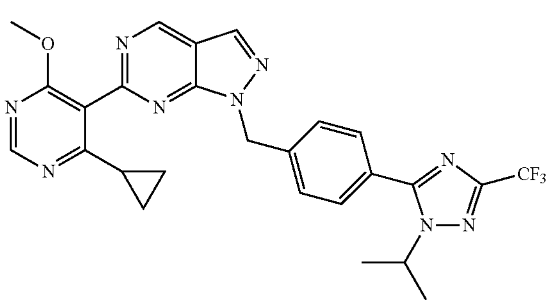 [SMILES: COc1ncnc(C2CC2)c1-c1ncc2cnn(Cc3ccc(-c4nc(C(F)(F)F)nn4C(C)C)cc3)c2n1] | I-38 and BB-4 | LC-MS (Method B) (ESI+): m/z 536.35 (M + H)+; 1H-NMR (400 MHz, DMSO-d6) δ 9.52 (s, 1H), 8.71 (s, 1H), 8.53 (s, 1H), 7.66 (d, J = 7.83 Hz, 2H), 7.49 (d, J = 7.83 Hz, 2H), 5.83 (s, 2H), 4.69 (td, J = 6.42, 13.08 Hz, 1H), 3.85 (s, 3H), 1.62-1.69 (m, 1H), 1.42 (d, J = 6.85 Hz, 6H), 1.03-1.08 (m, 2H), 0.85 (dd, J = 2.93, 7.34 Hz, 2H). |

| Example | Structure | Starting material | Analytical data |
|---|---|---|---|
| 59 | 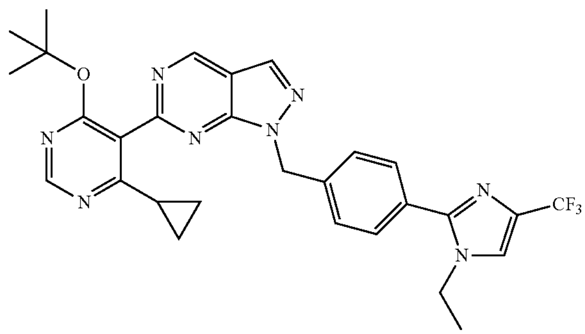 [SMILES: CCn1cc(C(F)(F)F)nc1-c1ccc(Cn2ncc3cnc(-c4c(OC(C)(C)C)ncnc4C4CC4)nc32)cc1] | I-5 and BB-12 | LC-MS (Method A) (ESI+): m/z 563 (M + H)+; 1H-NMR (300 MHz, CD$_3$OD) δ 9.40 (s, 1H), 8.57 (s, 1H), 8.41 (s, 1H), 7.78 (s, 1H), 7.50-7.57 (m, 4H), 5.82 (s, 2H), 4.07 (q, J = 7.2 Hz, 2H), 1.56 (m, 1H), 1.46 (s, 9H), 1.42 (t, J = 7.2 Hz, 3H), 1.11-1.14 (m, 2H), 0.85-0.89 (m, 2H). |
| 60 | 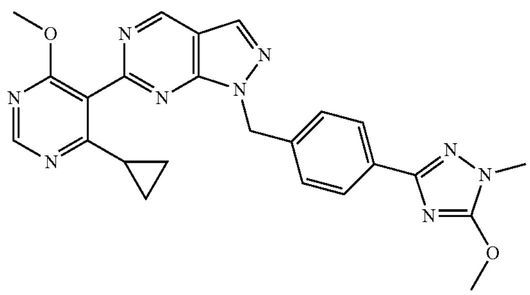 | I-51 and BB-4 | LC-MS (Method A) (ESI+): m/z 541 (M + H)+; 1H-NMR (300 MHz, DMSO-d$_6$) δ 9.51 (s, 1H), 8.72 (s, 1H), 8.51 (s, 1H), 7.84 (d, J = 8.1 Hz, 2H), 7.35 (d, J = 8.1 Hz, 2H), 5.73 (s, 2H), 4.07 (s, 3H), 3.85 (s, 3H), 3.59 (s, 3H), 1.64 (m, 1H), 1.01-1.06 (m, 2H), 0.82-0.89 (m, 2H). |
| 61 | 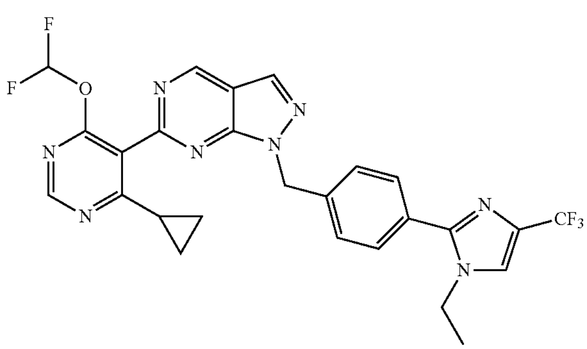 [SMILES: CCn1cc(C(F)(F)F)nc1-c1ccc(Cn2ncc3cnc(-c4c(OC(F)F)ncnc4C4CC4)nc32)cc1] | I-5 and BB-25 | LC-MS (Method A) (ESI+): m/z 557 (M + H)+; 1H-NMR (300 MHz, CD$_3$OD) δ 9.44 (s, 1H), 8.73 (s, 1H), 8.43 (s, 1H), 7.78 (s, 1H), 7.67 (t, J = 72.0 Hz, 1H), 7.43 (s, 4H), 5.82 (s, 2H), 4.06 (q, J = 7.2 Hz, 2H), 1.82 (m, 1H), 1.32 (t, J = 7.2 Hz, 3H), 1.22-1.26 (m, 2H), 0.95-1.02 (m, 2H). |
| 62 | 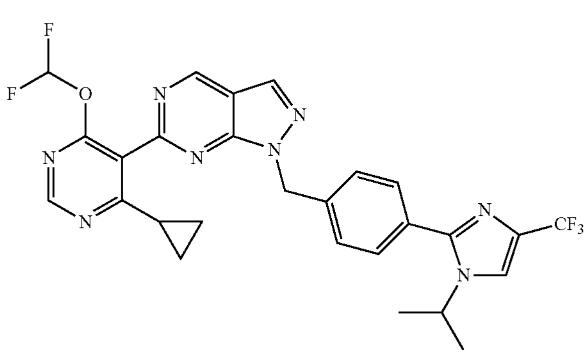 [SMILES: CC(C)n1cc(C(F)(F)F)nc1-c1ccc(Cn2ncc3cnc(-c4c(OC(F)F)ncnc4C4CC4)nc32)cc1] | I-6 and BB-25 | LC-MS (Method C) (ESI+): m/z 570.95 (M + H)+; 1H-NMR (400 MHz, DMSO-d$_6$) δ 9.51 (s, 1H), 8.72 (s, 1H), 8.52 (s, 1H), 8.16 (s, 1H), 7.64-7.94 (m, 1H), 7.52 (d, J = 7.98 Hz, 2H), 7.39 (d, J = 7.98 Hz, 2H), 5.79 (s, 2H), 4.42 (td, J = 6.54, 13.34 Hz, 1H), 1.56-1.64 (m, 1H), 1.37 (d, J = 6.48 Hz, 6H), 1.09 (d, J = 2.99 Hz, 2H), 0.88 (dd, J = 2.99, 7.48 Hz, 2H). |

| Example | Structure | Starting material | Analytical data |
|---|---|---|---|
| 63 | 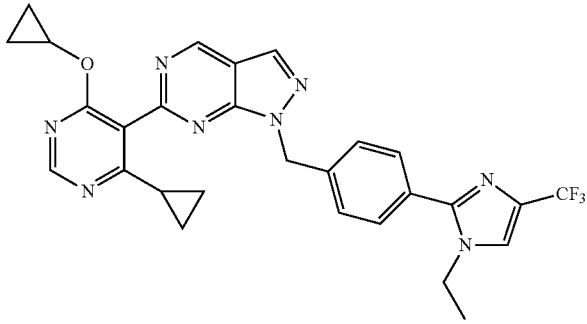 [SMILES: CCn1cc(C(F)(F)F)nc1-c1ccc(Cn2ncc3cnc(-c4c(OC5CC5)ncnc4C4CC4)nc32)cc1] | I-5 and BB-14 | LC-MS (Method A) (ESI+): m/z 547 (M + H)$^+$; $^1$H-NMR (300 MHz, CDCl$_3$) δ 9.32 (s, 1H), 8.75 (s, 1H), 8.24 (s, 1H), 7.45-7.54 (m, 4H), 7.36 (s, 1H), 5.75 (s, 2H), 4.38 (m, 1H), 4.02 (q, J = 7.2 Hz, 2H), 1.70 (m, 1H), 1.38-1.44 (t, J = 7.2 Hz, 3H), 1.21-1.29 (m, 2H), 0.85-0.91 (m, 2H), 0.71-0.77 (m, 2H), 0.55-0.65 (m, 2H). |
| 64 | 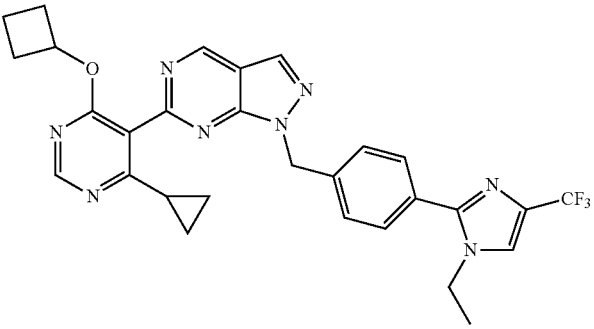 [SMILES: CCn1cc(C(F)(F)F)nc1-c1ccc(Cn2ncc3cnc(-c4c(OC5CCC5)ncnc4C4CC4)nc32)cc1] | I-5 and BB-13 | LC-MS (Method A) (ESI+): m/z 561 (M + H)$^+$; $^1$H-NMR (300 MHz, CD$_3$OD) δ 9.41 (s, 1H), 8.58 (s, 1H), 8.42 (s, 1H), 7.78 (s, 1H), 7.49-7.58 (m, 4H), 5.82 (s, 2H), 5.24 (m, 1H), 4.06 (q, J = 7.2 Hz, 2H), 2.32-2.38 (m, 2H), 1.90-1.97 (m, 2H), 1.62-1.68 (m, 3H), 1.34 (t, J = 7.2 Hz, 3H), 1.11-1.16 (m, 2H), 0.84-0.92 (m, 2H). |
| 65 | 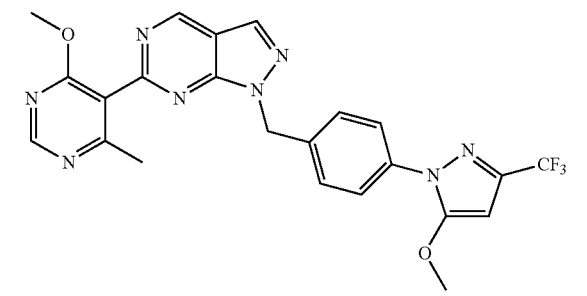 [SMILES: COc1ncnc(C)c1-c1ncc2cnn(Cc3ccc(-n4nc(C(F)(F)F)cc4OC)cc3)c2n1] | I-39 and BB-5 | LC-MS (Method A) (ESI+): m/z 497 (M + H)$^+$; $^1$H-NMR (300 MHz, CD$_3$OD) δ 9.39 (s, 1H), 8.74 (s, 1H), 8.41 (s, 1H), 7.64 (d, J = 8.7 Hz, 2H), 7.47 (d, J = 8.7 Hz, 2H), 6.20 (s, 1H), 5.77 (s, 2H), 3.99 (s, 3H), 3.95 (s, 3H), 2.28 (s, 3H). |
| 66 | 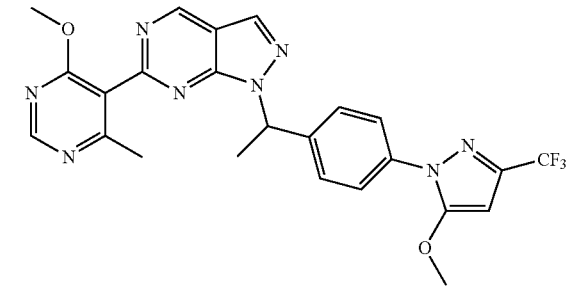 [SMILES: COc1ncnc(C)c1-c1ncc2cnn(C(C)c3ccc(-n4nc(C(F)(F)F)cc4OC)cc3)c2n1] | I-44 and BB-5 | LC-MS (Method A) (ESI+): m/z 511 (M + H)$^+$; $^1$H-NMR (300 MHz, CD$_3$OD) δ 9.36 (s, 1H), 8.73 (s, 1H), 8.42 (s, 1H), 7.62 (d, J = 8.7 Hz, 2H), 7.53 (d, J = 8.7 Hz, 2H), 6.32 (q, J = 6.9 Hz, 1H), 6.19 (s, 1H), 3.99 (s, 3H), 3.93 (s, 3H), 2.23 (s, 3H), 2.07 (d, J = 6.9 Hz, 3H). |
| 67 | 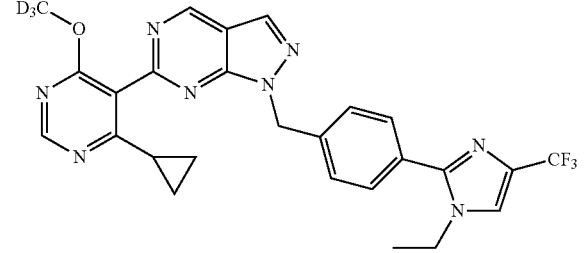 [SMILES: [2H]C([2H])([2H])Oc1ncnc(C2CC2)c1-c1ncc2cnn(Cc3ccc(-c4nc(C(F)(F)F)cn4CC)cc3)c2n1] | I-5 and BB-15 | LC-MS (Method A) (ESI+): m/z 524 (M + H)$^+$; $^1$H-NMR (300 MHz, CD$_3$OD) δ 9.40 (s, 1H), 8.64 (s, 1H), 8.42 (s, 1H), 7.78 (s, 1H), 7.50-7.58 (m, 4H), 5.81 (s, 2H), 4.07 (q, J = 7.5 Hz, 2H), 1.68 (m, 1H), 1.34 (t, J = 7.5 Hz, 3H), 1.13-1.19 (m, 2H), 0.91-0.94 (m, 2H). |

-continued

| Example | Structure | Starting material | Analytical data |
|---|---|---|---|
| 68 | 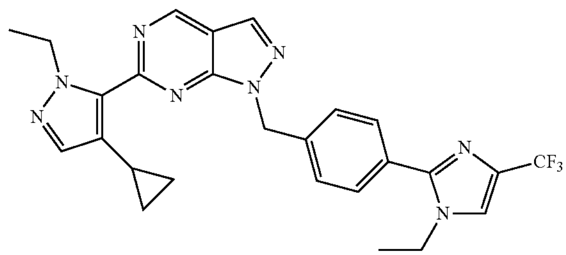 [SMILES: CCn1cc(C(F)(F)F)nc1-c1ccc(Cn2ncc3cnc(-c4c(C5CC5)cnn4CC)nc32)cc1] | I-5 and BB-32 | LC-MS (Method A) (ESI+): m/z 507 (M + H)+; 1H-NMR (300 MHz, CDCl$_3$) δ 9.29 (s, 1H), 8.21 (s 1H), 7.54 (d, J = 8.1 Hz, 2H), 7.44 (d, J = 8.1 Hz, 2H), 7.36 (s, 1H), 7.21 (s, 1H), 5.75 (s, 2H), 4.68 (q, J = 6.9 Hz, 2H), 4.03 (q, J = 6.9 Hz, 2H), 2.51 (m, 1H), 1.38-1.46 (m, 6H), 0.85-0.94 (m, 2H), 0.61-0.65 (m, 2H). |
| 69 | 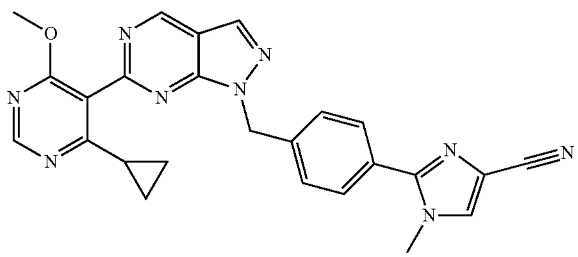 [SMILES: COc1ncnc(C2CC2)c1-c1ncc2cnn(Cc3ccc(-c4nc(C#N)cn4C)cc3)c2n1] | I-53 and BB-4 | LC-MS (Method A) (ESI+): m/z 464 (M + H)+; 1H-NMR (300 MHz, CD$_3$OD) δ 9.36 (s, 1H), 8.69 (s, 1H), 8.25 (s, 1H), 7.57 (d, J = 8.4 Hz, 2H), 7.39 (d, J = 8.4 Hz, 2H), 6.58 (s, 1H), 5.78 (s, 2H), 3.94 (s, 3H), 2.32 (s, 3H), 1.67 (m, 1H), 1.23-1.28 (m, 2H), 0.87-0.97 (m, 2H). |
| 70 | 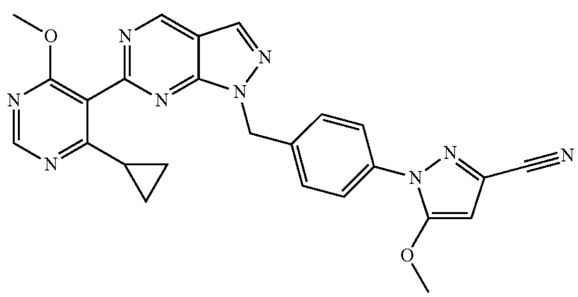 [SMILES: COc1ncnc(C2CC2)c1-c1ncc2cnn(Cc3ccc(-n4nc(C#N)cc4OC)cc3)c2n1] | I-45 and BB-4 | LC-MS (Method A) (ESI+): m/z 480 (M + H)+; 1H-NMR (300 MHz, CD$_3$OD) δ 9.34 (s, 1H), 8.69 (s, 1H), 8.23 (s, 1H), 7.63 (d, J = 8.4 Hz, 2H), 7.52 (d, J = 8.4 Hz, 2H), 6.04 (s, 1H), 5.75 (s, 2H), 3.96 (s, 3H), 3.94 (s, 3H), 1.65 (m, 1H), 1.20-1.29 (m, 2H), 0.81-0.92 (m, 2H). |
| 71 | 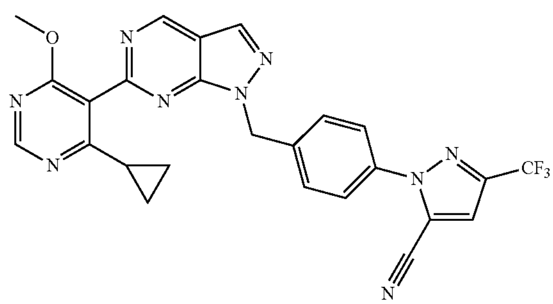 [SMILES: COc1ncnc(C2CC2)c1-c1ncc2cnn(Cc3ccc(-n4nc(C(F)(F)F)cc4C#N)cc3)c2n1] | I-54 and BB-4 | LC-MS (Method A) (ESI+): m/z 518 (M + H)+; 1H-NMR (300 MHz, CD$_3$OD) δ 9.41 (s, 1H), 8.63 (s, 1H) 8.43 (s, 1H), 7.73 (d, J = 8.4 Hz, 2H), 7.61 (s, 1H), 7.60 (d, J = 8.4 Hz, 2H), 5.85 (s, 2H), 3.91 (s, 3H), 1.65 (m, 1H), 1.12-1.18 (m, 2H), 0.85-0.92 (m, 2H). |
| 72 | 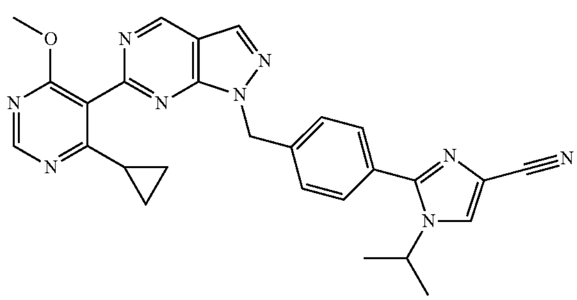 [SMILES: COc1ncnc(C2CC2)c1-c1ncc2cnn(Cc3ccc(-c4nc(C#N)cn4C(C)C)cc3)c2n1] | I-57 and BB-4 | LC-MS (Method C) (ESI+): m/z 492.15 (M + H)+; 1H-NMR (400 MHz, DMSO-d$_6$) δ 9.51 (s, 1H), 8.71 (s, 1H), 8.53 (s, 1H), 8.23 (s, 1H), 7.44-7.51 (m, 4H), 5.81 (s, 2H), 4.23 (td, J = 6.42, 13.08 Hz, 1H), 3.85 (s, 3H), 1.61-1.69 (m, 1H), 1.37 (d, J = 6.36 Hz, 6H), 1.02-1.08 (m, 2H), 0.84 (d, J = 3.91 Hz, 2H). |

-continued

| Example | Structure | Starting material | Analytical data |
|---|---|---|---|
| 73 | 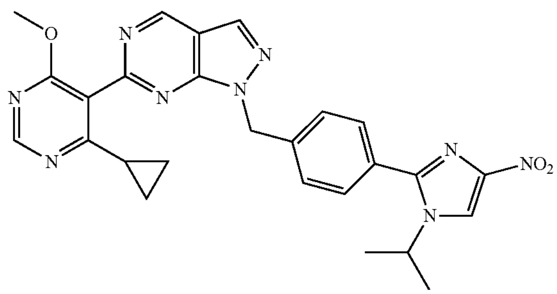 [SMILES: COc1ncnc(C2CC2)c1-c1ncc2cnn(Cc3ccc(-c4nc([N+](=O)[O-])cn4C(C)C)cc3)c2n1] | I-58 and BB-4 | LC-MS (Method C) (ESI+): m/z 512.35 (M + H)+; 1H-NMR (400 MHz, DMSO-d6) δ 9.52 (s, 1H), 8.71 (s, 1H), 8.54 (s, 1H), 8.19 (s, 1H), 7.40-7.49 (m, 4H), 5.81 (s, 2H), 3.91-3.99 (m, 1H), 3.85 (s, 3H), 1.63-1.70 (m, 1H), 1.34 (d, J = 6.98 Hz, 6H), 1.05 (td, J = 3.49, 6.98 Hz, 2H), 0.82-0.87 (m, 2H). |
| 74 | 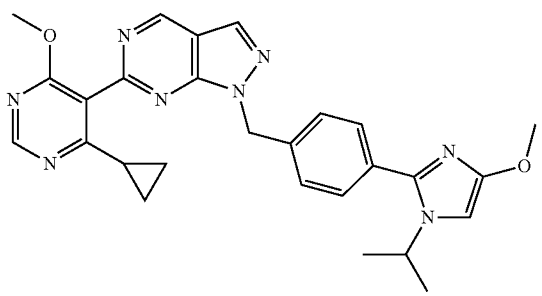 [SMILES: COc1cn(C(C)C)c(-c2ccc(Cn3ncc4cnc(-c5c(OC)ncnc5C5CC5)nc43)cc2)n1] | I-56 and BB-4 | LC-MS (Method B) (ESI+): m/z 497.60 (M + H)+; 1H-NMR (400 MHz, DMSO-d6) δ 9.50 (s, 1H), 8.71 (s, 1H), 8.51 (s, 1H), 7.41-7.45 (m, 2H), 7.35-7.39 (m, 2H), 6.75 (s, 1H), 5.75 (s, 2H), 4.33-4.39 (m, 2H), 3.85 (s, 3H), 3.68 (s, 3H), 1.32 (d, J = 6.85 Hz, 6H), 1.03-1.07 (m, 2H), 0.84 (dd, J = 3.18, 7.58 Hz, 2H). |
| 75 | 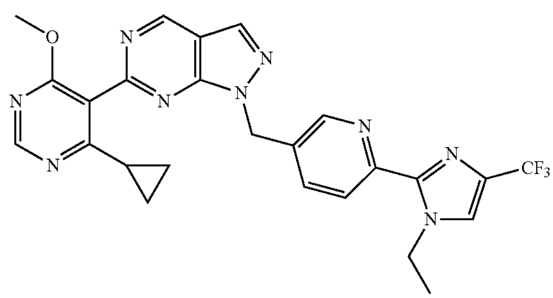 [SMILES: CCn1cc(C(F)(F)F)nc1-c1ccc(Cn2ncc3cnc(-c4c(OC)ncnc4C4CC4)nc32)cn1] | I-7 and BB-4 | LC-MS (Method A) (ESI+): m/z 522 (M + H)+; 1H-NMR (300 MHz, DMSO-d6) δ 9.52 (s, 1H), 8.73 (s, 1H), 8.69 (d, J = 1.8 Hz, 1H), 8.53 (s, 1H), 8.08 (s, 1H), 8.06 (d, J = 8.4 Hz, 1H), 7.85 (dd, J = 8.4, 2.1 Hz, 1H), 5.83 (s, 2H), 4.57 (q, J = 7.2 Hz, 2H), 3.86 (s, 3H), 1.67 (m, 1H), 1.34 (t, J = 7.2 Hz, 3H), 1.02-1.10 (m, 2H), 0.86-0.89 (m, 2H). |
| 76 | 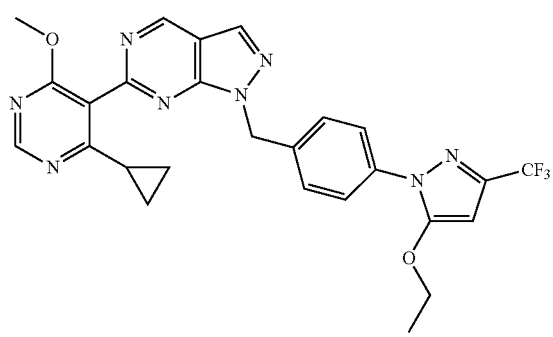 [SMILES: CCOc1cc(C(F)(F)F)nn1-c1ccc(Cn2ncc3cnc(-c4c(OC)ncnc4C4CC4)nc32)cc1] | I-40 and BB-4 | LC-MS (Method A) (ESI+): m/z 537 (M + H)+; 1H-NMR (300 MHz, CDCl3) δ 9.33 (s, 1H), 8.69 (s, 1H), 8.22 (s, 1H), 7.67 (d, J = 8.4Hz, 2H), 7.50 (d, J = 8.4 Hz, 2H), 5.90 (s, 1H), 5.74 (s, 2H), 4.19 (q, J = 7.2 Hz, 2H), 3.94 (s, 3H), 1.67 (m, 1H), 1.44 (t, J = 7.2 Hz, 3H), 1.20-1.28 (m, 2H), 0.82-0.91 (m, 2H). |
| 77 | 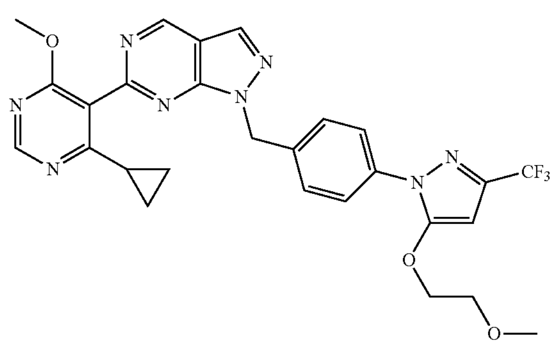 [SMILES: COCCOc1cc(C(F)(F)F)nn1-c1ccc(Cn2ncc3cnc(-c4c(OC)ncnc4C4CC4)nc32)cc1] | I-41 and BB-4 | LC-MS (Method A) (ESI+): m/z 567 (M + H)+; 1H-NMR (300 MHz, CDCl3) δ 9.33 (s, 1H), 8.69 (s, 1H), 8.23 (s, 1H), 7.68 (d, J = 8.7 Hz, 2H), 7.50 (d, J = 8.7 Hz, 2H), 5.94 (s, 1H), 5.73 (s, 2H), 4.26 (t, J = 4.5 Hz, 2H), 3.94 (s, 3H), 3.72 (t, J = 4.5 Hz, 2H), 3.38 (s, 3H), 1.65 (m, 1H), 1.24-1.26 (m, 2H), 0.87-0.91 (m, 2H). |

| Example | Structure | Starting material | Analytical data |
|---|---|---|---|
| 78 | 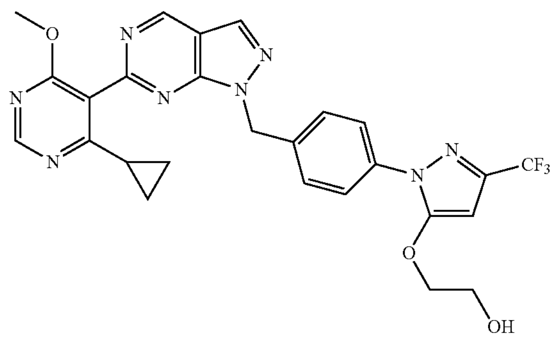 [SMILES: COc1ncnc(C2CC2)c1-c1ncc2cnn(Cc3ccc(-n4nc(C(F)(F)F)cc4OCCO)cc3)c2n1] | I-42 and BB-4 | LC-MS (Method A) (ESI+): m/z 553 (M + H)+; 1H-NMR (300 MHz, CDCl3) δ 9.34 (s, 1H), 8.69 (s, 1H), 8.23 (s, 1H), 7.65 (d, J = 8.7 Hz, 2H), 7.51 (d, J = 8.7 Hz, 2H), 5.95 (s, 1H), 5.74 (s, 2H), 4.25 (t, J = 4.5 Hz, 2H), 3.97 (m, 2H), 3.94 (s, 3H), 1.78 (t, J = 6.0 Hz, 2H), 1.66 (m, 1H), 1.22-1.26 (m, 2H), 0.87-0.91 (m, 2H). |
| 79 | 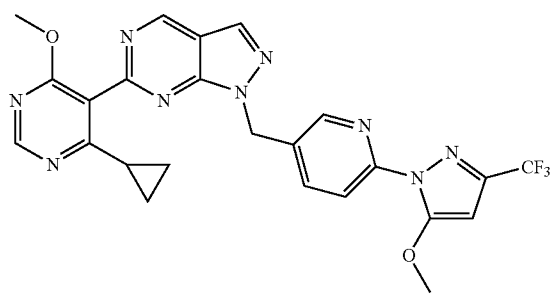 [SMILES: COc1ncnc(C2CC2)c1-c1ncc2cnn(Cc3ccc(-n4nc(C(F)(F)F)cc4OC)nc3)c2n1] | I-43 and BB-4 | LC-MS (Method A) (ESI+): m/z 524 (M + H)+; 1H-NMR (300 MHz, CD3OD) δ 9.40 (s, 1H), 8.64 (s, 1H), 8.58 (d, J = 1.5 Hz, 1H), 8.42 (s, 1H), 8.01 (dd, J = 8.4, 1.5 Hz, 1H), 7.71 (d, J = 8.4, 1H), 6.25 (s, 1H), 5.84 (s, 2H), 3.02 (s, 3H), 3.91 (s, 3H), 1.62 (m, 1H), 1.13-1.17 (m, 2H), 0.86-0.95 (m, 2H). |
| 80 | 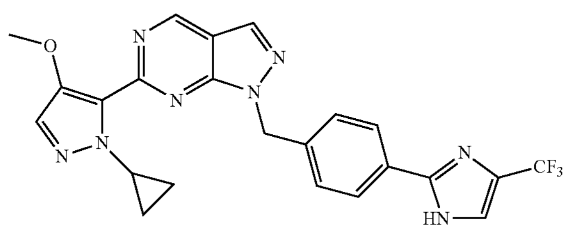 [SMILES: COc1cnn(C2CC2)c1-c1ncc2cnn(Cc3ccc(-c4nc(C(F)(F)F)c[nH]4)cc3)c2n1] | I-59 and BB-33 | LC-MS (Method A) (ESI+): m/z 481 (M + H)+; 1H-NMR (300 MHz, CD3OD) δ 9.34 (s, 1H), 8.35 (s, 1H), 7.85 (d, J = 8.4 Hz, 2H), 7.63 (s, 1H), 7.47 (d, J = 8.4 Hz, 2H), 7.42 (s, 1H), 5.79 (s, 2H), 4.18 (m, 1H), 3.88 (s, 3H), 0.91-0.97 (m, 2H), 0.72-0.81 (m, 2H). |
| 81 | 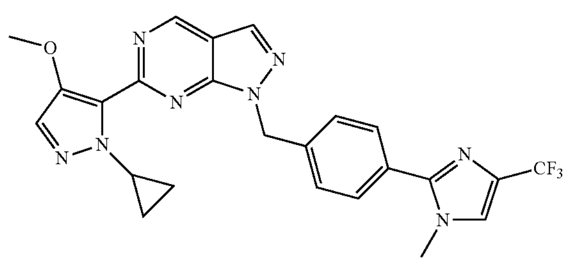 [SMILES: COc1cnn(C2CC2)c1-c1ncc2cnn(Cc3ccc(-c4nc(C(F)(F)F)cn4C)cc3)c2n1] | I-1 and BB-33 | LC-MS (Method A) (ESI+): m/z 495 (M + H)+; 1H-NMR (300 MHz, CD3OD) δ 9.35 (s, 1H), 8.35 (s, 1H), 7.67 (s, 1H), 7.60 (d, J = 8.1 Hz, 2H), 7.51 (d, J = 8.4 Hz, 2H), 7.43 (s, 1H), 5.82 (s, 2H), 4.25 (m, 1H), 3.88 (s, 3H), 3.73 (s, 3H), 0.95-1.01 (m, 2H), 0.72-0.85 (m, 2H). |
| 82 | 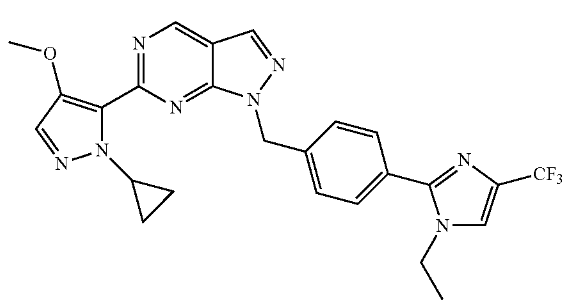 [SMILES: CCn1cc(C(F)(F)F)nc1-c1ccc(Cn2ncc3cnc(-c4c(OC)cnn4C4CC4)nc32)cc1] | I-5 and BB-33 | LC-MS (Method A) (ESI+): m/z 509 (M + H)+; 1H-NMR (300 MHz, CDCl3) δ 9.33 (s, 1H), 8.19 (s, 1H), 7.53 (d, J = 8.7 Hz, 2H), 7.44 (d, J = 8.7 Hz, 2H), 7.36 (s, 1H), 7.35 (s, 1H), 5.75 (s, 2H), 4.32 (m, 1H), 4.03 (q, J = 7.8 Hz, 2H), 3.94 (s, 3H), 1.38-1.45 (t, J = 7.8 Hz, 3H), 1.09-1.15 (m, 2H), 0.81-0.88 (m, 2H). |

| Example | Structure | Starting material | Analytical data |
|---|---|---|---|
| 83 | 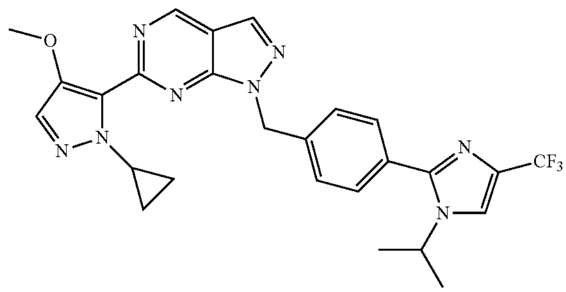 [SMILES: COc1cnn(C2CC2)c1-c1ncc2cnn(Cc3ccc(-c4nc(C(F)(F)F)cn4C(C)C)cc3)c2n1] | I-6 and BB-33 | LC-MS (Method A) (ESI+): m/z 523 (M + H)+; 1H-NMR (300 MHz, CD3OD) δ 9.34 (s, 1H), 8.35 (s, 1H) 7.89 (s, 1H), 7.51 (s, 4H), 7.42 (s, 1H), 5.83 (s, 2H), 4.47 (m, 1H), 4.23 (m, 1H), 3.88 (s, 3H), 1.41 (d, J = 6.9 Hz, 6H), 0.94-1.01 (m, 2H), 0.78-0.81 (m, 2H). |
| 84 | 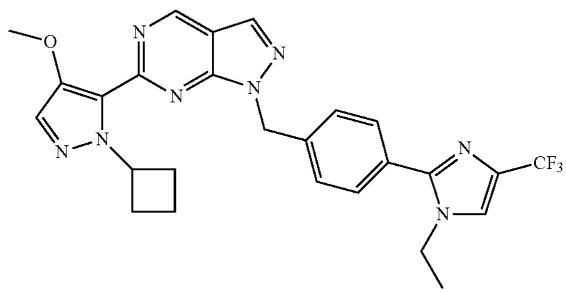 [SMILES: CCn1cc(C(F)(F)F)nc1-c1ccc(Cn2ncc3cnc(-c4c(OC)cnn4C4CCC4)nc32)cc1] | I-5 and BB-34 | LC-MS (Method A) (ESI+): m/z 523 (M + H)+; 1H-NMR (300 MHz, CD3OD) δ 9.34 (s, 1H), 8.34 (s, 1H), 7.77 (s, 1H), 7.52-7.61 (m, 5H), 5.84 (s, 2H), 5.65 (m, 1H), 4.03-4.12 (q, J = 7.2 Hz, 2H), 3.89 (s, 3H), 2.55-2.71 (m, 2H), 2.26-2.41 (m, 2H), 1.68-1.90 (m, 2H), 1.29-1.39 (t, J = 7.2 Hz, 3H). |
| 85 | 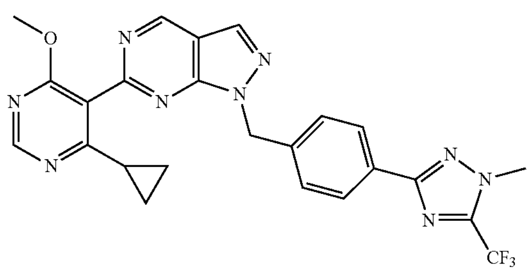 [SMILES: COc1ncnc(C2CC2)c1-c1ncc2cnn(Cc3ccc(-c4nc(C(F)(F)F)n(C)n4)cc3)c2n1] | I-52 and BB-4 | LC-MS (Method A) (ESI+): m/z 508 (M + H)+; 1H-NMR (300 MHz, CD3OD) δ 9.39 (s, 1H), 8.64 (s, 1H), 8.41 (s, 1H), 8.01 (d, J = 8.1 Hz, 2H), 7.44 (d, J = 8.1 Hz, 2H), 5.77 (s, 2H), 4.10 (s, 3H), 3.92 (s, 3H), 1.64 (m, 1H), 1.10-1.18 (m, 2H), 0.81-0.88 (m, 2H). |
| 86 | 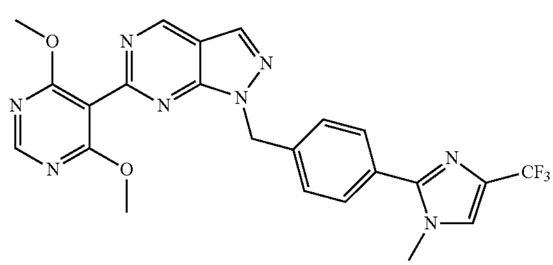 [SMILES: COc1ncnc(OC)c1-c1ncc2cnn(Cc3ccc(-c4nc(C(F)(F)F)cn4C)cc3)c2n1] | I-1 and BB-29 | LC-MS (Method B): (ESI+): m/z 497.15 (M + H)+; 1H-NMR (400 MHz, DMSO-d6) δ 9.45 (s, 1H), 8.65 (s, 1H), 8.49 (s, 1H), 7.92 (s, 1H), 7.69 (d, J = 7.82 Hz, 2H), 7.42 (d, J = 7.83 Hz, 2H), 5.75 (s, 2H), 3.88 (s, 6H), 3.75 (s, 3H). |
| 87 | 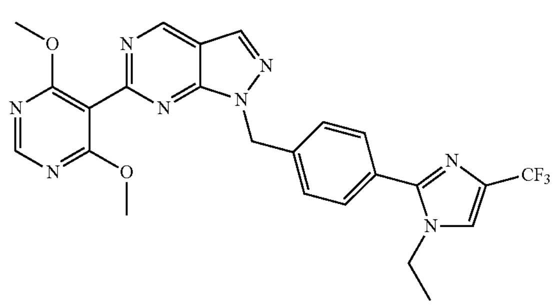 [SMILES: CCn1cc(C(F)(F)F)nc1-c1ccc(Cn2ncc3cnc(-c4c(OC)ncnc4OC)nc32)cc1] | I-5 and BB-29* | LC-MS (Method B) (ESI+): m/z 511.10 (M + H)+; 1H-NMR (400 MHz, DMSO-d6) δ 9.45 (s, 1H), 8.64 (s, 1H), 8.49 (s, 1H), 8.01 (s, 1H), 7.60 (d, J = 7.8 Hz, 2H), 7.42 (d, J = 7.8 Hz, 2H), 5.76 (s, 2H), 4.05 (q, J = 7.2 Hz, 2H), 3.87 (s, 6H), 1.29 (t, J = 7.1 Hz, 3H). |

| Example | Structure | Starting material | Analytical data |
|---|---|---|---|
| 88 | 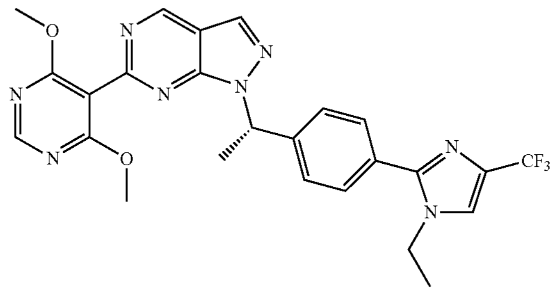 [SMILES: CCn1cc(C(F)(F)F)nc1-c1ccc([C@H](C)n2ncc3cnc(-c4c(OC)ncnc4OC)nc32)cc1] | I-28 and BB-29 | LC-MS (Method B) (ESI+): m/z 525.10 (M + H)+; $^1$H-NMR (400 MHz, DMSO-d6) δ 9.42 (s, 1H), 8.64 (s, 1H), 8.51 (s, 1H), 8.01 (s, 1H), 7.59 (d, J = 7.83 Hz, 2H), 7.49 (d, J = 7.83 Hz, 2H), 6.33 (q, J = 6.85 Hz, 1H), 4.04 (q, J = 7.17 Hz, 2H), 3.83-3.88 (m, 6H), 1.98 (d, J = 6.85 Hz, 3H), 1.29 (t, J = 7.34 Hz, 3H). |
| 89 | 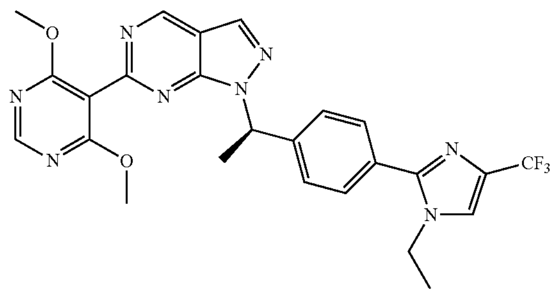 [SMILES: CCn1cc(C(F)(F)F)nc1-c1ccc([C@@H](C)n2ncc3cnc(-c4c(OC)ncnc4OC)nc32)cc1] | I-25 and BB-29 | LC-MS (Method B) (ESI+): m/z 525.15 (M + H)+; $^1$H-NMR (400 MHz, DMSO-d6) δ 9.43 (s, 1H), 8.64 (s, 1H), 8.51 (s, 1H), 8.01 (s, 1H), 7.59 (d, J = 7.78 Hz, 2H), 7.49 (d, J = 8.03 Hz, 2H), 6.33 (q, J = 6.78 Hz, 1H), 4.04 (q, J = 7.11 Hz, 2H), 3.85 (s, 6H), 1.98 (d, J = 7.03 Hz, 3H), 1.29 (t, J = 7.28 Hz, 3H). |
| 90 | 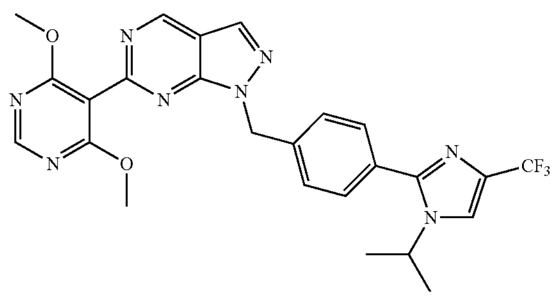 [SMILES: COc1ncnc(OC)c1-c1ncc2cnn(Cc3ccc(-c4nc(C(F)(F)F)cn4C(C)C)cc3)c2n1] | I-6 and BB-29 | LC-MS (Method B) (ESI+): m/z 525.20 (M + H)+; $^1$H-NMR (400 MHz, DMSO-d6) δ 9.45 (s, 1H), 8.64 (s, 1H), 8.49 (s, 1H), 8.16 (s, 1H), 7.53 (d, J = 8.28 Hz, 2H), 7.43 (d, J = 8.28 Hz, 2H), 5.76 (s, 2H), 4.42 (td, J = 6.40, 13.30 Hz, 1H), 3.87 (s, 6H), 1.37 (d, J = 6.78 Hz, 6H). |
| 91 | 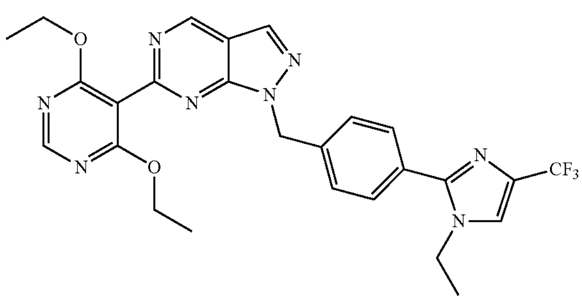 [SMILES: CCOc1ncnc(OCC)c1-c1ncc2cnn(Cc3ccc(-c4nc(C(F)(F)F)cn4CC)cc3)c2n1] | I-5 and BB-27 | LC-MS (Method C) (ESI+): m/z 539.10 (M + H)+; $^1$H-NMR (400 MHz, CDCl$_3$) δ 9.49 (s, 1H), 8.55 (s, 1H), 8.39 (s, 1H), 7.49-7.60 (m, 4H), 7.37 (s, 1H), 5.79 (s, 2H), 4.46-4.57 (m, 4H), 3.99-4.09 (m, 2H), 1.35-1.45 (m, 3H), 1.32 (t, J = 7.0 Hz, 6H). |
| 92* | 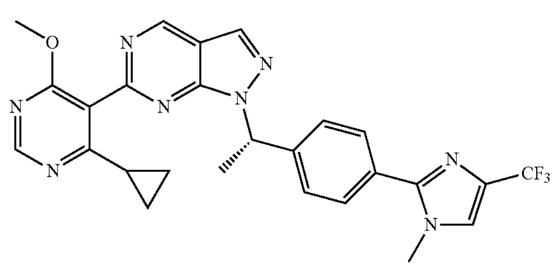 [SMILES: COc1ncnc(C2CC2)c1-c1ncc2cnn([C@@H](C)c3ccc(-c4nc(C(F)(F)F)cn4C)cc3)c2n1] | I-24 and BB-4 | LC-MS (Method B) (ESI+): m/z 521.10 (M + H; $^1$H-NMR (400 MHz, DMSO-d$_6$) δ 9.49 (s, 1H), 8.71 (s, 1H), 8.54 (s, 1H), 7.91 (s, 1H), 7.67 (d, J = 8.37 Hz, 2H), 7.48 (d, J = 8.37 Hz, 2H), 6.31-6.39 (m, 1H), 3.83 (s, 3H), 3.74 (s, 3H), 1.99 (d, J = 6.89 Hz, 3H), 1.57-1.66 (m, 1H), 1.05 (s, 2H), 0.78-0.88 (m, 2H). |

-continued

| Example | Structure | Starting material | Analytical data |
|---|---|---|---|
| 93* | 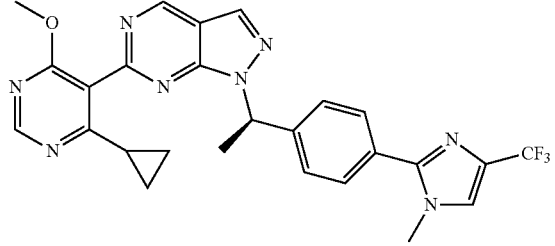 [SMILES: COc1ncnc(C2CC2)c1-c1ncc2cnn([C@H](C)c3ccc(-c4nc(C(F)(F)F)cn4C)cc3)c2n1] | I-24 and BB-4 | LC-MS (Method B) (ESI+); m/z 521.10 (M + H; $^1$H-NMR (400 MHz, DMSO-$d_6$) δ 9.49 (s, 1H), 8.71 (s, 1H), 8.54 (s, 1H), 7.91 (s, 1H), 7.67 (d, J = 8.37 Hz, 2H), 7.48 (d, J = 8.37 Hz, 2H), 6.35 (q, J = 6.89 Hz, 1H), 3.83 (s, 3H), 3.74 (s, 3H), 1.99 (d, J = 6.89 Hz, 3H), 1.56-1.66 (m, 1H), 1.04 (d, J = 3.94 Hz, 2H), 0.77-0.88 (m, 2H). |
| 94* | 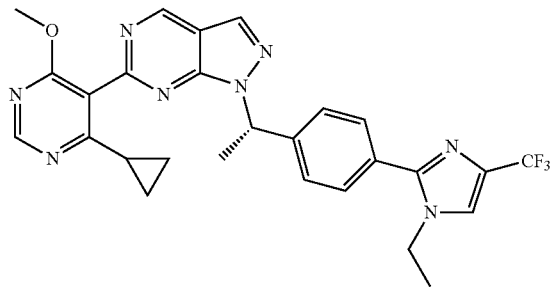 [SMILES: CCn1cc(C(F)(F)F)nc1-c1ccc([C@H](C)n2ncc3cnc(-c4c(OC)ncnc4C4CC4)nc32)cc1] | I-25 and BB-4 | LC-MS (Method B) (ESI+): m/z 535.10 (M + H)$^+$; $^1$H-NMR (400 MHz, DMSO-$d_6$) δ 9.49 (s, 1H), 8.70 (s, 1H), 8.54 (s, 1H), 8.01 (s, 1H), 7.58 (d, J = 7.9 Hz, 2H), 7.48 (d, J = 8.3 Hz, 2H), 6.35 (q, J = 7.0 Hz, 1H), 4.04 (q, J = 7.3 Hz, 2H), 3.83 (s, 3H), 2.00 (d, J = 7.0 Hz, 3H), 1.57-1.65 (m, 1H), 1.29 (t, J = 7.2 Hz, 3H), 1.04 (d, J = 3.1 Hz, 2H), 0.82 (d, J = 7.5 Hz, 2H). |
| 95* | 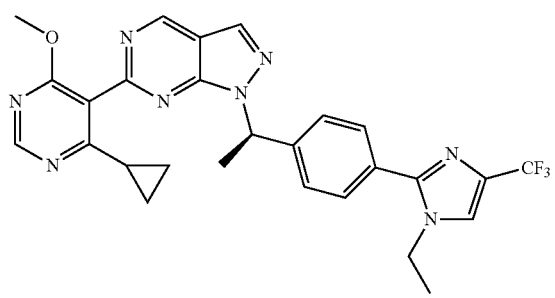 [SMILES: CCn1cc(C(F)(F)F)nc1-c1ccc([C@@H](C)n2ncc3cnc(-c4c(OC)ncnc4C4CC4)nc32)cc1] | I-25 and BB-4 | LC-MS (Method B) (ESI+); m/z 535.10 (M + H)$^+$; $^1$H-NMR (400 MHz, DMSO-$d_6$) δ 9.49 (s, 1H), 8.70 (s, 1H), 8.54 (s, 1H), 8.01 (s, 1H), 7.58 (d, J = 7.8 Hz, 2H), 7.48 (d, J = 7.8 Hz, 2H), 6.35 (q, J = 6.7 Hz, 1H), 4.04 (q, J = 6.8 Hz, 2H), 3.83 (s, 3H), 1.99 (d, J = 6.8 Hz, 3H), 1.60 (d, J = 3.9 Hz, 1H), 1.29 (t, J = 7.1 Hz, 3H), 1.04 (s, 2H), 0.82 (d, J = 6.8 Hz, 2H). |
| 96 | 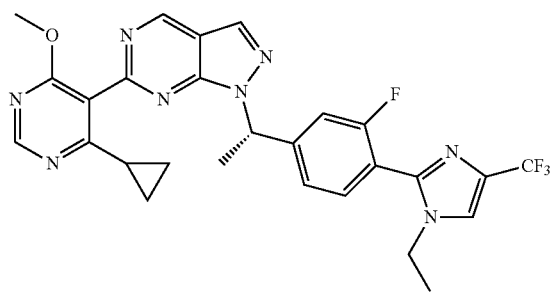 [SMILES: CCn1cc(C(F)(F)F)nc1-c1ccc([C@H](C)n2ncc3cnc(-c4c(OC)ncnc4C4CC4)nc32)cc1F] | I-27 and BB-4 | LC-MS (Method C) (ESI+): m/z 553.10 (M + H)$^+$; $^1$H-NMR (400 MHz, DMSO-$d_6$) δ 9.50 (s, 1H), 8.71 (s, 1H), 8.56 (s, 1H), 8.09 (s, 1H), 7.52 (t, J = 7.83 Hz, 1H), 7.42 (d, J = 11.25 Hz, 1H), 7.29 (dd, J = 1.22, 8.07 Hz, 1H), 6.39 (q, J = 6.85 Hz, 1H), 3.84-3.87 (m, 2H), 3.83 (s, 3H), 1.99 (d, J = 7.34 Hz, 3H), 1.57-1.66 (m, 1H), 1.24 (t, J = 7.34 Hz, 3H), 1.03-1.07 (m, 2H), 0.83 (d, J = 7.83 Hz, 2H). |
| 97 | 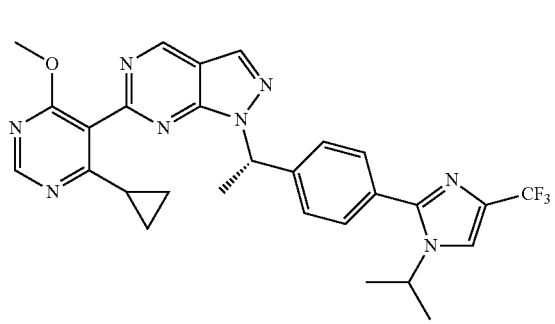 [SMILES: COc1ncnc(C2CC2)c1-c1ncc2cnn([C@@H](C)c3ccc(-c4nc(C(F)(F)F)cn4C(C)C)cc3)c2n1] | I-29 and BB-4 | LC-MS (Method C) (ESI+): m/z 549.10 (M + H)$^+$; $^1$H-NMR (400 MHz, DMSO-$d_6$) δ 9.49 (s, 1H), 8.71 (s, 1H), 8.54 (s, 1H), 8.16 (s, 1H), 7.46-7.55 (m, 4H), 6.36 (q, J = 6.98 Hz, 1H), 4.41 (td, J = 6.48, 12.96 Hz, 1H), 3.83 (s, 3H), 2.00 (d, J = 6.98 Hz, 3H), 1.58-1.65 (m, 1H), 1.37 (d, J = 6.48 Hz, 6H), 1.04 (d, J = 2.99 Hz, 2H), 0.76-0.87 (m, 2H). |

-continued

| Example | Structure | Starting material | Analytical data |
|---|---|---|---|
| 98 | 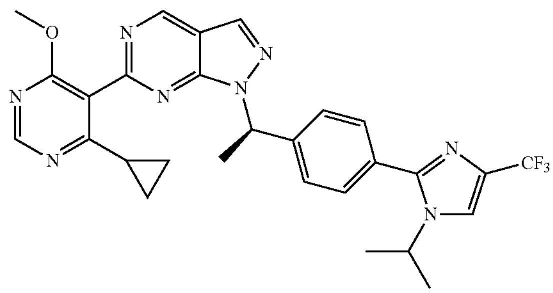 [SMILES: COc1ncnc(C2CC2)c1-c1ncc2cnn([C@H](C)c3ccc(-c4nc(C(F)(F)F)cn4C(C)C)cc3)c2n1] | I-30 and BB-4 | LC-MS (Method C) (ESI+): m/z 548.94 (M + H)+; 1H-NMR (400 MHz, DMSO-d6) δ 9.49 (s, 1H), 8.71 (s, 1H), 8.54 (s, 1H), 8.16 (s, 1H), 7.47-7.54 (m, 4H), 6.36 (d, J = 6.98 Hz, 1H), 4.41 (td, J = 6.36, 13.22 Hz, 1H), 3.83 (s, 3H), 2.00 (d, J = 6.98 Hz, 3H), 1.61 (d, J = 3.99 Hz, 1H), 1.37 (d, J = 6.48 Hz, 6H), 1.04 (d, J = 3.49 Hz, 2H), 0.78-0.87 (m, 2H). |
| 99* | 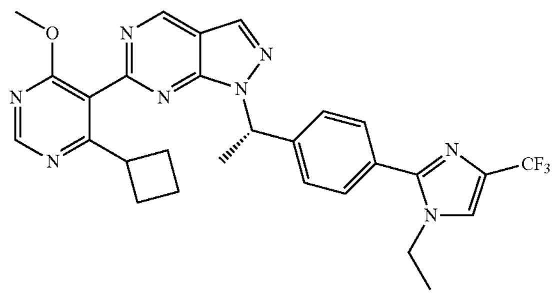 [SMILES: CCn1cc(C(F)(F)F)nc1-c1ccc([C@H](C)n2ncc3cnc(-c4c(OC)ncnc4C4CCC4)nc32)cc1] | I-25 and BB-20 | LC-MS (Method C) (ESI+): m/z 549.14 (M + H)+; 1H-NMR (400 MHz, DMSO-d6) δ 9.46 (s, 1H), 8.88 (s, 1H), 8.55 (s, 1H), 8.01 (s, 1H), 7.59 (d, J = 8.3 Hz, 2H), 7.44 (d, J = 8.3 Hz, 2H), 6.31 (q, J = 6.5 Hz, 1H), 4.04 (q, J = 7.3 Hz, 2H), 3.85 (s, 3H), 3.24-3.28 (m, 1H), 2.13-2.27 (m, 2H), 2.00 (d, J = 7.3 Hz, 3H), 1.58-1.78 (m, 4H), 1.29 (t, J = 7.3 Hz, 3H). |
| 100* | 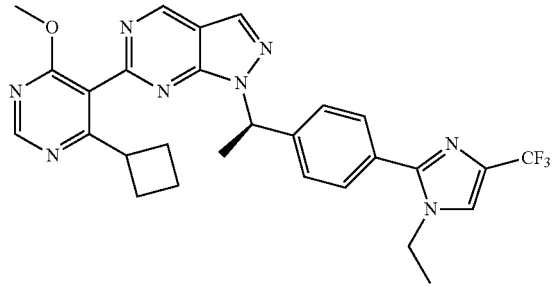 [SMILES: CCn1cc(C(F)(F)F)nc1-c1ccc([C@@H](C)n2ncc3cnc(-c4c(OC)ncnc4C4CCC4)nc32)cc1] | I-25 and BB-20 | LC-MS (Method C) (ESI+): m/z 549.14 (M + H)+; 1H-NMR (400 MHz, DMSO-d6) δ 9.46 (s, 1H), 8.88 (s, 1H), 8.55 (s, 1H), 8.01 (s, 1H), 7.59 (d, J = 8.3 Hz, 2H), 7.44 (d, J = 8.3 Hz, 2H), 6.31 (q, J = 6.8 Hz, 1H), 4.04 (q, J = 7.3 Hz, 2H), 3.85 (s, 3H), 3.24 3.29 (m, 1H), 2.12-2.27 (m, 2H), 2.00 (d, J = 6.8 Hz, 3H), 1.58-1.77 (m, 4H), 1.29 (t, J = 7.3 Hz, 3H). |
| 101 | 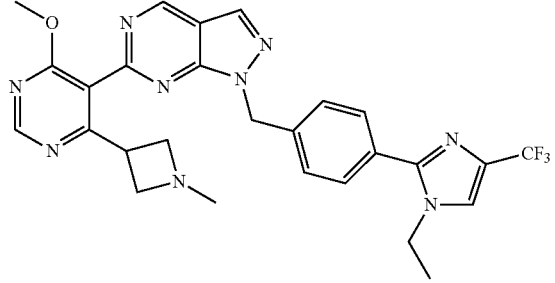 [SMILES: CCn1cc(C(F)(F)F)nc1-c1ccc(Cn2ncc3cnc(-c4c(OC)ncnc4C4CN(C)C4)nc32)cc1] | I-5 and BB-36 | LC-MS (Method B) (ESI+): m/z 550.15 (M + H)+; 1H-NMR (400 MHz, DMSO-d6) δ 9.48 (s, 1H), 8.90 (s, 1H), 8.54 (s, 1H), 8.01 (s, 1H), 7.61 (d, J = 7.98 Hz, 2H), 7.40 (d, J = 7.98 Hz, 2H), 5.78 (s, 2H), 4.06 (q, J = 7.15 Hz, 2H), 3.88 (s, 3H), 3.51 (t, J = 7.98 Hz, 1H), 3.05-3.16 (m, 4H), 2.07 (s, 3H), 1.29 (t, J = 7.23 Hz, 3H). |
| 102 | 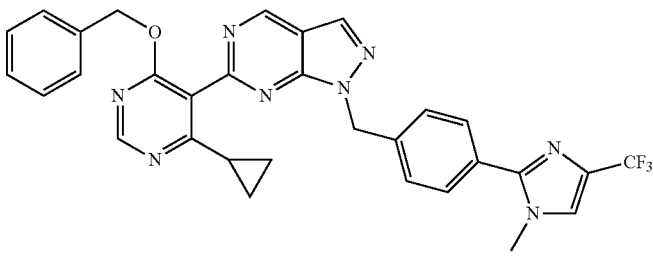 [SMILES: Cn1cc(C(F)(F)F)nc1-c1ccc(Cn2ncc3cnc(-c4c(OCc5ccccc5)ncnc4C4CC4)nc32)cc1] | I-1 and BB-17 | LC-MS (Method C) (ESI+): m/z 583.05 (M + H)+; 1H-NMR (400 MHz, DMSO-d6) δ 9.53 (s, 1H), 8.70 (s, 1H), 8.52 (s, 1H), 7.91 (s, 1H), 7.62 (d, J = 8.3 Hz, 2H), 7.38 (d, J = 8.3 Hz, 2H), 7.20-7.26 (m, 5H), 5.79 (s, 2H), 5.44 (s, 2H), 3.71 (s, 3H), 1.65-1.72 (m, 1H), 1.07 (s, 2H), 0.88 (dd, J = 3.2, 7.6 Hz, 2H). |

-continued

| Example | Structure | Starting material | Analytical data |
|---|---|---|---|
| 103 | 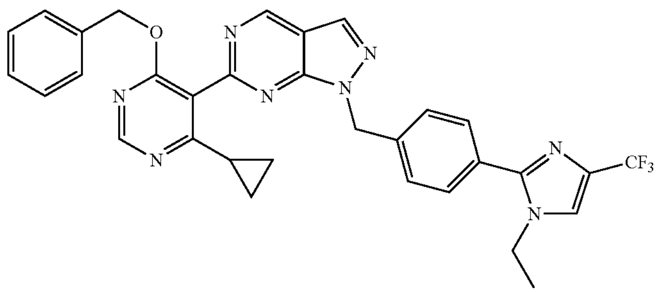 [SMILES: CCn1cc(C(F)(F)F)nc1-c1ccc(Cn2ncc3cnc(-c4c(OCc5ccccc5)ncnc4C4CC4)nc32)cc1] | I-5 and BB-17 | LC-MS (Method B) (ESI+): m/z 597.10 (M + H)+; 1H-NMR (400 MHz, DMSO-d$_6$) δ 9.53 (s, 1H), 8.70 (s, 1H), 8.53 (s, 1H), 8.00 (s, 1H), 7.54 (d, J = 8.3 Hz, 2H), 7.38 (d, J = 7.8 Hz, 2H), 7.18-7.29 (m, 5H), 5.80 (s, 2H), 5.44 (s, 2H), 4.01 (q, J = 7.3 Hz, 2H), 1.64-1.74 (m, 1H), 1.26 (t, J = 7.1 Hz, 3H), 1.07 (s, 2H), 0.82-0.91 (m, 2H). |
| 104 | 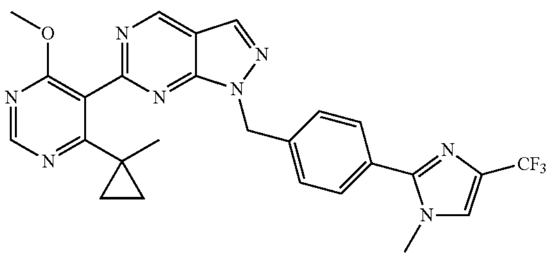 [SMILES: COc1ncnc(C2(C)CC2)c1-c1ncc2cnn(Cc3ccc(-c4nc(C(F)(F)F)cn4C)cc3)c2n1] | I-1 and BB-18 | LCMS (Method B) (ESI+): m/z 521.10 (M + H)+; 1H-NMR (400 MHz, DMSO-d6) δ 9.50 (s, 1H), 8.80 (s, 1H), 8.54 (s, 1H), 7.91 (s, 1H), 7.66 (d, J = 7.8 Hz, 2H), 7.33 (d, J = 8.3 Hz, 2H), 5.79 (s, 2H), 3.85 (s, 3H), 3.73 (s, 3H), 1.05 (s, 3H), 0.65 (s, 2H), 0.28-0.33 (m, 2H) |
| 105 | 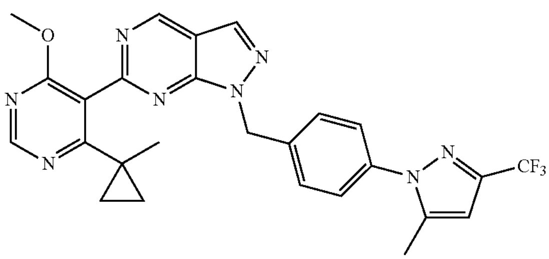 [SMILES: COc1ncnc(C2(C)CC2)c1-c1ncc2cnn(Cc3ccc(-n4nc(C(F)(F)F)cc4C)cc3)c2n1] | I-19 and BB-18 | LCMS (Method B) (ESI+): m/z 521.15 (M + H)+; 1H-NMR (400 MHz, DMSO-d6) δ 9.50 (s, 1H), 8.80 (s, 1H), 8.55 (s, 1H), 7.53 (d, J = 8.48 Hz, 2H), 7.37 (d, J = 8.48 Hz, 2H), 6.74 (s, 1H), 5.81 (s, 2H), 3.84 (s, 3H), 2.29 (s, 3H), 1.04 (s, 3H), 0.63-0.66 (m, 2H), 0.27-0.31 (m, 2H). |
| 106 | 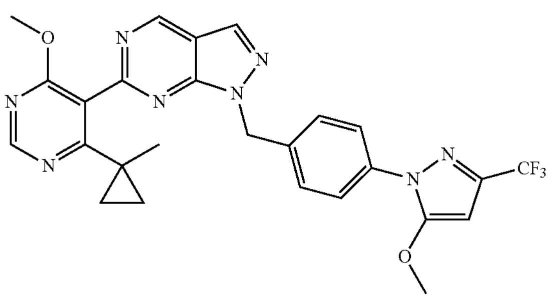 [SMILES: COc1ncnc(C2(C)CC2)c1-c1ncc2cnn(Cc3ccc(-n4nc(C(F)(F)F)cc4OC)cc3)c2n1] | I-39 and BB-18 | LCMS (Method B) (ESI+): m/z 537.05 (M + H)+; 1H-NMR (400 MHz, DMSO-d6) δ 9.49 (s, 1H), 8.80 (s, 1H), 8.53 (s, 1H), 7.58 (d, J = 8.48 Hz, 2H), 7.36 (d, J = 8.48 Hz, 2H), 6.45 (s, 1H), 5.76 (s, 2H), 3.96 (s, 3H), 3.84 (s, 3H), 1.04 (s, 3H), 0.62-0.67 (m, 2H), 0.27-0.33 (m, 2H). |
| 107 | 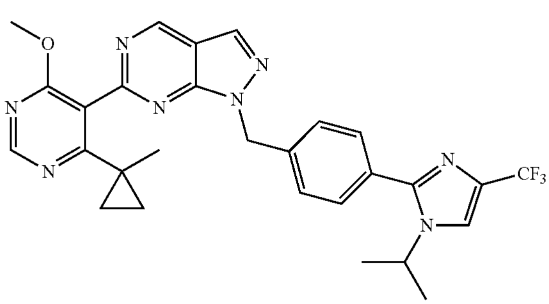 [SMILES: COc1ncnc(C2(C)CC2)c1-c1ncc2cnn(Cc3ccc(-c4nc(C(F)(F)F)cn4C(C)C)cc3)c2n1] | I-6 and BB-18 | LCMS (Method B) (ESI+): m/z 549.10 (M + H)+; 1H-NMR (400 MHz, DMSO-d6) δ 9.50 (s, 1H), 8.80 (s, 1H), 8.55 (s, 1H), 8.16 (s, 1H), 7.51 (d, J = 7.98 Hz, 2H), 7.33 (d, J = 7.98 Hz, 2H), 5.80 (s, 2H), 4.39 (td, J = 6.48, 12.96 Hz, 1H), 3.85 (s, 3H), 1.36 (d, J = 6.48 Hz, 6H), 1.04 (s, 3H), 0.61-0.66 (m, 2H), 0.27-0.31 (m, 2H). |

-continued

| Example | Structure | Starting material | Analytical data |
|---|---|---|---|
| 108 | 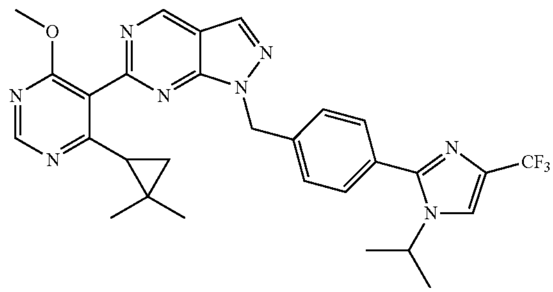 [SMILES: COc1ncnc(C2CC2(C)C)c1-c1ncc2cnn(Cc3ccc(-c4nc(C(F)(F)F)cn4C(C)C)cc3)c2n1] | I-6 and BB-19 | LCMS (Method B) (ESI+): m/z 563.10 (M + H)+; 1H-NMR (400 MHz, DMSO-d6) δ 9.52 (s, 1H), 8.77 (s, 1H), 8.54 (s, 1H), 8.16 (s, 1H), 7.52 (d, J = 7.83 Hz, 2H), 7.37-7.42 (m, 2H), 4.40 (td, J = 6.24, 12.96 Hz, 2H), 3.87 (s, 3H), 1.47-1.52 (m, 2H), 1.42-1.46 (m, 1H), 1.37 (d, J = 6.36 Hz, 6H), 0.86 (s, 3H), 0.69-0.74 (m, 1H), 0.64 (s, 3H). |
| 109 | 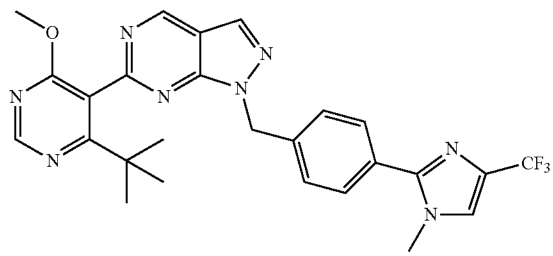 [SMILES: COc1ncnc(C(C)(C)C)c1-c1ncc2cnn(Cc3ccc(-c4nc(C(F)(F)F)cn4C)cc3)c2n1] | I-1 and BB-21 | LC-MS (Method B) (ESI+): m/z 523.10 (M + H)+; 1H-NMR (400 MHz, DMSO-d6) δ 9.47 (s, 1H), 8.85 (s, 1H), 8.53 (s, 1H), 7.92 (s, 1H), 7.65 (d, J = 7.8 Hz, 2H), 7.33 (d, J = 7.8 Hz, 2H), 5.55-5.89 (m, 2H), 3.80 (s, 3H), 3.73 (s, 3H), 0.99 (s, 9H). |
| 110 | 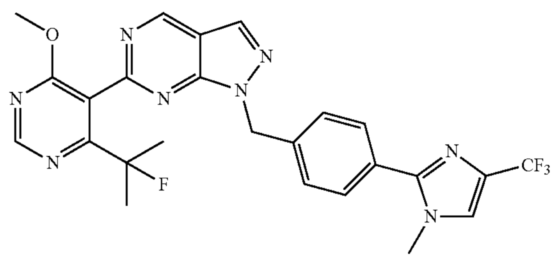 [SMILES: COc1ncnc(C(C)(C)F)c1-c1ncc2cnn(Cc3ccc(-c4nc(C(F)(F)F)cn4C)cc3)c2n1] | I-1 and BB-23 | LC-MS (Method B) (ESI+): m/z 527.15 (M + H)+; 1H-NMR (400 MHz, DMSO-d6) δ 9.41 (s, 1H), 8.90 (s, 1H), 8.48 (s, 1H), 7.92 (s, 1H), 7.66 (d, J = 7.8 Hz, 2H), 7.36 (d, J = 8.3 Hz, 2H), 5.65-5.84 (m, 2H), 3.87 (s, 3H), 3.74 (s, 3H), 1.56-1.68 (m, 6H). |
| 111 | 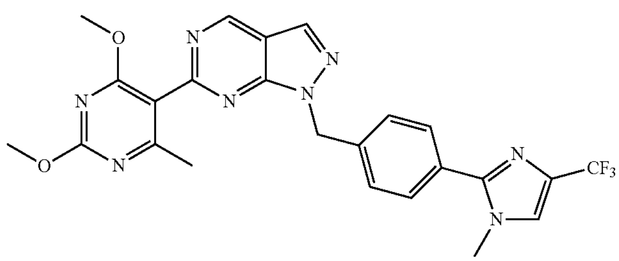 [SMILES: COc1nc(C)c(-c2ncc3cnn(Cc4ccc(-c5nc(C(F)(F)F)cn5C)cc4)c3n2)c(OC)n1] | I-1 and BB-24 | LC-MS (Method B) (ESI+): m/z 511.10 (M + H)+; 1H-NMR (400 MHz, DMSO-d6) δ 9.46 (s, 1H), 8.49 (s, 1H), 7.92 (s, 1H), 7.68 (d, J = 7.9 Hz, 2H), 7.42 (d, J = 7.9 Hz, 2H), 5.76 (s, 2H), 3.96 (s, 3H), 3.85 (s, 3H), 3.74 (s, 3H), 2.18 (s, 3H). |
| 112 | 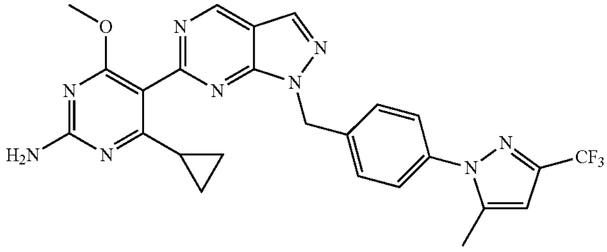 [SMILES: COc1nc(N)nc(C2CC2)c1-c1ncc2cnn(Cc3ccc(-n4nc(C(F)(F)F)cc4C)cc3)c2n1] | I-19 and BB-37 | LC-MS (Method A) (ESI+): m/z 522 (M + H)+; 1H-NMR (300 MHz, CDCl3) δ 9.30 (s, 1H), 8.19 (s, 1H), 7.54 (d, J = 8.4 Hz, 2H), 7.38 (d, J = 8.4 Hz, 2H), 6.43 (s, 1H), 5.76 (s, 2H), 4.87 (s, 2H), 3.85 (s, 3H), 2.31 (s, 3H), 1.71 (m, 1H), 1.09-1.17 (m, 2H), 0.69-0.78 (m, 2H). |

-continued

| Example | Structure | Starting material | Analytical data |
|---|---|---|---|
| 113 | 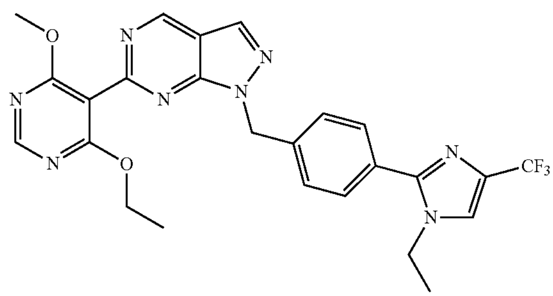 [SMILES: CCOc1ncnc(OC)c1-c1ncc2cnn(Cc3ccc(-c4nc(C(F)(F)F)cn4CC)cc3)c2n1] | I-5 and BB-29 | LC-MS (Method B) (ESI+): m/z 525.05 (M + H)+; 1H-NMR (400 MHz, DMSO-d6) δ 9.45 (s, 1H), 8.61 (s, 1H), 8.49 (s, 1H), 8.01 (s, 1H), 7.59 (d, J = 7.34 Hz, 2H), 7.41 (d, J = 7.83 Hz, 2H), 5.76 (s, 2H), 4.37 (q, J = 7.17 Hz, 2H), 4.04 (q, J = 7.01 Hz, 2H), 3.87 (s, 3H), 1.29 (t, J = 7.09 Hz, 3H), 1.14 (t, J = 7.09 Hz, 3H). |
| 114 | 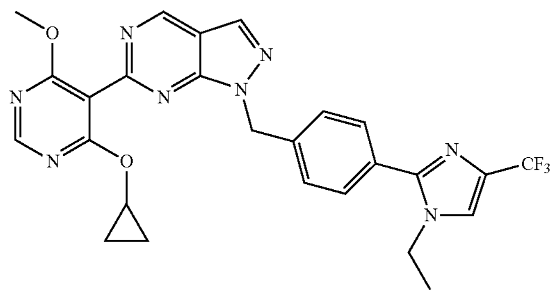 [SMILES: CCn1cc(C(F)(F)F)nc1-c1ccc(Cn2ncc3cnc(-c4c(OC)ncnc4OC4CC4)nc32)cc1] | I-5 and BB-30 | LC-MS (Method B) (ESI+): m/z 537.15 (M + H)+; 1H-NMR (400 MHz, DMSO-d6) δ 9.43 (s, 1H), 8.67 (s, 1H), 8.48 (s, 1H), 8.01 (s, 1H), 7.60 (d, J = 7.83 Hz, 2H), 7.39 (d, J = 8.31 Hz, 2H), 5.75 (s, 2H), 4.34-4.39 (m, 1H), 4.05 (q, J = 7.01 Hz, 2H), 3.88 (s, 3H), 1.30 (t, J = 7.34 Hz, 3H), 0.69 (q, J = 6.52 Hz, 2H), 0.45-0.50 (m, 2H). |
| 115 | 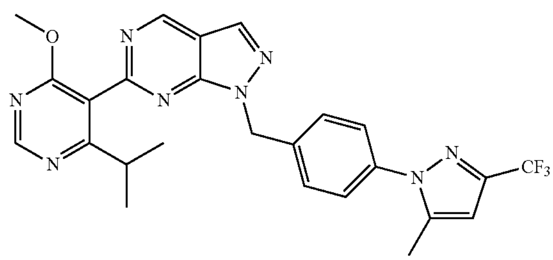 [SMILES: COc1ncnc(C(C)C)c1-c1ncc2cnn(Cc3ccc(-n4nc(C(F)(F)F)cc4C)cc3)c2n1] | I-19 and BB-22 | LC-MS (Method B) (ESI+): m/z 509.70 (M + H)+; 1H-NMR (400 MHz, DMSO-d6) δ 9.50 (s, 1H), 8.86 (s, 1H), 8.54 (s, 1H), 7.35-7.46 (m, 4H), 6.92 (s, 1H), 5.79 (s, 2H), 3.85 (s, 3H), 2.59-2.69 (m, 1H), 2.26 (s, 3H), 1.07 (d, J = 6.36 Hz, 6H). |
| 116 | 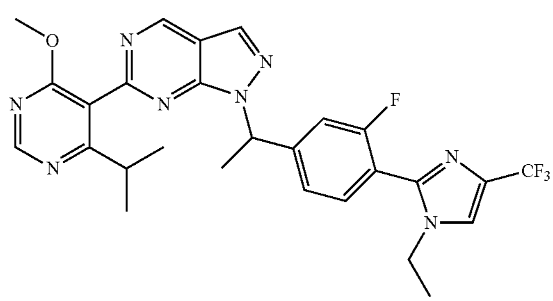 [SMILES: CCn1cc(C(F)(F)F)nc1-c1ccc(C(C)n2ncc3cnc(-c4c(OC)ncnc4C(C)C)nc32)cc1F] | I-26 and BB-22 | LC-MS (Method C) (ESI+): m/z 555.20 (M + H)+; 1H-NMR (400 MHz, DMSO-d6) δ 9.48 (s, 1H), 8.86 (s, 1H), 8.56 (s, 1H), 8.08 (s, 1H), 7.52 (t, J = 7.83 Hz, 1H), 7.38 (d, J = 11.25 Hz, 1H), 7.25 (d, J = 7.83 Hz, 1H), 6.35 (q, J = 6.85 Hz, 1H), 3.84 (s, 3H), 3.78-3.83 (m, 1H), 2.53-2.60 (m, 2H), 2.00 (d, J = 6.85 Hz, 3H), 1.24 (t, J = 7.34 Hz, 3H), 1.05 (t, J = 6.85 Hz, 6H). |
| 117 | 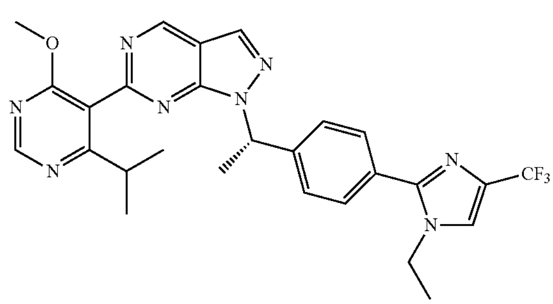 [SMILES: CCn1cc(C(F)(F)F)nc1-c1ccc([C@H](C)n2ncc3cnc(-c4c(OC)ncnc4C(C)C)nc32)cc1] | I-28 and BB-22 | LC-MS (Method B) (ESI+): m/z 537.18 (M + H)+; 1H-NMR (400 MHz, DMSO-d6) δ 9.47 (s, 1H), 8.86 (s, 1H), 8.54 (s, 1H), 8.00 (d, J = 1.00 Hz, 1H), 7.58 (d, J = 8.48 Hz, 2H), 7.43-7.47 (m, 2H), 6.28-6.35 (m, 1H), 4.03 (q, J = 7.48 Hz, 2H), 3.84 (s, 3H), 2.58 (dd, J = 6.48, 13.46 Hz, 1H), 2.00 (d, J = 6.98 Hz, 3H), 1.28 (t, J = 7.23 Hz, 3H), 1.05 (t, J = 7.48 Hz, 6H). |

-continued

| Example | Structure | Starting material | Analytical data |
|---|---|---|---|
| 118 | 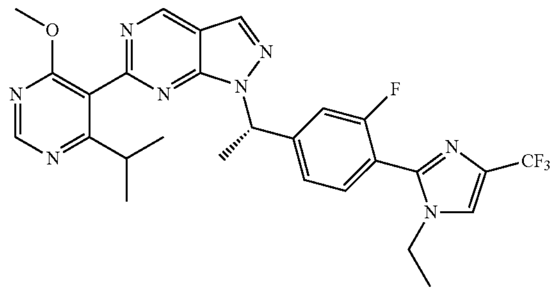 [SMILES: CCn1cc(C(F)(F)F)nc1-c1ccc([C@H](C)n2ncc3cnc(-c4c(OC)ncnc4C(C)C)nc32)cc1F] | I-27 and BB-22 | LC-MS (Method B) (ESI+): m/z 555.10 (M + H)+; 1H-NMR (400 MHz, DMSO-d6) δ 9.48 (s, 1H), 8.86 (s, 1H), 8.56 (s, 1H), 8.08 (s, 1H), 7.52 (t, J = 7.58 Hz, 1H), 7.38 (d, J = 11.25 Hz, 1H), 7.25 (d, J = 7.83 Hz, 1H), 6.31-6.40 (m, 1H), 3.84 (s, 3H), 3.78-3.83 (m, 1H), 2.53-2.65 (m, 2H), 2.00 (d, J = 6.85 Hz, 3H), 1.24 (t, J = 7.09 Hz, 3H), 1.05 (t, J = 6.85 Hz, 6H). |
| 119 | 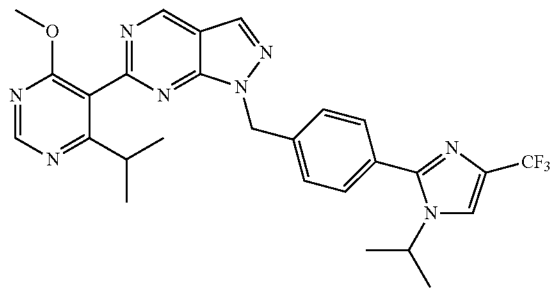 [SMILES: COc1ncnc(C(C)C)c1-c1ncc2cnn(Cc3ccc(-c4nc(C(F)(F)F)cn4C(C)C)cc3)c2n1] | I-6 and BB-22 | LC-MS (Method B) (ESI+): m/z 537.15 (M + H)+; 1H-NMR (400 MHz, DMSO-d6) δ 9.49 (s, 1H), 8.86 (s, 1H), 8.53 (s, 1H), 8.16 (s, 1H), 7.52 (d, J = 8.03 Hz, 2H), 7.40 (d, J = 8.03 Hz, 2H), 5.78 (s, 2H), 4.41 (td, J = 6.56, 13.24 Hz, 1H), 3.86 (s, 3H), 2.65 (td, J = 6.49, 13.36 Hz, 1H), 1.37 (d, J = 6.53 Hz, 6H), 1.08 (d, J = 6.78 Hz, 6H). |
| 120 | 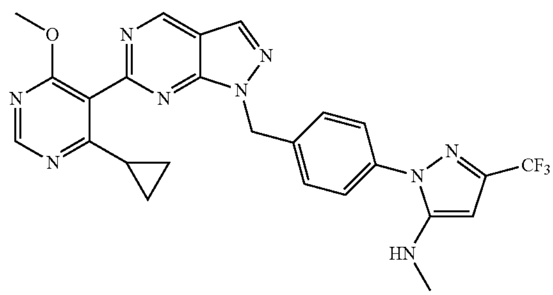 [SMILES: CNc1cc(C(F)(F)F)nn1-c1ccc(Cn2ncc3cnc(-c4c(OC)ncnc4C4CC4)nc32)cc1] | I-46 and BB-4 | LC-MS (Method C) (ESI+): m/z 522.10 (M + H)+; 1H-NMR (400 MHz, DMSO-d6) δ 9.50 (s, 1H), 8.72 (s, 1H), 8.51 (s, 1H), 7.45-7.53 (m, 4H), 5.88 (s, 2H), 5.77 (s, 2H), 3.86 (s, 3H), 2.65 (d, J = 4.99 Hz, 3H), 1.66 (td, J = 3.86, 8.23 Hz, 1H), 1.06 (d, J = 2.99 Hz, 2H), 0.88 (dd, J = 2.99, 7.48 Hz, 2H). |
| 121 | 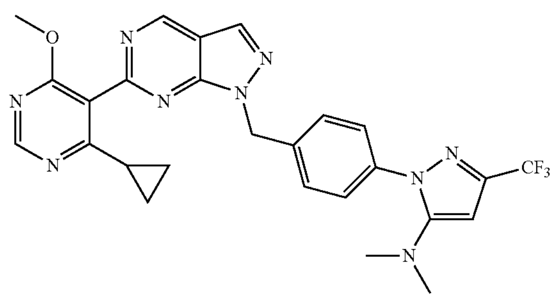 [SMILES: COc1ncnc(C2CC2)c1-c1ncc2cnn(Cc3ccc(-n4nc(C(F)(F)F)cc4N(C)C)cc3)c2n1] | I-48 and BB-4 | LC-MS (Method A) (ESI+): m/z 536 (M + H)+; 1H-NMR (300 MHz, CDCl3) δ 9.34 (s, 1H), 8.69 (s, 1H), 8.23 (s, 1H), 7.67 (d, J = 8.4 Hz, 2H), 7.50 (d, J = 8.4 Hz, 2H), 6.05 (s, 1H), 5.74 (s, 2H), 3.94 (s, 3H), 2.59 (s, 6H), 1.67 (m, 1H), 1.21-1.30 (m, 2H), 0.88-0.92 (m, 2H). |
| 122 | 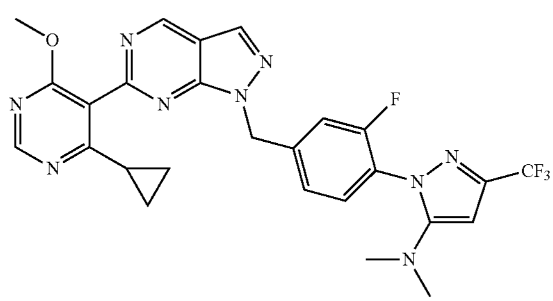 [SMILES: COc1ncnc(C2CC2)c1-c1ncc2cnn(Cc3ccc(-n4nc(C(F)(F)F)cc4N(C)C)c(F)c3)c2n1] | I-47 and BB-4 | LC-MS (Method C) (ESI+): m/z 554.05 (M + H)+; 1H-NMR (400 MHz, DMSO-d6) δ 9.52 (s, 1H), 8.71 (s, 1H), 8.55 (s, 1H), 7.60 (t, J = 7.98 Hz, 1H), 7.41 (dd, J = 1.25, 10.72 Hz, 1H), 7.21-7.26 (m, 1H), 6.35 (s, 1H), 5.83 (s, 2H), 3.84 (s, 3H), 2.48 (s, 6H), 1.62-1.69 (m, 1H), 1.05 (td, J = 3.49, 6.98 Hz, 2H), 0.82-0.89 (m, 2H). |

-continued

| Example | Structure | Starting material | Analytical data |
|---|---|---|---|
| 123 | 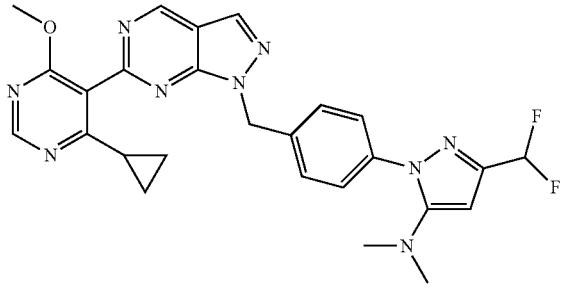 [SMILES: COc1ncnc(C2CC2)c1-c1ncc2cnn(Cc3ccc(-n4nc(C(F)F)cc4N(C)C)cc3)c2n1] | I-49 and BB-4 | LC-MS (Method B) (ESI+): m/z 518.35 (M + H)+; $^1$H-NMR (400 MHz, CD$_3$OD) δ 9.40 (s, 1H), 8.64 (s, 1H), 8.41 (s, 1H), 7.64 (d, J = 7.98 Hz, 2H), 7.50 (d, J = 8.48 Hz, 2H), 6.46-6.76 (m, 1H), 6.11 (s, 1H), 5.79 (s, 2H), 3.92 (s, 3H), 2.57 (s, 6H), 1.62-1.71 (m, 1H), 1.13-1.18 (m, 2H), 0.86-0.92 (m, 2H). |
| 125 | 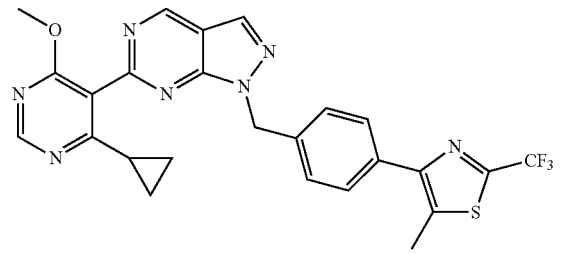 [SMILES: COc1ncnc(C2CC2)c1-c1ncc2cnn(Cc3ccc(-c4nc(C(F)(F)F)sc4C)cc3)c2n1] | I-60 and BB-4 | LC-MS (Method B) (ESI+): m/z 524.30 (M + H)+; $^1$H-NMR (400 MHz, DMSO-d$_6$) δ 9.51 (s, 1H), 8.71 (s, 1H), 8.52 (s, 1H), 7.65 (d, J = 7.83 Hz, 2H), 7.42 (d, J = 7.83 Hz, 2H), 5.77 (s, 2H), 3.85 (s, 3H), 2.62 (s, 3H), 1.61-1.69 (m, 1H), 1.03-1.08 (m, 2H), 0.82-0.88 (m, 2H). |
| 126 | 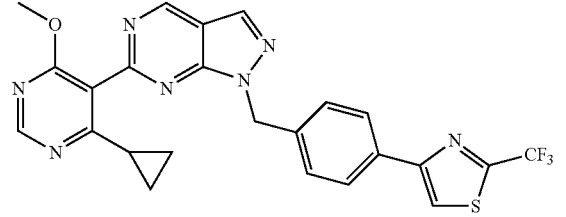 [SMILES: COc1ncnc(C2CC2)c1-c1ncc2cnn(Cc3ccc(-c4csc(C(F)(F)F)n4)cc3)c2n1] | I-61 and BB-4 | LC-MS (Method B) (ESI+): m/z 510.65 (M + H)+; $^1$H-NMR (400 MHz, DMSO-d$_6$) δ 9.50 (s, 1H), 8.71 (s, 1H), 8.56 (s, 1H), 8.51 (s, 1H), 7.94 (d, J = 7.98 Hz, 2H), 7.41 (d, J = 7.98 Hz, 2H), 5.75 (s, 2H), 3.85 (s, 3H), 1.60-1.68 (m, 1H), 1.03-1.08 (m, 2H), 0.82-0.88 (m, 2H). |
| 127 | 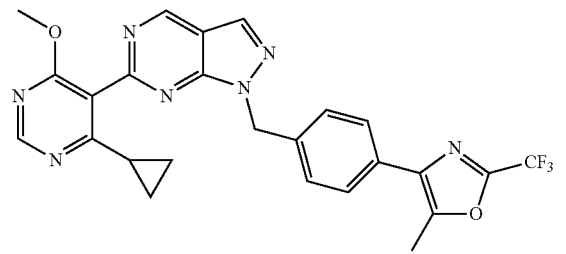 [SMILES: COc1ncnc(C2CC2)c1-c1ncc2cnn(Cc3ccc(-c4nc(C(F)(F)F)oc4C)cc3)c2n1] | I-62 and BB-4 | LC-MS (Method B) (ESI+): m/z 508.10 (M + H)+; $^1$H-NMR (400 MHz, DMSO-d$_6$) δ 9.50 (s, 1H), 8.71 (s, 1H), 8.51 (s, 1H), 7.65 (d, J = 8.31 Hz, 2H), 7.41 (d, J = 7.82 Hz, 2H), 5.75 (s, 2H), 3.85 (s, 3H), 2.61 (s, 3H), 1.61-1.68 (m, 1H), 1.03-1.08 (m, 2H), 0.82-0.88 (m, 2H). |
| 128 | 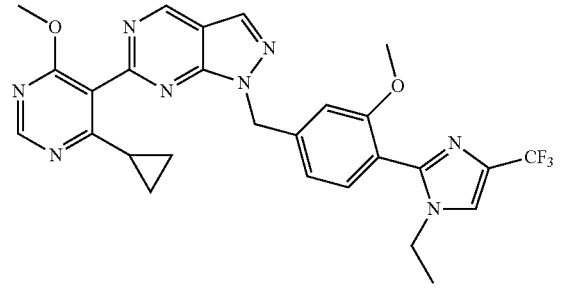 [SMILES: CCn1cc(C(F)(F)F)nc1-c1ccc(Cn2ncc3cnc(-c4c(OC)ncnc4C4CC4)nc32)cc1OC] | I-12 and BB-4 | LC-MS (Method B) (ESI+): m/z 551.10 (M + H)+; $^1$H-NMR(400 MHz, DMSO-d$_6$) δ 9.52 (s, 1H), 8.71 (s, 1H), 8.53 (s, 1H), 7.97 (s, 1H), 7.28 (d, J = 7.48 Hz, 1H), 7.20 (s, 1H), 6.85 (d, J = 7.98 Hz, 1H), 5.78 (s, 2H), 3.84 (s, 3H), 3.74-3.75 (m, 3H), 3.68-3.73 (m, 2H), 1.59-1.67 (m, 1H), 1.20 (t, J = 7.23 Hz, 3H), 1.03-1.08 (m, 2H), 0.84 (dd, J = 2.99, 7.48 Hz, 2H). |

-continued

| Example | Structure | Starting material | Analytical data |
|---|---|---|---|
| 129 | 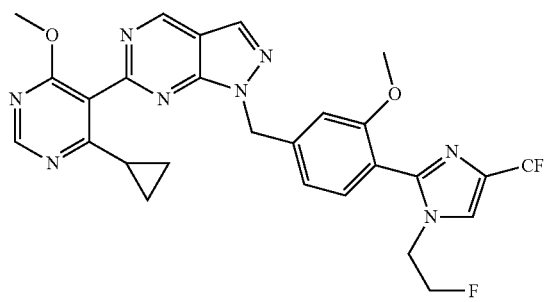 | I-13 and BB-4 | LC-MS (Method B) (ESI+): m/z 569.30 (M + H)+; 1H-NMR (400 MHz, DMSO-d6) δ 9.51 (s, 1H), 8.71 (s, 1H), 8.53 (s, 1H), 7.94 (s, 1H), 7.29 (d, J = 7.82 Hz, 1H), 7.21 (s, 1H), 6.86 (d, J = 7.34 Hz, 1H), 5.78 (s, 2H), 4.63 (t, J = 4.65 Hz, 1H), 4.51 (t, J = 4.40 Hz, 1H), 4.11 (t, J = 4.40 Hz, 1H), 4.04 (t, J = 4.40 Hz, 1H), 3.84 (s, 3H), 3.74 (s, 3H), 1.59-1.67 (m, 1H), 1.06 (d, J = 2.45 Hz, 2H), 0.85 (dd, J = 2.93, 7.83 Hz, 2H). |
| 130 | 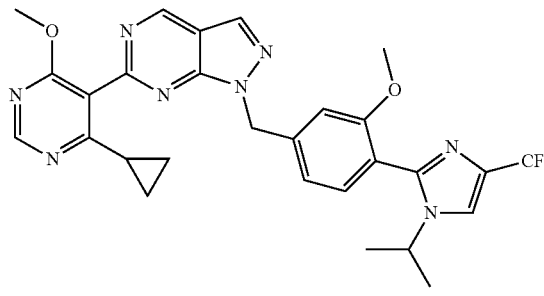 | I-14 and BB-4 | LC-MS (Method C) (ESI+): m/z 565.05 (M + H)+; 1H-NMR (400 MHz, DMSO-d6) δ 9.52 (s, 1H), 8.71 (s, 1H), 8.53 (s, 1H), 8.11 (s, 1H), 7.27 (d, J = 7.83 Hz, 1H), 7.20 (s, 1H), 6.85 (d, J = 7.34 Hz, 1H), 5.78 (s, 2H), 3.92-4.00 (m, 1H), 3.84 (s, 3H), 3.73 (s, 3H), 1.59-1.66 (m, 1H), 1.29 (d, J = 6.85 Hz, 6H), 1.02-1.07 (m, 2H), 0.81-0.87 (m, 2H). |
| 131 | 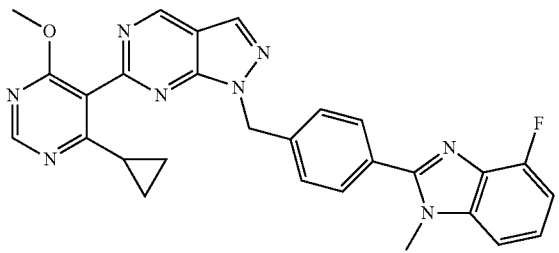 [SMILES: COc1ncnc(C2CC2)c1-c1ncc2cnn(Cc3ccc(-c4nc5c(F)cccc5n4C)cc3)c2n1] | I-63 and BB-4 | LC-MS (Method C) (ESI+): m/z 507.05 (M + H)+; 1H-NMR (400 MHz, DMSO-d6) δ 9.51 (s, 1H), 8.70 (s, 1H), 8.52 (s, 1H), 7.82 (d, J = 7.98 Hz, 2H), 7.44-7.49 (m, 3H), 7.25 (dt, J = 4.74, 8.10 Hz, 1H), 7.04 (dd, J = 8.23, 10.72 Hz, 1H), 5.81 (s, 2H), 3.85 (s, 3H), 3.84 (s, 3H), 1.62-1.70 (m, 1H), 1.02-1.08 (m, 2H), 0.81-0.89 (m, 2H). |
| 132 | 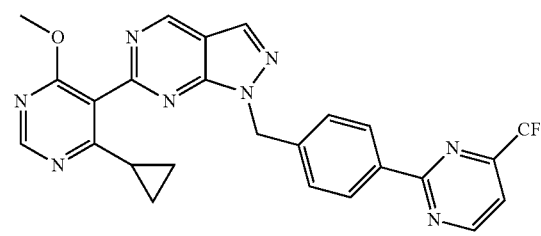 | I-64 and BB-4 | LC-MS (Method B) (ESI+): m/z 505.15 (M + H)+; 1H-NMR (400 MHz, DMSO-d6) δ 9.44 (br s, 1H), 9.14-9.17 (m, 1H), 8.63 (br s, 1H), 8.47 (br s, 1H), 8.28 (d, J = 7.48 Hz, 2H), 7.84 (br s, 1H), 7.41 (d, J = 6.48 Hz, 2H), 5.75 (br. s, 2H), 3.80 (br. s, 3H), 1.52-1.59 (m, 1H), 0.96-1.02 (m, 2H), 0.76-0.83 (m, 2H). |

*Stereochemistry of discrete enantiomers arbitrarily assigned after chiral SFC separation of racemate.

Example 133: Synthesis of 6-(4-Cyclopropyl-6-methoxy-2-methylpyrimidin-5-yl)-1-(4-(1-methyl-4-(trifluoromethyl)-1H-imidazol-2-yl)benzyl)-1H-pyrazolo[3,4-d]pyrimidine (133)

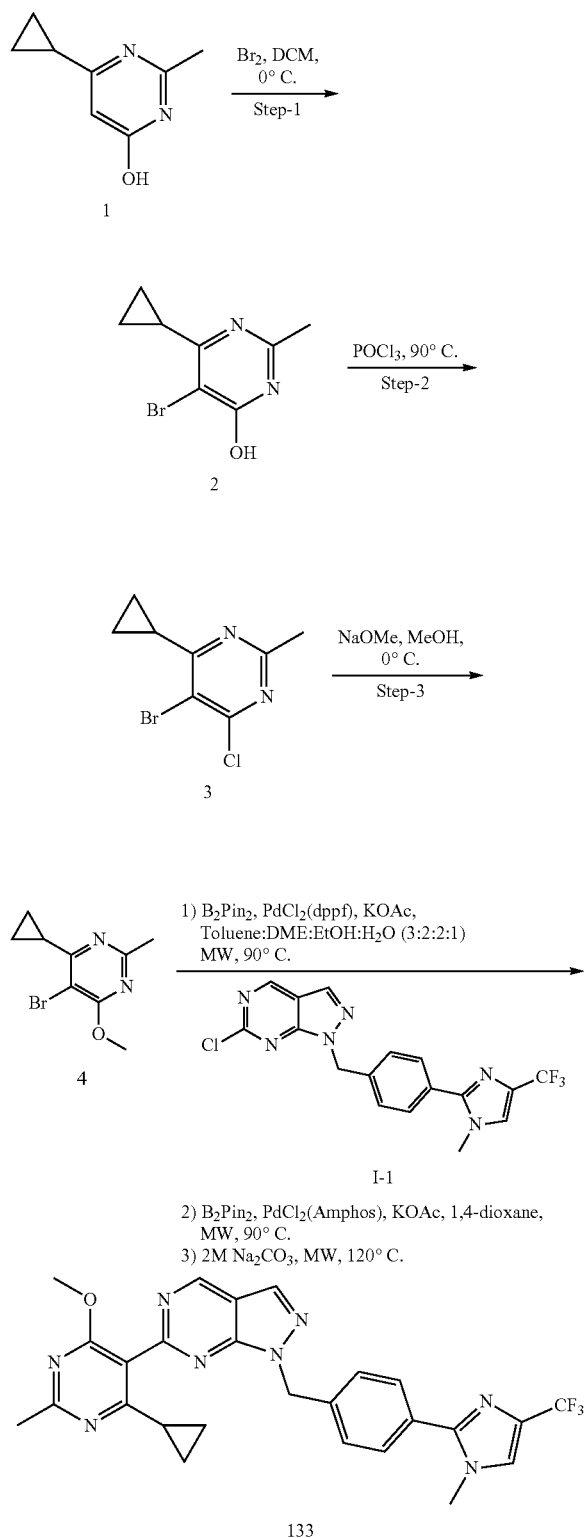

Step 1: Synthesis of 5-Bromo-6-cyclopropyl-2-methylpyrimidin-4-ol

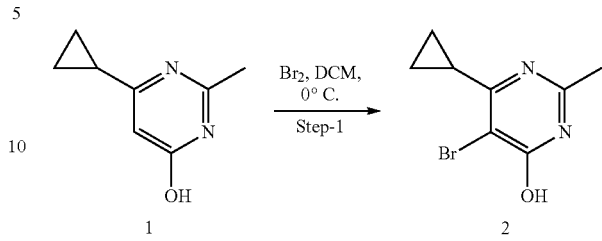

A solution of 6-cyclopropyl-2-methylpyrimidin-4-ol (2.0 g, 13.33 mmol) in DCM (50 mL) cooled to 0° C., was treated dropwise with bromine (0.75 mL, 14.66 mmol). The resulting mixture was stirred at 0° C. for 4 h. After completion of reaction (monitored by TLC), the reaction mixture was quenched with saturated sodium thiosulphate solution (50 mL). The aqueous layer was extracted with 10% methanol in DCM (3×50 mL). The combined organic layer was dried over anhydrous $Na_2SO_4$, filtered, and concentrated under reduced pressure resulting in the crude compound. The crude compound was purified by silica gel chromatography (0-10% methanol in DCM) to afford 1.50 g of the title compound. LC-MS (Method B) (ESI+): m/z 230.90 $(M+H)^+$; $^1$H-NMR (400 MHz, DMSO-$d_6$) δ 12.62 (br. s, 1H), 2.31 (td, J=6.17, 12.59 Hz, 1H), 2.20 (s, 3H), 0.96-1.02 (m, 4H).

Step 2: Synthesis of 5-Bromo-4-chloro-6-cyclopropyl-2-methylpyrimidine

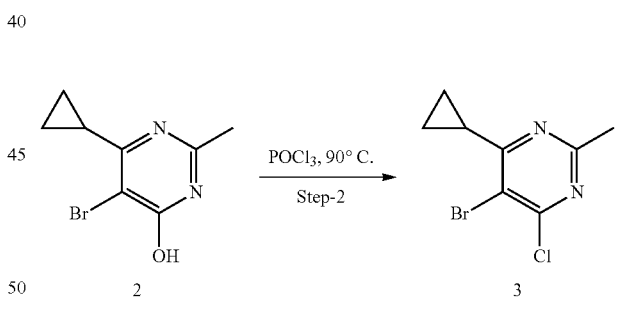

A solution of 5-bromo-6-cyclopropyl-2-methylpyrimidin-4-ol (1.5 g, 6.550 mmol) in $POCl_3$ (20 mL) was heated at 90° C. for 2 h. After completion of the reaction (monitored by TLC), the reaction mixture was quenched with ice and extracted with EA (3×50 mL). The combined organic layer was dried over anhydrous $Na_2SO_4$, filtered, and concentrated under vacuum. The crude compound was purified by column chromatography (silica gel; 0-20% EA in n-hexane) to afford 1.20 g of the title compound. LC-MS (Method B) (ESI+): m/z 248.95 $(M+H)^+$.

319

Step 3: Synthesis of
5-Bromo-4-cyclopropyl-6-methoxy-2-methylpyrimidine

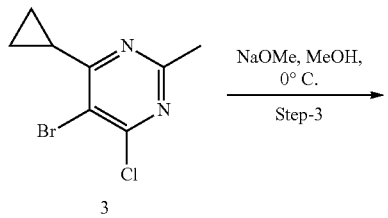

To an ice-cold solution of 5-bromo-4-chloro-6-cyclopropyl-2-methylpyrimidine (1.1 g, 4.453 mmol) in methanol (20 mL), was added 2 M sodium methoxide solution (20 mL). The reaction mixture was stirred at 0° C. for 2 h. After completion of reaction (monitored by TLC), the reaction mixture was quenched with ice cold water (50 mL) and EA (50 mL). The organic layer was separated, dried over anhydrous $Na_2SO_4$, filtered, and concentrated under vacuum. The crude compound was purified by column chromatography (silica gel; 0-10% EA in n-hexane) to afford 0.90 g the title compound. LC-MS (Method B) (ESI+): m/z 242.95 $(M+H)^+$; $^1$H-NMR (400 MHz, $CDCl_3$) δ 4.00 (s, 3H), 2.47-2.51 (m, 1H), 2.46 (s, 3H), 1.12-1.17 (m, 2H), 1.00-1.05 (m, 2H).

Step 4: Synthesis of 6-(4-Cyclopropyl-6-methoxy-2-methylpyrimidin-5-yl)-1-(4-(1-methyl-4-(trifluoromethyl)-1H-imidazol-2-yl)benzyl)-1H-pyrazolo[3,4-d]pyrimidine (133)

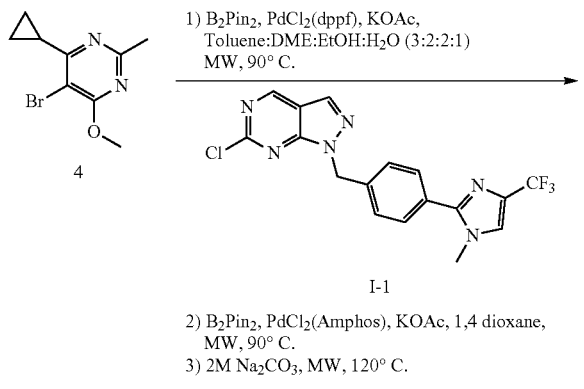

320

-continued

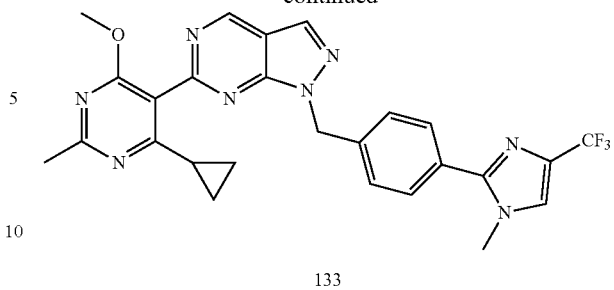

133

Step 1:

To a 30 mL microwave vial, was added 5-bromo-4-cyclopropyl-6-methoxy-2-methylpyrimidine (0.100 g, 0.411 mmol), bispinacolatodiboron (0.104 g, 0.411 mmol), KOAc (0.040 g, 0.41 mmol) and Toluene:DME:EtOH:$H_2O$ (3:2:2:1, 6 mL). The mixture was purged with argon for 20 min, whereupon $PdCl_2(dppf)$ (0.030 g, 0.041 mmol) was added. The reaction mixture was then heated in a microwave at 90° C. for 20 min. After completion of the reaction (monitored by TLC), the mixture was used without work-up in Step 3.

Step 2:

To another 30 mL microwave vial, was added 6-chloro-1-(4-(1-methyl-4-(trifluoromethyl)-1H-imidazol-2-yl)benzyl)-1H-pyrazolo[3,4-d]pyrimidine (0.160 g, 0.408 mmol), bispinacolatodiborane (0.103 g, 0.408 mmol), and KOAc (0.119 g, 1.224 mmol) in 1,4 dioxane (6 mL). The resulting mixture was purged with argon for 20 min, whereupon Pd(amphos)$Cl_2$ (0.028 g, 0.040 mmol) was added. The reaction mixture was then heated in a microwave at 90° C. for 20 min. After completion of the reaction (monitored by TLC), the reaction mixture was used without work up in Step 3.

Step 3:

Both the reaction mixtures from Step 1 and Step 2 were combined, and 2M aqueous $Na_2CO_3$ (4 mL) was added at room temperature. The resulting reaction mixture was heated in a microwave at 120° C. for 30 min. After completion of the reaction (monitored by TLC), the mixture was diluted with water (50 mL) and extracted with EA (3×30 mL). The combined organic layer was dried over anhydrous $Na_2SO_4$, filtered, and concentrated under reduced pressure. The crude compound was purified by silica gel chromatography (0-10% methanol in DCM) to afford 0.025 g of the title compound. LC-MS (Method B) (ESI+): m/z 521.10 $(M+H)^+$; $^1$H-NMR (400 MHz, DMSO-$d_6$) δ 9.48 (s, 1H), 8.50 (s, 1H), 7.91 (s, 1H), 7.67 (d, J=8.31 Hz, 2H), 7.41 (d, J=8.31 Hz, 2H), 5.76 (s, 2H), 3.82 (s, 3H), 3.74 (s, 3H), 2.50 (br. s, 3H, $OCH_3$ protons merged in residual solvent peak), 1.59-1.67 (m, 1H), 1.00-1.05 (m, 2H), 0.81 (dd, J=3.18, 7.58 Hz, 2H).

Example 134: Synthesis of 6-(4-Cyclopropyl-6-methoxypyrimidin-5-yl)-1-(4-(4-(trifluoromethyl)-1H-imidazol-2-yl)benzyl)-1H-pyrazolo[3,4-d]pyrimidine (134)

Step 1: Synthesis of 6-(4-Cyclopropyl-6-methoxypyrimidin-5-yl)-1-(4-(4-(trifluoromethyl)-1-((2-(trimethylsilyl)ethoxy)methyl)-1H-imidazol-2-yl)benzyl)-1H-pyrazolo[3,4-d]pyrimidine

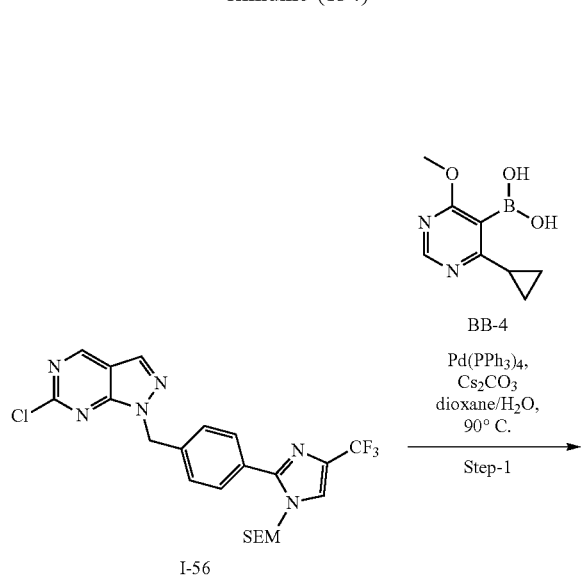

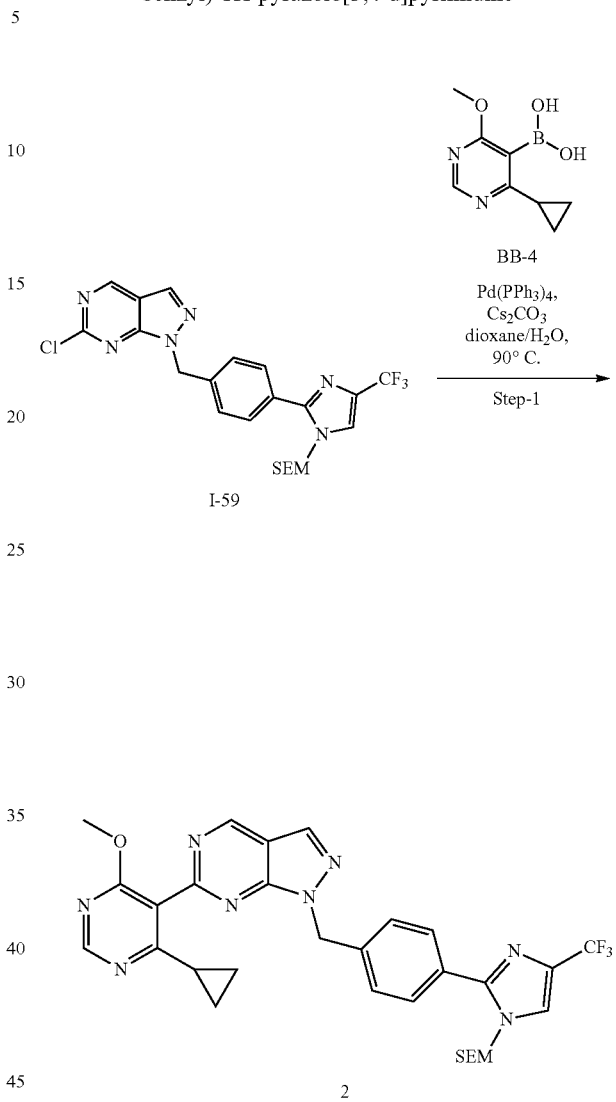

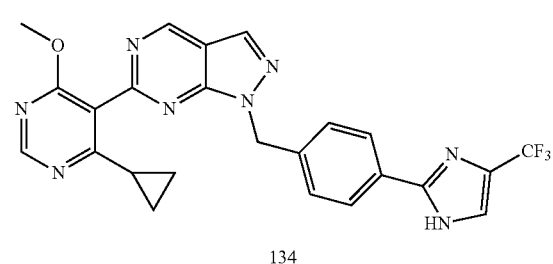

To a stirred solution of 6-chloro-1-(4-(4-(trifluoromethyl)-1-((2-(trimethylsilyl)ethoxy)methyl)-1H-imidazol-2-yl)benzyl)-1H-pyrazolo[3,4-d]pyrimidine I-59 (0.50 g, 0.98 mmol) and (4-cyclopropyl-6-methoxypyrimidin-5-yl)boronic acid (BB-4) (0.25 g, 1.27 mmol) in dioxane:H$_2$O (5:1, 12 mL), was added Cs$_2$CO$_3$ (0.801 g, 2.46 mmol). The reaction mixture was degassed with argon for 10 min followed by addition of Pd(PPh$_3$)$_4$ (0.113 g, 0.09 mmol). The reaction mixture was degassed with argon for 5 min and heated to 90° C. for 12 h. Progress of the reaction was monitored by TLC and LCMS. After completion, the reaction mixture was diluted with water (100 mL) and extracted with EA (2×200 mL). The combined organic layer was washed with brine (200 mL), dried over anhydrous sodium sulfate, filtered, and concentrated under reduced pressure. The crude compound was purified by silica gel chromatography using 10-30% EA in hexane to afford 0.41 g of the title compound. LC-MS (Method B) (ESI+): m/z 623.25 (M+H)$^+$.

323

Step 2: Synthesis of 6-(4-Cyclopropyl-6-methoxy-pyrimidin-5-yl)-1-(4-(4-(trifluoromethyl)-1H-imidazol-2-yl)benzyl)-1H-pyrazolo[3,4-d]pyrimidine (134)

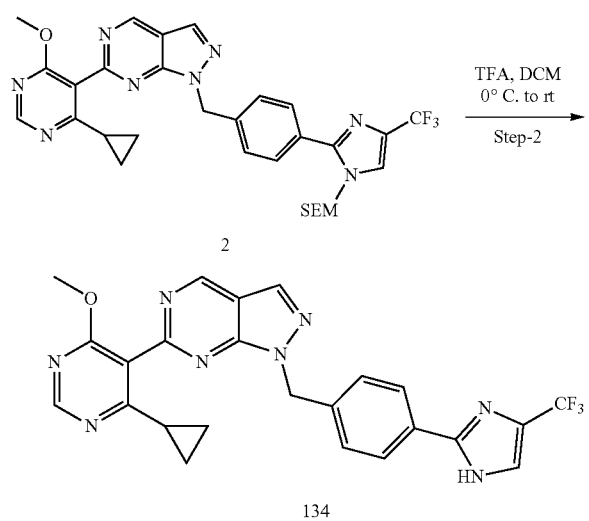

To a stirred solution of 6-(4-cyclopropyl-6-methoxypyrimidin-5-yl)-1-(4-(4-(trifluoromethyl)-1-((2-(trimethylsilyl)ethoxy)methyl)-1H-imidazol-2-yl)benzyl)-1H-pyrazolo[3,4-d]pyrimidine (0.07 g, 0.11 mmol) in DCM (5 mL) at 0° C., was slowly added TFA (2 mL), and the reaction mixture was stirred at room temperature for 4 h. Progress of the reaction was monitored by TLC. After completion, the reaction mixture was concentrated under reduced pressure. To the residue, water was added, adjusted to pH=7 using NaHCO$_3$ solution, and extracted with EA. The organic layer was dried over anhydrous sodium sulfate, filtered, and concentrated under reduced pressure. The crude compound was purified by silica gel chromatography using 0-40% EA in hexane to afford 0.025 g of the title compound. LC-MS (Method C) (ESI+): m/z 493.05 (M+H)$^+$; $^1$H-NMR (400 MHz, DMSO-d$_6$) δ 13.17 (s, 1H), 9.50 (s, 1H), 8.71 (s, 1H), 8.51 (s, 1H), 7.88-7.94 (m, 3H), 7.40 (d, J=7.8 Hz, 2H), 5.74 (s, 2H), 3.86 (s, 3H), 1.66 (s, 1H), 1.06 (s, 2H), 0.86 (d, J=3.9 Hz, 2H).

Example 135: Synthesis of 6-(4-(azetidin-3-yl)-6-methoxypyrimidin-5-yl)-1-(4-(1-ethyl-4-(trifluoromethyl)-1H-imidazol-2-yl)benzyl)-1H-pyrazolo[3,4-d]pyrimidine (135)

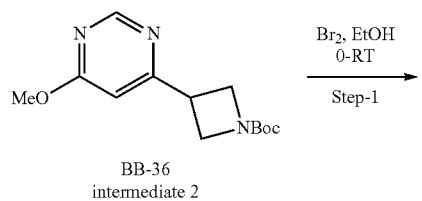

324

-continued

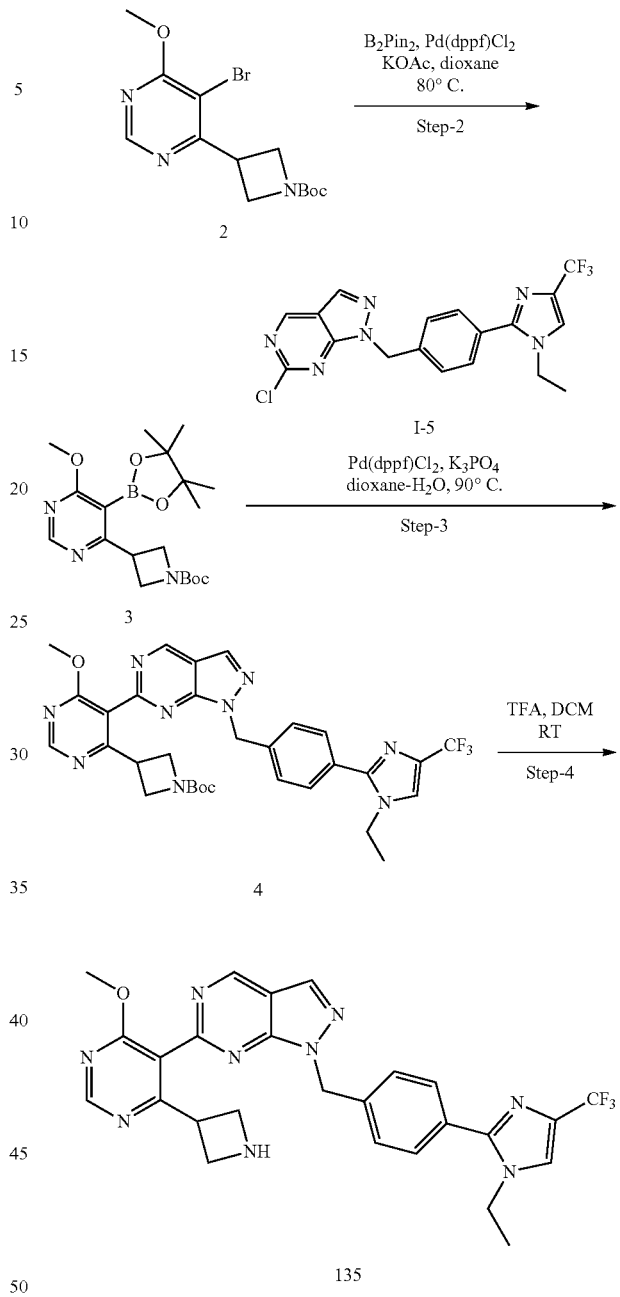

Step 1: Synthesis of tert-butyl 3-(5-bromo-6-methoxypyrimidin-4-yl)azetidine-1-carboxylate

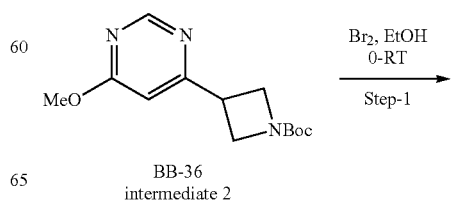

-continued

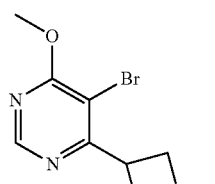

2

To a stirred solution of tert-butyl 3-(6-methoxypyrimidin-4-yl)azetidine-1-carboxylate (10.0 g, 37.7 mmol) in ethanol (200 mL) was added bromine (9.0 g, 57 mmol) at 0° C. The resulting mixture was then allowed to warm to rt and stirred for 16 h. Progress of the reaction was monitored by TLC. After completion, the reaction mixture was concentrated under reduced pressure. The resulting residue was dissolved in aqueous ammonia solution (30 mL) and extracted with EA (200 mL). The organic layer was separated, dried over anhydrous sodium sulfate, filtered and concentrated under reduced pressure. The crude compound was purified by silica gel chromatography using 10-50% EA in n hexane to afford title compound (10.0 g). LC-MS (Method C) (ESI+): m/z 289.90 (M+H)$^+$; $^1$H-NMR (400 MHz, DMSO-d$_6$) δ 8.77 (s, 1H), 4.15-4.21 (m, 3H), 4.05-4.10 (m, 2H), 4.01 (s, 3H), 1.38 (s, 9H).

Step 2: Synthesis of tert-butyl 3-(6-methoxy-5-(4,4,5,5-tetramethyl-1,3,2-dioxaborolan-2-yl)pyrimidin-4-yl)azetidine-1-carboxylate

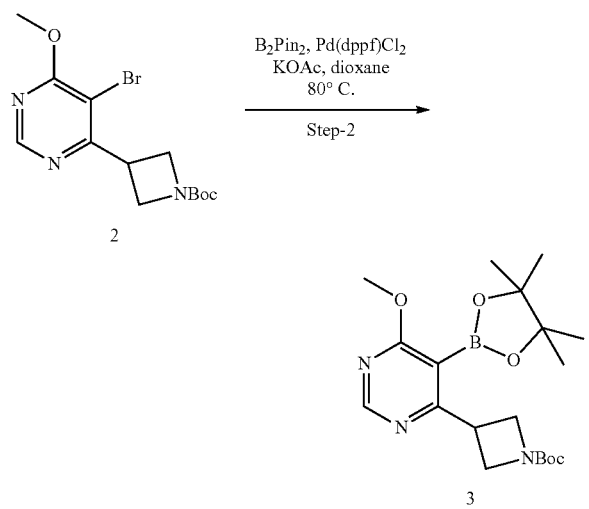

To a stirred solution of tert-butyl 3-(5-bromo-6-methoxypyrimidin-4-yl)azetidine-1-carboxylate 2 (5.0 g, 14.5 mmol) and B$_2$Pin$_2$ (11.1 g, 43.6 mmol) in dioxane (50 mL) was added and KOAc (4.26 g, 43.6 mmol) and the reaction mixture was degassed with argon gas for 15 min. To the resulting reaction mixture was added Pd(dppf)Cl$_2$-DCM (2.36 g, 2.90 mmol) and then the mixture was heated in sealed tube at 80° C. for 2 h. Progress of the reaction was monitored by TLC. After completion, the reaction mixture was cooled to room temperature, diluted with EA (100 mL) and filtered through a pad of Celite. The filtrate was concentrated under reduced pressure and the crude residue was purified by silica gel chromatography using 10-30% EA in n hexane to afford the title compound (3.9 g). LC-MS (Method C) (ESI+): m/z 392.10 (M+H)$^+$; $^1$H-NMR (400 MHz, DMSO-d$_6$) δ 7.93 (s, 1H), 4.05-4.15 (m, 3H), 3.90-3.94 (m, 2H), 3.89 (s, 3H), 1.38 (s, 9H), 1.16 (s, 12H).

Step 3: Synthesis of tert-butyl 3-(5-(1-(4-(1-ethyl-4-(trifluoromethyl)-1H-imidazol-2-yl)benzyl)-1H-pyrazolo[3,4-d]pyrimidin-6-yl)-6-methoxypyrimidin-4-yl)azetidine-1-carboxylate

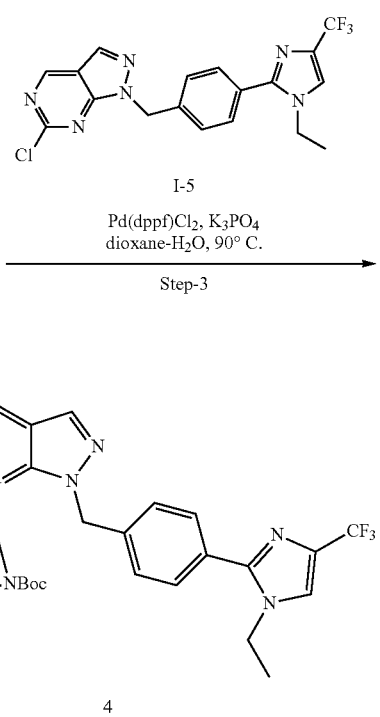

To a stirred solution of tert-butyl 3-(6-methoxy-5-(4,4,5,5-tetramethyl-1,3,2-dioxaborolan-2-yl)-pyrimidin-4-yl)azetidine-1-carboxylate 3 (1.0 g, 2.6 mmol) in dioxane (20 mL) and water (10 mL) was added I-5 (1.03 g, 2.6 mmol) and potassium phosphate (0.811 g, 3.83 mmol)) at room temperature. The resulting reaction mixture was degassed with argon gas for 30 min, and then treated with X-Phos-Pd-G2 (0.200 g, 0.255 mmol) and X-Phos (0.243 g, 0.511 mmol) at room temperature. The reaction mixture was then heated in sealed tube at 90° C. for 1 h. Progress of the reaction was monitored by TLC. After completion, the reaction mixture was cooled to room temperature, diluted with water (20 mL) and extracted with EA (100 mL). The organic layer was separated, dried over anhydrous sodium sulfate, filtered and concentrated under reduced pressure. The crude compound was purified by silica gel chromatography using 10-100% EA in n hexane to afford title compound (0.714 g). LC-MS (Condition 03) (ESI+): m/z 636.12 (M+H)$^+$; $^1$H-NMR (400 MHz, DMSO-d$_6$) δ 9.49 (s, 1H), 8.97 (s, 1H), 8.54 (s, 1H), 8.01 (s, 1H), 7.61 (d, J=7.83 Hz, 2H), 7.41 (d, J=7.83 Hz, 2H), 5.77 (s, 2H), 4.04 (q, J=7.34 Hz, 3H), 3.90 (s, 3H), 3.74-3.87 (m, 3H), 3.61-3.71 (m, 2H), 1.31 (s, 9H), 1.24-1.29 (m, 2H).

Step 5: Synthesis of 6-(4-(azetidin-3-yl)-6-methoxy-pyrimidin-5-yl)-1-(4-(1-ethyl-4-(trifluoromethyl)-1H-imidazol-2-yl)benzyl)-1H-pyrazolo[3,4-d]pyrimidine (135)

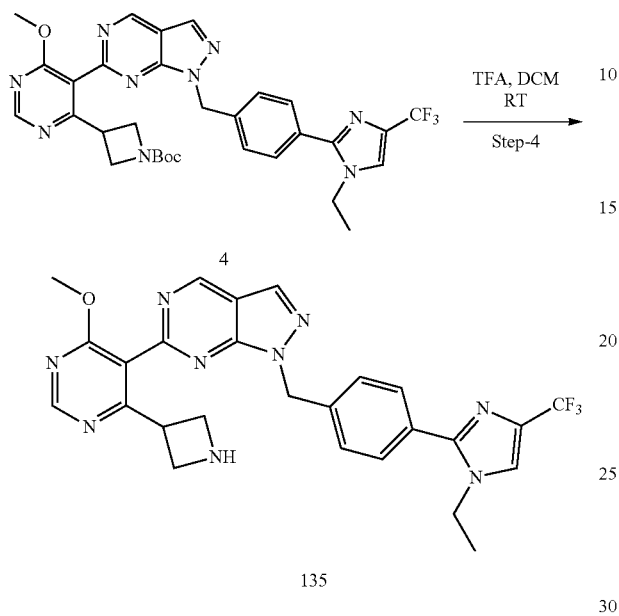

To a stirred solution of tert-butyl 3-(5-(1-(4-(1-ethyl-4-(trifluoromethyl)-1H-imidazol-2-yl)benzyl)-1H-pyrazolo[3,4-d]pyrimidin-6-yl)-6-methoxypyrimidin-4-yl)azetidine-1-carboxylate 4 (0.250 g, 0.393 mmol) in DCM (20 mL) was added TFA (0.224 g, 1.97 mmol) at 0° C. The resulting solution was further stirred at room temperature for 4 h. Progress of the reaction was monitored by TLC. After completion, the reaction mixture was concentrated under reduced pressure. The remaining residue was dissolved in DCM (10 mL) and the pH was adjusted to 9 using aqueous ammonia solution (10 mL). The organic layer was separated, dried over anhydrous sodium sulfate, filtered and concentrated under reduced pressure. The crude compound was purified by silica gel chromatography using 0-10% methanol in DCM to afford title compound (0.050 g). LC-MS (Method B) (ESI+): m/z 536.15 (M+H)$^+$; $^1$H-NMR (400 MHz, DMSO-d$_6$) δ 9.41 (br s, 1H), 8.94 (br s, 1H), 8.49 (br s, 1H), 7.88 (br s, 1H), 7.54 (d, J=7.82 Hz, 2H), 7.38 (d, J=7.34 Hz, 2H), 5.71 (br. s, 2H), 4.16-4.24 (m, 2H), 3.92-4.02 (m, 6H), 3.86 (br s, 3H), 1.23 (d, J=6.85 Hz, 3H).

Example 136: Synthesis of 6-(4-Cyclopropyl-6-methoxypyrimidin-5-yl)-1-(4-(1-(trifluoromethyl)-5,6,7,8-tetrahydroimidazo[1,5-a]pyrazin-3-yl)benzyl)-1H-pyrazolo[3,4-d]pyrimidine (136)

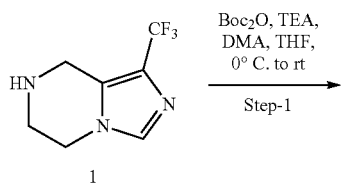

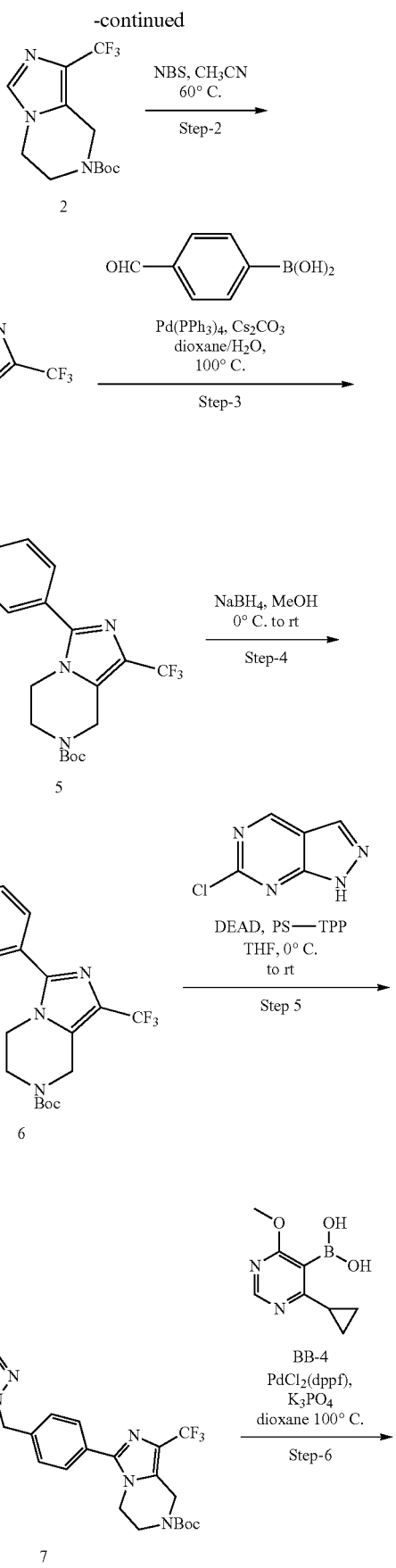

329

-continued

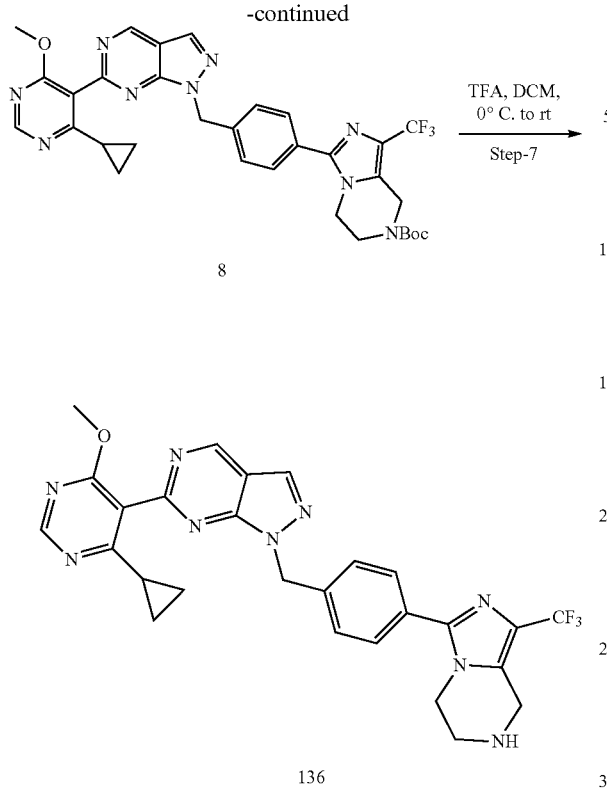

8

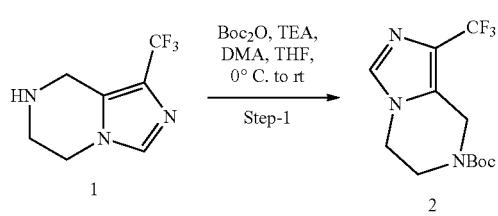 [SMILES: FC(F)(F)c1ncn2c1CNCC2 ; CC(C)(C)OC(=O)N1CCn2cnc(C(F)(F)F)c2C1]

136

Step 1: Synthesis of tert-Butyl 1-(trifluoromethyl)-5,6-dihydroimidazo[1,5-a]pyrazine-7(8H)-carboxylate

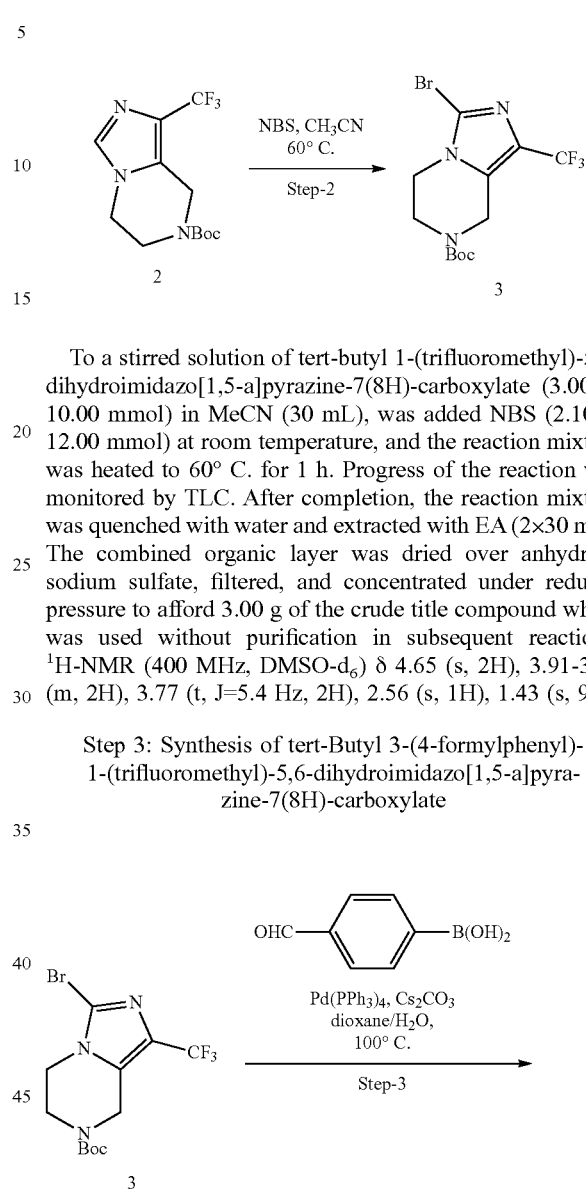

To a stirred solution of 1-(trifluoromethyl)-5,6,7,8-tetrahydroimidazo[1,5-a]pyrazine (2.00 g, 10.40 mmol) in THF (20 mL) at 0° C., were added triethyl amine (2.10 g, 20.80 mmol) followed by DMAP (0.12 g, 1.00 mmol), and the reaction mixture was stirred for 10 min. To the resulting reaction mixture, Boc₂O (3.42 g, 15.70 mmol) was added and the reaction mixture was stirred at room temperature for 15 h. Progress of the reaction was monitored by TLC. After completion, the reaction mixture was quenched with water and extracted with EA (3×20 mL). The combined organic layer was dried over anhydrous sodium sulfate, filtered, and concentrated under reduced pressure. The crude compound was purified by silica gel chromatography using 0-30% EA in hexane followed by washing with n-pentane to afford 3.00 g of the title compound. LC-MS (Method B) (ESI+): m/z 292.05 (M+H)⁺; ¹H-NMR (400 MHz, DMSO-d₆) δ 7.82 (s, 1H), 4.66 (s, 2H), 4.09 (t, J=5.4 Hz, 2H), 3.73 (t, J=5.4 Hz, 2H), 1.43 (s, 9H).

330

Step 2: Synthesis of tert-Butyl 3-bromo-1-(trifluoromethyl)-5,6-dihydroimidazo[1,5-a]pyrazine-7(8H)-carboxylate

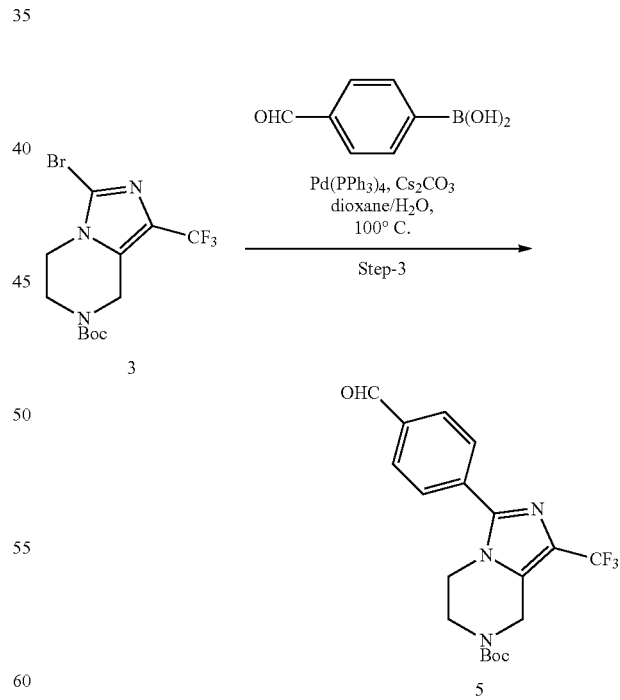

To a stirred solution of tert-butyl 1-(trifluoromethyl)-5,6-dihydroimidazo[1,5-a]pyrazine-7(8H)-carboxylate (3.00 g, 10.00 mmol) in MeCN (30 mL), was added NBS (2.10 g, 12.00 mmol) at room temperature, and the reaction mixture was heated to 60° C. for 1 h. Progress of the reaction was monitored by TLC. After completion, the reaction mixture was quenched with water and extracted with EA (2×30 mL). The combined organic layer was dried over anhydrous sodium sulfate, filtered, and concentrated under reduced pressure to afford 3.00 g of the crude title compound which was used without purification in subsequent reactions. ¹H-NMR (400 MHz, DMSO-d₆) δ 4.65 (s, 2H), 3.91-3.96 (m, 2H), 3.77 (t, J=5.4 Hz, 2H), 2.56 (s, 1H), 1.43 (s, 9H).

Step 3: Synthesis of tert-Butyl 3-(4-formylphenyl)-1-(trifluoromethyl)-5,6-dihydroimidazo[1,5-a]pyrazine-7(8H)-carboxylate A mixture of tert-butyl 3-bromo-1-(trifluoromethyl)-5,6-dihydroimidazo[1,5-a]pyrazine-7(8H)-carboxylate (3.00 g, 8.10 mmol), (4-formylphenyl)boronic acid (1.45 g, 9.70 mmol), and aq. 2M Cs₂CO₃ (5.28 g, 16.20 mmol) in dioxane (30 mL), was degassed with argon for 15 min. To the resulting reaction mixture, Pd(PPh$_3$)$_4$ (0.92 g, 0.81 mmol) was added, and the reaction mixture was heated to 100° C. for 16 h. Progress of the reaction was monitored by TLC. After completion, the reaction mixture was diluted with water (50 mL) and extracted with EA (2×30 mL). The combined organic layer was dried over anhydrous sodium sulfate, filtered, and concentrated under reduced pressure. The crude compound was purified by silica gel chromatography using 0-30% EA in hexane to afford 1.40 g of the title compound. LC-MS (Method B) (ESI+): m/z 396.00 (M+H)$^+$; $^1$H-NMR (400 MHz, DMSO-d$_6$) δ 10.09 (s, 1H), 7.95-8.06 (m, 4H), 4.78 (s, 2H), 4.26 (d, J=4.4 Hz, 2H), 3.73 (s, 2H), 1.46 (s, 9H).

Step 4: Synthesis of tert-Butyl 3-(4-(hydroxymethyl)phenyl)-1-(trifluoromethyl)-5,6-dihydroimidazo[1,5-a]pyrazine-7(8H)-carboxylate

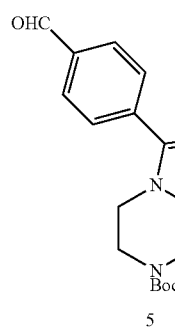

To a stirred solution of tert-butyl 3-(4-formylphenyl)-1-(trifluoromethyl)-5,6-dihydroimidazo[1,5-a]pyrazine-7(8H)-carboxylate (1.40 g, 3.50 mmol) in MeOH (20 mL) at 0° C., was added NaBH$_4$ (0.20 g, 5.30 mmol), and the reaction mixture was stirred at room temperature for 1 h. Progress of the reaction was monitored by TLC. After completion, the reaction mixture was concentrated under reduced pressure. The residue obtained was quenched with water (20 mL) and extracted with DCM (2×20 mL). The combined organic layer was dried over anhydrous sodium sulfate, filtered, and concentrated under reduced pressure to afford 1.20 g of the title compound, which was used in subsequent reactions without further purification. LC-MS (Method B) (ESI+): m/z 397.95 (M+H)$^+$; $^1$H-NMR (400 MHz, DMSO-d$_6$) δ 7.68 (d, J=8.0 Hz, 2H), 7.44 (d, J=8.0 Hz, 2H), 5.31 (t, J=5.5 Hz, 1H), 4.75 (s, 2H), 4.57 (d, J=5.5 Hz, 2H), 4.17 (t, J=5.0 Hz, 2H), 3.71 (d, J=4.5 Hz, 2H), 1.45 (s, 9H).

Step 5: Synthesis of tert-Butyl 3-(4-((6-chloro-1H-pyrazolo[3,4-d]pyrimidin-1-yl)methyl)phenyl)-1-(trifluoromethyl)-5,6-dihydroimidazo[1,5-a]pyrazine-7(8H)-carboxylate

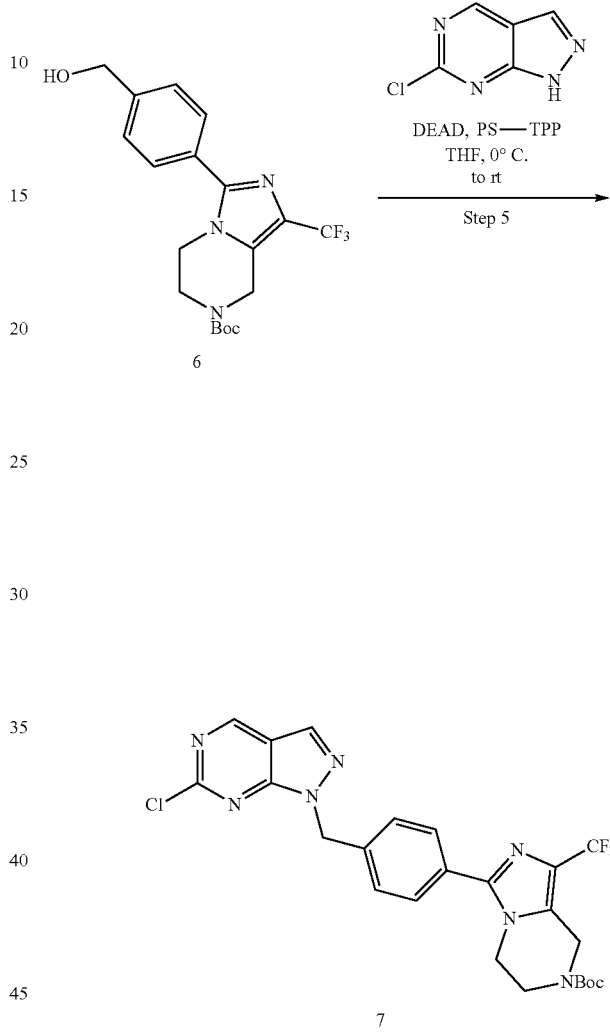

To a stirred solution of tert-butyl 3-(4-(hydroxymethyl)phenyl)-1-(trifluoromethyl)-5,6-dihydroimidazo-[1,5-a]pyrazine-7(8H)-carboxylate (1.20 g, 3.02 mmol) and 6-chloro-1H-pyrazolo[3,4-d]pyrimidine (0.41 g, 2.72 mmol) in THF (20 mL) at 0° C., was added polymer bound triphenyl phosphine (2.37 g, 9.06 mmol), and the reaction mixture was stirred for 25 min. To the resulting reaction mixture, diethyl azodicarboxylate (DEAD) (1.05 g, 6.04 mmol) was added, and the reaction mixture was stirred at room temperature for 16 h. Progress of the reaction was monitored by TLC. After completion, the reaction mixture was filtered through Celite, and the filtrate was concentrated under reduced pressure. The crude compound was purified by silica gel chromatography using 0-40% EA in hexane to afford 0.50 g of the title compound. LC-MS (Method B) (ESI+): m/z 534.10 (M+H)$^+$; $^1$H-NMR (400 MHz, DMSO-d$_6$) δ 9.32 (s, 1H), 8.52 (s, 1H), 7.69 (d, J=8.3 Hz, 2H), 7.38 (d, J=7.8 Hz, 2H), 5.72 (s, 2H), 4.74 (s, 2H), 4.15 (s, 2H), 3.68 (s, 2H), 1.44 (s, 9H).

Step 6: Synthesis of tert-Butyl 3-(4-((6-(4-cyclopropyl-6-methoxypyrimidin-5-yl)-1H-pyrazolo[3,4-d]pyrimidin-1-yl)methyl)phenyl)-1-(trifluoromethyl)-5,6-dihydroimidazo[1,5-a]pyrazine-7(8H)-carboxylate

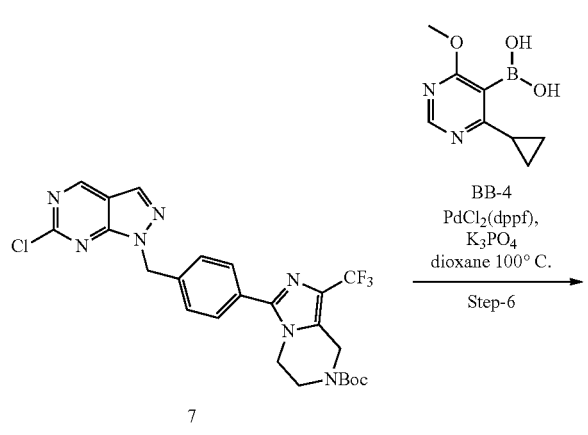

A mixture of tert-butyl 3-(4-((6-chloro-1H-pyrazolo[3,4-d]pyrimidin-1-yl)methyl)phenyl)-1-(trifluoromethyl)-5,6-dihydroimidazo[1,5-a]pyrazine-7(8H)-carboxylate (0.30 g, 0.50 mmol), (4-cyclopropyl-6-methoxypyrimidin-5-yl)boronic acid (0.11 g, 0.60 mmol), and 2M aq. K$_3$PO$_4$ solution (0.318 g, 1.50 mmol) in dioxane (5 mL), was degassed with argon for 5 min. To the resulting reaction mixture, was added PdCl$_2$(dppf) (0.04 g, 0.05 mmol), and the reaction mixture was heated to 100° C. for 16 h. Progress of the reaction was monitored by TLC. After completion, the reaction mixture was diluted with water and extracted with EA (2×30 mL). The combined organic layer was dried over anhydrous sodium sulfate, filtered, and concentrated under reduced pressure. The crude compound was purified by silica gel chromatography using 0-60% EA in hexane to afford 0.20 g of the title compound. LC-MS (Method B) (ESI+): m/z 648.3 (M+H)$^+$; $^1$H-NMR (400 MHz, DMSO-d$_6$) δ 9.50 (s, 1H), 8.71 (s, 1H), 8.51 (s, 1H), 7.67 (d, J=7.8 Hz, 2H), 7.42 (d, J=7.8 Hz, 2H), 5.75-5.79 (m, 2H), 4.74 (s, 2H), 4.14 (s, 2H), 3.86 (s, 3H), 3.68 (s, 2H), 1.44 (s, 9H), 1.65 (s, 1H), 1.06 (s, 2H), 0.87 (d, J=4.4 Hz, 2H).

Step 7: Synthesis of 6-(4-Cyclopropyl-6-methoxypyrimidin-5-yl)-1-(4-(1-(trifluoromethyl)-5,6,7,8-tetrahydroimidazo[1,5-a]pyrazin-3-yl)benzyl)-1H-pyrazolo[3,4-d]pyrimidine (136)

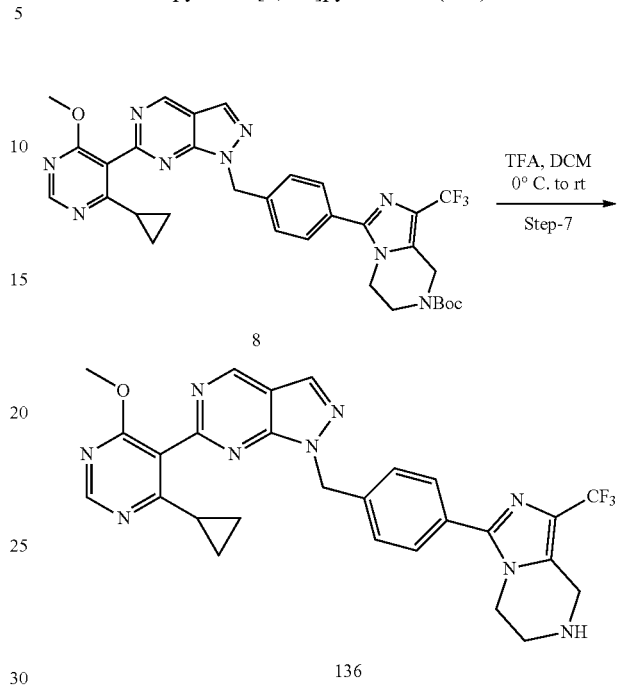

To a stirred solution of tert-butyl 3-(4-((6-(4-cyclopropyl-6-methoxypyrimidin-5-yl)-1H-pyrazolo[3,4-d]pyrimidin-1-yl)methyl)phenyl)-1-(trifluoromethyl)-5,6-dihydroimidazo[1,5-a]pyrazine-7(8H)-carboxylate (0.20 g, 0.40 mmol) in DCM (5 mL) at 0° C., was slowly added TFA (0.097 g, 0.80 mmol), and the reaction mixture was stirred at room temperature for 2 h. Progress of the reaction was monitored by TLC. After completion, the reaction mixture was concentrated under reduced pressure. The residue thus obtained was dissolved in water, basified with 2N NaHCO$_3$ solution, and extracted with EA (2×10 mL). The combined organic layer was dried over anhydrous sodium sulfate, filtered, and concentrated under reduced pressure. The crude compound was purified by prep-HPLC to afford 0.052 g of the title compound. LC-MS (Method B) (ESI+): m/z 548.10 (M+H)$^+$; $^1$H-NMR (400 MHz, DMSO-d$_6$) δ 9.50 (s, 1H), 8.71 (s, 1H), 8.51 (s, 1H), 7.66 (d, J=8.0 Hz, 2H), 7.40 (d, J=8.0 Hz, 2H), 5.76 (s, 2H), 4.03 (s, 2H), 3.98 (s, 2H), 3.85 (s, 3H), 2.94-2.99 (m, 2H), 1.61-1.69 (m, 1H), 1.06 (s, 2H), 0.85 (dd, J=3.0, 7.5 Hz, 2H).

General Procedures for the Synthesis of N-Alkylimidazoles by Functionalization of Example 134:

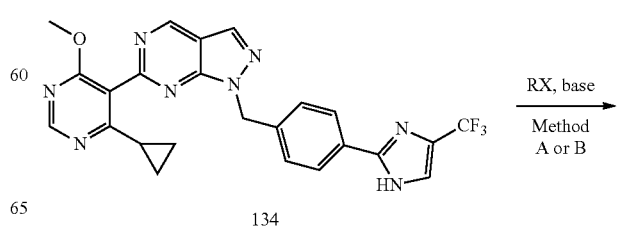

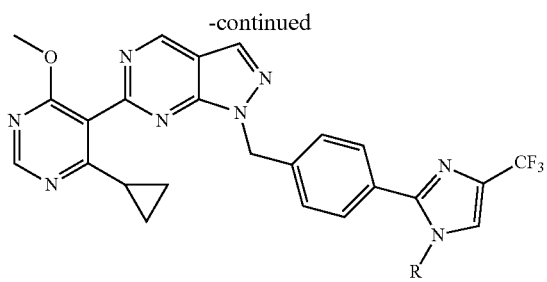

Examples 137-147

Example 134 can be alkylated by Method A or Method B below to afford N-functionalized imidazoles.

General Procedure:

Method-A:

To an ice cooled solution of 6-(4-cyclopropyl-6-methoxy-pyrimidin-5-yl)-1-(4-(4-(trifluoromethyl)-1H-imidazol-2-yl)benzyl)-1H-pyrazolo[3,4-d]pyrimidine (134) (1 eq) in DMF (5 mL) was added NaH (60% dispersion in mineral oil) (1.2 eq) portion wise, and the reaction mixture was stirred at same temperature for 10 min. To the resulting reaction mixture was added alkyl halides (1.20 eq) and stirring was continued at room temperature for 16 h. Progress of the reaction was monitored by TLC and LCMS. After completion, the reaction mixture was diluted with water (50 mL) and extracted with EA (2×200 mL). The combined organic layer was dried over anhydrous sodium sulfate, filtered, and concentrated under reduced pressure. The crude compounds were purified by prep HPLC to afford the title compounds.

Method-B:

To a stirred solution of 6-(4-cyclopropyl-6-methoxypyrimidin-5-yl)-1-(4-(4-(trifluoromethyl)-1H-imidazol-2-yl)benzyl)-1H-pyrazolo[3,4-d]pyrimidine (134) (1 eq) in DMF (5 mL) were added $Cs_2CO_3$ (1 eq) and alkyl halide 1 (1 eq) sequentially. The reaction mixture was heated to 90° C. for 12 h. Progress of the reaction was monitored by TLC and LCMS. After completion, the reaction mixture was diluted with water (50 mL) and extracted with EA (2×100 mL). The combined organic layer was washed with cold water (3×50 mL), dried over anhydrous sodium sulfate, filtered, and concentrated under reduced pressure. The crude compounds thus obtained were purified by prep HPLC to afford the title compounds.

| Example | Structure | Method | Analytical data |
|---|---|---|---|
| 137 | 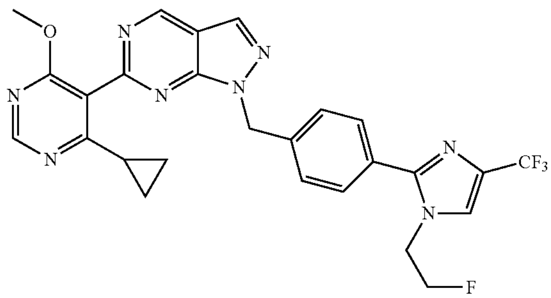 [SMILES: COc1ncnc(C2CC2)c1-c1ncc2cnn(Cc3ccc(-c4nc(C(F)(F)F)cn4CCF)cc3)c2n1] | A | LC-MS (Method C) (ESI+): m/z 539.10 (M + H)+; $^1$H-NMR (400 MHz, DMSO-$d_6$) δ 9.51 (s, 1H), 8.71 (s, 1H), 8.52 (s, 1H), 8.02 (s, 1H), 7.58 (d, J = 7.8 Hz, 2H), 7.42 (d, J = 7.8 Hz, 2H), 5.78 (s, 2H), 4.77 (t, J = 4.6 Hz, 1H), 4.65 (t, J = 4.6 Hz, 1H), 4.39 (t, J = 4.6 Hz, 1H), 4.32 (t, J = 4.4 Hz, 1H), 3.85 (s, 3H), 1.62-1.69 (m, 1H), 1.06 (s, 2H), 0.86 (dd, J = 3.2, 7.6 Hz, 2H). |
| 138 | 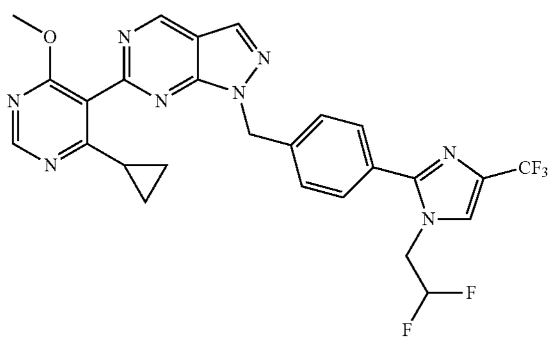 [SMILES: COc1ncnc(C2CC2)c1-c1ncc2cnn(Cc3ccc(-c4nc(C(F)(F)F)cn4CC(F)F)cc3)c2n1] | B | LC-MS (Method B) (ESI+): m/z 557.15 (M + H)+; $^1$H-NMR (400 MHz, DMSO-$d_6$) δ 9.51 (s, 1H), 8.71 (s, 1H), 8.52 (s, 1H), 7.98 (s, 1H), 7.58 (d, J = 7.83 Hz, 2H), 7.43 (d, J = 8.31 Hz, 2H), 6.19-6.48 (m, 1H), 5.79 (s, 2H), 4.50-4.62 (m, 2H), 3.85 (s, 3H), 1.65 (dt, J = 4.16, 7.95 Hz, 1H), 1.03-1.10 (m, 2H), 0.81-0.89 (m, 2H). |
| 139 | 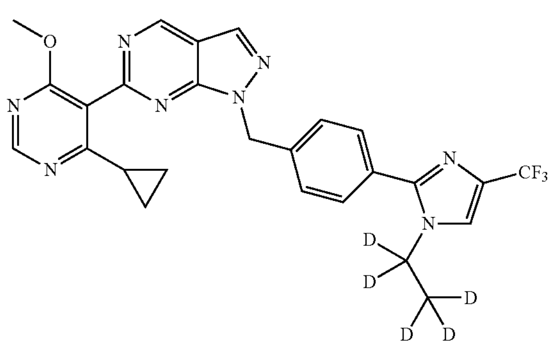 [SMILES: [2H]C([2H])([2H])C([2H])([2H])n1cc(C(F)(F)F)nc1-c1ccc(Cn2ncc3cnc(-c4c(OC)ncnc4C4CC4)nc32)cc1] | B | LC-MS (Method A) (ESI+): m/z 526 (M + H)+; $^1$H-NMR (300 MHz, $CD_3OD$) δ 9.40 (s, 1H), 8.64 (s, 1H), 8.41 (s, 1H), 7.77 (s, 1H), 7.51-7.58 (m, 4H), 5.81 (s, 2H), 3.92 (s, 3H), 1.66 (m, 1H), 1.10-1.18 (m, 2H), 0.85-0.92 (m, 2H). |

-continued

| Example | Structure | Method | Analytical data |
|---|---|---|---|
| 140 | 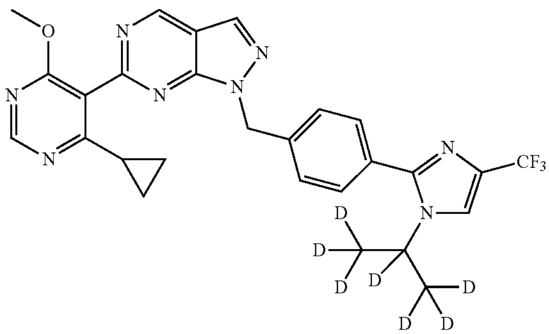 [SMILES: [2H]C([2H])([2H])C([2H])(n1cc(C(F)(F)F)nc1-c1ccc(Cn2ncc3cnc(-c4c(OC)ncnc4C4CC4)nc32)cc1)C([2H])([2H])[2H]] | B | LC-MS (Method A) (ESI+): m/z 542 (M + H)+; 1H-NMR (300 MHz, CD3OD) δ 9.40 (s, 1H), 8.64 (s, 1H), 8.41 (s, 1H), 7.89 (s, 1H), 7.48-7.53 (m, 4H), 5.81 (s, 2H), 3.92 (s, 3H), 1.68 (m, 1H), 1.12-1.30 (m, 2H), 0.85-0.92 (m, 2H). |
| 141 | 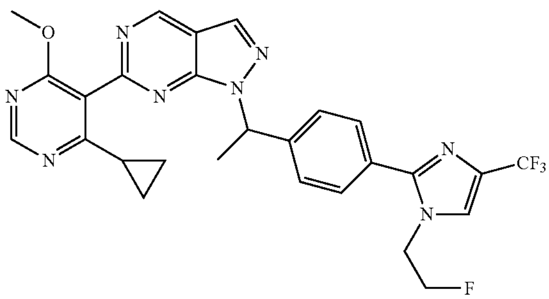 [SMILES: COc1ncnc(C2CC2)c1-c1ncc2cnn(C(C)c3ccc(-c4nc(C(F)(F)F)cn4CCF)cc3)c2n1] | A | LC-MS (Method B) (ESI+): m/z 553.20 (M + H)+; 1H-NMR (400 MHz, DMSO-d6) δ 9.49 (s, 1H), 8.71 (s, 1H), 8.54 (s, 1H), 8.01 (s, 1H), 7.55-7.60 (m, 2H), 7.49 (d, J = 8.31 Hz, 2H), 6.35 (q, J = 6.85 Hz, 1H), 4.77 (t, J = 4.40 Hz, 1H), 4.65 (t, J = 4.40 Hz, 1H), 4.38 (t, J = 4.16 Hz, 1H), 4.31 (t, J = 4.40 Hz, 1H), 3.83 (s, 3H), 1.99 (d, J = 7.34 Hz, 3H), 1.57-1.66 (m, 1H), 1.00-1.06 (m, 2H), 0.83 (d, J = 6.36 Hz, 2H). |
| 142 | 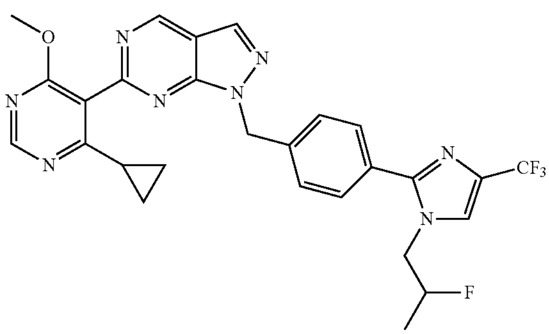 [SMILES: COc1ncnc(C2CC2)c1-c1ncc2cnn(Cc3ccc(-c4nc(C(F)(F)F)cn4CC(C)F)cc3)c2n1] | B | LC-MS (Method B) (ESI+): m/z 553.35 (M + H)+; 1H-NMR (400 MHz, DMSO-d6) δ 9.51 (s, 1H), 8.71 (s, 1H), 8.52 (s, 1H), 7.99 (s, 1H), 7.59 (d, J = 7.82 Hz, 2H), 7.42 (d, J = 8.31 Hz, 2H), 5.79 (s, 2H), 4.28-4.37 (m, 1H), 4.22-4.26 (m, 1H), 3.85 (s, 3H), 1.62-1.70 (m, 1H), 1.25 (d, J = 5.87 Hz, 2H), 1.19 (d, J = 6.36 Hz, 2H), 1.02-1.09 (m, 2H), 0.82-0.89 (m, 2H). |
| 143 | 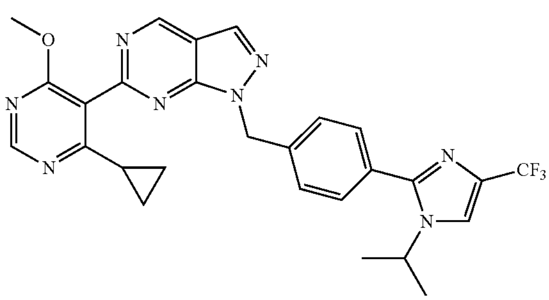 [SMILES: COc1ncnc(C2CC2)c1-c1ncc2cnn(Cc3ccc(-c4nc(C(F)(F)F)cn4C(C)C)cc3)c2n1] | A | LC-MS (Method C) (ESI+): m/z 535.00 (M + H)+; 1H-NMR (400 MHz, DMSO-d6) δ 9.49 (s, 1H), 8.69 (s, 1H), 8.50 (s, 1H), 8.14 (s, 1H), 7.51 (d, J = 7.8 Hz, 2H), 7.40 (d, J = 7.8 Hz, 2H), 5.77 (s, 2H), 4.45-4.34 (m, 1H), 3.83 (s, 3H), 1.60-1.67 (m, 1H), 1.35 (d, J = 6.8 Hz, 6H), 1.04 (s, 2H), 0.83 (dd, J = 3.2, 7.6 Hz, 2H). |
| 144 | 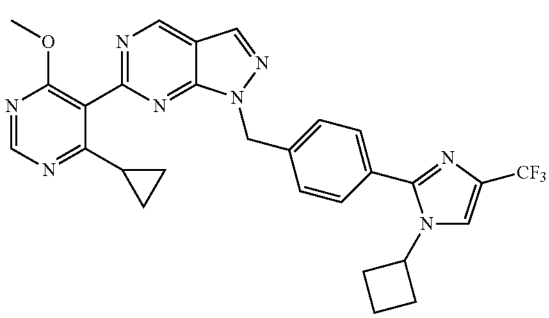 [SMILES: COc1ncnc(C2CC2)c1-c1ncc2cnn(Cc3ccc(-c4nc(C(F)(F)F)cn4C4CCC4)cc3)c2n1] | B | LC-MS (Method C) (ESI+): m/z 547.00 (M + H)+; 1H-NMR (400 MHz, DMSO-d6) δ 9.51 (s, 1H), 8.71 (s, 1H), 8.53 (s, 1H), 8.27 (s, 1H), 7.52 (d, J = 7.8 Hz, 2H), 7.41 (d, J = 7.8 Hz, 2H), 5.79 (s, 2H), 4.65-4.76 (m, 1H), 3.85 (s, 3H), 2.29-2.42 (m, 4H), 1.61-1.78 (m, 3H), 1.06 (s, 2H), 0.85 (dd, J = 2.9, 7.3 Hz, 2H). |

-continued

| Example | Structure | Method | Analytical data |
|---|---|---|---|
| 145 | 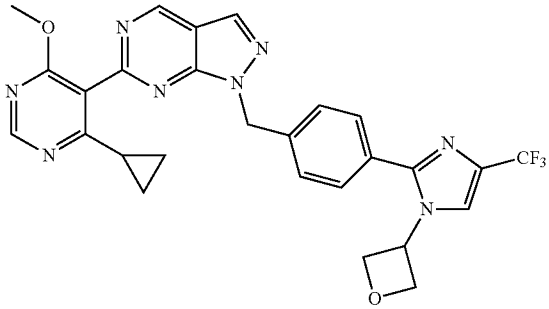 [SMILES: COc1ncnc(C2CC2)c1-c1ncc2cnn(Cc3ccc(-c4nc(C(F)(F)F)cn4C4COC4)cc3)c2n1] | B | LC-MS (Method C) (ESI+); m/z 548.95 (M + H)+; $^1$H-NMR (400 MHz, DMSO-d$_6$) δ 9.51 (s, 1H), 8.71 (s, 1H), 8.53 (s, 1H), 8.47 (s, 1H), 7.47-7.50 (m, 2H), 7.39-7.44 (m, 2H), 5.79 (s, 2H), 5.43-5.51 (m, 1H), 4.81-4.86 (m, 2H), 4.75-4.80 (m, 2H), 3.86 (s, 3H), 1.62-1.70 (m, 1H), 1.07 (d, J = 3.0 Hz, 2H), 0.86 (dd, J = 3.0, 7.9 Hz, 2H). |
| 146 | 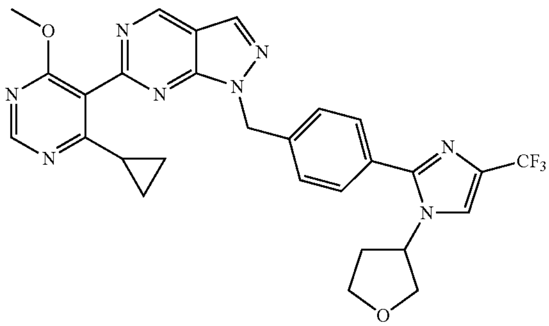 [SMILES: COc1ncnc(C2CC2)c1-c1ncc2cnn(Cc3ccc(-c4nc(C(F)(F)F)cn4C4CCOC4)cc3)c2n1] | B | LC-MS (Method C) (ESI+); m/z 563.15 (M + H)+; $^1$H-NMR (400 MHz, DMSO-d$_6$) δ 9.45 (s, 1H), 8.64 (s, 1H), 8.47 (s, 1H), 7.76-7.82 (m, 1H), 7.50 (d, J = 7.83 Hz, 2H), 7.39 (d, J = 7.82 Hz, 2H), 5.74 (br. s, 2H), 4.80-4.85 (m, 1H), 3.81 (s, 3H), 3.65-3.76 (m, 3H), 2.32-2.44 (m, 2H), 1.98-2.07 (m, 1H), 1.55-1.63 (m, 1H), 0.99-1.04 (m, 2H), 0.83 (d, J = 4.40 Hz, 2H). |
| 147 | 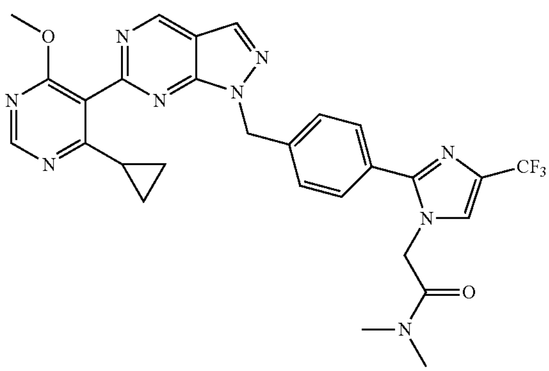 [SMILES: COc1ncnc(C2CC2)c1-c1ncc2cnn(Cc3ccc(-c4nc(C(F)(F)F)cn4CC(=O)N(C)C)cc3)c2n1] | B | LC-MS (Method B) (ESI+): m/z 578.10 (M + H)+; $^1$H-NMR (400 MHz, DMSO-d$_6$) δ 9.50 (s, 1H), 8.72 (s, 1H), 8.51 (s, 1H), 7.80 (s, 1H), 7.48-7.52 (m, 2H), 7.41 (d, J = 7.8 Hz, 2H), 5.76 (s, 2H), 5.04 (s, 2H), 3.85 (s, 3H), 2.94 (s, 3H), 2.82 (s, 3H), 1.62-1.70 (m, 1H), 1.06 (s, 2H), 0.86 (dd, J = 3.2, 7.6 Hz, 2H). |

Example 148: Synthesis of 2-(4-(((6-(4-cyclopropyl-6-methoxypyrimidin-5-yl)-1H-pyrazolo[3,4-d]pyrimidin-1-yl)methyl)phenyl)-1-ethyl-1H-imidazole-4-carbonitrile (148)

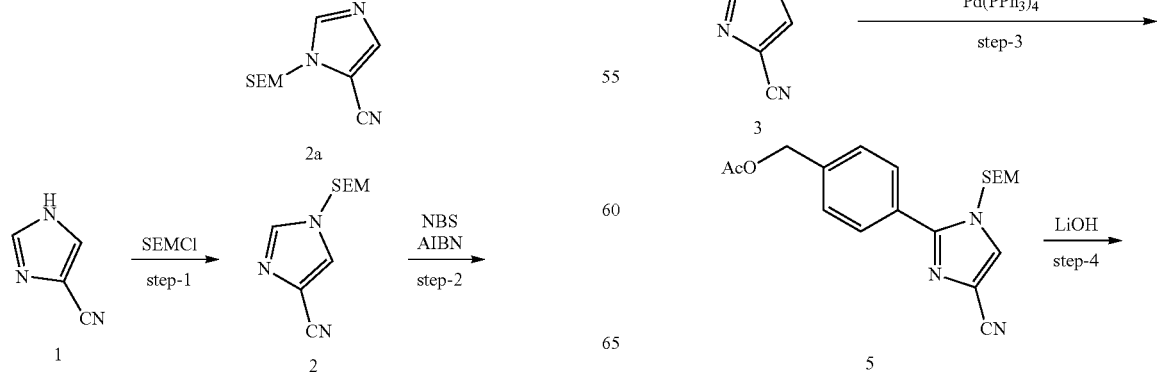

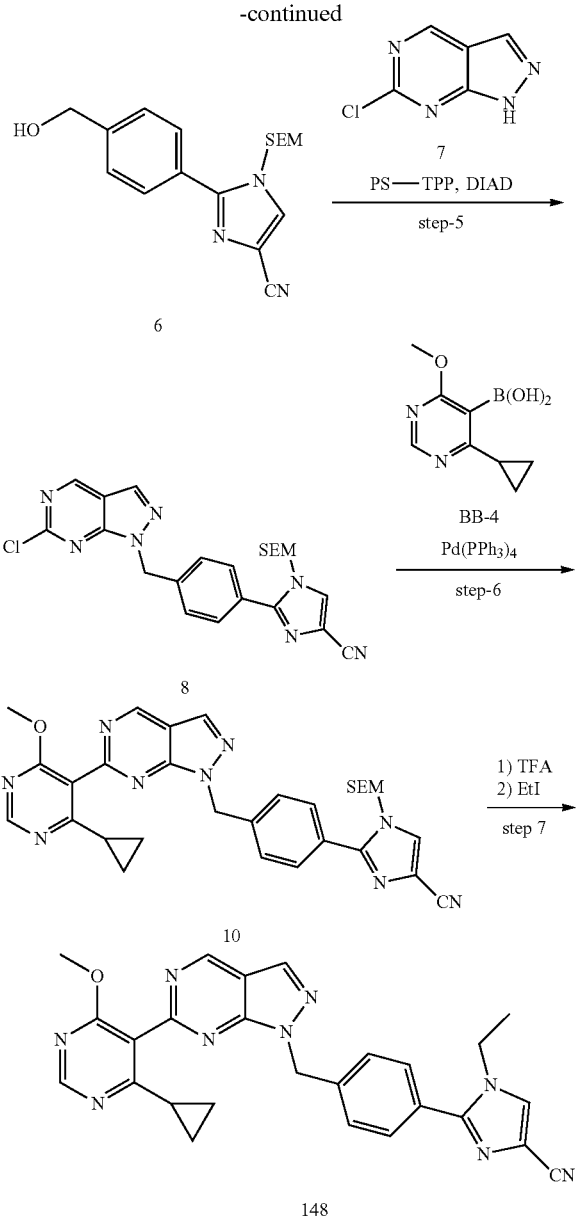

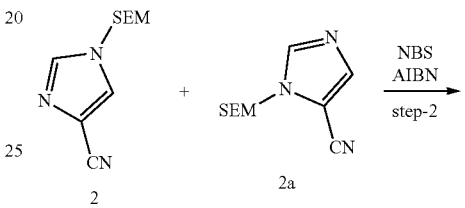

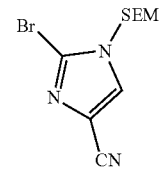

in acetone (20 mL) at 10° C., was added SEMCl (1.98 g, 11.8 mmol) dropwise over 30 min, while the internal temperature was kept below 15° C. The reaction was then allowed to warm to rt and stirred overnight. After the reaction was completed, the reaction was quenched by cold water (50 mL) and extracted with EA (50 mL×3). The combined organic layer was dried over sodium sulfate (30 g), filtered and concentrated. The concentrated residue was purified by silica gel chromatography (eluent: EA/n-Hex=1/4) to afford 1.3 g of a mixture of the title compound and its regioisomer 2a. LC-MS (Method A) (ESI+): m/z 224 (M+H)$^+$.

Step 2: Synthesis of 2-bromo-1-((2-(trimethylsilyl)ethoxy)methyl)-1H-imidazole-4-carbonitrile A solution of 1-((2-(trimethylsilyl)ethoxy)methyl)-1H-imidazole-4-carbonitrile 2 and 1-((2-(trimethyl silyl)ethoxy)methyl)-1H-imidazole-5-carbonitrile 2a (1.30 g, 5.83 mmol) in CCl$_4$ (30 mL) at 60° C. was added NBS (1.14 g, 6.41 mmol) portion-wise over 5 min. An exothermic reaction was observed, and the internal temperature increased to 75° C. After addition, the reaction was stirred at 60° C. overnight. The reaction was allowed to cool to rt, and the resulting suspension was filtered. The filter cake was washed with CCl$_4$ (20 mL). The combined filtrate was washed with a saturated NaHCO$_3$ solution (60 mL). After separation, the organic layer was dried over sodium sulfate (30 g), filtered and concentrated. The residue was purified by silica gel chromatography (eluent: EA/n-Hex=1/10) to afford 800 mg of the title compound. LC-MS (Method A) (ESI+): m/z 324 (M+Na)$^+$; $^1$H-NMR (300 MHz, CDCl$_3$) δ 7.63 (s, 1H), 5.30 (s, 2H), 3.55 (t, J=8.1 Hz, 2H), 0.93 (t, J=8.1 Hz, 2H), 0.05 (s, 9H).

Step 1: Synthesis of 1-((2-(trimethylsilyl)methyl)-1H-imidazole-4-carbonitrile and 1-((2-(trimethyl silyl)ethoxy)methyl)-1H-imidazole-5-carbonitrile

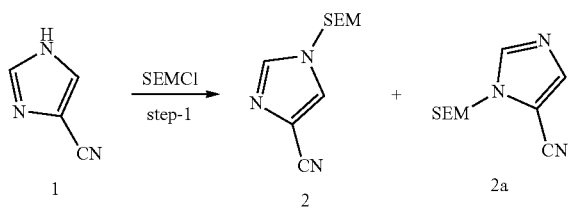 [SMILES: N#Cc1c[nH]cn1 ; "SEMCl" ; C[Si](C)(C)CCOCn1cnc(C#N)c1 ; C[Si](C)(C)CCOCn1cncc1C#N]

To a suspension of 1H-imidazole-4-carbonitrile (1 g, 10.76 mmol) and potassium carbonate (2.96 g, 21.5 mmol)

Step 3: Synthesis of 4-(4-cyano-1-((2-(trimethylsilyl)ethoxy)methyl)-1H-imidazol-2-yl)benzyl acetate

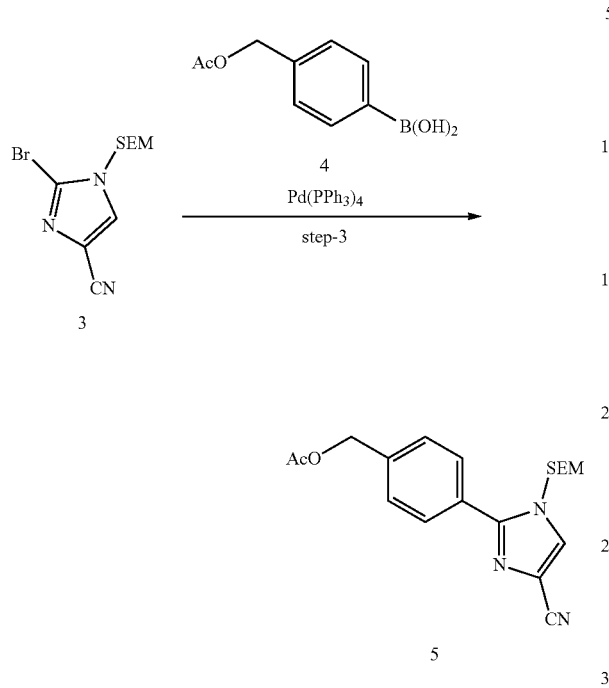

To a solution of 2-bromo-1-((2-(trimethylsilyl)methyl)-1H-imidazole-4-carbonitrile 3 (800 mg, 2.48 mmol) in 1,4-dioxane/H₂O (20 mL, 20:1) was added 4-(acetoxymethyl)phenyl)boronic acid (568 mg, 2.93 mmol), K₃PO₄·3H₂O (2.12 g, 7.98 mmol), and Pd(PPh₃)₄ (307 mg, 0.27 mmol) in one portion. The reaction was then stirred at 110° C. overnight. The reaction was cooled to rt and quenched with water (50 mL). The resulting mixture was extracted with EA (50 mL×3). The organic layer was dried over sodium sulfate (100 g), filtered and concentrated. The residue was purified by silica gel chromatography (eluent: EA/n-Hex=1/3) to afford 650 mg of the title compound. LC-MS (Method A) (ESI+): m/z 372 (M+H)⁺; ¹H-NMR (300 MHz, CDCl₃) δ 7.76 (d, J=8.1 Hz, 2H), 7.65 (s, 1H), 7.46 (d, J=8.1 Hz, 2H), 5.28 (s, 2H), 5.16 (s, 2H), 3.58 (t, J=8.4 Hz, 2H), 2.12 (s, 3H), 0.94 (t, J=8.4 Hz, 2H), 0.05 (s, 9H).

Step 4: Synthesis of 2-(4-(hydroxymethyl)phenyl)-1-((2-(trimethylsilyl)ethoxy)methyl)-1H-imidazole-4-carbonitrile

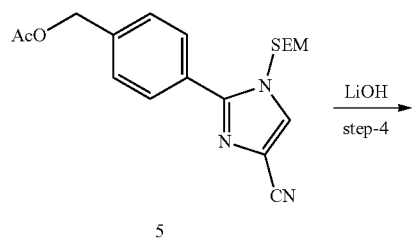

To a solution of 4-(4-cyano-1-((2-(trimethylsilyl)ethoxy)methyl)-1H-imidazol-2-yl)benzyl acetate 5 (650 mg, 1.75 mmol) in 1:1 THF/water (10 mL) was added LiOH H₂O (150 mg, 3.50 mmol) in one portion. The reaction was stirred at rt for 4 h. After the reaction was completed as indicated by TLC analysis, the reaction was adjusted to pH 8 with a dilute HCl solution and extracted with EA (50 mL×2). The combined organic layer was dried with sodium sulfate (30 g), filtered and concentrated to afford 690 mg of the crude title compound. LC-MS (Method A) (ESI+): m/z 330 (M+H)⁺; ¹H-NMR (300 MHz, CDCl₃) δ 7.75 (d, J=7.8 Hz, 2H), 7.65 (s, 1H), 7.49 (d, J=7.8 Hz, 2H), 5.28 (s, 2H), 4.78 (d, J=5.1 Hz, 2H), 3.57 (t, J=8.1 Hz, 2H), 1.80 (t, J=5.1 Hz, 1H), 0.94 (t, J=8.1 Hz, 2H), 0.05 (s, 9H).

Step 5: Synthesis of 2-(4-((6-chloro-1H-pyrazolo[3,4-d]pyrimidin-1-yl)methyl)phenyl)-1-((2-(trimethylsilyl)ethoxy)methyl)-1H-imidazole-4-carbonitrile

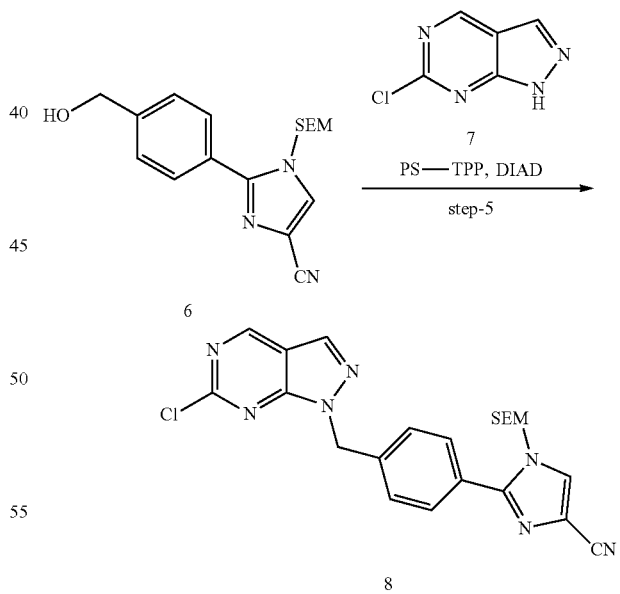

The compound was synthesized according to the procedure for the preparation of common intermediate I-47. LC-MS (Method A) (ESI+): m/z 466 (M+H)⁺; ¹H-NMR (300 MHz, CDCl₃) δ 9.06 (s, 1H), 8.19 (s, 1H), 7.76 (d, J=8.4 Hz, 2H), 7.64 (s, 1H), 7.47 (d, J=8.4 Hz, 2H), 5.70 (s, 2H), 5.26 (s, 2H), 3.57 (t, J=8.1 Hz, 2H), 0.93 (t, J=8.1 Hz, 2H), 0.05 (s, 9H).

Step 6: Synthesis of 2-(4-((6-(4-cyclopropyl-6-methoxypyrimidin-5-yl)-1H-pyrazolo[3,4-d]pyrimidin-1-yl)methyl)phenyl)-1-((2-(trimethylsilyl)ethoxy)methyl)-1H-imidazole-4-carbonitrile

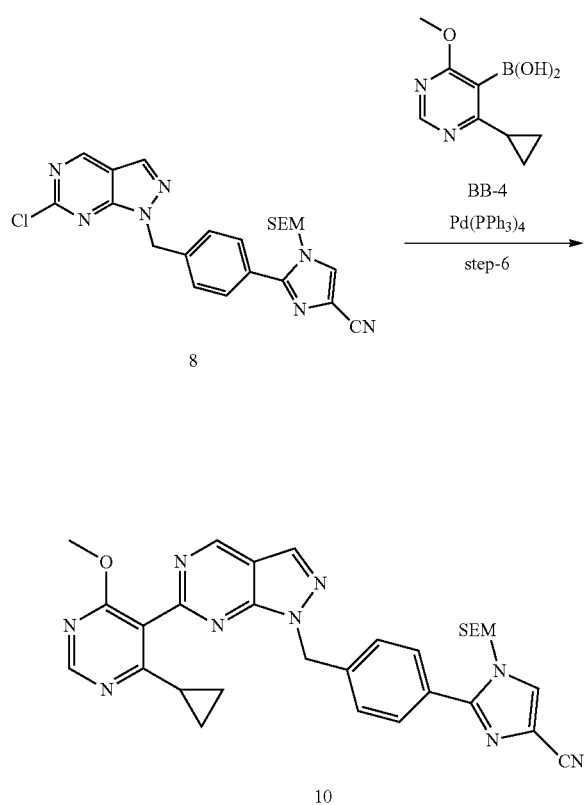

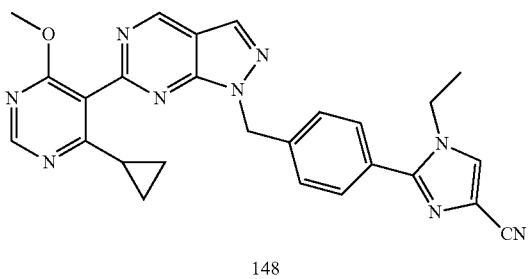

148

A solution of 2-(4-((6-(4-cyclopropyl-6-methoxypyrimidin-5-yl)-1H-pyrazolo[3,4-d]pyrimidin-1-yl) methyl)phenyl)-1-((2-(trimethylsilyl)ethoxy)methyl)-1H-imidazole-4-carbonitrile 10 (400 mg, 0.69 mmol) in TFA (10 mL) was stirred at rt for 3 h. After the reaction was complete based on TLC analysis, the reaction was concentrated to dryness in vacuo. The residue was dissolved in EA (50 mL) and neutralized with a saturated sodium bicarbonate solution. After separation, the aqueous phase was extracted with EA (50 mL×2). The combined organic layer was dried, filtered and concentrated to give 400 mg of crude deprotected intermediate.

To a solution of the deprotected intermediate (180 mg, 0.40 mmol) in DMF (10 mL) was added cesium carbonate (156 mg, 0.48 mmol) and EtI (75 mg, 0.48 mmol). The reaction was stirred at 40° C. for 5 h. After the reaction was complete as indicated by TLC analysis, the reaction was quenched with water (30 mL) and extracted with EA (50 mL×3). The organic layer was washed with water (20 mL), dried with sodium sulfate (50 g), filtered and concentrated. The residue was purified by preparative HPLC (Method A) to afford 53 mg of the title compound. LC-MS (Method A) (ESI+): m/z 478 (M+H)$^+$; $^1$H-NMR (300 MHz, CD$_3$OD) δ 9.40 (s, 1H), 8.64 (s, 1H), 8.42 (s, 1H), 8.06 (s, 1H), 7.51-7.62 (m, 4H), 5.81 (s, 2H), 4.09 (q, J=7.2 Hz, 2H), 3.91 (s, 3H), 1.60-1.75 (m, 1H), 1.34 (t, J=7.2 Hz, 3H), 1.10-1.20 (m, 2H), 0.83-0.94 (m, 2H).

The compound was synthesized according to the General Experimental Procedure 1. LC-MS (Method A) (ESI+): m/z 580 (M+H)$^+$; $^1$H-NMR (300 MHz, CDCl$_3$) δ 9.35 (s, 1H), 8.69 (s, 1H), 8.24 (s, 1H), 7.66-7.78 (m, 2H), 7.64 (s, 1H), 7.42-7.58 (m, 2H), 5.77 (s, 2H), 5.25 (s, 2H), 3.95 (s, 3H), 3.58 (t, J=8.4 Hz, 2H), 1.64-1.75 (m, 1H), 1.20-1.31 (m, 2H), 0.83-0.99 (m, 4H), 0.05 (s, 9H).

Step 7: Synthesis of 2-(4-((6-(4-cyclopropyl-6-methoxypyrimidin-5-yl)-1H-pyrazolo[3,4-d]pyrimidin-1-yl)methyl)phenyl)-1-ethyl-1H-imidazole-4-carbonitrile (148)

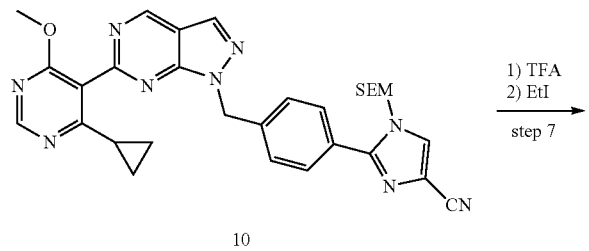

Example 149: Synthesis of 6-(2-Isopropylphenyl)-1-(4-(1-(1-methylazetidin-3-yl)-4-(trifluoromethyl)-1H-imidazol-2-yl)benzyl)-1H-pyrazolo[3,4-d]pyrimidine (149)

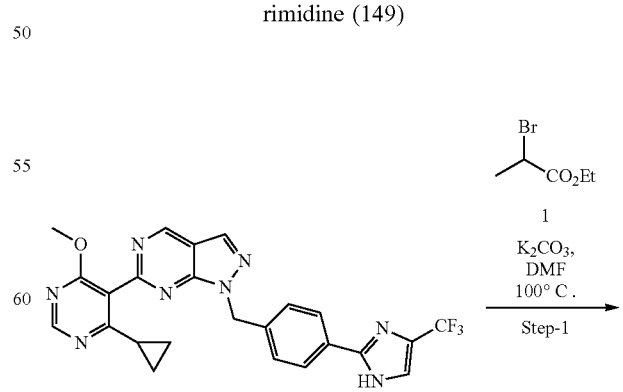

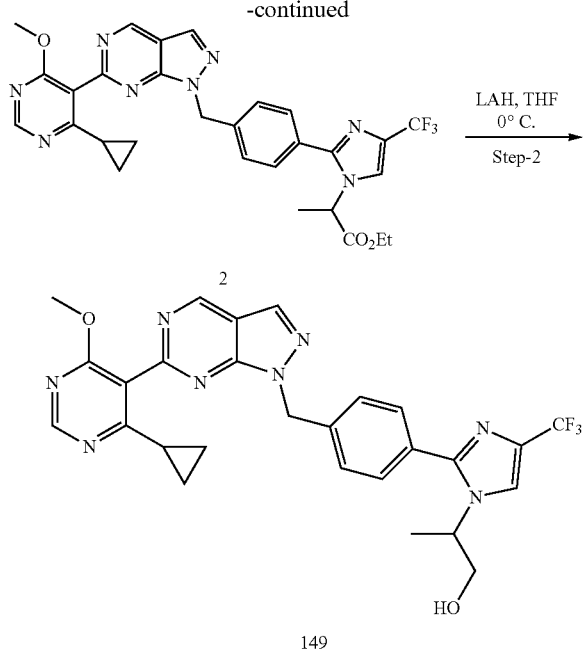

Step 1: Synthesis of ethyl 2-(2-(4-((6-(4-cyclopropyl-6-methoxypyrimidin-5-yl)-1H-pyrazolo[3,4-d]pyrimidin-1-yl)methyl)phenyl)-4-(trifluoromethyl)-1H-imidazol-1-yl)propanoate To a stirred solution of 6-(4-cyclopropyl-6-methoxypyrimidin-5-yl)-1-(4-(4-(trifluoromethyl)-1H-imidazol-2-yl)benzyl)-1H-pyrazolo[3,4-d]pyrimidine (134) (0.320 g, 0.650 mmol) in DMF (10 mL), was added $K_2CO_3$ (0.224 g, 1.63 mmol) and ethyl 2-bromopropanoate 1 (0.141 g, 0.780 mmol) at room temperature. The reaction mixture was heated at 100° C. for 16 h. Progress of the reaction was monitored by TLC. After completion, the reaction mixture was cooled to room temperature and quenched with water (10 mL) and extracted with EA (3×5 mL). The organic layer was dried over anhydrous sodium sulfate, filtered and concentrated under reduced pressure. The crude compound was purified by silica gel chromatography using 0-10% MeOH in DCM to afford the title compound (0.240 g). LC-MS (Method C) (ESI+): m/z 593.1 (M+H)$^+$; $^1$H-NMR (400 MHz, DMSO-d$_6$) δ 9.51 (s, 1H), 8.71 (s, 1H), 8.52 (s, 1H), 8.15 (br s, 1H), 7.95 (s, 1H), 7.47-7.51 (m, 2H), 7.41-7.45 (m, 2H), 5.78 (s, 2H), 5.06-5.13 (m, 2H), 4.01-4.08 (m, 2H), 3.85 (s, 3H), 1.68 (d, J=6.98 Hz, 3H), 1.02-1.08 (m, 4H), 0.82-0.88 (m, 2H).

Step 2: Synthesis of 2-(2-(4-((6-(4-cyclopropyl-6-methoxypyrimidin-5-yl)-1H-pyrazolo[3,4-d]pyrimidin-1-yl)methyl)phenyl)-4-(trifluoromethyl)-1H-imidazol-1-yl)propan-1-ol (149)

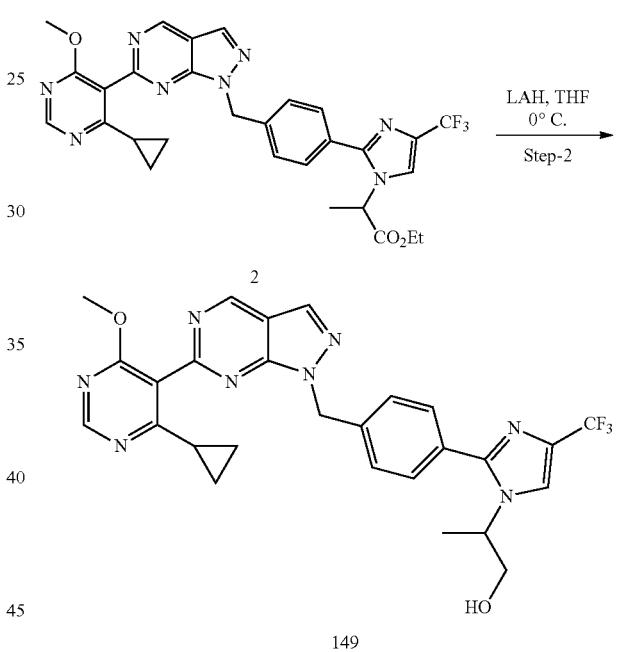

To an ice cooled solution of ethyl 2-(2-(4-((6-(4-cyclopropyl-6-methoxypyrimidin-5-yl)-1H-pyrazolo[3,4-d]pyrimidin-1-yl)methyl)phenyl)-4-(trifluoromethyl)-1H-imidazol-1-yl)propanoate 2 (0.175 g, 0.296 mmol) in THF (3 mL), was added LAH (0.022 g, 0.59 mmol). The resulting mixture was then stirred for 5 h. Progress of the reaction was monitored by TLC. After completion, the reaction mixture was quenched with EA (10 mL), filtered through a pad of Celite and washed with EA (5 mL). The filtrate was concentrated under reduced pressure to give the crude compound which was purified by prep HPLC (Method C) to afford the title compound (0.042 g). LC-MS (Method C) (ESI+): m/z 551.14 (M+H)$^+$; $^1$H-NMR (400 MHz, DMSO-d$_6$) δ 9.44 (s, 1H), 8.64 (s, 1H), 8.45-8.50 (m, 1H), 8.00 (br s, 1H), 7.53 (d, J=7.98 Hz, 2H), 7.37 (d, J=7.48 Hz, 2H), 5.73 (br s, 2H), 4.28 (d, J=4.99 Hz, 1H), 3.81 (s, 3H), 3.51-3.62 (m, 3H), 1.54-1.63 (m, 1H), 1.25 (d, J=6.48 Hz, 3H), 0.98-1.06 (m, 2H), 0.81-0.86 (m, 2H).

Example 150: Synthesis of 6-(4-cyclopropyl-6-methoxypyrimidin-5-yl)-1-(4-(1-(1-methoxypropan-2-yl)-4-(trifluoromethyl)-1H-imidazol-2-yl)benzyl)-1H-pyrazolo[3,4-d]pyrimidine (150)

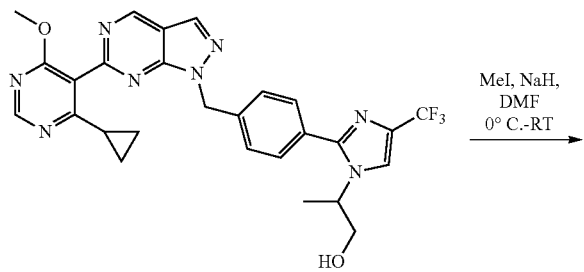

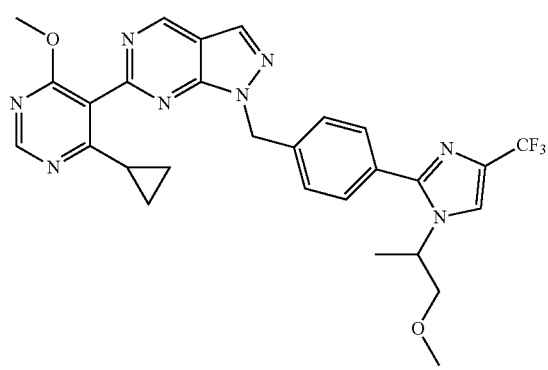

150

To a stirred solution of 2-(2-(4-((6-(4-cyclopropyl-6-methoxypyrimidin-5-yl)-1H-pyrazolo[3,4-d]-pyrimidin-1-yl)methyl)phenyl)-4-(trifluoromethyl)-1H-imidazol-1-yl)propan-1-ol (149) (0.050 g, 0.090 mmol) in DMF (1.5 mL) at 0° C. was added NaH (0.005 g, 0.14 mmol), and the mixture was stirred for 30 min. To the resulting reaction mixture was added MeI (0.011 mL, 0.19 mmol) and the reaction was further stirred at room temperature for 16 h. Progress of the reaction was monitored by TLC. After completion, the reaction mixture was quenched with ice cold water (5 mL) and extracted with EA (4×5 mL). The combined organic layer was dried over anhydrous sodium sulfate, filtered and concentrated under reduced pressure. The crude compound was purified by preparative HPLC (Method E) to afford the title compound (0.025 g). LC-MS (Method C) (ESI+): m/z 565 (M+H)+; $^1$H-NMR (400 MHz, DMSO-$d_6$) δ 9.51 (s, 1H), 8.71 (s, 1H), 8.52 (s, 1H), 8.15 (s, 1H), 7.55 (d, J=7.98 Hz, 2H), 7.42 (d, J=7.98 Hz, 2H), 5.78 (s, 2H), 4.45 (d, J=3.49 Hz, 1H), 3.85 (s, 3H), 3.57-3.64 (m, 1H), 3.50 (dd, J=4.24, 10.22 Hz, 1H), 3.11 (s, 3H), 1.66 (dt, J=3.99, 7.73 Hz, 1H), 1.33 (d, J=6.98 Hz, 3H), 1.03-1.08 (m, 2H), 0.86 (dd, J=2.99, 7.48 Hz, 2H).

Example 151: Synthesis of 6-(4-cyclopropyl-6-methoxypyrimidin-5-yl)-1-(4-(1-(1-fluoropropan-2-yl)-4-(trifluoromethyl)-1H-imidazol-2-yl)benzyl)-1H-pyrazolo[3,4-d]pyrimidine (151)

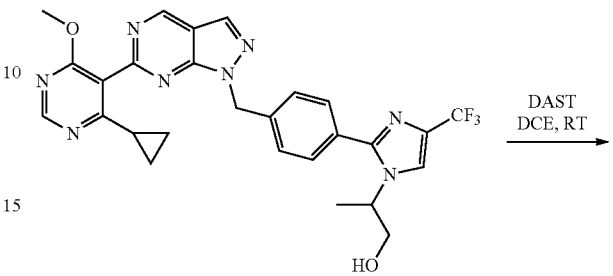

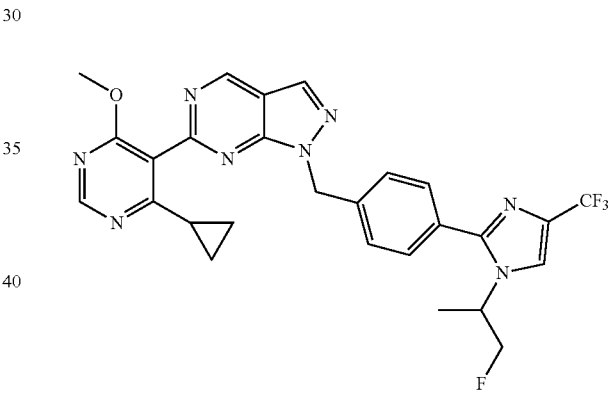

151

To a stirred solution of 2-(2-(4-((6-(4-cyclopropyl-6-methoxypyrimidin-5-yl)-1H-pyrazolo[3,4-d]-pyrimidin-1-yl)methyl)phenyl)-4-(trifluoromethyl)-1H-imidazol-1-yl)propan-1-ol (149) (0.120 g, 0.2181 mmol) in DCE (10 mL) was added DAST (0.140 g, 0.872 mmol) at room temperature. The resulting mixture was stirred for 4 h. Progress of the reaction was monitored by TLC. After completion, the reaction mixture was diluted with water (10 mL) and extracted with DCM (20 mL). The organic layer was dried over anhydrous sodium sulfate, filtered and concentrated under reduced pressure. The crude compound was purified by silica gel chromatography using 0-10% methanol in DCM to afford the title compound (0.090 g). LC-MS (Method B) (ESI+): m/z 553.20 (M+H)+; $^1$H-NMR (400 MHz, DMSO-$d_6$) δ 9.51 (s, 1H), 8.71 (s, 1H), 8.52 (s, 1H), 8.22 (s, 1H), 7.50-7.54 (m, 2H), 7.44 (d, J=8.31 Hz, 2H), 5.79 (s, 2H), 4.54-4.72 (m, 3H), 3.85 (s, 3H), 1.62-1.71 (m, 1H), 1.38 (d, J=6.36 Hz, 3H), 1.03-1.09 (m, 2H), 0.83-0.89 (m, 2H).

Example 152: Synthesis of 6-(2-Isopropylphenyl)-1-(4-(1-(1-methylazetidin-3-yl)-4-(trifluoromethyl)-1H-imidazol-2-yl)benzyl)-1H-pyrazolo[3,4-d]pyrimidine (152)

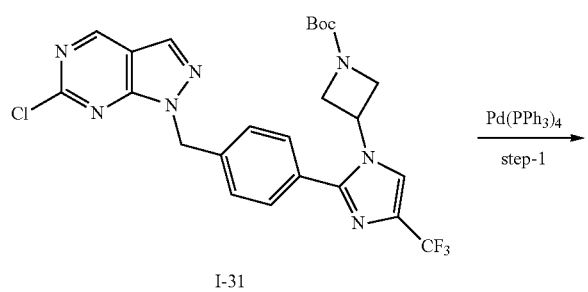

I-31

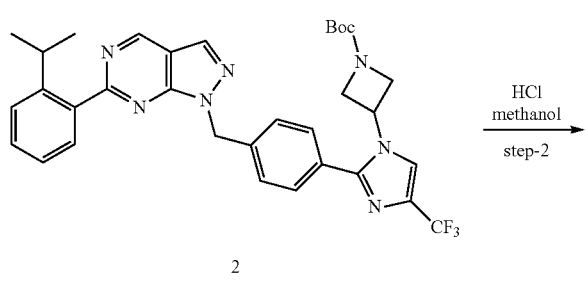

2

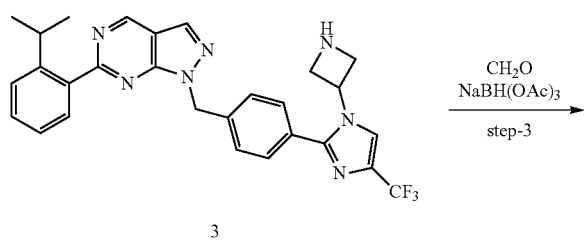

3

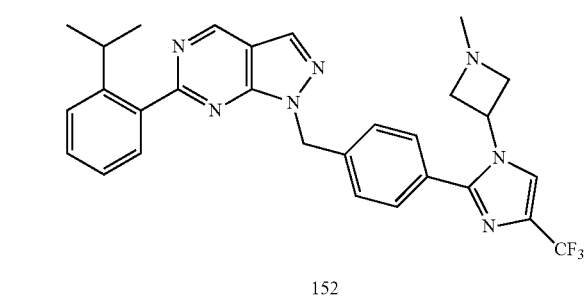

152

Step 1: Synthesis of tert-Butyl 3-(2-(4-((6-(2-isopropylphenyl)-1H-pyrazolo[3,4-d]pyrimidin-1-yl)methyl)phenyl)-4-(trifluoromethyl)-1H-imidazol-1-yl)azetidine-1-carboxylate

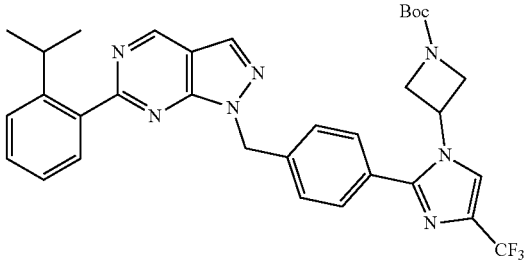 [SMILES: CC(C)c1ccccc1-c1ncc2cnn(Cc3ccc(-c4nc(C(F)(F)F)cn4C4CN(C(=O)OC(C)(C)C)C4)cc3)c2n1]

Under nitrogen atmosphere, a mixture of tert-butyl 3-(2-(4-((6-chloro-1H-pyrazolo[3,4-d]pyrimidin-1-yl)methyl)phenyl)-4-(trifluoromethyl)-1H-imidazol-1-yl)azetidine-1-carboxylate (I-31) (0.26 g, 0.49 mmol), $K_3PO_4$ (0.39 g, 1.47 mmol), (2-isopropylphenyl)boronic acid, and Pd(PPh$_3$)$_4$ (57 mg, 10 mol %) in dioxane (9 mL) and water (0.9 mL), was stirred at 90° C. for 3 hours. The mixture was then cooled to room temperature, diluted with water (10 mL), and extracted with EA (100 mL×3). The combined organic layer was dried over anhydrous $Na_2SO_4$ (20 g), filtered and concentrated in vacuo. The residue was purified by silica gel chromatography (EA:n-Hex=1:10 to 1:4) to afford 280 mg of the title compound. $^1$H-NMR (300 MHz, CDCl$_3$) δ 9.31 (s, 1H), 8.21 (s, 1H), 7.73 (s, 1H), 7.64-7.71 (m, 3H), 7.52-7.56 (m, 2H), 7.42-7.50 (m, 3H), 5.76 (s, 2H), 5.01 (m, 1H), 4.35-4.40 (m, 2H), 4.05-4.13 (m, 2H), 3.56 (m, 1H), 1.45 (s, 9H), 1.26 (d, J=7.2 Hz, 6H).

Step 2: Synthesis of 1-(4-(1-(Azetidin-3-yl)-4-(trifluoromethyl)-1H-imidazol-2-yl)benzyl)-6-(2-isopropylphenyl)-1H-pyrazolo[3,4-d]pyrimidine

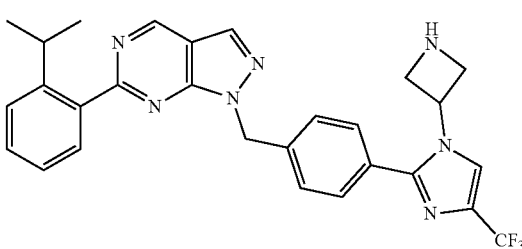

To a solution of tert-butyl 3-(2-(4-((6-(2-isopropylphenyl)-1H-pyrazolo[3,4-d]pyrimidin-1-yl)methyl) phenyl)-4-(trifluoromethyl)-1H-imidazol-1-yl)azetidine-1-carboxylate (0.25 g, 0.41 mmol) in DCM (15 mL), was added TFA (3 mL). The mixture was stirred at room temperature for 3 hours, and then concentrated in vacuo. The crude product was used for the next step directly. LC-MS (ESI): m/z 518 (M+H)$^+$.

Step 3: Synthesis of 6-(2-Isopropylphenyl)-1-(4-(1-(1-methylazetidin-3-yl)-4-(trifluoromethyl)-1H-imidazol-2-yl)benzyl)-1H-pyrazolo[3,4-d]pyrimidine (152)

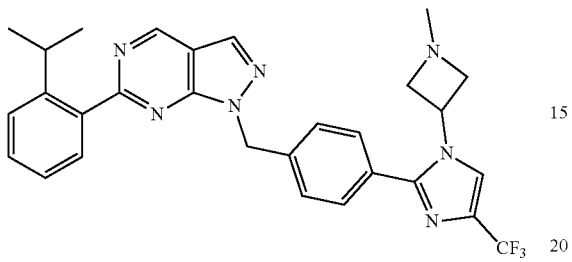

To a solution of 3-(2-(4-((6-(2-isopropylphenyl)-1H-pyrazolo[3,4-d]pyrimidin-1-yl)methyl)phenyl)-4-(trifluoromethyl)-1H-imidazol-1-yl)azetidin-1-ium 2,2,2-trifluoroacetate (TFA salt) (0.20 g, 0.41 mmol) in DCM (10 mL) at room temperature, was added an aqueous 37% formaldehyde solution (2.04 mL) and NaBH(OAc)$_3$ (0.17 g, 0.82 mmol) in one portion. After the reaction was stirred at room temperature for 30 min, an additional 70 mg of NaBH(OAc)$_3$ was added. After an additional 1 hour, the reaction was quenched with water (20 mL) and extracted with DCM (50 ml×3). The combined organic layer was dried over anhydrous Na$_2$SO$_4$ (20 g), filtered and concentrated in vacuo. The residue was purified by silica gel chromatography (DCM:MeOH=100:1 to 20:1) to give 38 mg of the title compound. LC-MS (Method A) (ESI): m/z 532 (M+H)$^+$; $^1$H-NMR (300 MHz, CDCl$_3$) δ 9.31 (s, 1H), 8.21 (s, 1H), 7.82 (s, 1H), 7.72 (d, J=7.5 Hz, 1H), 7.41-7.71 (m, 6H), 7.33 (m, 1H), 5.75 (s, 2H), 4.78-4.82 (m, 1H), 3.60-3.65 (m, 2H), 3.55 (m, 1H), 3.31-3.36 (m, 2H), 2.37 (s, 3H), 1.26-1.28 (d, J=6.9 Hz, 6H).

The following example was prepared from BB-4 according to Example 152:

Example 154: Synthesis of 1-(4-(1-Cyclopropyl-4-(trifluoromethyl)-1H-imidazol-2-yl)benzyl)-6-(4-cyclopropyl-6-methoxypyrimidin-5-yl)-1H-pyrazolo[3,4-d]pyrimidine (154)

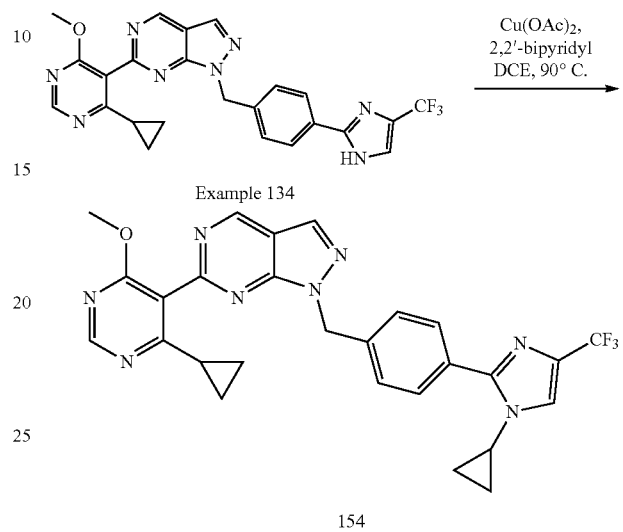

To a stirred solution of 6-(4-cyclopropyl-6-methoxypyrimidin-5-yl)-1-(4-(4-(trifluoromethyl)-1H-imidazol-2-yl)benzyl)-1H-pyrazolo[3,4-d]pyrimidine (134) (0.20 g, 0.40 mmol) and cyclopropyl boronic acid (0.052 g, 0.60 mmol) in DCE (20 mL), was added Cu(OAc)$_2$ (0.108 g, 0.60 mmol) and 2,2'-bipyridyl (0.074 g, 0.48 mmol). The reaction mixture was degassed by oxygen for 30 min and then heated at 90° C. under oxygen balloon pressure for 16 h. Progress of the reaction was monitored by TLC. After completion, the reaction mixture was filtered through Celite bed, washed with DCM, and the filtrate was concentrated under reduced pressure. The crude compound was purified by column chromatography using 0-2% MeOH in DCM to get the impure compound which was further purified by prep. HPLC to afford 0.042 g of the title compound. LC-MS (Method C) (ESI+): m/z 533.05 (M+H)$^+$; $^1$H-NMR (400 MHz, DMSO-d$_6$) 9.51 (s, 1H), 8.71 (s, 1H), 8.53 (s, 1H), 7.92 (s, 1H), 7.85 (d, J=7.8 Hz, 2H), 7.40 (d, J=8.3 Hz, 2H), 5.78 (s, 2H), 3.85 (s, 3H), 3.67-3.74 (m, 1H), 1.62-1.69 (m, 1H), 1.06 (s, 2H), 0.92-1.00 (m, 2H), 0.83-0.91 (m, 4H).

| Example | Structure | Analytical data |
|---|---|---|
| 153 | 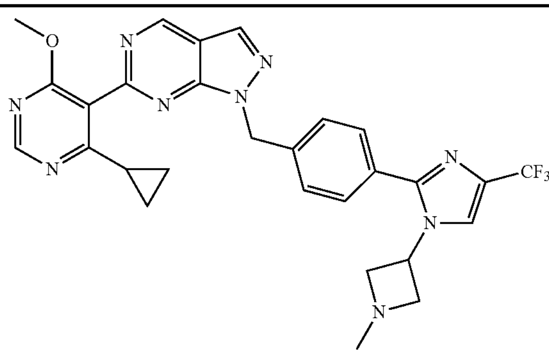 | LC-MS (Method A) (ESI+): m/z 561 (M + H)$^+$; $^1$H-NMR (300 MHz, CD$_3$OD) δ 9.41 (s, 1H), 8.65 (s, 1H), 8.42 (s, 1H), 8.30 (s, 1H), 7.50-7.58 (m, 4H), 5.82 (s, 2H), 5.38 (m, 1H), 4.40-4.52 (m, 4H), 3.92 (s, 3H), 2.98 (s, 3H), 1.78 (m, 1H), 1.12-1.20 (m, 2H), 0.88-0.95 (m, 2H). |

General Procedure for the Preparation of Aminopyrimidines: Synthesis of 6-Cyclopropyl-N,N-dimethyl-5-(1-(4-(1-methyl-4-(trifluoromethyl)-1H-imidazol-2-yl)benzyl)-1H-pyrazolo[3,4-d]pyrimidin-6-yl)pyrimidin-4-amine (155)

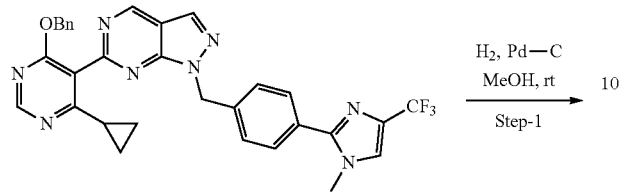

Example 102

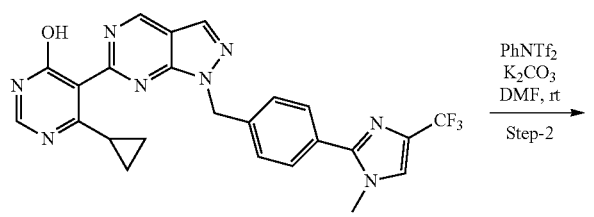

2

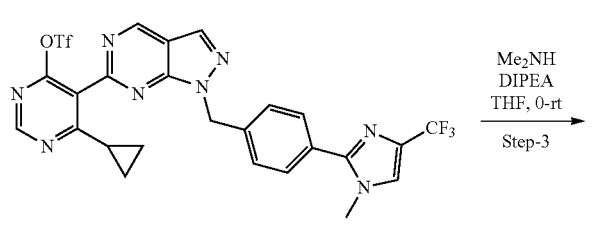

3

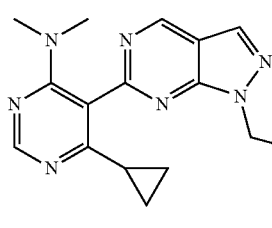

155

Step 1: Synthesis of 6-Cyclopropyl-5-(1-(4-(1-methyl-4-(trifluoromethyl)-1H-imidazol-2-yl)benzyl)-1H-pyrazolo[3,4-d]pyrimidin-6-yl)pyrimidin-4-ol

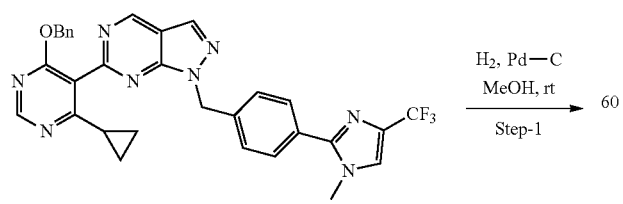

Example 102

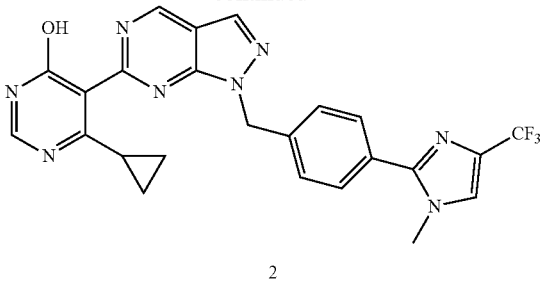

2

To a stirred solution of 6-(4-(benzyloxy)-6-cyclopropylpyrimidin-5-yl)-1-(4-(1-methyl-4-(trifluoromethyl)-1H-imidazol-2-yl)benzyl)-1H-pyrazolo[3,4-d]pyrimidine (102) (0.32 g, 0.55 mmol) in MeOH (5 mL) was added Pd/C (0.10 g) under nitrogen atmosphere, and the reaction mixture was stirred under $H_2$ atmosphere at room temperature for 2 h. Progress of the reaction was monitored by TLC. After completion, the reaction mixture was filtered through Celite, and the filtrate was concentrated under reduced pressure. The crude compound was purified by silica gel chromatography using 7-10% MeOH in DCM to afford 0.215 g of the title compound. LC-MS (Method B) (ESI+): m/z 493.00 (M+H)$^+$; $^1$H-NMR (400 MHz, DMSO-$d_6$) δ 12.62 (s, 1H), 9.47 (s, 1H), 8.48 (s, 1H), 8.17 (s, 1H), 7.91 (s, 1H), 7.67 (d, J=7.9 Hz, 2H), 7.40 (d, J=8.4 Hz, 2H), 5.77 (s, 2H), 3.74 (s, 3H), 1.46-1.54 (m, 1H), 0.97-1.02 (m, 2H), 0.74-0.80 (n, 2H).

Step 2: Synthesis of 6-Cyclopropyl-5-(1-(4-(1-methyl-4-(trifluoromethyl)-1H-imidazol-2-yl)benzyl)-1H-pyrazolo[3,4-d]pyrimidin-6-yl)pyrimidin-4-yl trifluoromethanesulfonate

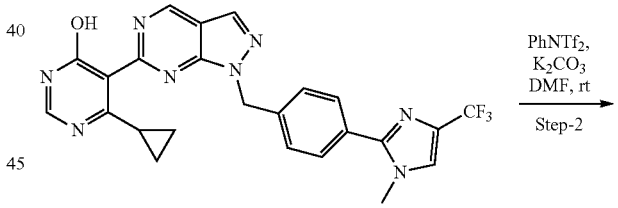

2

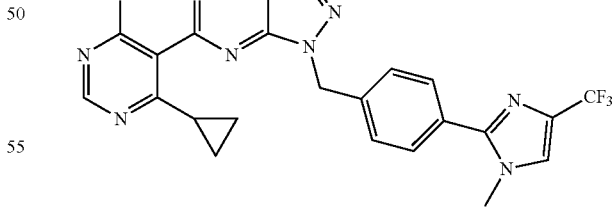

3

To a stirred solution of 6-cyclopropyl-5-(1-(4-(1-methyl-4-(trifluoromethyl)-1H-imidazol-2-yl)benzyl)-1H-pyrazolo[3,4-d]pyrimidin-6-yl)pyrimidin-4-ol (0.20 g, 0.41 mmol) in DMF (5 mL), was added $K_2CO_3$ (0.168 g, 1.22 mmol). N-Phenyl-bis(trifluoromethanesulfonimide) (0.217 g, 0.61 mmol) was then added and the reaction mixture was stirred at room temperature for 16 h. Progress of the reaction was monitored by TLC. After completion, the reaction mixture was diluted with H₂O (20 mL) and extracted with EA (2×20 mL). The combined organic layer was washed with cold H₂O (25 mL) and brine (25 mL), dried over anhydrous sodium sulfate, filtered, and concentrated under reduced pressure. The crude compound was purified by silica gel chromatography using 1-2% MeOH in DCM to afford 0.13 g of the title compound. LC-MS (Method B) (ESI+): m/z 625.00 (M+H)⁺; ¹H-NMR (400 MHz, DMSO-d₆) δ 9.62 (s, 1H), 9.09 (s, 1H), 8.61 (s, 1H), 7.92 (s, 1H), 7.67 (d, J=7.9 Hz, 2H), 7.40 (d, J=7.9 Hz, 2H), 5.81 (s, 2H), 3.74 (s, 3H), 2.26-2.30 (m, 1H), 1.25 (s, 2H), 1.09-1.14 (m, 2H).

Step 3: Synthesis of 6-Cyclopropyl-N,N-dimethyl-5-(1-(4-(1-methyl-4-(trifluoromethyl)-1H-imidazol-2-yl)benzyl)-1H-pyrazolo[3,4-d]pyrimidin-6-yl)pyrimidin-4-amine (Example 155)

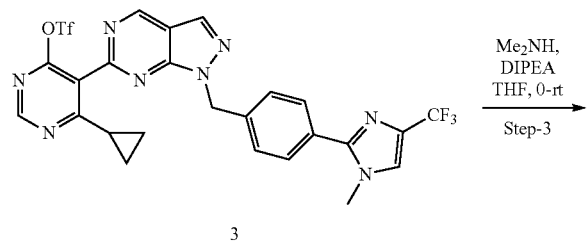

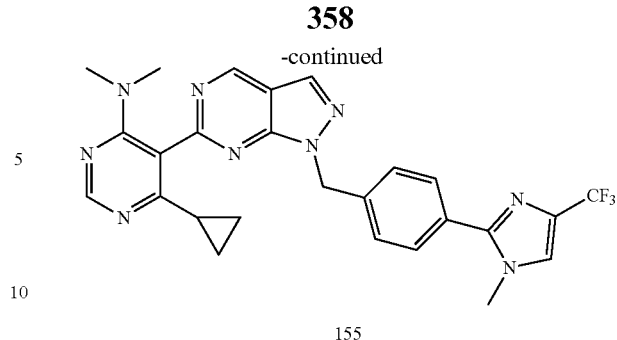

155

To an ice cooled solution of 6-cyclopropyl-5-(1-(4-(1-methyl-4-(trifluoromethyl)-1H-imidazol-2-yl)benzyl)-1H-pyrazolo[3,4-d]pyrimidin-6-yl)pyrimidin-4-yl trifluoromethanesulfonate (1 eq) in dry THF (2 mL), were added DIPEA (2 eq) and Me₂NH (2 eq) sequentially. The resulting mixture was stirred at room temperature for 1 h. Progress of the reaction was monitored by TLC. After completion, the reaction mixture was diluted with water (10 mL) and extracted with EA (2×15 mL). The combined organic layer was dried over anhydrous sodium sulfate, filtered, and concentrated under reduced pressure. The crude compound was triturated with n-pentane (10 mL), filtered, and the solid thus obtained was further purified prep HPLC to afford mg of the title compound. LC-MS (Method B) (ESI+): m/z 520.15 (M+H)⁺; ¹H-NMR (400 MHz, DMSO-d₆) δ 9.49 (s, 1H), 8.51 (s, 1H), 8.41 (s, 1H), 7.92 (s, 1H), 7.67 (d, J=7.8 Hz, 2H), 7.36 (d, J=8.3 Hz, 2H), 5.78 (s, 2H), 3.74 (s, 3H), 2.61 (s, 6H), 1.58-1.66 (m, 1H), 0.93-0.97 (m, 2H), 0.67-0.70 (m, 2H).

The following compounds were prepared from the appropriate amines according to the method described for Example 155:

| Example | Structure | Analytical data |
|---|---|---|
| 156 | 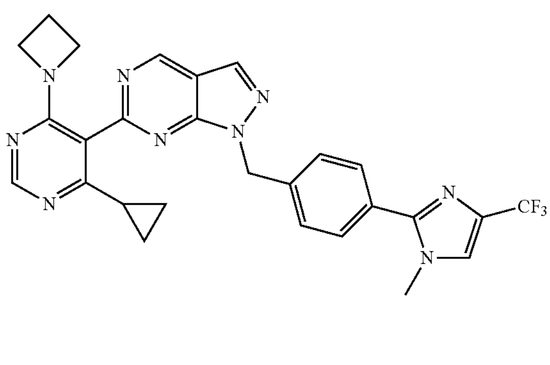 [SMILES: Cn1cc(C(F)(F)F)nc1-c1ccc(Cn2ncc3cnc(-c4c(C5CC5)ncnc4N4CCC4)nc32)cc1] | LC-MS (Method B) (ESI+): m/z 532.10 (M + H)⁺; ¹H-NMR (400 MHz, DMSO-d₆) δ 9.49 (s, 1H), 8.52 (s, 1H), 8.37 (s, 1H), 7.92 (s, 1H), 7.68 (d, J = 7.8 Hz, 2H), 7.39 (d, J = 8.3 Hz, 2H), 5.80 (s, 2H), 3.74 (s, 3H), 3.44 (d, J = 8.3 Hz, 4H), 1.93-2.03 (m, 2H), 1.43-1.52 (m, 1H), 0.96 (s, 2H), 0.67-0.74 (m, 2H). |
| 157 | 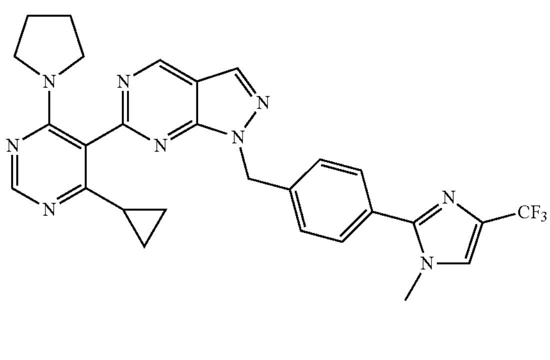 [SMILES: Cn1cc(C(F)(F)F)nc1-c1ccc(Cn2ncc3cnc(-c4c(C5CC5)ncnc4N4CCCC4)nc32)cc1] | LC-MS (Method B) (ESI+): m/z 546.15 (M + H)⁺; ¹H-NMR (400 MHz, DMSO-d₆) δ 9.47 (s, 1H), 8.52 (s, 1H), 8.38 (s, 1H), 7.91 (s, 1H), 7.66 (d, J = 8.3 Hz, 2H), 7.33 (d, J = 8.3 Hz, 2H), 5.79 (s, 2H), 3.74 (s, 3H), 2.89 (s, 4H), 1.58 (s, 4H), 1.36-1.44 (m, 1H), 0.95 (s, 2H), 0.66 (dd, J = 2.9, 7.8 Hz, 2H). |

| Example | Structure | Analytical data |
|---|---|---|
| 158 | 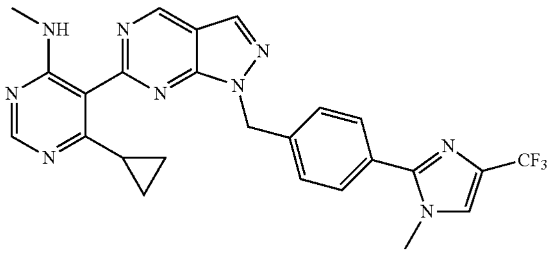 | LC-MS (Method B) (ESI+): m/z 506.15 (M + H)+; 1H-NMR (400 MHz, DMSO-d6) δ 9.50 (s, 1H), 8.52 (s, 1H), 8.37 (s, 1H), 7.92 (s, 1H), 7.67 (d, J = 7.8 Hz, 2H), 7.42 (d, J = 7.8 Hz, 2H), 6.98 (d, J = 4.4 Hz, 1H), 5.78 (s, 2H), 3.74 (s, 3H), 2.80 (d, J = 4.4 Hz, 3H), 1.77-1.85 (m, 1H), 0.98 (s, 2H), 0.71 (dd, J = 3.2, 7.1 Hz, 2H). |
| 159 | 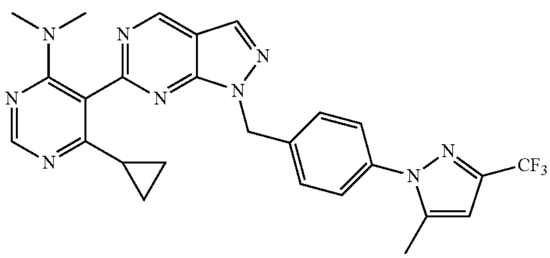 | LC-MS (Method A) (ESI+): m/z 494 (M + H)+; 1H-NMR (300 MHz, CDCl3) □ 9.39 (s, 1H), 8.44 (s, 1H), 8.42 (s, 1H), 7.46-7.54 (m, 4H), 6.57 (s, 1H), 5.82 (s, 2H), 2.71 (s, 6H), 2.31 (s, 3H), 2.13 (s, 3H). |

Example 160: Synthesis of 6-Cyclopropyl-5-(1-(4-(1-methyl-4-(trifluoromethyl)-1H-imidazol-2-yl)benzyl)-1H-pyrazolo[3,4-d]pyrimidin-6-yl)pyrimidin-4-yl trifluoromethanesulfonate (160)

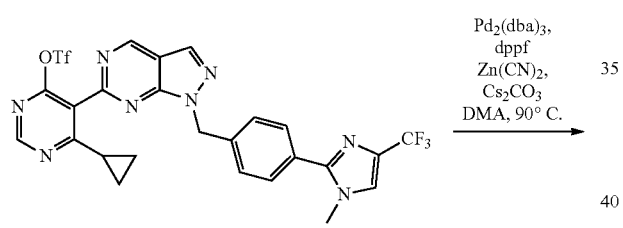

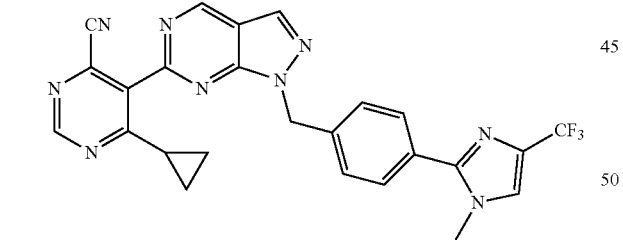

To a stirred solution of 6-cyclopropyl-5-(1-(4-(1-methyl-4-(trifluoromethyl)-1H-imidazol-2-yl)benzyl)-1H-pyrazolo[3,4-d]pyrimidin-6-yl)pyrimidin-4-yltrifluoromethanesulfonate (0.15 g, 0.24 mmol) in DMA (5 mL), was added Zn(CN)2 (0.141 g, 1.20 mmol) and Cs2CO3 (0.156 g, 0.48 mmol). The mixture was then degassed with argon for 10 min, whereupon, Pd2(dba)3 (0.022 g, 0.024 mmol) and dppf (0.013 g, 0.024 mmol) were added. The reaction mixture was heated to 90° C. for 16 h. Progress of the reaction was monitored by TLC. After completion, the reaction mixture was concentrated under reduced pressure. The residue obtained was dissolved in Et2O (50 mL), filtered through Celite, and washed with Et2O (20 mL). The organic layer was concentrated under reduced pressure and the crude compound was purified by SFC to afford 0.037 g of the title compound. LC-MS (Method C) (ESI+): m/z 501.95 (M+H)+; 1H-NMR (400 MHz, DMSO-d6) δ 9.65 (s, 1H), 9.28 (s, 1H), 8.63 (s, 1H), 7.92 (s, 1H), 7.67 (d, J=7.8 Hz, 2H), 7.46 (d, J=7.8 Hz, 2H), 5.83 (s, 2H), 3.74 (s, 3H), 2.38-2.45 (m, 1H), 1.23 (s, 2H), 1.09-1.16 (m, 2H).

Example 161: Synthesis of 6-(4-cyclopropyl-6-methoxypyrimidin-5-yl)-1-(4-(1-isopropyl-4-(trifluoromethyl)-1H-imidazol-2-yl)benzyl)-N,N-dimethyl-1H-pyrazolo[3,4-d]pyrimidin-4-amine (161)

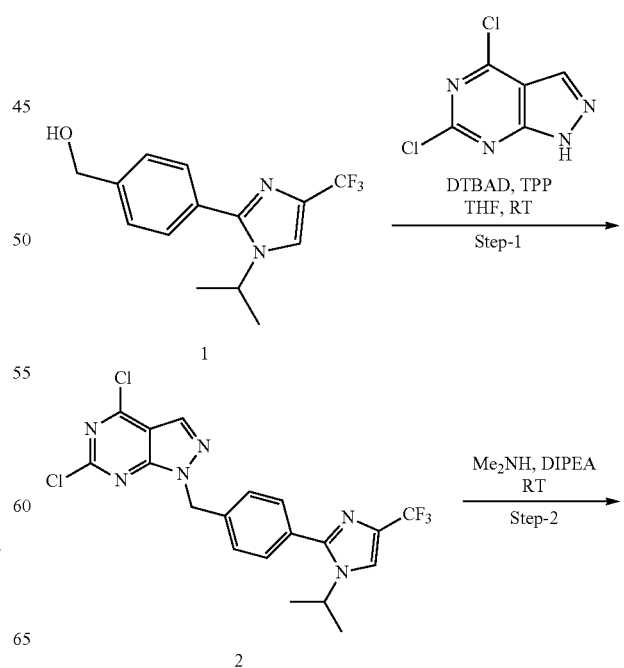

361

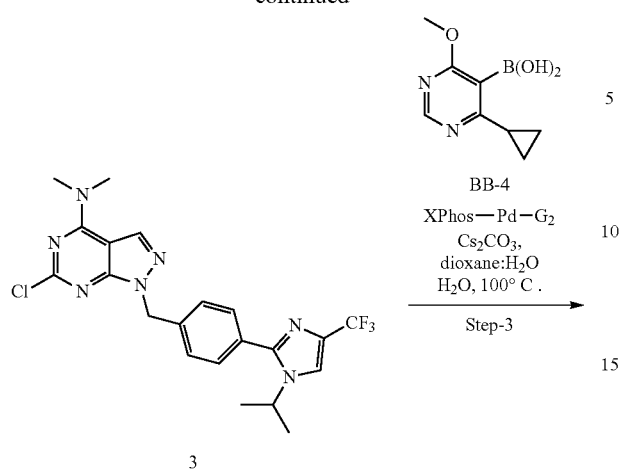

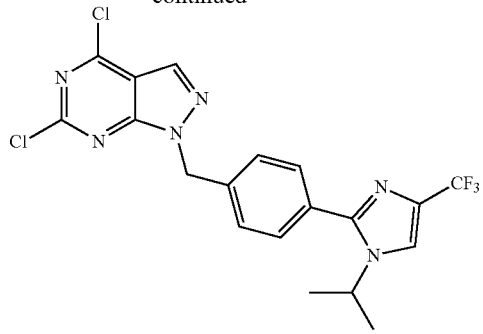

362

-continued

To a stirred solution of (4-(1-isopropyl-4-(trifluoromethyl)-1H-imidazol-2-yl)phenyl)methanol 1 (1.0 g, 3.52 mmol), 4,6-dichloro-1H-pyrazolo[3,4-d]pyrimidine (0.665 g, 0.352 mmol) and TPP (1.84 g, 7.04 mmol) in THF (10 mL), was added DTBAD (1.61 g, 7.04 mmol) portion-wise at room temperature. The resulting mixture was stirred for 2 h. Progress of the reaction was monitored by TLC. After completion, the reaction mixture was concentrated under reduced pressure to dryness resulting in the crude compound. The crude compound was purified by silica gel chromatography using 0-40% EA in hexane to afford the title compound (0.230 g). LC-MS (Method B) (ESI+): m/z 455.10 (M)+; $^1$H-NMR (400 MHz, DMSO-$d_6$) δ 8.63 (s, 1H), 8.17 (s, 1H), 7.54 (d, J=7.83 Hz, 2H), 7.40 (d, J=7.83 Hz, 2H), 5.73-5.77 (m, 2H), 4.43 (td, J=6.72, 12.96 Hz, 1H), 1.38 (d, J=6.85 Hz, 6H).

Step 2: Synthesis of 6-chloro-1-(4-(1-isopropyl-4-(trifluoromethyl)-1H-imidazol-2-yl)benzyl)-N,N-dimethyl-1H-pyrazolo[3,4-d]pyrimidin-4-amine Step 1: Synthesis of 4,6-dichloro-1-(4-(1-isopropyl-4-(trifluoromethyl)-1H-imidazol-2-yl)benzyl)-1H-pyrazolo[3,4-d]pyrimidine

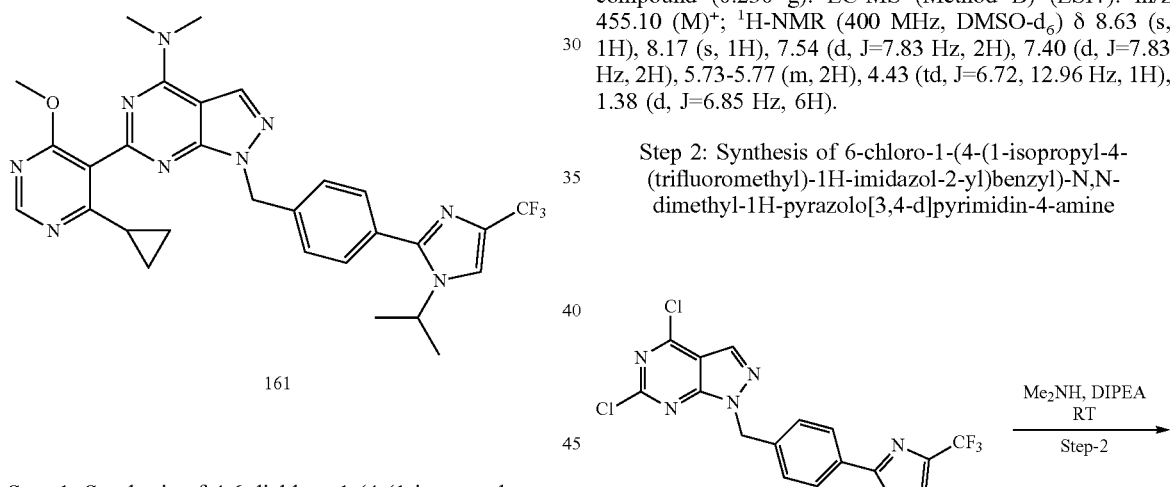

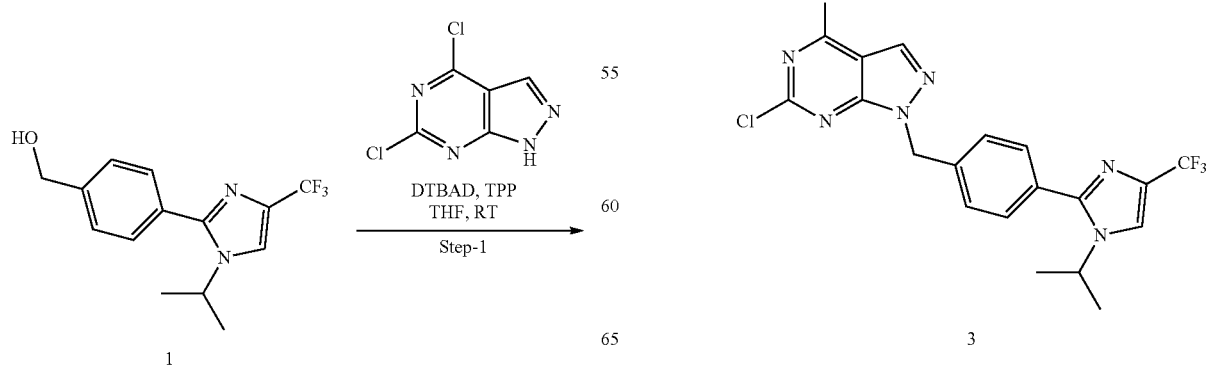

To a stirred solution of 4,6-dichloro-1-(4-(1-isopropyl-4-(trifluoromethyl)-1H-imidazol-2-yl)benzyl)-1H-pyrazolo[3,4-d]pyrimidine (0.230 g, 0.506 mmol) in THF (12 mL), was added DIPEA (0.263 mL, 1.519 mmol) at room temperature. To the resulting mixture was added dimethylamine (2M solution in THF, 0.506 mL, 1.01 mmol) and the reaction was stirred for 16 h. Progress of the reaction was monitored by TLC. After completion, the reaction mixture was diluted with water (20 mL) and extracted with EA (3×5 mL). The combined organic layer was dried over anhydrous sodium sulfate, filtered and concentrated under reduced pressure. The crude compound was purified by silica gel chromatography using 0-50% EA in hexane to afford the title compound (0.200 g). LC-MS (Method B) (ESI+): m/z 464.08 (M+H)+; 1H-NMR (400 MHz, DMSO-d6) δ 8.31 (s, 1H), 8.17 (s, 1H), 7.53 (d, J=7.83 Hz, 2H), 7.32 (d, J=7.83 Hz, 2H), 5.57 (s, 2H), 4.10 (q, J=5.22 Hz, 1H), 3.42 (br s, 3H), 3.26 (br s, 3H), 1.38 (d, J=6.36 Hz, 6H).

Step 3: Synthesis of 6-(4-cyclopropyl-6-methoxypyrimidin-5-yl)-1-(4-(1-isopropyl-4-(trifluoromethyl)-1H-imidazol-2-yl)benzyl)-N,N-dimethyl-1H-pyrazolo[3,4-d]pyrimidin-4-amine (161)

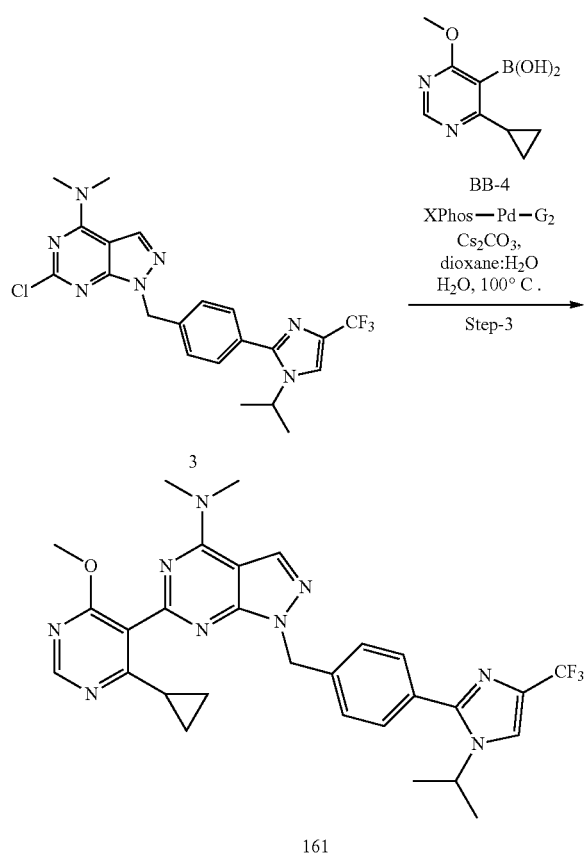

To a stirred solution of 6-chloro-1-(4-(1-isopropyl-4-(trifluoromethyl)-1H-imidazol-2-yl)benzyl)-N,N-dimethyl-1H-pyrazolo[3,4-d]pyrimidin-4-amine 3 (0.090 g, 0.194 mmol) and (4-cyclopropyl-6-methoxypyrimidin-5-yl)boronic acid BB-4 (0.041 g, 0.213 mmol) in dioxane:H2O (3:1 mL), was added Cs2CO3 (0.158 g, 0.485 mmol) at room temperature. The resulting mixture was degassed with argon for 5 min, and then treated with X-Phos (0.018 g, 0.038 mmol) and X-Phos-Pd-G2 (0.015 g, 0.019 mmol). The mixture was further degassed with argon for 5 min, and then heated at 100° C. for 8 h. Progress of the reaction was monitored by TLC. After completion, the reaction mixture was cooled to room temperature, diluted with water (100 mL) and extracted with EA (2×100 mL). The combined organic layer was separated, dried over anhydrous sodium sulfate, filtered and concentrated under reduced pressure. The crude compound was purified by silica gel chromatography using 0-50% EA in hexane to afford (0.070 g) of the title compound. This material was dissolved in dioxane (7 mL) and stirred with PS-Thiol silica (0.007 g). The resulting slurry was heated to 100° C. for 2 h, then cooled to room temperature, filtered and concentrated under reduced pressure to afford the title compound (0.050 g).

This material was further purified by prep HPLC (Method C) to afford the title compound (0.020 g). LC-MS (Method B) (ESI+): m/z 578.30 (M+H)+; 1H-NMR (400 MHz, DMSO-d6) δ 8.61 (s, 1H), 8.29 (s, 1H), 8.11 (s, 1H), 7.47 (d, J=7.83 Hz, 2H), 7.34 (d, J=7.83 Hz, 2H), 5.59 (s, 2H), 4.38 (td, J=6.24, 12.96 Hz, 1H), 3.83 (s, 3H), 3.19-3.47 (m, 6H), 1.70-1.80 (m, 1H), 1.35 (d, J=6.36 Hz, 6H), 0.96-1.02 (m, 2H), 0.80-0.86 (m, 2H).

Preparation of I-65: Synthesis of 1-(4-(5-bromo-1-ethyl-4-(trifluoromethyl)-1H-imidazol-2-yl)benzyl)-6-(4-cyclopropyl-6-methoxypyrimidin-5-yl)-1H-pyrazolo[3,4-d]pyrimidine (I-65)

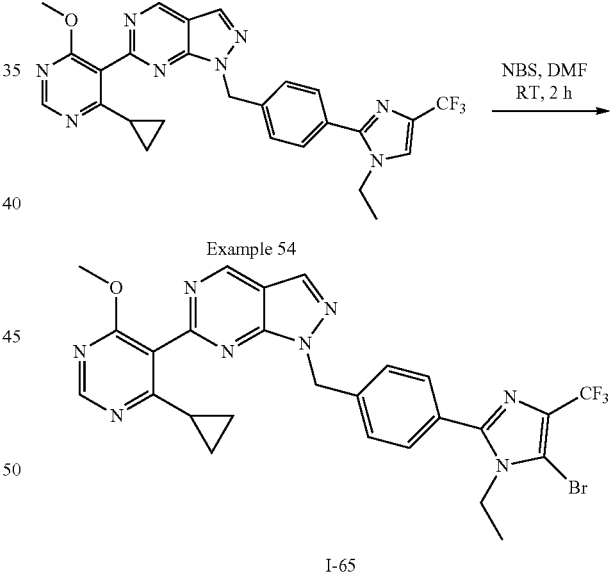

To a stirred solution of 6-(4-cyclopropyl-6-methoxypyrimidin-5-yl)-1-(4-(1-ethyl-4-(trifluoromethyl)-1H-imidazol-2-yl) benzyl)-1H-pyrazolo[3,4-d]pyrimidine (54) (1.80 g, 3.461 mmol) in DMF (10 mL) was added NBS (1.23 g, 6.923 mmol) in one lot at room temperature. The resulting mixture was stirred for 2 h and progress of the reaction was monitored by TLC. After completion, the reaction mixture was quenched with ice cold water (15 mL) and extracted with EA (3×15 mL). The combined organic layer was dried over anhydrous sodium sulfate, filtered and concentrated under reduced pressure. The crude compound thus obtained was purified by silica gel chromatography using 0-50% EA in hexane as eluent to afford the title compound (1.00 g). LC-MS (Method B) (ESI+): m/z 600.40 (M+H)+; ¹H-NMR (400 MHz, DMSO-d$_6$) δ 9.51 (s, 1H), 8.71 (s, 1H), 8.53 (s, 1H), 7.54-7.64 (m, 3H), 7.43 (d, J=7.98 Hz, 1H), 5.80 (s, 2H), 4.00-4.08 (m, 2H), 3.85 (s, 2H), 1.62-1.69 (m, 1H), 1.24 (t, J=7.23 Hz, 3H), 1.17 (t, J=7.23 Hz, 1H), 1.02-1.08 (m, 2H), 0.83-0.88 (m, 2H).

The following Example compounds were prepared from the appropriate building blocks according to the method described for I-65:

| Example | Structure | Analytical data |
|---|---|---|
| 162 | 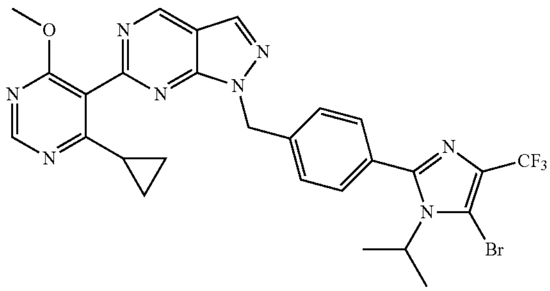 [SMILES: COc1ncnc(C2CC2)c1-c1ncc2cnn(Cc3ccc(-c4nc(C(F)(F)F)c(Br)n4C(C)C)cc3)c2n1] | LC-MS (Method B) (ESI+): m/z 613.30 (M + H)+; ¹H-NMR (400 MHz, DMSO-d$_6$) δ 9.51 (s, 1H), 8.71 (s, 1H), 8.53 (s, 1H), 7.46-7.53 (m, 2H), 7.39-7.45 (m, 2H), 5.80 (s, 2H), 4.51-4.60 (m, 1H), 3.85 (s, 3H), 1.65 (dt, J = 3.91, 8.07 Hz, 1H), 1.49 (d, J = 7.34 Hz, 6H), 1.02-1.09 (m, 2H), 0.85 (dd, J = 3.42, 7.83 Hz, 2H). |
| 163 | 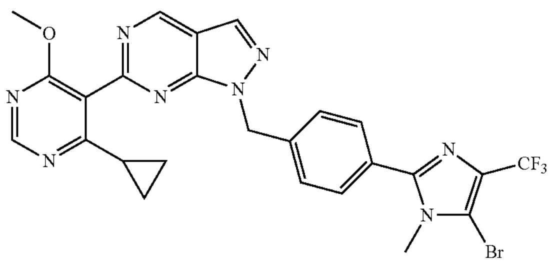 [SMILES: COc1ncnc(C2CC2)c1-c1ncc2cnn(Cc3ccc(-c4nc(C(F)(F)F)c(Br)n4C)cc3)c2n1] | LC-MS (Method C) (ESI+): m/z 584.90 (M + H)+; ¹H-NMR (400 MHz, DMSO-d$_6$) δ 9.51 (s, 1H), 8.71 (s, 1H), 8.52 (s, 1H), 7.64 (d, J = 7.98 Hz, 2H), 7.44 (d, J = 8.48 Hz, 2H), 5.79 (s, 2H), 3.85 (s, 3H), 3.65 (s, 3H), 1.65 (ddd, J = 4.49, 7.85, 12.09 Hz, 1H), 1.03-1.09 (m, 2H), 0.86 (dd, J = 2.99, 7.98 Hz, 2H). |

Example 164: Synthesis of 6-(4-cyclopropyl-6-methoxypyrimidin-5-yl)-1-(4-(1-ethyl-5-methoxy-4-(trifluoromethyl)-1H-imidazol-2-yl)benzyl)-1H-pyrazolo[3,4-d]pyrimidine (164)

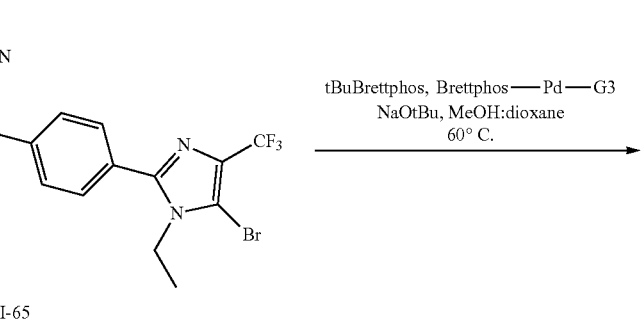

I-65 tBuBrettphos, Brettphos—Pd—G3
NaOtBu, MeOH:dioxane
60° C.

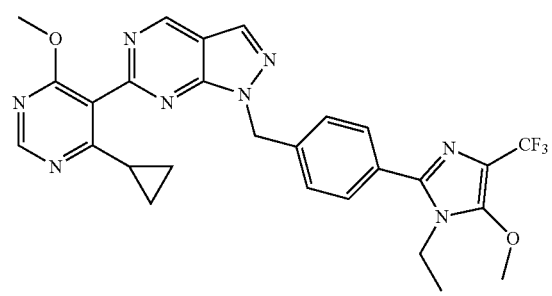

164

To a stirred solution of 1-(4-(5-bromo-1-ethyl-4-(trifluoromethyl)-1H-imidazol-2-yl)benzyl)-6-(4-cyclopropyl-6-methoxypyrimidin-5-yl)-1H-pyrazolo[3,4-d]pyrimidine I-65 (0.100 g, 0.167 mmol) in dioxane:MeOH (1.2:0.3 mL) was added NaOtBu (0.032 g, 0.334 mmol). The mixture was then degassed with argon for 10 min. To the reaction mixture was added tert-butyl-Brettphos (0.002 g, 0.003 mmol) and tert-butyl-BrettphosPd-G$_3$ (0.003 g, 0.003 mmol) at room temperature, and the mixture was further degassed with argon for 5 min. The reaction mixture was then heated at 60° C. for 48 h. Progress of the reaction was monitored by TLC. After completion, the reaction mixture was concentrated under reduced pressure. The crude compound was purified by silica gel chromatography eluting with 0-2% methanol in DCM followed by re-purification using preparative HPLC (Method B) to afford the title compound (0.014 g). LC-MS (Method B) (ESI+): m/z 551.25 (M+H)$^+$; $^1$H-NMR (400 MHz, DMSO-d$_6$) δ 9.51 (s, 1H), 8.71 (s, 1H), 8.52 (s, 1H), 7.58 (d, J=8.31 Hz, 2H), 7.40 (d, J=8.31 Hz, 2H), 5.78 (s, 2H), 3.97 (s, 3H), 3.90-3.96 (m, 2H), 3.85 (s, 3H), 1.61-1.69 (m, 1H), 1.17 (t, J=7.09 Hz, 3H), 1.03-1.08 (m, 2H), 0.83-0.88 (m, 2H).

The following compounds were prepared from the appropriate building blocks according to the method described for Example 164:

Example 167: Synthesis of 6-(4-cyclopropyl-6-methoxypyrimidin-5-yl)-1-(4-(1-ethyl-5-methyl-4-(trifluoromethyl)-1H-imidazol-2-yl)benzyl)-1H-pyrazolo[3,4-d]pyrimidine (167)

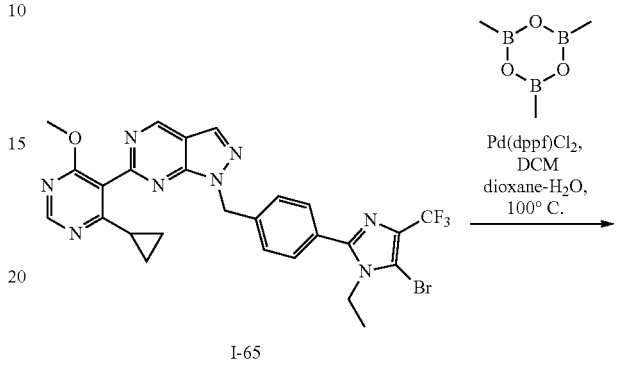

I-65

| Example | Structure | Analytical data |
|---|---|---|
| 165 | 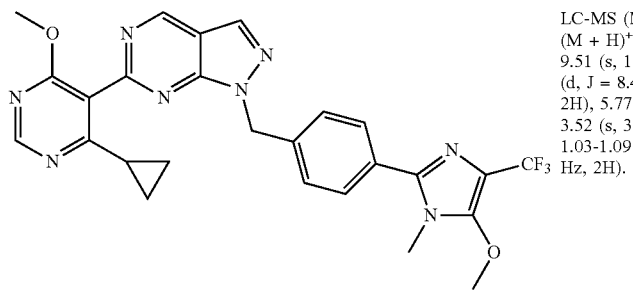 | LC-MS (Method C) (ESI+): m/z 537.04 (M + H)$^+$; $^1$H-NMR (400 MHz, DMSO-d$_6$) δ 9.51 (s, 1H), 8.71 (s, 1H), 8.52 (s, 1H), 7.64 (d, J = 8.48 Hz, 2H), 7.41 (d, J = 7.98 Hz, 2H), 5.77 (s, 2H), 3.94 (s, 3H), 3.85 (s, 3H), 3.52 (s, 3H), 1.65 (dt, J = 4.24, 8.10 Hz, 1H), 1.03-1.09 (m, 2H), 0.86 (dd, J = 3.24, 7.73 Hz, 2H). |
| 166 | 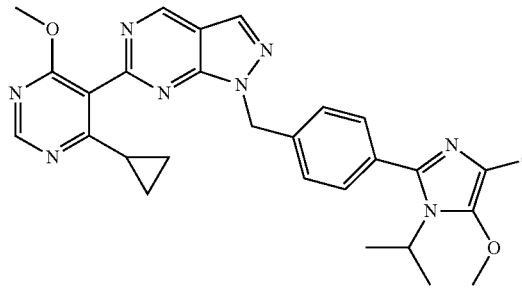 | LC-MS (Method B) (ESI+): m/z 565.40 (M + H)$^+$; $^1$H-NMR (400 MHz, DMSO-d$_6$) δ 9.51 (s, 1H), 8.71 (s, 1H), 8.52 (s, 1H), 7.44-7.48 (m, 2H), 7.38-7.43 (m, 2H), 5.78 (s, 2H), 4.33 (td, J = 6.92, 13.59 Hz, 1H), 3.98 (s, 3H), 3.85 (s, 3H), 1.62-1.70 (m, 1H), 1.40 (d, J = 6.98 Hz, 6H), 1.06 (d, J = 2.49 Hz, 2H), 0.85 (dd, J = 3.24, 7.73 Hz, 2H). |

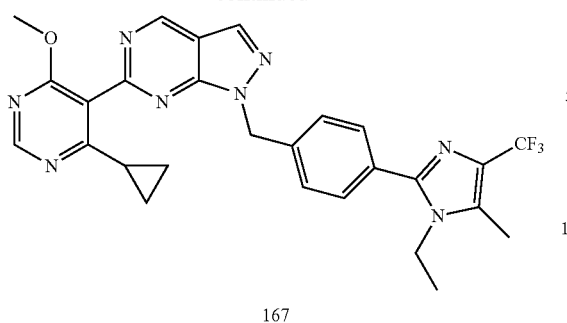

167

To a stirred solution of 1-(4-(5-bromo-1-ethyl-4-(trifluoromethyl)-1H-imidazol-2-yl)benzyl)-6-(4-cyclopropyl-6-methoxypyrimidin-5-yl)-1H-pyrazolo[3,4-d]pyrimidine I-65 (0.200 g, 0.334 mmol) and trimethyl boroxine (0.031 g, 0.502 mmol) in dioxane (6 mL) and water (2 ml), was added and K₂CO₃ (0.090 g, 0.668 mmol) at room temperature and the reaction mixture was degassed with argon gas for 15 min. To the resulting reaction mixture was added Pd(dppf)Cl₂-DCM (0.014 g, 0.016 mmol) at room temperature. The reaction mixture was heated in a sealed tube at 100° C. for 6 h. Progress of the reaction was monitored by TLC. After completion, the reaction mixture was cooled to room temperature and filtered through Celite and washed EA (5 mL). The filtrate obtained was concentrated under reduced pressure. The resulting crude compound was purified by prep. HPLC (Method B) to give the title compound. To a stirred solution of compound 168 (0.70 g) in dioxane (7 mL), was added SP thiol silica (0.007 g). The resulting reaction mixture was heated to 100° C. for 1 h, then cooled to room temperature, filtered and concentrated under reduced pressure to afford the title compound (0.027 g). LC-MS (Method B) (ESI+): m/z 535.15 (M+H)⁺; ¹H-NMR (400 MHz, DMSO-d₆) δ 9.51 (s, 1H), 8.71 (s, 1H), 8.52 (s, 1H), 7.55 (d, J=7.82 Hz, 2H), 7.41 (d, J=7.82 Hz, 2H), 5.79 (s, 2H), 3.92-4.01 (m, 2H), 3.85 (s, 3H), 2.37 (br s, 3H), 1.66 (d, J=3.42 Hz, 1H), 1.19 (t, J=7.09 Hz, 3H), 1.02-1.08 (m, 2H), 0.85 (d, J=3.91 Hz, 2H).

Preparation of Common Intermediate I-63: Synthesis of 6-(4-cyclopropyl-6-methoxypyrimidin-5-yl)-1H-pyrazolo[3,4-d]pyrimidine (I-66)

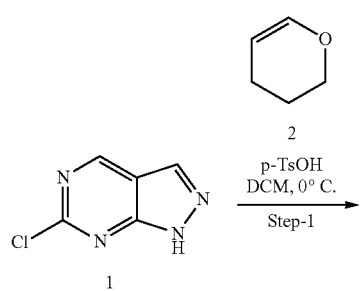

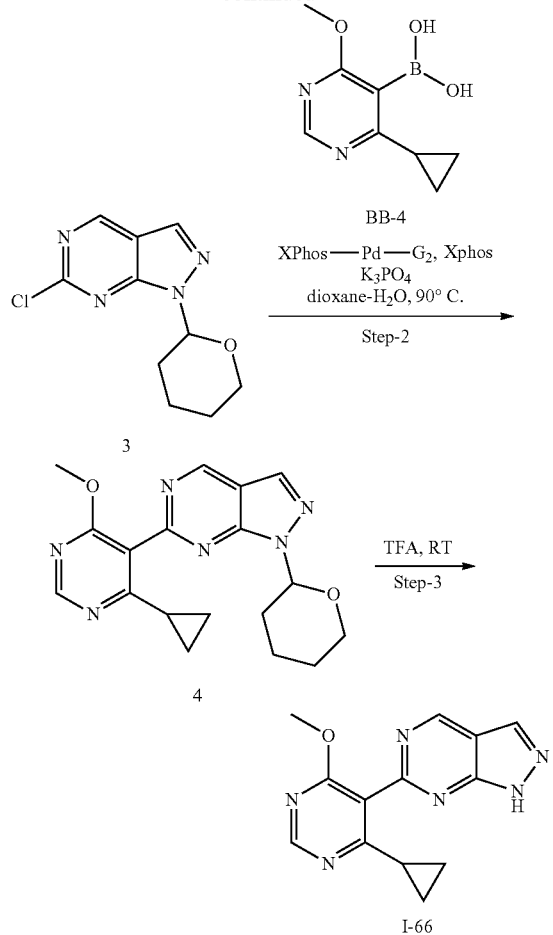

Step 1: Synthesis of 6-chloro-1-(tetrahydro-2H-pyran-2-yl)-1H-pyrazolo[3,4-d]pyrimidine

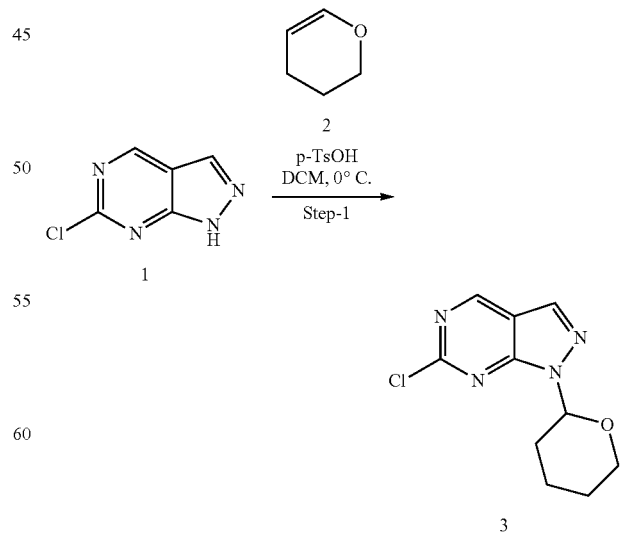

To a stirred solution of 6-chloro-1H-pyrazolo[3,4-d]pyrimidine 1 (2.5 g, 16.2 mmol) in DCM (50 mL), was added p-TsOH (0.418 g, 2.43 mmol) at room temperature. The resulting mixture was stirred for 5 min, and then 3,4-dihydro-2H-pyran 2 (2.29 g, 3.24 mmol) was added dropwise at 0° C. After addition, the mixture was stirred for 1 h at the same temperature. Progress of the reaction was monitored by TLC. After completion, the reaction mixture was quenched with saturated NaHCO$_3$ solution (50 mL). The organic layer was separated, dried over anhydrous sodium sulfate, filtered and concentrated under reduced pressure. The crude compound was purified by silica gel chromatography using 10-20% EA in hexane to afford the title compound (3.0 g). $^1$H-NMR (400 MHz, DMSO-d$_6$) δ 9.31-9.29 (m, 1H), 8.50 (s, 1H), 5.94 (dd, J=2.4, 10.3 Hz, 1H), 3.98-3.92 (m, 1H), 3.77-3.69 (m, 1H), 2.48-2.36 (m, 1H), 2.07-1.98 (m, 1H), 1.97-1.89 (m, 1H), 1.84-1.71 (m, 1H), 1.62-1.54 (m, 2H).

Step 2: Synthesis of 6-(4-cyclopropyl-6-methoxypyrimidin-5-yl)-1-(tetrahydro-2H-pyran-2-yl)-1H-pyrazolo[3,4-d]pyrimidine

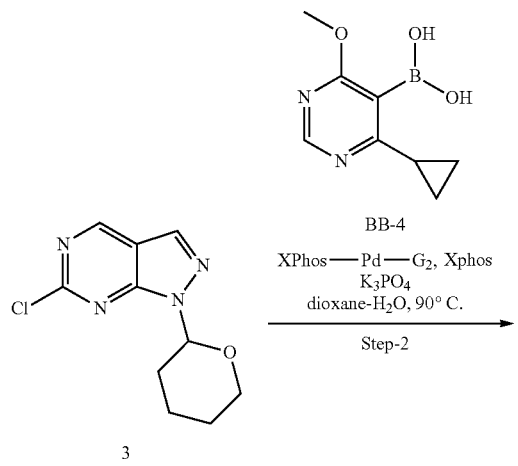
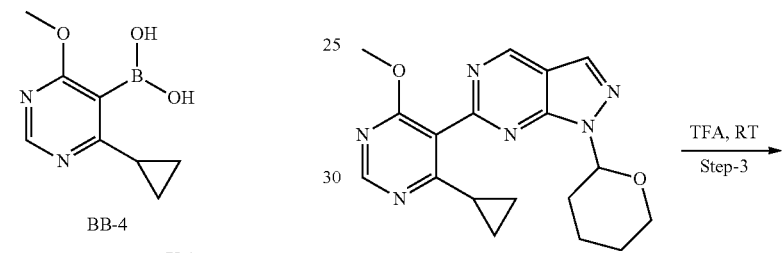

To a stirred solution of 6-chloro-1-(tetrahydro-2H-pyran-2-yl)-1H-pyrazolo[3,4-d]pyrimidine 3 (2.5 g, 10.5 mmol) and (4-cyclopropyl-6-methoxypyrimidin-5-yl)boronic acid BB-4 (2.03 g, 10.5 mmol) in dioxane:H$_2$O (3:1, 40 mL), was added K$_3$PO$_4$ (2.43 g, 11.4 mmol) at room temperature. The reaction mixture was purged with argon for 30 min, and then treated with XPhos-Pd-G2 (0.818 g, 1.04 mmol) and XPhos (0.991 g, 2.08 mmol) at room temperature. The resulting mixture was heated to 90° C. in a sealed tube for 1 h. Progress of the reaction was monitored by TLC. After completion, the reaction mixture was cooled to room temperature, diluted with water (50 mL) and extracted with EA (50 mL). The organic layer was separated, dried over anhydrous sodium sulfate and concentrated under reduced pressure. The crude compound was purified by silica gel chromatography using 10-40% EA in hexane to afford the title compound 4 (3.00 g). To a stirred solution of compound 4 (3.00 g) in dioxane (10 mL), was added SP thiol silica (0.250 g). The resulting reaction mixture was heated to 100° C. for 1 h, and then cooled to room temperature, filtered and concentrated under reduced pressure to afford the title compound (2.92 g). LC-MS (Method C) (ESI+): m/z 353.05 (M+H)$^+$; $^1$H-NMR (400 MHz, DMSO-d$_6$) δ 9.49 (s, 1H), 8.72 (s, 1H), 8.51 (s, 1H), 3.97-3.90 (m, 1H), 3.84 (s, 3H), 3.76-3.68 (m, 1H), 2.05-1.98 (m, 3H), 1.86-1.71 (m, 1H), 1.63-1.52 (m, 3H), 1.20-1.15 (m, 1H), 1.11-1.02 (m, 2H), 0.90-0.86 (m, 2H).

Step 3: Synthesis of 6-(4-cyclopropyl-6-methoxypyrimidin-5-yl)-1H-pyrazolo[3,4-d]pyrimidine (I-66)

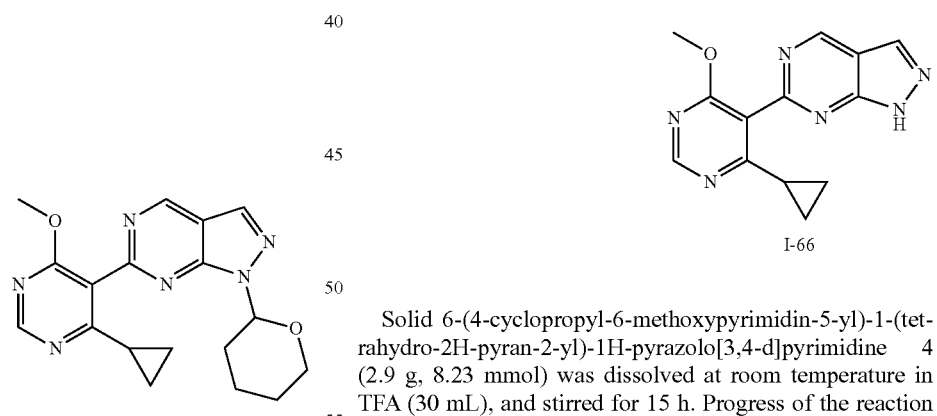

Solid 6-(4-cyclopropyl-6-methoxypyrimidin-5-yl)-1-(tetrahydro-2H-pyran-2-yl)-1H-pyrazolo[3,4-d]pyrimidine 4 (2.9 g, 8.23 mmol) was dissolved at room temperature in TFA (30 mL), and stirred for 15 h. Progress of the reaction was monitored by TLC. After completion, the reaction mixture was concentrated under reduced pressure. The residue was diluted with DCM (50 mL) and was basified to pH 8 using saturated NaHCO$_3$ solution (10 mL). The organic layer was separated, dried over anhydrous sodium sulfate, filtered and concentrated under reduced pressure. The crude compound was purified by silica gel chromatography using 10-20% EA in hexane to afford the title compound (1.87 g). LC-MS (Method C) (ESI+): m/z 268.95 (M+H)$^+$; $^1$H-NMR (400 MHz, DMSO-d$_6$) δ 14.20 (br s, 1H), 9.46 (s, 1H), 8.69 (s, 1H), 8.43 (s, 1H), 3.83 (s, 3H), 1.67-1.59 (m, 1H), 1.05 (td, J=3.7, 7.1 Hz, 2H), 0.91-0.84 (m, 2H).

Example 168: Synthesis of (S)-6-(4-cyclopropyl-6-methoxypyrimidin-5-yl)-1-(1-(4-(1-(2-fluoroethyl)-4-(trifluoromethyl)-1H-imidazol-2-yl)-3-methoxyphenyl)ethyl)-1H-pyrazolo[3,4-d]pyrimidine (168)

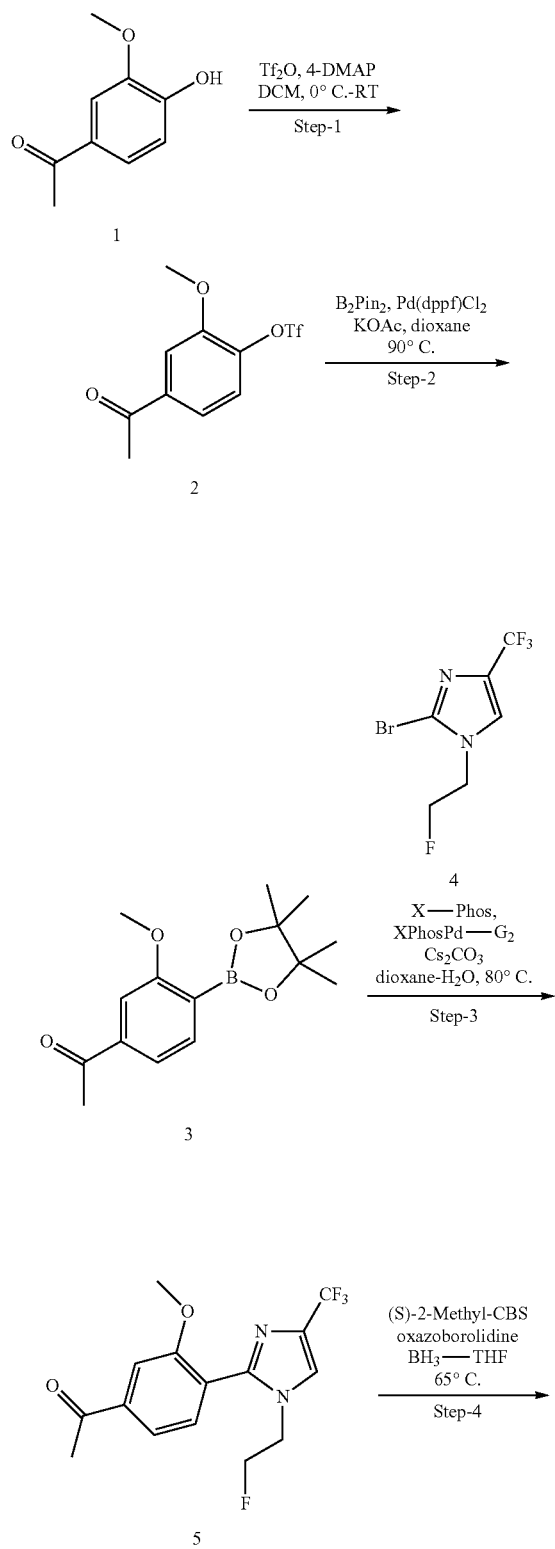

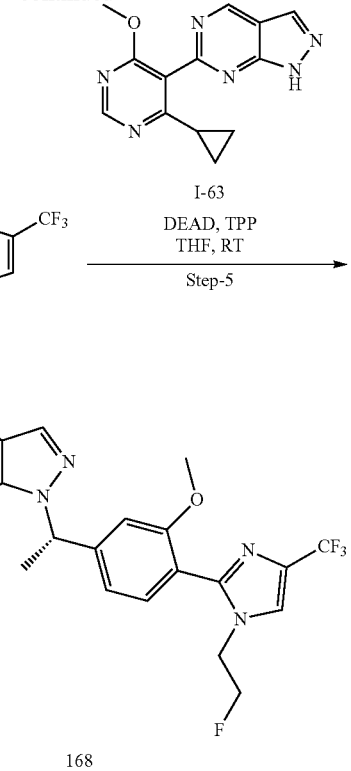

Step 1: Synthesis of 4-acetyl-2-methoxyphenyl trifluoromethanesulfonate

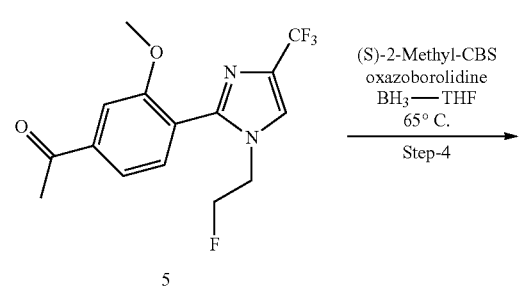

To a stirred solution of 1-(4-hydroxy-3-methoxyphenyl)ethan-1-one 1 (3 g, 18 mmol) in DCM (60 mL) was added 4-dimethylanminopyridine (3.3 g, 27 mmol) at 0° C. To the resulting reaction mixture was added triflic anhydride (6.1 g, 22 mmol) dropwise. Upon complete addition, the mixture was further stirred at 0° C. for 1 h. Progress of the reaction was monitored by TLC. After completion, the reaction mixture was quenched with 1N HCl (50 mL) and extracted with DCM (50 mL). The organic layer was separated, dried over anhydrous sodium sulfate, filtered and concentrated under reduced pressure. The crude compound was purified by silica gel chromatography using 0-20% EA in hexane as eluent to afford the title compound (4.57 g). ¹H-NMR (400 MHz, CDCl₃) δ 7.66 (d, J=1.96 Hz, 1H), 7.57 (dd, J=1.96, 8.31 Hz, 1H), 7.32 (d, J=8.31 Hz, 1H), 3.99 (s, 3H), 2.61-2.64 (m, 3H).

Step 2: Synthesis of 1-(3-methoxy-4-(4,4,5,5-tetramethyl-1,3,2-dioxaborolan-2-yl)phenyl)ethan-1-one

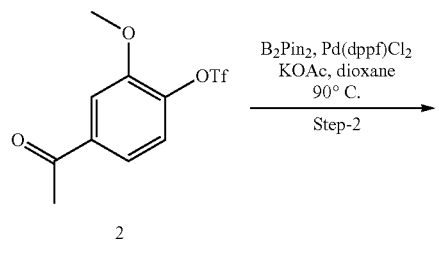

Step 3: Synthesis of 1-(4-(1-(2-fluoroethyl)-4-(trifluoromethyl)-1H-imidazol-2-yl)-3-methoxyphenyl)ethan-1-one

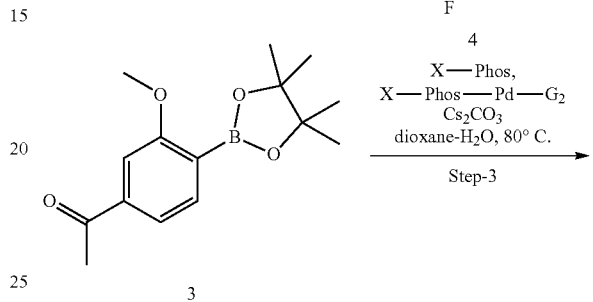

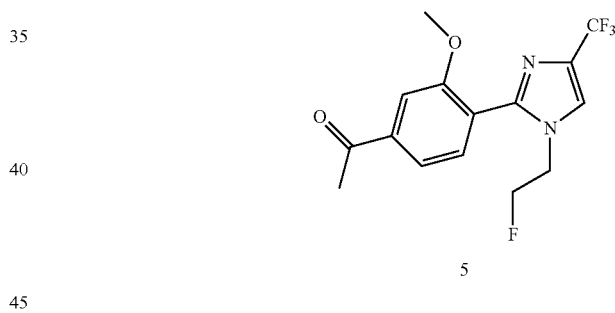

To a stirred solution of 4-acetyl-2-methoxyphenyl trifluoromethanesulfonate 2 (4.5 g, 15.1 mmol) and bis(pinacolato)diborane (19.15 g, 75.44 mmol) in dioxane (100 mL), was added potassium acetate (4.44 g, 45.2 mmol). The resulting mixture was degassed with argon for 10 min, and then treated with Pd(dppf)Cl₂ (0.044 g, 1.508 mmol) at room temperature. The reaction mixture was then heated in a sealed tube at 90° C. for 2 h. Progress of the reaction was monitored by TLC. After completion, the reaction mixture was cooled to room temperature and filtered through a pad of Celite. The filtrate was diluted with water (100 mL) and extracted with EA (2×50 mL). The combined organic layer was dried over anhydrous sodium sulfate, filtered and concentrated under reduced pressure. The crude compound was purified by silica gel chromatography using 0-15% EA in hexane as eluent to afford 3 (2.07 g). LC-MS (Method C) (ESI+): m/z 277.26 (M+H)⁺; ¹H-NMR (400 MHz, CDCl₃) δ 7.73 (d, J=7.34 Hz, 1H), 7.49 (dd, J=1.22, 7.58 Hz, 1H), 7.42-7.45 (m, 1H), 3.89 (s, 3H), 2.61 (s, 3H), 1.37 (s, 12H).

To a stirred solution of 2-bromo-1-(2-fluoroethyl)-4-(trifluoromethyl)-1H-imidazole 4 (2.0 g, 7.24 mmol) and 1-(3-methoxy-4-(4,4,5,5-tetramethyl-1,3,2-dioxaborolan-2-yl)phenyl)ethan-1-one 3 (1.89 g, 7.24 mmol) in dioxane:H₂O (4:1, 50 mL), was added Cs₂CO₃ (3.53 g, 10.96 mmol). The resulting mixture was purged with argon for 10 min, and then treated with XPhos-Pd-G2 (0.284 g, 0.362 mmol) and XPhos (0.345 g, 0.724 mmol) at room temperature. The reaction mixture was then heated to 80° C. in a sealed tube for 2 h. Progress of the reaction was monitored by TLC. After completion, the reaction mixture was cooled to room temperature, diluted with water (50 mL) and extracted with EA (2×25 mL). The combined organic layer was dried over anhydrous sodium sulfate and concentrated under reduced pressure. The crude compound was purified by silica gel chromatography using 0-30% EA in hexane as eluent to afford the title compound (2.0 g). LC-MS (Method B) (ESI+): m/z 331.10 (M+H)⁺; ¹H-NMR (400 MHz, DMSO-d₆) δ 8.01 (s, 1H), 7.67-7.72 (m, 1H), 7.62 (s, 1H), 7.53 (d, J=7.83 Hz, 1H), 4.49-4.67 (m, 2H), 4.08-4.20 (m, 2H), 3.89 (s, 3H), 2.63-2.70 (m, 4H).

Step 4: Synthesis of (R)-1-(4-(1-(2-fluoroethyl)-4-(trifluoromethyl)-1H-imidazol-2-yl)-3-methoxyphenyl)ethan-1-ol

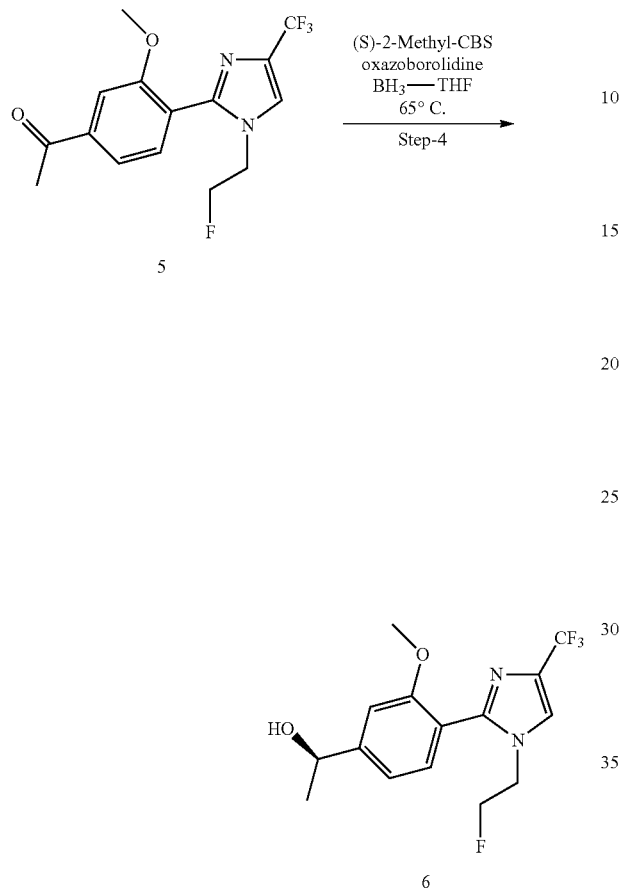

To a stirred solution of 1-(4-(1-(2-fluoroethyl)-4-(trifluoromethyl)-1H-imidazol-2-yl)-3-methoxyphenyl)ethan-1-one 5 (1.5 g, 4.5 mmol) in THF (30 mL) was added (S)-2-Methyl-CBS-oxazoborolidine (0.9 mL, 0.91 mmol) at room temperature. The mixture was then heated at 45° C. for 1 h. To the resulting reaction mixture was added borane-DMS (0.689 mg, 9.08 mmol), and the mixture was heated at 65° C. for 1 h. Progress of the reaction was monitored by TLC. After completion, the reaction mixture was cooled to room temperature, slowly quenched with methanol (50 mL) and concentrated under reduced pressure. The crude residue obtained was diluted with 1N HCl (20 mL) and extracted with EA (2×25 mL). The combined organic layer was dried over anhydrous sodium sulfate and concentrated under reduced pressure. The crude compound was purified by silica gel chromatography using 10-60% EA in hexane as eluent to afford the title compound (1.04 g). LC-MS (Method B) (ESI+): m/z 333.4 (M+H)+; 1H-NMR (400 MHz, DMSO-d6) δ 7.94 (s, 1H), 7.28 (d, J=7.83 Hz, 1H), 7.15 (s, 1H), 7.04 (d, J=7.34 Hz, 1H), 5.31 (d, J=3.91 Hz, 1H), 4.74-4.83 (m, 1H), 4.67 (t, J=4.40 Hz, 1H), 4.55 (t, J=4.65 Hz, 1H), 4.14 (t, J=4.40 Hz, 1H), 4.07 (t, J=4.65 Hz, 1H), 3.80 (s, 3H), 1.37 (d, J=6.36 Hz, 3H).

Step 5: Synthesis of (S)-6-(4-cyclopropyl-6-methoxypyrimidin-5-yl)-1-(1-(4-(1-(2-fluoroethyl)-4-(trifluoromethyl)-1H-imidazol-2-yl)-3-methoxyphenyl)ethyl)-1H-pyrazolo[3,4-d]pyrimidine (168)

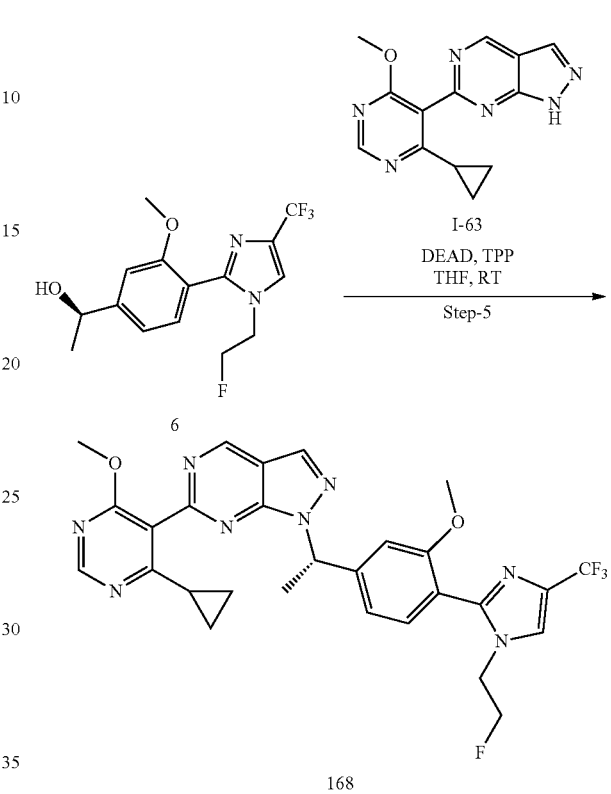

To a stirred solution of (R)-1-(4-(1-(2-fluoroethyl)-4-(trifluoromethyl)-1H-imidazol-2-yl)-3-methoxyphenyl)ethan-1-ol 6 (0.400 g, 1.20 mmol), 6-(4-cyclopropyl-6-methoxypyrimidin-5-yl)-1H-pyrazolo[3,4-d]pyrimidine 1-66 (0.322 g, 1.20 mmol) and triphenylphosphine (0.470 g, 1.80 mmol) in THF (4 mL), was added DEAD (0.133 g, 1.80 mmol) at room temperature. The resulting mixture was stirred for 30 min, and progress of the reaction was monitored by TLC. After completion, the reaction mixture was concentrated under reduced pressure. The crude residue obtained was diluted with water (30 mL) and extracted with EA (2×25 mL). The combined organic layer was dried over anhydrous sodium sulfate, filtered and concentrated under reduced pressure. The crude compound was purified by silica gel chromatography using 10-70% EA in hexane as eluent to afford impure compound that was further purified by prep HPLC (Method D) and chiral SFC purification (Method B) to afford the title compound (0.200 g). LC-MS (Method B) (ESI+): m/z 583.25 (M+H)+; 1H-NMR (400 MHz, DMSO-d6) δ 9.49 (s, 1H), 8.71 (s, 1H), 8.55 (s, 1H), 7.93 (s, 1H), 7.28 (d, J=7.83 Hz, 1H), 6.97 (d, J=7.83 Hz, 1H), 6.30-6.38 (m, 1H), 4.63 (t, J=4.40 Hz, 1H), 4.51 (t, J=4.40 Hz, 1H), 4.11 (d, J=3.91 Hz, 1H), 4.04 (d, J=4.40 Hz, 1H), 3.82 (s, 3H), 3.74 (s, 3H), 2.00 (d, J=6.85 Hz, 3H), 1.55-1.64 (m, 2H), 1.01-1.07 (m, 2H), 0.77-0.88 (m, 2H).

The following compound was prepared from the appropriate building blocks according to the method described for Example 168:

| Example | Structure | Analytical data |
|---|---|---|
| 169 | 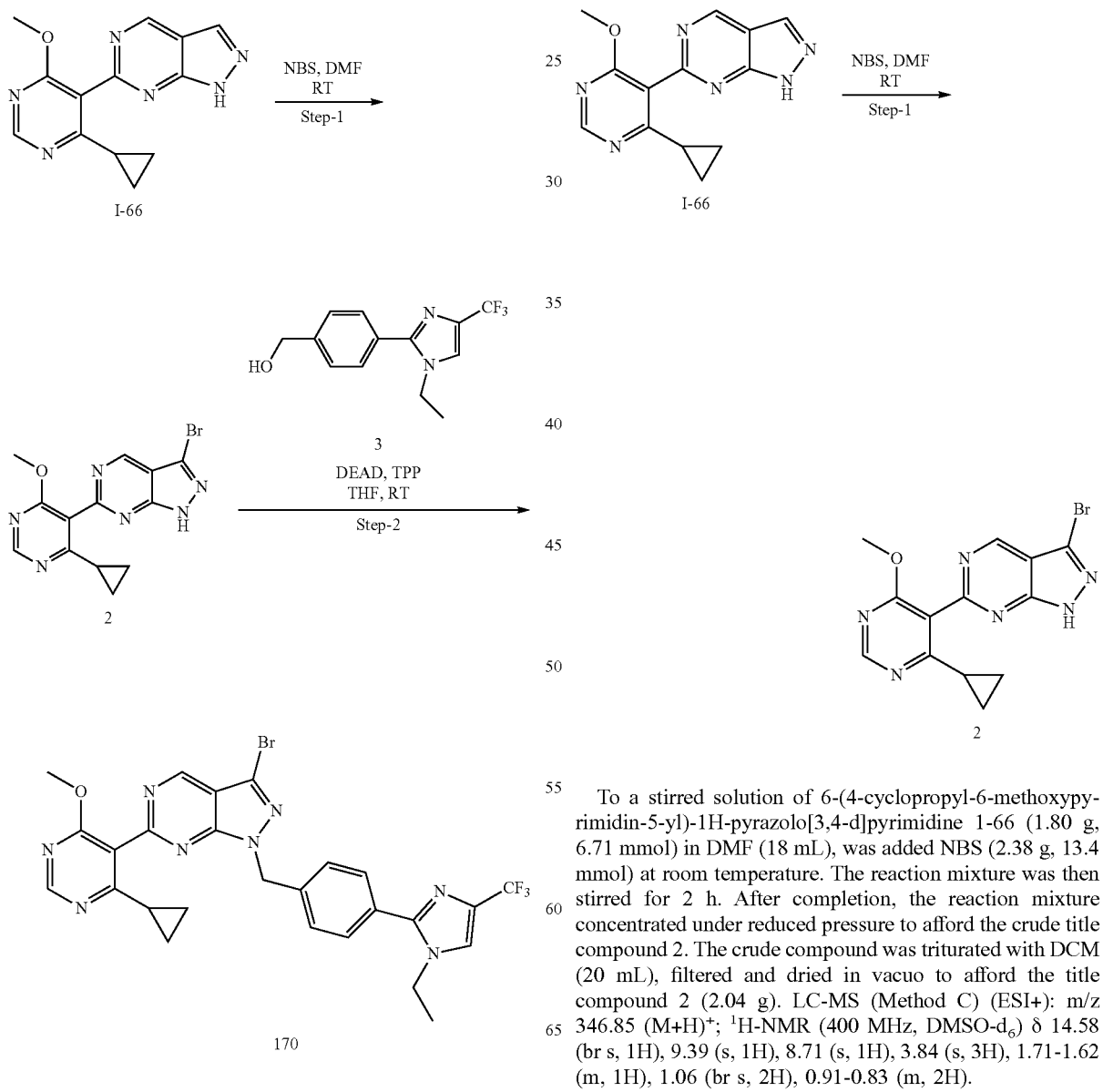 | LC-MS (Method B) (ESI+): m/z 553.30 (M + H)+, 1H-NMR (400 MHz, DMSO-d6) δ 9.49 (s, 1H), 8.70 (s, 1H), 8.54 (s, 1H), 8.01 (s, 1H), 7.56-7.59 (m, 2H), 7.48 (d, J = 8.31 Hz, 2H), 6.35 (q, J = 6.85 Hz, 1H), 4.77 (t, J = 4.65 Hz, 1H), 4.65 (t, J = 4.40 Hz, 1H), 4.38 (t, J = 4.65 Hz, 1H), 4.31 (t, J = 4.40 Hz, 1H), 3.83 (s, 3H), 1.99 (d, J = 6.85 Hz, 3H), 1.57-1.65 (m, 1H), 1.04 (d, J = 4.40 Hz, 2H), 0.83 (d, J = 6.36 Hz, 2H). |

Example 170: Synthesis of 3-bromo-6-(4-cyclopropyl-6-methoxypyrimidin-5-yl)-1-(4-(1-ethyl-4-(trifluoromethyl)-1H-imidazol-2-yl)benzyl)-1H-pyrazolo[3,4-d]pyrimidine (170)

Step 1: Synthesis of 3-bromo-6-(4-cyclopropyl-6-methoxypyrimidin-5-yl)-1H-pyrazolo[3,4-d]pyrimidine To a stirred solution of 6-(4-cyclopropyl-6-methoxypyrimidin-5-yl)-1H-pyrazolo[3,4-d]pyrimidine 1-66 (1.80 g, 6.71 mmol) in DMF (18 mL), was added NBS (2.38 g, 13.4 mmol) at room temperature. The reaction mixture was then stirred for 2 h. After completion, the reaction mixture concentrated under reduced pressure to afford the crude title compound 2. The crude compound was triturated with DCM (20 mL), filtered and dried in vacuo to afford the title compound 2 (2.04 g). LC-MS (Method C) (ESI+): m/z 346.85 (M+H)+; 1H-NMR (400 MHz, DMSO-d6) δ 14.58 (br s, 1H), 9.39 (s, 1H), 8.71 (s, 1H), 3.84 (s, 3H), 1.71-1.62 (m, 1H), 1.06 (br s, 2H), 0.91-0.83 (m, 2H).

Step 2: Synthesis of Synthesis of 3-bromo-6-(4-cyclopropyl-6-methoxypyrimidin-5-yl)-1-(4-(1-ethyl-4-(trifluoromethyl)-1H-imidazol-2-yl)benzyl)-1H-pyrazolo[3,4-d]pyrimidine (170)

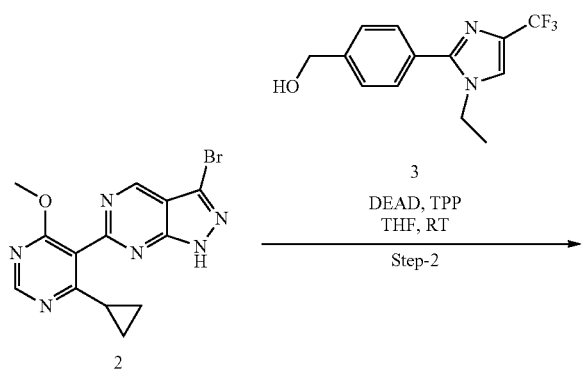

To a stirred mixture of (4-(1-ethyl-4-(trifluoromethyl)-1H-imidazol-2-yl)phenyl)methanol 3 (1.55 g, 5.74 mmol), 3-bromo-6-(4-cyclopropyl-6-methoxypyrimidin-5-yl)-1H-pyrazolo[3,4-d]pyrimidine 2 (2.00 g, 5.740 mmol) and triphenylphosphine (2.26 g, 8.611 mmol) in THF (20 mL) was added DEAD (1.50 g, 8.611 mmol) at room temperature. The resulting mixture was then stirred for 1 h. Progress of the reaction was monitored by TLC. After completion, the reaction mixture was diluted with water (50 mL) and extracted with EA (2×50 mL). The combined organic layer was dried over anhydrous sodium sulfate, filtered and concentrated under reduced pressure. The crude compound was purified by silica gel chromatography using 10-60% EA in n-hexane as eluent to afford the title compound (2.41 g). LC-MS (Method B) (ESI+): m/z 599.15 (M+H)$^+$; $^1$H-NMR (400 MHz, DMSO-d$_6$) δ 9.44 (s, 1H), 8.72 (s, 1H), 8.02 (s, 1H), 7.61 (d, J=7.83 Hz, 2H), 7.45 (d, J=7.83 Hz, 2H), 5.77 (s, 2H), 4.05 (q, J=7.34 Hz, 2H), 3.86 (s, 3H), 1.70 (dd, J=3.67, 8.07 Hz, 1H), 1.30 (t, J=7.34 Hz, 3H), 1.04-1.09 (m, 2H), 0.83-0.89 (m, 2H).

The following compound was prepared from the appropriate building blocks according to the method described for Example 170:

| Example | Structure | Analytical data |
|---|---|---|
| 171 | 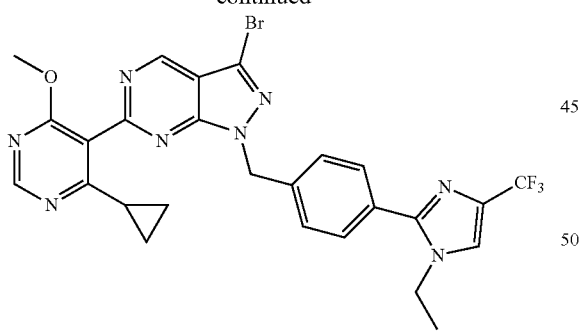 | LC-MS (Method C) (ESI+): m/z 599.08 (M + H)$^+$; $^1$H-NMR (400 MHz, DMSO-d$_6$) δ 9.41 (s, 1H), 8.71 (s, 1H), 7.91 (s, 1H), 7.69 (d, J = 7.34 Hz, 2H), 7.49 J = 8.31 Hz, 2H), 6.35 (q, J = 6.85 Hz, 1H), 3.84 (s, 3H), 3.74 (s, 3H), 1.98 (d, J = 6.85 Hz, 3H), 1.61-1.70 (m, 1H), 1.02-1.07 (m, 2H), 0.80-0.87 (m, 2H). |

Example 172: Synthesis of 6-(4-cyclopropyl-6-methoxypyrimidin-5-yl)-1-(4-(1-ethyl-4-(trifluoromethyl)-1H-imidazol-2-yl)benzyl)-1H-pyrazolo[3,4-d]pyrimidine-3-carbonitrile (172)

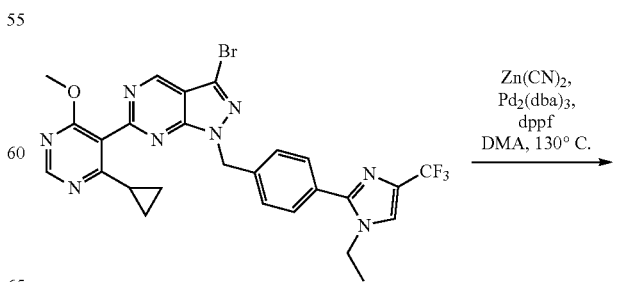

Example 170

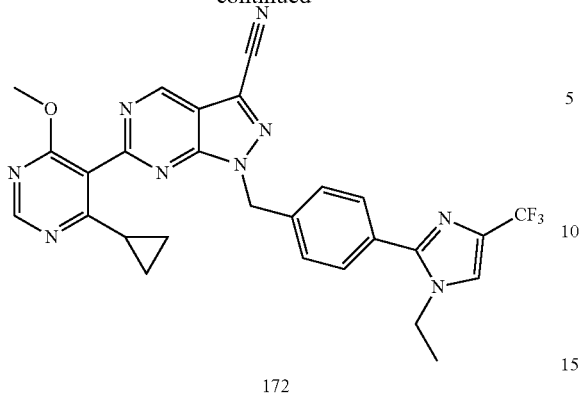

172

To a stirred solution of 3-bromo-6-(4-cyclopropyl-6-methoxypyrimidin-5-yl)-1-(4-(1-ethyl-4-(trifluoromethyl)-1H-imidazol-2-yl)benzyl)-1H-pyrazolo[3,4-d]pyrimidine (170) (0.200 g, 0.334 mmol) in DMA (10 mL), was added zinc cyanide (0.078 g, 0.67 mmol) at room temperature. The resulting mixture was degassed with argon for 30 min, and then treated with 1,1'-bis(diphenylphosphino)ferrocene (0.044 g, 0.080 mmol) and $Pd_2(dba)_3$ (0.036 g, 0.040 mmol) at room temperature. The reaction mixture was heated in sealed tube at 130° C. for 1 h. The reaction mixture was cooled to room temperature and treated with aqueous ammonia solution (20 mL) for 30 min. Progress of the reaction was monitored by TLC. After completion, the reaction mixture was extracted with DCM (20 mL). The organic layer was separated, washed with water (10 mL) and brine (10 mL). The organic layer was then dried over anhydrous sodium sulfate, filtered and concentrated under reduced pressure. The crude compound was treated with PS-Thiol metal scavenger resin in in THF, filtered and concentrated in vacuo. The resulting residue was purified by silica gel chromatography using 0-40% EA in hexane as eluent to obtain the impure compound which was further re-purified by preparative HPLC (Method B) to afford the title compound (0.070 g). LC-MS (Method C) (ESI+): m/z 546.10 $(M+H)^+$; $^1$H-NMR (400 MHz, DMSO-$d_6$) 9.80 (s, 1H), 8.74 (s, 1H), 8.03 (d, J=1.47 Hz, 1H), 7.62 (d, J=8.31 Hz, 2H), 7.49 (d, J=8.31 Hz, 2H), 5.92 (s, 2H), 4.05 (q, J=7.34 Hz, 2H), 3.86 (s, 3H), 1.70 (ddd, J=4.65, 7.95, 12.35 Hz, 1H), 1.30 (t, J=7.09 Hz, 3H), 1.06-1.11 (m, 2H), 0.83-0.89 (m, 2H).

Example 173: Synthesis of (S)-6-(4-cyclopropyl-6-methoxypyrimidin-5-yl)-1-(5-(1-isopropyl-4-(trifluoromethyl)-1H-imidazol-2-yl)-2,3-dihydro-1H-inden-1-yl)-1H-pyrazolo[3,4-d]pyrimidine (173)

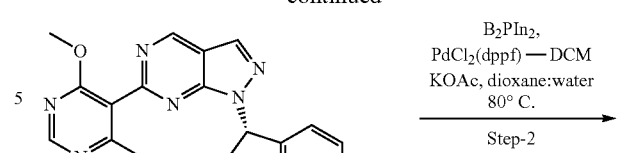

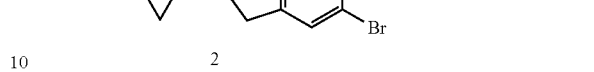

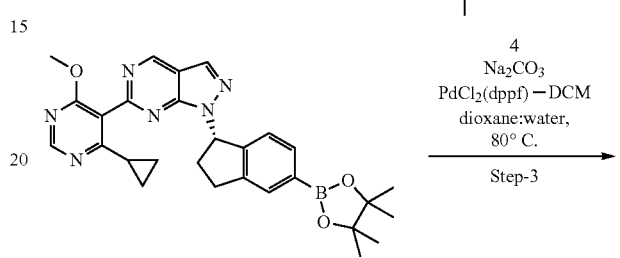

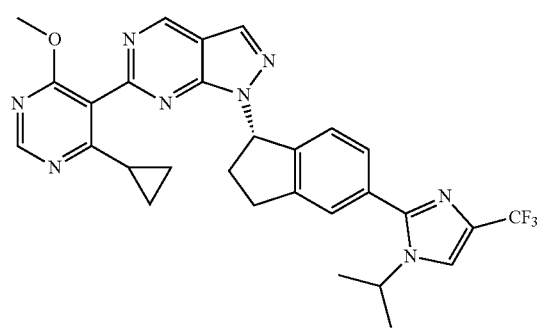

173

Step 1: Synthesis of (S)-1-(5-bromo-2,3-dihydro-1H-inden-1-yl)-6-(4-cyclopropyl-6-methoxypyrimidin-5-yl)-1H-pyrazolo[3,4-d]pyrimidine

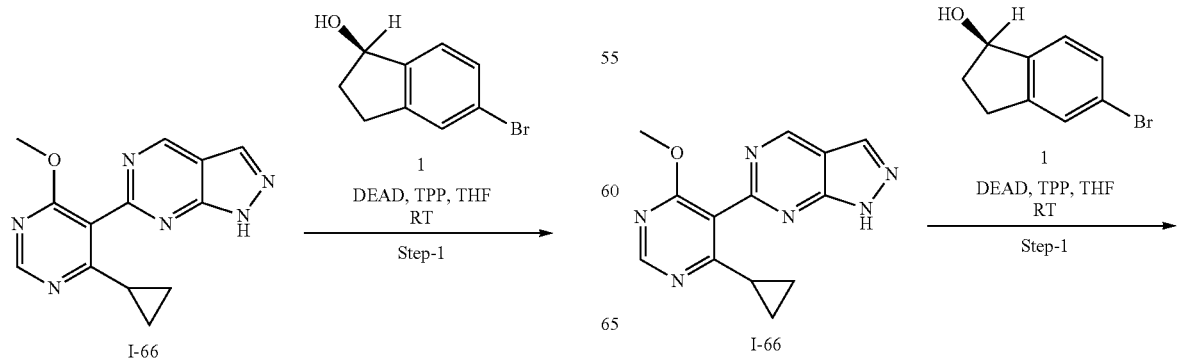

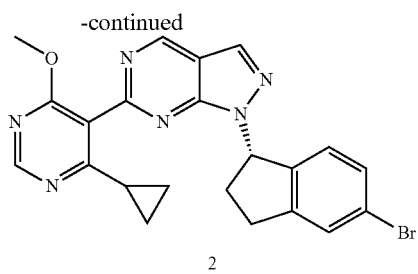

To a stirred solution of 6-(4-cyclopropyl-6-methoxypyrimidin-5-yl)-1H-pyrazolo[3,4-d]pyrimidine 1-66 (0.800 g, 2.98 mmol) in THF (8 mL) at 0° C., was added (R)-5-bromo-2,3-dihydro-1H-inden-1-ol 1 (0.635 g, 2.98 mmol), DEAD (0.777 g, 4.47 mmol) and TPP (1.17 g, 4.47 mmol). The reaction mixture was allowed to warm to room temperature and was then stirred for 1 h. Progress of the reaction was monitored by TLC. After completion, the reaction mixture was quenched with water (20 mL) and extracted with EA (3×15 mL). The organic layer was dried over anhydrous sodium sulfate, filtered and concentrated under reduced pressure. The crude compound was purified by silica gel chromatography eluting with 10-90% EA in hexane to afford the title compound (0.897 g). LC-MS (Method B) (ESI+): m/z 463.00 (M+).

Step 2: Synthesis of (S)-6-(4-cyclopropyl-6-methoxypyrimidin-5-yl)-1-(5-(4,4,5,5-tetramethyl-1,3,2-dioxaborolan-2-yl)-2,3-dihydro-1H-inden-1-yl)-1H-pyrazolo[3,4-d]pyrimidine

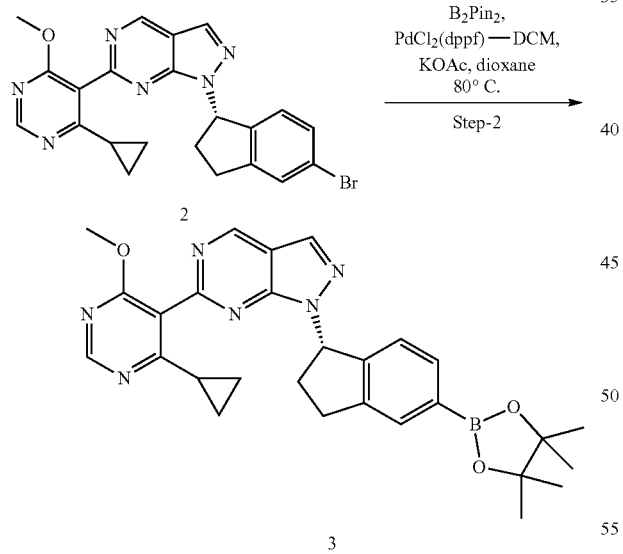

To a stirred solution of (S)-1-(5-bromo-2,3-dihydro-1H-inden-1-yl)-6-(4-cyclopropyl-6-methoxypyrimidin-5-yl)-1H-pyrazolo[3,4-d]pyrimidine 2 (0.800 g, 1.72 mmol) in dioxane (30 mL) was added KOAc (0.506 g, 5.16 mmol) and $B_2Pin_2$ (2.19 g, 8.62 mmol). The resulting mixture was degassed with argon for 10 min, and then treated with $PdCl_2$(dppf)-DCM (0.140 g, 0.171 mmol) at room temperature. The reaction mixture was then heated at 80° C. for 3 h. Progress of the reaction was monitored by TLC. After completion, the reaction mixture was filtered through a pad of Celite. The filtrate was diluted with water (50 mL) and EA (50 mL). The organic layer was separated, dried over anhydrous sodium sulfate, filtered and concentrated under reduced pressure. The crude compound was purified by silica gel chromatography eluting with 0-40% EA in hexane to afford the title compound (0.550 g). LC-MS (Method C) (ESI+); m/z 511.25 (M+H)$^+$; $^1$H-NMR (400 MHz, DMSO-$d_6$) δ 9.48 (s, 1H), 8.71 (s, 1H), 8.43 (s, 1H), 7.65 (s, 1H), 7.42 (d, J=7.48 Hz, 1H), 6.91 (d, J=7.48 Hz, 1H), 6.56 (t, J=7.23 Hz, 1H), 3.87 (s, 3H), 3.21-3.29 (m, 2H), 3.04 (td, J=7.73, 15.46 Hz, 1H), 2.60-2.76 (m, 3H), 1.64-1.72 (m, 1H), 1.16 (s, 6H), 1.07 (s, 6H), 0.89 (t, J=6.73 Hz, 2H).

Step 3: Synthesis of (S)-6-(4-cyclopropyl-6-methoxypyrimidin-5-yl)-1-(5-(1-isopropyl-4-(trifluoromethyl)-1H-imidazol-2-yl)-2,3-dihydro-1H-inden-1-yl)-1H-pyrazolo[3,4-d]pyrimidine (173)

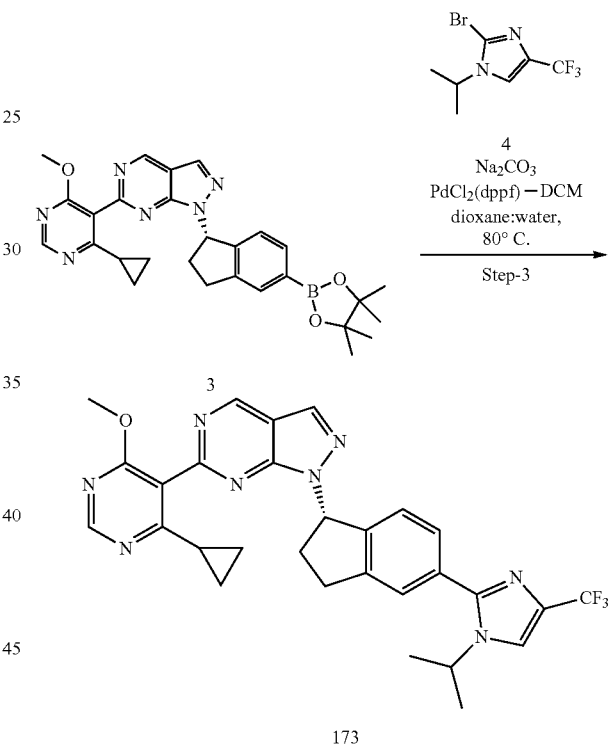

To a stirred solution of (S)-6-(4-cyclopropyl-6-methoxypyrimidin-5-yl)-1-(5-(4,4,5,5-tetramethyl-1,3,2-dioxaborolan-2-yl)-2,3-dihydro-1H-inden-1-yl)-1H-pyrazolo[3,4-d]pyrimidine 3 (0.500 g, 0.979 mmol) in dioxane:H$_2$O (25:10 mL), was added Na$_2$CO$_3$ (0.155 g, 1.47 mmol) and 2-bromo-1-isopropyl-4-(trifluoromethyl)-1H-imidazole 4 (0.252 g, 0.979 mmol) at room temperature. The resulting mixture was degassed with argon for 10 min, and then treated with PdCl$_2$(dppf)-DCM (0.080 g, 0.097 mmol) at room temperature. The reaction was further degassed with argon for 10 min, and then heated at 80° C. for 2 h. Progress of the reaction was monitored by TLC. After completion, the reaction mixture was diluted with H$_2$O (50 mL) and EA (50 mL). The combined organic layer was dried over anhydrous sodium sulfate, filtered and concentrated under reduced pressure. The crude compound was purified by silica gel chromatography using 10-90% EA in hexane as eluent.

Re-purification of impure compound thus obtained by preparative HPLC (Method D) afforded 173. To the stirred solution of 173 (0.090 g) in dioxane (9 mL), was added SP thiol silica (0.009 g). The resulting reaction mixture was heated to 100° C. for 2 h. The reaction mixture was cooled to room temperature, filtered and concentrated under reduced pressure to afford the title compound (0.040 g). LC-MS (Method B) (ESI+): m/z 561.35 (M+H)+; 1H-NMR (400 MHz, DMSO-d6) δ 9.50 (s, 1H), 8.72 (s, 1H), 8.46 (s, 1H), 8.16 (s, 1H), 7.55 (s, 1H), 7.31 (d, J=7.48 Hz, 1H), 7.07 (d, J=7.98 Hz, 1H), 4.47 (td, J=6.67, 13.09 Hz, 1H), 3.88 (s, 3H), 3.06-3.17 (m, 2H), 2.64-2.82 (m, 3H), 1.68-1.76 (m, 1H), 1.39 (d, J=6.48 Hz, 6H), 1.06-1.10 (m, 2H), 0.91 (td, J=3.74, 7.48 Hz, 2H).

The following compounds were prepared from the appropriate building blocks according to the method described for Example 173:

| Example | Structure | Analytical data |
|---|---|---|
| 174 | 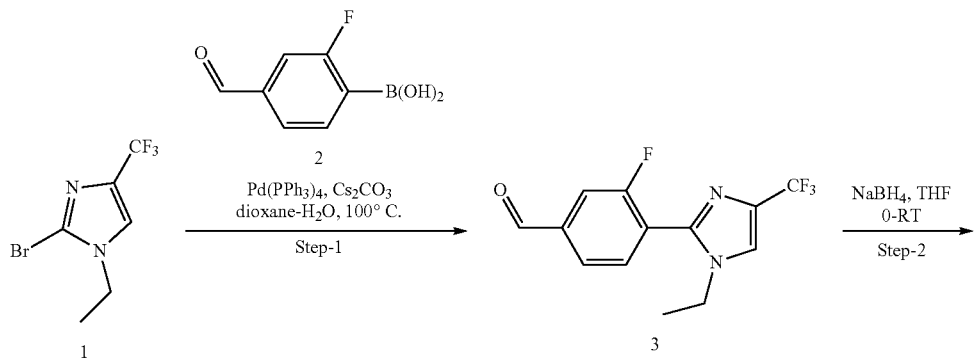 | LC-MS (Method B) (ESI+): m/z 561.25 (M + H)+; 1H-NMR (400 MHz, DMSO-d6) δ 9.51 (s, 1H), 8.72 (s, 1H), 8.46 (s, 1H), 8.16 (s, 1H), 7.55 (s, 1H), 7.31 (d, J = 7.98 Hz, 1H), 7.08 (d, J = 7.98 Hz, 1H), 4.47 (td, J = 6.67, 13.09 Hz, 1H), 3.88 (s, 3H), 3.07-3.18 (m, 2H), 2.65-2.81 (m, 3H), 1.72 (tt, J = 4.11, 8.10 Hz, 1H), 1.37-1.42 (m, 6H), 1.06-1.11 (m, 2H), 0.91 (td, J = 3.74, 7.48 Hz, 2H). |

Example 175: Synthesis of 6-(4-cyclopropyl-6-methoxypyrimidin-5-yl)-1-(4-(1-ethyl-4-(trifluoromethyl)-1H-imidazol-2-yl)-3-fluorobenzyl)-3-methoxy-1H-pyrazolo[3,4-d]pyrimidine (175)

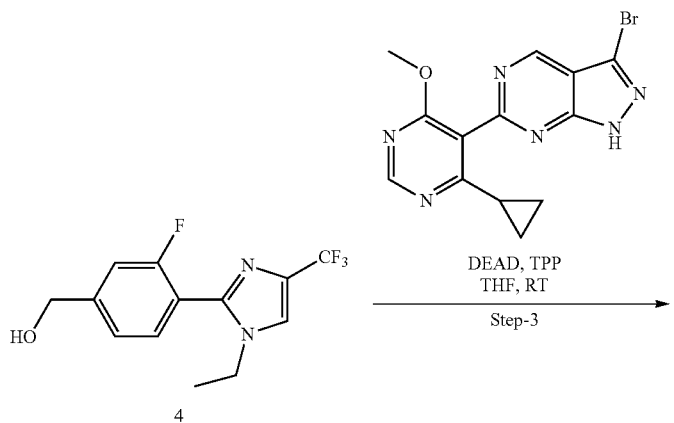

-continued

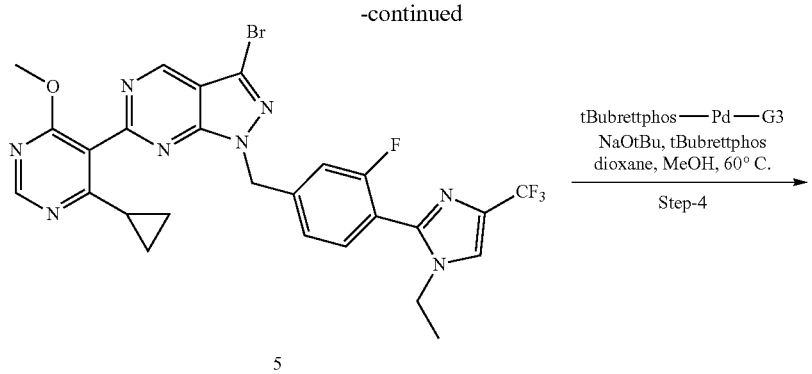

5

175

Step 1: Synthesis of 4-(1-ethyl-4-(trifluoromethyl)-1H-imidazol-2-yl)-3-fluorobenzaldehyde

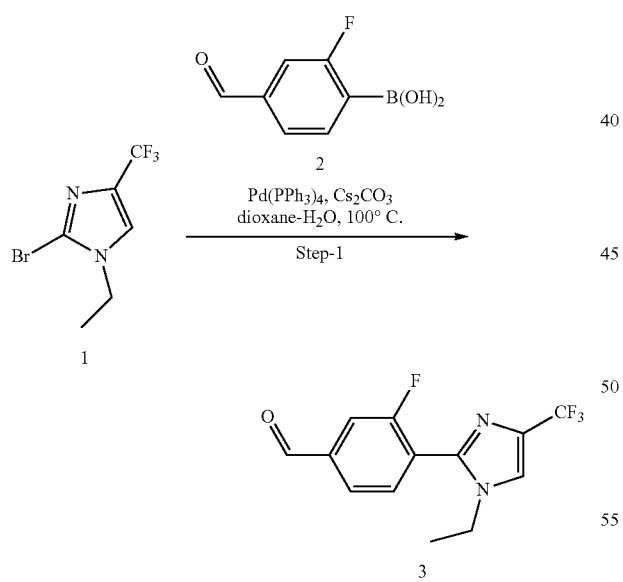

To a stirred solution of 2-bromo-1-ethyl-4-(trifluoromethyl)-1H-imidazole 1 (1.50 g, 6.17 mmol) in dioxane:$H_2O$ (5:1) (18 mL), was added $Cs_2CO_3$ (4.0 g, 12.3 mmol) and (2-fluoro-4-formylphenyl)-boronic acid 2 (1.24 g, 7.41 mmol). The resulting mixture was degassed with argon for 5 min., and then treated with Pd(PPh$_3$)$_4$ (0.709 g, 0.617 mmol) at room temperature. The reaction mixture was heated in a sealed tube at 100° C. for 16 h. Progress of the reaction was monitored by TLC. After completion, the reaction mixture was cooled to room temperature, diluted with water (50 mL) and extracted with EA (2×60 mL). The combined organic layer was dried over anhydrous sodium sulfate, filtered and concentrated under reduced pressure. The crude compound was purified by silica gel using 10-30% EA in hexane to afford the title compound (0.400 g). LC-MS (Method B) (ESI+): m/z 286.9 (M+H)$^+$; $^1$H-NMR (400 MHz, DMSO-d$_6$) δ 10.09 (s, 1H), 8.19 (s, 1H), 7.92 (d, J=7.83 Hz, 2H), 7.81-7.87 (m, 1H), 3.94 (q, J=7.34 Hz, 2H), 1.29 (t, J=7.34 Hz, 3H).

Step 2: Synthesis of (4-(1-ethyl-4-(trifluoromethyl)-1H-imidazol-2-yl)-3-fluorophenyl)methanol

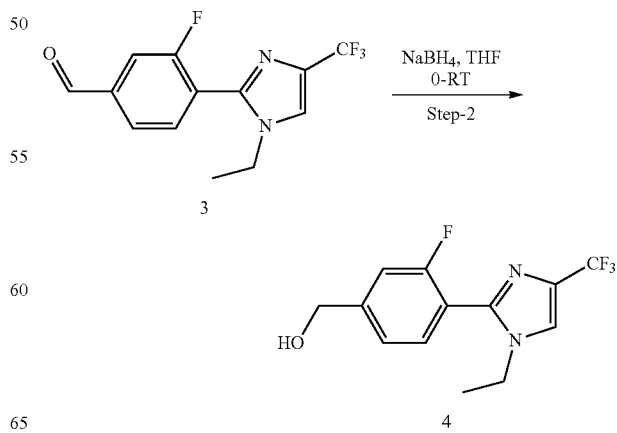

To a stirred solution of 4-(1-ethyl-4-(trifluoromethyl)-1H-imidazol-2-yl)-3-fluorobenzaldehyde 3 (0.400 g, 1.398 mmol) in methanol (5 mL) at 0° C., was added sodium borohydride (0.053 g, 1.398 mmol). The reaction mixture was allowed to warm to room temperature, and then stirred for 2 h. Progress of the reaction was monitored by TLC. After completion, the reaction mixture was quenched with water (10 mL) and concentrated under reduced pressure. The remaining residue was dissolved in water (20 mL) and extracted with EA (2×30 mL). The combined organic layer was dried over anhydrous sodium sulfate, filtered and concentrated under reduced pressure. The crude compound was purified by silica gel chromatography using 0-50% EA in hexane as eluent to afford the title compound (0.250 g). LC-MS (Method B) (ESI+): m/z 289.0 (M+H)$^+$; $^1$H-NMR (400 MHz, DMSO-d$_6$) δ 8.09 (s, 1H), 7.51 (t, J=7.83 Hz, 1H), 7.28-7.34 (m, 2H), 5.45 (br s, 1H), 4.60 (br s, 2H), 3.88 (q, J=7.01 Hz, 2H), 1.26 (t, J=7.09 Hz, 3H).

Step 3: Synthesis of 3-bromo-6-(4-cyclopropyl-6-methoxypyrimidin-5-yl)-1-(4-(1-ethyl-4-(trifluoromethyl)-1H-imidazol-2-yl)-3-fluorobenzyl)-1H-pyrazolo[3,4-d]pyrimidine

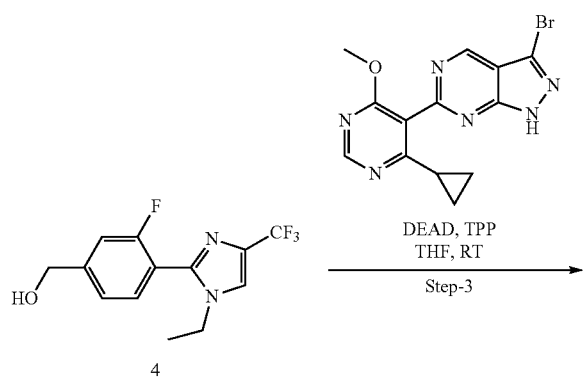

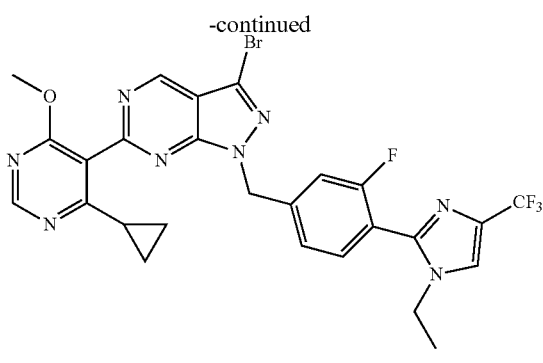

To a stirred solution of (4-(1-ethyl-4-(trifluoromethyl)-1H-imidazol-2-yl)-3-fluorophenyl)methanol 4 (0.250 g, 0.868 mmol) in THF (5 mL), was added 3-bromo-6-(4-cyclopropyl-6-methoxypyrimidin-5-yl)-1H-pyrazolo[3,4-d]pyrimidine (Intermediate 2, Example 170) (0.301 g, 0.868 mmol), DEAD (0.226 g, 1.302 mmol) and TPP (0.341 g, 1.302 mmol). The reaction mixture was stirred at room temperature for 1 h. Progress of the reaction was monitored by TLC. After completion, the reaction mixture was quenched with water (20 mL) and extracted with EA (2×20 mL). The organic layer was dried over anhydrous sodium sulfate, filtered and concentrated under reduced pressure. The crude compound was purified by silica gel chromatography eluting with 0-40% EA in hexane the title compound (0.200 g). LC-MS (Method B) (ESI+): m/z 619.05 (M+H)$^+$; $^1$H-NMR (400 MHz, DMSO-d$_6$) δ 9.45 (s, 1H), 8.72 (s, 1H), 8.09 (s, 1H), 7.55 (t, J=7.83 Hz, 1H), 7.38 (d, J=10.76 Hz, 1H), 7.28 (d, J=6.85 Hz, 1H), 5.81 (s, 2H), 3.86 (s, 3H), 3.84-3.85 (m, 2H), 1.72 (td, J=4.03, 7.58 Hz, 1H), 1.25 (t, J=7.34 Hz, 3H), 1.04-1.09 (m, 2H), 0.85 (dd, J=2.93, 7.83 Hz, 2H).

Step 4: Synthesis of 6-(4-cyclopropyl-6-methoxypyrimidin-5-yl)-1-(4-(1-ethyl-4-(trifluoromethyl)-1H-imidazol-2-yl)-3-fluorobenzyl)-3-methoxy-1H-pyrazolo[3,4-d]pyrimidine (175)

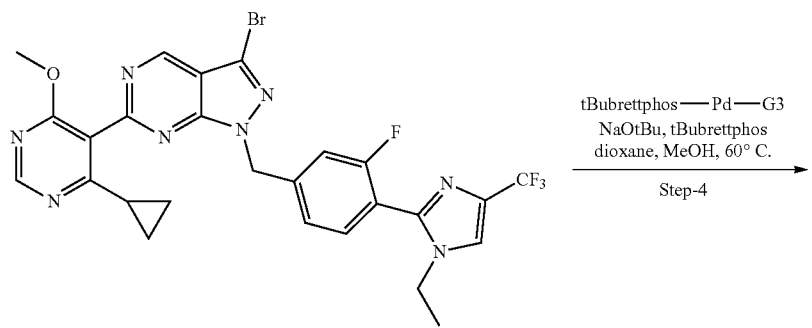

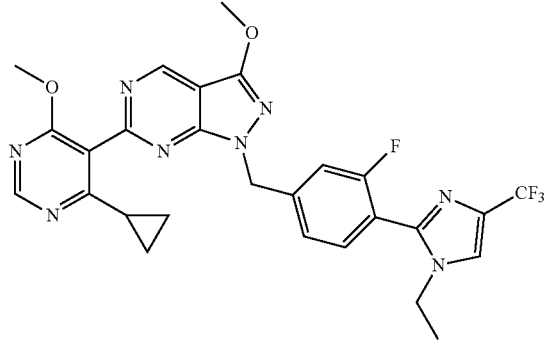

175

To a stirred solution of 3-bromo-6-(4-cyclopropyl-6-methoxypyrimidin-5-yl)-1-(4-(1-ethyl-4-(trifluoromethyl)-1H-imidazol-2-yl)-3-fluorobenzyl)-1H-pyrazolo[3,4-d]pyrimidine 5 (0.180 g, 0.292 mmol) in dioxane:H₂O (4:1) (12.5 mL), was added sodium tert-butoxide (0.042 g, 0.438 mmol) and then methanol (2.5 mL). The resulting mixture was degassed with argon for 15 min, then treated with tert-butyl brettphos-Pd-G3 (0.024 g, 0.029 mmol) and tert-butyl-Brettphos (0.028 g, 0.058 mmol) at room temperature. The reaction mixture was then heated in a sealed tube at 60° C. for 16 h. Progress of the reaction was monitored by TLC. After completion, the reaction mixture was cooled to room temperature, diluted with water (20 mL) and extracted with EA (2×60 mL). The combined organic layer was dried over anhydrous sodium sulfate, filtered and concentrated under reduced pressure. The crude compound was purified by silica gel chromatography using 1-5% methanol in DCM as eluent. The product thus obtained was slurried with PS-Thiol silica in THF at 100° C. for 2 h, then filtered. The filtrate was concentrated in vacuo to afford the title compound (0.025 g). LC-MS (Method C) (ESI+): m/z 569.15 (M+H)+; $^1$H-NMR (400 MHz, CD₃OD) δ 9.21 (s, 1H), 8.63 (s, 1H), 7.84 (s, 1H), 7.50 (t, J=7.48 Hz, 1H), 7.29-7.36 (m, 2H), 5.63 (s, 2H), 4.13-4.18 (m, 3H), 3.93-3.97 (m, 2H), 3.92 (s, 3H), 1.70 (ddd, J=4.49, 8.10, 12.34 Hz, 1H), 1.32 (t, J=7.23 Hz, 3H), 1.14-1.19 (m, 2H), 0.88-0.94 (m, 2H).

The following compounds were prepared from the appropriate building blocks and reagents according to the method described for Example 175:

| Example | Structure | Analytical data |
| --- | --- | --- |
| 176 | 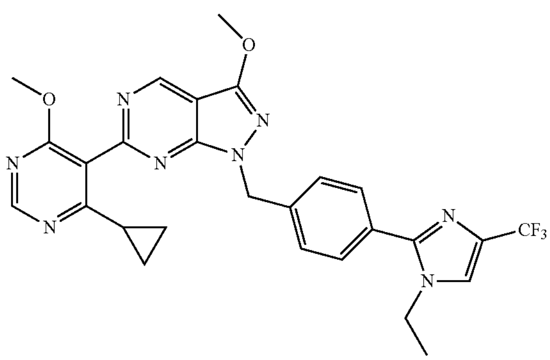 [SMILES: CCn1cc(C(F)(F)F)nc1-c1ccc(Cn2nc(OC)c3cnc(-c4c(OC)ncnc4C4CC4)nc32)cc1] | LC-MS (Method C) (ESI+): m/z 551.15 (M + H)+; $^1$H-NMR (400 MHz, DMSO-d₆) δ 9.35 (s, 1H), 8.70 (s, 1H), 8.02 (s, 1H), 7.59 (d, J = 8.0 Hz, 2H), 7.40 (d, J = 8.5 Hz, 2H), 5.60 (s, 2H), 4.08 (s, 3H), 4.10-4.02 (m, 2H), 3.85 (s, 3H), 1.70-1.63 (m, 1H), 1.30 (t, J = 7.2 Hz, 3H), 1.07-1.03 (m, 2H), 0.89-0.83 (m, 2H). |
| 177 | 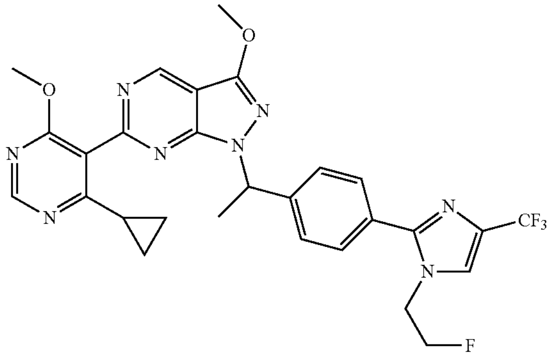 [SMILES: COc1ncnc(C2CC2)c1-c1ncc2c(OC)nn(C(C)c3ccc(-c4nc(C(F)(F)F)cn4CCF)cc3)c2n1] | LC-MS (Method C) (ESI+): m/z 583.10 (M + H)+; $^1$H-NMR (400 MHz, DMSO-d₆) δ 9.32 (s, 1H), 8.69 (s, 1H), 8.02 (s, 1H), 7.57 (d, J = 8.31 Hz, 2H), 7.47-7.52 (m, 2H), 6.16-6.24 (m, 1H), 4.77 (t, J = 4.40 Hz, 1H), 4.66 (t, J = 4.40 Hz, 1H), 4.39 (t, J = 4.16 Hz, 1H), 4.32 (d, J = 3.91 Hz, 1H), 4.12 (s, 3H), 3.83 (s, 3H), 1.93 (d, J = 6.85 Hz, 3H), 1.58-1.65 (m, 1H), 1.00-1.06 (m, 2H), 0.83 (d, J = 7.34 Hz, 2H). |

| Example | Structure | Analytical data |
|---|---|---|
| 178 | 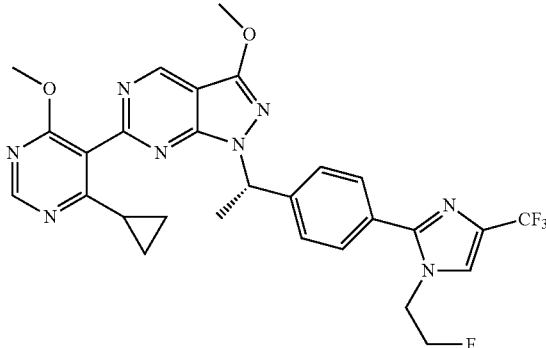 | LC-MS (Method B) (ESI+): m/z 583.15 (M + H)+; $^1$H-NMR (400 MHz, DMSO-$d_6$) δ 9.32 (s, 1H), 8.69 (s, 1H), 8.02 (s, 1H), 7.55-7.60 (m, 2H), 7.50 (d, J = 8.31 Hz, 2H), 6.20 (q, J = 7.01 Hz, 1H), 4.77 (d, J = 4.40 Hz, 1H), 4.64-4.68 (m, 1H), 4.39 (t, J = 4.65 Hz, 1H), 4.32 (t, J = 4.40 Hz, 1H), 4.12 (s, 3H), 3.84 (s, 3H), 1.93 (d, J = 7.34 Hz, 3H), 1.58-1.66 (m, 1H), 1.04 (d, J = 3.42 Hz, 2H), 0.83 (d, J = 5.38 Hz, 2H). |
| 179 | 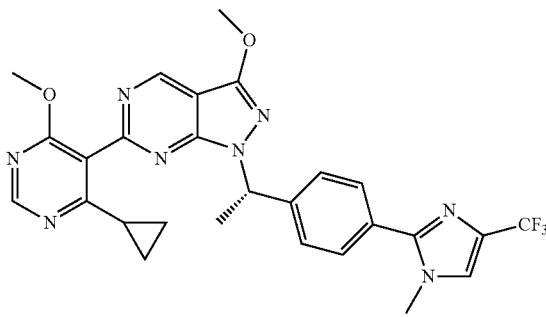 [SMILES: COc1ncnc(C2CC2)c1-c1ncc2c(OC)nn([C@@H](C)c3ccc(-c4nc(C(F)(F)F)cn4C)cc3)c2n1] | LC-MS (Method C) (ESI+): m/z 551.14 (M + H)+; $^1$H-NMR (400 MHz, DMSO-$d_6$) δ 9.32 (s, 1H), 8.70 (s, 1H), 7.92 (s, 1H), 7.67 (d, J = 7.83 Hz, 2H), 7.49 (d, J = 7.83 Hz, 2H), 6.16-6.23 (m, 1H), 4.12 (s, 3H), 3.84 (s, 3H), 3.75 (s, 3H), 1.93 (d, J = 6.85 Hz, 3H), 1.58-1.66 (m, 1H), 1.02-1.07 (m, 2H), 0.82-0.86 (m, 2H). |
| 180 | 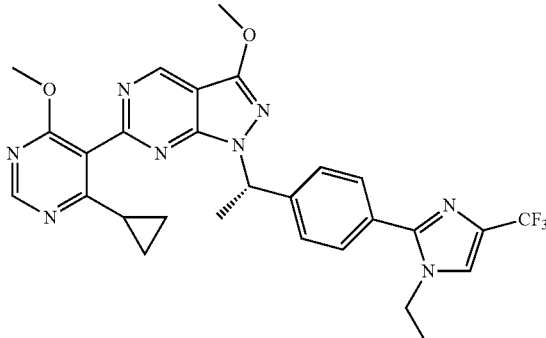 | LC-MS (Method C) (ESI+): m/z 565.10 (M + H)+; $^1$H-NMR (400 MHz, DMSO-$d_6$) δ 9.32 (s, 1H), 8.69 (s, 1H), 8.01 (s, 1H), 7.58 (d, J = 7.98 Hz, 2H), 7.49 (d, J = 8.48 Hz, 2H), 6.20 (q, J = 6.81 Hz, 1H), 4.12 (s, 3H), 4.05 (q, J = 6.98 Hz, 2H), 3.84 (s, 3H), 1.93 (d, J = 6.98 Hz, 3H), 1.58-1.66 (m, 1H), 1.30 (t, J = 7.23 Hz, 3H), 1.04 (d, J = 2.49 Hz, 2H), 0.83 (d, J = 7.48 Hz, 2H). |
| 181 | 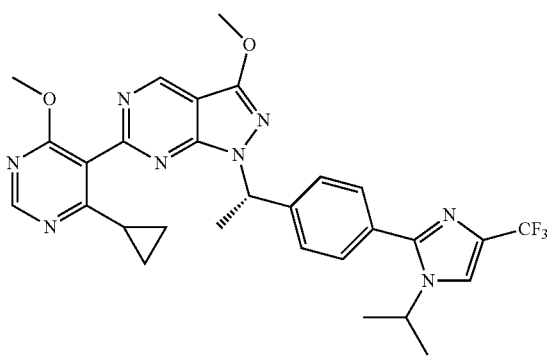 [SMILES: COc1ncnc(C2CC2)c1-c1ncc2c(OC)nn([C@@H](C)c3ccc(-c4nc(C(F)(F)F)cn4C(C)C)cc3)c2n1] | LC-MS (Method B) (ESI+): m/z 579.35 (M + H)+; $^1$H-NMR (400 MHz, DMSO-$d_6$) δ 9.33 (s, 1H), 8.69 (s, 1H), 8.16 (s, 1H), 7.47-7.54 (m, 4H), 6.17-6.24 (m, 1H), 4.42 (td, J = 6.60, 13.21 Hz, 1H), 4.12 (s, 3H), 3.84 (s, 3H), 1.93 (d, J = 7.34 Hz, 3H), 1.59-1.66 (m, 1H), 1.38 (dd, J = 1.71, 6.60 Hz, 6H), 1.04 (d, J = 3.91 Hz, 2H), 0.78-0.87 (m, 2H). |

-continued

| Example | Structure | Analytical data |
|---|---|---|
| 182 | 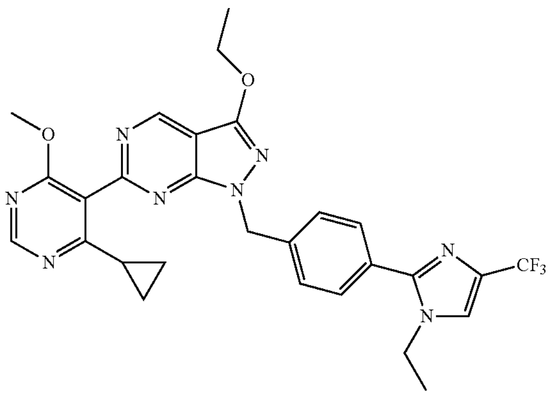 [SMILES: CCOc1nn(Cc2ccc(-c3nc(C(F)(F)F)cn3CC)cc2)c2nc(-c3c(OC)ncnc3C3CC3)ncc12] | LC-MS (Method B) (ESI+): m/z 565.35 (M + H)+; 1H-NMR (400 MHz, DMSO-d6) δ 9.34 (s, 1H), 8.70 (s, 1H), 8.01 (s, 1H), 7.59 (d, J = 7.82 Hz, 2H), 7.39 (d, J = 7.82 Hz, 2H), 5.59 (s, 2H), 4.46 (q, J = 6.85 Hz, 2H), 4.05 (q, J = 7.34 Hz, 2H), 3.85 (s, 3H), 1.63-1.70 (m, 1H), 1.42 (t, J = 7.09 Hz, 3H), 1.29 (t, J = 7.34 Hz, 3H), 1.02-1.08 (m, 2H), 0.82-0.89 (m, 2H). |
| 183 | 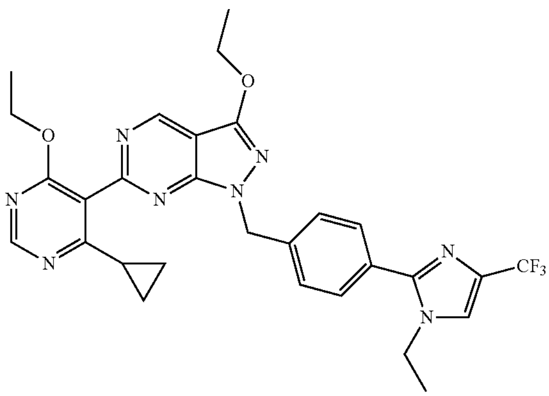 [SMILES: CCOc1ncnc(C2CC2)c1-c1ncc2c(OCC)nn(Cc3ccc(-c4nc(C(F)(F)F)cn4CC)cc3)c2n1] | LC-MS (Method B) (ESI+): m/z 579.35 (M + H)+; 1H-NMR (400 MHz, DMSO-d6) δ 9.34 (s, 1H), 8.67 (s, 1H), 8.02 (s, 1H), 7.58 (d, J = 7.98 Hz, 2H), 7.37 (d, J = 7.98 Hz, 2H), 5.60 (s, 2H), 4.46 (q, J = 6.98 Hz, 2H), 4.34 (q, J = 6.98 Hz, 2H), 4.05 (q, J = 6.98 Hz, 2H), 1.62-1.70 (m, 1H), 1.42 (t, J = 6.98 Hz, 3H), 1.29 (t, J = 7.23 Hz, 3H), 1.13 (t, J = 6.98 Hz, 3H), 1.02-1.08 (m, 2H), 0.85 (dd, J = 2.99, 7.48 Hz, 2H). |
| 184 | 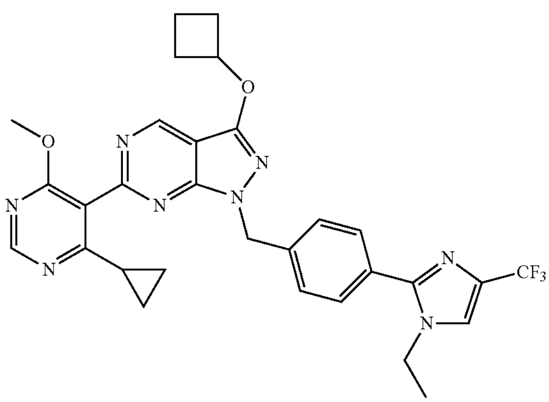 [SMILES: CCn1cc(C(F)(F)F)nc1-c1ccc(Cn2nc(OC3CCC3)c3cnc(-c4c(OC)ncnc4C4CC4)nc32)cc1] | LC-MS (Method B) (ESI+): m/z 591.35 (M + H)+; 1H-NMR (400 MHz, DMSO-d6) δ 9.33 (s, 1H), 8.70 (s, 1H), 8.01 (s, 1H), 7.59 (d, J = 7.83 Hz, 2H), 7.39 (d, J = 8.31 Hz, 2H), 5.58 (s, 2H), 5.16 (m, J = 7.21 Hz, 1H), 4.05 (q, J = 7.34 Hz, 2H), 3.85 (s, 3H), 2.42-2.47 (m, 2H), 2.18 (td, J = 9.78, 19.56 Hz, 2H), 1.82 (q, J = 10.27 Hz, 1H), 1.62-1.72 (m, 2H), 1.29 (t, J = 7.34 Hz, 3H), 1.02-1.07 (m, 2H), 0.82-0.88 (m, 2H). |
| 185 | 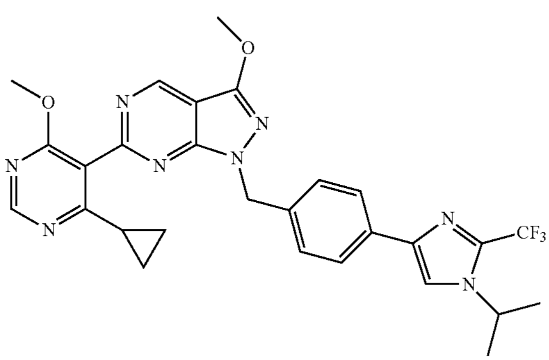 [SMILES: COc1ncnc(C2CC2)c1-c1ncc2c(OC)nn(Cc3ccc(-c4cn(C(C)C)c(C(F)(F)F)n4)cc3)c2n1] | LC-MS (Method B) (ESI+): m/z 565.35 (M + H)+; 1H-NMR (400 MHz, DMSO-d6) δ 9.34 (s, 1H), 8.70 (s, 1H), 8.24 (s, 1H), 7.75 (d, J = 8.31 Hz, 2H), 7.31 (d, J = 8.31 Hz, 2H), 5.51 (s, 2H), 4.56 (td, J = 6.42, 13.08 Hz, 1H), 4.07 (s, 3H), 3.86 (s, 3H), 1.67 (dd, J = 3.91, 7.83 Hz, 1H), 1.48 (d, J = 6.36 Hz, 6H), 1.03-1.10 (m, 2H), 0.87 (dd, J = 2.93, 7.34 Hz, 2H). |

Example 186: Synthesis of 3-(azetidin-1-yl)-6-(4-cyclopropyl-6-methoxypyrimidin-5-yl)-1-(4-(1-ethyl-4-(trifluoromethyl)-1H-imidazol-2-yl)benzyl)-1H-pyrazolo[3,4-d]pyrimidine (186)

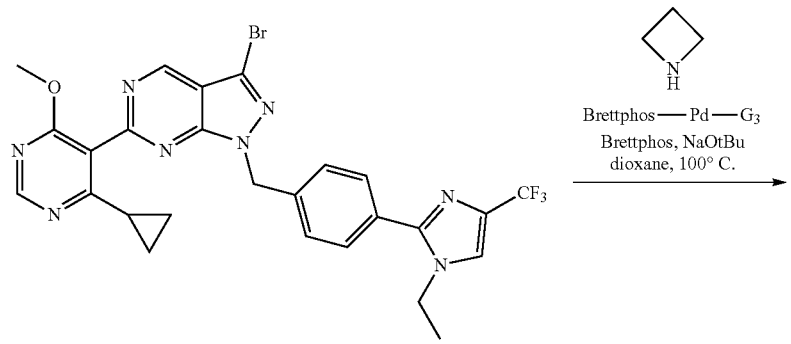

Example 170

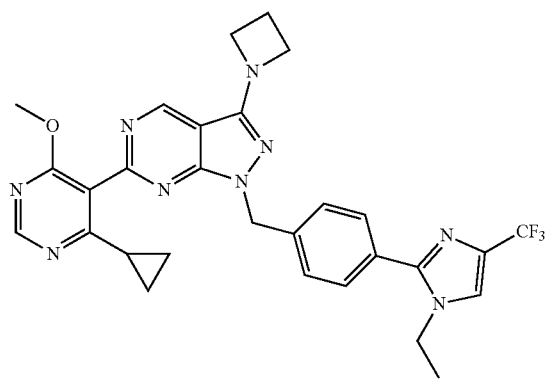

186

To a stirred solution of 3-bromo-6-(4-cyclopropyl-6-methoxypyrimidin-5-yl)-1-(4-(1-ethyl-4-(trifluoromethyl)-1H-imidazol-2-yl)benzyl)-1H-pyrazolo[3,4-d]pyrimidine 170 (0.150 g, 0.250 mmol) and azetidine (0.143 g, 2.51 mmol) in dioxane (6 mL), was added NaOtBu (0.036 g, 0.38 mmol) and the mixture was degassed with argon for 10 min. To the resulting reaction mixture was added Brettphos (0.027 g, 0.050 mmol) and Brettphos-Pd-G₃ (0.023 g, 0.025 mmol) at room temperature. The resulting mixture was degassed with argon for 5 min, and then heated at 100° C. for 2 h. Progress of the reaction was monitored by TLC. After completion, the reaction mixture of was diluted with water (100 mL) and extracted with EA (2×100 mL). The combined organic layer was dried over anhydrous sodium sulfate, filtered and concentrated under reduced pressure. The crude compound was purified by silica gel chromatography eluting with 0-50% EA in n-hexane. The product obtained (0.080 g) was dissolved in dioxane (8 mL) and treated with PS-Thiol silica (0.008 g). The resulting mixture was heated to 100° C. for 2 h, then cooled to room temperature, filtered and concentrated under reduced pressure to remove metal contamination. The solid thus obtained was then purified by preparative HPLC (Method B) to afford the title compound (0.035 g). LC-MS (Method B) (ESI+): m/z 576.30 (M+H)$^+$; $^1$H-NMR (400 MHz, DMSO-d$_6$) δ 9.21 (s, 1H), 8.69 (s, 1H), 8.01 (s, 1H), 7.58 (d, J=8.31 Hz, 2H), 7.37 (d, J=7.83 Hz, 2H), 5.52 (s, 2H), 4.17 (t, J=7.34 Hz, 4H), 4.02-4.09 (m, 2H), 3.85 (s, 3H), 2.42-2.47 (m, 2H), 1.62-1.71 (m, 1H), 1.30 (t, J=7.09 Hz, 3H), 1.02-1.07 (m, 2H), 0.86 (dd, J=3.18, 7.58 Hz, 2H).

Example 187: Synthesis of 6-(4-cyclopropyl-6-methoxypyrimidin-5-yl)-1-(4-(1-ethyl-4-(trifluoromethyl)-1H-imidazol-2-yl) benzyl)-3-methyl-1H-pyrazolo[3,4-d]pyrimidine (187)

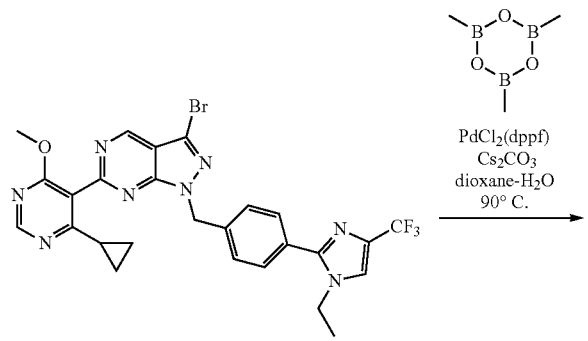

Example 170

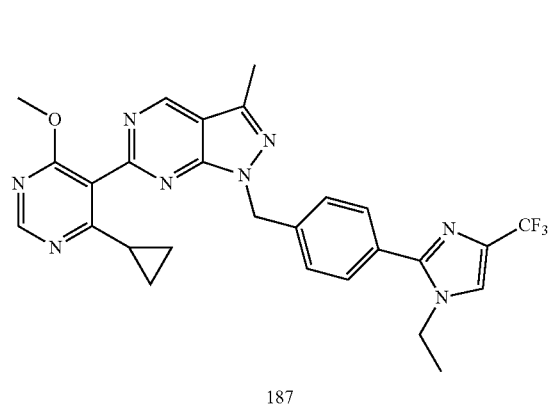

187

To a stirred solution of 3-bromo-6-(4-cyclopropyl-6-methoxypyrimidin-5-yl)-1-(4-(1-ethyl-4-(trifluoromethyl)-1H-imidazol-2-yl)benzyl)-1H-pyrazolo[3,4-d]pyrimidine 170 (0.200 g, 0.334 mmol) and trimethyl boroxine (0.031 g, 1.00 mmol) in dioxane (10 mL) and water (5 ml) was added and Cs$_2$CO$_3$ (0.162 g, 0.5016 mmol) at room temperature. The mixture was degassed with argon for 15 min and then treated with Pd(dppf)Cl$_2$.DCM (0.054 g, 0.066 mmol) at room temperature. The reaction mixture was then heated in sealed tube at 90° C. for 1 h. Progress of the reaction was monitored by TLC. After completion, the reaction mixture was cooled to room temperature, diluted with EA (20 mL) and water (10 mL). The organic layer was dried over anhydrous sodium sulfate, filtered and concentrated under reduced pressure. To the stirred solution of the crude compound (0.70 g) in dioxane (7 mL) was added SP thiol silica (0.007 g). The resulting reaction mixture was heated to 100° C. for 1 h, cooled to room temperature, filtered and concentrated under reduced pressure. The crude compound was then purified by preparative HPLC (Method D) to afford the title compound (0.050 g). LC-MS (Method C) (ESI+): m/z 535.15 (M+H)$^+$; $^1$H-NMR (400 MHz, DMSO-d$_6$) δ 9.47 (s, 1H), 8.71 (s, 1H), 8.02 (s, 1H), 7.59 (d, J=8.48 Hz, 2H), 7.40 (d, J=7.98 Hz, 2H), 5.69 (s, 2H), 4.05 (q, J=6.98 Hz, 2H), 3.85 (s, 3H), 2.63 (s, 3H), 1.60-1.68 (m, 1H), 1.29 (t, J=7.23 Hz, 3H), 1.03-1.07 (m, 2H), 0.85 (dd, J=3.24, 7.23 Hz, 2H).

Example 188: Synthesis of (S)-1-(1-(4-(5-bromo-1-methyl-4-(trifluoromethyl)-1H-imidazol-2-yl)phenyl)ethyl)-6-(4-cyclopropyl-6-methoxypyrimidin-5-yl)-3-methoxy-1H-pyrazolo[3,4-d]pyrimidine (188)

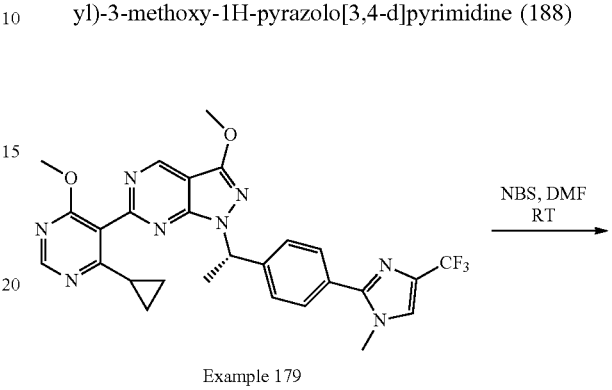

Example 179

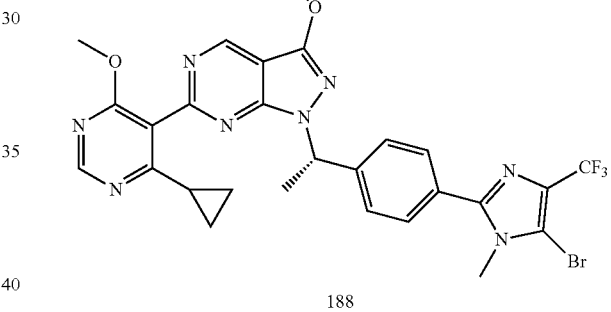

188

To a stirred solution of (S)-6-(4-cyclopropyl-6-methoxypyrimidin-5-yl)-3-methoxy-1-(1-(4-(1-methyl-4-(trifluoromethyl)-1H-imidazol-2-yl)phenyl)ethyl)-1H-pyrazolo[3,4-d]pyrimidine 179 (0.220 g, 0.400 mmol) in DMF (4 mL) was added NBS (0.142 g, 0.800 mmol) at room temperature, and the reaction mixture was stirred for 16 h. Progress of the reaction was monitored by TLC. After completion, the reaction mixture was concentrated under reduced pressure, diluted with water (10 mL) and extracted with EA (2×20 mL). The combined organic layer was dried over anhydrous sodium sulfate, filtered and concentrated under reduced pressure. The crude compound was purified by silica gel chromatography using with 0-40% EA in n-hexane as eluent followed by additional chiral purification (Method A) to afford the title compound (0.035 g). LC-MS (Method B) (ESI+): m/z 629.15 (M+H)$^+$; $^1$H-NMR (400 MHz, DMSO-d$_6$) δ 9.32 (s, 1H), 8.69 (s, 1H), 7.63 (d, J=8.31 Hz, 2H), 7.51 (d, J=8.31 Hz, 2H), 6.20 (q, J=7.17 Hz, 1H), 4.12 (s, 3H), 3.84 (s, 3H), 3.65 (s, 3H), 1.93 (d, J=7.34 Hz, 3H), 1.58-1.67 (m, 1H), 1.04 (d, J=3.42 Hz, 2H), 0.84 (dd, J=2.20, 7.58 Hz, 2H).

The following compounds were prepared from the appropriate building blocks according to the method described for Example 188:

| Example | Structure | Analytical data |
|---|---|---|
| 189 | 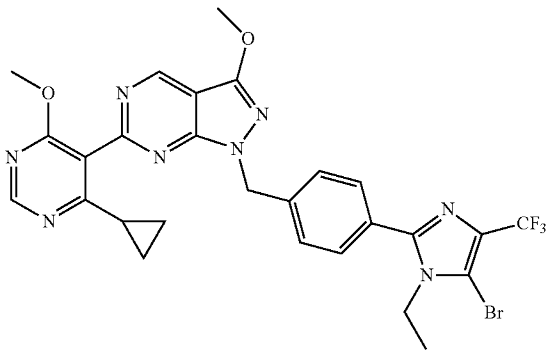 [SMILES: CCn1c(-c2ccc(Cn3nc(OC)c4cnc(-c5c(OC)ncnc5C5CC5)nc43)cc2)nc(C(F)(F)F)c1Br] | LC-MS (Method B) (ESI+): m/z 631.25 (M + H)⁺; ¹H-NMR (400 MHz, DMSO-d₆) δ 9.36 (s, 1H), 8.70 (s, 1H), 7.59 (d, J = 8.31 Hz, 2H), 7.42 (d, J = 7.83 Hz, 2H), 5.62 (s, 2H), 4.08 (s, 3H), 4.01-4.07 (m, 2H), 3.85 (s, 3H), 1.62-1.71 (m, 1H), 1.25 (t, J = 7.34 Hz, 3H), 1.05 (d, J = 2.93 Hz, 2H), 0.86 (dd, J = 2.93, 7.83 Hz, 2H). |

Example 190: Synthesis of 6-(4-cyclopropyl-6-methoxypyrimidin-5-yl)-1-(4-(1-ethyl-4-(trifluoromethyl)-1H-imidazol-2-yl)benzyl)-3-(methylthio)-1H-pyrazolo[3,4-d]pyrimidine (190)

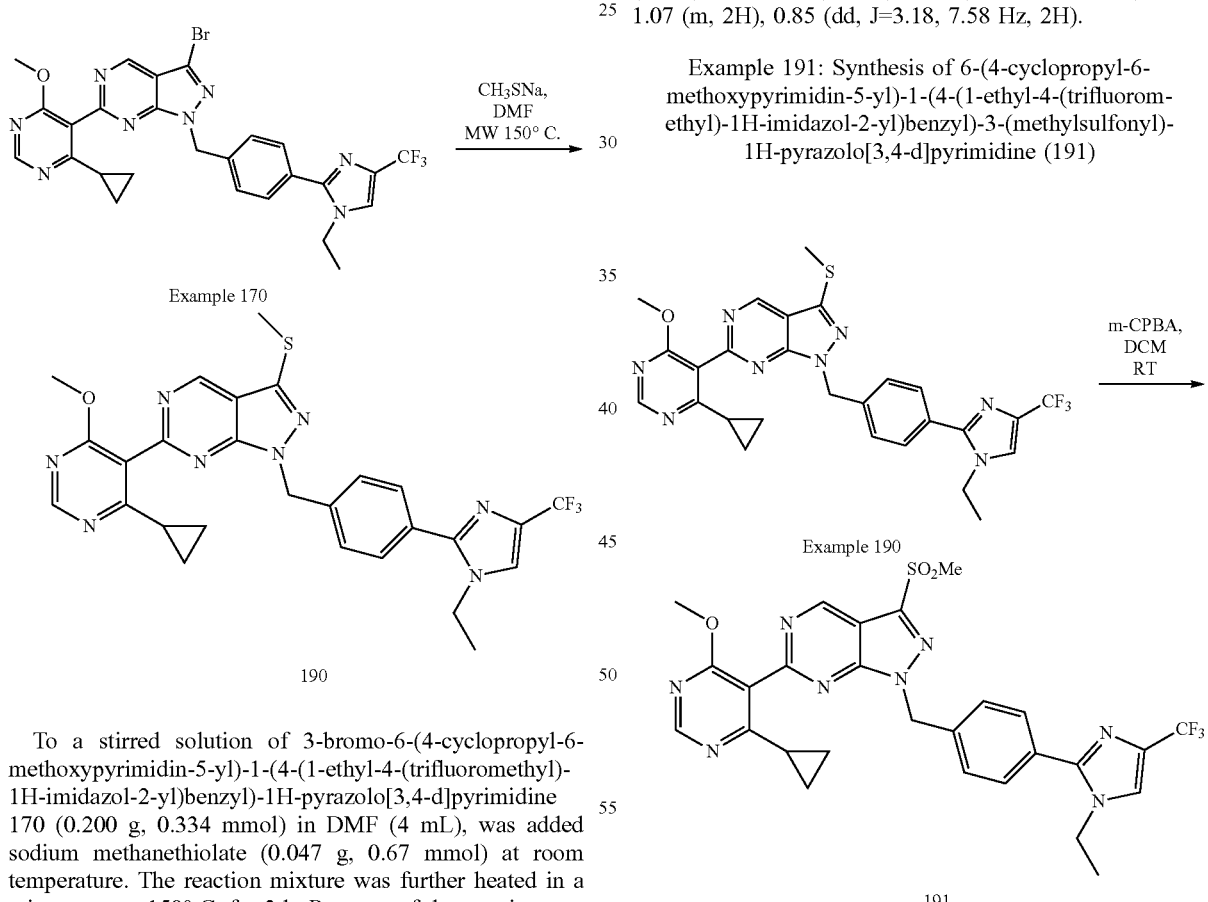

To a stirred solution of 3-bromo-6-(4-cyclopropyl-6-methoxypyrimidin-5-yl)-1-(4-(1-ethyl-4-(trifluoromethyl)-1H-imidazol-2-yl)benzyl)-1H-pyrazolo[3,4-d]pyrimidine 170 (0.200 g, 0.334 mmol) in DMF (4 mL), was added sodium methanethiolate (0.047 g, 0.67 mmol) at room temperature. The reaction mixture was further heated in a microwave at 150° C. for 2 h. Progress of the reaction was monitored by TLC. After completion, the reaction mixture of was diluted with ice cold water (50 mL) and extracted with EA (2×100 mL). The combined organic layer was washed with ice cold water (2×150 mL), dried over anhydrous sodium sulfate, filtered and concentrated under reduced pressure. The crude compound was purified by silica gel chromatography eluting with 0-40% EA in n-hexane followed by additional purification using preparative HPLC (Method B) to afford the title compound (0.025 g). LC-MS (Method B) (ESI+): m/z 567.30 (M+H)⁺; ¹H-NMR (400 MHz, DMSO-d₆) δ 9.47 (s, 1H), 8.71 (s, 1H), 8.02 (s, 1H), 7.60 (d, J=8.31 Hz, 2H), 7.42 (d, J=8.31 Hz, 2H), 5.73 (s, 2H), 4.05 (q, J=7.34 Hz, 2H), 3.85 (s, 3H), 2.72 (s, 3H), 1.64-1.71 (m, 1H), 1.29 (t, J=7.34 Hz, 3H), 1.02-1.07 (m, 2H), 0.85 (dd, J=3.18, 7.58 Hz, 2H).

Example 191: Synthesis of 6-(4-cyclopropyl-6-methoxypyrimidin-5-yl)-1-(4-(1-ethyl-4-(trifluoromethyl)-1H-imidazol-2-yl)benzyl)-3-(methylsulfonyl)-1H-pyrazolo[3,4-d]pyrimidine (191)

To an ice cooled solution of 6-(4-cyclopropyl-6-methoxy-pyrimidin-5-yl)-1-(4-(1-ethyl-4-(trifluoro-methyl)-1H-imidazol-2-yl)benzyl)-3-(methylthio)-1H-pyrazolo[3,4-d]pyrimidine 190 (0.150 g, 0.265 mmol) in DCM (15 mL) was added m-CPBA (0.182 g, 1.06 mmol). The resulting mixture was allowed to attain room temperature and was further stirred for 2 h. Progress of the reaction was monitored by TLC. After completion, the reaction mixture was diluted with water (100 mL) and extracted with DCM (2×100 mL). The combined organic layer was dried over anhydrous sodium sulfate, filtered and concentrated under reduced pressure. The crude compound was purified by silica gel chromatography using 0-50% EA in n-hexane followed by repurification by preparative HPLC (Method B) to afford the title compound (0.030 g). LC-MS (Method B) (ESI+): m/z 599.20 (M+H)+; $^1$H-NMR (400 MHz, DMSO-d$_6$) δ 9.67 (s, 1H), 8.74 (s, 1H), 8.02 (s, 1H), 7.62 (d, J=8.31 Hz, 2H), 7.50 (d, J=8.31 Hz, 2H), 5.93 (s, 2H), 4.05 (q, J=7.17 Hz, 2H), 3.86 (s, 3H), 3.53 (s, 3H), 1.69-1.76 (m, 1H), 1.30 (t, J=7.09 Hz, 3H), 1.06-1.10 (m, 2H), 0.86 (dd, J=3.42, 7.83 Hz, 2H).

Example 192: Synthesis of 6-(4-cyclopropyl-6-methoxypyrimidin-5-yl)-1-(4-(1-ethyl-4-(trifluoromethyl)-1H-imidazol-2-yl)benzyl)-3-((4-methoxybenzyl)thio)-1H-pyrazolo[3,4-d]pyrimidine (192)

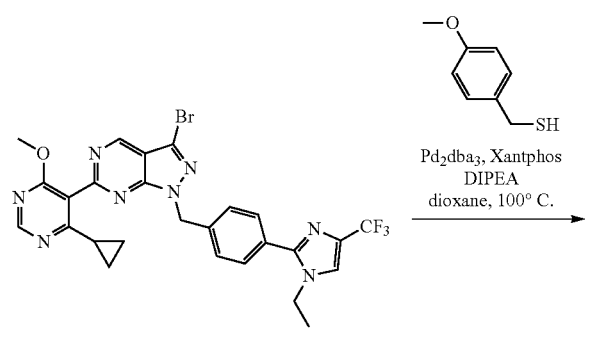

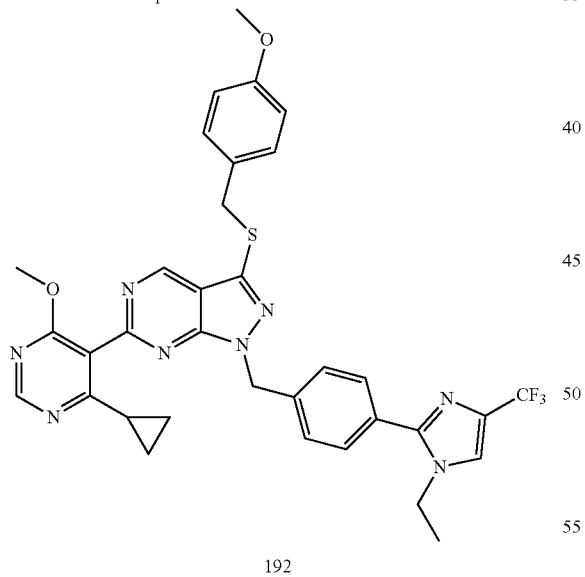

To a stirred solution of 3-bromo-6-(4-cyclopropyl-6-methoxypyrimidin-5-yl)-1-(4-(1-ethyl-4-(trifluoromethyl)-1H-imidazol-2-yl)benzyl)-1H-pyrazolo[3,4-d]pyrimidine 170 (0.300 g, 0.501 mmol) and (4-methoxyphenyl)methanethiol (0.115 g, 0.752 mmol) in dioxane (10 mL), was added DIPEA (0.620 mL, 3.51 mmol). The resulting solution was degassed with argon for 10 min, then treated with Xantphos (0.020 g, 0.035 mmol) and Pd$_2$(dba)$_3$ (0.032 g, 0.035 mmol) at room temperature. The mixture was further degassed with argon for 5 min, and then heated at 100° C. for 16 h. Progress of the reaction was monitored by TLC. After completion, the reaction mixture was diluted with water (100 mL) and extracted with EA (2×100 mL). The combined organic layer was dried over anhydrous sodium sulfate, filtered and concentrated under reduced pressure. The crude compound was purified by silica gel chromatography using 0-30% EA in n-hexane as eluent to afford the title compound (0.300 g). LC-MS (Method B) (ESI+): m/z 673.30 (M+H)+; $^1$H-NMR (400 MHz, DMSO-d$_6$) δ 9.28 (d, J=1.96 Hz, 1H), 8.70 (d, J=1.96 Hz, 1H), 8.03 (s, 1H), 7.62 (d, J=6.85 Hz, 2H), 7.41 (d, J=7.34 Hz, 2H), 7.22 (d, J=7.34 Hz, 2H), 6.74 (d, J=6.85 Hz, 2H), 5.74 (s, 2H), 4.40 (s, 2H), 4.03-4.11 (m, 2H), 3.85 (s, 3H), 3.65 (s, 3H), 1.59-1.67 (m, 1H), 1.27-1.33 (m, 3H), 1.02-1.07 (m, 2H), 0.83-0.88 (m, 2H).

Example 193: Synthesis of 6-(4-cyclopropyl-6-methoxypyrimidin-5-yl)-1-(4-(1-((methylsulfonyl)methyl)-4-(trifluoromethyl)-1H-imidazol-2-yl)benzyl)-1H-pyrazolo[3,4-d]pyrimidine (193)

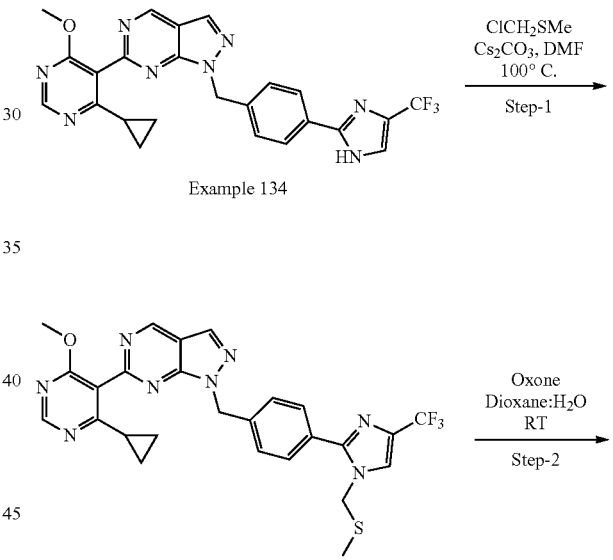

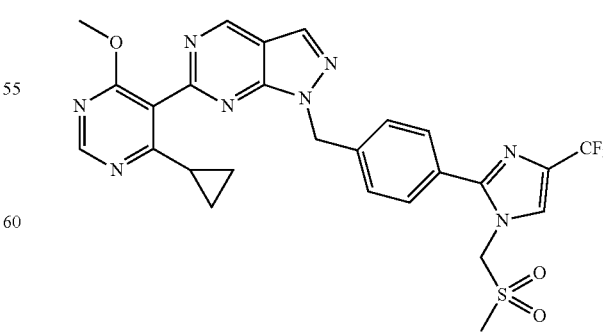

Step 1: Synthesis of 6-(4-cyclopropyl-6-methoxypyrimidin-5-yl)-1-(4-(1-((methylthio)methyl)-4-(trifluoromethyl)-1H-imidazol-2-yl)benzyl)-1H-pyrazolo[3,4-d]pyrimidine

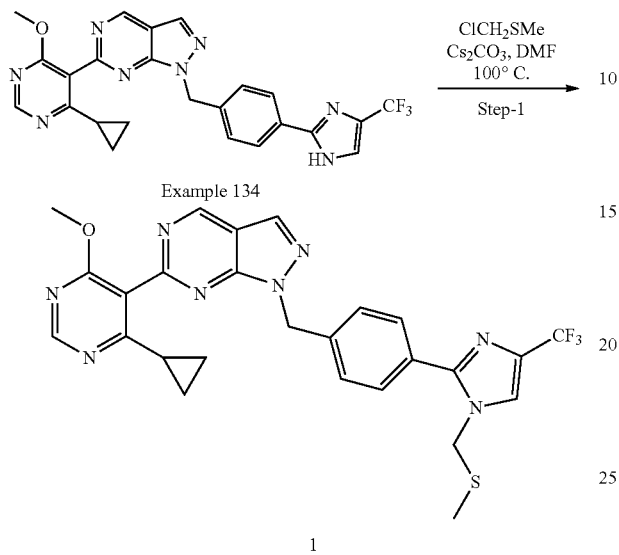

To a stirred solution of 6-(4-cyclopropyl-6-methoxypyrimidin-5-yl)-1-(4-(4-(trifluoromethyl)-1H-imidazol-2-yl)benzyl)-1H-pyrazolo[3,4-d]pyrimidine 134 (0.200 g, 0.406 mmol) and (chloromethyl)(methyl)sulfane (0.078 g, 0.813 mmol) in DMF (2 mL), was added cesium carbonate (0.397 g, 1.219 mmol) at room temperature. The reaction mixture was heated at 100° C. for 2 h. Progress of the reaction was monitored by TLC. After completion, the reaction mixture was diluted with ice cold water (100 mL) and extracted with EA (2×100 mL). The combined organic layer was washed with water (3×100 mL), dried over anhydrous sodium sulfate, filtered and concentrated under reduced pressure. The crude compound was purified by preparative HPLC (Method B) to afford the title compound (0.080 g). LC-MS (Method B) (ESI+): m/z 553.20 (M+H)+; $^1$H-NMR (400 MHz, DMSO-$d_6$) δ 9.51 (s, 1H), 8.71 (s, 1H), 8.52 (s, 1H), 8.06 (s, 1H), 7.67 (d, J=8.31 Hz, 2H), 7.42 (d, J=7.83 Hz, 2H), 5.78 (s, 2H), 5.22 (s, 2H), 3.85 (s, 3H), 2.01 (s, 3H), 1.61-1.69 (m, 1H), 1.03-1.07 (m, 2H), 0.86 (d, J=4.40 Hz, 2H).

Step 2: Synthesis of 6-(4-cyclopropyl-6-methoxypyrimidin-5-yl)-1-(4-(1-((methylsulfonyl)methyl)-4-(trifluoromethyl)-1H-imidazol-2-yl)benzyl)-1H-pyrazolo[3,4-d]pyrimidine (193)

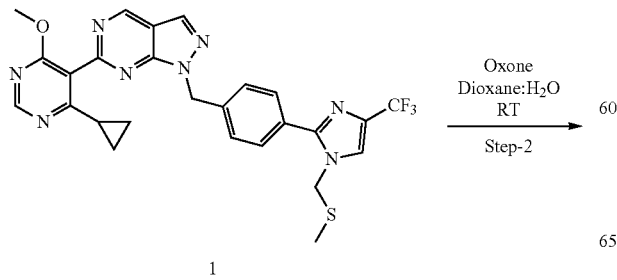

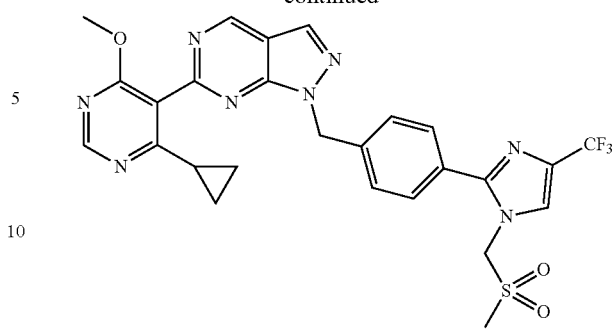

To a stirred solution of 6-(4-cyclopropyl-6-methoxypyrimidin-5-yl)-1-(4-(1-((methylthio)methyl)-4-(trifluoromethyl)-1H-imidazol-2-yl)benzyl)-1H-pyrazolo[3,4-d]pyrimidine 1 (0.070 g, 0.126 mmol) in dioxane:H$_2$O (3:1 mL), was added Oxone (0.233 g, 0.380 mmol) at room temperature. The mixture was stirred for 1 h, and progress of the reaction was monitored by TLC. After completion, the reaction mixture was diluted with water (50 mL) and extracted with EA (2×50 mL). The combined organic layer was dried over anhydrous sodium sulfate, filtered and concentrated under reduced pressure. The crude compound was purified by silica gel chromatography using 0-5% methanol in DCM and was then repurified by preparative HPLC (Method B) purification to afford the title compound (0.018 g). LC-MS (Method B) (ESI+): m/z 585.10 (M+H)+; $^1$H-NMR (400 MHz, DMSO-$d_6$) δ 9.51 (s, 1H), 8.71 (s, 1H), 8.52 (s, 1H), 7.99 (s, 1H), 7.69 (d, J=7.98 Hz, 2H), 7.44 (d, J=7.98 Hz, 2H), 5.79 (s, 2H), 5.63 (s, 2H), 3.85 (s, 3H), 3.04 (s, 3H), 1.63-1.70 (m, 1H), 1.03-1.07 (m, 2H), 0.84-0.92 (m, 2H).

Example 194: Synthesis of (2-(4-((6-(4-cyclopropyl-6-methoxypyrimidin-5-yl)-1H-pyrazolo[3,4-d]pyrimidin-1-yl)methyl)phenyl)-1-ethyl-1H-imidazol-4-yl)methanol (194)

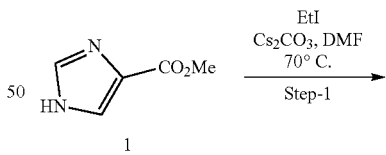

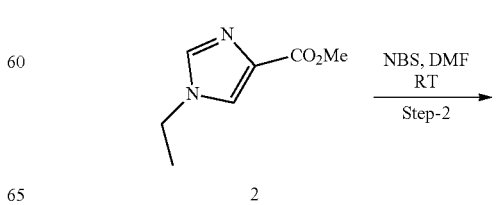

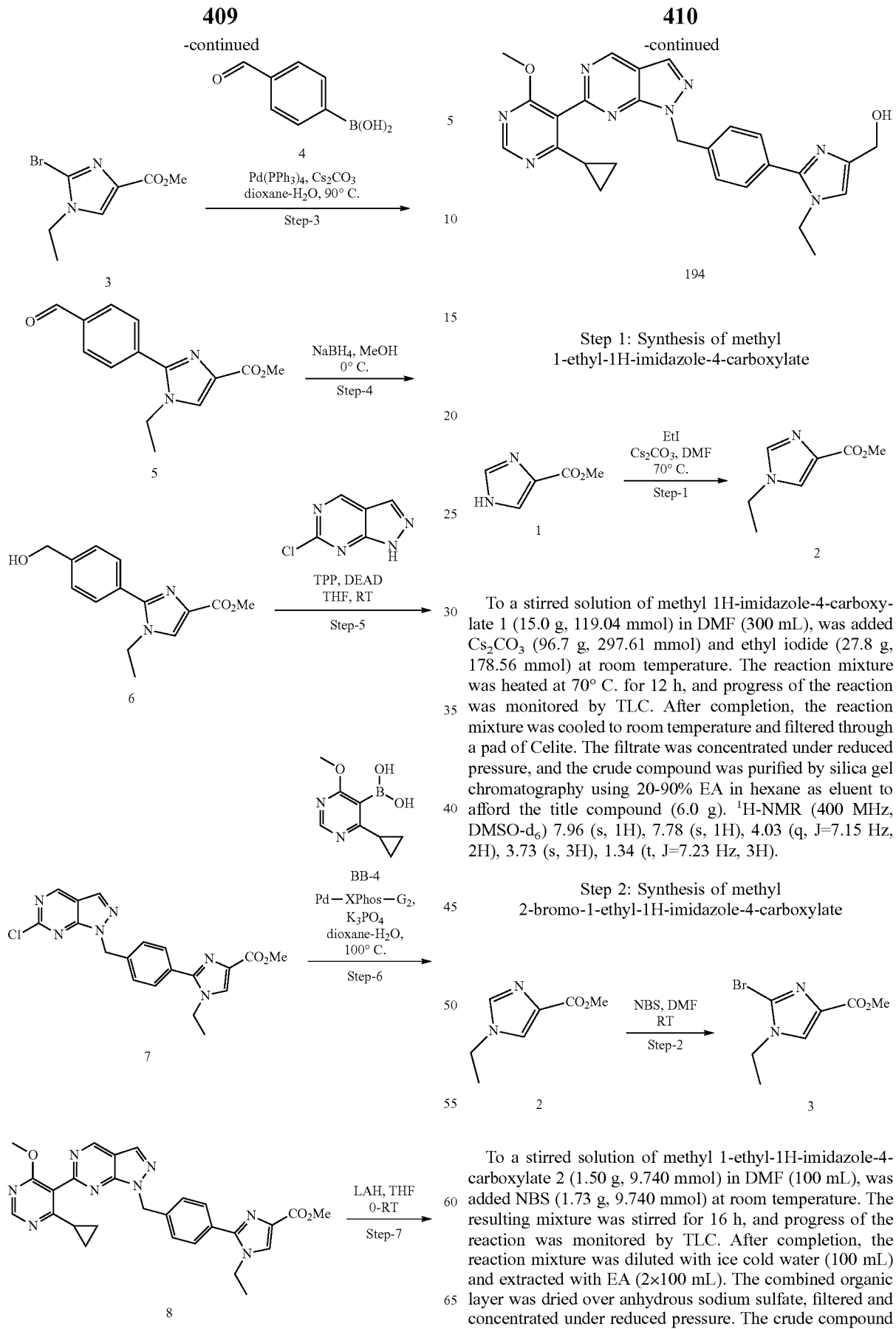

Step 1: Synthesis of methyl 1-ethyl-1H-imidazole-4-carboxylate

To a stirred solution of methyl 1H-imidazole-4-carboxylate 1 (15.0 g, 119.04 mmol) in DMF (300 mL), was added $Cs_2CO_3$ (96.7 g, 297.61 mmol) and ethyl iodide (27.8 g, 178.56 mmol) at room temperature. The reaction mixture was heated at 70° C. for 12 h, and progress of the reaction was monitored by TLC. After completion, the reaction mixture was cooled to room temperature and filtered through a pad of Celite. The filtrate was concentrated under reduced pressure, and the crude compound was purified by silica gel chromatography using 20-90% EA in hexane as eluent to afford the title compound (6.0 g). $^1$H-NMR (400 MHz, DMSO-$d_6$) 7.96 (s, 1H), 7.78 (s, 1H), 4.03 (q, J=7.15 Hz, 2H), 3.73 (s, 3H), 1.34 (t, J=7.23 Hz, 3H).

Step 2: Synthesis of methyl 2-bromo-1-ethyl-1H-imidazole-4-carboxylate

To a stirred solution of methyl 1-ethyl-1H-imidazole-4-carboxylate 2 (1.50 g, 9.740 mmol) in DMF (100 mL), was added NBS (1.73 g, 9.740 mmol) at room temperature. The resulting mixture was stirred for 16 h, and progress of the reaction was monitored by TLC. After completion, the reaction mixture was diluted with ice cold water (100 mL) and extracted with EA (2×100 mL). The combined organic layer was dried over anhydrous sodium sulfate, filtered and concentrated under reduced pressure. The crude compound was purified by silica gel chromatography using 0-5% methanol in DCM as eluent to afford the title compound (1.50 g). LC-MS (Method B) (ESI+): m/z 234.95 (M+H)+.

Step 3: Synthesis of methyl 1-ethyl-2-(4-formylphenyl)-1H-imidazole-4-carboxylate

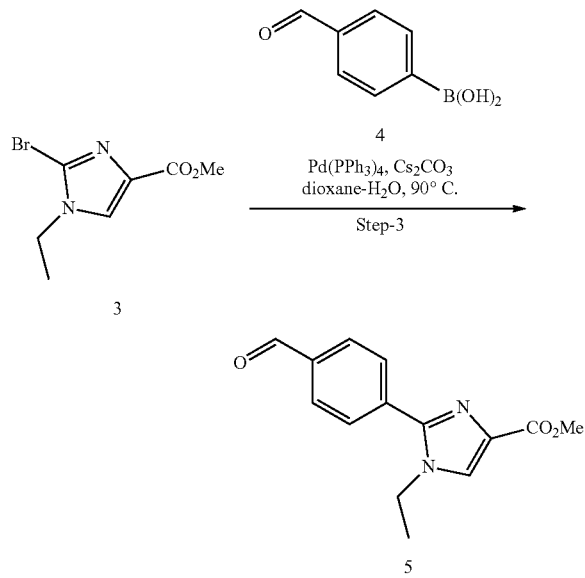

To a stirred solution of methyl 2-bromo-1-ethyl-1H-imidazole-4-carboxylate 3 (1.00 g, 4.291 mmol) in dioxane: H₂O (90:30 mL) was added Cs₂CO₃ (3.42 g, 10.72 mmol) and (4-formylphenyl)boronic acid 4 (0.77 g, 5.149 mmol). The resulting mixture was degassed with argon for 30 min, and then treated with Pd(PPh₃)₄ (0.097 g, 0.085 mmol) at room temperature. The reaction mixture was then heated in a sealed tube at 90° C. for 16 h. Progress of the reaction was monitored by TLC. After completion, the reaction mixture was cooled to room temperature, diluted with water (50 mL) and extracted with EA (2×50 mL). The combined organic layer was dried over anhydrous sodium sulfate, filtered and concentrated under reduced pressure. The crude compound was purified by silica gel chromatography using 20-80% EA in hexane as eluent to afford the title compound (1.0 g). LC-MS (Method B) (ESI+): m/z 259 (M+H)+.

Step 4: Synthesis of methyl 1-ethyl-2-(4-(hydroxymethyl)phenyl)-1H-imidazole-4-carboxylate

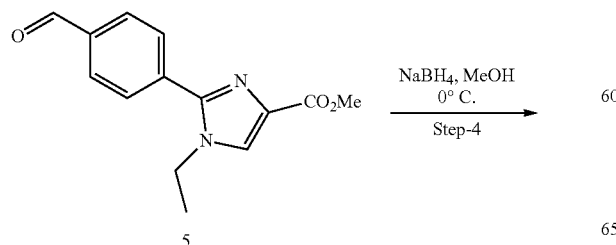

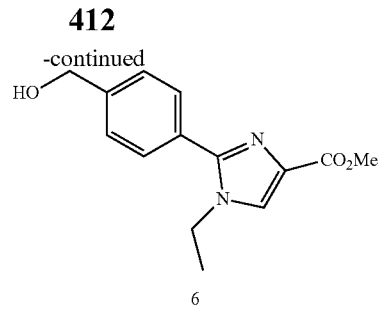

To a stirred solution of methyl 1-ethyl-2-(4-formylphenyl)-1H-imidazole-4-carboxylate 5 (1.0 g, 3.875 mmol) in methanol (40 mL) at 0° C., was added sodium borohydride (0.073 g, 1.937 mmol). The reaction mixture was allowed to warm to room temperature and stirred for 30 min. Progress of the reaction was monitored by TLC. After completion, the reaction mixture was quenched with water (10 mL) and concentrated under reduced pressure. The remaining residue was dissolved in water (20 mL) and extracted with EA (2×100 mL). The combined organic layer was dried over anhydrous sodium sulfate, filtered and concentrated under reduced pressure to afford the title compound (0.960 g). LC-MS (Method B) (ESI+): m/z 261 (M+H)+; ¹H-NMR (400 MHz, DMSO-d₆) δ 7.89 (s, 1H), 7.39-7.44 (m, 2H), 7.31-7.36 (m, 2H), 5.29 (t, J=5.73 Hz, 1H), 4.57 (d, J=5.49 Hz, 2H), 3.82 (q, J=6.98 Hz, 2H), 3.57 (s, 3H), 1.12 (t, J=7.23 Hz, 3H).

Step 5: Synthesis of methyl 2-(4-((6-chloro-1H-pyrazolo[3,4-d]pyrimidin-1-yl)methyl)phenyl)-1-ethyl-1H-imidazole-4-carboxylate

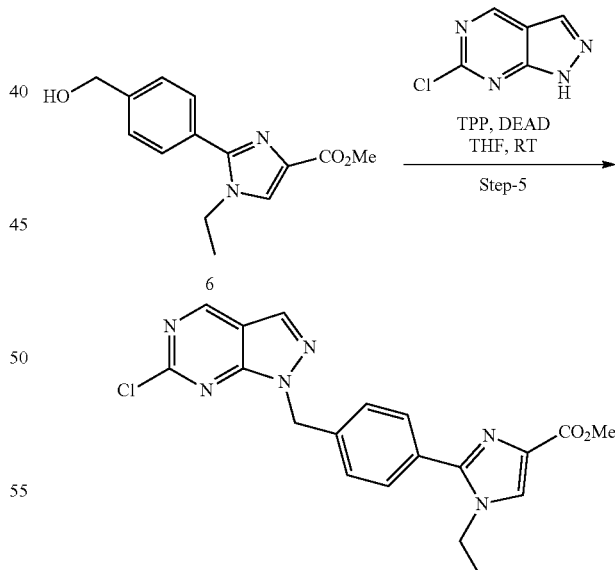

To a stirred solution of methyl 1-ethyl-2-(4-(hydroxymethyl)phenyl)-1H-imidazole-4-carboxylate 6 (0.900 g, 3.461 mmol) in THF (20 mL) at 0° C., was added 6-chloro-1H-pyrazolo[3,4-d]pyrimidine (0.533 g, 3.461 mmol), DEAD (0.887 g, 5.192 mmol) and TPP (1.33 g, 5.192 mmol). The reaction mixture was allowed to warm to room temperature and stirred for 1 h. Progress of the reaction was monitored by TLC. After completion, the reaction mixture was quenched with water (20 mL) and extracted with EA (2×100 mL). The combined organic layer was dried over anhydrous sodium sulfate, filtered and concentrated under reduced pressure. The crude compound was purified by silica gel chromatography using 20-70% EA in hexane as eluent to afford the title compound (1.20 g). LC-MS (Method B) (ESI+): m/z 396.9 (M+H)$^+$.

Step 6: Synthesis of methyl 2-(4-((6-(4-cyclopropyl-6-methoxypyrimidin-5-yl)-1H-pyrazolo[3,4-d]pyrimidin-1-yl)methyl)phenyl)-1-ethyl-1H-imidazole-4-carboxylate

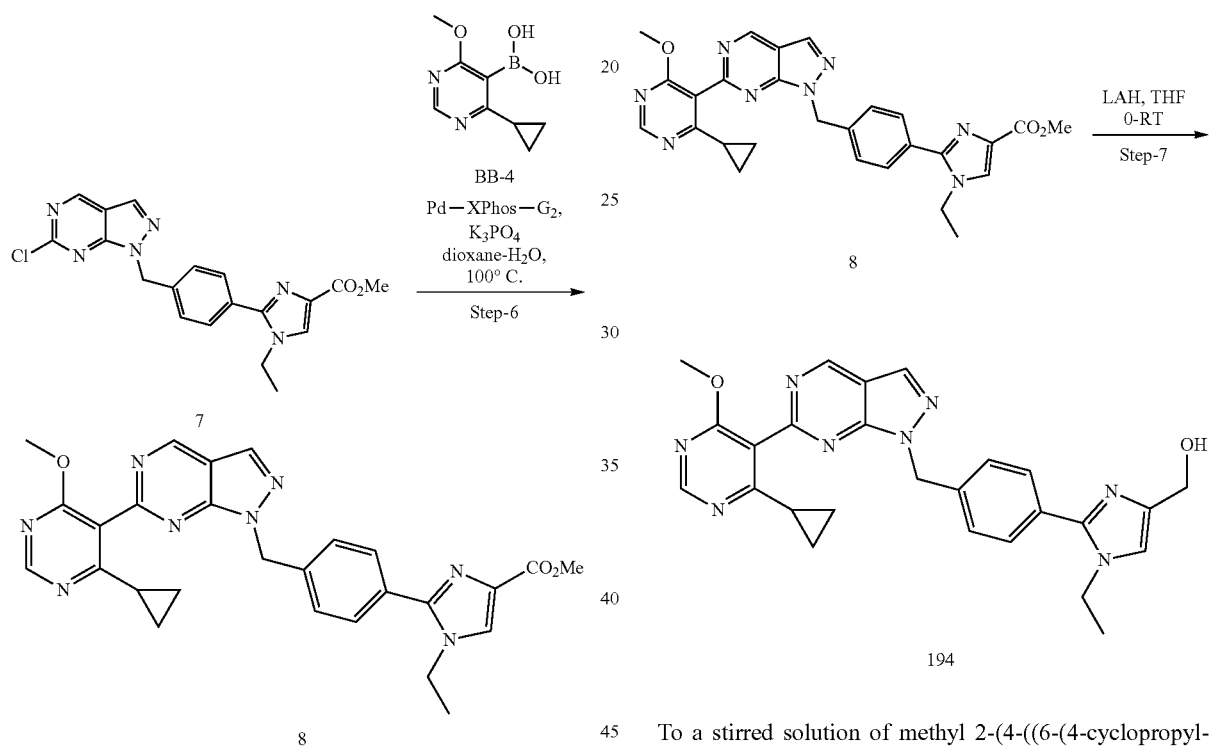

To a stirred solution of methyl 2-(4-((6-chloro-1H-pyrazolo[3,4-d]pyrimidin-1-yl)methyl)phenyl)-1-ethyl-1H-imidazole-4-carboxylate 7 (1.2 g, 3.03 mmol) in dioxane:H$_2$O (20:4 mL) was added K$_3$PO$_4$ (0.320 g, 1.51 mmol) and (4-cyclopropyl-6-methoxypyrimidin-5-yl)boronic acid (BB-4) (1.59 g, 7.58 mmol) at room temperature. The resulting mixture was degassed with argon for 30 min, then treated with X-phos (0.288 g, 0.606 mmol) and X-phos-Pd-G2 (0.118 g, 0.1515 mmol) at room temperature. The mixture was subsequently degassed with argon for 10 min. The reaction mixture was then heated in a sealed tube at 100° C. for 16 h. Progress of the reaction was monitored by TLC. After completion, the reaction mixture was quenched with H$_2$O (20 mL) and extracted with EA (2×100 mL). The combined organic layer was dried over anhydrous sodium sulfate, filtered and concentrated under reduced pressure. The crude compound was purified by silica gel chromatography using 0-80% EA in hexane as eluent, followed by concentration in vacuo to afford intermediate 8 (1.50 g). To a stirred solution of 8 (1.50 g) in dioxane (15 mL) was added SP thiol silica (0.150 g). The resulting reaction mixture was heated to 100° C. for 2 h. The reaction mixture was then cooled to room temperature, filtered and concentrated under reduced pressure to afford the title compound (1.20 g). LC-MS (Method B) (ESI+): m/z 511.30 (M+H)$^+$; $^1$H-NMR (400 MHz, DMSO-d$_6$) δ 9.51 (s, 1H), 8.71 (s, 1H), 8.53 (s, 1H), 7.88 (s, 1H), 7.33-7.39 (m, 4H), 5.78 (s, 2H), 3.85 (s, 3H), 3.78 (q, J=7.01 Hz, 2H), 3.54 (s, 3H), 1.65 (d, J=4.40 Hz, 1H), 1.03-1.12 (m, 5H), 0.85 (dd, J=2.93, 4.40 Hz, 2H).

Step 7: Synthesis of (2-(4-((6-(4-cyclopropyl-6-methoxypyrimidin-5-yl)-1H-pyrazolo[3,4-d]pyrimidin-1-yl)methyl)phenyl)-1-ethyl-1H-imidazol-4-yl)methanol (194)

To a stirred solution of methyl 2-(4-((6-(4-cyclopropyl-6-methoxypyrimidin-5-yl)-1H-pyrazolo[3,4-d]pyrimidin-1-yl)methyl)phenyl)-1-ethyl-1H-imidazole-4-carboxylate 8 (0.070 g, 0.1372 mmol) in THF (20 mL) at 0° C., was slowly added a 1.0 M solution of LAH in THF (0.260 mL, 0.260 mmol). The reaction mixture was allowed to warm to room temperature, and then stirred for 1 h. Progress of the reaction was monitored by TLC. After completion, the reaction mixture was quenched with saturated Na$_2$SO$_4$ solution (10 mL) and filtered through Celite. The filtrate was concentrated under reduced pressure, and the resulting crude compound was purified by preparative HPLC to afford the title compound (0.025 g). LC-MS (Method B) (ESI+): m/z 483.30 (M+H)$^+$; $^1$H-NMR (400 MHz, DMSO-d$_6$) δ 9.51 (s, 1H), 8.71 (s, 1H), 8.52 (s, 1H), 7.69 (s, 1H), 7.36-7.43 (m, 4H), 5.76 (s, 2H), 4.71 (t, J=5.24 Hz, 1H), 4.14 (d, J=4.99 Hz, 2H), 3.87-3.93 (m, 2H), 3.85 (s, 3H), 1.66 (d, J=3.99 Hz, 1H), 1.11 (t, J=6.98 Hz, 3H), 1.04-1.07 (m, 2H), 0.82-0.88 (m, 2H).

The following compound was prepared from the appropriate building blocks according to the method described for Example 194:

| Example | Structure | Analytical data |
|---|---|---|
| 195 | 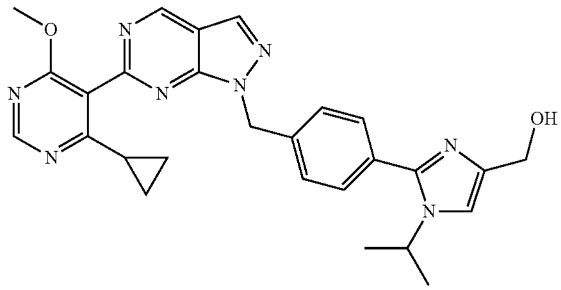 [SMILES: COc1ncnc(C2CC2)c1-c1ncc2cnn(Cc3ccc(-c4nc(CO)cn4C(C)C)cc3)c2n1] | LC-MS (Method C) (ESI+): m/z 497.20 (M + H)+; 1H-NMR (400 MHz, DMSO-d6) δ 9.51 (s, 1H), 8.71 (s, 1H), 8.52 (s, 1H), 7.84 (s, 1H), 7.37 (q, J = 7.65 Hz, 4H), 5.76 (s, 2H), 4.66 (t, J = 4.99 Hz, 1H), 4.12 (d, J = 5.49 Hz, 2H), 3.85 (s, 3H), 1.64-1.71 (m, 2H), 1.31 (d, J = 6.98 Hz, 6H), 1.04-1.08 (m, 2H), 0.85 (d, J = 4.49 Hz, 2H). |

Example 196: Synthesis of 6-(4-cyclopropyl-6-methoxypyrimidin-5-yl)-1-(4-(4-(difluoromethyl)-1-ethyl-1H-imidazol-2-yl)benzyl)-1H-pyrazolo[3,4-d]pyrimidine (196)

Step 1: Synthesis of 2-(4-((6-(4-cyclopropyl-6-methoxypyrimidin-5-yl)-1H-pyrazolo[3,4-d]pyrimidin-1-yl)methyl)phenyl)-1-ethyl-1H-imidazole-4-carbaldehyde

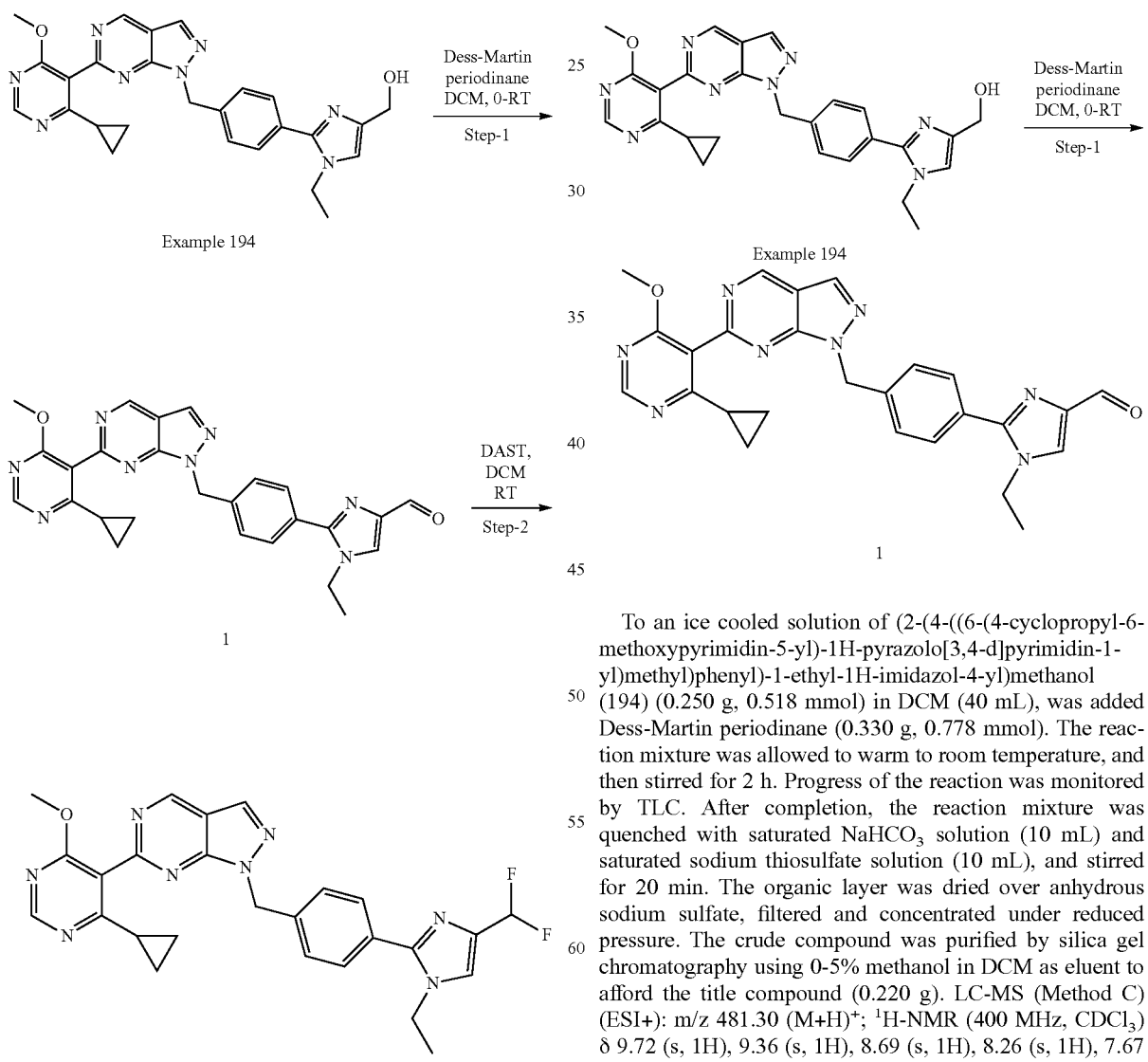

To an ice cooled solution of (2-(4-((6-(4-cyclopropyl-6-methoxypyrimidin-5-yl)-1H-pyrazolo[3,4-d]pyrimidin-1-yl)methyl)phenyl)-1-ethyl-1H-imidazol-4-yl)methanol (194) (0.250 g, 0.518 mmol) in DCM (40 mL), was added Dess-Martin periodinane (0.330 g, 0.778 mmol). The reaction mixture was allowed to warm to room temperature, and then stirred for 2 h. Progress of the reaction was monitored by TLC. After completion, the reaction mixture was quenched with saturated NaHCO3 solution (10 mL) and saturated sodium thiosulfate solution (10 mL), and stirred for 20 min. The organic layer was dried over anhydrous sodium sulfate, filtered and concentrated under reduced pressure. The crude compound was purified by silica gel chromatography using 0-5% methanol in DCM as eluent to afford the title compound (0.220 g). LC-MS (Method C) (ESI+): m/z 481.30 (M+H)+; 1H-NMR (400 MHz, CDCl3) δ 9.72 (s, 1H), 9.36 (s, 1H), 8.69 (s, 1H), 8.26 (s, 1H), 7.67 (s, 1H), 7.56 (d, J=7.98 Hz, 2H), 7.37 (d, J=8.48 Hz, 2H), 5.79 (s, 2H), 3.94 (s, 3H), 3.86-3.93 (m, 2H), 1.31 (t, J=7.23 Hz, 3H), 1.23-1.28 (m, 3H), 0.85-0.91 (m, 2H).

Step 2: Synthesis of 6-(4-cyclopropyl-6-methoxypyrimidin-5-yl)-1-(4-(4-(difluoromethyl)-1-ethyl-1H-imidazol-2-yl)benzyl)-1H-pyrazolo[3,4-d]pyrimidine (196)

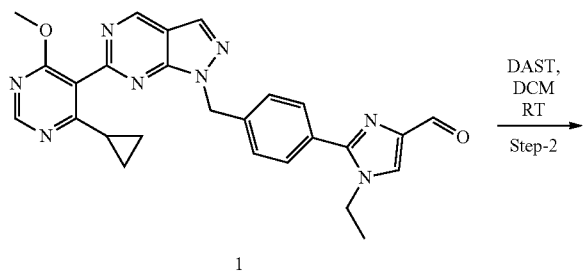

DCM (2×20 mL). The combined organic layer was dried over anhydrous sodium sulfate, filtered and concentrated under reduced pressure. The crude compound was first purified by silica gel chromatography using 0-25% EA in hexane as eluent. The impure compound thus obtained was then purified by preparative HPLC (Method B) to afford the title compound (0.035 g). LC-MS (Method B) (ESI+): m/z 503.30 (M+H)$^+$; $^1$H-NMR (400 MHz, DMSO-$d_6$) δ 9.51 (s, 1H), 8.71 (s, 1H), 8.53 (s, 1H), 7.90 (s, 1H), 7.39 (q, J=7.99 Hz, 4H), 6.47-6.75 (m, 1H), 5.79 (s, 2H), 3.86-3.90 (m, 2H), 3.85 (s, 3H), 1.66 (td, J=3.55, 7.58 Hz, 1H), 1.12 (t, J=7.09 Hz, 3H), 1.03-1.08 (m, 2H), 0.84 (dd, J=2.93, 7.34 Hz, 2H).

The following compounds were prepared from the appropriate building blocks according to the method described for Example 196:

| Example | Structure | Analytical data |
|---|---|---|
| 197 | 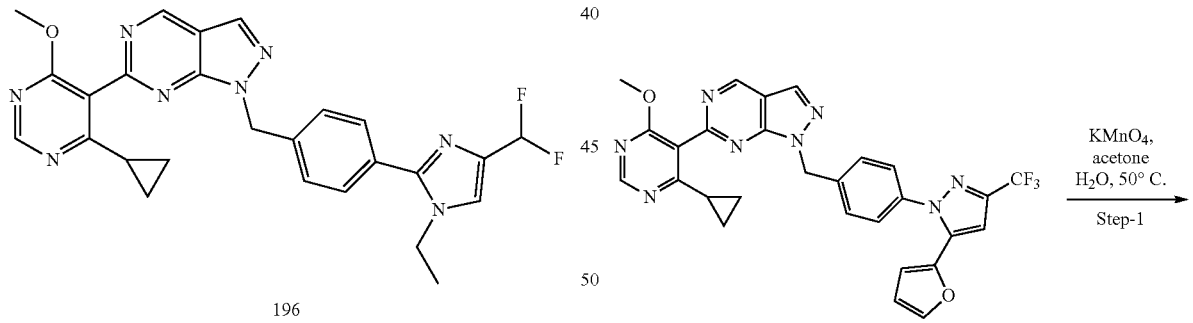 | LC-MS (Method C) (ESI+): m/z 517.15 (M + H)$^+$; $^1$H-NMR (400 MHz, DMSO-$d_6$) δ 9.52 (s, 1H), 8.71 (s, 1H), 8.53 (s, 1H), 8.04 (s, 1H), 7.39-7.42 (m, 2H), 7.32-7.36 (m, 2H), 6.44-6.72 (m, 1H), 5.79 (s, 2H), 4.06 (td, J = 6.73, 13.46 Hz, 1H), 3.85 (s, 3H), 1.62-1.70 (m, 1H), 1.33 (d, J = 6.48 Hz, 6H), 1.05 (d, J = 3.49 Hz, 2H), 0.84 (dd, J = 3.24, 7.73 Hz, 2H). |

Example 198: Synthesis of (1-(4-((6-(4-cyclopropyl-6-methoxypyrimidin-5-yl)-1H-pyrazolo[3,4-d]pyrimidin-1-yl)methyl)phenyl)-3-(trifluoromethyl)-1H-pyrazol-5-yl)methanol (198)

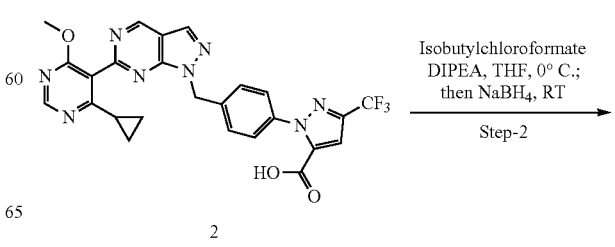

To a stirred solution 2-(4-((6-(4-cyclopropyl-6-methoxypyrimidin-5-yl)-1H-pyrazolo[3,4-d]pyrimidin-1-yl)methyl)phenyl)-1-ethyl-1H-imidazole-4-carbaldehyde 1 (0.200 g, 0.416 mmol) in DCM (20 mL), was added DAST (0.335 g, 2.08 mmol) at room temperature. The resulting mixture was stirred for 2 h, and progress of the reaction was monitored by TLC. After completion, the reaction mixture was diluted with saturated NaHCO₃ solution (20 mL) and extracted with -continued

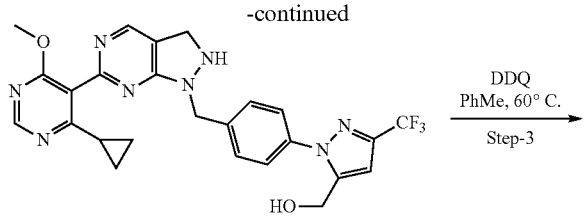
3

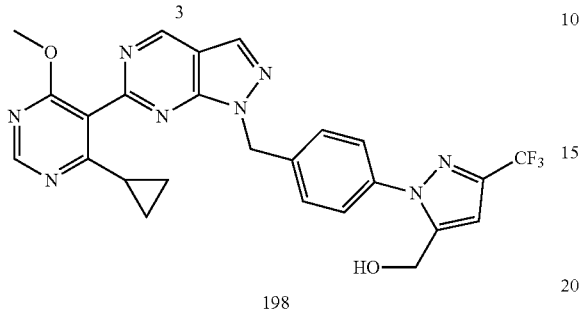
198

Step 1: Synthesis of 1-(4-(((6-(4-cyclopropyl-6-methoxypyrimidin-5-yl)-1H-pyrazolo[3,4-d]pyrimidin-1-yl)methyl)phenyl)-3-(trifluoromethyl)-1H-pyrazole-5-carboxylic Acid

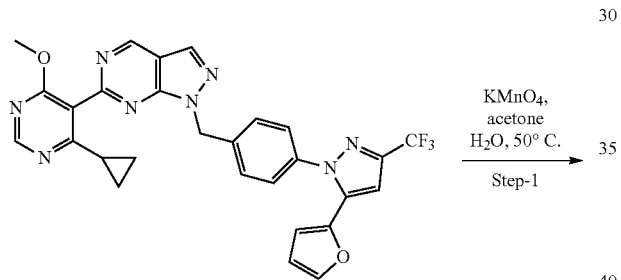
Example 30

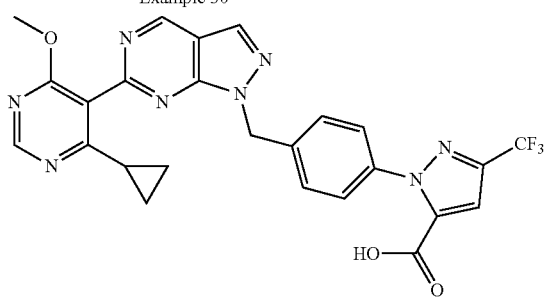
2

To a stirred solution of 6-(4-cyclopropyl-6-methoxypyrimidin-5-yl)-1-(4-(5-(furan-2-yl)-3-(trifluoromethyl)-1H-pyrazol-1-yl)benzyl)-1H-pyrazolo[3,4-d]pyrimidine (Example 30) (1.00 g, 2.25 mmol) in acetone:water (2:1, 30 mL) was added KMnO₄ (0.707 g, 4.48 mmol) at room temperature. The reaction mixture was then heated at 50° C. for 4 h. Progress of the reaction was monitored by TLC. After completion, the reaction mixture was cooled to room temperature and diluted with H₂O (50 mL). The suspension was filtered, and the filtrate obtained was concentrated under reduced pressure. The aqueous layer was washed with DCM (2×10 mL) and the pH was adjusted to 5 using 1N HCl solution. The solid precipitate was filtered, washed with water and dried in an oven at 60° C. for 2 h to afford the title compound (0.350 g). LC-MS (Method B) (ESI+): m/z 537.30 (M+H)⁺; ¹H-NMR (400 MHz, DMSO-d₆) δ 9.51 (s, 1H), 8.71 (s, 1H), 8.53 (s, 1H), 7.38-7.52 (m, 6H), 5.80 (s, 2H), 3.85 (s, 3H), 1.65 (d, J=3.99 Hz, 1H), 1.02-1.07 (m, 2H), 0.83-0.89 (m, 2H).

Step 2: Synthesis of (1-(4-(((6-(4-cyclopropyl-6-methoxypyrimidin-5-yl)-2,3-dihydro-1H-pyrazolo[3,4-d]pyrimidin-1-yl)methyl)phenyl)-3-(trifluoromethyl)-1H-pyrazol-5-yl)methanol

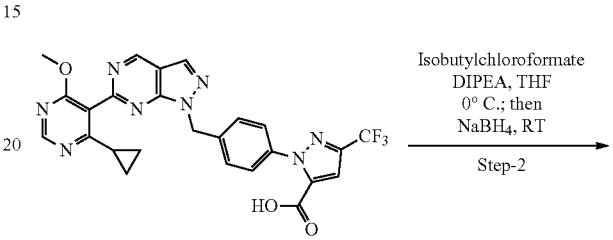
2

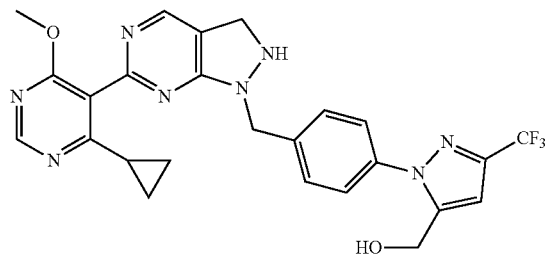
3

To an ice cooled solution of 1-(4-(((6-(4-cyclopropyl-6-methoxypyrimidin-5-yl)-1H-pyrazolo[3,4-d]pyrimidin-1-yl)methyl)phenyl)-3-(trifluoromethyl)-1H-pyrazole-5-carboxylic acid 2 (0.300 g, 0.559 mmol) in THF (10 mL), was added DIPEA (0.145 mL, 0.838 mmol) and isobutyl chloroformate (0.080 mL, 0.62 mmol) drop-wise. The resulting mixture was stirred for 30 min. To the resulting reaction mixture was added sodium borohydride (0.021 g, 0.56 mmol) in one portion at the same temperature. Then the reaction mixture was allowed to warm to room temperature and stirred for an additional 1 h. Progress of the reaction was monitored by TLC. After completion, the reaction mixture was concentrated under reduced pressure, then diluted with EA (20 mL) and water (20 mL). The organic layer was dried over anhydrous sodium sulfate, filtered and concentrated under reduced pressure. The crude compound was purified by silica gel chromatography eluting with 0-10% methanol in DCM to afford the title compound (0.050 g). LC-MS (Method B) (ESI+): m/z 525.30 (M+H)⁺; ¹H-NMR (400 MHz, DMSO-d₆) δ 8.62 (s, 1H), 7.99 (s, 1H), 7.58 (d, J=8.31 Hz, 2H), 7.35 (d, J=8.31 Hz, 2H), 7.15 (s, 1H), 6.88 (s, 1H), 5.58 (t, J=5.38 Hz, 1H), 5.25 (s, 2H), 4.74 (s, 2H), 4.49 (d, J=5.38 Hz, 2H), 3.93 (s, 3H), 2.10-2.18 (m, 1H), 0.94-1.05 (m, 4H).

Step 3: Synthesis of (1-(4-((6-(4-cyclopropyl-6-methoxypyrimidin-5-yl)-1H-pyrazolo[3,4-d]pyrimidin-1-yl)methyl)phenyl)-3-(trifluoromethyl)-1H-pyrazol-5-yl)methanol (198)

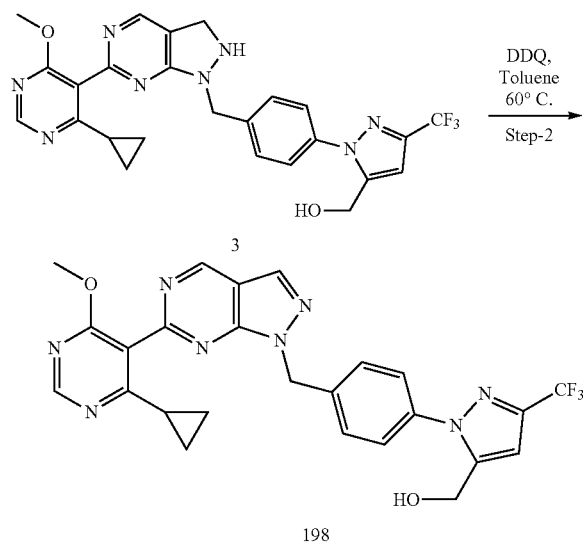

To a stirred solution of (1-(4-((6-(4-cyclopropyl-6-methoxypyrimidin-5-yl)-2,3-dihydro-1H-pyrazolo[3,4-d]pyrimidin-1-yl)methyl)phenyl)-3-(trifluoromethyl)-1H-pyrazol-5-yl)methanol 3 (0.040 g, 0.076 mmol) in toluene (4 mL), was added DDQ (0.026 g, 0.114 mmol) and the reaction mixture was heated at 60° C. for 1 h. Progress of the reaction was monitored by TLC. After completion, the reaction mixture was concentrated under reduced pressure. Purification of the crude compound by silica gel chromatography using 0-90% EA in hexane as eluent afforded impure compound which was further purified by preparative HPLC purification (Method D) to afford the title compound (0.022 g). LC-MS (Method B) (ESI+): m/z 523.25 (M+H)+; $^1$H-NMR (400 MHz, DMSO-$d_6$) δ 9.51 (s, 1H), 8.71 (s, 1H), 8.52 (s, 1H), 7.61 (d, J=7.83 Hz, 2H), 7.46 (d, J=8.31 Hz, 2H), 6.88 (s, 1H), 5.80 (s, 2H), 5.57 (t, J=5.38 Hz, 1H), 4.48 (d, J=5.38 Hz, 2H), 3.85 (s, 3H), 1.62-1.69 (m, 1H), 1.02-1.07 (m, 2H), 0.86 (dd, J=3.18, 7.58 Hz, 2H).

Example 199: Synthesis of 2-(4-((6-(4-cyclopropyl-6-methoxypyrimidin-5-yl)-1H-pyrazolo[3,4-d]pyrimidin-1-yl)methyl)phenyl)-1-isopropyl-1H-imidazol-4-amine (199)

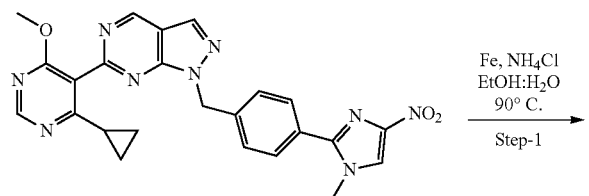

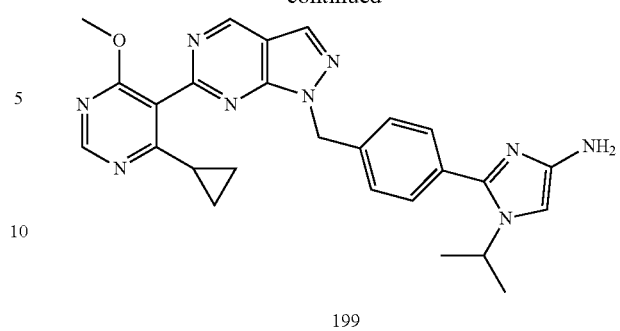

To a stirred solution of 6-(4-cyclopropyl-6-methoxypyrimidin-5-yl)-1-(4-(1-isopropyl-4-nitro-1H-imidazol-2-yl)benzyl)-1H-pyrazolo[3,4-d]pyrimidine (Example 73) (0.130 g, 0.254 mmol) in EtOH:H$_2$O (4:2 mL) was added ammonium chloride (0.067 g, 1.27 mmol) and iron powder (0.069 g, 1.27 mmol) at room temperature. The reaction mixture was heated in a sealed tube at 90° C. for 2 h. Progress of the reaction was monitored by TLC. After completion, the reaction mixture was cooled to room temperature and concentrated under reduced pressure. The crude residue obtained was diluted with water (10 mL) and extracted with DCM (2×20 mL). The combined organic layer was dried over anhydrous sodium sulfate, filtered and concentrated under reduced pressure. The crude compound was purified by silica gel chromatography using 0-5% MeOH in DCM to afford the title compound (0.550 g). LC-MS (Method B) (ESI+): m/z 482.05 (M+H)+; $^1$H-NMR (400 MHz, DMSO-$d_6$) δ 9.49 (s, 1H), 8.71 (s, 1H), 8.50 (s, 1H), 7.46 (s, 1H), 7.36 (d, J=8.48 Hz, 2H), 7.25 (d, J=7.98 Hz, 2H), 5.71 (s, 2H), 4.11-4.18 (m, 1H), 4.09 (s, 2H), 3.85 (s, 3H), 1.27 (d, J=6.48 Hz, 6H), 1.03-1.09 (m, 3H), 0.83-0.89 (m, 2H).

Example 200: Synthesis of 1-(4-(5-(azetidin-3-yloxy)-3-(trifluoromethyl)-1H-pyrazol-1-yl)benzyl)-6-(4-cyclopropyl-6-methoxypyrimidin-5-yl)-1H-pyrazolo[3,4-d]pyrimidine (200)

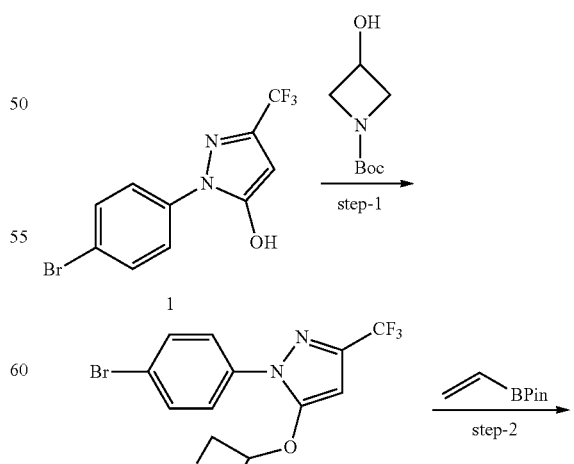

423

-continued

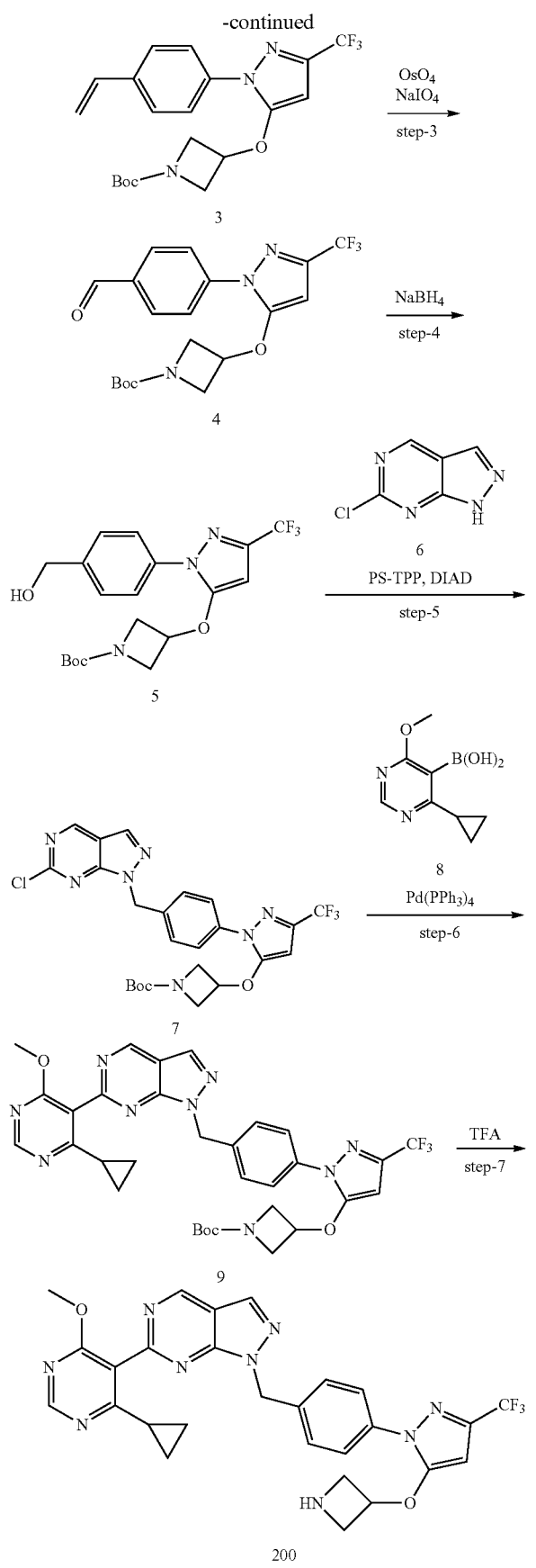

424

Step 1: Synthesis of tert-butyl 3-((1-(4-bromophenyl)-3-(trifluoromethyl)-1H-pyrazol-5-yl)oxy)azetidine-1-carboxylate

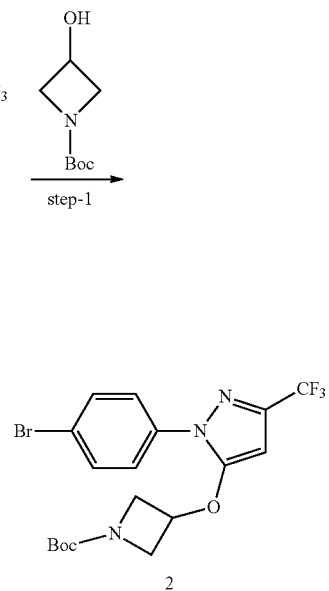

To a solution of 1-(4-bromophenyl)-3-(trifluoromethyl)-1H-pyrazol-5-ol (I-39, intermediate 3) (550 mg, 1.63 mmol) in THF (10 mL) at 0° C. was added tert-butyl 3-hydroxyazetidine-1-carboxylate (339 mg, 1.96 mmol) and PS-TPP (2.18 g, 4.52 mmol) in one portion. After the reaction was stirred at 0° C. for 10 min, DIAD (495 mg, 2.45 mmol) was added to the reaction dropwise over 2 min. The reaction was stirred at 0° C. for 10 min, then warmed to room temperature and stirred overnight. After the reaction was complete as indicated by TLC analysis, the mixture was quenched with water (20 mL) and extracted with EA (20 mL×3). The organic layer was dried over sodium sulfate (20 g), filtered and concentrated. The resulting residue was purified by silica gel chromatography (eluent: PE/EA=50/1 to 25/1) to yield 420 mg of the title compound. LC-MS (Method A) (ESI+): m/z 462, 464 (M+H)$^+$; $^1$H-NMR (300 MHz, CDCl$_3$) δ 7.60 (s, 4H), 5.74 (s, 1H), 4.94 (m, 1H), 4.31-4.39 (m, 2H), 4.04-4.19 (m, 2H), 1.45 (s, 9H).

Step 2: Synthesis of tert-butyl 3-((3-(trifluoromethyl)-1-(4-vinylphenyl)-1H-pyrazol-5-yl)oxy)azetidine-1-carboxylate

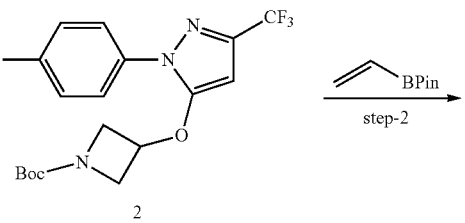

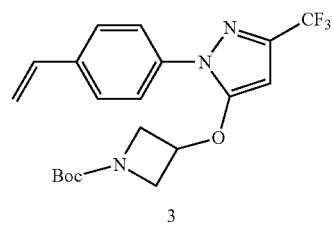

To a solution of tert-butyl 3-((1-(4-bromophenyl)-3-(trifluoromethyl)-1H-pyrazol-5-yl)oxy)azetidine-1-carboxylate 2 (370 mg, 0.80 mmol) in toluene (6 mL) was added tributyl(vinyl)stannane (382 mg, 1.20 mmol) and Pd(PPh$_3$)$_4$ (92 mg, 0.08 mmol). The reaction was then stirred at 90° C. overnight. After the reaction was complete as indicated by LC-MS analysis, the mixture was quenched with water (10 mL) and extracted with EA (15 mL×2). The combined organic was dried over sodium sulfate (30 g), filtered and concentrated. The resulting residue was purified by silica gel chromatography (eluent: PE/EA=30/1 to 20/1) to yield 300 mg of the title compound. LC-MS (Method A) (ESI+): m/z 410 (M+H)$^+$; $^1$H-NMR (300 MHz, CDCl$_3$) δ 7.65 (d, J=8.7 Hz, 2H), 7.50 (d, J=8.7 Hz, 2H), 6.78 (m, 1H), 5.75-5.79 (m, 2H), 5.32 (d, J=7.2 Hz, 1H), 4.92 (m, 1H), 4.30-4.39 (m, 2H), 4.05-4.20 (m, 2H), 1.45 (s, 9H).

Step 3: Synthesis of tert-butyl 3-((1-(4-formylphenyl)-3-(trifluoromethyl)-1H-pyrazol-5-yl)oxy)azetidine-1-carboxylate

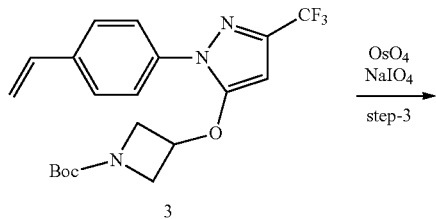

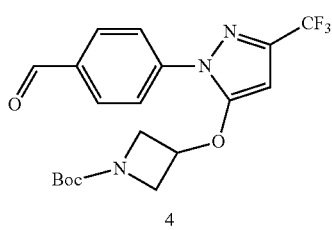

The compound was synthesized according to the procedure for the preparation of common intermediate I-33. LC-MS (Method A) (ESI+): m/z 434.19 (M+Na)$^+$.

Step 4: Synthesis of tert-butyl 3-((1-(4-(hydroxymethyl)phenyl)-3-(trifluoromethyl)-1H-pyrazol-5-yl)oxy)azetidine-1-carboxylate

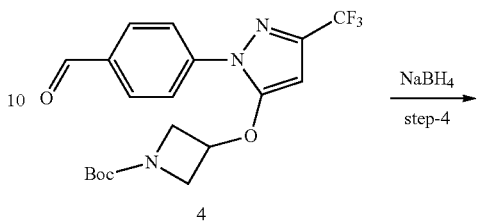

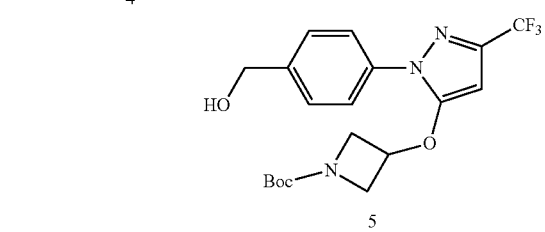

The compound was synthesized according to the procedure for the preparation of common intermediate I-33. LC-MS (Method A) (ESI+): m/z 414 (M+Na)$^+$; $^1$H-NMR (300 MHz, CDCl$_3$) δ 7.68 (d, J=8.1 Hz, 2H), 7.48 (d, J=8.1 Hz, 2H), 5.75 (s, 1H), 4.94 (m, 1H), 4.76 (d, J=5.4 Hz, 2H), 4.30-4.35 (m, 2H), 4.04-4.13 (m, 2H), 1.85 (m, 1H), 1.45 (s, 9H).

Step 5: Synthesis of tert-butyl 3-((1-(4-((6-chloro-1H-pyrazolo[3,4-d]pyrimidin-1-yl)methyl)phenyl)-3-(trifluoromethyl)-1H-pyrazol-5-yl)oxy)azetidine-1-carboxylate

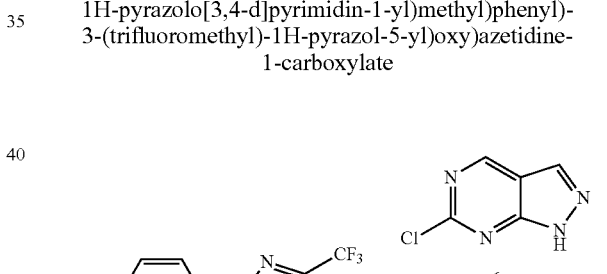

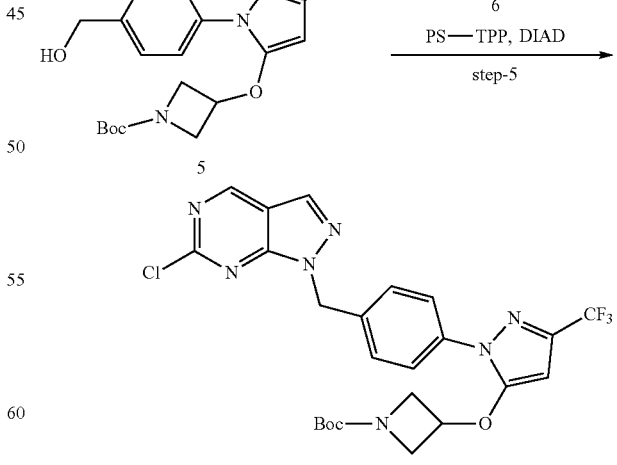

The compound was synthesized according to the procedure described in Example 148. LC-MS (Method A) (ESI+): m/z 572.00 (M+Na)$^+$.

427

Step 6: Synthesis of 3-((1-(4-((6-(4-cyclopropyl-6-methoxypyrimidin-5-yl)-1H-pyrazolo[3,4-d]pyrimidin-1-yl)methyl)phenyl)-3-(trifluoromethyl)-1H-pyrazol-5-yl)oxy)azetidine-1-carboxylate

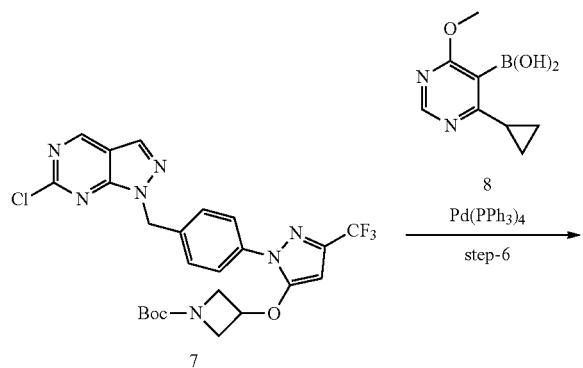

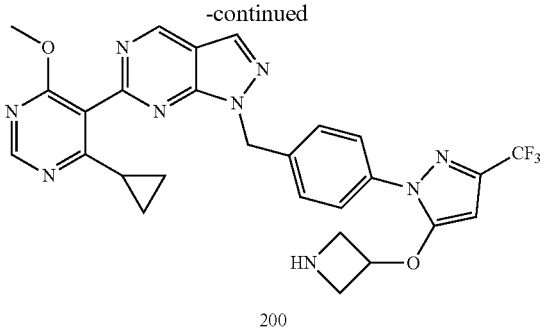

The compound was synthesized according to procedure of General Experimental Procedure 1. LC-MS (Method A) (ESI+): m/z 664 (M+H)+.

Step 7: Synthesis of 1-(4-(5-(azetidin-3-yloxy)-3-(trifluoromethyl)-1H-pyrazol-1-yl)benzyl)-6-(4-cyclopropyl-6-methoxypyrimidin-5-yl)-1H-pyrazolo[3,4-d]pyrimidine (200)

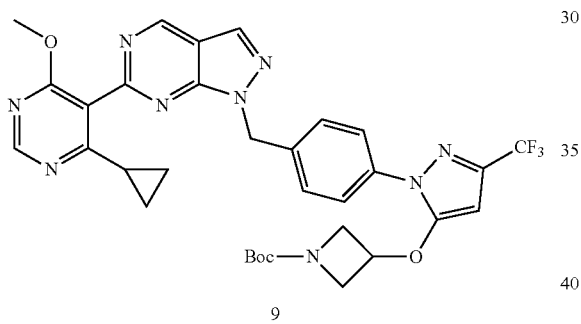

428

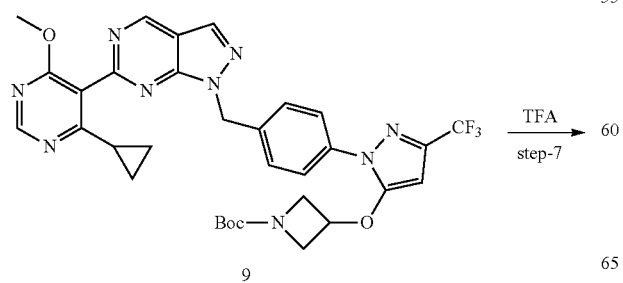

To a solution of tert-butyl 3-((1-(4-((6-(4-cyclopropyl-6-methoxypyrimidin-5-yl)-1H-pyrazolo[3,4-d]pyrimidin-1-yl)methyl)phenyl)-3-(trifluoromethyl)-1H-pyrazol-5-yl)oxy)azetidine-1-carboxylate 9 (90 mg, 0.14 mmol) in DCM (10 mL) and TFA (1 mL) was stirred at rt for 1 h. After the reaction was complete as indicated by TLC analysis, the mixture was quenched with water (10 mL) and the pH was adjusted to 8 with a sodium carbonate solution. The mixture was extracted with DCM (10 mL×3), and the organic layer was dried over sodium sulfate (30 g), filtered and concentrated. The residue was purified by preparative HPLC (Method A) to afford 24.6 mg of the title compound. LC-MS (Method A) (ESI+): m/z 564 (M+H)+; $^1$H-NMR (300 MHz, CD$_3$OD) (9.40 (s, 1H), 8.64 (s, 1H), 8.41 (s, 1H), 7.68 (d, J=8.4 Hz, 2H), 7.51 (d, J=8.4 Hz, 2H), 6.06 (s, 1H), 5.79 (s, 2H), 5.12 (m, 1H), 3.95-4.02 (m, 2H), 3.92 (s, 3H), 3.65-3.71 (m, 2H), 1.65 (m, 1H), 1.09-1.19 (m, 2H), 0.85-0.92 (m, 2H).

Example 201: Synthesis of 2-(4-cyclopropyl-6-methoxypyrimidin-5-yl)-7-(4-(1-methyl-4-(trifluoromethyl)-1H-imidazol-2-yl)benzyl)-7H-pyrrolo[2,3-d]pyrimidine (201)

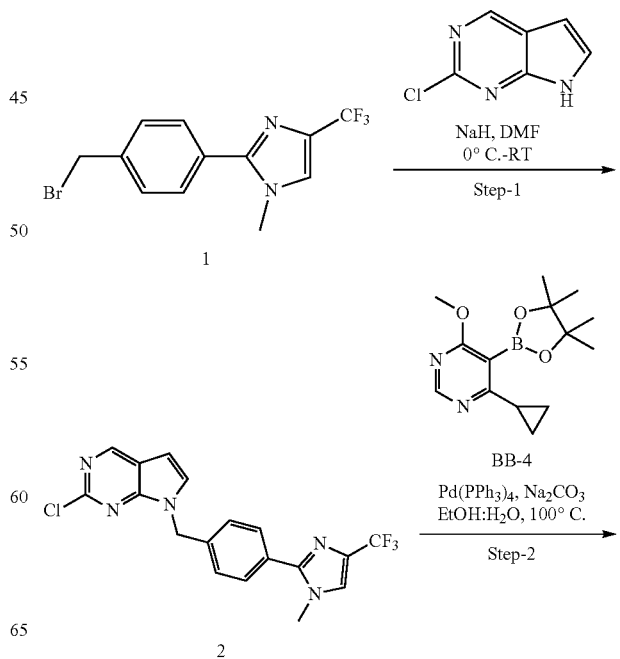

429

-continued

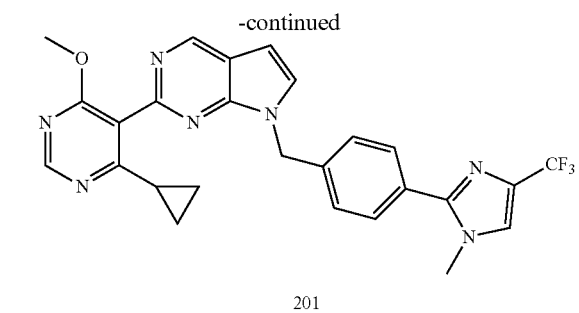

201

Step 1: Synthesis of 2-chloro-7-(4-(1-methyl-4-(trifluoromethyl)-1H-imidazol-2-yl)benzyl)-7H-pyrrolo[2,3-d]pyrimidine

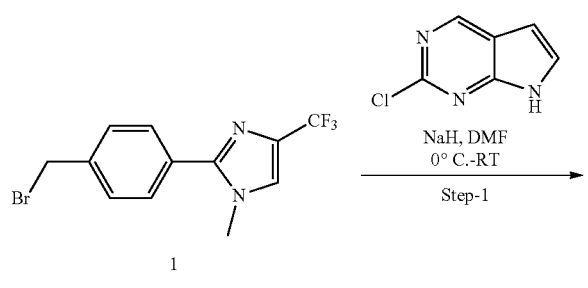

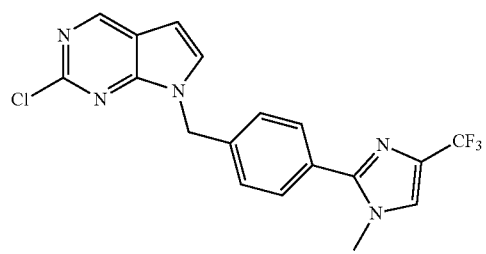

2

To an ice cooled solution of 2-chloro-7H-pyrrolo[2,3-d]pyrimidine (0.140 g, 0.914 mmol) in DMF (5 mL) was added 60% dispersion of sodium hydride in oil (0.073 g, 1.83 mmol) portion-wise. The resulting mixture was stirred for 30 min and was then treated with 2-(4-(bromomethyl)phenyl)-1-methyl-4-(trifluoromethyl)-1H-imidazole 1 (0.292 g, 0.914 mmol). The mixture was further stirred for 2 h at room temperature. Progress of the reaction was monitored by TLC. After completion, the reaction mixture was quenched with ice water (10 mL) and extracted with EA (2×25 mL). The combined organic layer was washed with cold water (10 mL) followed by brine (10 mL), dried over anhydrous sodium sulfate, filtered and concentrated under reduced pressure. The crude compound was purified by silica gel chromatography using 30-50% EA in n-hexane to afford the title compound (0.260 g). LC-MS (Method B) (ESI+): m/z 391.90 (M+H)+.

430

Step 2: Synthesis of 2-(4-cyclopropyl-6-methoxypyrimidin-5-yl)-7-(4-(1-methyl-4-(trifluoromethyl)-1H-imidazol-2-yl)benzyl)-7H-pyrrolo[2,3-d]pyrimidine (201)

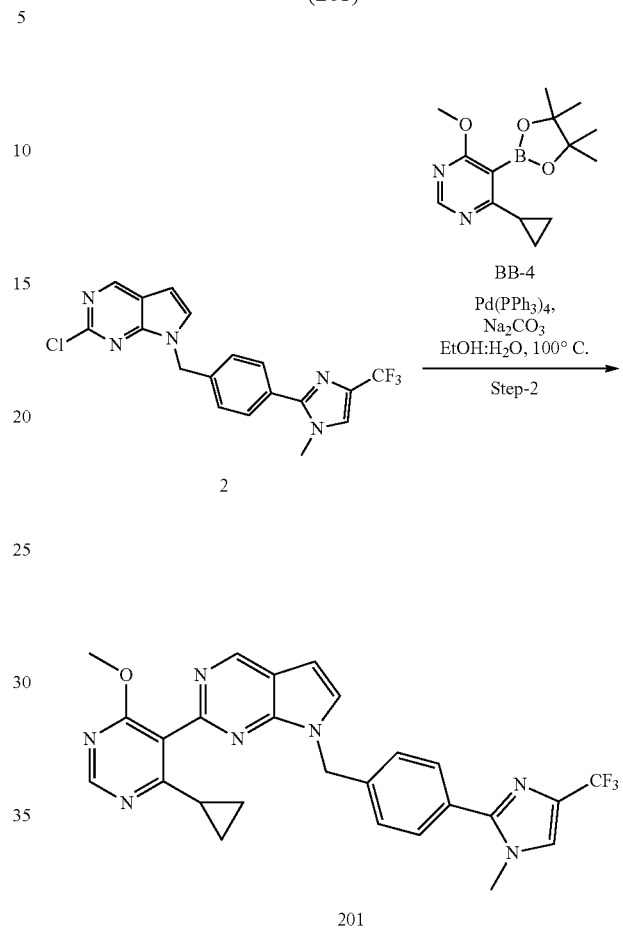

To a stirred solution of 4-cyclopropyl-6-methoxy-5-(4,4,5,5-tetramethyl-1,3,2-dioxaborolan-2-yl)pyrimidine BB-4 (0.243 g, 0.880 mmol) and 2-chloro-7-(4-(1-methyl-4-(trifluoromethyl)-1H-imidazol-2-yl)benzyl)-7H-pyrrolo[2,3-d]pyrimidine 2 (0.230 g, 0.587 mmol) in ethanol:H$_2$O (10:2 mL) was added Na$_2$CO$_3$ (0.186 g, 1.76 mmol) at room temperature. The resulting mixture was degassed with argon for 10 min and then treated with Pd(PPh$_3$)$_4$ (0.034 g, 0.029 mmol) at room temperature. The mixture was further degassed with argon for 5 min, and then heated in microwave at 100° C. for 2 h. Progress of the reaction was monitored by TLC. After completion, the reaction mixture was diluted with EA (25 mL) and filtered through a pad of Celite. The organic layer was separated, washed with brine, dried over anhydrous sodium sulfate, filtered and concentrated under reduced pressure. The crude compound was purified by silica gel chromatography using 0-50% EA in n-hexane followed by repurification by preparative HPLC (Method B) to afford the title compound (0.032 g). LC-MS (Method B) (ESI+): m/z 506.15 (M+H)+; $^1$H-NMR (400 MHz, DMSO-d$_6$) δ 9.16 (s, 1H), 8.67 (s, 1H), 7.92 (s, 1H), 7.85 (d, J=3.42 Hz, 1H), 7.66 (d, J=7.83 Hz, 2H), 7.40 (d, J=8.31 Hz, 2H), 6.76 (d, J=3.42 Hz, 1H), 5.57 (s, 2H), 3.83 (s, 3H), 3.73 (s, 3H), 1.60-1.66 (m, 1H), 1.00-1.04 (m, 2H), 0.81 (dd, J=3.18, 7.58 Hz, 2H).

Example 202: General Procedure for the Synthesis of Imidazolopyrimidines Preparation of 2-(2-Isopropylphenyl)-9-(4-(1-methyl-4-(trifluoromethyl)-1H-imidazol-2-yl)benzyl)-9H-purine (202)

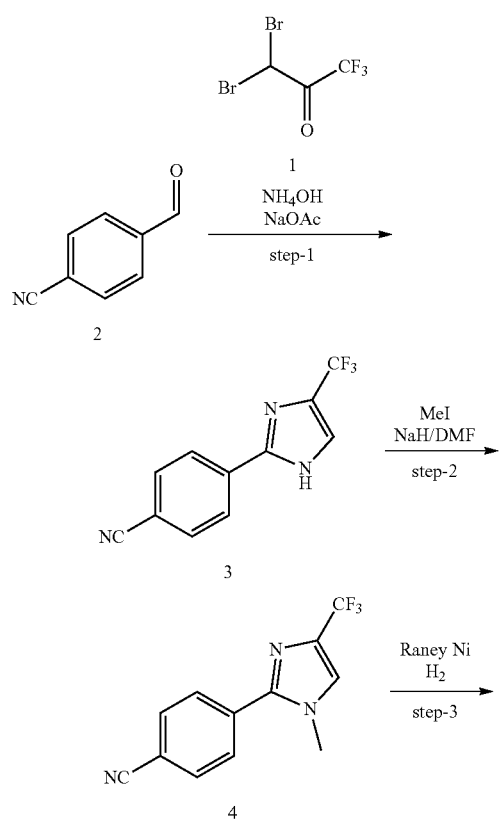

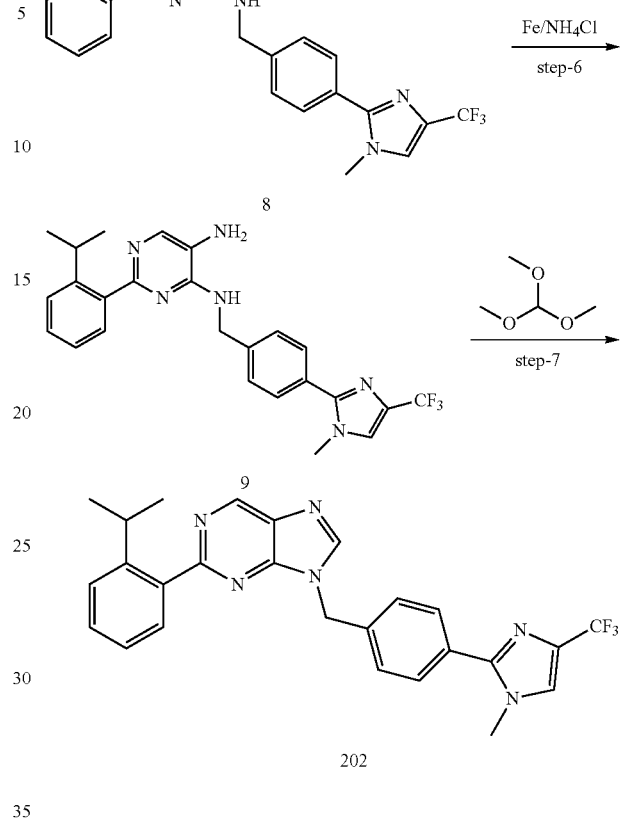

Step 1: Synthesis of 4-(4-(Trifluoromethyl)-1H-imidazol-2-yl)benzonitrile

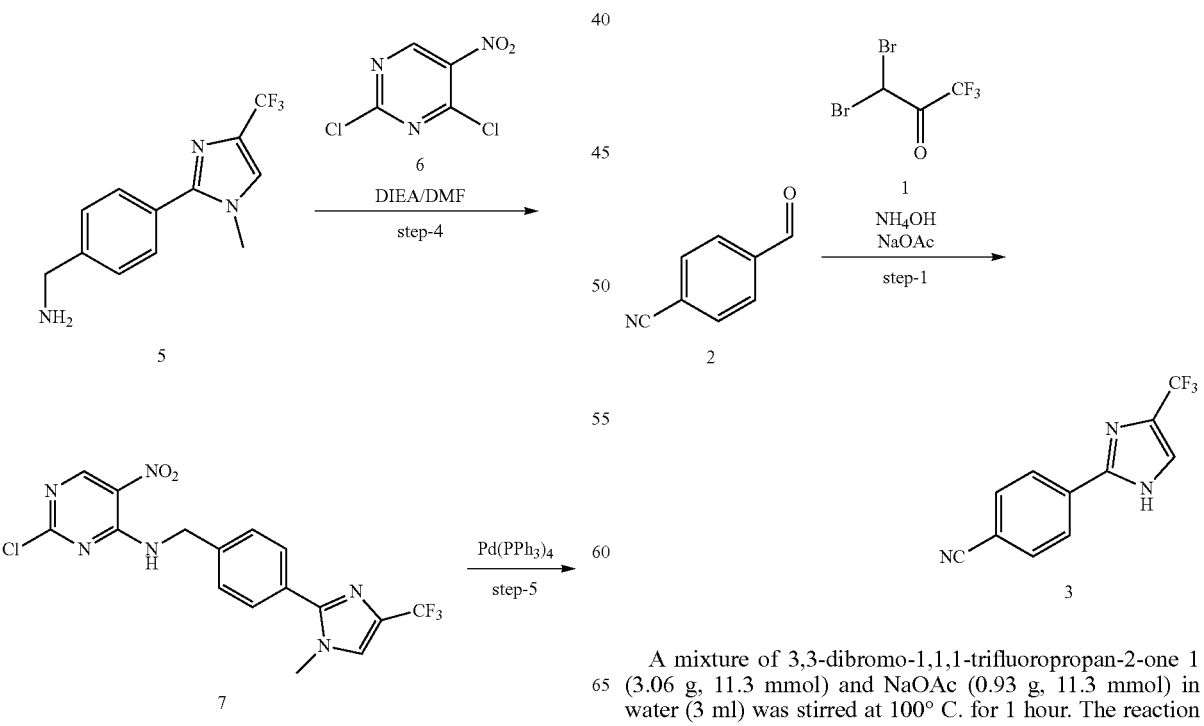

A mixture of 3,3-dibromo-1,1,1-trifluoropropan-2-one 1 (3.06 g, 11.3 mmol) and NaOAc (0.93 g, 11.3 mmol) in water (3 ml) was stirred at 100° C. for 1 hour. The reaction was cooled to room temperature and a mixture of 4-formylbenzonitrile 2 (1.5 g, 11.3 mmol) in methanol (50 ml) and NH₄OH (10 ml) were added to the reaction subsequently. The resulting reaction mixture was stirred at room temperature for 40 min, and then at 100° C. for 2 hours. The mixture was then cooled to room temperature and quenched with water (100 mL), and then extracted with EA (100 mL×2). The combined organic layer was dried with Na₂SO₄ (30 g), filtered and concentrated to dryness to afford the crude product that was purified by column chromatography (eluent: EA/n-Hex=1:10 to 1:5) to afford 1.5 g of the title compound. LC-MS (Method A) (ESI+): m/z 238 (M+H)⁺; ¹H-NMR (300 MHz, DMSO-d₆) δ 13.55 (br s, 1H), 8.14 (d, J=8.1 Hz, 1H), 8.07 (s, 1H), 7.97 (d, J=8.1 Hz, 1H).

Step 2: Synthesis of 4-(1-Methyl-4-(trifluoromethyl)-1H-imidazol-2-yl)benzonitrile

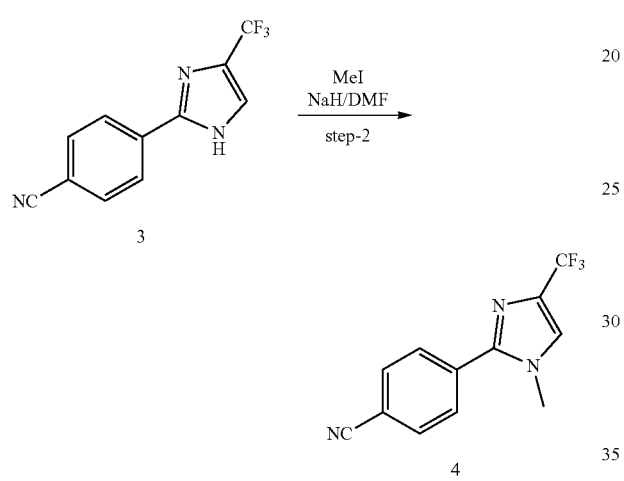

To a solution of 4-(4-(trifluoromethyl)-1H-imidazol-2-yl)benzonitrile 3 (1.37 g, 5.8 mmol) in THF (15 mL) at 0° C., was added NaH (290 mg, 7.25 mmol) portion-wise over 2 min. After addition, the resulting suspension was stirred at 0° C. for 1 hour. MeI (1.03 g, 7.25 mmol) was then added dropwise over 2 min, and the mixture was stirred at 0° C. for an additional 2.5 hours. The reaction was then quenched with a saturated NH₄Cl solution (30 mL) and extracted with EA (50 mL×2). The combined organic layer was dried with Na₂SO₄ (30 g), filtered and concentrated to dryness. The residue was purified by column chromatography (eluent:EA/n-Hex=1:10 to 1:5) to afford 700 mg of the title compound. LC-MS (Method A) (ESI+): m/z 252 (M+H); ¹H-NMR (300 MHz, CDCl₃) (7.76-7.83 (m, 4H), 7.38 (s, 1H), 3.83 (s, 3H).

Step 3: Synthesis of (4-(1-Methyl-4-(trifluoromethyl)-1H-imidazol-2-yl)phenyl)methanamine

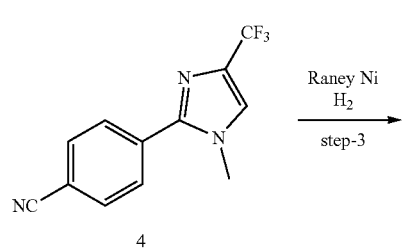

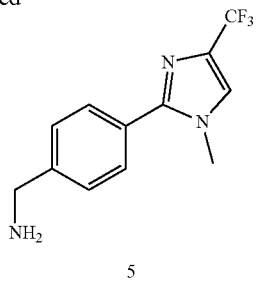

A suspension of 4-(1-methyl-4-(trifluoromethyl)-1H-imidazol-2-yl)benzonitrile 4 (2.5 g, 9.9 mmol) and Raney Ni (2 g, wet solid) in EA (100 mL) and NH₃.H₂O (0.5 mL), was hydrogenated using a H₂ balloon (1 atm). After the reaction was stirred at room temperature for 2.5 hours, the suspension was filtered through a pad of Celite. The filter cake was washed with EA (10 mL), and the filtrate was concentrated to dryness to afford 2.5 g of the crude title compound. LC-MS (Method A) (ESI+): m/z 256 (M+H)⁺; ¹H-NMR (300 MHz, CDCl₃) δ 7.60 (d, J=8.1 Hz, 1H), 7.46 (d, J=8.1 Hz, 1H), 7.31 (s, 1H), 3.95 (s, 2H), 3.77 (s, 3H).

Step 4: Synthesis of 2-Chloro-N-(4-(1-methyl-4-(trifluoromethyl)-1H-imidazol-2-yl)benzyl)-5-nitro-pyrimidin-4-amine

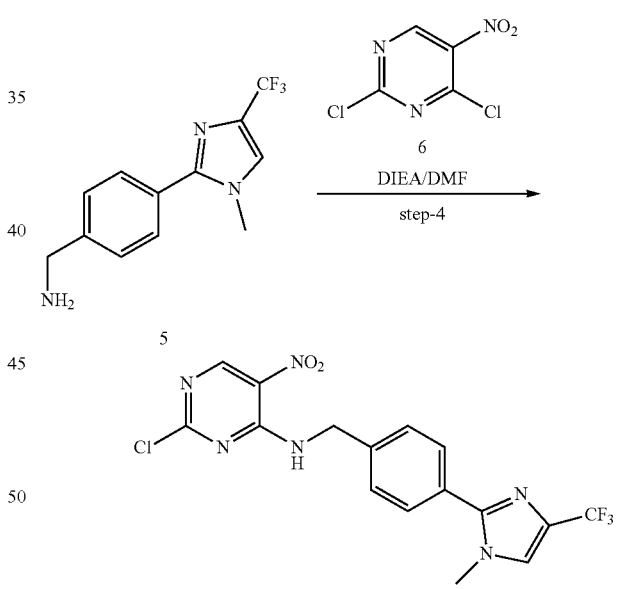

A mixture of (4-(1-methyl-4-(trifluoromethyl)-1H-imidazol-2-yl)phenyl)methanamine 5 (0.87 g, 3.4 mmol), 2,4-dichloro-5-nitropyrimidine 6 (0.66 g, 3.4 mmol) and DIEA (0.88 g, 6.8 mmol) in DMF (12 mL) was stirred at rt for 30 min. The mixture was then quenched with water and extracted with EA (50 mL×3). The combined organic layer was washed with water (30 mL), dried over anhydrous Na₂SO₄ (30 g), filtered and concentrated in vacuo. The residue was purified by silica gel chromatography (eluent: EA:n-Hex=1:20 to 1:4) to give 480 mg of the title compound. ¹H-NMR (300 MHz, CDCl₃) δ 9.09 (s, 1H), 8.74 (br s, 1H), 7.66 (d, J=8.1 Hz, 2H), 7.48 (d, J=8.1 Hz, 2H), 7.33 (s, 1H), 4.91 (d, J=6.0 Hz, 2H), 3.79 (s, 3H).

Step 5: Synthesis of 2-(2-Isopropylphenyl)-N-(4-(1-methyl-4-(trifluoromethyl)-1H-imidazol-2-yl)benzyl)-5-nitropyrimidin-4-amine

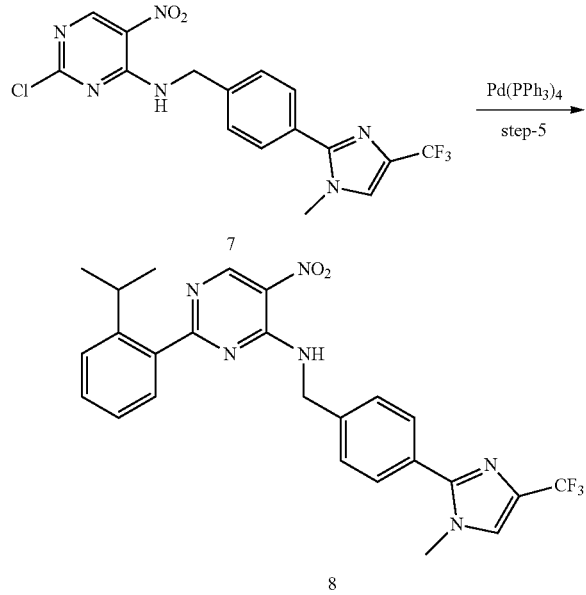

A mixture of 2-chloro-N-(4-(1-methyl-4-(trifluoromethyl)-1H-imidazol-2-yl) benzyl)-5-nitropyrimidin-4-amine 7 (0.30 g, 0.74 mmol), $K_3PO_4$ (0.47 g, 2.2 mmol), Pd(dppf)$Cl_2$ (121 mg, 20 mol %) and (2-isopropylphenyl)boronic acid (0.24 g, 1.5 mmol) in DME (18 mL) was stirred at 80° C. for 3 hours. The mixture was then cooled to room temperature and diluted with water (20 mL), and subsequently extracted with EA (50 mL×3). The combined organic layer was dried over anhydrous $Na_2SO_4$ (20 g), filtered and concentrated in vacuo. The residue was purified by silica gel chromatography (eluent: EA:n-Hex=1:10 to 1:5) to give 300 mg of the title compound. LC-MS (Method A) (ESI): m/z 497 (M+H)$^+$.

Step 6: Synthesis of 2-(2-Isopropylphenyl)-N4-(4-(1-methyl-4-(trifluoromethyl)-1H-imidazol-2-yl)benzyl)pyrimidine-4,5-diamine

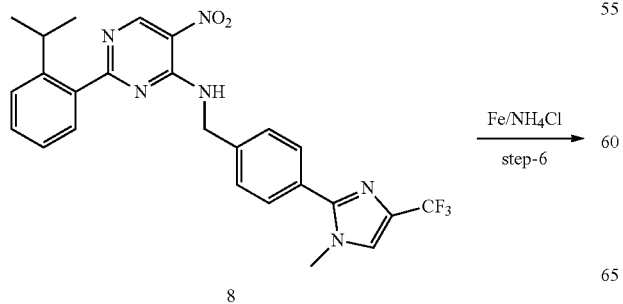

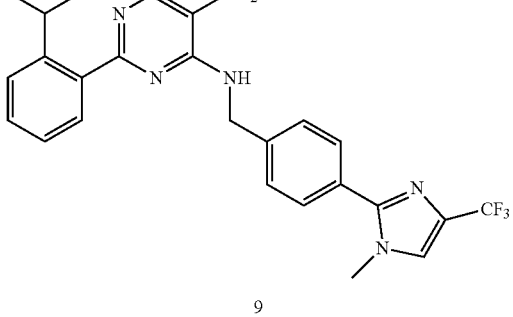

To a solution of 2-(2-isopropylphenyl)-N-(4-(1-methyl-4-(trifluoromethyl)-1H-imidazol-2-yl)benzyl)-5-nitropyrimidin-4-amine 8 (0.28 g, 0.56 mmol) in EtOH (30 mL), was added $FeCl_3$ (18 mg, 0.11 mmol), $N_2H_4$ (1.13 g, 17.9 mmol) and charcoal (0.11 g) under $N_2$ atmosphere. The resulting mixture was stirred at 70° C. for 2 hours, and then the suspension was filtered through a pad of Celite. The filter cake was washed with EA (30 mL). The filtrate was diluted with water (50 mL) and extracted with EA (50 mL×3). The combined organic layer was washed with water (20 mL) and dried over anhydrous $Na_2SO_4$ (30 g), filtered and concentrated in vacuo. The residue was purified by silica gel chromatography (eluent: EA:n-Hex=1:10 to 2:1) to give 330 mg of the title compound. LC-MS (Method A) (ESI+): m/z 467 (M+H)$^+$.

Step 7: Synthesis of 2-(2-Isopropylphenyl)-9-(4-(1-methyl-4-(trifluoromethyl)-1H-imidazol-2-yl)benzyl)-9H-purine (202)

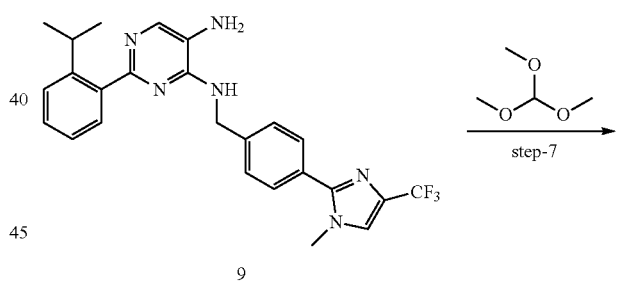

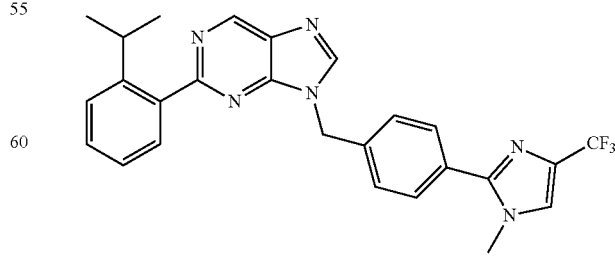

To a solution of 2-(2-isopropylphenyl)-N4-(4-(1-methyl-4-(trifluoromethyl)-1H-imidazol-2-yl) benzyl)pyrimidine-4,5-diamine 9 (60 mg, 0.13 mmol) in dioxane (4.8 mL), was added methanesulfonic acid (0.30 mg, 2.5%) and trimethoxymethane (1.2 mL) in one portion. After addition, the reaction was stirred at 80° C. for 1 hour. The reaction was then cooled to room temperature, quenched with water (10 mL), and extracted with EA (20 mL×3). The combined organic layer was dried over anhydrous Na$_2$SO$_4$ (20 g), filtered and concentrated in vacuo. The residue was purified by preparative HPLC (Method A) to give 28 mg of the title compound. LC-MS (Method A) (ESI+): m/z 477 (M+H)$^+$; $^1$H-NMR (300 MHz, CD$_3$OD) δ 9.18 (s, 1H), 8.69 (s, 1H), 7.64-7.68 (m, 3H), 7.53-7.56 (m, 3H), 7.40-7.48 (m, 2H), 7.27 (m, 1H), 5.66 (s, 2H), 3.74 (s, 3H), 3.37 (m, 1H), 1.16 (d, J=6.9 Hz, 6H).

The following compound was prepared according to the General Experimental Procedure 202:

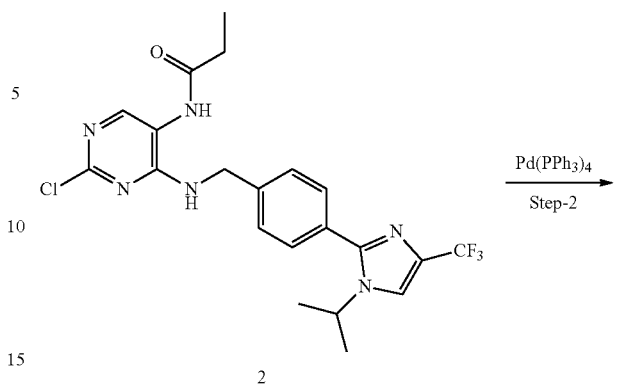

| Example | Structure | Analytical data |
|---|---|---|
| 203 | 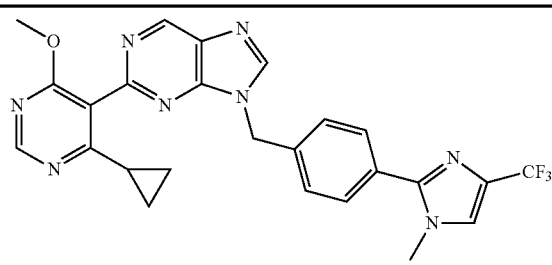 | LC-MS (Method A) (ESI+): m/z 507 (M + H)$^+$; $^1$H-NMR (300 MHz, CD$_3$OD) δ 9.23 (s, 1H), 8.75 (s, 1H), 8.63 (s, 1H), 7.64-7.69 (m, 3H), 7.58 (d, J = 8.1 Hz, 2H), 5.67 (s, 2H), 3.90 (s, 3H), 3.75 (s, 3H), 1.65 (m, 1H), 1.13-1.15 (m, 2H), 0.85-0.88 (m, 2H). |
| 204 | 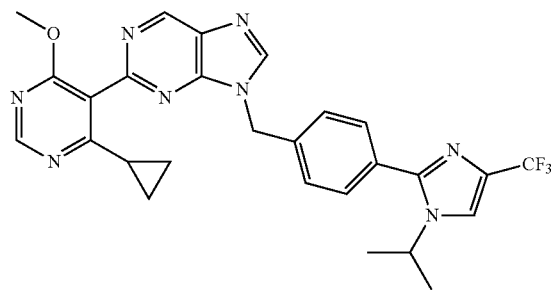 [SMILES: COc1ncnc(C2CC2)c1-c1ncc2ncn(Cc3ccc(-c4nc(C(F)(F)F)cn4C(C)C)cc3)c2n1] | LC-MS (Method C) (ESI+): m/z 535.15 (M + H)$^+$; $^1$H-NMR (400 MHz, DMSO-d$_6$) δ 9.32 (s, 1H), 8.86 (s, 1H), 8.68 (s, 1H), 8.17 (s, 1H), 7.48-7.57 (m, 4H), 5.63 (s, 2H), 4.41 (td, J = 6.48, 12.96 Hz, 1H), 3.83 (s, 3H), 1.58-1.65 (m, 1H), 1.37 (d, J = 6.48 Hz, 6H), 1.00-1.05 (m, 2H), 0.77-0.84 (m, 2H). |

Example 205: Preparation of 2-(4-cyclopropyl-6-methoxypyrimidin-5-yl)-8-ethyl-9-(4-(1-isopropyl-4-(trifluoromethyl)-1H-imidazol-2-yl)benzyl)-9H-purine (205)

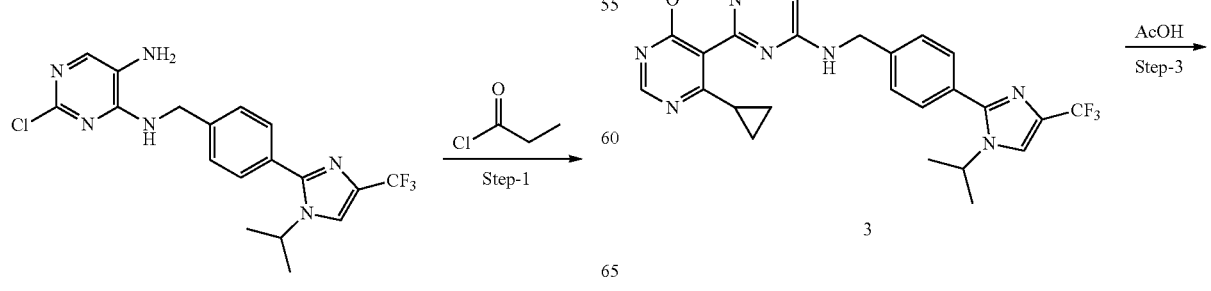

439

-continued

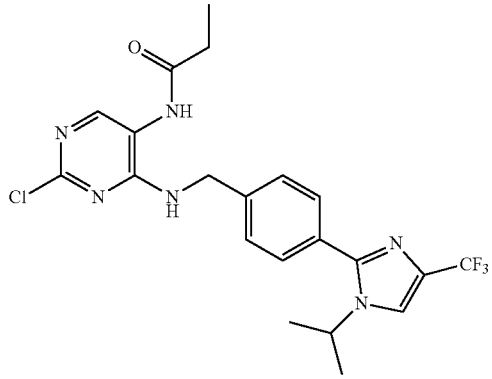

205

Synthesis of 2-chloro-N4-(4-(1-isopropyl-4-(trifluoromethyl)-1H-imidazol-2-yl)benzyl)pyrimidine-4,5-diamine

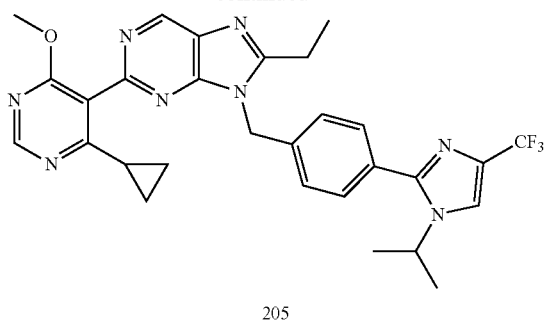

1

The compound was synthesized according to General Experimental Procedure 202. LC-MS (Method A) (ESI+): m/z 411 (M+H)⁺; ¹H-NMR (300 MHz, CDCl₃) δ 7.59 (s, 1H), 7.47 (d, J=8.4 Hz, 2H), 7.39-7.42 (m, 3H), 5.61 (br s, 1H), 4.71 (d, J=5.7 Hz, 2H), 4.49-4.58 (m, 1H), 3.22 (br s, 2H), 1.45 (d, J=6.6 Hz, 6H).

Step 1: Synthesis of N-(2-chloro-4-((4-(1-isopropyl-4-(trifluoromethyl)-1H-imidazol-2-yl)benzyl)amino)pyrimidin-5-yl)propionamide

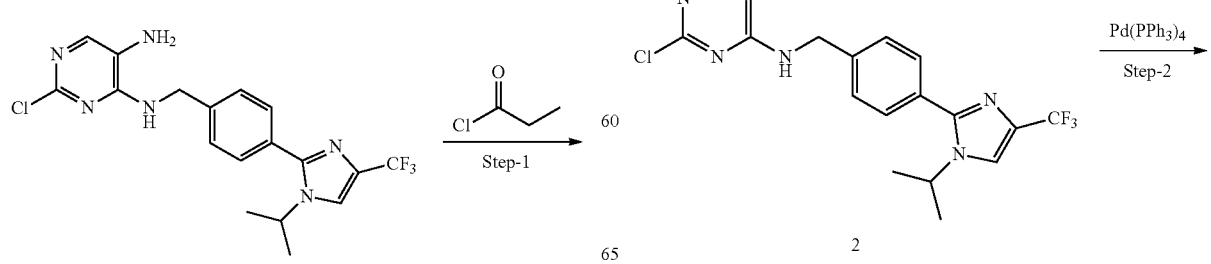

440

-continued

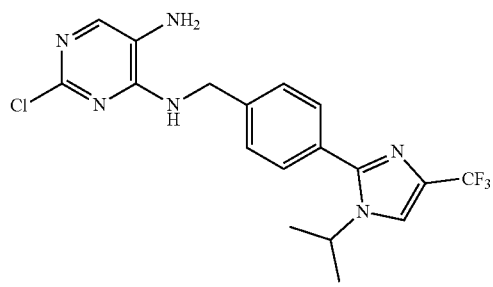

2

To a solution of 2-chloro-N⁴-(4-(1-isopropyl-4-(trifluoromethyl)-1H-imidazol-2-yl)benzyl)pyrimidine-4,5-diamine 1 (250 mg, 0.61 mmol) in anhydrous THF (10 mL) was added propionyl chloride (65 mg, 0.70 mmol) dropwise over 2 min. The resulting mixture was stirred at rt for 1 h. After the reaction was completed as indicated by TLC analysis, the reaction was quenched with an aqueous NaHCO₃ solution (10 mL) and extracted with EA (20 mL×2). The combined organic layer was dried with Na₂SO₄, filtered and concentrated. The residue was purified by silica gel chromatography (PE/EA=3/1 to 1/1) to provide 320 mg of the title compound. LC-MS (Method A) (ESI+): m/z 467 (M+H)⁺; ¹H-NMR (300 MHz, CDCl₃) δ 8.27 (s, 1H), 7.98 (s, 1H), 7.44 (s, 1H), 7.31-7.38 (m, 4H), 6.13 (m, 1H), 4.65 (d, J=5.7 Hz, 2H), 4.48 (m, 1H), 2.40 (q, J=7.5 Hz, 2H), 1.41-1.46 (d, J=6.6 Hz, 6H), 1.25 (t, J=7.5 Hz, 3H).

Step 2: Synthesis of N-(4'-cyclopropyl-4-((4-(1-isopropyl-4-(trifluoromethyl)-1H-imidazol-2-yl)benzyl)amino)-6'-methoxy-[2,5'-bipyrimidin]-5-yl)propionamide

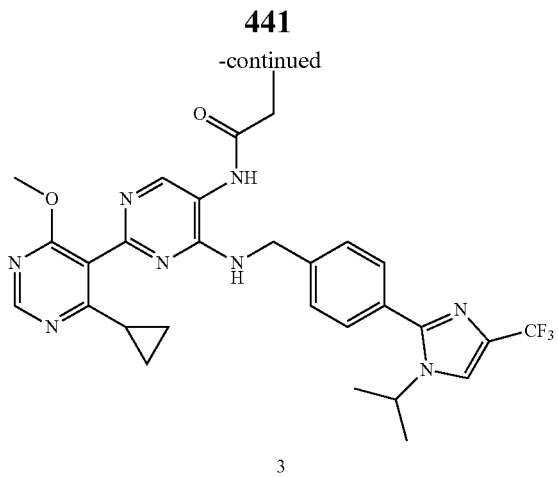

3

The compound was synthesized according to General Experimental Procedure 1. LC-MS (Method A) (ESI+): m/z 581 (M+H)+; 1H-NMR (300 MHz, CDCl3) δ 8.60 (s, 1H), 8.26 (s, 1H), 7.40-7.42 (m, 6H), 6.10 (m, 1H), 4.75 (d, J=5.4 Hz, 2H), 4.50 (m, 1H), 3.91 (s, 3H), 2.43 (q, J=7.2 Hz, 2H), 2.10-2.13 (m, 1H), 1.41-1.46 (m, 6H), 1.26-1.28 (m, 4H), 0.85-0.89 (m, 2H).

Step 3: Synthesis of 2-(4-cyclopropyl-6-methoxypyrimidin-5-yl)-8-ethyl-9-(4-(1-isopropyl-4-(trifluoromethyl)-1H-imidazol-2-yl)benzyl)-9H-purine (205)

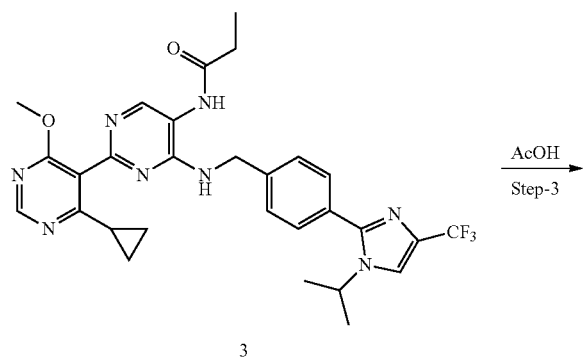

A solution of N-(4'-cyclopropyl-4-((4-(1-isopropyl-4-(trifluoromethyl)-1H-imidazol-2-yl)benzyl)amino)-6'-methoxy-[2,5'-bipyrimidin]-5-yl)propionamide 3 (80 mg, 0.14 mmol) in AcOH (5 mL) was stirred at reflux for 7 h. After the reaction was complete as indicated by TLC analysis, the reaction was concentrated to dryness. The residue was dissolved in EA (50 mL) was washed with an aqueous NaHCO3 solution (20 mL). The organic layer was dried, filtered and concentrated to give a crude product. The crude product was purified by preparative HPLC (Method A) to give 57 mg of the title compound. LC-MS (Method A) (ESI+): m/z 563 (M+H)+; 1H-NMR (300 MHz, CD3OD) δ 9.11 (s, 1H), 8.61 (s, 1H), 7.91 (s, 1H), 7.54 (d, J=8.1 Hz, 2H), 7.44 (d, J=8.1 Hz, 2H), 5.67 (s, 2H), 4.52 (m, 1H), 3.91 (s, 3H), 3.03 (q, J=7.5 Hz, 2H), 1.68 (m, 1H), 1.38-1.44 (m, 9H), 1.10-1.18 (m, 2H), 0.84-0.92 (m, 2H).

The following compounds were prepared according to the General Experimental Procedure 205:

| Example | Structure | Analytical data |
| --- | --- | --- |
| 206 | ![structure] | LC-MS (Method A) (ESI+): m/z 521 (M + H)+; 1H-NMR (300 MHz, CD3OD) δ 9.10 (s, 1H), 8.62 (s, 1H), 7.61-7.70 (m, 3H), 7.46 (d, J = 8.1 Hz, 2H), 5.65 (s, 2H), 3.91 (s, 3H), 3.75 (s, 3H), 2.70 (s, 3H), 1.65-1.75 (m, 1H), 1.10-1.19 (m, 2H), 0.85-0.93 (m, 2H). |

| Example | Structure | Analytical data |
|---|---|---|
| 207 | 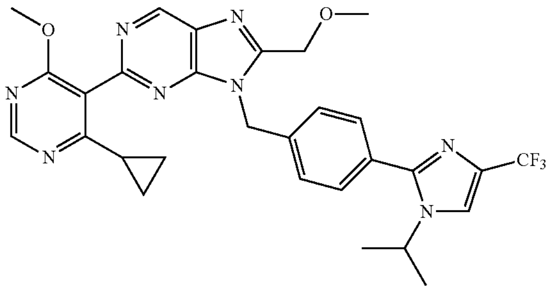 [SMILES: COCc1nc2cnc(-c3c(OC)ncnc3C3CC3)nc2n1Cc1ccc(-c2nc(C(F)(F)F)cn2C(C)C)cc1] | LC-MS (Method A) (ESI+): m/z 579 (M + H)+; 1H-NMR (300 MHz, CDCl3) δ 9.26 (s, 1H), 8.67 (s, 1H), 7.51 (d, J = 7.5 Hz, 2H), 7.40-7.44 (m, 3H), 5.67 (s, 2H), 4.70 (s, 2H), 4.48 (m, 1H), 3.94 (s, 3H), 3.42 (s, 3H), 1.65-1.70 (m, 1H), 1.43 (d, J = 6.6 Hz, 6H), 1.20-1.30 (m, 2H), 0.85-0.89 (m, 2H). |
| 208 | 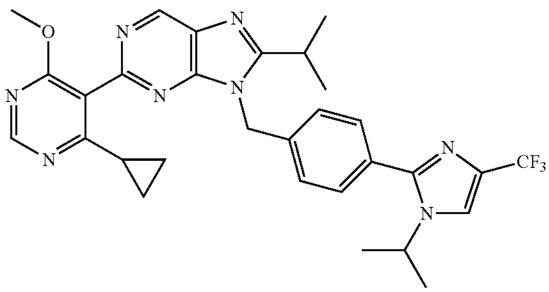 [SMILES: COc1ncnc(C2CC2)c1-c1ncc2nc(C(C)C)n(Cc3ccc(-c4nc(C(F)(F)F)cn4C(C)C)cc3)c2n1] | LC-MS (Method A) (ESI+): m/z 577 (M + H)+; 1H-NMR (300 MHz, CD3OD) δ 9.11 (s, 1H), 8.61 (s, 1H), 7.90 (s, 1H), 7.54 (d, J = 8.4 Hz, 2H), 7.43 (d, J = 8.4 Hz, 2H), 5.72 (s, 2H), 4.50 (m, 1H), 3.91 (s, 3H), 3.45 (m, 1H), 1.64-1.72 (m, 1H), 1.42 (d, J = 6.6 Hz, 6H), 1.36 (d, J = 6.9 Hz, 6H), 1.12-1.20 (m, 2H), 0.83-0.90 (m, 2H). |
Example 209: Synthesis of 2-(4-cyclopropyl-6-methoxypyrimidin-5-yl)-8-ethyl-9-(4-(5-methyl-3-(trifluoromethyl)-1H-pyrazol-1-yl)benzyl)-9H-purine (209)
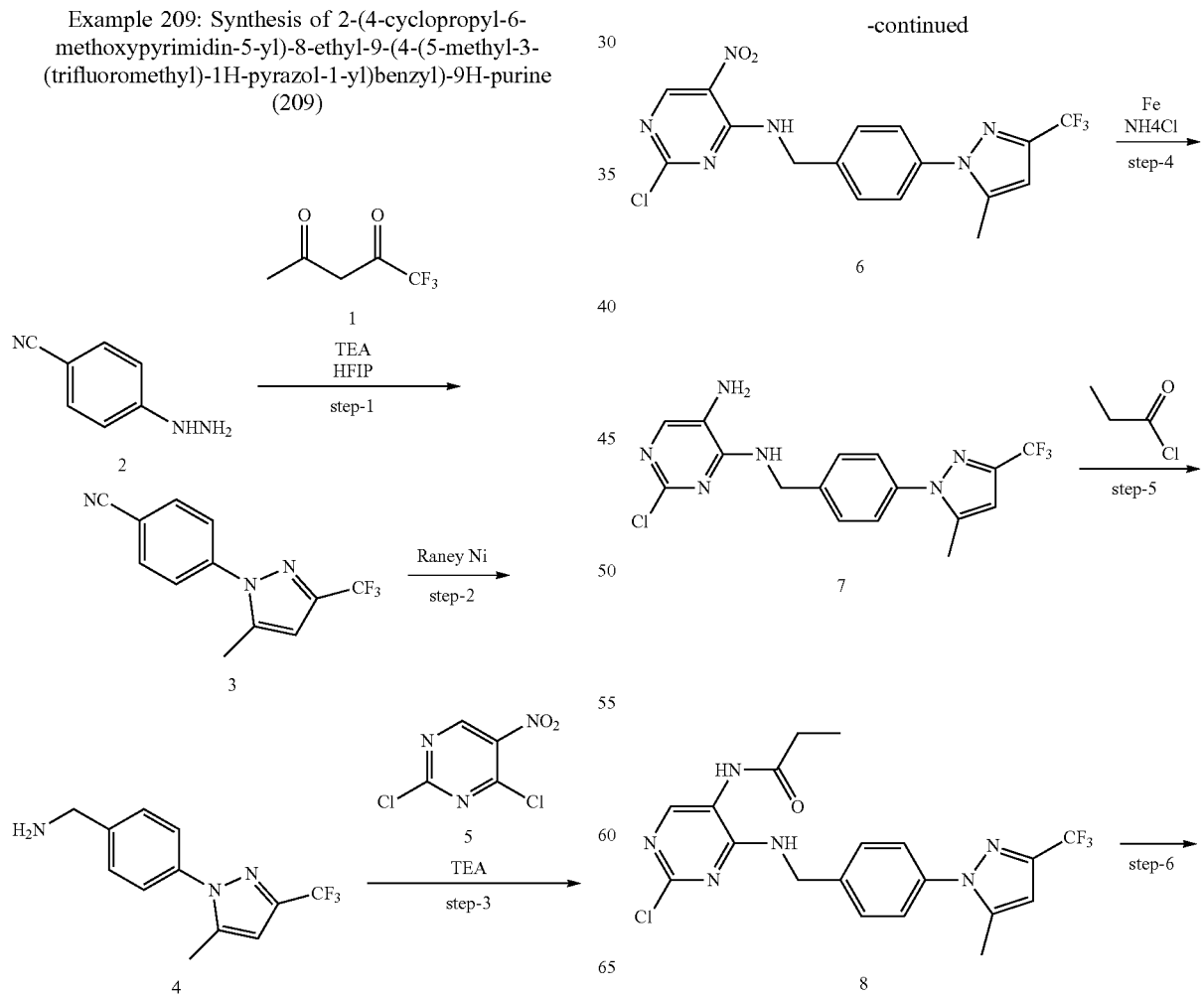

445

-continued

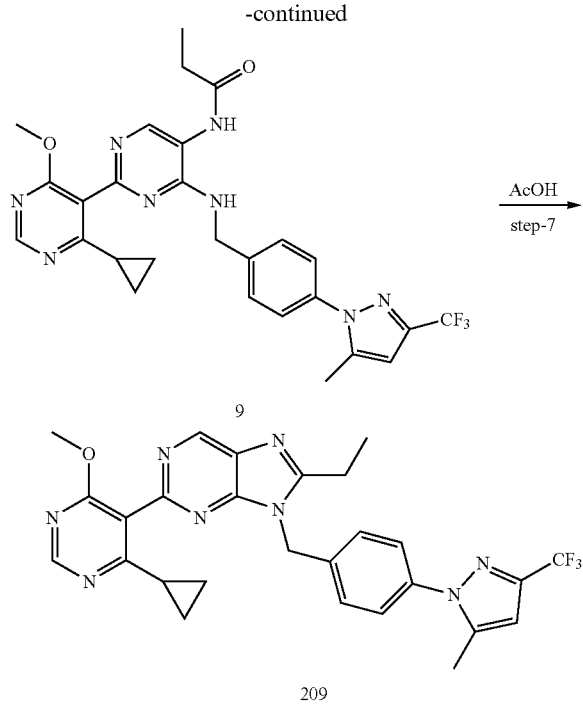

209

Step 1: Synthesis of 4-(5-methyl-3-(trifluoromethyl)-1H-pyrazol-1-yl)benzonitrile The compound was synthesized according to the procedure for the preparation of common intermediate I-19. LC-MS (Method A) (ESI+): m/z 252 (M+H)+; 1H-NMR (300 MHz, CDCl3) δ 7.79-7.85 (d, J=8.7 Hz, 2H), 7.65 (d, J=8.7 Hz, 2H), 6.53 (s, 1H), 2.45 (s, 3H).

446

Step 2: Synthesis of (4-(5-methyl-3-(trifluoromethyl)-1H-pyrazol-1-yl)phenyl)methanamine

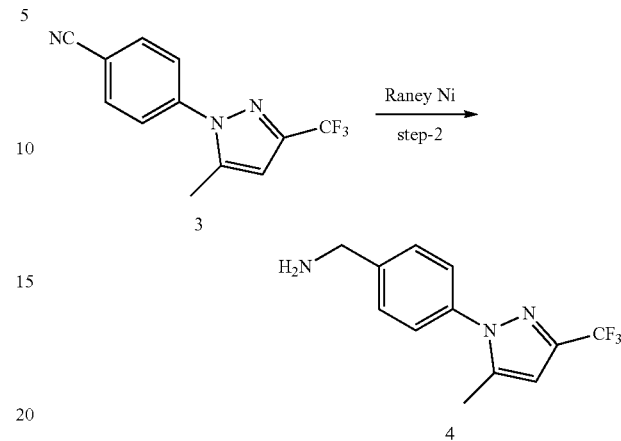

The compound was synthesized according to the procedure of Example 202. LC-MS (Method A) (ESI+): m/z 256 (M+H)+; 1H-NMR (300 MHz, CDCl3) δ 7.39-7.47 (m, 4H), 6.46 (s, 1H), 3.96 (s, 2H), 2.34 (s, 3H).

Step 3: Synthesis of 2-chloro-N-(4-(5-methyl-3-(trifluoromethyl)-1H-pyrazol-1-yl)benzyl)-5-nitropyrimidin-4-amine

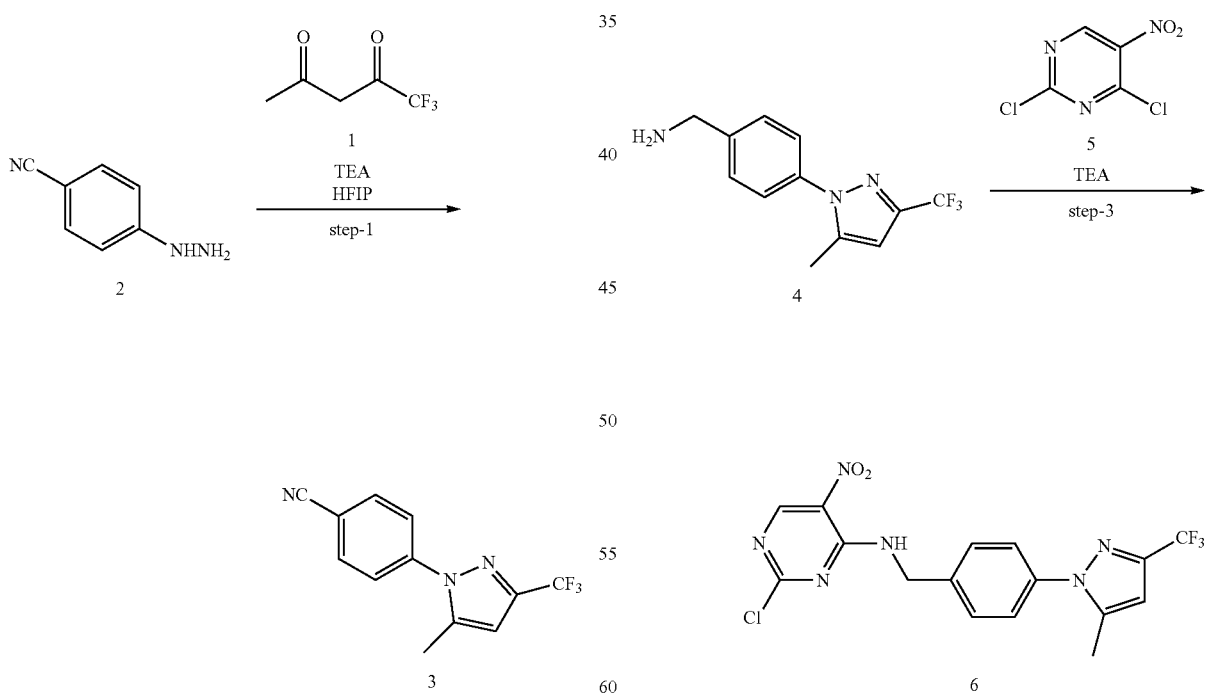

The compound was synthesized according to the procedure of Example 202. LC-MS (Method A) (ESI+): m/z 413 (M+H)+; 1H-NMR (300 MHz, CDCl3) δ 9.10 (s, 1H), 8.73 (s, 1H), 7.45-7.53 (m, 4H), 6.48 (s, 1H), 4.91 (d, J=6.0 Hz, 2H), 2.37 (s, 3H).

Step 4: Synthesis of 2-chloro-N4-(4-(5-methyl-3-(trifluoromethyl)-1H-pyrazol-1-yl)benzyl)pyrimidine-4,5-diamine

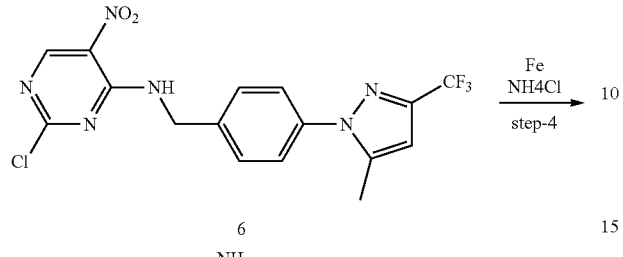

6

7

The compound was synthesized according to the procedure of Example 202. LC-MS (Method A) (ESI+): m/z 383 (M+H)$^+$; $^1$H-NMR (300 MHz, CDCl$_3$) δ 7.65 (s, 1H), 7.48 (d, J=8.4 Hz, 2H), 7.41 (d, J=8.4 Hz, 2H), 6.47 (s, 1H), 5.43 (br s, 1H), 4.74 (d, J=5.7 Hz, 2H), 3.07 (br s, 2H), 2.36 (s, 3H).

Step 5: Synthesis of N-(2-chloro-4-((4-(5-methyl-3-(trifluoromethyl)-1H-pyrazol-1-yl)benzyl)amino)pyrimidin-5-yl)propionamide

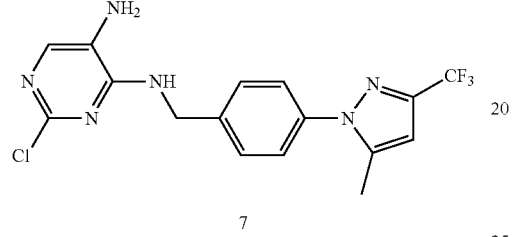

7

8

The compound was synthesized according to the procedure of Example 205. LC-MS (Method A) (ESI+): m/z 439 (M+H)$^+$; $^1$H-NMR (300 MHz, CD$_3$OD) δ 8.23 (s, 1H), 7.58 (d, J=8.4 Hz, 2H), 7.49 (d, J=8.4 Hz, 2H), 6.59 (s, 1H), 4.84 (s, 2H), 2.49 (q, J=7.5 Hz, 2H), 2.34 (s, 3H), 1.20 (t, J=7.5 Hz, 3H).

Step 6: Synthesis of N-(4'-cyclopropyl-6'-methoxy-4-((4-(5-methyl-3-(trifluoromethyl)-1H-pyrazol-1-yl)benzyl)amino)-[2,5'-bipyrimidin]-5-yl)propionamide

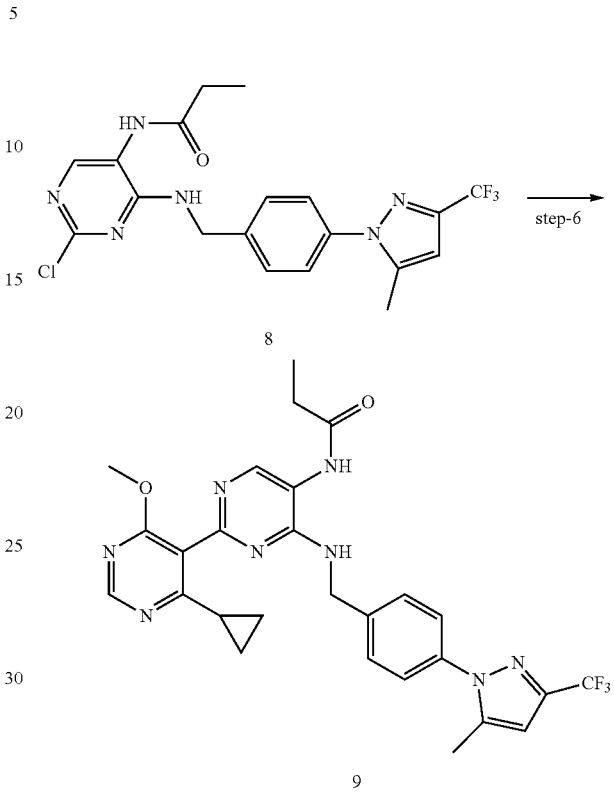

8

9

The compound was synthesized according to Example 205. LC-MS (Method A) (ESI+): m/z 553 (M+H)$^+$; $^1$H-NMR (300 MHz, CD$_3$OD) δ 8.53 (s, 1H), 8.18 (s, 1H), 7.53 (d, J=8.4 Hz, 2H), 7.42 (d, J=8.4 Hz, 2H), 6.57 (s, 1H), 4.78 (s, 2H), 3.88 (s, 3H), 2.52 (q, J=7.5 Hz, 2H), 2.32 (s, 3H), 1.72 (m, 1H), 1.24 (t, J=7.5 Hz, 3H), 1.03-1.10 (m, 2H), 0.78-0.92 (m, 2H).

Step 7: Synthesis of 2-(4-cyclopropyl-6-methoxypyrimidin-5-yl)-8-ethyl-9-(4-(5-methyl-3-(trifluoromethyl)-1H-pyrazol-1-yl)benzyl)-9H-purine (209)

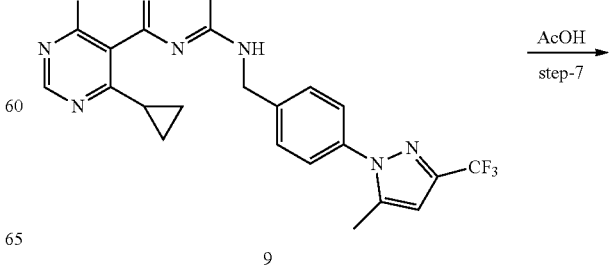

9

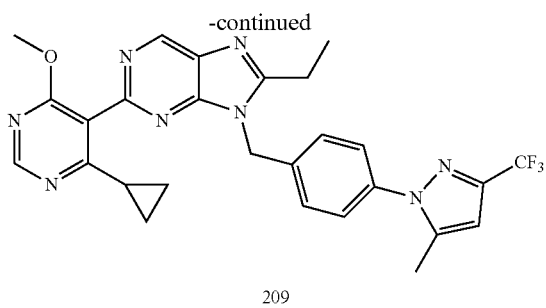

209

The compound was synthesized according to the procedure of Example 205. LC-MS (ESI+): m/z 535 (M+H)⁺; ¹H-NMR (300 MHz, CD₃OD) δ 9.11 (s, 1H), 8.61 (s, 1H), 7.44-7.52 (m, 4H), 6.57 (s, 1H), 5.67 (s, 2H), 3.91 (s, 3H), 3.04 (q, J=7.2 Hz, 2H), 2.32 (s, 3H), 1.68 (m, 1H), 1.41 (t, J=7.2 Hz, 3H), 1.10-1.16 (m, 2H), 0.84-0.89 (m, 2H).

The following examples were prepared according to the procedure of Example 209 using either trimethylorthoformate or the appropriate acid chlorides:

| Example | Structure | Analytical data |
|---|---|---|
| 210 | 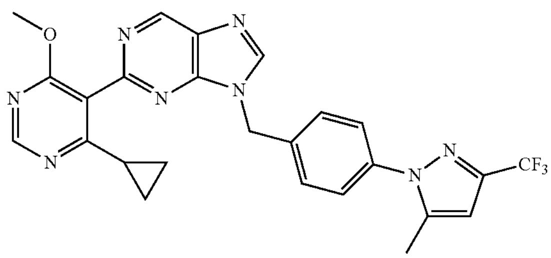 [SMILES: COc1ncnc(C2CC2)c1-c1ncc2ncn(Cc3ccc(-n4nc(C(F)(F)F)cc4C)cc3)c2n1] | LC-MS (Method A) (ESI+): m/z 507 (M + H)⁺; ¹H-NMR (300 MHz, CD₃OD) δ 9.23 (s, 1H), 8.76 (s, 1H), 8.62 (s, 1H), 7.61 (d, J = 8.1 Hz, 2H), 7.51 (d, J = 8.4 Hz, 2H), 6.57 (s, 1H), 5.68 (s, 2H), 3.90 (s, 3H), 2.32 (s, 3H), 1.62 (m, 1H), 1.10-1.18 (m, 2H), 0.85-0.91 (m, 2H). |
| 211 | 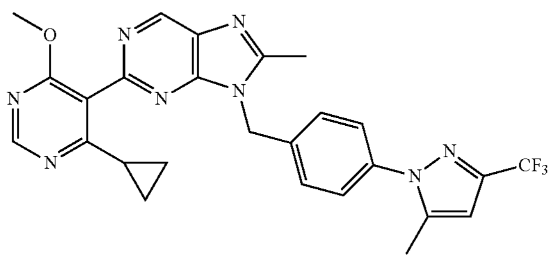 [SMILES: COc1ncnc(C2CC2)c1-c1ncc2nc(C)n(Cc3ccc(-n4nc(C(F)(F)F)cc4C)cc3)c2n1] | LC-MS (Method A) (ESI+): m/z 521 (M + H)⁺; ¹H-NMR (300 MHz, CD₃OD) δ 9.10 (s, 1H), 8.62 (s, 1H), 7.40-7.55 (m, 4H), 6.58 (s, 1H), 5.67 (s, 2H), 3.91 (s, 3H), 2.71 (s, 3H), 2.33 (s, 3H), 1.69 (m, 1H), 1.10-1.19 (m, 2H), 0.85-0.91 (m, 2H). |
| 212 | 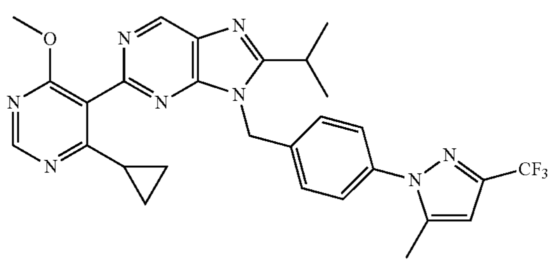 [SMILES: COc1ncnc(C2CC2)c1-c1ncc2nc(C(C)C)n(Cc3ccc(-n4nc(C(F)(F)F)cc4C)cc3)c2n1] | LC-MS (Method A) (ESI+): m/z 549 (M + H)⁺; ¹H-NMR (300 MHz, CD₃OD) δ 9.11 (s, 1H), 8.61 (s, 1H), 7.53 (d, J = 8.1 Hz, 2H), 7.46 (d, J = 8.1 Hz, 2H), 6.58 (s, 1H), 5.72 (s, 2H), 3.91 (s, 3H), 3.42 (m, 1H), 2.32 (s, 3H), 1.66 (m, 1H), 1.36 (d, J = 6.9 Hz, 6H), 1.10-1.18 (m, 2H), 0.84-0.92 (m, 2H). |
| 213 | 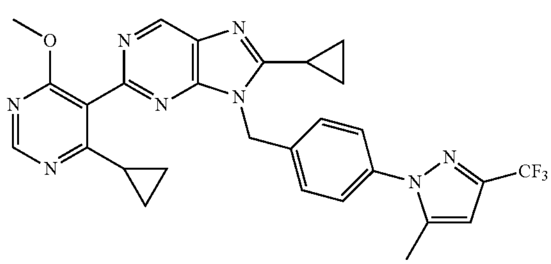 [SMILES: COc1ncnc(C2CC2)c1-c1ncc2nc(C3CC3)n(Cc3ccc(-n4nc(C(F)(F)F)cc4C)cc3)c2n1] | LC-MS (Method A) (ESI+): m/z 547 (M + H)⁺; ¹H-NMR (300 MHz, CDCl₃) δ 9.13 (s, 1H), 8.66 (s, 1H), 7.44 (s, 4H), 6.48 (s, 1H), 5.66 (s, 2H), 3.81 (s, 3H), 2.32 ( s, 3H), 1.99 (m, 1H), 1.78 (m, 1H), 1.29-1.33 (m, 2H), 1.1.15-1.26 (m, 4H), 0.82-0.91 (m, 2H). |

| Example | Structure | Analytical data |
|---|---|---|
| 214 | 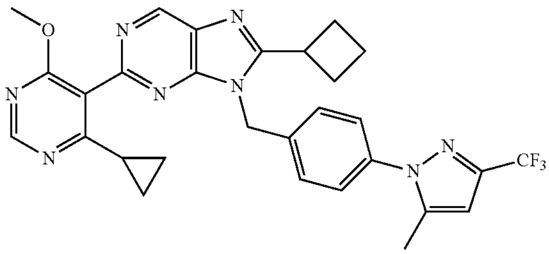 [SMILES: COc1ncnc(C2CC2)c1-c1ncc2nc(C3CCC3)n(Cc3ccc(-n4nc(C(F)(F)F)cc4C)cc3)c2n1] | LC-MS (Method A) (ESI+): m/z 561 (M + H)$^+$; $^1$H-NMR (300 MHz, CDCl$_3$) δ 9.25 (s, 1H), 8.66 (s, 1H), 7.42 (d, J = 8.4 Hz, 2H), 7.33 (d, J = 8.4 Hz, 2H), 6.46 (s, 1H), 5.48 (s, 2H), 3.92 (s, 3H), 3.69 (m, 1H), 2.51-2.62 (m, 2H), 2.35-2.42 (m, 2H), 2.31 (m, 3H), 2.05-2.21 (m, 2H), 1.68 (m, 1H), 1.19-1.26 (m, 2H), 0.81-0.91 (m, 2H). |

Example 215: Synthesis of 5-(4-cyclopropyl-6-methoxypyrimidin-5-yl)-3-(4-(1-methyl-4-(trifluoromethyl)-1H-imidazol-2-yl)benzyl)-3H-[1,2,3]triazolo[4,5-d]pyrimidine (215)

Step 1: Synthesis of 5-chloro-3-(4-(1-methyl-4-(trifluoromethyl)-1H-imidazol-2-yl)benzyl)-3H-[1,2,3]triazolo[4,5-d]pyrimidine

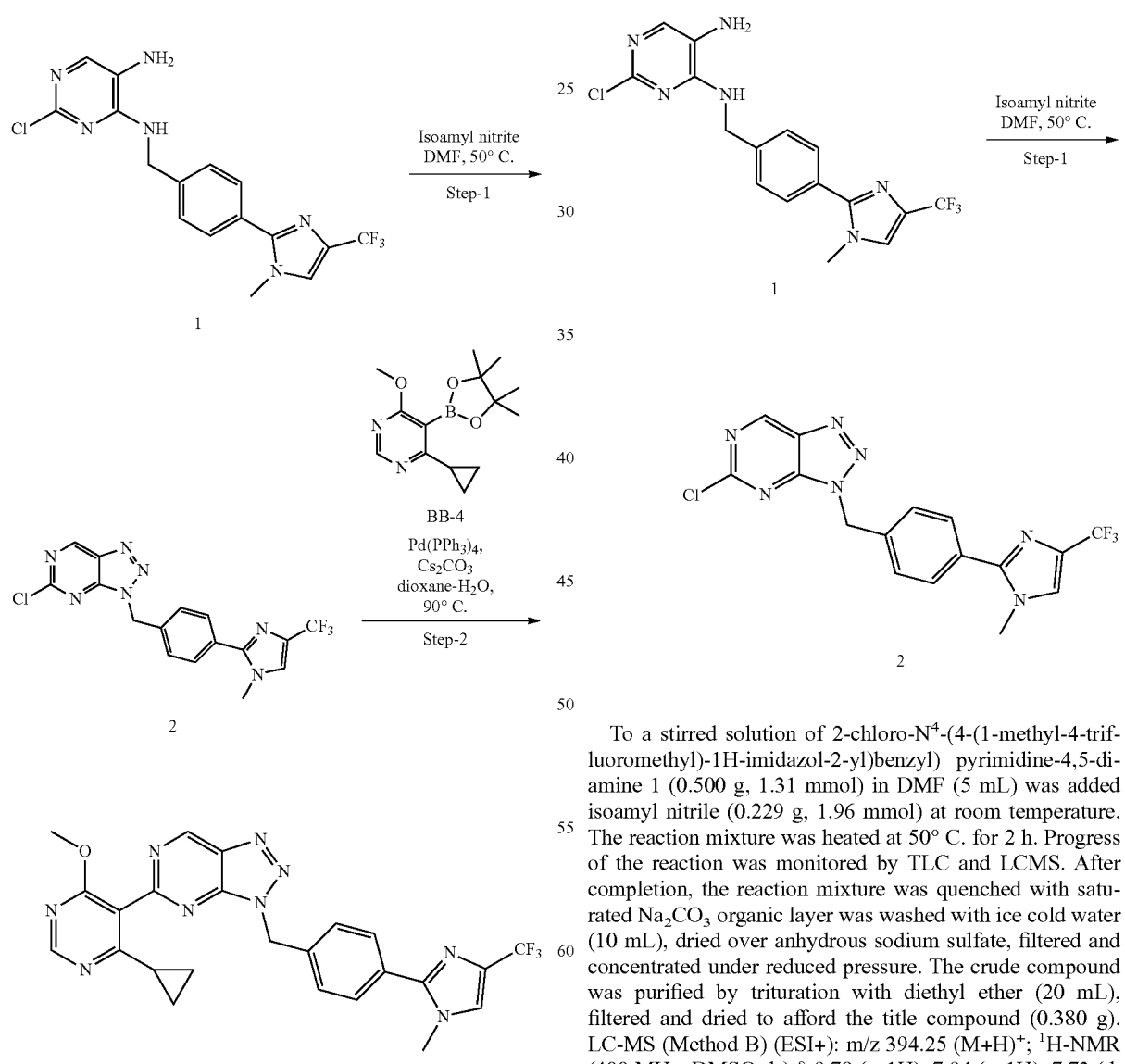

To a stirred solution of 2-chloro-N$^4$-(4-(1-methyl-4-trifluoromethyl)-1H-imidazol-2-yl)benzyl) pyrimidine-4,5-diamine 1 (0.500 g, 1.31 mmol) in DMF (5 mL) was added isoamyl nitrile (0.229 g, 1.96 mmol) at room temperature. The reaction mixture was heated at 50° C. for 2 h. Progress of the reaction was monitored by TLC and LCMS. After completion, the reaction mixture was quenched with saturated Na$_2$CO$_3$ organic layer was washed with ice cold water (10 mL), dried over anhydrous sodium sulfate, filtered and concentrated under reduced pressure. The crude compound was purified by trituration with diethyl ether (20 mL), filtered and dried to afford the title compound (0.380 g). LC-MS (Method B) (ESI+): m/z 394.25 (M+H)$^+$; $^1$H-NMR (400 MHz, DMSO-d$_6$) δ 9.78 (s, 1H), 7.94 (s, 1H), 7.73 (d, J=8.31 Hz, 2H), 7.51 (d, J=8.31 Hz, 2H), 6.03 (s, 2H), 3.76 (s, 3H).

Step 2: Synthesis of 5-(4-cyclopropyl-6-methoxypyrimidin-5-yl)-3-(4-(1-methyl-4-(trifluoromethyl)-1H-imidazol-2-yl)benzyl)-3H-[1,2,3]triazolo[4,5-d]pyrimidine (215)

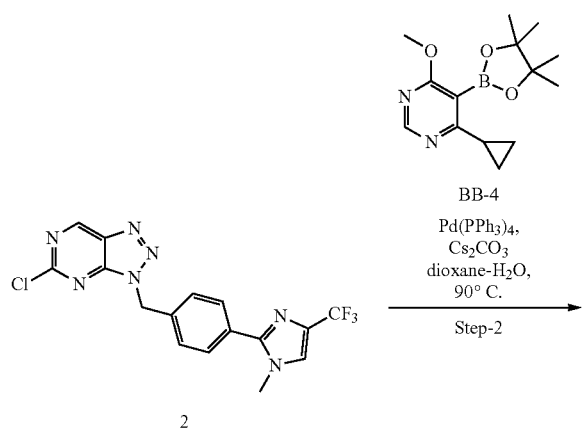

Example 216 and 217: Synthesis of 5-bromo-2-(4-cyclopropyl-6-methoxypyrimidin-5-yl)-7-(3-fluoro-4-(1-isopropyl-4-(trifluoromethyl)-1H-imidazol-2-yl)benzyl)-7H-pyrrolo[2,3-d]pyrimidine (216) and 2-(4-cyclopropyl-6-methoxypyrimidin-5-yl)-7-(3-fluoro-4-(1-isopropyl-4-(trifluoromethyl)-1H-imidazol-2-yl)benzyl)-5,7-dihydro-6H-pyrrolo[2,3-d]pyrimidin-6-one (217)

To a stirred solution of 5-chloro-3-(4-(1-methyl-4-(trifluoromethyl)-1H-imidazol-2-yl)benzyl)-3H-[1,2,3]triazolo[4,5-d]pyrimidine 2 (0.150 g, 0.380 mmol) in dioxane:H$_2$O (5:1 mL) was added cesium carbonate (0.308 g, 0.950 mmol), 4-cyclopropyl-6-methoxy-5-(4,4,5,5-tetramethyl-1,3,2-dioxaborolan-2-yl)pyrimidine BB-4 (0.157 g, 0.571 mmol) at room temperature. The resulting mixture was degassed with argon for 10 min, and then treated with Pd(PPh$_3$)$_4$ (0.065 g, 0.057 mmol) at room temperature. The mixture was further degassed with argon for 10 min, and then heated at 90° C. for 16 h. Progress of the reaction was monitored by TLC. After completion, the reaction mixture was quenched with H$_2$O (20 mL) and extracted with EA (2×20 mL). The combined organic layer was dried over anhydrous sodium sulfate, filtered and concentrated under reduced pressure. The crude compound was purified by preparative HPLC (Method D) to afford the title compound (0.050 g). LC-MS (Method B) (ESI+): m/z 508.20 (M+H)$^+$; $^1$H-NMR (400 MHz, DMSO-d$_6$) δ 9.94 (s, 1H), 8.73 (s, 1H), 7.93 (s, 1H), 7.72 (d, J=8.31 Hz, 2H), 7.54 (d, J=8.31 Hz, 2H), 6.09 (s, 2H), 3.85 (s, 3H), 3.75 (s, 3H), 1.69 (td, J=3.79, 8.07 Hz, 1H), 1.05-1.09 (m, 2H), 0.85 (dd, J=2.93, 7.83 Hz, 2H).

455
-continued

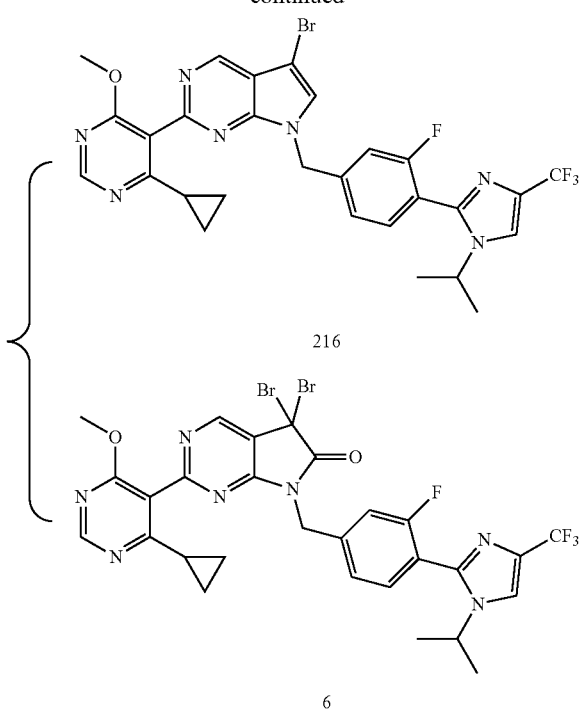

456
-continued

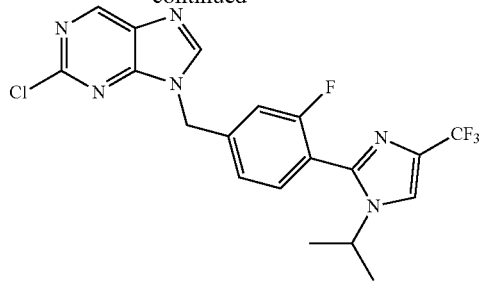

The compound was synthesized according to the general procedure for the synthesis of common intermediate I-8. LC-MS (Method A) (ESI+): m/z 438 (M+H)$^+$; $^1$H-NMR (300 MHz, CDCl$_3$) δ 8.86 (s, 1H), 7.53 (t, J=7.5 Hz, 1H), 7.44 (s, 1H), 7.19 (s, 1H), 7.12 (d, J=7.8 Hz, 1H), 6.97 (d, J=10.2 Hz, 1H), 6.65 (d, J=3.6 Hz, 1H), 5.49 (s, 2H), 4.23 (m, 1H), 1.41 (d, J=6.6 Hz, 6H).

Step 2: Synthesis of 2-(4-cyclopropyl-6-methoxypyrimidin-5-yl)-7-(3-fluoro-4-(1-isopropyl-4-(trifluoromethyl)-1H-imidazol-2-yl)benzyl)-7H-pyrrolo[2,3-d]pyrimidine

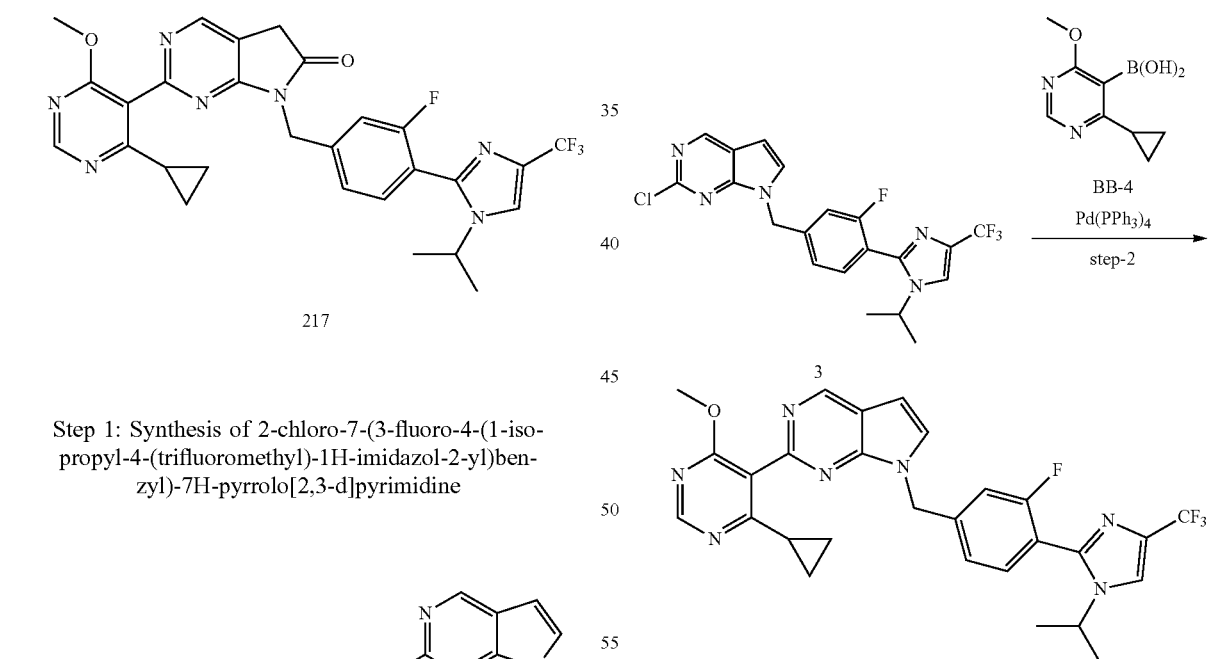

Step 1: Synthesis of 2-chloro-7-(3-fluoro-4-(1-isopropyl-4-(trifluoromethyl)-1H-imidazol-2-yl)benzyl)-7H-pyrrolo[2,3-d]pyrimidine

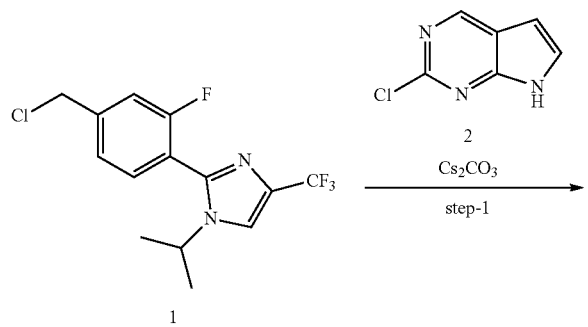

The compound was synthesized according to General Experimental Procedure 1. LC-MS (Method A) (ESI+): m/z 552 (M+H)$^+$; $^1$H-NMR (300 MHz, CDCl$_3$) δ 9.16 (s, 1H), 8.66 (s, 1H), 7.52 (t, J=7.2 Hz, 1H), 7.43 (s, 1H), 7.28 (s, 1H), 7.20 (d, J=8.1 Hz, 1H), 7.10 (d, J=9.6 Hz, 1H), 6.69 (d, J=3.6 Hz, 1H), 5.54 (s, 2H), 4.19 (m, 1H), 3.93 (s, 3H), 1.72 (m, 1H), 1.40 (d, J=6.6 Hz, 6H), 1.19-1.25 (m, 2H), 0.82-0.89 (m, 2H).

Step 2: Synthesis of 5,5-dibromo-2-(4-cyclopropyl-6-methoxypyrimidin-5-yl)-7-(3-fluoro-4-(1-isopropyl-4-(trifluoromethyl)-1H-imidazol-2-yl)benzyl)-5,7-dihydro-6H-pyrrolo[2,3-d]pyrimidin-6-one (6) and 5-bromo-2-(4-cyclopropyl-6-methoxypyrimidin-5-yl)-7-(3-fluoro-4-(1-isopropyl-4-(trifluoromethyl)-1H-imidazol-2-yl)benzyl)-7H-pyrrolo[2,3-d]pyrimidine (216)

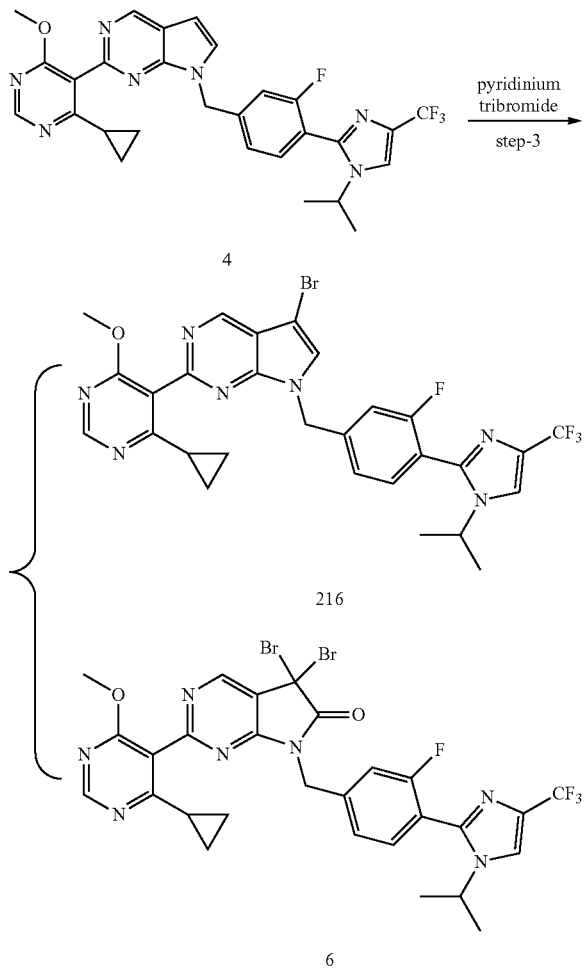

A solution of 2-(4-cyclopropyl-6-methoxypyrimidin-5-yl)-7-(3-fluoro-4-(1-isopropyl-4-(trifluoromethyl)-1H-imidazol-2-yl)benzyl)-7H-pyrrolo[2,3-d]pyrimidine (60 mg, 0.11 mmol) in AcOH (1 mL) and t-BuOH (2 ml) was added pyridinium bromide perbromide (104 mg, 0.33 mmol) in one portion. The resulting mixture was stirred at rt for 5 h. After the reaction was complete as indicated by TLC analysis, the reaction was concentrated to dryness. The residue was dissolved in EA (10 mL) and washed with an aqueous NaHCO$_3$ solution (10 mL). The organic layer was dried, filtered and concentrated. The residue was purified by flash silica chromatography (PE/EA=2/1) to provide 14 mg of (5-bromo-2-(4-cyclopropyl-6-methoxypyrimidin-5-yl)-7-(3-fluoro-4-(1-isopropyl-4-(trifluoromethyl)-1H-imidazol-2-yl)benzyl)-7H-pyrrolo[2,3-d]pyrimidine) 216 and 47 mg of 5,5-dibromo-2-(4-cyclopropyl-6-methoxypyrimidin-5-yl)-7-(3-fluoro-4-(1-isopropyl-4-(trifluoromethyl)-1H-imidazol-2-yl)benzyl)-5,7-dihydro-6H-pyrrolo[2,3-d]pyrimidin-6-one 6 containing some impurities.

Analytical data of 5-bromo-2-(4-cyclopropyl-6-methoxypyrimidin-5-yl)-7-(3-fluoro-4-(1-isopropyl-4-(trifluoromethyl)-1H-imidazol-2-yl)benzyl)-7H-pyrrolo[2,3-d]pyrimidine 216

LC-MS (Method A) (ESI+): m/z 630 (M+H)$^+$; $^1$H-NMR (300 MHz, CD$_3$OD) δ 9.03 (s, 1H), 8.62 (s, 1H), 7.96 (s, 1H), 7.87 (s, 1H), 7.48 (t, J=7.5 Hz, 1H), 7.31 (d, J=9.0 Hz, 1H), 5.62 (s, 2H), 4.21 (m, 1H), 3.91 (s, 3H), 1.66 (m, 1H), 1.40 (d, J=6.6 Hz, 6H), 1.19-1.25 (m, 2H), 0.82-0.89 (m, 2H).

Analytical data of 5,5-dibromo-2-(4-cyclopropyl-6-methoxypyrimidin-5-yl)-7-(3-fluoro-4-(1-isopropyl-4-(trifluoromethyl)-1H-imidazol-2-yl)benzyl)-5,7-dihydro-6H-pyrrolo[2,3-d]pyrimidin-6-one 6

LC-MS (Method A)(ESI+): m/z 724, 726, 728 (M+H)$^+$.

Step 4: Synthesis of 2-(4-cyclopropyl-6-methoxypyrimidin-5-yl)-7-(3-fluoro-4-(1-isopropyl-4-(trifluoromethyl)-1H-imidazol-2-yl)benzyl)-5,7-dihydro-6H-pyrrolo[2,3-d]pyrimidin-6-one (217)

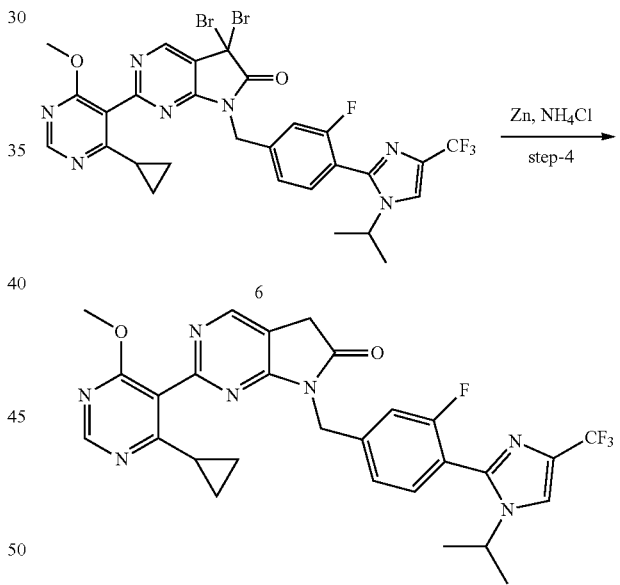

A solution of 5,5-dibromo-2-(4-cyclopropyl-6-methoxypyrimidin-5-yl)-7-(3-fluoro-4-(1-isopropyl-4-(trifluoromethyl)-1H-imidazol-2-yl)benzyl)-5,7-dihydro-6H-pyrrolo[2,3-d]pyrimidin-6-one 6 (47 mg, 0.065 mmol) in THF (1.5 mL) and a saturated aqueous NH$_4$Cl solution (1.5 ml) was added Zn powder (65 mg, 0.26 mmol) in one portion. The resulting mixture was stirred at rt for 1.5 h. After the reaction was complete as indicated by TLC analysis, the reaction was quenched with H$_2$O (1 mL) and extracted with EA (3 mL×3). The combined organic layer was dried with Na$_2$SO$_4$, filtered and concentrated. The residue was purified by preparative HPLC (Method A) to give 7 mg of the title compound. LC-MS (Method A) (ESI+): m/z 568 (M+H)$^+$;

¹H-NMR (300 MHz, CDCl₃) δ 8.66 (s, 1H), 8.52 (s, 1H), 7.35-7.52 (m, 4H), 5.02 (s, 2H), 4.23 (m, 1H), 3.93 (s, 3H), 3.68 (s, 2H), 1.75 (m, 1H), 1.40 (d, J=6.6 Hz, 6H), 1.22-1.26 (m, 2H), 0.87-0.95 (m, 2H).

Example 218

Deubiquitination Assay for USP1/UAF1 Activity and Inhibitor Testing

Certain Compounds of the Disclosure were assessed for USP1/UAF1 activity in a Ubiquitin Rhodamine assay modified from those described previously.

Deubiquitinase activity was measured using ubiquitin-rhodamine 110 as a substrate. Cleavage of the amide bond between rhodamine and the c-terminal glycine of ubiquitin yields an increase in fluorescence signal. The assay was conducted in 20 ul total volume of assay buffer (50 mM Tris-HCl, pH 7.8, 0.5 mM EDTA, 0.01% Bovine Serum Albumin, 1 mM DTT, 0.01% Tween-20), and 0.05 nM USP1/UAF1 enzyme. Reaction was initiated by addition of 150 nM Ubiquitin-rhodamine (Boston Biochem) substrate.

Compounds, dissolved in DMSO were tested in dose response format, beginning at 10 uM.

Compounds depicted below were added to enzyme/assay buffer mix and incubated 10 min. Substrate mix was added, and reaction mix was read in kinetic mode for 30 min at Ex480/Em540 and IC50 response curves were plotted.

Data for all assay formats was calculated as percent inhibition compared with control wells. Percent inhibition was calculated using the following equation: % inhibition=100×[1−(X−min)/(max−min)], where X is the raw data readout, min is the average of the no enzyme control wells (n=32), max is the average of the DMSO control well (n=32). IC$_{50}$ values were calculated using the standard four parameter curve fitting algorithm in either Prism GraphPad (La Jolla, Calif.) software, or Collaborative Drug Discovery (Burlingame, Calif.) CDD Vault. See Chem. Biol. 20(1): 55-62 (Jan. 24, 2013); Bioorg. Med. Chem. Lett. 23(20): 5660-5666 (Oct. 15, 2013).

The following Compounds of the Disclosure inhibit USP1 activity with the IC$_{50}$ values shown in Table 2, Table 3, and Table 4 below.

TABLE 2

| Compound Structure | USP1 IC$_{50}$ |
|---|---|
| 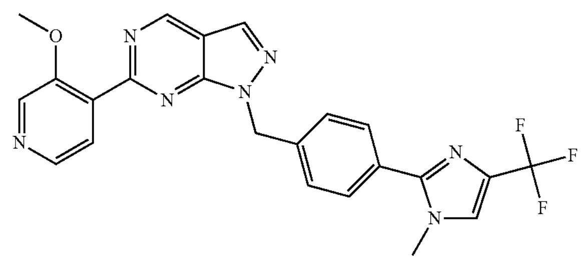 [SMILES: COc1cnccc1-c1ncc2cnn(Cc3ccc(-c4nc(C(F)(F)F)cn4C)cc3)c2n1] | + |
|  | ++ |
|  | ++ |

TABLE 2-continued

| Compound Structure | USP1 IC$_{50}$ |
|---|---|
| 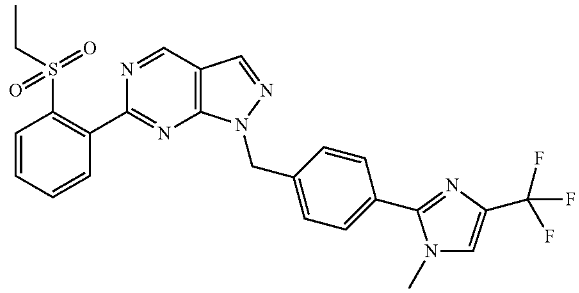 [SMILES: CCS(=O)(=O)c1ccccc1-c1ncc2cnn(Cc3ccc(-c4nc(C(F)(F)F)cn4C)cc3)c2n1] | ++ |
| | +++ |
| | +++ |
| | +++ |
| | +++ |
| | +++ |

TABLE 2-continued

| Compound Structure | USP1 IC$_{50}$ |
|---|---|
| | +++ |
| | +++ |
| | +++ |
| | +++ |
| | +++ |
| | +++ |

TABLE 2-continued

| Compound Structure | USP1 IC$_{50}$ |
|---|---|
| | +++ |
| | +++ |
| | ++++ |
| | ++++ |
| | ++++ |
| | ++++ |

TABLE 2-continued

| Compound Structure | USP1 IC$_{50}$ |
|---|---|
| | ++++ |
| | ++++ |
| | ++++ |
| | ++++ |

USP1 IC$_{50}$:

"+" indicates 200 nM or greater;

"++" indicates 100 nM to less than 200 nM;

"+++" indicates 10 nM to less than 100 nM;

"++++" indicates less than 10 nM.

TABLE 3

| Compound Structure | USP1 IC$_{50}$ |
|---|---|
| (structure) | ++++ |
| (structure) | ++++ |
| (structure) | ++++ |
| (structure) | ++++ |
| (structure) | ++++ |

TABLE 3-continued

| Compound Structure | USP1 IC$_{50}$ |
|---|---|
| | +++ |
| | +++ |
| | +++ |
| | +++ |
| | +++ |

TABLE 3-continued

| Compound Structure | USP1 IC$_{50}$ |
|---|---|
| | +++ |
| | +++ |
| | +++ |
| | +++ |
| | +++ |

TABLE 3-continued

| Compound Structure | USP1 IC$_{50}$ |
|---|---|
| | +++ |
| | +++ |
| | +++ |
| | +++ |
| | +++ |

TABLE 3-continued
| Compound Structure | USP1 IC$_{50}$ |
|---|---|
| 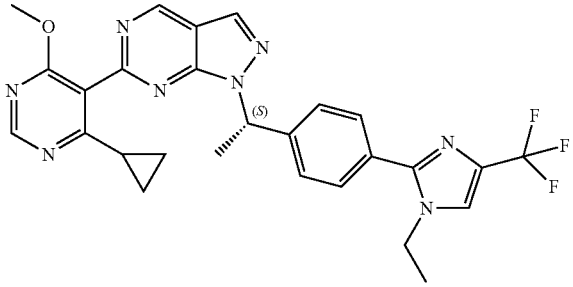 | +++ |
| 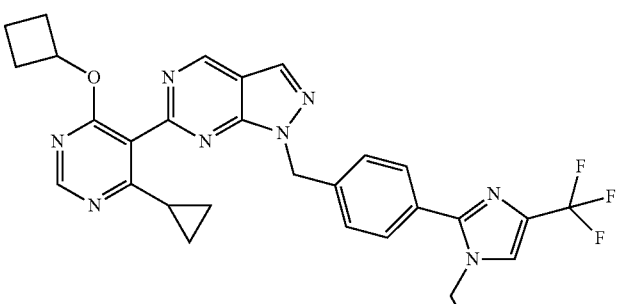 | +++ |
| 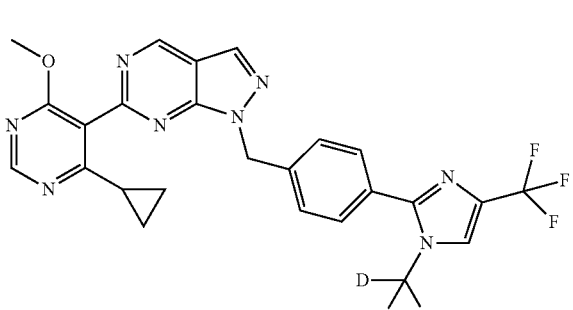 | +++ |
| 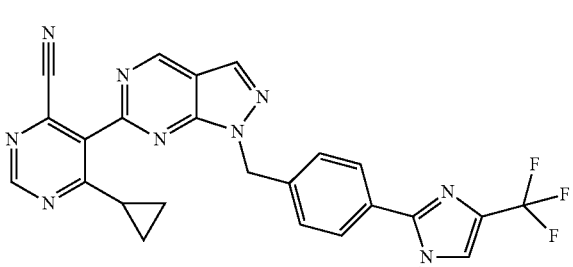 | +++ |
| 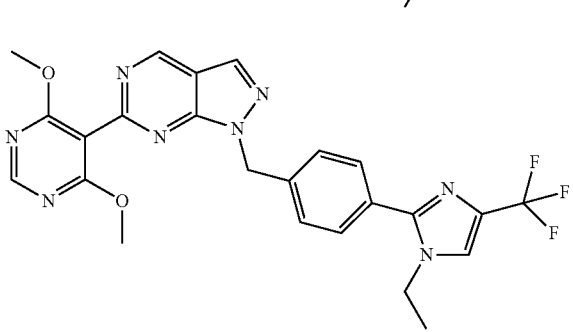 | +++ |

TABLE 3-continued

| Compound Structure | USP1 IC$_{50}$ |
|---|---|
| | +++ |
| | +++ |
| | +++ |
| | +++ |
| | +++ |
| | +++ |

TABLE 3-continued

| Compound Structure | USP1 IC$_{50}$ |
| --- | --- |
| | +++ |
| | +++ |
| | +++ |
| | +++ |
| | +++ |

TABLE 3-continued

| Compound Structure | USP1 IC$_{50}$ |
|---|---|
| | +++ |
| | +++ |
| | +++ |
| | +++ |
| | +++ |

TABLE 3-continued

| Compound Structure | USP1 IC$_{50}$ |
|---|---|
| | +++ |
| | +++ |
| | +++ |
| | +++ |
| | +++ |

TABLE 3-continued

| Compound Structure | USP1 IC$_{50}$ |
|---|---|
| | +++ |
| | +++ |
| | +++ |
| | ++ |
| | ++ |

TABLE 3-continued

| Compound Structure | USP1 IC$_{50}$ |
|---|---|
| | ++ |
| | ++ |
| | ++ |
| 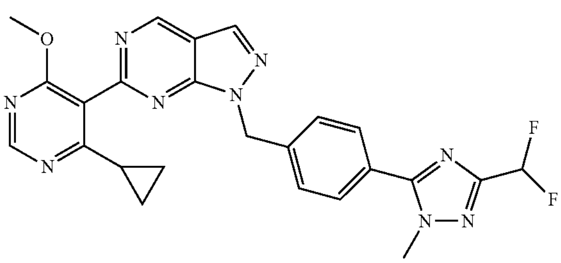 [SMILES: COc1ncnc(C2CC2)c1-c1ncc2cnn(Cc3ccc(-c4nc(C(F)F)nn4C)cc3)c2n1] | + |

TABLE 3-continued

| Compound Structure | USP1 IC$_{50}$ |
|---|---|
| | + |
| | + |
| | + |
| | + |

TABLE 3-continued

| Compound Structure | USP1 IC$_{50}$ |
|---|---|
| | + |
| | + |
| | + |
| | + |
| | + |

TABLE 3-continued

| Compound Structure | USP1 IC$_{50}$ |
|---|---|
| (structure) | + |
| (structure) | + |
| (structure) | + |
| (structure) | N/A |

USP1 IC$_{50}$:
"+" indicates 200 nM or greater;
"++" indicates 100 nM to less than 200 nM;
"+++" indicates 10 nM to less than 100 nM;
"++++" indicates less than 10 nM.

TABLE 4
| Compound Structure | USP1 IC$_{50}$ |
|---|---|
| 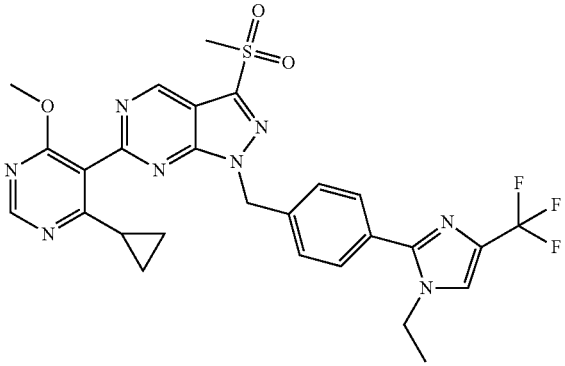 [SMILES: CCn1cc(C(F)(F)F)nc1-c1ccc(Cn2nc(S(C)(=O)=O)c3cnc(-c4c(OC)ncnc4C4CC4)nc32)cc1] | N/A |
| 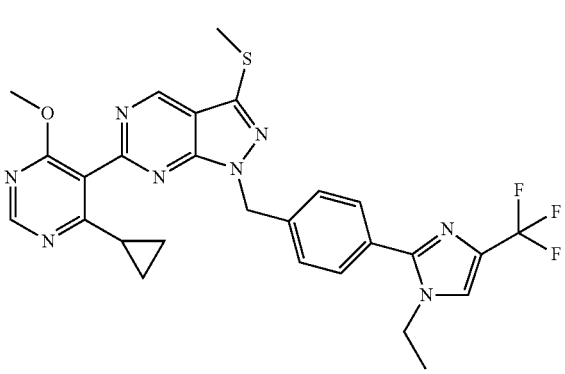 | +++ |
| 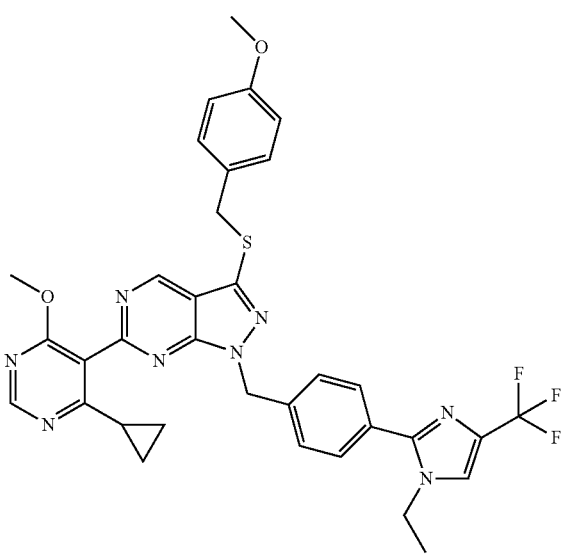 [SMILES: CCn1cc(C(F)(F)F)nc1-c1ccc(Cn2nc(SCc3ccc(OC)cc3)c3cnc(-c4c(OC)ncnc4C4CC4)nc32)cc1] | +++ |
| 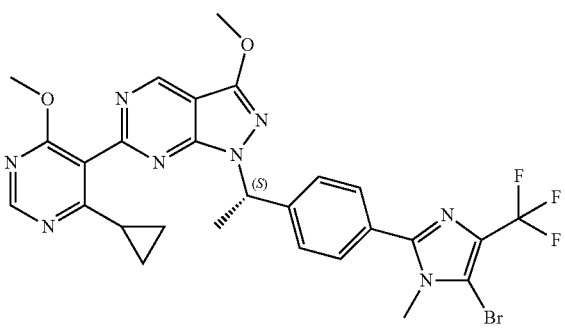 | +++ |

TABLE 4-continued
| Compound Structure | USP1 IC$_{50}$ |
| --- | --- |
| 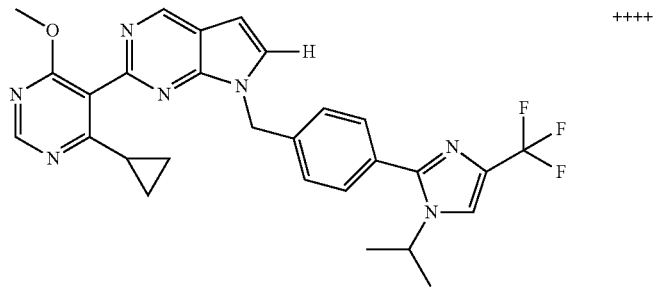 | ++++ |
| 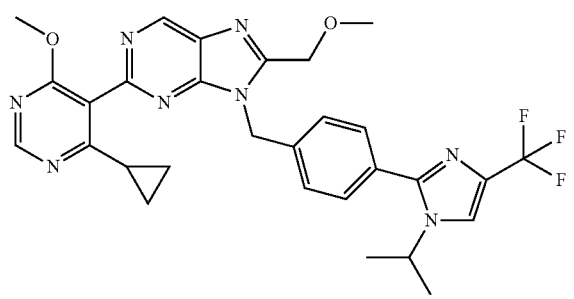 [SMILES: COCc1nc2cnc(-c3c(OC)ncnc3C3CC3)nc2n1Cc1ccc(-c2nc(C(F)(F)F)cn2C(C)C)cc1] | +++ |
| 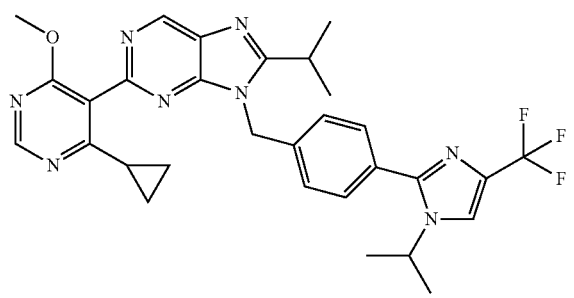 [SMILES: COc1ncnc(C2CC2)c1-c1ncc2nc(C(C)C)n(Cc3ccc(-c4nc(C(F)(F)F)cn4C(C)C)cc3)c2n1] | +++ |
| 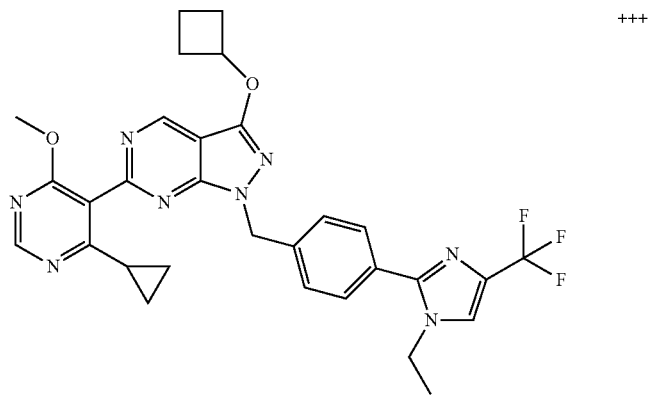 | +++ |

TABLE 4-continued

| Compound Structure | USP1 IC$_{50}$ |
|---|---|
| | +++ |
| | +++ |
| | +++ |
| | +++ |

TABLE 4-continued
| Compound Structure | USP1 IC$_{50}$ |
|---|---|
| 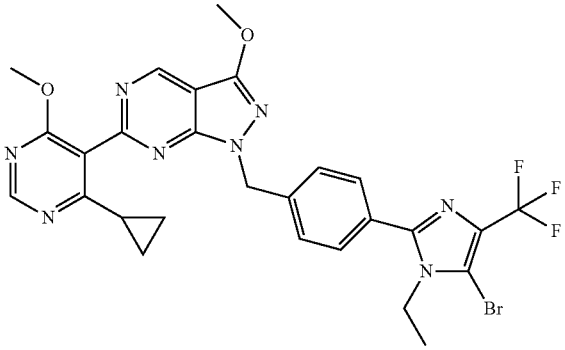 [SMILES: CCn1c(-c2ccc(Cn3nc(OC)c4cnc(-c5c(OC)ncnc5C5CC5)nc43)cc2)nc(C(F)(F)F)c1Br] | +++ |
| 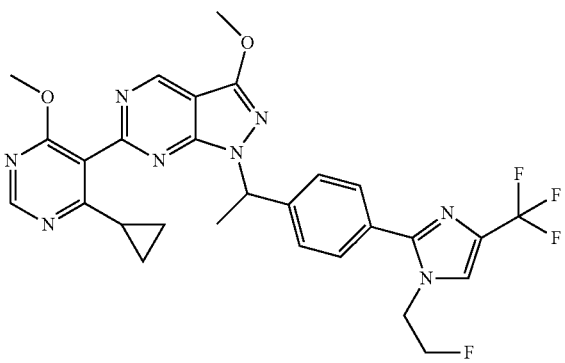 [SMILES: COc1ncnc(C2CC2)c1-c1ncc2c(OC)nn(C(C)c3ccc(-c4nc(C(F)(F)F)cn4CCF)cc3)c2n1] | +++ |
| 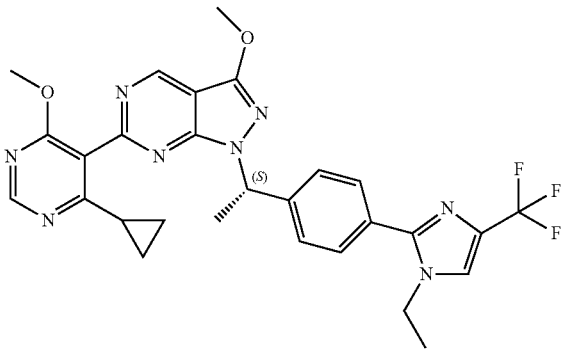 | +++ |
| 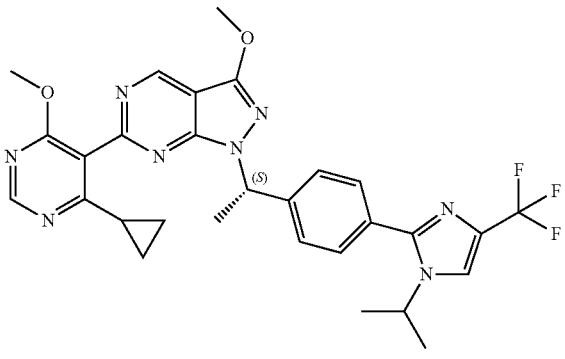 | +++ |

TABLE 4-continued

| Compound Structure | USP1 IC$_{50}$ |
|---|---|
| | +++ |
| | +++ |
| | +++ |
| | +++ |

TABLE 4-continued

| Compound Structure | USP1 IC$_{50}$ |
|---|---|
| | +++ |
| | +++ |
| 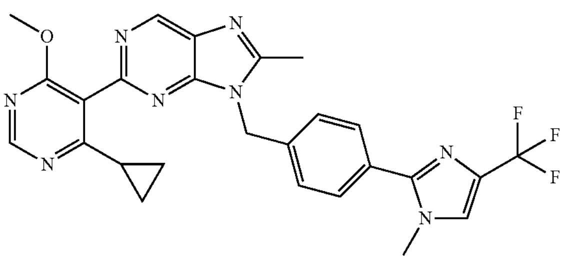 [SMILES: COc1ncnc(C2CC2)c1-c1ncc2nc(C)n(Cc3ccc(-c4nc(C(F)(F)F)cn4C)cc3)c2n1] | ++ |
| | +++ |
| | +++ |

TABLE 4-continued

| Compound Structure | USP1 IC$_{50}$ |
|---|---|
| (structure) | ++ |
| (structure) | +++ |
| (structure) | +++ |
| (structure) | +++ |
| (structure) | +++ |
| (structure) | + |

TABLE 4-continued

| Compound Structure | USP1 IC$_{50}$ |
|---|---|
| 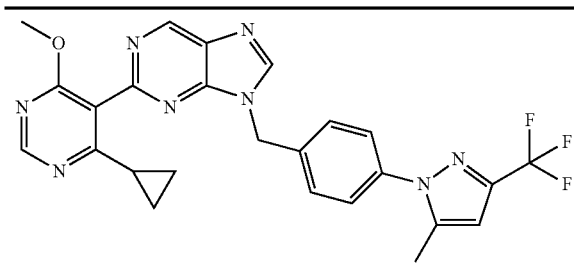 | ++ |
| 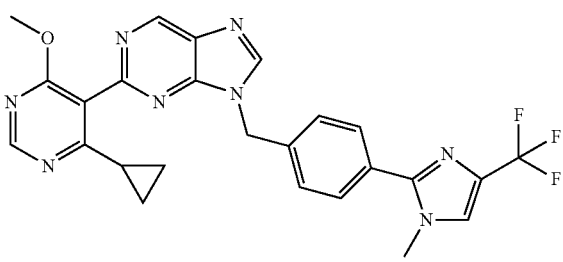 [SMILES: COc1ncnc(C2CC2)c1-c1ncc2ncn(Cc3ccc(-c4nc(C(F)(F)F)cn4C)cc3)c2n1] | ++ |
| 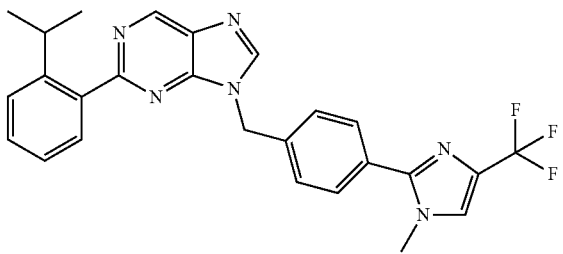 [SMILES: CC(C)c1ccccc1-c1ncc2ncn(Cc3ccc(-c4nc(C(F)(F)F)cn4C)cc3)c2n1] | +++ |

USP1 IC$_{50}$ $_{50}$:
"+" indicates 200 nM or greater;
"++" indicates 100 nM to less than 200 nM;
"+++" indicates 10 nM to less than 100 nM;
"++++" indicates less than 10 nM.

Example 219

P53 and BRCA Mutations Correlate with Sensitivity to USP1 Inhibitors

To identify cancers that are sensitive to USP1 inhibitors, p53 mutation status and BRCA mutation status were evaluated in cancer cell lines that were either sensitive or insensitive to USP1 inhibitors.

In these experiments, two different assay formats were used. The first assay format, termed the long-term proliferation assay (LTP), involved plating cancer cell lines in 6-well plates at very low density in a media volume of 3 ml with the goal of not splitting for at least 10 days (typically 5 k-20 k cells/well). Cells were plated on day −1 and on Day 0, the wells were treated with DMSO or increasing concentrations of USP1 inhibitor. Throughout the assay, cells treated with DMSO were checked for confluency and if the cell confluency reached 80%, the cells were split back to 20-40%. The ratio required to achieve this was then applied to the other wells treated with USP1 inhibitor. Media was changed every 3-4 days containing appropriate concentrations of DMSO or USP1 inhibitor. At the end of the experiment, cell growth was measured using CellTiter-Glo® (Promega) reagent and the results detected using a SynergyHTX plate reader. The second assay format was the colony formation assay (CFA). This assay required first establishing what cell plating density enabled the development of clearly interspersed colonies on a six-well plate when left to grow for around 14 days. Once this density had been identified, cells were plated on day −1 and on day 0 the wells were treated with DMSO or increasing concentrations of USP1 inhibitor. Media was changed on day 8 containing appropriate concentrations of DMSO or USP1 inhibitor. At or around day 14 when clearly interspersed colonies were visible in the DMSO treated wells, the cells were fixed and stained using 0.1% crystal violet in 10% ethanol for 20 minutes at room temperature. The plates were imaged then the amount of crystal violet stain in each well was quantified by extracting the crystal violet into 10% acetic acid and the absorbance measured at 565 nm. The results are shown in the table below.

TABLE 5

| Tissue | Long term proliferation - USP1 inhibitor sensitive? (<316 nM) | Colony Formation Assay - USP1 inhibitor sensitive? (<316 nM) | BRCA1 | BRCA2 | p53 | ATM |
|---|---|---|---|---|---|---|
| Breast | Yes | Yes | Mutant | WT | Mutant | WT |
| Ovary | Yes | Yes | Mutant | WT | Mutant | WT |
| Ovary | — | Yes | Mutant | WT | Mutant | WT |
| Ovary | — | Yes | WT | WT | Mutant | WT |
| Ovary | Yes | Yes | WT | WT | Mutant | WT |
| Ovary | Yes | — | WT | WT | Mutant | WT |
| Breast | Yes | — | Mutant | WT | Mutant | WT |
| Breast | Yes | — | Mutant | Mutant | Mutant | WT |
| Ovary | — | No | WT | WT | Mutant | WT |
| Breast | | No | WT | WT | Mutant | WT |
| Ovary | — | No | WT | WT | WT | WT |
| Ovary | — | No | WT | WT | WT | WT |
| Ovary | No | — | WT | WT | WT | WT |
| Breast | No | No | Mutant | — | Mutant | WT |
| Breast | No | — | Mutant | WT | Mutant | WT |
| Ovary | No | No | Mutant | WT | Mutant | WT |
| Ovary | No | — | WT | WT | Mutant | Mutant |
| Ovary | — | No | WT | WT | WT | WT |
| Melanoma | — | No | WT | WT | WT | WT |
| Bone | — | No | WT | WT | Mutant | WT |
| Bone | — | No | WT | WT | Mutant | WT |
| Bone | — | No | WT | WT | Mutant | WT |
| Bone | — | No | WT | WT | WT | WT |
| Melanoma | — | No | WT | WT | WT | WT |
| Bone | — | No | WT | Mutant | WT | WT |
| Lung | — | Yes | WT | Mutant | Mutant | WT |
| Uterus | — | No | WT | Mutant | Mutant | Mutant |
| Bladder | — | Yes | WT | WT | WT | WT |
| Bone | — | No | WT | WT | WT | WT |
| Bone | — | No | WT | WT | WT | WT |
| Bone | — | No | WT | WT | Mutant | WT |
| Bone | — | No | WT | WT | WT | WT |
| Bone | — | No | WT | WT | WT | WT |
| Bone | — | No | WT | WT | WT | WT |
| Nervous System | — | No | WT | WT | WT | WT |
| Nervous System | — | No | WT | WT | WT | WT |
| Nervous System | — | No | WT | WT | WT | Mutant |
| Nervous System | — | No | WT | WT | WT | WT |
| Nervous System | — | No | WT | WT | WT | WT |
| Skin | — | No | WT | WT | WT | WT |
| Soft Tissue | — | No | WT | WT | WT | WT |
| Uterus | — | No | WT | WT | WT | Mutant |
| Colon* | — | Yes | WT | Mutant | WT | Mutant |
| Lung* | — | Yes | WT | WT | WT | WT |
| Colon | — | No | WT | WT | WT | Mutant |
| Nervous System | — | No | WT | WT | WT | Mutant |
| Breast | — | No | WT | WT | WT | Mutant |
| Lung* | — | Yes | WT | WT | Mutant | Mutant |
| Lung | — | No | WT | WT | WT | Mutant |
| Colon* | — | Yes | WT | WT | Mutant | Mutant |
| Bladder | — | No | WT | WT | WT | Mutant |
| Colon | — | No | WT | Mutant | Mutant | WT |
| Ovary | — | No | WT | WT | Mutant | WT |
| Pancreas | — | No | WT | Mutant | WT | WT |
| Colon* | — | Yes | WT | Mutant | WT | WT |
| Colon | — | No | WT | Mutant | WT | WT |
| Colon* | — | Yes | WT | Mutant | Mutant | WT |
| Head & Neck | — | No | WT | WT | Mutant | WT |
| Pancreas | — | No | WT | Mutant | WT | WT |
| Cervix | — | No | WT | Mutant | WT | WT |
| Breast | — | No | WT | Mutant | Mutant | WT |
| Breast | — | No | Mutant | WT | WT | WT |
| Uterus | — | No | WT | WT | WT | WT |
| Breast | — | No | WT | WT | WT | WT |
| Bone | — | No | WT | WT | WT | WT |
| Bone | — | No | WT | WT | WT | WT |
| Ovary | — | No | WT | Mutant | WT | WT |
| Breast | — | No | WT | WT | Mutant | WT |
| Ovary | — | No | WT | WT | Mutant | WT |
| Breast | — | No | WT | WT | Mutant | WT |
| Breast | — | No | WT | WT | WT | WT |
| Breast | — | No | WT | Mutant | Mutant | Mutant |
| Breast | — | No | WT | Mutant | Mutant | WT |
| Breast | — | No | WT | WT | Mutant | Mutant |

TABLE 5-continued

| Tissue | Long term proliferation - USP1 inhibitor sensitive? (<316 nM) | Colony Formation Assay - USP1 inhibitor sensitive? (<316 nM) | BRCA status | | | |
|---|---|---|---|---|---|---|
| | | | BRCA1 | BRCA2 | p53 | ATM |
| Breast | — | No | WT | WT | WT | WT |
| Head & Neck | — | No | WT | WT | Mutant | WT |
| Ovary* | — | Yes | WT | WT | Mutant | WT |
| Skin* | — | Yes | WT | WT | WT | Mutant |
| Esophagus | — | No | WT | WT | Mutant | WT |
| Head & Neck | — | No | WT | WT | Mutant | WT |
| Esophagus | — | No | WT | Mutant | Mutant | WT |
| Head & Neck | — | No | WT | WT | Mutant | WT |
| Bladder* | — | Yes | WT | WT | Mutant | WT |

*USP1 inhibitor sensitivity reported based on one experiment.

These results indicate that p53 mutant cancers have increased sensitivity to USP1 inhibitors and that BRCA mutant cancers have increased sensitivity to USP1 inhibitors. It has previously been reported that p53 status determines PARP inhibitor sensitization (Sa et al. Genome Biology, (2019) 20:253) and that BRCA1/2 status predicts the efficacy of PARP inhibitors in the clinic (Audeh et al. Lancet (2010) 376 (9737), 245-51). In addition, these results indicate that ATM mutant cancers may have increased sensitivity to USP1 inhibitors. It has previously been reported that cancer cells with mutations in ATM are sensitive to PARP inhibitors (Wang et al. Translational Oncology (2017) 10, 190-196). Thus, USP1 inhibitors may be effective in combination with PARP inhibitors.

Example 220

Solubility Determination

Certain Compounds of the Disclosure were assessed for ADME solubility at pH 2.0 and pH 7.4.

Stock solutions were prepared by adding each compound to DMSO at a concentration of 10 mM. Samples were prepared by adding 50 µL of each stock solution to separate vials. The vials were loaded onto a 96-well rack and dried. 500 µL of Phosphate Buffered Saline (PBS) pH 7.4 or PBS pH 2.0 were added into each vial. The vials were then shaken at 25° C. and 1,100 rpm for 24 hours.

After 24 hours, the vials were centrifuged at 3220 G and 25° C. for 30 minutes. The supernatant fluid was analyzed by LC-MS/MS against a standard of known concentration. The solubility of each sample was then calculated using the equation below:

$$[Sample] = \frac{1}{n} * \sum (Calculated\ Conc.\ sample \times DF\ sample)$$

where DF is the dilution factor.

The following Compounds of the Disclosure have the ADME solubility values shown in Table 5 below.

TABLE 6

| Sample | Solubility at pH 2.0 (uM) | Solubility at pH 7.4 (uM) |
|---|---|---|
| 1 | + | + |
| 2 | ++ | + |
| 3 | ++ | + |
| 4 | ++ | + |
| 5 | ++ | + |
| 6 | ++ | + |
| 7 | + | + |
| 9 | ++ | ++ |
| 10 | + | + |
| 11 | ++ | ++ |
| 12 | ++ | ++ |
| 13 | + | + |
| 14 | ++ | + |
| 15 | ++ | ++ |
| 16 | ++ | + |
| 17 | + | + |
| 18 | + | + |
| 19 | ++ | ++ |
| 20 | + | + |
| 21 | + | + |
| 22 | ++ | + |
| 23 | + | + |
| 24 | + | + |
| 25 | + | + |
| 26 | ++ | + |
| 27 | + | + |
| 28 | + | + |
| 29 | + | + |
| 30 | + | + |
| 32 | ++ | + |
| 33 | ++ | ++ |
| 34 | + | + |
| 35 | + | + |
| 37 | + | + |
| 38 | + | + |
| 39 | ++ | + |
| 40 | ++ | + |
| 42 | ++ | ++ |
| 43 | + | ++ |
| 44 | + | + |
| 45 | + | + |
| 46 | + | + |
| 47 | ++ | ++ |
| 48 | ++ | + |
| 49 | + | + |
| 50 | + | + |
| 51 | ++ | + |
| 52 | + | + |
| 53 | + | + |
| 54 | + | + |
| 56 | ++ | + |
| 57 | ++ | ++ |
| 58 | + | + |
| 59 | + | + |
| 61 | + | + |
| 63 | ++ | + |
| 64 | + | + |
| 67 | ++ | + |

TABLE 6-continued

| Sample | Solubility at pH 2.0 (uM) | Solubility at pH 7.4 (uM) |
|---|---|---|
| 68 | + | + |
| 69 | ++ | ++ |
| 70 | + | + |
| 71 | + | + |
| 74 | ++ | ++ |
| 75 | + | + |
| 76 | + | + |
| 77 | + | + |
| 78 | + | + |
| 79 | + | + |
| 81 | + | + |
| 82 | + | + |
| 83 | ++ | + |
| 84 | + | + |
| 85 | + | + |
| 86 | ++ | ++ |
| 87 | ++ | ++ |
| 88 | ++ | ++ |
| 89 | ++ | ++ |
| 90 | ++ | ++ |
| 91 | ++ | + |
| 92 | ++ | ++ |
| 93 | ++ | ++ |
| 94 | ++ | + |
| 95 | ++ | + |
| 96 | + | + |
| 97 | ++ | + |
| 98 | ++ | ++ |
| 99 | ++ | + |
| 100 | ++ | + |
| 101 | ++ | + |
| 104 | ++ | ++ |
| 105 | ++ | + |
| 106 | + | + |
| 107 | ++ | ++ |
| 108 | ++ | + |
| 109 | + | + |
| 110 | ++ | ++ |
| 111 | ++ | + |
| 112 | ++ | + |
| 113 | ++ | ++ |
| 114 | ++ | ++ |
| 115 | + | + |
| 116 | ++ | + |
| 117 | ++ | ++ |
| 118 | + | + |
| 119 | + | ++ |
| 120 | + | + |
| 121 | + | + |
| 122 | + | + |
| 123 | + | + |
| 124 | + | + |
| 125 | + | + |
| 126 | + | + |
| 127 | + | + |
| 128 | ++ | ++ |
| 129 | ++ | + |
| 131 | ++ | + |
| 133 | ++ | ++ |
| 134 | + | + |
| 136 | ++ | + |
| 137 | ++ | ++ |
| 138 | ++ | ++ |
| 139 | ++ | ++ |
| 140 | + | + |
| 141 | ++ | + |
| 142 | ++ | + |
| 143 | + | + |
| 144 | + | + |
| 145 | ++ | ++ |
| 146 | ++ | ++ |
| 148 | + | + |
| 150 | ++ | ++ |
| 151 | ++ | ++ |
| 152 | ++ | ++ |
| 153 | ++ | ++ |
| 154 | + | + |
| 159 | ++ | ++ |
| 160 | + | + |
| 162 | + | + |
| 163 | + | + |
| 164 | ++ | + |
| 165 | + | + |
| 166 | + | + |
| 167 | ++ | + |
| 169 | ++ | + |
| 170 | + | + |
| 172 | + | + |
| 173 | + | + |
| 174 | + | + |
| 175 | + | + |
| 176 | ++ | + |
| 177 | + | + |
| 178 | + | + |
| 180 | + | + |
| 181 | ++ | + |
| 182 | + | + |
| 183 | + | + |
| 184 | + | + |
| 185 | + | + |
| 186 | ++ | ++ |
| 187 | + | + |
| 188 | + | + |
| 189 | + | + |
| 190 | + | + |
| 192 | + | + |
| 198 | + | + |
| 200 | ++ | ++ |
| 201 | ++ | + |
| 202 | ++ | + |
| 203 | ++ | ++ |
| 204 | ++ | ++ |
| 205 | ++ | ++ |
| 206 | ++ | + |
| 207 | ++ | ++ |
| 208 | + | + |
| 209 | ++ | ++ |
| 210 | ++ | ++ |
| 211 | ++ | ++ |
| 212 | + | + |
| 213 | + | + |
| 214 | + | + |
| 215 | ++ | ++ |
| 218 | + | + |
| 219 | + | + |

Solubility: "+" indicates less than 10 μM; "++" indicates 10 μM or greater.

Example 221

Liver Microsomal Stability

Certain Compounds of the Disclosure were assessed for ADME metabolic stability in human liver microsomes (HLM) and rat liver microsomes (RLM).

Samples were prepared by adding 222.5 μL of a master solution (100 mM phosphate buffer and 1 mg/mL liver microsomes (HLM or RLM)) and 25 μL of a 10 mM NADPH solution to incubation plates, which were then warmed for 10 min. Each compound was separately dissolved in DMSO to prepare 10 mM stock solutions, which were then diluted to 100 μM with acetonitrile. A reaction was started by adding 2.5 μL of the 100 μM solution of each compound to separate incubation plates such that the final concentration of for each compound in each plate was 1 μM.

25 μL aliquots of each sample were taken at 0.5, 5, 10, 15, 20 and 30 minutes, and the reaction was stopped by adding 5 volumes of cold acetonitrile with IS (100 nM alprazolam, 200 nM caffeine and 100 nM tolbutamide). The samples were then centrifuged at 3,220 G for 30 minutes, and 100 μL of the supernatant fluid was mixed with 100 μL of ultra-pure H₂O.

The samples were then analyzed by LC-MS/MS. Peak areas were determined from extracted ion chromatograms. Slope values (k) were determined by linear regression of the natural logarithm of the remaining percentage of the compound vs. incubation time curve. The in vitro half-life (in vitro $t_{1/2}$) was determined from the slope value using the following equation:

$$\text{in vitro } t_{1/2} = -(0.693/k).$$

The in vitro half-life (min) was converted into the in vitro intrinsic clearance (in vitro $CL_{int}$, in μL/min/mg protein) using the following equation:

$$\text{in vitro } CL_{int} = \left(\frac{0.693}{(t_{1/2})}\right) * \left(\frac{\text{volume of incubation } (\mu L)}{\text{amount of proteins (mg)}}\right)$$

The following Compounds of the Disclosure have the ADME metabolic stability values shown in Table 6 below.

TABLE 7

| Sample | $t_{1/2}$ (min) in HLM | $t_{1/2}$ (min) in RLM |
|---|---|---|
| 1 | + | + |
| 2 | + | + |
| 3 | ++ | ++ |
| 4 | + | + |
| 5 | + | + |
| 6 | + | + |
| 7 | ++ | + |
| 9 | + | + |
| 10 | + | + |
| 11 | + | + |
| 12 | + | ++ |
| 13 | ++ | ++ |
| 14 | ++ | ++ |
| 15 | + | + |
| 16 | + | + |
| 17 | ++ | ++ |
| 18 | ++ | ++ |
| 19 | ++ | ++ |
| 20 | ++ | ++ |
| 21 | + | + |
| 22 | + | + |
| 23 | ++ | + |
| 24 | + | + |
| 25 | + | + |
| 26 | ++ | + |
| 27 | ++ | ++ |
| 28 | ++ | ++ |
| 29 | ++ | ++ |
| 30 | + | + |
| 32 | + | + |
| 33 | ++ | ++ |
| 34 | ++ | ++ |
| 35 | ++ | ++ |
| 37 | ++ | ++ |
| 38 | + | + |
| 39 | + | + |
| 40 | + | + |
| 42 | + | + |
| 43 | + | + |
| 44 | + | + |
| 45 | + | + |
| 46 | + | + |
| 47 | + | + |
| 48 | ++ | ++ |
| 49 | ++ | ++ |
| 50 | ++ | ++ |
| 51 | ++ | ++ |
| 52 | ++ | + |
| 53 | ++ | ++ |
| 54 | + | + |
| 56 | ++ | ++ |
| 57 | ++ | ++ |
| 58 | ++ | ++ |
| 59 | + | + |
| 61 | ++ | + |
| 63 | ++ | + |
| 64 | + | + |
| 67 | ++ | ++ |
| 68 | + | + |
| 69 | + | + |
| 70 | ++ | + |
| 71 | ++ | ++ |
| 74 | + | + |
| 75 | ++ | ++ |
| 76 | ++ | ++ |
| 77 | + | + |
| 78 | ++ | ++ |
| 79 | ++ | ++ |
| 81 | + | + |
| 82 | + | + |
| 83 | + | + |
| 84 | + | + |
| 85 | ++ | ++ |
| 86 | ++ | ++ |
| 87 | ++ | ++ |
| 88 | ++ | + |
| 89 | ++ | ++ |
| 90 | ++ | ++ |
| 91 | + | + |
| 92 | + | ++ |
| 93 | + | + |
| 94 | ++ | + |
| 95 | ++ | + |
| 96 | ++ | ++ |
| 97 | ++ | ++ |
| 98 | ++ | + |
| 99 | + | + |
| 100 | + | + |
| 101 | + | + |
| 104 | + | + |
| 105 | ++ | ++ |
| 106 | ++ | ++ |
| 107 | ++ | ++ |
| 108 | + | + |
| 109 | + | + |
| 110 | + | ++ |
| 111 | + | ++ |
| 112 | ++ | ++ |
| 113 | ++ | + |
| 114 | + | + |
| 115 | + | + |
| 116 | + | + |
| 117 | + | + |
| 118 | ++ | + |
| 119 | ++ | ++ |
| 120 | + | + |
| 121 | + | + |
| 122 | + | + |
| 123 | + | + |
| 124 | + | + |
| 125 | ++ | ++ |
| 127 | ++ | ++ |
| 128 | ++ | + |
| 129 | ++ | ++ |
| 131 | ++ | ++ |
| 133 | + | + |
| 134 | ++ | ++ |
| 136 | + | + |
| 137 | ++ | ++ |
| 138 | ++ | ++ |
| 139 | ++ | ++ |
| 140 | ++ | ++ |
| 141 | ++ | ++ |
| 142 | ++ | + |
| 143 | ++ | ++ |

TABLE 7-continued

| Sample | $t_{1/2}$ (min) in HLM | $t_{1/2}$ (min) in RLM |
|---|---|---|
| 144 | ++ | + |
| 145 | ++ | + |
| 146 | + | + |
| 148 | + | + |
| 150 | + | + |
| 151 | ++ | ++ |
| 152 | + | + |
| 153 | + | + |
| 154 | ++ | ++ |
| 159 | + | + |
| 160 | ++ | ++ |
| 162 | ++ | ++ |
| 163 | ++ | ++ |
| 164 | + | + |
| 165 | ++ | ++ |
| 166 | + | + |
| 167 | + | + |
| 169 | ++ | ++ |
| 170 | ++ | + |
| 172 | ++ | + |
| 173 | ++ | ++ |
| 174 | ++ | ++ |
| 175 | ++ | ++ |
| 176 | ++ | ++ |
| 177 | ++ | ++ |
| 178 | ++ | ++ |
| 180 | ++ | ++ |
| 181 | ++ | ++ |
| 182 | ++ | ++ |
| 183 | + | + |
| 184 | + | + |
| 185 | ++ | ++ |
| 186 | + | + |
| 187 | ++ | + |
| 188 | ++ | ++ |
| 189 | ++ | ++ |
| 190 | + | + |
| 192 | + | + |
| 198 | ++ | ++ |
| 200 | ++ | ++ |
| 201 | + | + |
| 202 | + | + |
| 203 | + | + |
| 204 | ++ | + |
| 205 | ++ | ++ |
| 206 | + | ++ |
| 207 | + | ++ |
| 208 | ++ | ++ |
| 209 | + | ++ |
| 210 | ++ | ++ |
| 211 | + | ++ |
| 212 | ++ | ++ |
| 213 | ++ | ++ |
| 214 | ++ | ++ |
| 215 | ++ | + |
| 218 | ++ | + |
| 219 | ++ | ++ |

HLM/RLM Stability $t_{1/2}$: "+" indicates less than 25 minutes; "++" indicates 25 minutes or greater.

Example 222

USP1 is Required for the Viability of a Subset of Cancer Cell Lines

To perform CRISPR-Cas9 gene depletion screens, approximately 500 cancer cell lines were engineered to express Cas9 and were subsequently infected with lentivirus expressing guide RNAs targeting every gene in the genome. After 14 days, cells were harvested, genomic DNA was extracted, and Illumina Sequencing was used to determine guide representation, and a "dropout" score was used to measure the depletion of guides targeting each gene in each cell line. A lower dropout score indicates a greater sensitivity to loss of the gene. The dropout scores for USP1 in various cell lines are presented in FIG. 1. These data demonstrate that guides targeting USP1 were depleted in a subset of ovarian cancer and breast cancer cell lines, indicating that USP1 is required for viability of these lines (FIG. 1). Breast cancer cell lines are shown in white, and ovarian cancer cell lines are shown in black. Seven out of the nine most sensitive breast lines were triple negative breast cancer (TNBC), but some TNBC lines were insensitive to loss of USP1.

USP1 is a deubiquitinase protein that removes ubiquitin from mono-ubiquitinated PCNA (FIG. 2) and FANCD2. CRISPR-Cas9 genetic depletion or pharmacological inhibition of USP1 results in increased mono-ubiquitination of both PCNA and FANCD2.

Example 223

Rad18 Levels Correlate with Sensitivity to Loss of USP1

Figure 2:
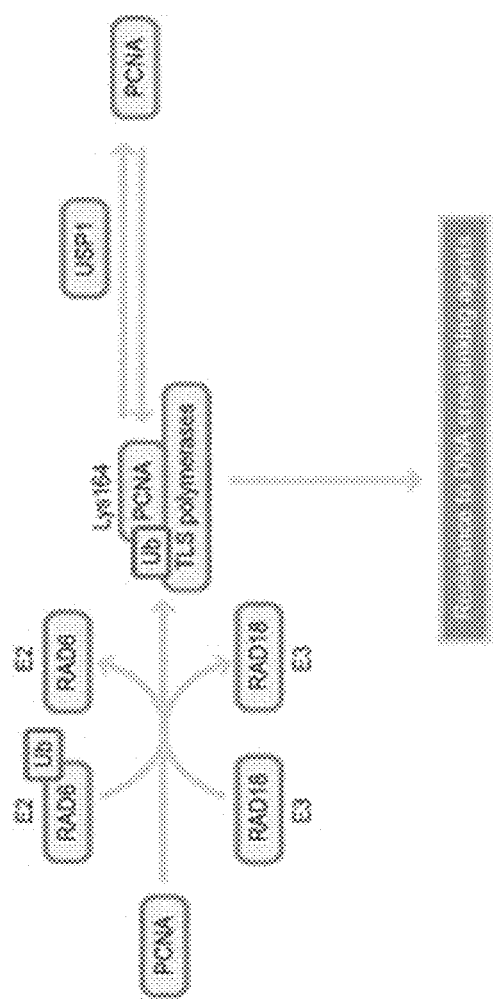
FIG. 2 provides a schematic of PCNA ubiquitination from Jacquemont C. and Taniguchi T., *BMC Biochemistry* 8 (Suppl 1):S10 (2007). The E3 ligase Rad18 mono-ubiquitinates PCNA. USP1 deubiquitnates mono-ubiquitinated PCNA.

To identify features that may predict sensitivity to loss of USP1, gene expression was analyzed across all of the approximately 500 cell lines. Rad18 mRNA levels were found to correlate with sensitivity to loss of USP1. Rad18 is the E3 ubiquitin ligase that ubiquitinates PCNA (FIG. 2). It has previously been reported that knockdown of Rad18 resulted in a loss of mono-ubiquitinated PCNA and that this rescued the replication fork instability induced by USP1 inhibition in homologous-recombination deficient tumors with BRCA1 and BRCA2 mutations. (Lim K. et al., "USP1 is required for replication fork stability in BRCA1-deficient tumors," AACR 2018 Meeting, Abstract 333/14.) Therefore, it was surprising that the USP1-sensitive cell lines included BRCA1/2 wild-type cell lines as well as BRCA1/2 mutant cell lines (FIG. 1).

Figure 3:
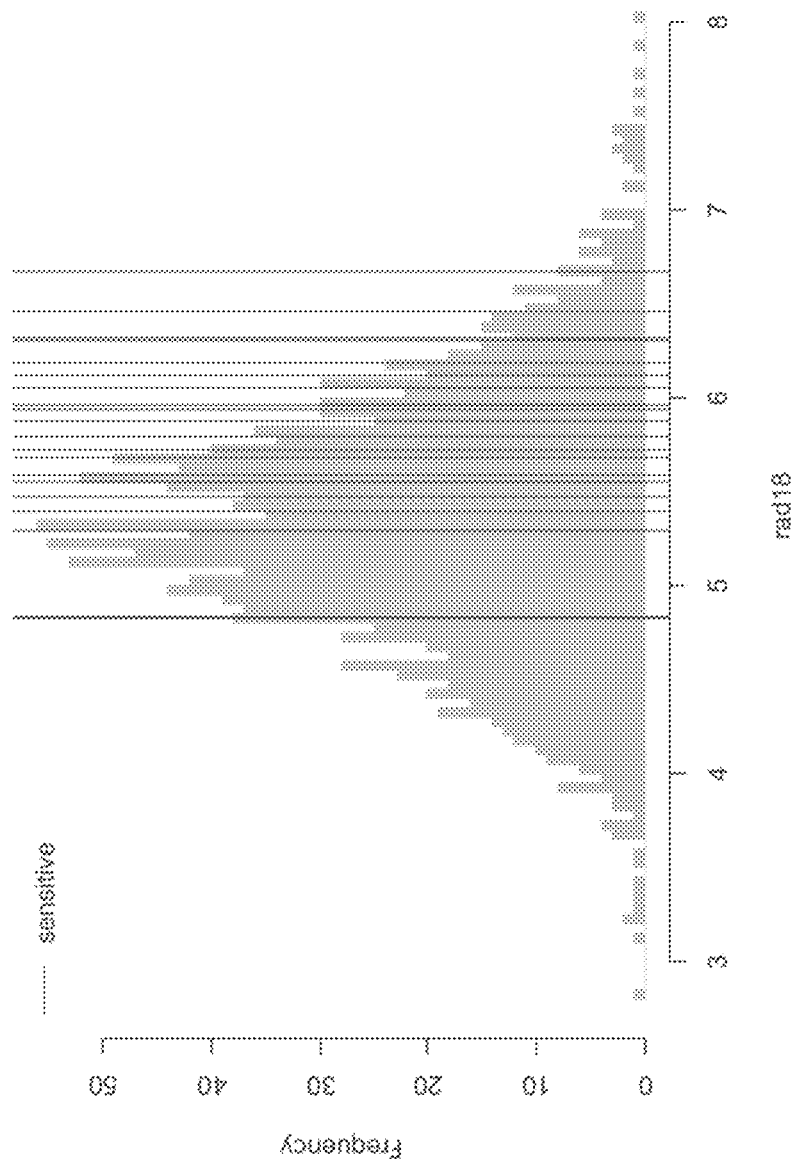
FIG. 3 shows the distribution of Rad18 mRNA expression across approximately 500 cancer cell lines. The x-axis shows normalized Rad18 mRNA expression values, and y-axis shows the number of cell lines that have the expression value indicated on the x-axis. The 20 cell lines with the lowest USP1 dropout scores are shown in the dark bars reaching to the top of the graph.
Figure 4:
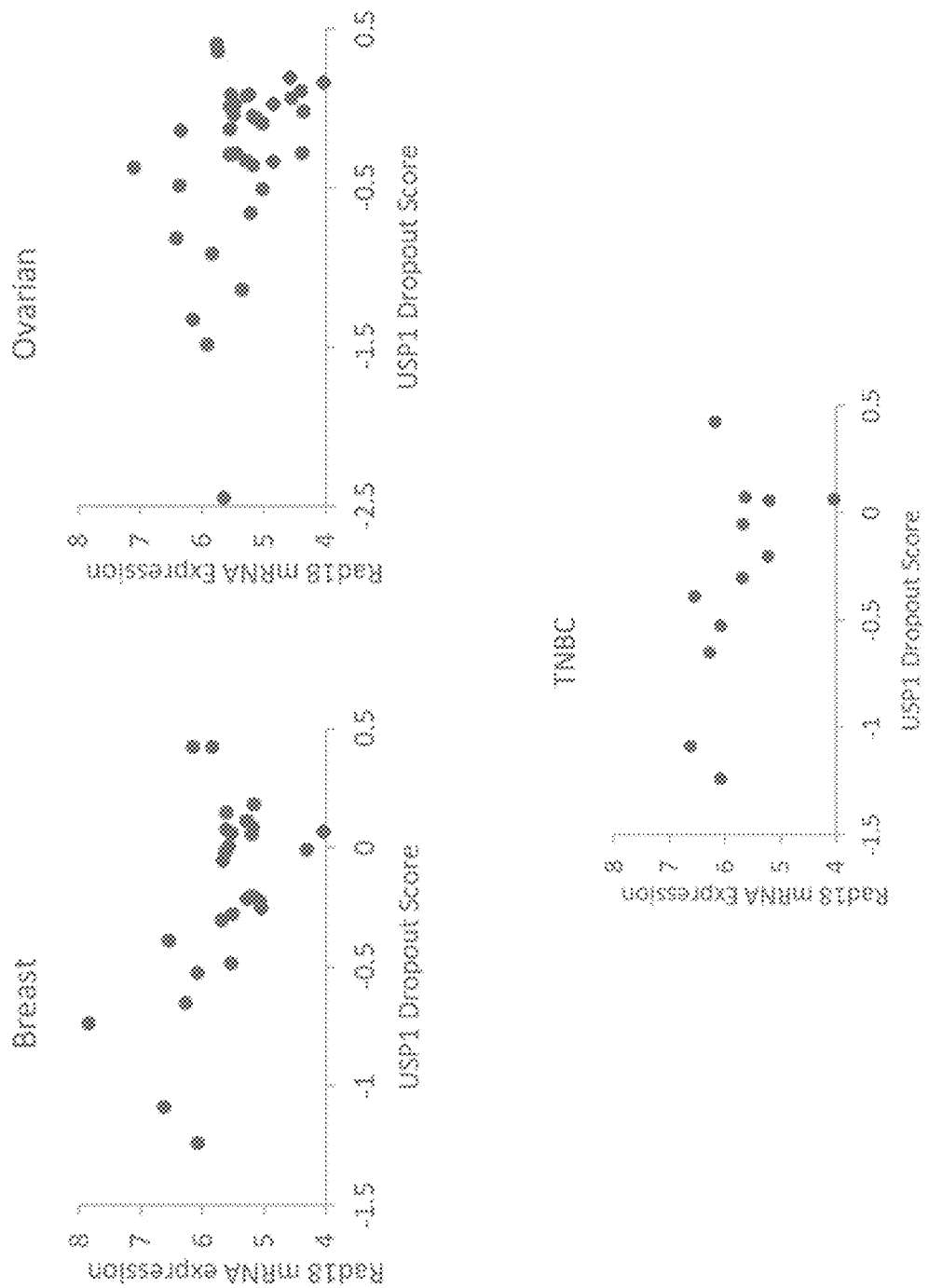
FIG. 4 provides plots showing USP1 dropout scores across Rad18 mRNA expression levels in breast cancer cell lines (top left), ovarian cancer cell lines (top right), and triple negative breast cancer cell lines (bottom).

RAD18 had not previously been proposed as even a potential biomarker for USP1-inhibitor sensitivity, and, as demonstrated herein, Rad18 can be detected in both USP1-sensitive and USP1-insensitive tumors (see FIGS. 3-6). However, the cell lines that were most sensitive to USP1 inhibitors also tended to have high Rad18 levels. FIG. 3 shows a histogram of Rad18 mRNA expression across approximately 500 cell lines, and the 20 lines with the lowest USP1 dropout score indicated in the dark bars reaching to the top of the graph. Similarly, FIG. 4 shows that USP1 dropout scores correlated with Rad18 mRNA expression levels in both breast (including TNBC) and ovarian cancer lines.

Figure 5:
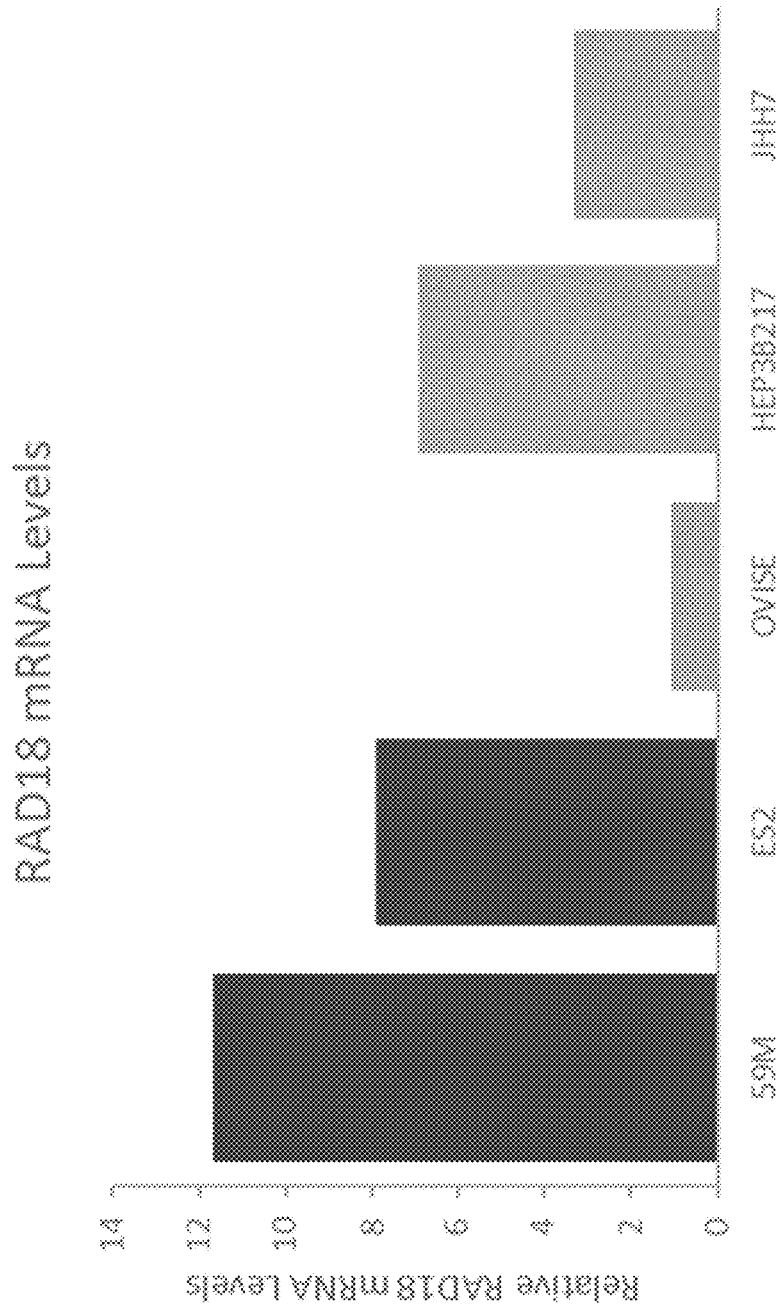
FIG. 5 shows Rad18 mRNA levels in USP1 sensitive cell lines (59M and ES2) and insensitive cell lines (OVISE, JHH7, and HEP3B217) as measured by qRT-PCT, normalized to GAPDH expression, and normalized to OVISE.
Figure 6:
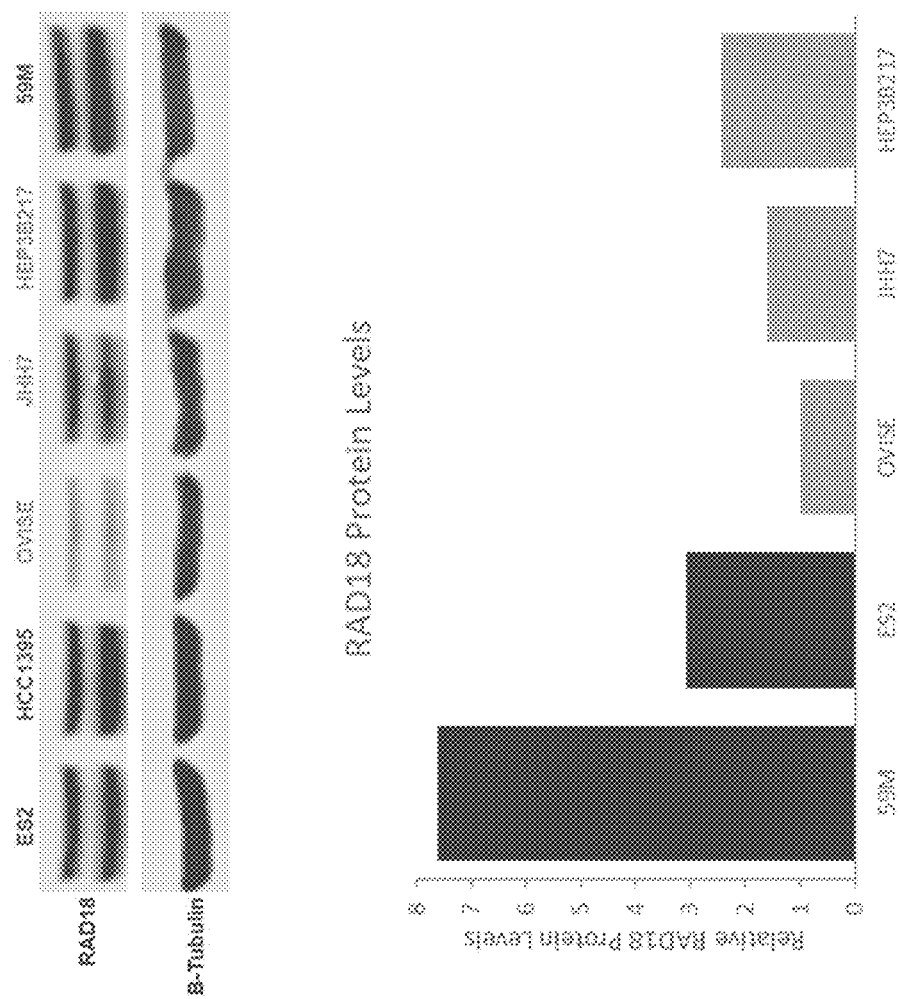
FIG. 6 shows RAD18 protein levels in the USP1 sensitive cell lines (59M and ES2) and insensitive cell lines (OVISE, JHH7, and HEP3B217). The top panel shows the protein levels in a Western blot, and the bottom panel provides quantitation of the Western blot protein levels. "HCC1395" in the Western assay (top panel) was determined to be contaminated with another cell line and therefore not used in the quantitation (bottom panel).

To further analyze the correlation of Rad18 levels and sensitivity to USP1 inhibitors, Rad18 mRNA and protein levels were analyzed in a panel of USP1-sensitive and -insensitive lines. The sensitive cell lines were 59M (a BRCA1/2 wildtype ovarian cancer line) and ES2 (a BRCA1/2 wildtype ovarian cancer line). The insensitive cell lines were OVISE (a BRCA1/2 wildtype ovarian cancer line), Hep3B217 (a BRCA1/2 wildtype liver cancer line), and JHH7 (a BRCA1/2 wildtype liver cancer line). Rad18 mRNA levels were determined using quantitative reverse transcription PCR (qRT-PCR), and sensitive lines were observed to have higher expression of Rad18 mRNA (FIG. 5). Rad18 protein levels were examined by western blot in the same cell lines, and a sensitive lines were also observed to have higher expression of Rad18 protein levels (FIG. 6).

These data demonstrate that while Rad18 can be detected in both USP1-sensitive and USP1-insensitive tumors, elevated Rad18 mRNA and protein levels are correlated with USP1-sensitivity.

Example 224

Rad18 Deletion Rescues USP1 Deletion

Figure 7:
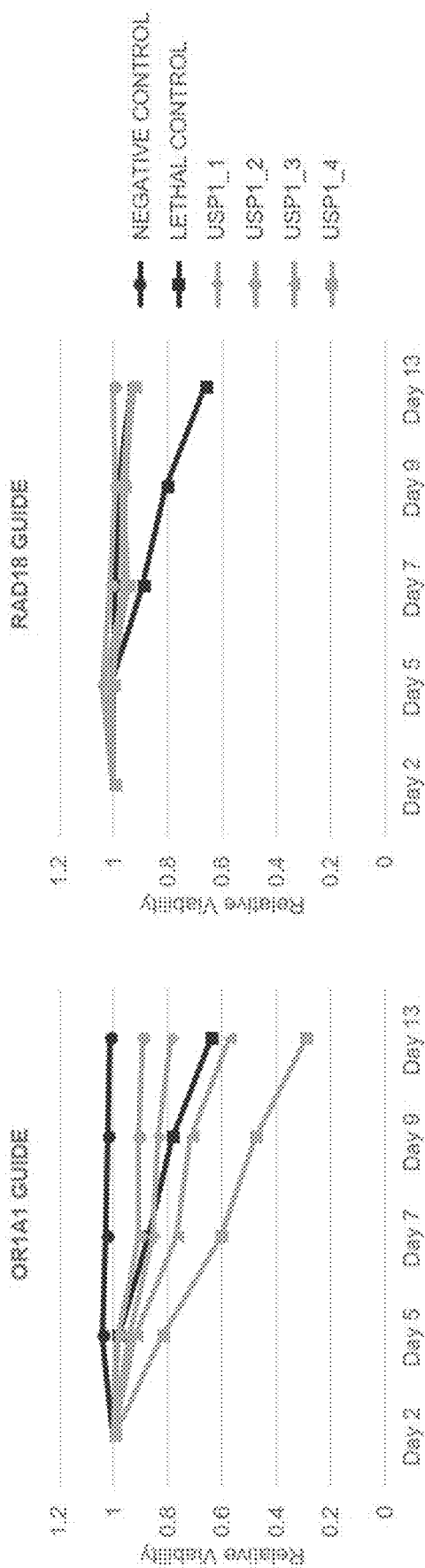
FIG. 7. provides graphs demonstrating that deletion of Rad18 rescues deletion of USP1. The graphs show the relative cell viability in OR1A1 (negative control) knockout cells (left panel) or Rad18 knockout cells (right panel) with the addition of guides against OR1A1 negative control ("negative control"), EEF2 pan lethal positive control ("lethal control"), or 4 different USP1 guides ("USP1_1," "USP1_2," "USP1_3," and "USP1_4").

Rad18 was found to play a functional role in sensitivity to USP1 loss. ES2 cells were infected with lentivirus expressing Cas9, then electroporated with ribonucleoproteins containing Cas9 protein and either a negative control guide (OR1A1) or a guide targeting Rad18. The cells were subsequently infected with lentivirus expressing guides against a negative control (OR1A1), a positive lethal control (EEF2), or one of four different USP1-targeting guides. In the negative control cells, treatment with USP1-targeted guides decreases viability. However, genetic depletion of Rad18 reversed the cell viability effects of USP1 loss. (FIG. 7.) These data demonstrate that Rad18 deletion rescues USP1 deletion.

Having now fully described this invention, it will be understood by those of ordinary skill in the art that the same can be performed within a wide and equivalent range of conditions, formulations, and other parameters without affecting the scope of the invention or any embodiment thereof.

Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

All patents and publications cited herein are fully incorporated by reference herein in their entirety.

What is claimed is:
1. A compound having Formula I:

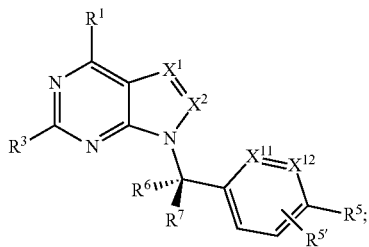

I or a pharmaceutically acceptable salt or solvate thereof, wherein:

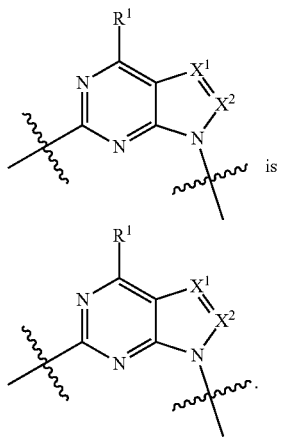

is each of $R^1$ and $R^2$ is independently selected from hydrogen, halo, cyano, optionally substituted alkyl, optionally substituted alkenyl, and optionally substituted alkynyl;

$R^3$ is an optionally substituted phenyl, optionally substituted pyridyl, optionally substituted pyrimidinyl, optionally substituted pyrazinyl, optionally substituted pyridazinyl, or optionally substituted pyrazolyl;

each of $X^{11}$ and $X^{12}$ is independently selected from N and CH;

$R^{5'}$ is selected from hydrogen, optionally substituted $(C_1-C_6)$ alkyl, optionally substituted $(C_2-C_6)$ alkenyl, optionally substituted $(C_2-C_6)$ alkynyl, optionally substituted $(C_1-C_6)$ alkoxy, $(C_1-C_6)$ haloalkyl, $(C_1-C_6)$ haloalkoxy, $(C_1-C_6)$ hydroxyalkyl, cyano, halo, sulfonamido, —C(=O)$R^{23}$, —C(=O)O$R^{24}$, —N$R^{32a}R^{32b}$, —N$R^{31a}$C(=O)$R^{25}$, —N$R^{31a}$C(=O)N$R^{31a}R^{31b}$—C(=O)N$R^{31a}R^{31b}$, —S(O)$_2R^{27}$, —N$R^{31a}$SO$_2R^{27}$, optionally substituted $(C_6-C_{14})$ aryl, optionally substituted $(C_6-C_{14})$ ar-$(C_1-C_2)$ alkyl, optionally substituted heteroaryl, optionally substituted heteroar-$(C_1-C_2)$ alkyl, optionally substituted $(C_3-C_8)$ cycloalkyl, optionally substituted $((C_3-C_8)$ cycloalkyl)-$(C_1-C_2)$ alkyl, optionally substituted heterocyclo, optionally substituted heterocyclo-$(C_1-C_2)$ alkyl, optionally substituted —O—$(C_6-C_{14})$ aryl, optionally substituted —O—$(C_6-C_{14})$ ar-$(C_1-C_2)$ alkyl, optionally substituted O-heteroaryl, optionally substituted —O-heteroar-$(C_1-C_2)$ alkyl, optionally substituted —O—$(C_3-C_8)$ cycloalkyl, optionally substituted —O—$((C_3-C_8)$ cycloalkyl)-$(C_1-C_2)$ alkyl, optionally substituted —O-heterocyclo, optionally substituted —O-heterocyclo-$(C_1-C_2)$ alkyl;

$R^5$ is selected from optionally substituted $(C_1-C_6)$ alkyl, optionally substituted $(C_2-C_6)$ alkenyl, optionally substituted $(C_2-C_6)$ alkynyl, optionally substituted $(C_1-C_6)$ alkoxy, $(C_1-C_6)$ haloalkyl, $(C_1-C_6)$ haloalkoxy, $(C_1-C_6)$ hydroxyalkyl, cyano, halo, sulfonamido, —C(=O)$R^{23}$, —C(=O)O$R^{24}$, —N$R^{32a}R^{32b}$—N$R^{31a}$C(=O)$R^{25}$, —N$R^{31a}$C(=O)N$R^{31a}R^{31b}$, —C(=O)N$R^{31a}R^{31b}$, —S(O)$_2R^{27}$, —N$R^{31a}$SO$_2R^{27}$, optionally substituted $(C_6-C_{14})$ aryl, optionally substituted $(C_6-C_{14})$ ar-$(C_1-C_2)$ alkyl, optionally substituted heteroaryl, optionally substituted heteroar-$(C_1-C_2)$ alkyl, optionally substituted $(C_3-C_8)$ cycloalkyl, optionally substituted $((C_3-C_8)$ cycloalkyl)-$(C_1-C_2)$ alkyl, optionally substituted heterocyclo, optionally substituted heterocyclo-$(C_1-C_2)$ alkyl, optionally substituted —O—$(C_6-C_{14})$ aryl, optionally substituted —O—$(C_6-C_{14})$ ar-$(C_1-C_2)$ alkyl, optionally substituted O-heteroaryl, optionally substituted —O-heteroar-($C_1$-$C_2$) alkyl, optionally substituted —O—($C_3$-$C_8$) cycloalkyl, optionally substituted —O—(($C_3$-$C_8$) cycloalkyl)-($C_1$-$C_2$) alkyl, optionally substituted O-heterocyclo, optionally substituted —O-heterocyclo-($C_1$-$C_2$) alkyl; or one of $R^5$ and one of $R^{5'}$ on adjacent atoms are taken together with the atoms to which they are attached to form an optionally substituted ($C_6$-$C_{14}$) aryl ring; or one of $R^5$ and one of $R^{5'}$ on adjacent atoms are taken together with the atoms to which they are attached to form an optionally substituted heteroaryl ring; or one of $R^5$ and one of $R^{5'}$ on adjacent atoms are taken together with the atoms to which they are attached to form an optionally substituted ($C_3$-$C_8$) cycloalkyl ring; or one of $R^5$ and one of $R^{5'}$ on adjacent atoms are taken together with the atoms to which they are attached to form an optionally substituted heterocycloalkyl ring; or one of $R^5$ and one of $R^{5'}$ on adjacent atoms on the same atom to which they are attached are taken together to form an optionally substituted spirocycloalkyl ring; or one of $R^5$ and one of $R^{5'}$ on adjacent atoms on the same atom to which they are attached are taken together to form an optionally substituted spiroheterocycloalkyl ring;

each of $R^6$ and $R^7$ is independently selected from hydrogen, halo, cyano, optionally substituted alkyl, optionally substituted alkenyl, and optionally substituted alkynyl;

$R^{23}$ is selected from the group consisting of hydrogen, optionally substituted alkyl, optionally substituted alkenyl, optionally substituted alkynyl, amino, alkylamino, dialkylamino, cycloalkylamino, hydroxyalkyl, (amino)alkyl, (alkylamino)alkyl, (dialkylamino)alkyl, (cycloalkylamino)alkyl, (cycloalkyl)alkyl, aralkyl, (heterocyclo)alkyl, (heteroaryl)alkyl, (amino)(hydroxy)alkyl, (aralkylamino)alkyl, optionally substituted heterocyclo, optionally substituted heteroaryl, optionally substituted aryl, and optionally substituted cycloalkyl;

$R^{31a}$ and $R^{31b}$ are each independently selected from the group consisting of hydrogen, optionally substituted alkyl, optionally substituted alkenyl, optionally substituted alkynyl, hydroxyalkyl, (amino)alkyl, (alkylamino)alkyl, (dialkylamino)alkyl, alkoxyalkyl, cycloalkyl, (cycloalkyl)alkyl, (heterocyclo)alkyl, aralkyl, and (heteroaryl)alkyl; and each of $R^{24}$, $R^{25}$, $R^{27}$, $R^{32a}$, and $R^{32b}$ is independently selected from the group consisting of hydrogen, optionally substituted alkyl, optionally substituted alkenyl, optionally substituted alkynyl, amino, alkylamino, dialkylamino, cycloalkylamino, hydroxyalkyl, (amino)alkyl, (alkylamino)alkyl, (dialkylamino)alkyl, (cycloalkylamino)alkyl, (cycloalkyl)alkyl, aralkyl, (heterocyclo)alkyl, (heteroaryl)alkyl, (amino)(hydroxy)alkyl, (aralkylamino)alkyl, alkoxyalkyl, optionally substituted heterocyclo, optionally substituted heteroaryl, optionally substituted aryl, and optionally substituted cycloalkyl.

2. The compound of claim 1, or a pharmaceutically acceptable salt or solvate thereof, wherein $R^3$ is an optionally substituted phenyl, an optionally substituted pyrid-3-yl, an optionally substituted pyrid-4-yl, an optionally substituted pyrimidin-5-yl, or an optionally substituted pyrazol-5-yl.

3. The compound of claim 2, wherein $R^3$ is substituted and the substituents are independently selected from methoxy, deuteromethoxy, ethoxy, isopropoxy, t-butoxy, difluoromethoxy, 2-fluoroethoxy, 2-methoxyethoxy, cyclopropoxy, cyclobutoxy, (tetrahydrofuran-3-yl)oxy, benzyloxy, methyl, ethyl, isopropyl, 2-fluoroisopropyl, t-butyl, cyclopropyl, cyclobutyl, methylcyclopropyl, pyrrolidin-1-yl, azetidin-1-yl, methylamino, dimethylamino, cyano, halo, methylthio, methylsulfonyl, and ethylsulfonyl.

4. The compound of claim 1, or a pharmaceutically acceptable salt or solvate thereof, wherein $R^3$ is selected from the group consisting of:

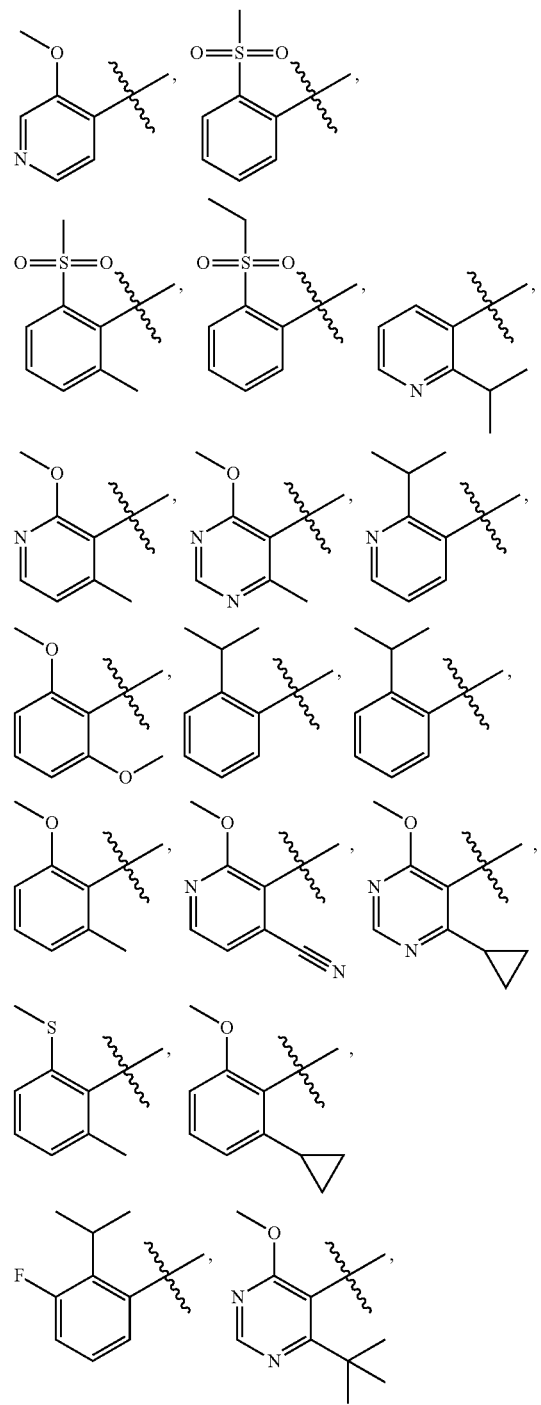

531
-continued
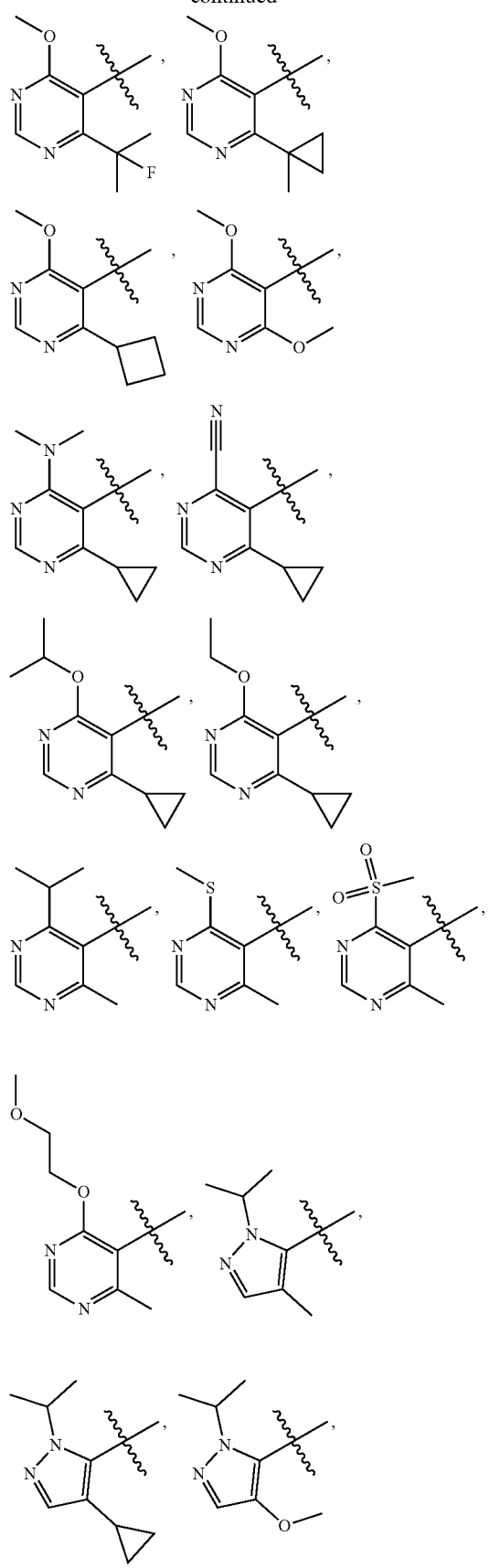
532
-continued
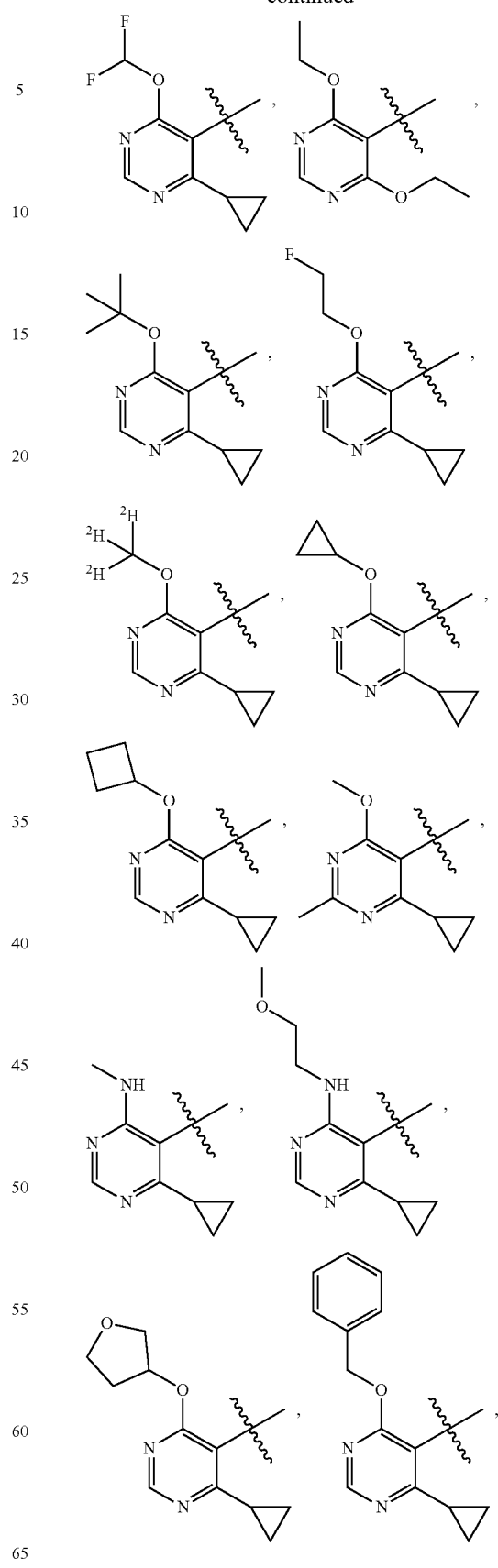

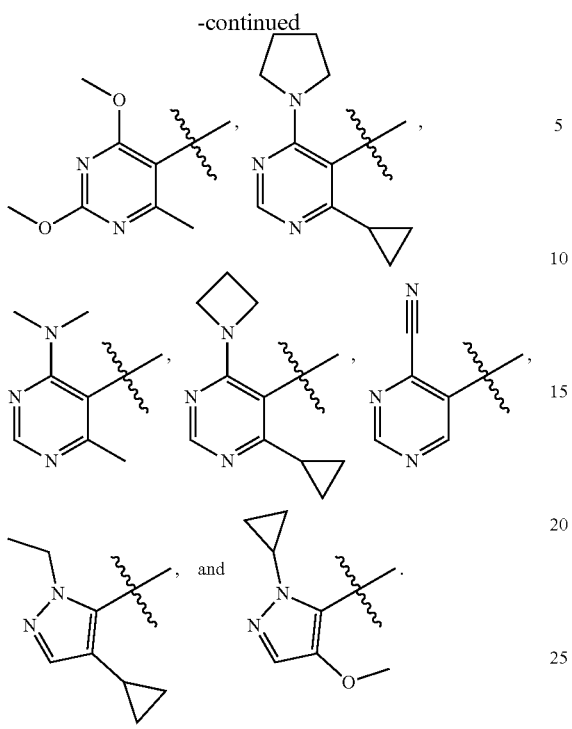

5. The compound of claim 1, or a pharmaceutically acceptable salt or solvate thereof, wherein $R^5$ is selected from optionally substituted $(C_6-C_{14})$ aryl, optionally substituted $(C_6-C_{14})$ ar-$(C_1-C_2)$ alkyl, optionally substituted heteroaryl, optionally substituted heteroar-$(C_1-C_2)$ alkyl, optionally substituted $(C_3-C_8)$ cycloalkyl, optionally substituted $((C_3-C_8)$ cycloalkyl)-$(C_1-C_2)$ alkyl, optionally substituted heterocyclo, optionally substituted heterocyclo-$(C_1-C_2)$ alkyl.

6. The compound of claim 1, or a pharmaceutically acceptable salt or solvate thereof, wherein $R^5$ is an optionally substituted pyrrolyl, optionally substituted imidazolyl, optionally substituted pyrazolyl, optionally substituted triazolyl, or optionally substituted tetrazolyl.

7. The compound of claim 6, wherein $R^5$ is substituted and the substituents are independently selected from halo, methyl, ethyl, isopropyl, cyclopropyl, cyclobutyl, methoxy, ethoxy, triazolyl, cyano, optionally substituted alkyl, amino, alkylamino, dialkylamino, difluoromethyl, trifluoromethyl, methylsulfonyl, oxetan-3-yl, and methylazetidinyl.

8. The compound of claim 1, or a pharmaceutically acceptable salt or solvate thereof, wherein $R^5$ is selected from the group consisting of:

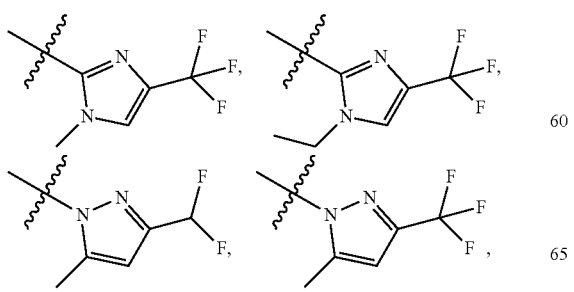

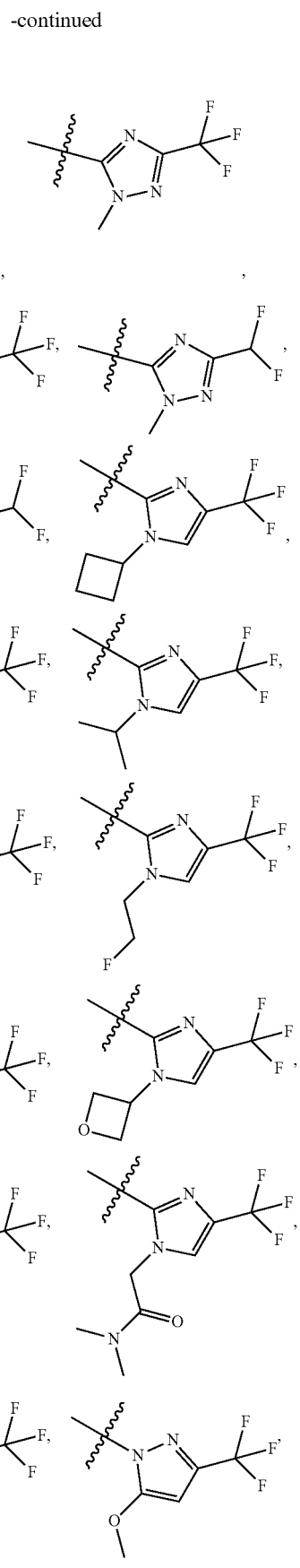

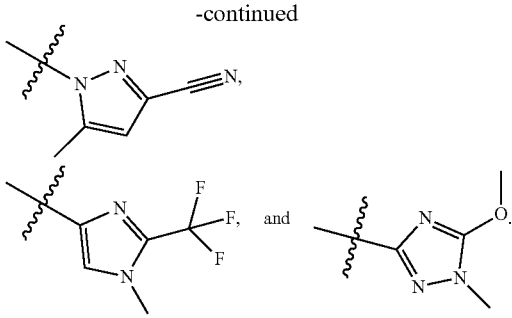

9. The compound of claim 1, or a pharmaceutically acceptable salt or solvate thereof, having a Formula II:

II

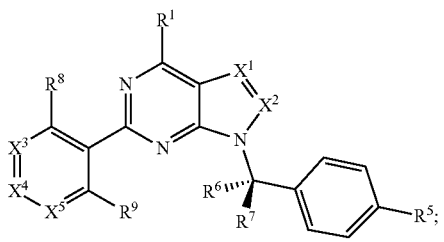

wherein:
$X^1$ is $CR^2$;
$X^2$ is N;
$X^3$ is selected from N and $CR^{11}$;
$X^4$ is selected from N and $CR^{11}$;
$X^5$ is selected from N and $CR^{12}$; and
each of $R^8$, $R^9$, $R^{10}$, $R^{11}$, and $R^{12}$ is independently selected from the group consisting of hydrogen, halo, nitro, cyano, hydroxy, amino, alkylamino, dialkylamino, haloalkyl, hydroxyalkyl, alkoxy, haloalkoxy, aryloxy, heteroaryloxy, aralkyl aralkyloxy, alkylthio, carboxamido, sulfonamido, alkylcarbonyl, arylcarbonyl, alkylsulfonyl, arylsulfonyl, carboxy, carboxyalkyl, alkyl, optionally substituted cycloalkyl, alkenyl, alkynyl, optionally substituted aryl, optionally substituted heteroaryl, optionally substituted heterocyclo, alkoxyalkyl, (amino)alkyl, hydroxyalkylamino, (alkylamino)alkyl, (dialkylamino)alkyl, (cyano)alkyl, (carboxamido)alkyl, mercaptoalkyl, (heterocyclo)alkyl, (cycloalkylamino)alkyl, ($C_{1-4}$ haloalkoxy)alkyl, or (heteroaryl)alkyl.

10. The compound of claim 9, or a pharmaceutically acceptable salt or solvate thereof, having Formula III, Formula IV, Formula V, Formula VI, or Formula VIa:

III

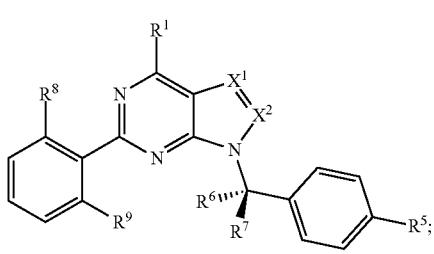

IV

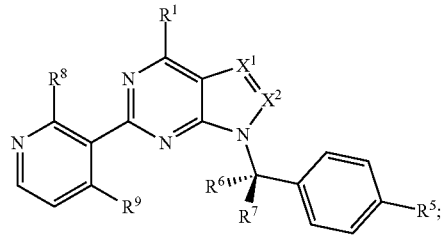

V

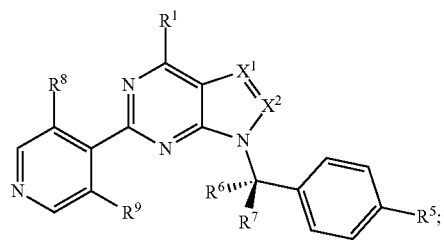

VI

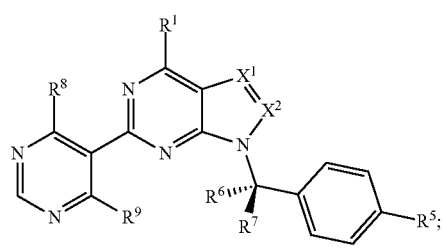

VIa

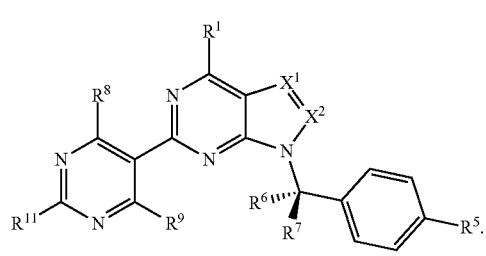

11. The compound of claim 9, or a pharmaceutically acceptable salt or solvate thereof, wherein $R^5$ is:

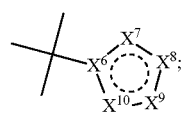

wherein:
$X^6$ is selected from $NR^{13}$ and $CR^{18}$;
$X^7$ is selected from $NR^{14}$ and $CR^{19}$;
$X^8$ is selected from $NR^{15}$ and $CR^{20}$;
$X^9$ is selected from $NR^{16}$ and $CR^{21}$;
$X^{10}$ is selected from $NR^{17}$ and $CR^{22}$;
each of $R^{13}$, $R^{14}$, $R^{15}$, $R^{16}$, and $R^{17}$ is absent, or independently selected from hydrogen, halo, methyl, ethyl, isopropyl, cyclopropyl, methoxy, triazolyl, cyano, optionally substituted alkyl, amino, alkylamino, dialkylamino, difluoromethyl, trifluoromethyl, methylsulfonyl, and methylazetidinyl; and
each of $R^{18}$, $R^{19}$, $R^{20}$, $R^{21}$, and $R^{22}$ is independently selected from hydrogen, halo, methyl, ethyl, isopropyl, cyclopropyl, methoxy, triazolyl, cyano, optionally substituted alkyl, amino, alkylamino, dialkylamino, difluoromethyl, trifluoromethyl, methylsulfonyl, and methylazetidinyl.

12. The compound of claim 11, or a pharmaceutically acceptable salt or solvate thereof, having Formula VII, Formula VIII, Formula IX, Formula X, Formula XI, or Formula XII:

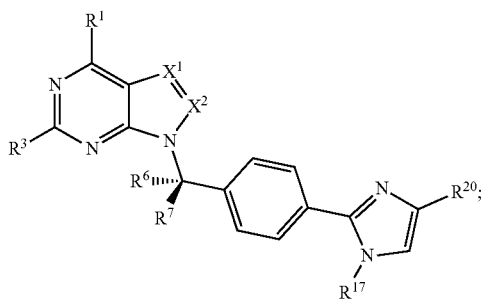

VII

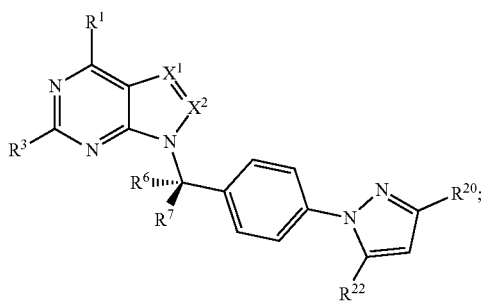

VIII

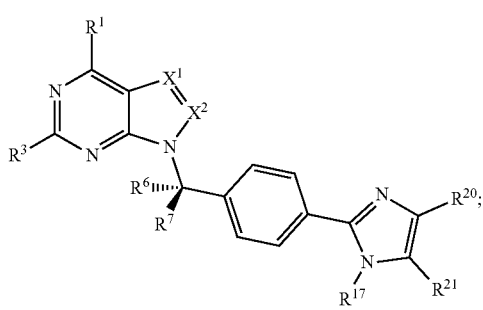

IX

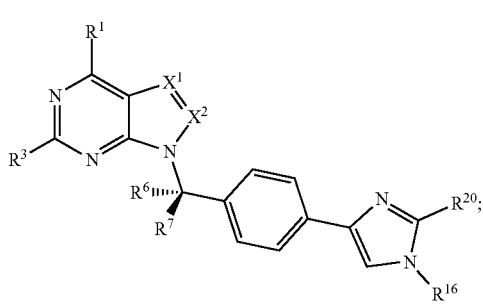

X

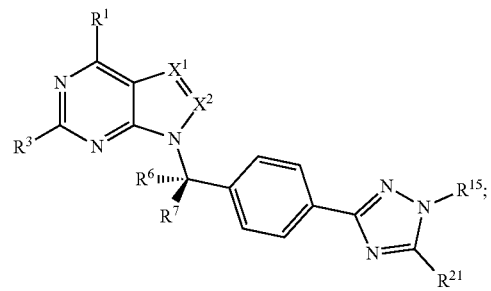

XI

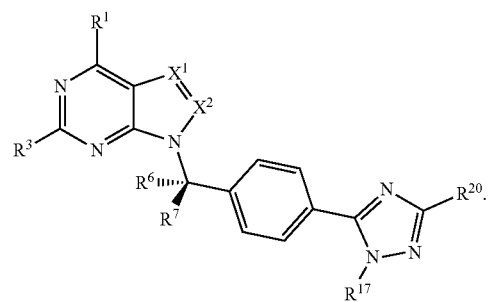

XII

13. A compound selected from the group consisting of:
6-(3-methoxypyridin-4-yl)-1-(4-(1-methyl-4-(trifluoromethyl)-1H-imidazol-2-yl)benzyl)-1H-pyrazolo[3,4-d]pyrimidine;
1-(4-(1-methyl-4-(trifluoromethyl)-1H-imidazol-2-yl)benzyl)-6-(2-(methylsulfonyl)-phenyl)-1H-pyrazolo[3,4-d]pyrimidine;
1-(4-(1-methyl-4-(trifluoromethyl)-1H-imidazol-2-yl)benzyl)-6-(2-methyl-6-(methylsulfonyl)phenyl)-1H-pyrazolo[3,4-d]pyrimidine;
6-(2-(ethylsulfonyl)phenyl)-1-(4-(1-methyl-4-(trifluoromethyl)-1H-imidazol-2-yl)benzyl)-1H-pyrazolo[3,4-d]pyrimidine;
1-(4-(3-(difluoromethyl)-5-methyl-1H-pyrazol-1-yl)benzyl)-6-(2-isopropylpyridin-3-yl)-1H-pyrazolo[3,4-d]pyrimidine;
6-(2-methoxy-4-methylpyridin-3-yl)-1-(4-(1-methyl-4-(trifluoromethyl)-1H-imidazol-2-yl)benzyl)-1H-pyrazolo[3,4-d]pyrimidine;
6-(4-methoxy-6-methylpyrimidin-5-yl)-1-(4-(1-methyl-4-(trifluoromethyl)-1H-imidazol-2-yl)benzyl)-1H-pyrazolo[3,4-d]pyrimidine;
6-(2-isopropylpyridin-3-yl)-1-(4-(5-methyl-3-(trifluoromethyl)-1H-pyrazol-1-yl)benzyl)-1H-pyrazolo[3,4-d]pyrimidine;
6-(2,6-dimethoxyphenyl)-1-(4-(1-methyl-4-(trifluoromethyl)-1H-imidazol-2-yl)benzyl)-1H-pyrazolo[3,4-d]pyrimidine;
6-(2-methoxyphenyl)-1-(4-(1-methyl-4-(trifluoromethyl)-1H-imidazol-2-yl)benzyl)-1H-pyrazolo[3,4-d]pyrimidine;
6-(2-isopropylphenyl)-1-(4-(5-methyl-3-(trifluoromethyl)-1H-pyrazol-1-yl)benzyl)-1H-pyrazolo[3,4-d]pyrimidine;
6-(2-methoxy-6-methylphenyl)-1-(4-(1-methyl-4-(trifluoromethyl)-1H-imidazol-2-yl)benzyl)-1H-pyrazolo[3,4-d]pyrimidine;
2-methoxy-3-(1-(4-(1-methyl-4-(trifluoromethyl)-1H-imidazol-2-yl)benzyl)-1H-pyrazolo[3,4-d]pyrimidin-6-yl)isonicotinonitrile;

2-(2-isopropylphenyl)-9-(4-(1-methyl-4-(trifluoromethyl)-1H-imidazol-2-yl)benzyl)-9H-purine;

6-(4-cyclopropyl-6-methoxypyrimidin-5-yl)-1-(4-(1-methyl-4-(trifluoromethyl)-1H-imidazol-2-yl)benzyl)-1H-pyrazolo[3,4-d]pyrimidine;

6-(2-isopropylpyridin-3-yl)-1-(4-(1-methyl-4-(trifluoromethyl)-1H-imidazol-2-yl)benzyl)-1H-pyrazolo[3,4-d]pyrimidine;

1-(4-(1-methyl-4-(trifluoromethyl)-1H-imidazol-2-yl)benzyl)-6-(2-methyl-6-(methylthio)phenyl)-1H-pyrazolo[3,4-d]pyrimidine;

6-(4-cyclopropyl-6-methoxypyrimidin-5-yl)-1-(4-(5-methyl-3-(trifluoromethyl)-1H-pyrazol-1-yl)benzyl)-1H-pyrazolo[3,4-d]pyrimidine;

6-(2-cyclopropyl-6-methoxyphenyl)-1-(4-(1-methyl-4-(trifluoromethyl)-1H-imidazol-2-yl)benzyl)-1H-pyrazolo[3,4-d]pyrimidine;

6-(2-isopropylphenyl)-1-(4-(1-(1-methylazetidin-3-yl)-4-(trifluoromethyl)-1H-imidazol-2-yl)benzyl)-1H-pyrazolo[3,4-d]pyrimidine;

6-(2-isopropylphenyl)-1-(1-(4-(1-methyl-4-(trifluoromethyl)-1H-imidazol-2-yl)phenyl)ethyl)-1H-pyrazolo[3,4-d]pyrimidine;

6-(2-isopropylphenyl)-4-methyl-1-(4-(1-methyl-4-(trifluoromethyl)-1H-imidazol-2-yl)benzyl)-1H-pyrazolo[3,4-d]pyrimidine;

6-(3-fluoro-2-isopropylphenyl)-1-(4-(1-methyl-4-(trifluoromethyl)-1H-imidazol-2-yl)benzyl)-1H-pyrazolo[3,4-d]pyrimidine;

6-(2-isopropylphenyl)-3-methyl-1-(4-(1-methyl-4-(trifluoromethyl)-1H-imidazol-2-yl)benzyl)-1H-pyrazolo[3,4-d]pyrimidine;

6-(2-isopropylphenyl)-1-(4-(1-methyl-4-(trifluoromethyl)-1H-imidazol-2-yl)benzyl)-1H-pyrazolo[3,4-d]pyrimidine;

6-(4-(tert-butyl)-6-methoxypyrimidin-5-yl)-1-(4-(1-methyl-4-(trifluoromethyl)-1H-imidazol-2-yl)benzyl)-1H-pyrazolo[3,4-d]pyrimidine;

6-(4-(2-fluoropropan-2-yl)-6-methoxypyrimidin-5-yl)-1-(4-(1-methyl-4-(trifluoromethyl)-1H-imidazol-2-yl)benzyl)-1H-pyrazolo[3,4-d]pyrimidine;

6-(4-methoxy-6-(1-methylcyclopropyl)pyrimidin-5-yl)-1-(4-(1-methyl-4-(trifluoromethyl)-1H-imidazol-2-yl)benzyl)-1H-pyrazolo[3,4-d]pyrimidine;

6-(4-cyclobutyl-6-methoxypyrimidin-5-yl)-1-(4-(1-methyl-4-(trifluoromethyl)-1H-imidazol-2-yl)benzyl)-1H-pyrazolo[3,4-d]pyrimidine;

(S)-6-(4-cyclopropyl-6-methoxypyrimidin-5-yl)-1-(1-(4-(1-methyl-4-(trifluoromethyl)-1H-imidazol-2-yl)phenyl)ethyl)-1H-pyrazolo[3,4-d]pyrimidine;

(R)-6-(4-cyclopropyl-6-methoxypyrimidin-5-yl)-1-(1-(4-(1-methyl-4-(trifluoromethyl)-1H-imidazol-2-yl)phenyl)ethyl)-1H-pyrazolo[3,4-d]pyrimidine;

6-(4-cyclopropyl-6-ethoxypyrimidin-5-yl)-1-(4-(1-methyl-4-(trifluoromethyl)-1H-imidazol-2-yl)benzyl)-1H-pyrazolo[3,4-d]pyrimidine;

6-(4-cyclopropyl-6-isopropoxypyrimidin-5-yl)-1-(4-(1-methyl-4-(trifluoromethyl)-1H-imidazol-2-yl)benzyl)-1H-pyrazolo[3,4-d]pyrimidine;

6-cyclopropyl-5-(1-(4-(1-methyl-4-(trifluoromethyl)-1H-imidazol-2-yl)benzyl)-1H-pyrazolo[3,4-d]pyrimidin-6-yl)pyrimidine-4-carbonitrile;

6-cyclopropyl-N,N-dimethyl-5-(1-(4-(1-methyl-4-(trifluoromethyl)-1H-imidazol-2-yl)benzyl)-1H-pyrazolo[3,4-d]pyrimidin-6-yl)pyrimidin-4-amine;

6-(4,6-dimethoxypyrimidin-5-yl)-1-(4-(1-methyl-4-(trifluoromethyl)-1H-imidazol-2-yl)benzyl)-1H-pyrazolo[3,4-d]pyrimidine;

6-(4-cyclopropyl-6-methoxypyrimidin-5-yl)-1-(4-(1-ethyl-4-(trifluoromethyl)-1H-imidazol-2-yl)benzyl)-1H-pyrazolo[3,4-d]pyrimidine;

6-(4-isopropyl-6-methylpyrimidin-5-yl)-1-(4-(5-methyl-3-(trifluoromethyl)-1H-pyrazol-1-yl)benzyl)-1H-pyrazolo[3,4-d]pyrimidine;

1-(4-(5-methyl-3-(trifluoromethyl)-1H-pyrazol-1-yl)benzyl)-6-(4-methyl-6-(methylthio)pyrimidin-5-yl)-1H-pyrazolo[3,4-d]pyrimidine;

2-(4-cyclopropyl-6-methoxypyrimidin-5-yl)-8-methyl-9-(4-(5-methyl-3-(trifluoromethyl)-1H-pyrazol-1-yl)benzyl)-9H-purine;

1-(4-(5-methyl-3-(trifluoromethyl)-1H-pyrazol-1-yl)benzyl)-6-(4-methyl-6-(methylsulfonyl)pyrimidin-5-yl)-1H-pyrazolo[3,4-d]pyrimidine;

6-(4-(2-methoxyethoxy)-6-methylpyrimidin-5-yl)-1-(4-(5-methyl-3-(trifluoromethyl)-1H-pyrazol-1-yl)benzyl)-1H-pyrazolo[3,4-d]pyrimidine;

6-(1-isopropyl-4-methyl-1H-pyrazol-5-yl)-1-(4-(5-methyl-3-(trifluoromethyl)-1H-pyrazol-1-yl)benzyl)-1H-pyrazolo[3,4-d]pyrimidine;

6-(1-isopropyl-4-methoxy-1H-pyrazol-5-yl)-1-(4-(5-methyl-3-(trifluoromethyl)-1H-pyrazol-1-yl)benzyl)-1H-pyrazolo[3,4-d]pyrimidine;

6-(4-cyclopropyl-1-isopropyl-1H-pyrazol-5-yl)-1-(4-(5-methyl-3-(trifluoromethyl)-1H-pyrazol-1-yl)benzyl)-1H-pyrazolo[3,4-d]pyrimidine;

2-(4-cyclopropyl-6-methoxypyrimidin-5-yl)-7-(4-(1-methyl-4-(trifluoromethyl)-1H-imidazol-2-yl)benzyl)-7H-pyrrolo[2,3-d]pyrimidine;

5-(4-cyclopropyl-6-methoxypyrimidin-5-yl)-3-(4-(1-methyl-4-(trifluoromethyl)-1H-imidazol-2-yl)benzyl)-3H-[1,2,3]triazolo[4,5-d]pyrimidine;

6-(4,6-diethoxypyrimidin-5-yl)-1-(4-(1-ethyl-4-(trifluoromethyl)-1H-imidazol-2-yl)benzyl)-1H-pyrazolo[3,4-d]pyrimidine;

6-(4-cyclopropyl-6-methoxypyrimidin-5-yl)-1-(4-(1-(trifluoromethyl)-5,6,7,8-tetrahydroimidazo[1,5-a]pyrazin-3-yl)benzyl)-1H-pyrazolo[3,4-d]pyrimidine;

6-(4-cyclopropyl-6-methoxypyrimidin-5-yl)-1-(4-(1-methyl-5-(trifluoromethyl)-1H-1,2,4-triazol-3-yl)benzyl)-1H-pyrazolo[3,4-d]pyrimidine;

6-(1-cyclopropyl-4-methoxy-1H-pyrazol-5-yl)-1-(4-(1-ethyl-4-(trifluoromethyl)-1H-imidazol-2-yl)benzyl)-1H-pyrazolo[3,4-d]pyrimidine;

6-(4-cyclopropyl-6-methoxypyrimidin-5-yl)-1-((6-(5-methoxy-3-(trifluoromethyl)-1H-pyrazol-1-yl)pyridin-3-yl)methyl)-1H-pyrazolo[3,4-d]pyrimidine;

(R)-6-(4-cyclobutyl-6-methoxypyrimidin-5-yl)-1-(1-(4-(1-ethyl-4-(trifluoromethyl)-1H-imidazol-2-yl)phenyl)ethyl)-1H-pyrazolo[3,4-d]pyrimidine;

(S)-6-(4-cyclobutyl-6-methoxypyrimidin-5-yl)-1-(1-(4-(1-ethyl-4-(trifluoromethyl)-1H-imidazol-2-yl)phenyl)ethyl)-1H-pyrazolo[3,4-d]pyrimidine;

(R)-6-(4-cyclopropyl-6-methoxypyrimidin-5-yl)-1-(1-(4-(1-ethyl-4-(trifluoromethyl)-1H-imidazol-2-yl)phenyl)ethyl)-1H-pyrazolo[3,4-d]pyrimidine;

(S)-6-(4-cyclopropyl-6-methoxypyrimidin-5-yl)-1-(1-(4-(1-ethyl-4-(trifluoromethyl)-1H-imidazol-2-yl)phenyl)ethyl)-1H-pyrazolo[3,4-d]pyrimidine;

6-(4-cyclopropyl-6-methoxypyrimidin-5-yl)-1-(4-(1-methyl-2-(trifluoromethyl)-1H-imidazol-4-yl)benzyl)-1H-pyrazolo[3,4-d]pyrimidine;

6-(4-(2-fluoropropan-2-yl)-6-methoxypyrimidin-5-yl)-1-(4-(1-methyl-4-(trifluoromethyl)-1H-imidazol-2-yl)benzyl)-1H-pyrazolo[3,4-d]pyrimidine;

6-(4-cyclopropyl-6-methoxypyrimidin-5-yl)-1-(4-(5-ethoxy-3-(trifluoromethyl)-1H-pyrazol-1-yl)benzyl)-1H-pyrazolo[3,4-d]pyrimidine;

6-(4-cyclopropyl-6-methoxypyrimidin-5-yl)-1-((6-(1-ethyl-4-(trifluoromethyl)-1H-imidazol-2-yl)pyridin-3-yl)methyl)-1H-pyrazolo[3,4-d]pyrimidine;

1-(4-((6-(4-cyclopropyl-6-methoxypyrimidin-5-yl)-1H-pyrazolo[3,4-d]pyrimidin-1-yl)methyl)phenyl)-5-methyl-1H-pyrazole-3-carbonitrile;

6-(4-cyclopropyl-1-ethyl-1H-pyrazol-5-yl)-1-(4-(1-ethyl-4-(trifluoromethyl)-1H-imidazol-2-yl)benzyl)-1H-pyrazolo[3,4-d]pyrimidine;

6-(4-cyclopropyl-6-(methoxy-d3)pyrimidin-5-yl)-1-(4-(1-ethyl-4-(trifluoromethyl)-1H-imidazol-2-yl)benzyl)-1H-pyrazolo[3,4-d]pyrimidine;

6-cyclopropyl-5-(1-(4-(1-methyl-4-(trifluoromethyl)-1H-imidazol-2-yl)benzyl)-1H-pyrazolo[3,4-d]pyrimidin-6-yl)pyrimidine-4-carbonitrile;

6-(4-cyclopropoxy-6-cyclopropylpyrimidin-5-yl)-1-(4-(1-ethyl-4-(trifluoromethyl)-1H-imidazol-2-yl)benzyl)-1H-pyrazolo[3,4-d]pyrimidine;

6-(4-cyclobutoxy-6-cyclopropylpyrimidin-5-yl)-1-(4-(1-ethyl-4-(trifluoromethyl)-1H-imidazol-2-yl)benzyl)-1H-pyrazolo[3,4-d]pyrimidine;

6-(4-cyclopropyl-6-(difluoromethoxy)pyrimidin-5-yl)-1-(4-(1-ethyl-4-(trifluoromethyl)-1H-imidazol-2-yl)benzyl)-1H-pyrazolo[3,4-d]pyrimidine;

6-(4-cyclopropyl-6-methoxy-2-methylpyrimidin-5-yl)-1-(4-(1-methyl-4-(trifluoromethyl)-1H-imidazol-2-yl)benzyl)-1H-pyrazolo[3,4-d]pyrimidine;

6-(4-cyclopropyl-6-methoxypyrimidin-5-yl)-1-(4-(1-(oxetan-3-yl)-4-(trifluoromethyl)-1H-imidazol-2-yl)benzyl)-1H-pyrazolo[3,4-d]pyrimidine;

6-(4-(tert-butyl)-6-methoxypyrimidin-5-yl)-1-(4-(1-methyl-4-(trifluoromethyl)-1H-imidazol-2-yl)benzyl)-1H-pyrazolo[3,4-d]pyrimidine;

6-(4-(tert-butoxy)-6-cyclopropylpyrimidin-5-yl)-1-(4-(1-ethyl-4-(trifluoromethyl)-1H-imidazol-2-yl)benzyl)-1H-pyrazolo[3,4-d]pyrimidine;

6-(4-cyclopropyl-6-(2-fluoroethoxy)pyrimidin-5-yl)-1-(4-(1-ethyl-4-(trifluoromethyl)-1H-imidazol-2-yl)benzyl)-1H-pyrazolo[3,4-d]pyrimidine;

6-(4-cyclopropyl-6-methoxypyrimidin-5-yl)-1-(4-(1-(methyl-d3)-4-(trifluoromethyl)-1H-imidazol-2-yl)benzyl)-1H-pyrazolo[3,4-d]pyrimidine;

1-(4-(1-cyclobutyl-4-(trifluoromethyl)-1H-imidazol-2-yl)benzyl)-6-(4-cyclopropyl-6-methoxypyrimidin-5-yl)-1H-pyrazolo[3,4-d]pyrimidine;

6-(4,6-dimethoxypyrimidin-5-yl)-1-(4-(1-ethyl-4-(trifluoromethyl)-1H-imidazol-2-yl)benzyl)-1H-pyrazolo[3,4-d]pyrimidine;

6-(4-cyclopropyl-6-methoxypyrimidin-5-yl)-1-(4-(1-isopropyl-4-(trifluoromethyl)-1H-imidazol-2-yl)benzyl)-1H-pyrazolo[3,4-d]pyrimidine;

1-(4-(1-cyclopropyl-4-(trifluoromethyl)-1H-imidazol-2-yl)benzyl)-6-(4-cyclopropyl-6-methoxypyrimidin-5-yl)-1H-pyrazolo[3,4-d]pyrimidine;

6-(4-cyclopropyl-6-methoxypyrimidin-5-yl)-1-(4-(1-(2-fluoroethyl)-4-(trifluoromethyl)-1H-imidazol-2-yl)benzyl)-1H-pyrazolo[3,4-d]pyrimidine;

6-(4-cyclopropyl-6-methoxypyrimidin-5-yl)-1-(4-(4-(trifluoromethyl)-1H-imidazol-2-yl)benzyl)-1H-pyrazolo[3,4-d]pyrimidine;

6-(4-cyclopropyl-6-methoxypyrimidin-5-yl)-1-(3-fluoro-4-(1-methyl-4-(trifluoromethyl)-1H-imidazol-2-yl)benzyl)-1H-pyrazolo[3,4-d]pyrimidine;

6-(4-cyclopropyl-6-methoxypyrimidin-5-yl)-1-(2-fluoro-4-(1-methyl-4-(trifluoromethyl)-1H-imidazol-2-yl)benzyl)-1H-pyrazolo[3,4-d]pyrimidine;

6-(2,4-dimethoxy-6-methylpyrimidin-5-yl)-1-(4-(1-methyl-4-(trifluoromethyl)-1H-imidazol-2-yl)benzyl)-1H-pyrazolo[3,4-d]pyrimidine;

6-(4-cyclopropyl-6-methoxypyrimidin-5-yl)-1-(4-(5-methoxy-3-(trifluoromethyl)-1H-pyrazol-1-yl)benzyl)-1H-pyrazolo[3,4-d]pyrimidine;

6-(4-cyclopropyl-6-(2-methoxyethoxy)pyrimidin-5-yl)-1-(4-(1-methyl-4-(trifluoromethyl)-1H-imidazol-2-yl)benzyl)-1H-pyrazolo[3,4-d]pyrimidine;

6-(4-cyclopropyl-6-(2-methoxyethoxy)pyrimidin-5-yl)-1-(4-(5-methyl-3-(trifluoromethyl)-1H-pyrazol-1-yl)benzyl)-1H-pyrazolo[3,4-d]pyrimidine;

6-(4-methoxy-6-(1-methylcyclopropyl)pyrimidin-5-yl)-1-(4-(1-methyl-4-(trifluoromethyl)-1H-imidazol-2-yl)benzyl)-1H-pyrazolo[3,4-d]pyrimidine;

6-(1-isopropyl-4-methyl-1H-pyrazol-5-yl)-1-(4-(5-methyl-3-(trifluoromethyl)-1H-pyrazol-1-yl)benzyl)-1H-pyrazolo[3,4-d]pyrimidine;

(S)-6-(4-cyclopropyl-6-methoxypyrimidin-5-yl)-1-(1-(4-(1-methyl-4-(trifluoromethyl)-1H-imidazol-2-yl)phenyl)ethyl)-1H-pyrazolo[3,4-d]pyrimidine;

(R)-6-(4-cyclopropyl-6-methoxypyrimidin-5-yl)-1-(1-(4-(1-methyl-4-(trifluoromethyl)-1H-imidazol-2-yl)phenyl)ethyl)-1H-pyrazolo[3,4-d]pyrimidine;

6-(4-cyclobutyl-6-methoxypyrimidin-5-yl)-1-(4-(1-methyl-4-(trifluoromethyl)-1H-imidazol-2-yl)benzyl)-1H-pyrazolo[3,4-d]pyrimidine;

6-(4-cyclopropyl-6-isopropoxypyrimidin-5-yl)-1-(4-(1-methyl-4-(trifluoromethyl)-1H-imidazol-2-yl)benzyl)-1H-pyrazolo[3,4-d]pyrimidine;

6-(4-isopropyl-6-methylpyrimidin-5-yl)-1-(4-(5-methyl-3-(trifluoromethyl)-1H-pyrazol-1-yl)benzyl)-1H-pyrazolo[3,4-d]pyrimidine;

6-(4-cyclopropyl-6-ethoxypyrimidin-5-yl)-1-(4-(1-methyl-4-(trifluoromethyl)-1H-imidazol-2-yl)benzyl)-1H-pyrazolo[3,4-d]pyrimidine;

N,N,6-trimethyl-5-(1-(4-(5-methyl-3-(trifluoromethyl)-1H-pyrazol-1-yl)benzyl)-1H-pyrazolo[3,4-d]pyrimidin-6-yl)pyrimidin-4-amine;

1-(4-(5-methyl-3-(trifluoromethyl)-1H-pyrazol-1-yl)benzyl)-6-(4-methyl-6-(methylthio)pyrimidin-5-yl)-1H-pyrazolo[3,4-d]pyrimidine;

6-(4-cyclopropyl-6-methoxypyrimidin-5-yl)-1-(4-(1-ethyl-4-(trifluoromethyl)-1H-imidazol-2-yl)benzyl)-1H-pyrazolo[3,4-d]pyrimidine;

6-(4,6-dimethoxypyrimidin-5-yl)-1-(4-(1-methyl-4-(trifluoromethyl)-1H-imidazol-2-yl)benzyl)-1H-pyrazolo[3,4-d]pyrimidine;

6-(4-(2-methoxyethoxy)-6-methylpyrimidin-5-yl)-1-(4-(5-methyl-3-(trifluoromethyl)-1H-pyrazol-1-yl)benzyl)-1H-pyrazolo[3,4-d]pyrimidine;

6-(4-cyclopropyl-6-methoxypyrimidin-5-yl)-1-(4-(1-(1-methylazetidin-3-yl)-4-(trifluoromethyl)-1H-imidazol-2-yl)benzyl)-1H-pyrazolo[3,4-d]pyrimidine;

6-(4-methoxy-6-methylpyrimidin-5-yl)-1-(4-(5-methyl-3-(trifluoromethyl)-1H-pyrazol-1-yl)benzyl)-1H-pyrazolo[3,4-d]pyrimidine;

3-(1-(4-(5-methyl-3-(trifluoromethyl)-1H-pyrazol-1-yl)benzyl)-1H-pyrazolo[3,4-d]pyrimidin-6-yl)picolinonitrile;

6-(4-cyclopropyl-6-methoxypyrimidin-5-yl)-1-(4-(3-(difluoromethyl)-5-methyl-1H-pyrazol-1-yl)benzyl)-1H-pyrazolo[3,4-d]pyrimidine;

6-cyclopropyl-N-methyl-5-(1-(4-(1-methyl-4-(trifluoromethyl)-1H-imidazol-2-yl)benzyl)-1H-pyrazolo[3,4-d]pyrimidin-6-yl)pyrimidin-4-amine;

1-(4-(5-methoxy-3-(trifluoromethyl)-1H-pyrazol-1-yl)benzyl)-6-(4-methoxy-6-methylpyrimidin-5-yl)-1H-pyrazolo[3,4-d]pyrimidine;

6-(4-cyclopropyl-6-((tetrahydrofuran-3-yl)oxy)pyrimidin-5-yl)-1-(4-(1-methyl-4-(trifluoromethyl)-1H-imidazol-2-yl)benzyl)-1H-pyrazolo[3,4-d]pyrimidine;

6-(4-(benzyloxy)-6-cyclopropylpyrimidin-5-yl)-1-(4-(1-ethyl-4-(trifluoromethyl)-1H-imidazol-2-yl)benzyl)-1H-pyrazolo[3,4-d]pyrimidine;

6-(4-cyclopropyl-6-methoxypyrimidin-5-yl)-1-(4-(3-(difluoromethyl)-1-methyl-1H-1,2,4-triazol-5-yl)benzyl)-1H-pyrazolo[3,4-d]pyrimidine;

6-(4-(benzyloxy)-6-cyclopropylpyrimidin-5-yl)-1-(4-(1-methyl-4-(trifluoromethyl)-1H-imidazol-2-yl)benzyl)-1H-pyrazolo[3,4-d]pyrimidine;

6-(4-cyclopropyl-6-methoxypyrimidin-5-yl)-1-(4-(5-methoxy-1-methyl-1H-1,2,4-triazol-3-yl)benzyl)-1H-pyrazolo[3,4-d]pyrimidine;

2-(2-(4-((6-(4-cyclopropyl-6-methoxypyrimidin-5-yl)-1H-pyrazolo[3,4-d]pyrimidin-1-yl)methyl)phenyl)-4-(trifluoromethyl)-1H-imidazol-1-yl)-N,N-dimethylacetamide;

6-cyclopropyl-N,N-dimethyl-5-(1-(4-(1-methyl-4-(trifluoromethyl)-1H-imidazol-2-yl)benzyl)-1H-pyrazolo[3,4-d]pyrimidin-6-yl)pyrimidin-4-amine;

6-(4-cyclopropyl-6-methoxypyrimidin-5-yl)-1-(4-(5-(difluoromethyl)-1-methyl-1H-1,2,4-triazol-3-yl)benzyl)-1H-pyrazolo[3,4-d]pyrimidine;

6-(4-cyclopropyl-6-(pyrrolidin-1-yl)pyrimidin-5-yl)-1-(4-(1-methyl-4-(trifluoromethyl)-1H-imidazol-2-yl)benzyl)-1H-pyrazolo[3,4-d]pyrimidine;

6-(4-(azetidin-1-yl)-6-cyclopropylpyrimidin-5-yl)-1-(4-(1-methyl-4-(trifluoromethyl)-1H-imidazol-2-yl)benzyl)-1H-pyrazolo[3,4-d]pyrimidine; and 5-(4-cyclopropyl-6-methoxypyrimidin-5-yl)-3-(4-(1-methyl-4-(trifluoromethyl)-1H-imidazol-2-yl)benzyl)-3H-[1,2,3]triazolo[4,5-d]pyrimidine;

or a pharmaceutically acceptable salt or solvate thereof.

14. A pharmaceutical composition comprising the compound of claim 1, or a pharmaceutically acceptable salt or solvate thereof, and a pharmaceutically acceptable carrier.

15. The compound of claim 6, wherein $R^5$ is an optionally substituted imidazolyl.

16. The compound of claim 2, wherein $R^3$ is an optionally substituted pyrimidin-5-yl.

17. The compound of claim 13, wherein the compound is 6-(4-cyclopropyl-6-methoxypyrimidin-5-yl)-1-(4-(1-isopropyl-4-(trifluoromethyl)-1H-imidazol-2-yl)benzyl)-1H-pyrazolo[3,4-d]pyrimidine or a pharmaceutically acceptable salt or solvate thereof.

18. The compound of claim 13, wherein the compound is 6-(4-cyclopropyl-6-methoxypyrimidin-5-yl)-1-(4-(1-methyl-4-(trifluoromethyl)-1H-imidazol-2-yl)benzyl)-1H-pyrazolo[3,4-d]pyrimidine, or a pharmaceutically acceptable salt or solvate thereof.

19. The compound of claim 13, wherein the compound is 6-(4-cyclopropyl-6-methoxypyrimidin-5-yl)-1-(4-(5-methyl-3-(trifluoromethyl)-1H-pyrazol-1-yl)benzyl)-1H-pyrazolo[3,4-d]pyrimidine, or a pharmaceutically acceptable salt or solvate thereof.

20. A pharmaceutical composition comprising the compound of claim 17, or a pharmaceutically acceptable salt or solvate thereof, and a pharmaceutically acceptable carrier.

21. A pharmaceutical composition comprising the compound of claim 18, or a pharmaceutically acceptable salt or solvate thereof, and a pharmaceutically acceptable carrier.

22. A pharmaceutical composition comprising the compound of claim 19, or a pharmaceutically acceptable salt or solvate thereof, and a pharmaceutically acceptable carrier.

23. The compound of claim 12, wherein each of $R^1$, $R^6$, and $R^7$ are hydrogen.

24. The compound of claim 10, or a pharmaceutically acceptable salt or solvate thereof, having Formula VIa:

VIa

25. The compound of claim 24, wherein $R^8$ is optionally substituted cycloalkyl, $R^9$ is alkoxy, and $R^{11}$ is hydrogen.

26. The compound of claim 12, or a pharmaceutically acceptable salt or solvate thereof, having Formula IX:

IX

27. The compound of claim 26, wherein $R^{17}$ is optionally substituted alkyl, $R^{20}$ is optionally substituted alkyl, and $R^{21}$ is hydrogen.

28. The compound of claim 27, wherein $R^{17}$ is isopropyl, $R^{20}$ is trifluoroalkyl, and $R^{21}$ is hydrogen.

29. The compound of claim 1, wherein each of $R^1$, $R^{5'}$, $R^6$, and $R^7$ are hydrogen.

30. The compound of claim 1, wherein each of $X^{11}$ and $X^{12}$ are CH.

31. The compound of claim 29, wherein each of $X^{11}$ and $X^{12}$ are CH.

32. The compound of claim 31, wherein $R^3$ is optionally substituted pyrimidin-5-yl.

33. The compound of claim 31, wherein $R^3$ is selected from the group consisting of:

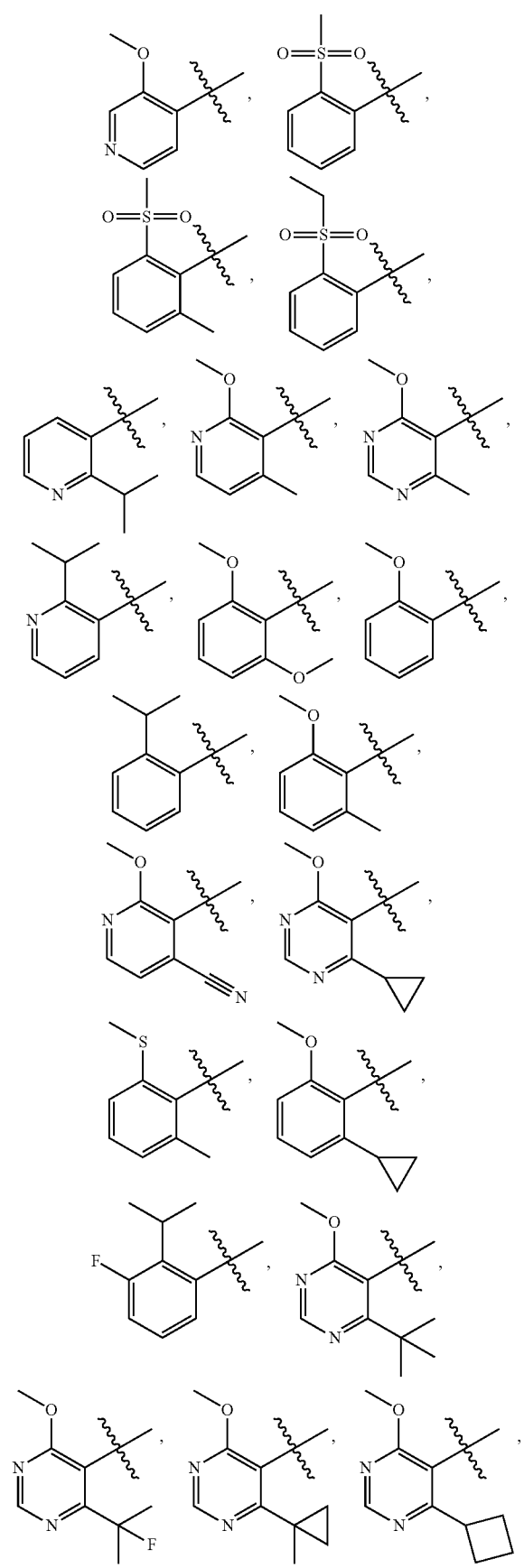
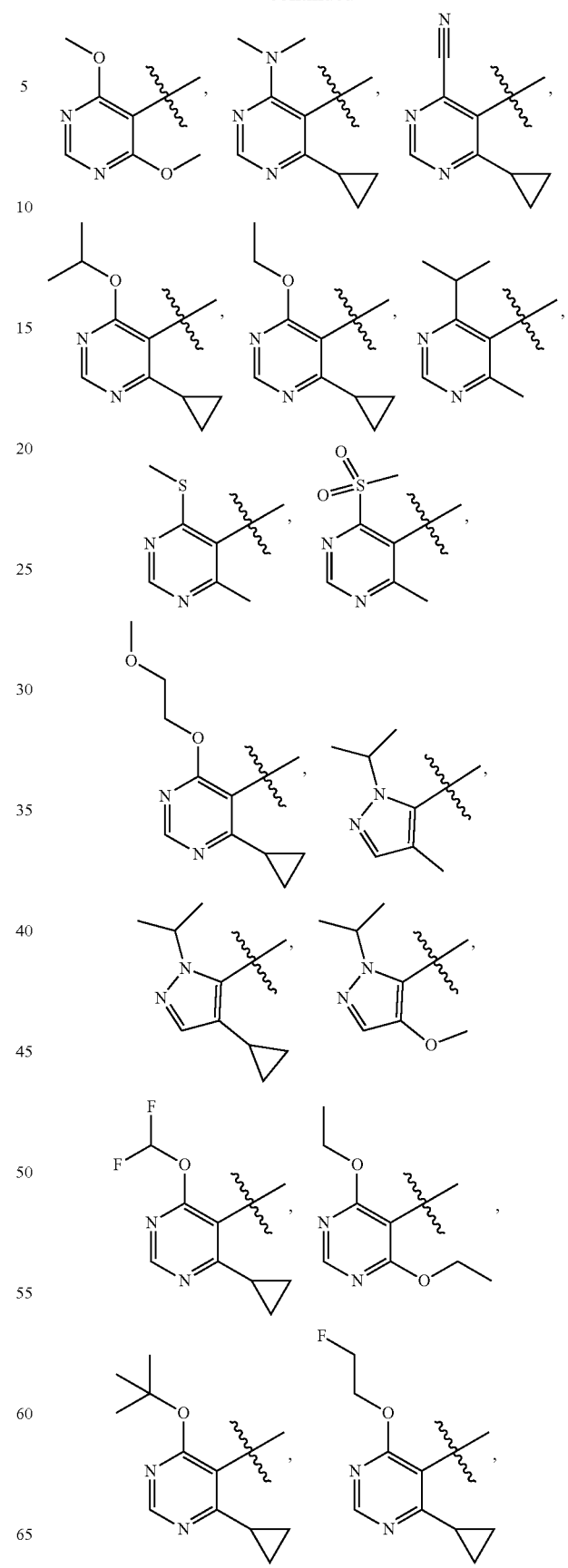

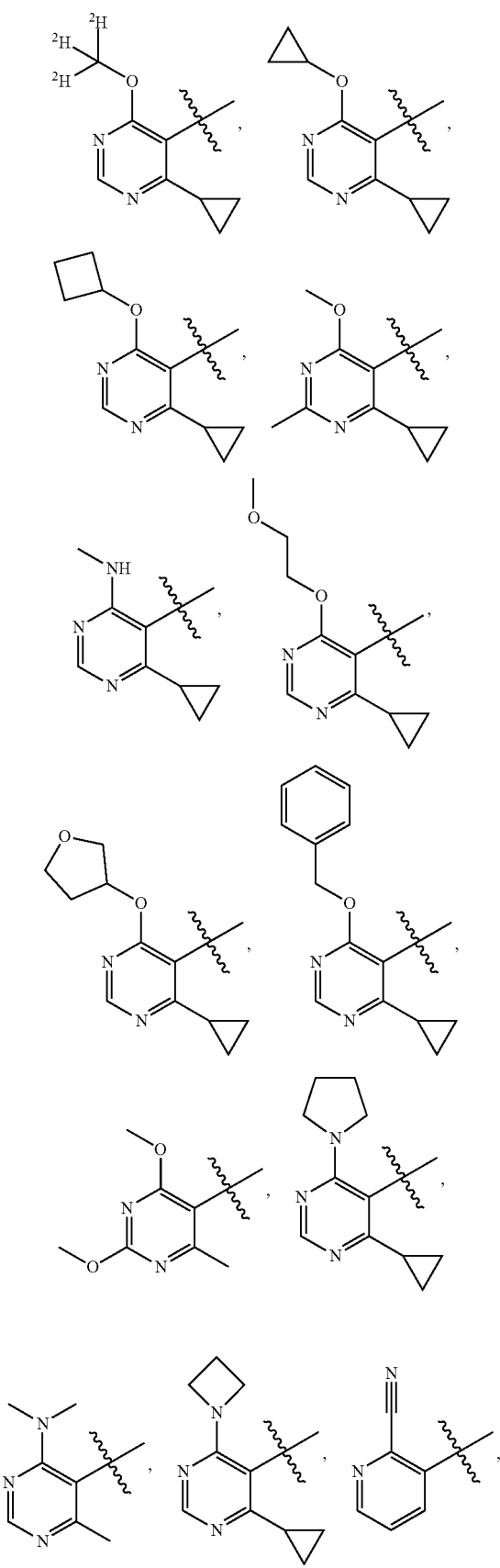
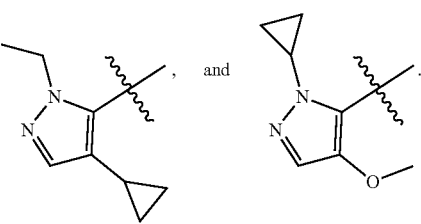
34. The compound of claim 31, wherein R⁵ is optionally substituted imidazolyl.
35. The compound of claim 32, wherein R⁵ is optionally substituted imidazolyl.
36. The compound of claim 33, wherein R⁵ is optionally substituted imidazolyl.
37. The compound of claim 31, wherein R⁵ is selected from the group consisting of:
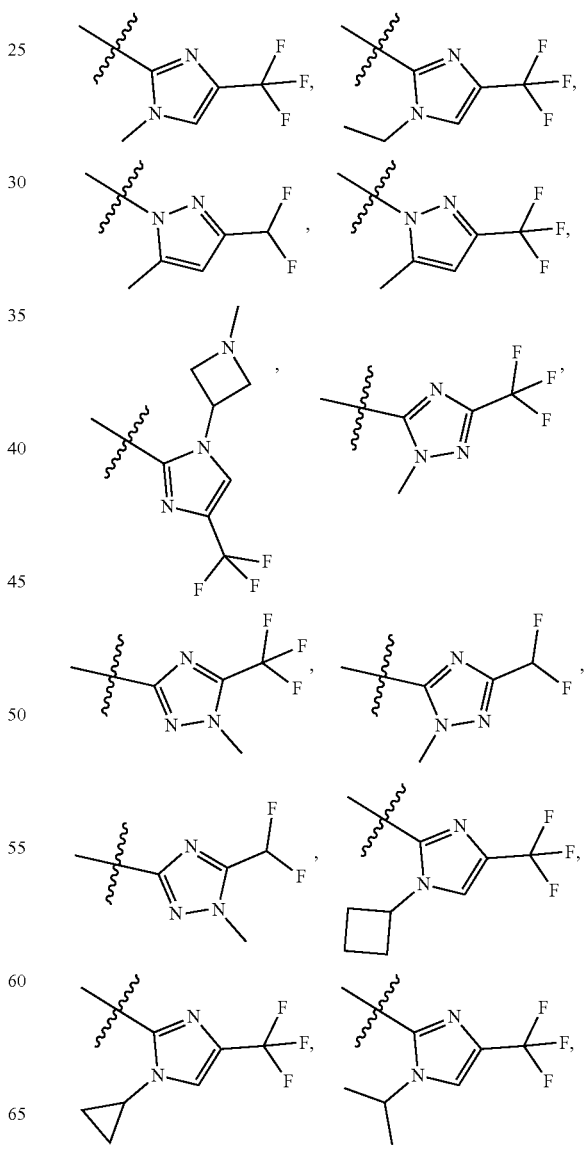

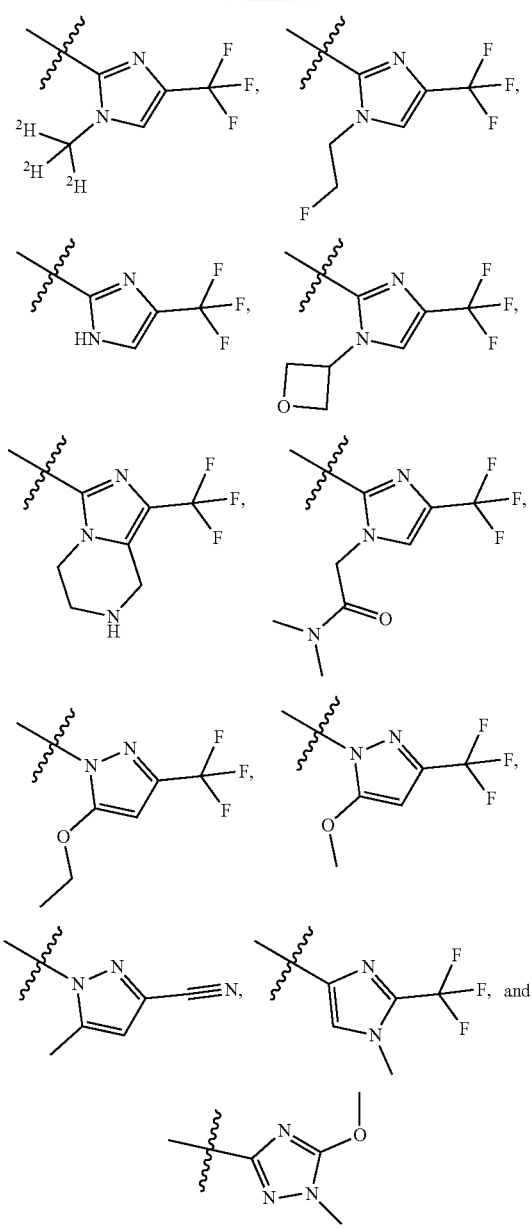
38. The compound of claim 34, wherein $R^5$ is selected from the group consisting of:
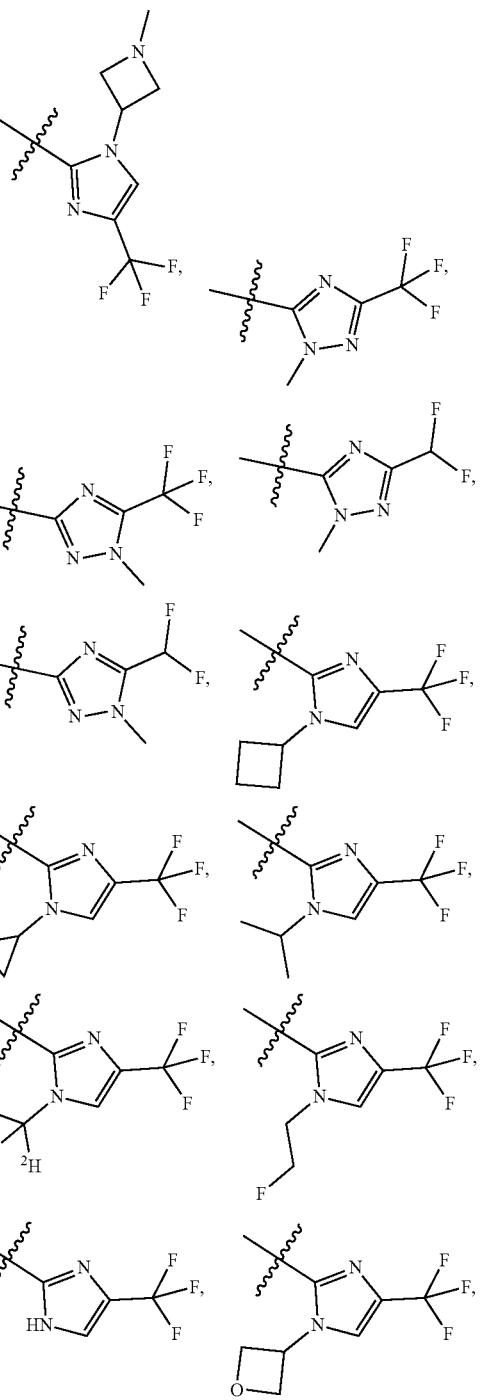

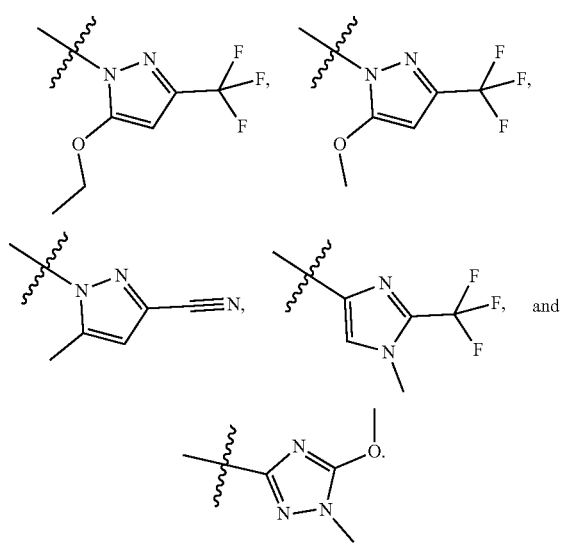
39. The compound of claim 35, wherein R⁵ is selected from the group consisting of:
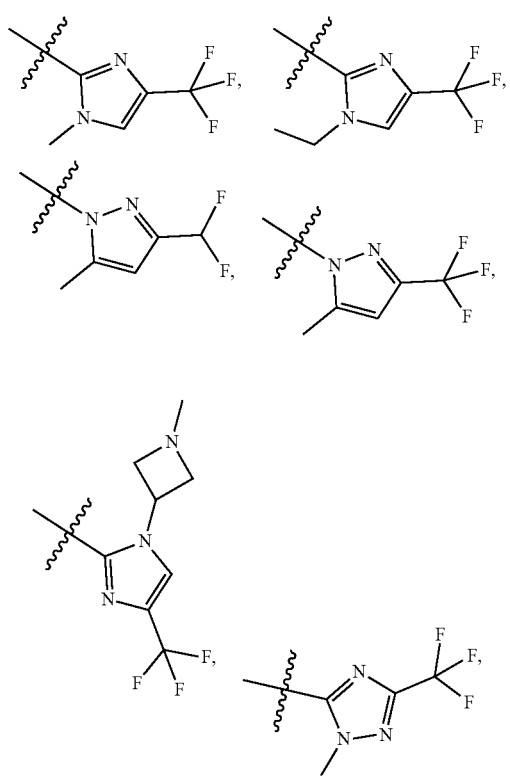
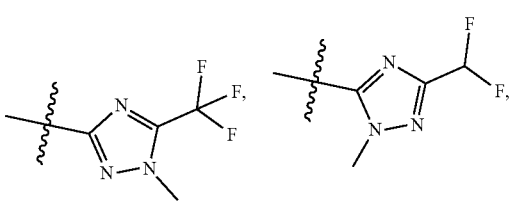
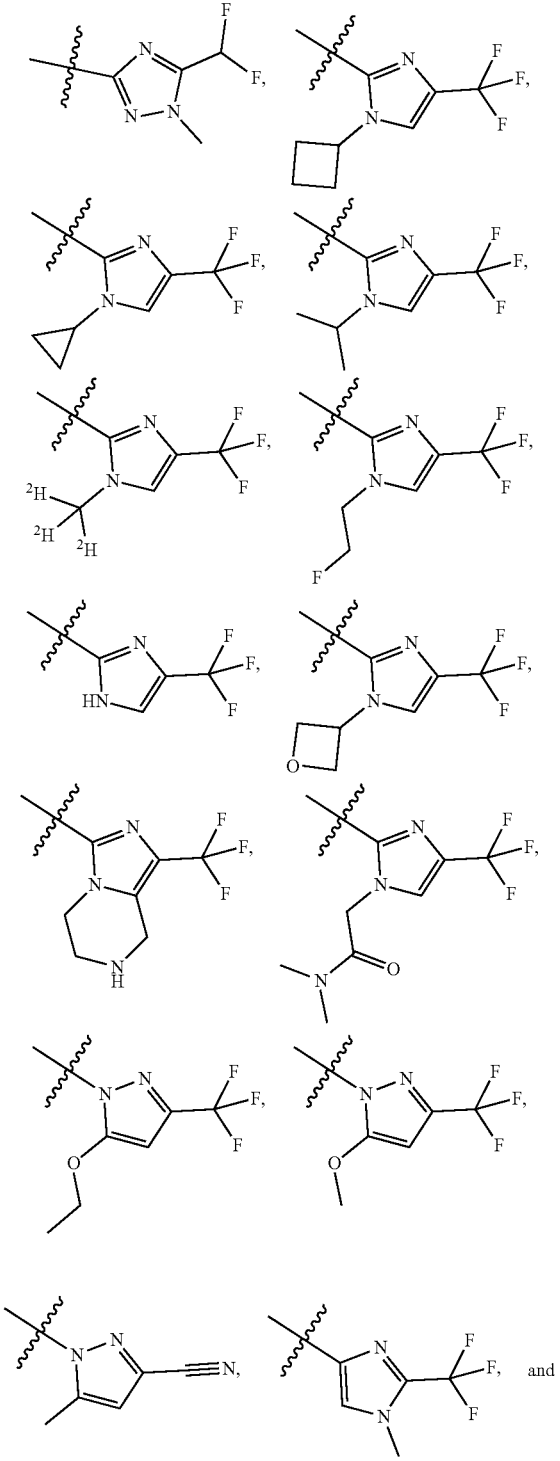

40. A compound having Formula I:

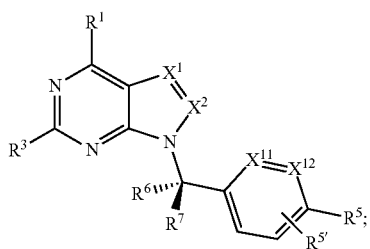

or a pharmaceutically acceptable salt or solvate thereof
each of $X^1$ and $X^2$ is independently selected from N and $CR^2$;
each of $R^1$ and $R^2$ is independently selected from hydrogen, halo, cyano, optionally substituted alkyl, optionally substituted alkenyl, and optionally substituted alkynyl;
$R^3$ is selected from the group consisting of:

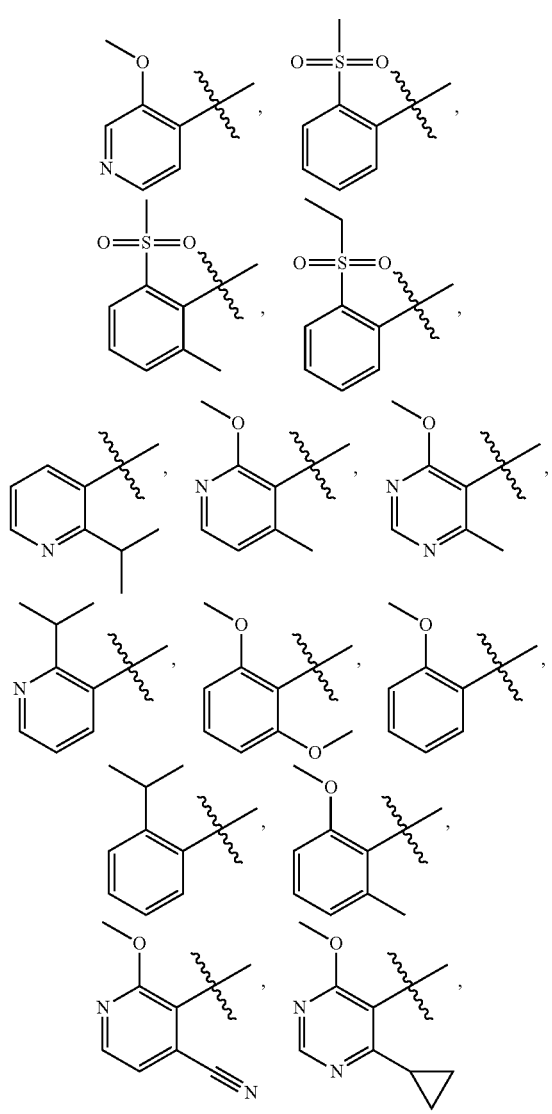

-continued

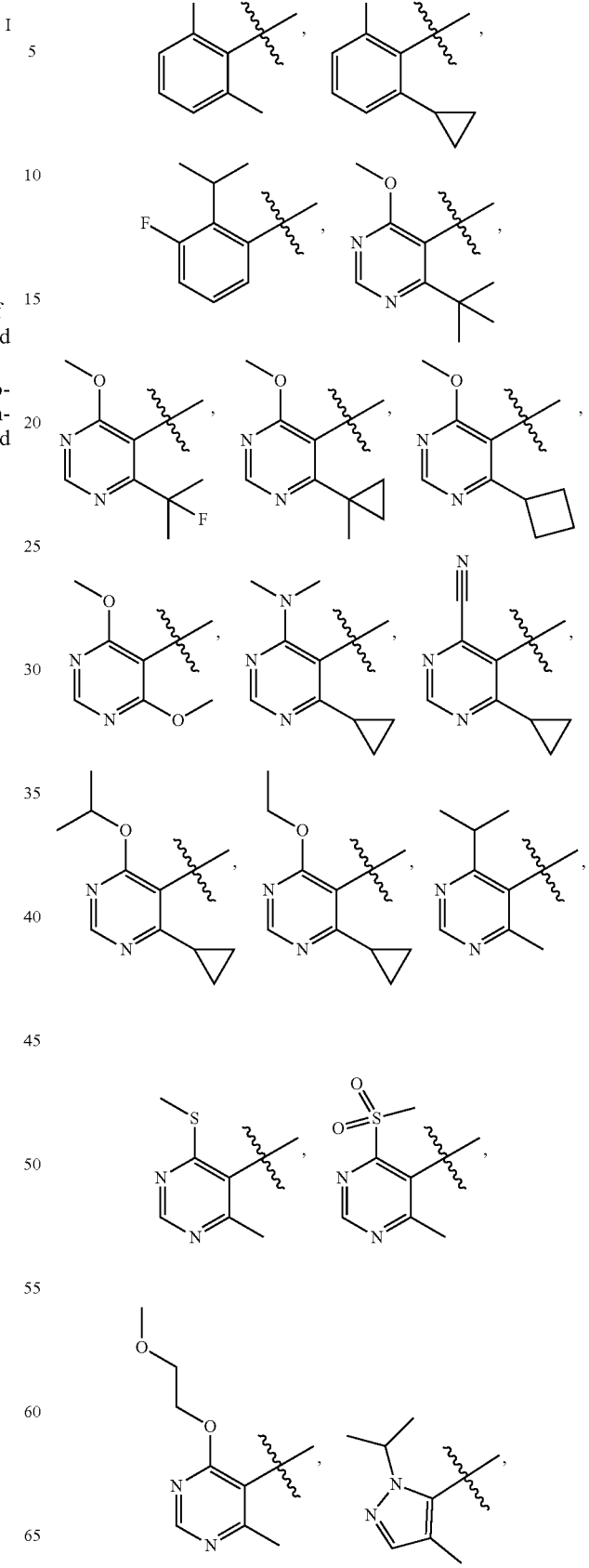

555
-continued

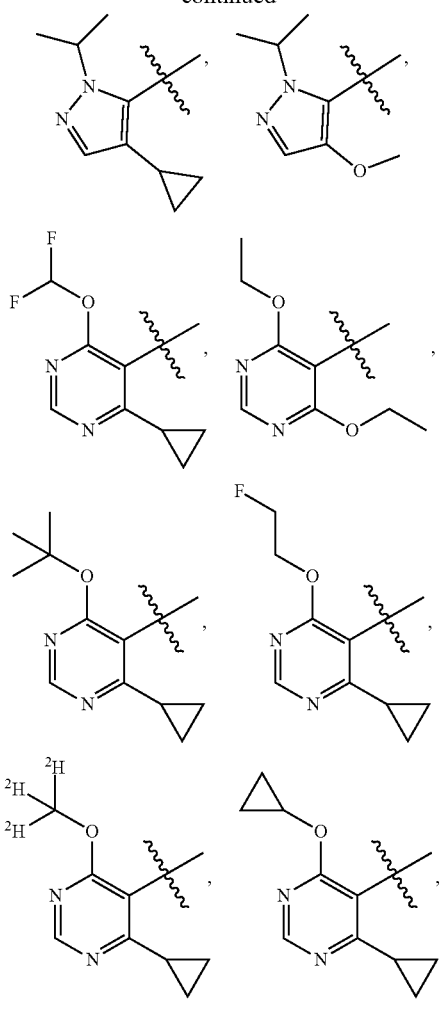

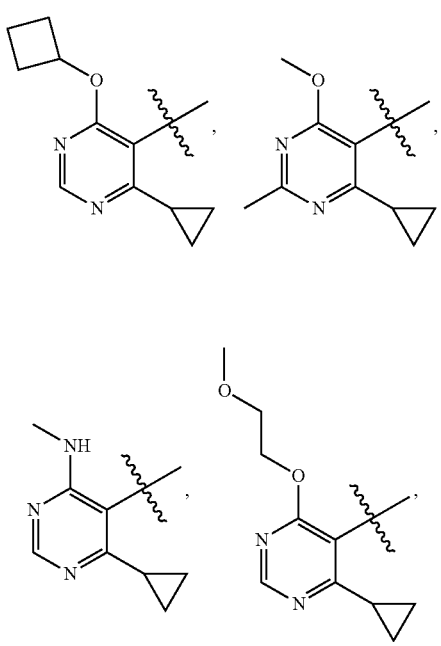

556
-continued

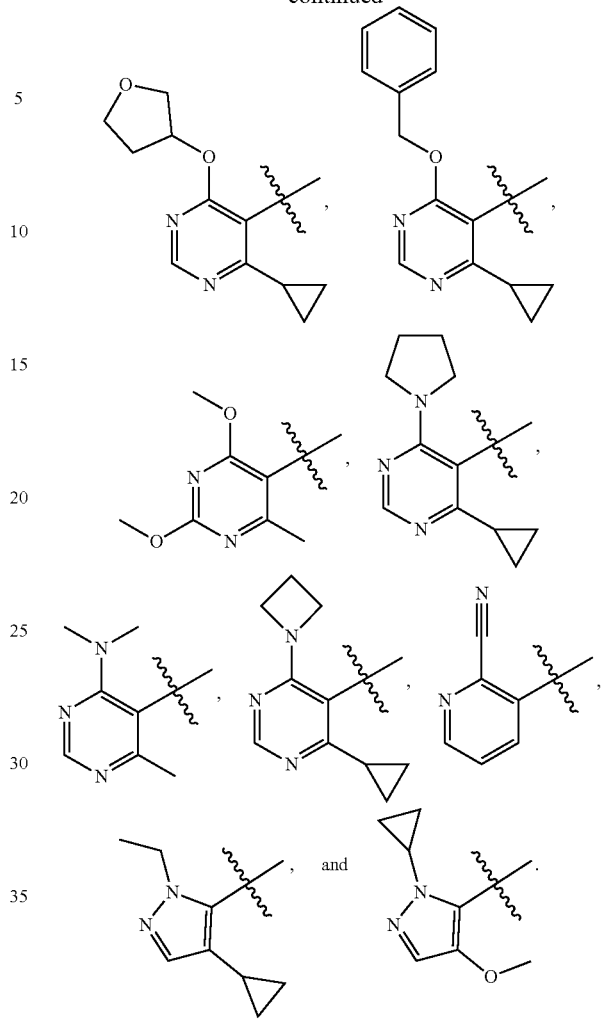

each of $X^{11}$ and $X^{12}$ is independently selected from N and CH;

$R^{5'}$ is selected from hydrogen, optionally substituted ($C_1$-$C_6$) alkyl, optionally substituted ($C_2$-$C_6$) alkenyl, optionally substituted ($C_2$-$C_6$) alkynyl, optionally substituted ($C_1$-$C_6$) alkoxy, ($C_1$-$C_6$) haloalkyl, ($C_1$-$C_6$) haloalkoxy, ($C_1$-$C_6$) hydroxyalkyl, cyano, halo, sulfonamido, —C(=O)$R^{23}$, —C(=O)O$R^{24}$, —N$R^{32a}R^{32b}$, —N$R^{31a}$C(=O)$R^{25}$, —N$R^{31a}$C(=O)N$R^{31a}R^{31b}$—C(=O)N$R^{31a}R^{31b}$, —S(O)$_2R^{27}$—N$R^{31a}$SO$_2R^{27}$, optionally substituted ($C_6$-$C_{14}$) aryl, optionally substituted ($C_6$-$C_{14}$) ar-($C_1$-$C_2$) alkyl, optionally substituted heteroaryl, optionally substituted heteroar-($C_1$-$C_2$) alkyl, optionally substituted ($C_3$-$C_8$) cycloalkyl, optionally substituted (($C_3$-$C_8$) cycloalkyl)-($C_1$-$C_2$) alkyl, optionally substituted heterocyclo, optionally substituted heterocyclo-($C_1$-$C_2$) alkyl, optionally substituted —O—($C_6$-$C_{14}$) aryl, optionally substituted —O—($C_6$-$C_{14}$) ar-($C_1$-$C_2$) alkyl, optionally substituted —O-heteroaryl, optionally substituted —O-heteroar-($C_1$-$C_2$) alkyl, optionally substituted —O—($C_3$-$C_8$) cycloalkyl, optionally substituted —O—(($C_3$-$C_8$) cycloalkyl)-($C_1$-$C_2$) alkyl, optionally substituted —O-heterocyclo, optionally substituted —O-heterocyclo-($C_1$-$C_2$) alkyl;

$R^5$ is selected from optionally substituted ($C_1$-$C_6$) alkyl, optionally substituted ($C_2$-$C_6$) alkenyl, optionally substituted (C₂-C₆) alkynyl, optionally substituted (C₁-C₆) alkoxy, (C₁-C₆) haloalkyl, (C₁-C₆) haloalkoxy, (C₁-C₆) hydroxyalkyl, cyano, halo, sulfonamido, —C(=O)R²³, —C(=O)OR²⁴, NR³²ᵃR³²ᵇ, —NR³¹ᵃC(=O)R²⁵, —NR³¹ᵃC(=O)NR³¹ᵃR³¹ᵇ, —C(=O)NR³¹ᵃR³¹ᵇ, S(O)₂R²⁷, —NR³¹ᵃSO₂R²⁷, optionally substituted (C₆-C₁₄) aryl, optionally substituted (C₆-C₁₄) ar-(C₁-C₂) alkyl, optionally substituted heteroaryl, optionally substituted heteroar-(C₁-C₂) alkyl, optionally substituted (C₃-C₈) cycloalkyl, optionally substituted ((C₃-C₈) cycloalkyl)-(C₁-C₂) alkyl, optionally substituted heterocyclo, optionally substituted heterocyclo-(C₁-C₂) alkyl, optionally substituted —O—(C₆-C₁₄) aryl, optionally substituted —O—(C₆-C₁₄) ar-(C₁-C₂) alkyl, optionally substituted —O-heteroaryl, optionally substituted —O-heteroar-(C₁-C₂) alkyl, optionally substituted —O—(C₃-C₈) cycloalkyl, optionally substituted —O—((C₃-C₈) cycloalkyl)-(C₁-C₂) alkyl, optionally substituted —O-heterocyclo, optionally substituted —O-heterocyclo-(C₁-C₂) alkyl; or one of R⁵ and one of R⁵' on adjacent atoms are taken together with the atoms to which they are attached to form an optionally substituted (C₆-C₁₄) aryl ring; or one of R⁵ and one of R⁵' on adjacent atoms are taken together with the atoms to which they are attached to form an optionally substituted heteroaryl ring; or one of R⁵ and one of R⁵' on adjacent atoms are taken together with the atoms to which they are attached to form an optionally substituted (C₃-C₈) cycloalkyl ring; or one of R⁵ and one of R⁵' on adjacent atoms are taken together with the atoms to which they are attached to form an optionally substituted heterocycloalkyl ring; or one of R⁵ and one of R⁵' on adjacent atoms on the same atom to which they are attached are taken together to form an optionally substituted spirocycloalkyl ring; or one of R⁵ and one of R⁵' on adjacent atoms on the same atom to which they are attached are taken together to form an optionally substituted spiroheterocycloalkyl ring;

each of R⁶ and R⁷ is independently selected from hydrogen, halo, cyano, optionally substituted alkyl, optionally substituted alkenyl, and optionally substituted alkynyl;

R²³ is selected from the group consisting of hydrogen, optionally substituted alkyl, optionally substituted alkenyl, optionally substituted alkynyl, amino, alkylamino, dialkylamino, cycloalkylamino, hydroxyalkyl, (amino)alkyl, (alkylamino)alkyl, (dialkylamino)alkyl, (cycloalkylamino)alkyl, (cycloalkyl)alkyl, aralkyl, (heterocyclo)alkyl, (heteroaryl)alkyl, (amino)(hydroxy)alkyl, (aralkylamino)alkyl, optionally substituted heterocyclo, optionally substituted heteroaryl, optionally substituted aryl, and optionally substituted cycloalkyl;

R³¹ᵃ and R³¹ᵇ are each independently selected from the group consisting of hydrogen, optionally substituted alkyl, optionally substituted alkenyl, optionally substituted alkynyl, hydroxyalkyl, (amino)alkyl, (alkylamino)alkyl, (dialkylamino)alkyl, alkoxyalkyl, cycloalkyl, (cycloalkyl)alkyl, (heterocyclo)alkyl, aralkyl, and (heteroaryl)alkyl; and each of R²⁴, R²⁵, R²⁷, R³²ᵃ, and R³²b is independently selected from the group consisting of hydrogen, optionally substituted alkyl, optionally substituted alkenyl, optionally substituted alkynyl, amino, alkylamino, dialkylamino, cycloalkylamino, hydroxyalkyl, (amino)alkyl, (alkylamino)alkyl, (dialkylamino)alkyl, (cycloalkylamino)alkyl, (cycloalkyl)alkyl, aralkyl, (heterocyclo)alkyl, (heteroaryl)alkyl, (amino)(hydroxy)alkyl, (aralkylamino)alkyl, alkoxyalkyl, optionally substituted heterocyclo, optionally substituted heteroaryl, optionally substituted aryl, and optionally substituted cycloalkyl.

41. The compound of claim 40, wherein R³ is

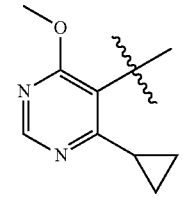

42. A compound having Formula I:

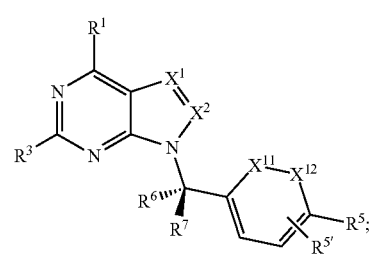

I or a pharmaceutically acceptable salt or solvate thereof, wherein:

each of X¹ and X² is independently selected from N and CR²;

each of R¹ and R² is independently selected from hydrogen, halo, cyano, optionally substituted alkyl, optionally substituted alkenyl, and optionally substituted alkynyl;

R³ is an optionally substituted phenyl, optionally substituted pyridyl, optionally substituted pyrimidinyl, optionally substituted pyrazinyl, optionally substituted pyridazinyl, or optionally substituted pyrazolyl;

each of X¹¹ and X¹² is independently selected from N and CH;

R⁵' is selected from hydrogen, optionally substituted (C₁-C₆) alkyl, optionally substituted (C₂-C₆) alkenyl, optionally substituted (C₂-C₆) alkynyl, optionally substituted (C₁-C₆) alkoxy, (C₁-C₆) haloalkyl, (C₁-C₆) haloalkoxy, (C₁-C₆) hydroxyalkyl, cyano, halo, sulfonamido, —C(=O)R²³, —C(=O)OR²⁴, —NR³²ᵃR³²ᵇ, —NR³¹ᵃC(=O)R²⁵, —NR³¹ᵃC(=O)NR³¹ᵃR³¹ᵇ, —C(=O)NR³¹ᵃR³¹ᵇ, —S(O)₂R²⁷, —NR³¹ᵃSO₂R²⁷, optionally substituted (C₆-C₁₄) aryl, optionally substituted (C₆-C₁₄) ar-(C₁-C₂) alkyl, optionally substituted heteroaryl, optionally substituted heteroar-(C₁-C₂) alkyl, optionally substituted (C₃-C₈) cycloalkyl, optionally substituted ((C₃-C₈) cycloalkyl)-(C₁-C₂) alkyl, optionally substituted heterocyclo, optionally substituted heterocyclo-(C₁-C₂) alkyl, optionally substituted —O—(C₆-C₁₄) aryl, optionally substituted —O—(C₆-C₁₄) ar-(C₁-C₂) alkyl, optionally substituted —O-heteroaryl, optionally substituted —O-heteroar-(C₁-C₂) alkyl, optionally substituted —O—(C₃-C₈) cycloalkyl, optionally substituted —O—((C₃-C₈)

cycloalkyl)-($C_1$-$C_2$) alkyl, optionally substituted —O-heterocyclo, optionally substituted —O-heterocyclo-($C_1$-$C_2$) alkyl;

$R^5$ is selected from optionally substituted ($C_6$-$C_{14}$) aryl, optionally substituted ($C_6$-$C_{14}$) ar-($C_1$-$C_2$) alkyl, optionally substituted heteroaryl, optionally substituted heteroar-($C_1$-$C_2$) alkyl, optionally substituted ($C_3$-$C_8$) cycloalkyl, optionally substituted (($C_3$-$C_8$) cycloalkyl)-($C_1$-$C_2$) alkyl, optionally substituted heterocyclo, optionally substituted heterocyclo-($C_1$-$C_2$) alkyl;

each of $R^6$ and $R^7$ is independently selected from hydrogen, halo, cyano, optionally substituted alkyl, optionally substituted alkenyl, and optionally substituted alkynyl;

$R^{23}$ is selected from the group consisting of hydrogen, optionally substituted alkyl, optionally substituted alkenyl, optionally substituted alkynyl, amino, alkylamino, dialkylamino, cycloalkylamino, hydroxyalkyl, (amino)alkyl, (alkylamino)alkyl, (dialkylamino)alkyl, (cycloalkylamino)alkyl, (cycloalkyl)alkyl, aralkyl, (heterocyclo)alkyl, (heteroaryl)alkyl, (amino)(hydroxy)alkyl, (aralkylamino)alkyl, optionally substituted heterocyclo, optionally substituted heteroaryl, optionally substituted aryl, and optionally substituted cycloalkyl;

$R^{31a}$ and $R^{31b}$ are each independently selected from the group consisting of hydrogen, optionally substituted alkyl, optionally substituted alkenyl, optionally substituted alkynyl, hydroxyalkyl, (amino)alkyl, (alkylamino)alkyl, (dialkylamino)alkyl, alkoxyalkyl, cycloalkyl, (cycloalkyl)alkyl, (heterocyclo)alkyl, aralkyl, and (heteroaryl)alkyl; and each of $R^{24}$, $R^{25}$, $R^{27}$, $R^{32a}$, and $R^{32b}$ is independently selected from the group consisting of hydrogen, optionally substituted alkyl, optionally substituted alkenyl, optionally substituted alkynyl, amino, alkylamino, dialkylamino, cycloalkylamino, hydroxyalkyl, (amino)alkyl, (alkylamino)alkyl, (dialkylamino)alkyl, (cycloalkylamino)alkyl, (cycloalkyl)alkyl, aralkyl, (heterocyclo)alkyl, (heteroaryl)alkyl, (amino)(hydroxy)alkyl, (aralkylamino)alkyl, alkoxyalkyl, optionally substituted heterocyclo, optionally substituted heteroaryl, optionally substituted aryl, and optionally substituted cycloalkyl.

43. The compound of claim 42, wherein $R^5$ is selected from the group consisting of:

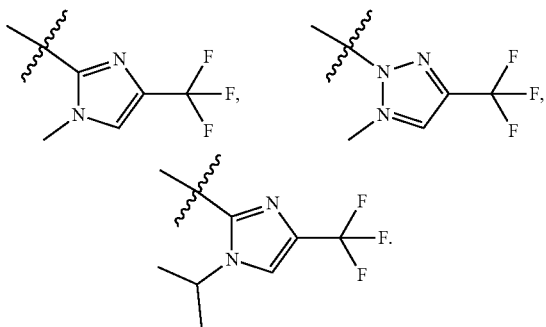

44. The compound of claim 43, wherein $R^5$ is

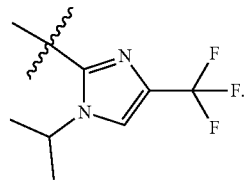

45. A compound having Formula I:

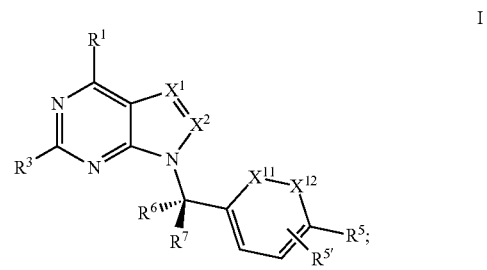

or a pharmaceutically acceptable salt or solvate thereof, wherein:

each of $X^1$ and $X^2$ is independently selected from N and $CR^2$;

each of $R^1$ and $R^2$ is independently selected from hydrogen, halo, cyano, optionally substituted alkyl, optionally substituted alkenyl, and optionally substituted alkynyl;

$R^3$ is an optionally substituted phenyl, optionally substituted pyridyl, optionally substituted pyrimidinyl, optionally substituted pyrazinyl, optionally substituted pyridazinyl, or optionally substituted pyrazolyl;

each of $X^{11}$ and $X^{12}$ is independently selected from N and CH;

$R^{5'}$ is selected from hydrogen, optionally substituted ($C_1$-$C_6$) alkyl, optionally substituted ($C_2$-$C_6$) alkenyl, optionally substituted ($C_2$-$C_6$) alkynyl, optionally substituted ($C_1$-$C_6$) alkoxy, ($C_1$-$C_6$) haloalkyl, ($C_1$-$C_6$) haloalkoxy, ($C_1$-$C_6$) hydroxyalkyl, cyano, halo, sulfonamido, —C(=O)$R^{23}$, —C(=O)O$R^{24}$, —NR$^{32a}$R$^{32b}$, —NR$^{31a}$C(=O)$R^{25}$, —NR$^{31a}$C(=O)NR$^{31a}$R$^{31b}$, —C(=O)NR$^{31a}$R$^{31b}$, —S(O)$_2$R$^{27}$, —NR$^{31a}$SO$_2$R$^{27}$, optionally substituted ($C_6$-$C_{14}$) aryl, optionally substituted ($C_6$-$C_{14}$) ar-($C_1$-$C_2$) alkyl, optionally substituted heteroaryl, optionally substituted heteroar-($C_1$-$C_2$) alkyl, optionally substituted ($C_3$-$C_8$) cycloalkyl, optionally substituted (($C_3$-$C_8$) cycloalkyl)-($C_1$-$C_2$) alkyl, optionally substituted heterocyclo, optionally substituted heterocyclo-($C_1$-$C_2$) alkyl, optionally substituted —O—($C_6$-$C_{14}$) aryl, optionally substituted —O—($C_6$-$C_{14}$) ar-($C_1$-$C_2$) alkyl, optionally substituted —O-heteroaryl, optionally substituted —O-heteroar-($C_1$-$C_2$) alkyl, optionally substituted —O— ($C_3$-$C_8$) cycloalkyl, optionally substituted —O—(($C_3$-$C_8$) cycloalkyl)-($C_1$-$C_2$) alkyl, optionally substituted —O-heterocyclo, optionally substituted —O-heterocyclo-($C_1$-$C_2$) alkyl;

$R^5$ is an optionally substituted pyrrolyl, optionally substituted imidazolyl, optionally substituted pyrazolyl, optionally substituted triazolyl, or optionally substituted tetrazolyl;

each of $R^6$ and $R^7$ is independently selected from hydrogen, halo, cyano, optionally substituted alkyl, optionally substituted alkenyl, and optionally substituted alkynyl;

$R^{23}$ is selected from the group consisting of hydrogen, optionally substituted alkyl, optionally substituted alkenyl, optionally substituted alkynyl, amino, alkylamino, dialkylamino, cycloalkylamino, hydroxyalkyl, (amino)alkyl, (alkylamino)alkyl, (dialkylamino)alkyl, (cycloalkylamino)alkyl, (cycloalkyl)alkyl, aralkyl, (heterocyclo)alkyl, (heteroaryl)alkyl, (amino)(hydroxy)alkyl, (aralkylamino)alkyl, optionally substituted heterocyclo, optionally substituted heteroaryl, optionally substituted aryl, and optionally substituted cycloalkyl;

$R^{31a}$ and $R^{31b}$ are each independently selected from the group consisting of hydrogen, optionally substituted alkyl, optionally substituted alkenyl, optionally substituted alkynyl, hydroxyalkyl, (amino)alkyl, (alkylamino)alkyl, (dialkylamino)alkyl, alkoxyalkyl, cycloalkyl, (cycloalkyl)alkyl, (heterocyclo)alkyl, aralkyl, and (heteroaryl)alkyl; and each of $R^{24}$, $R^{25}$, $R^{27}$, $R^{32a}$, and $R^{32b}$ is independently selected from the group consisting of hydrogen, optionally substituted alkyl, optionally substituted alkenyl, optionally substituted alkynyl, amino, alkylamino, dialkylamino, cycloalkylamino, hydroxyalkyl, (amino)alkyl, (alkylamino)alkyl, (dialkylamino)alkyl, (cycloalkylamino)alkyl, (cycloalkyl)alkyl, aralkyl, (heterocyclo)alkyl, (heteroaryl)alkyl, (amino)(hydroxy)alkyl, (aralkylamino)alkyl, alkoxyalkyl, optionally substituted heterocyclo, optionally substituted heteroaryl, optionally substituted aryl, and optionally substituted cycloalkyl.

* * * * *

UNITED STATES PATENT AND TRADEMARK OFFICE
CERTIFICATE OF CORRECTION

PATENT NO. : 11,485,736 B2
APPLICATION NO. : 16/721079
DATED : November 1, 2022
INVENTOR(S) : Brenneman et al.

It is certified that error appears in the above-identified patent and that said Letters Patent is hereby corrected as shown below:

In the Specification

In Column 3, Line 9, delete "one of $R^5$ and one of $R^5$ on adjacent atoms are taken" and insert -- one of $R^5$ and one of $R^{5'}$ on adjacent atoms are taken --, therefor.

In Column 14, Line 52, delete "$R^5$," and insert -- $R^{15}$, --, therefor.

In Column 25, Line 17, delete "deubiquitnates" and insert -- deubiquitinates --, therefor.

In Column 33, Line 25, delete "the the" and insert -- the -- at each occurrence throughout the Patent.

In Column 52, Line 67, delete "3-(1-(4-(5-methyl-3-(trifluoromethyl)-1H-pyrazol-yl)benzyl)-H-pyrazolo[3,4-d]pyrimidin-6-yl)picolinonitrile" and insert -- 3-(1-(4-(5-methyl-3-(trifluoromethyl)-1H-pyrazol-1-yl)benzyl)-1H-pyrazolo[3,4-d]pyrimidin-6-yl)picolinonitrile --, therefor.

In Column 69, Line 59, delete "Examplary" and insert -- Exemplary --, therefor.

In Column 69, Line 61, delete "inhibiton," and insert -- inhibition, --, therefor.

In Column 73, Line 3, delete "flurophore" and insert -- fluorophore --, therefor.

In Column 73, Line 7, delete "flurophore" and insert -- fluorophore --, therefor.

In Column 73, Line 14, delete "Deubicuitination" and insert -- Deubiquitination --, therefor.

In Column 75, Lines 38-39, delete "homolgous-recombination" and insert -- homologous-recombination --, therefor.

In Column 76, Line 10, delete "Lippencott" and insert -- Lippincott --, therefor.

Signed and Sealed this
Sixth Day of June, 2023

Katherine Kelly Vidal
*Director of the United States Patent and Trademark Office*

CERTIFICATE OF CORRECTION (continued)
U.S. Pat. No. 11,485,736 B2

In Column 76, Line 54, delete "benzylalkonium" and insert -- benzalkonium --, therefor.

In Column 80, Line 53, delete "Diethylazodicarboxylate" and insert -- Diethyl azodicarboxylate --, therefor.

In Column 136, Line 13, delete "(7.85" and insert -- δ 7.85 --, therefor.

In Column 136, Line 66, delete "(7.70" and insert -- δ 7.70 --, therefor.

In Column 137, Line 5, delete "(7.93" and insert -- δ 7.93 --, therefor.

In Column 139, Line 21, delete "(8.06" and insert -- δ 8.06 --, therefor.

In Column 139, Line 47, delete "(7.72" and insert -- δ 7.72 --, therefor.

In Column 150, Lines 15-19, delete " 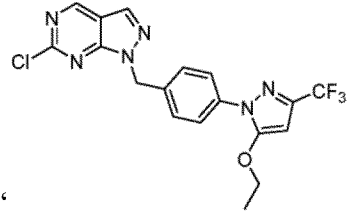 " and insert -- 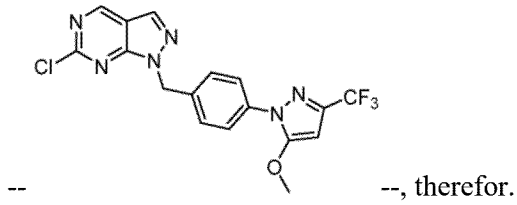 --, therefor.

In Column 163, Line 66, delete "(8.19" and insert -- δ 8.19 --, therefor.

In Column 175, Line 8, delete "I/O)" and insert -- 1/0) --, therefor.

In Column 188, Line 20, after "DMSO-$d_6$)" insert -- δ --.

In Column 211, Line 66, delete "(7.67" and insert -- δ 7.67 --, therefor.

In Column 224, Line 27, delete "6H)" and insert -- 6H). --, therefor.

In Column 226, Line 35, delete "(6.69-6.79" and insert -- δ 6.69-6.79 --, therefor.

In Column 235, Line 43, delete "3H)" and insert -- 3H). --, therefor.

In Column 237, Line 3, delete "2H)" and insert -- 2H). --, therefor.

In Column 254, Line 66, delete "(8.88" and insert -- δ 8.88 --, therefor.

In Column 256, Line 3, delete "B$_3$Pin$_2$," and insert -- B$_2$Pin$_2$, --, therefor.

In Column 258, Line 16, delete "B₃Pin₂," and insert -- B₂Pin₂, --, therefor.

In Column 264, Line 26, delete "(9.30" and insert -- δ 9.30 --, therefor.

In Column 291, Line 2, delete " 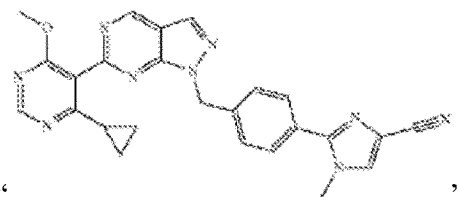 " and insert
-- 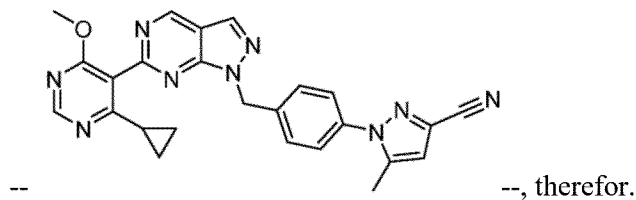 --, therefor.

In Column 306, Line 10, delete "2H)" and insert -- 2H). --, therefor.

In Column 354, Line 46, after "DMSO-d₆)" insert -- δ --.

In Column 356, Line 30, delete "(n," and insert -- (m, --, therefor.

In Column 374, Line 60, delete "4-dimethylanminopyridine" and insert
-- 4-dimethylaminopyridine --, therefor.

In Column 410, Line 41, after "DMSO-d₆)" insert -- δ --.

In Column 447, Step 4, Line 1, delete "NH4Cl" and insert -- NH₄Cl --, therefor.

In Column 452, Line 59, after "Na₂CO₃" insert -- solution (20 mL) slowly under stirring and extracted with EA (2 x 10 mL). The combined --.

In Column 467, Line 5, delete "IC₅₀ ₅₀:" and insert -- IC₅₀: --, therefor.

In Column 511, Line 4, delete "IC₅₀ ₅₀:" and insert -- IC₅₀: --, therefor.

In the Claims

In Column 527, Claim 1, Lines 52-60, delete " 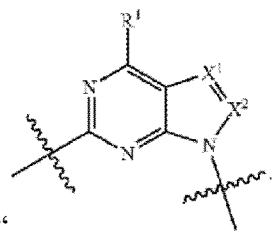 " and insert -- 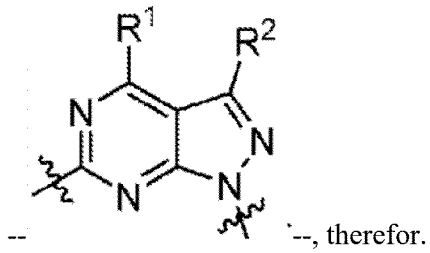 --, therefor.
In Column 529, Claim 1, Line 16, delete "$R^5$ and one of $R^5$ on adjacent atoms" and insert -- $R^5$ and one of $R^{5'}$ on adjacent atoms --, therefor.
In Column 530, Claim 4, Lines 37-43, delete " 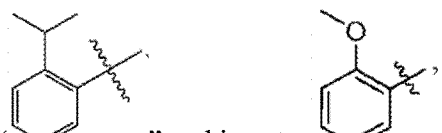 --, therefor.
In Column 532, Claim 4, Lines 41-51, delete " 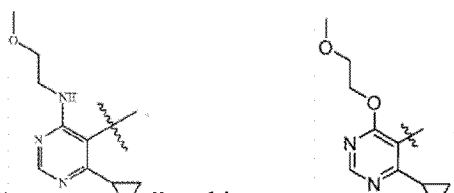 --, therefor.
In Column 533, Claim 4, Lines 11-19, delete " 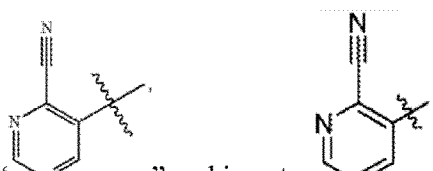 --, therefor.
In Column 536, Claim 11, Lines 46-50, delete " 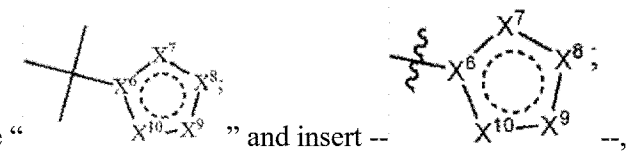 --, therefor.

CERTIFICATE OF CORRECTION (continued)

In Column 546, Claim 33, Lines 27-39, delete "  " and insert -- 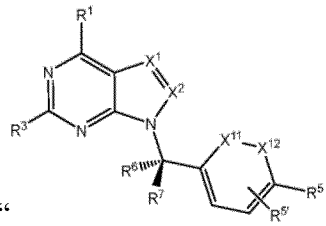 --, therefor.

In Column 558, Claim 42, Lines 21-31, delete " 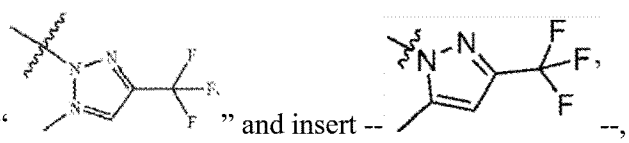 " and insert -- 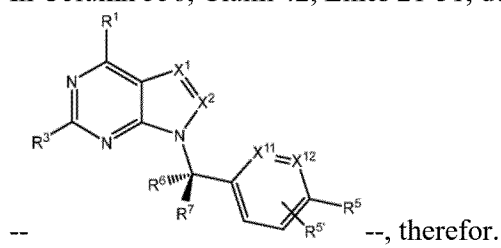 --, therefor.

In Column 559, Claim 43, Lines 52-57, delete "  " and insert --  --, therefor.

In Column 560, Claim 45, Lines 21-24, delete " 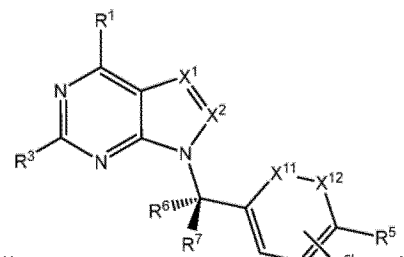 " and insert -- 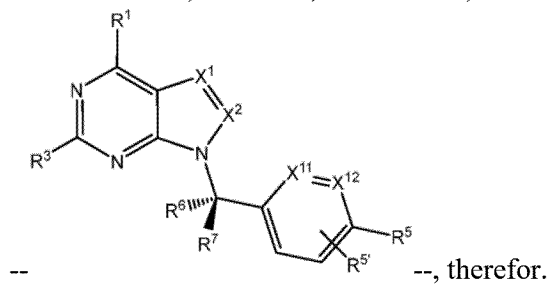 --, therefor.